(12) United States Patent
Picataggio et al.

(10) Patent No.: US 8,093,037 B2
(45) Date of Patent: Jan. 10, 2012

(54) ENGINEERED MICROORGANISMS WITH ENHANCED FERMENTATION ACTIVITY

(75) Inventors: Stephen Picataggio, Carlsbad, CA (US); Kirsty Anne Lily Salmon, Carlsbad, CA (US); Jose Miguel LaPlaza, Carlsbad, CA (US)

(73) Assignee: Verdezyne, Inc., Carlsbad, CA (US)

( * ) Notice: Subject to any disclaimer, the term of this patent is extended or adjusted under 35 U.S.C. 154(b) by 0 days.

(21) Appl. No.: 13/045,841

(22) Filed: Mar. 11, 2011

(65) Prior Publication Data

US 2011/0229959 A1    Sep. 22, 2011

Related U.S. Application Data

(63) Continuation of application No. PCT/US2010/041618, filed on Jul. 9, 2010.

(60) Provisional application No. 61/224,430, filed on Jul. 9, 2009, provisional application No. 61/316,780, filed on Mar. 23, 2010, provisional application No. 61/334,097, filed on May 12, 2010.

(51) Int. Cl.
    *C12N 1/15*    (2006.01)
(52) U.S. Cl. .................................... 435/254.21
(58) Field of Classification Search .................... None
    See application file for complete search history.

(56) References Cited

U.S. PATENT DOCUMENTS

| | | | |
|---|---|---|---|
| 4,490,468 A | 12/1984 | Gong et al. |
| 4,683,195 A | 7/1987 | Mullis et al. |
| 4,683,202 A | 7/1987 | Mullis |
| 4,965,188 A | 10/1990 | Mullis et al. |
| 5,232,841 A | 8/1993 | Hashimoto et al. |
| 5,268,273 A | 12/1993 | Buckholz |
| 5,389,529 A | 2/1995 | Panayotatos et al. |
| 5,470,719 A | 11/1995 | Meng et al. |
| 5,595,899 A | 1/1997 | Sato |
| 5,656,493 A | 8/1997 | Mullis et al. |
| 5,712,114 A | 1/1998 | Mankovich et al. |
| 5,766,891 A | 6/1998 | Shuman |
| 5,786,186 A | 7/1998 | Lancashire et al. |
| 5,789,210 A | 8/1998 | Ho et al. |
| 5,798,237 A | 8/1998 | Picataggio et al. |
| 5,843,760 A | 12/1998 | Zhang et al. |
| 5,846,818 A | 12/1998 | Robinson et al. |
| 5,888,732 A | 3/1999 | Hartley et al. |
| 5,932,474 A | 8/1999 | Tsien et al. |
| 5,935,837 A | 8/1999 | Rasmussen |
| 6,008,378 A | 12/1999 | Tsien et al. |
| 6,054,271 A | 4/2000 | Tsien et al. |
| 6,143,557 A | 11/2000 | Hartley et al. |
| 6,171,861 B1 | 1/2001 | Hartley et al. |
| 6,270,969 B1 | 8/2001 | Hartley et al. |
| 6,277,608 B1 | 8/2001 | Hartley et al. |
| 6,288,302 B1 | 9/2001 | Yu et al. |
| 6,333,181 B1 | 12/2001 | Ingram et al. |
| 6,451,569 B1 | 9/2002 | Tsien et al. |
| 6,475,768 B1 | 11/2002 | Otero et al. |
| 6,566,107 B1 | 5/2003 | Zhang |
| 6,720,140 B1 | 4/2004 | Hartley et al. |
| 7,198,933 B2 | 4/2007 | Zeikus et al. |
| 7,226,735 B2 | 6/2007 | Jeffries et al. |
| 7,285,403 B2 | 10/2007 | Jeffries et al. |
| 7,432,085 B2 | 10/2008 | Hara et al. |
| 7,514,247 B2 | 4/2009 | Rush |
| 7,527,927 B1 | 5/2009 | Ho et al. |
| 7,622,284 B2 | 11/2009 | Op Den Camp et al. |
| 7,670,823 B1 | 3/2010 | Hartley et al. |
| 2002/0007051 A1 | 1/2002 | Cheo et al. |
| 2003/0083373 A1 | 5/2003 | Tsien et al. |
| 2004/0142435 A1 | 7/2004 | Gunji et al. |
| 2004/0142456 A1 | 7/2004 | Jeffries et al. |
| 2005/0112590 A1 | 5/2005 | Van Den Boom et al. |
| 2005/0287592 A1 | 12/2005 | Kless |
| 2006/0115878 A1 | 6/2006 | Hara et al. |
| 2006/0216804 A1 | 9/2006 | Karhumaa et al. |
| 2006/0228789 A1 | 10/2006 | Jeffries et al. |
| 2006/0234364 A1 | 10/2006 | Rajgarhia et al. |
| 2006/0281908 A1 | 12/2006 | Callen et al. |
| 2007/0082386 A1 | 4/2007 | Gorwa-Grausland |
| 2007/0141690 A1 | 6/2007 | Karhumaa et al. |
| 2008/0014620 A1 | 1/2008 | Op Den Camp et al. |
| 2008/0085341 A1 | 4/2008 | Dai et al. |
| 2008/0187973 A1 | 8/2008 | Viitanen et al. |
| 2008/0261287 A1 | 10/2008 | Winkler et al. |
| 2009/0221078 A1 | 9/2009 | Caimi et al. |
| 2009/0246857 A1 | 10/2009 | Ho et al. |
| 2009/0311771 A1 | 12/2009 | Boles et al. |
| 2010/0028975 A1 | 2/2010 | Gorwa-Grauslund |
| 2010/0035306 A1 | 2/2010 | Op Den Camp et al. |
| 2010/0120105 A1 | 5/2010 | Anthony |
| 2010/0146842 A1 | 6/2010 | Dumenil |

(Continued)

FOREIGN PATENT DOCUMENTS

EP    1468093    10/2004

(Continued)

OTHER PUBLICATIONS

Fong et al., "Directed evolution of D-2-keto-3-deoxy-6-phosphogluconate adolase to new variants fot the efficient synthesis of D- and L-sugars," Chemistry & Biochemistry, 2000, vol. 7, No. 11, pp. 873-883.
Fuhrman et al., :Rapid accumulation of intracellular 2-keto-3-deoxy-6-phosphogluconate in an Entner-Doudoroff aldolase mutant results in bacteriostasis. FEMS Microbiology Letters 1998, vol. 159, Issue 2, pp. 261-266.
International Search Report and Written Opinion mailed: Jun. 3, 2011 in International Application No. PCT/US2010/041607 filed on: Jul. 9, 2010 and published as: WO/2011/006126 on: Jan. 13, 2011.
U.S. Appl. No. 60/587,583, filed Jul. 14, 2004, Wieslaw.
Ding et al., "Identification, expression, and characterization of the highly conserved d-xylose isomerase in animals," Acta Biochim Biophys Sin (2009) 41 (2): 116-122.
Madhavan et al., "Xylose isomerase from polycentric fungus Orpinomyces: gene sequencing, cloning, and expression in *Saccharomyces cerevisiae* for bioconversion of xylose to ethanol," Appl Microbiol Biotechnol (2009) 82:1067-1078.

(Continued)

*Primary Examiner* — Nashaat Nashed
(74) *Attorney, Agent, or Firm* — Grant Anderson LLP

(57) ABSTRACT

Provided herein are genetically modified microorganisms that have enhanced fermentation activity, and methods for making and using such microorganisms.

19 Claims, 37 Drawing Sheets

U.S. PATENT DOCUMENTS

| | | | |
|---|---|---|---|
| 2010/0146843 | A1 | 6/2010 | Dumenil |
| 2011/0165660 | A1 | 7/2011 | Picataggio et al. |
| 2011/0165661 | A1 | 7/2011 | Picataggio et al. |

FOREIGN PATENT DOCUMENTS

| | | |
|---|---|---|
| KR | 10-0697551 | 3/2007 |
| WO | WO 95/13362 | 5/1995 |
| WO | WO 95/25799 | 9/1995 |
| WO | WO 96/19497 | 6/1996 |
| WO | WO 97/42307 | 11/1997 |
| WO | WO 98/56943 | 12/1998 |
| WO | WO 99/21013 | 4/1999 |
| WO | WO 2009/109631 | 9/2001 |
| WO | WO 03/062430 | 7/2003 |
| WO | WO 2004/099381 | 11/2004 |
| WO | WO 2005/023998 | 3/2005 |
| WO | WO 2005/091733 | 10/2005 |
| WO | WO 2006/096130 | 9/2006 |
| WO | WO 2007/028811 | 3/2007 |
| WO | WO 2009/109630 | 9/2009 |
| WO | WO 2009/109633 | 9/2009 |
| WO | WO 2009/109634 | 9/2009 |
| WO | WO 2010/074677 | 7/2010 |
| WO | WO 2010/079065 | 7/2010 |
| WO | WO 2010/079067 | 7/2010 |
| WO | WO 2011/006126 | 1/2011 |
| WO | WO 2011/006136 | 1/2011 |

OTHER PUBLICATIONS

Akbergenov et al., "ARC-1, a sequence element complementary to an internal 18S rRNA segment, enhances translation efficiency in plants when present in the leader or intercistronic region of mRNAs," Nucleic Acids Research 32: 239-247 (2004).

Alani et al., "A method for gene disruption that allows repeated use of URA3 selection in the construction of multiply disrupted yeast strains", Genetics 116(4):541-545 Aug. 1987.

Alper et al., "Engineering yeast transcription machinery for improved ethanol tolerance and production," Science, American Association for the Advancement of Science, Washington, DC, US, vol. 314, No. 5805, Dec. 8, 2006, pp. 1565-1568.

Brat et al, Functional Expression of a Bacterial Xylose Isomerase in *Saccharomyces cerevisiae* (Applied and Evnironmental Microbiol., Apr. 2009; p. 2304-2311; vol. 75, No. 8).

Capone et al., Amber, ochre and opal suppressor tRNA genes derived from a human serine tRNA gene. EMBO J. 4:213, 1985.

Cheriyan et al., "Mutagenesis of the phosphate-binding pocket of KDPG aldolase enhances selectivity for hydrophobic substrates," Protein Science 16:2368-2377, 2007.

Coppella et al., "A Detailed Analysis of *Saccharomyces cerevkiae* Growth Kinetics in Batch, Fed-batch, and Hollow-fiber Bioreactors," The Chemical Engineering Journal, 41 (1989) B27-B35.

Current Protocols in Molecular Biology, John Wiley & Sons, N.Y., 6.3.1-6.3.6 (1989).

De Graaf Albert A et al., "Metabolic state of Zymomonas mobilis in glucose-, fructose-, and xylose-fed continuous cultures as analyzed by 13C- and 31P-NMR spectroscopy" Archives of Microbiology, Springer, DE, vol. 171. No. 6, May 1, 1999, pp. 371-385.

Deshpande, Mukund V., "Ethanol production from cellulose by coupled saccharification/fermentation using *Saccharomyces cerevisiae* and cellulase complex from *Sclerotium rolfsii* UV-8 mutant.," Appl. Biochem. Biotechnol., 36:227-234 (1992).

Eggertsson, et al., "Transfer ribonucleic acid-mediated suppression of termination codons in *Escherichia coli*." (1988) Microbiological Review 52(3):354-374.

Gallie et al., "The 5'-leader sequence of tobacco mosaic virus RNA enhances the expression of foreign gene transcripts in vitro and in vivo," Nucleic Acids Research 15: 3257-3273 (1987).

Gallie, "The 5'-leader of tobacco mosaic virus promotes translation through enhanced recruitment of elF4F," Nucleic Acids Research 30: 3401-3411 (2002).

Hitchman et al., "Hexanoate Synthase, a Specialized Type I Fatty Acid Synthase in Aflatoxin B1 Biosynthesis," Bioorganic Chemistry 29, 293-307 (2001).

Hill, Craig, "Automating nucleic acid amplification tests" IVD Technology Magazine, published Nov./Dec. 2000, downloaded from: http://www.devicelink.com/ivdt/archive/00/11/007.

Innis et al., eds, (1990) PCR Protocols: A Guide to Methods and Applications (Table of Contents).

International Search Report and Written Opinion mailed: Mar. 11, 2011 in International Application No. PCT/US2010/041618 filed on: Jul. 9, 2010 and published as: on.

Jeffries, Thomas W., "Engineering yeasts for xylose metabolism," Current Opinion in Biotechnology 2006, 17:320-326.

Kuyper et al., "High-level functional expression of a fungal xylose isomerase: the key to efficient ethanolic fermentation of xylose by *Saccharomyces cerevisiae*?" FEMS Yeast Res., 4:69-78 [2003].

Landy, "Mechanistic and structural complexity in the site-specific recombination pathways of Int and FLP," Curr. Opin. Biotech. 3:699-707 (1993).

Larkin, et al., "Clustal W and Clustal X version 2.0," Bioinformatics 2007 23(21): 2947-2948.

Larsen et al., "Computationally Optimized DNA Assembly of synthetic genes," Int. J. Bioinform. Res. Appl; 2008:4[3]; 324-336.

Meyers & Miller, "Optimal alignments in linear space," CABIOS 4: 11-17 (1989).

Mignone et al., "Untranslated regions of mRNAs," Genome Biology 3(3): reviews0004.1-0001.10 (2002).

Mignone et al., "UTRdb and UTRsite: a collection of sequences and regulatory motifs of the untranslated regions of eukaryotic mRNAs," Nucleic Acids Research 33: D141-D146 (2005).

Mumberg D, et al., "Regulatable promoters of *Saccharomyces cerevisiae*: comparison of transcriptional activity and their use for heterologous expression," Nucleic Acids Res. 22: 5767-5768, 1994.

Mumberg et al., "Yeast vectors for the controlled expression of heterologous proteins in different genetic backgrounds," 1995, Gene 156: 119-122.

Needleman & Wunsch,"A general method applicable to the search for similarities in the Amino Acid Sequence of two proteins." J. Mol. Biol. 48: 443-453 (1970).

Nelson et al., "Simultaneous detection of multiple nucleic acid targets in a homogeneous format," Biochemistry Jun. 25, 1996;35(25):8429-8438.

Ost et al., "Rational re-design of the substrate binding site of £avocytochrome P450 BM3," FEBS Letters 486(2000) 173-177.

Paulous et al., "Comparison of the capacity of different viral internal ribosome entry segments to direct translation initiation in poly(A)-dependent reticulocyte lysates," Nucleic Acids Research 31: 722-733 (2003).

Sambrook et al., (1989) Revised ed. of: "Molecular cloning, A Laboratory Manual," 1982 by Maniatis, Fritsch, Sambrook, Maniatis, "Molecular Cloning: a Laboratory Manual; Cold Spring Harbor Laboratory, Cold Spring Harbor, N.Y." Table of contents.

Sauer, B., "Site-specific recombination: developments and applications," Curr. Opin. Biotech. 5:521-527 (1994).

Sekiguchi and Shuman, "Requirements for noncovalent binding of vaccinia topoisomerase I to duplex DNA," Nucl. Acids Res. 22:5360-5365, 1994.

Shaloiko et al., "Effective non-viral leader for cap-independent translation in a eukaryotic cell-free system," Biotechnology and Bioengineeringvol. 88, Issue 6, pp. 730-739, (2004).

Shuman, "Site-specific interaction of vaccinia virus topoisomerase I with duplex DNA. Minimal DNA substrate for strand cleavage in vitro," J. Biol. Chem. 266:11372-11379, 1991.

Sikorski RS, Boeke JD., "In vitro mutagenesis and plasmid shuffling: From cloned gene to mutant yeast," Methods Enzymol. 194: 302-318, 1991.

Tjalsma et al., "Signal peptide-dependent protein transport in *Bacillus subtilis*: a genome-based survey of the secretome," Microbiol. Molec. Biol. Rev. 64: 515-547 (2000).

Vincent et al., "Helicase-dependent isothermal DNA amplification". EMBO reports 5 (8): 795-800 (2004).

Winzeler EA, et al. "Functional characterization of the *S. cerevisiae* genome by gene deletion and parallel analysis," Science 285: 901-906, 1999.

Broun et al., Catalytic plasticity of fatty acid modification enzymes underlying chemical diversity of plant lipids. Science, 1998, vol. 282: 1315-1317.

Chica et al., Semi-rational approaches to engineering enzyme activity: combining the benefits of directed evolution and rational design. Curro Opi. Biotechnol., 2005, vol. 16: 378-384.

Devos et al., Practical limits of function prediction. Proteins: Structure, Function, and Genetics. 2000, vol. 41: 98-107.

Kimchi-Sarfaty et al., A "Silent" polymorphism in the MDR1 gene changes substrate specificty. SCIENCE, 2007, vol. 315: 525-528.

Kisselev L., Polypeptide release factors in prokaryotes and eukaryotes: same function, different structure. Structure, 2002, vol. 10: 8-9.

Nackley et al., Human Caechol-O-Methytransferase haplotypes modulate protein expression by altering mRNA secondary structure. SCIENCE, 2006, vol. 314: 1930-1933.

Sauna et al., Silent polymorhisms speak: How they affect pharmacogenomics and the treatment of cancer. Cancer Res., 2007, vol. 67(20): 9609-9612.

Seffernick et al., Melamine deaminase and Atrazine chlorohydrolase: 98 percent identical but functionally different. J. Bacteriol., 2001, vol. 183 (8): 2405-2410.

Sen et al., Developments in directed evolution for improving enzyme functions. Appl. Biochem. Biotechnol., 2007, vol. 143: 212-223.

Whisstock et al., Prediction of protein function from protein sequence. Q. Rev. Biophysics., 2003, vol. 36 (3): 307-340.

Wishart et al., A single mutation converts a novel phosphotyrosine binding domain into a dual-specificity phosphatase. J. Biol. Chem., 1995, vol. 270(45): 26782-26785.

Witkowski et al., Conversion of b-ketoacyl synthase to a Malonyl Decarboxylase by replacement of the active cysteine with glutamine. Biochemistry, 1999, vol. 38: 11643-11650.

Office Action mailed on: Sep. 19, 2011 in U.S. Appl. No. 13/045,855 filed on: Mar. 11, 2011, and published as: 2011-0165661 on Jul. 7, 2011.

Score Search Results for U.S. Appl. No. 13/045,847 cited in Office Action dated: Sep. 19, 2011 as Temple et al., J. Bacteriol, 1994 vol: 176, 4700-4709; Accession # P31961; Q9HZ45.

Score Search Results for U.S. Appl. No. 13/045,847 cited in Office Action dated Sep. 19, 2011 as DeSouza et al, Accession # U17155 and GI 577838 (1994).

Score Search Results of U.S. Appl. No. 13/045,847 cited in Office Action dated: Sep. 19, 2011 as Borneman et al., FEMS Yeast Res, 2008, vol. 8: 1185-1195; Accession # B5VK90.

Score Search Results of U.S. Appl. No. 13/045,847 cited in Office Action dated: Sep. 19, 2011 as Nogae et al., Gene, 1990, vol. 96: 161-169; Cited as Accession # P11412; D6W0V2.

Thurston, B., et al., "Pentose utilization by the ruminal bacteria *Ruminococcus albus*," Applied and Environmental Microbiology, vol. 60, No. 4, pp. 1087-1092 (1994).

Aurilia, V., et al., "Organisation and variable incidence of genes concerned with the utilization of xylans in the rumen celluolytic bacterium *Ruminococcus Flavefaciens*," Anerobe, vol. 6, No. 6, pp. 333-340.

Office Action mailed on: Oct. 18, 2011 in U.S. Appl. No. 13/045,829 filed on: Mar. 12, 2011, and published as: 2011-0224416 on Sep. 15, 2011.

DNA Sequence Alignment for ZM4 Native, ZM4 Matched, ZM4 HR and *E.coli* Eda

```
ZM4_NATIVE      ATGCGTGAT-----ATCGATTCCGTAATGCGTT-TGGCA------CCGGT
ZM4_MATCHED     ATGAGGGAT-----ATTGATAGTGTGATGAGGT-TAGCC------CCTGT
ZM4_HR          ATGAGAGAC-----ATTGATTCTGTTATGAGAT-TGGCT------CCAGT
ECOLI_NATIVE    ATGAAAAACTGGAAAACAAGTGCAGAATCAATCCTGACCACCGGCCCGGT
                ***        *    *   *       **    *   *      ** **

ZM4_NATIVE      TATGCCGGTCCTCGTCATTGAAGATATTGCTGATGCAAAACCTATCGCAG
ZM4_MATCHED     TATGCCTGTTCTCGTTATTGAAGATATTGCAGATGCCAAACCTATTGCCG
ZM4_HR          TATGCCAGTCTTGGTTATAGAAGATATAGCTGATGCTAAGCCAATTGCTG
ECOLI_NATIVE    TGTACCGGTTATCGTGGTAAAAAAACTGGAACACGCGGTGCCGATGGCAA
                * * ** **   * **   ** *   **   *  *      ** ** **

ZM4_NATIVE      AAGCTTTGGTTGCTGGTGGTCTGAACGTTCTTGAAGTAACGCTTCGCACC
ZM4_MATCHED     AAGCACTCGTTGCAGGTGGTCTAAACGTTCTAGAAGTGACACTAAGGACT
ZM4_HR          AGGCTTTGGTTGCTGGTGGTTTAAATGTTTTGGAAGTTACATTGAGAACT
ECOLI_NATIVE    AAGCGTTGGTTGCTGGTGGGGTGCGCGTTCTGGAAGTGACTCTGCGTACC
                * **   * ***** *****  *    *** * *****  **   *  **

ZM4_NATIVE      CCTTGTGCTCTTGAAGCCATCAAGATCATG---AAAGAAGTTCCGGGTGC
ZM4_MATCHED     CCTTGTGCACTAGAAGCTATTAAGATTATG---AAGGAAGTTCCTGGTGC
ZM4_HR          CCATGTGCTTTGGAAGCTATTAAAATTATG---AAGGAAGTTCCAGGTGC
ECOLI_NATIVE    GAGTGTGCAGTTGACGCTATCCGTGCTATCGCCAAAGAAGTGCCTGAAGC
                    *****  *   **  **  * ** ** **   ** ***** **  **

ZM4_NATIVE      CGTTGTTGGTGCCGGTACGGTTCTGAACGCAAAAATGCTCGACCAAGCTC
ZM4_MATCHED     TGTTGTTGGTGCTGGTACAGTTCTAAACGCCAAAATGCTCGACCAGGCAC
ZM4_HR          TGTTGTTGGTGCTGGTACTGTTTTAAACGCTAAAATGTTGGATCAAGCTC
ECOLI_NATIVE    GATTGTGGGTGCCGGTACGGTGCTGAATCCACAGCAGCTGGCAGAAGTCA
                 **** ***** *****  ** *  **    * * *   *  * *  * *

ZM4_NATIVE      AGGAAGCTGGTTGCG-AATTTTTCGTTAGCCCGGGTCTGACCG--CTGAC
ZM4_MATCHED     AAGAAGCAGGTTGCG-AATTTTTCGTTTCACCTGGTCTAACTG--CCGAC
ZM4_HR          AAGAAGCTGGTTGTG-AGTTCTTTGTATCACCAGGTTTGACTG--CTGAT
ECOLI_NATIVE    CTGAAGCGGGT-GCACAGTTCGCAATTAGCCCGGGTCTGACCGAGCCG-C
                  **** ***  *   * **    *  * ** *** * ** *    *  *

ZM4_NATIVE      CTCGGCAAGCATGCTGTTGCCCAGAAAGCAGCTTTGCTT---CCAGGTGT
ZM4_MATCHED     CTCGGAAAGCACGCAGTTGCTCAAAAAGCCGCATTACTA---CCCGGTGT
ZM4_HR          TTGGGAAAACATGCTGTTGCTCAAAAAGCGGCTCTTCTA---CCAGGGGT
ECOLI_NATIVE    TGCTGAAA----GCTGCTACCGAAGGGACTATTCCTCTGATTCCGGGGAT
                 * **     ** *  * *  *  *         **  **  **    *

ZM4_NATIVE      TGCTAATGCTGCTGATGTGATGCTTGGTCTTGACCTTGGTCTTGATCGCT
ZM4_MATCHED     TGCAAATGCAGCAGATGTGATGCTAGGTCTAGACCTAGGTCTAGATAGGT
ZM4_HR          TGCTAATGCTGCTGATGTTATGTTGGGATTGGATTTGGGTTTGGATAGAT
ECOLI_NATIVE    CAGCACTGTTTCCGAACTGATGCTGGGTATGGACTACGGTTTGAAAGAGT
                 * **    * *   * ** ***   **  **   * *** * *    *

ZM4_NATIVE      TCAAATTCTTCCCGGCTGAAAATATCGGTGGTTTACCTGCCCTGAAGTCC
ZM4_MATCHED     TCAAGTTCTTCCCTGCCGAAAACATTGGTGGTCTACCTGCTCTAAAGAGT
ZM4_HR          TTAAATTCTTCCCAGCTGAAAATATAGGTGGTTTGCCAGCTTTAAAATCT
```

FIG. 6A

```
ECOLI_NATIVE        TCAAATTCTTCCCGGCTGAAGCTAACGGCGGCGTGAAAGCCCTGCAGGCG
                    *  ** ******** ** ***    *  ** **  *    ** *    *

ZM4_NATIVE          ATGGCT--TCTGTTTTCCGTCAGGTTCGTTTCTGCCCGACCGGCGGTATC
ZM4_MATCHED         ATGGCA--TCAGTTTTCAGGCAAGTTAGGTTCTGCCCTACTGGAGGTATA
ZM4_HR              ATGGCT--TCTGTTTTTAGACAAGTTAGATTTTGTCCAACTGGAGGAATT
ECOLI_NATIVE        ATCGCGGGTCCGTTCTCC--CAGGTCCGTTTCTGCCCGACGGGTGGTATT
                    ** **    ** *** *    ** **    * ** ** ** ** ** **

ZM4_NATIVE          ACCCCGACGTCAGCTCCTAAATATCTTG-----AAAACCCGTCCATTCTT
ZM4_MATCHED         ACTCCTACAAGTGCACCTAAATATCTAG-----AAAACCCTAGTATTCTA
ZM4_HR              ACTCCGACTTCTGCTCCAAAATATTTGG-----AAAATCCATCTATTTTG
ECOLI_NATIVE        TCTCCGGCTAACTACCGTGACTACCTGGCGCTGAAAAGC-----GTGCTG
                    * **   *     *   *  *  * **          ****  *    * *

ZM4_NATIVE          TGCGTCGGTGGTAGCTGGGTTGTTCCGGCTGGCAAACCAGATGTCG-CAA
ZM4_MATCHED         TGCGTTGGTGGTTCATGGGTTGTTCCTGCCGGAAAACCCGATGTTG-CCA
ZM4_HR              TGTGTTGGTGGTTCTTGGGTTGTTCCAGCGGGTAAACCAGATGTTG-CGA
ECOLI_NATIVE        TGCATCGGTGGTTCCTGGCTGGTTCCGGCAGATGCGCTGGAAGCGGGCGA
                    ** *  ****** ** * ***** *****  *      ** *  *  * *

ZM4_NATIVE          AAATCACGGCACTCGCTAAAGAAGCTTCTG---CTTTCAAGCGCGCTGCT
ZM4_MATCHED         AAATTACAGCCCTCGCAAAAGAAGCAAGTG---CATTCAAGAGGGCAGCA
ZM4_HR              AAATTACTGCTTTGGCTAAAGAGGCTTCAG---CTTTTAAAAGAGCTGCT
ECOLI_NATIVE        TTACGACCGCATT-ACTAAGCTGGCGCGTGAAGCTGTAGAAGGCGCTA-A
                    * ** **  *   * *  **   **     * **  * * ** ** *

ZM4_NATIVE          GTTGCC
ZM4_MATCHED         GTTGCT
ZM4_HR              GTGGCG
ECOLI_NATIVE        GCTG--
                    *  *
```

FIG. 6A (Cont.)

Protein Sequence Alignment for ZM4 Native, ZM4 Matched, ZM4 HR and *E.coli* Eda

```
ZM4_NATIVE      MR----DIDSVMRLAPVMPVLVIEDIADAKPIAEALVAGGLNVLEVTLRTPCALEAIK-I
ZM4_MATCHED     MR----DIDSVMRLAPVMPVLVIEDIADAKPIAEALVAGGLNVLEVTLRTPCALEAIK-I
ZM4_HR          MR----DIDSVMRLAPVMPVLVIEDIADAKPIAEALVAGGLNVLEVTLRTPCALEAIK-I
ECOLI_NATIVE    MKNWKTSAESILTTGPVVPVIVVKKLEHAVPMAKALVAGGVRVLEVTLRTECAVDAIRAI
                *:    . :*::  .**:**:*:..: .* *:*:*******:.******* **::**: *

ZM4_NATIVE      MKEVPGAVVGAGTVLNAKMLDQAQEAGCEFFVSPGLTADLGKHAVAQKAALLPGVANAAD
ZM4_MATCHED     MKEVPGAVVGAGTVLNAKMLDQAQEAGCEFFVSPGLTADLGKHAVAQKAALLPGVANAAD
ZM4_HR          MKEVPGAVVGAGTVLNAKMLDQAQEAGCEFFVSPGLTADLGKHAVAQKAALLPGVANAAD
ECOLI_NATIVE    AKEVPEAIVGAGTVLNPQQLAEVTEAGAQFAISPGLTEPLLKAATEGTIPLIPGISTVSE
                 **** *:********.: * :. ***.:* :*****  * * *. . .*:**::..::

ZM4_NATIVE      VMLGLDLGLDRFKFFPAENIGGLPALKSMASVFRQVRFCPTGGITPTSAPKYLENPSILC
ZM4_MATCHED     VMLGLDLGLDRFKFFPAENIGGLPALKSMASVFRQVRFCPTGGITPTSAPKYLENPSILC
ZM4_HR          VMLGLDLGLDRFKFFPAENIGGLPALKSMASVFRQVRFCPTGGITPTSAPKYLENPSILC
ECOLI_NATIVE    LMLGMDYGLKEFKFFPAEANGGVKALQAIAGPFSQVRFCPTGGISPANYRDYLALKSVLC
                :***:* **..******* **:  **: ::*.  * ***********:: .** *:**

ZM4_NATIVE      VGGSWVVPAG--KP-DVAKITALAKEASAFKRAAVA
ZM4_MATCHED     VGGSWVVPAG--KP-DVAKITALAKEASAFKRAAVA
ZM4_HR          VGGSWVVPAG--KP-DVAKITALAKEASAFKRAAVA
ECOLI_NATIVE    IGGSWLVPADALEAGDYDRITKLAREA--VEGAKL-
                :****:***.  :. *  :** **:**    .: * :
```

FIG. 6B

DNA Sequence Alignment for ZM4 Native, ZM4 Matched, ZM4 HR and *E.coli* Edd

```
ZM4_NATIVE      ATGACTGATCTGCATTCAACGGTAGAAAAGGTTACCGCGCGCGTTATTGAACGCTCGCGG
ZM4_MATCHED     ATGACGGATCTACATAGTACAGTGGAGAAGGTTACTGCCAGGGTTATTGAAAGGAGTAGG
ZM4_HR          ATGACGGATTTGCATTCAACTGTTGAGAAAGTAACTGCTAGAGTAATTGAAAGATCAAGG
ECOLI_NATIVE    ATGA---ATCCACA----ATTGTTACGC--GTAACAAATCGAATCATTGAACGTTCGCGC
                ****    **  **      * **        ** **     *  * ******  *   *

ZM4_NATIVE      GAAACCCGTAAGGCTTATCTGGATTTGATCCAGTATGAGCGGGAAAA----AGGCGTAGA
ZM4_MATCHED     GAAACTAGGAAGGCATATCTAGATTTAATTCAATATGAGAGGGAAAA----AGGAGTGGA
ZM4_HR          GAAACTAGAAAGGCTTATTTGGATTTGATACAATATGAGAGGGAAAA----AGGTGTTGA
ECOLI_NATIVE    GAGACTCGCTCTGCTTATCTCGCCCGGATAGAACA----AGCGAAAACTTCGACCGTTCA
                ** **   *   ** ***  * *        **   *    * *****        **  *

ZM4_NATIVE      CCGTCCAAACCTGTCCTGTAGTAACCTTGCTCATGGCTTTGCGGC-TATGAAT--GGTGA
ZM4_MATCHED     CAGGCCCAACCTAAGTTGTAGCAACCTAGCACATGGATTCGCCGC-AATGAAT--GGTGA
ZM4_HR          TAGACCAAATTTGTCTTGTTCTAATTTGGCTCATGGTTTTGCTGC-TATGAAT--GGTGA
ECOLI_NATIVE    TCGTTCGCAGTTGGCATGCGGTAACCTGGCACACGGTTTCGCTGCCTGCCAGCCAGAAGA
                   *   *   *   *    **  **  * **  ** ** ** **      *     * **

ZM4_NATIVE      CAAGCCAGCTTTGCGCGACTTCAACCGCATGA--ATATCGGCGTCGTGACTTCCTACAAC
ZM4_MATCHED     CAAGCCCGCATTAAGGGACTTCAACAGGATGA--ATATTGGAGTTGTGACGAGTTACAAC
ZM4_HR          TAAACCAGCTTTGAGAGATTTTAATAGAATGA--ATATAGGTGTAGTTACTTCTTATAAT
ECOLI_NATIVE    CAAAGCCTCTTTGAAAAGCAT--GTTGCGTAACAATATCGCCATCATCACCTCCTATAAC
                  **   *  *  *       *        *      ****  *      *   **  **

ZM4_NATIVE      GATATGTTGTCGGCTCATGAACCATATTATCGCTATCCGGAG--CAGATGAAAGTATTTG
ZM4_MATCHED     GATATGTTAAGTGCACATGAACCCTATTATAGGTATCCTGAG--CAAATGAAGGTGTTTG
ZM4_HR          GATATGTTGTCTGCTCATGAACCATATTATAGATATCCAGAA--CAAATGAAGGTTTTTG
ECOLI_NATIVE    GACATGCTCTCCGCGCACCAGCCTTATGAACACTATCCAGAAATCATTCGTAAAGCCCTG
                ** ***  *   ** **  ** **  * *  *  ***** *        **    *  **

ZM4_NATIVE      CTCGCGAAGTTGGCGCAACGGTTCAGGTCGCCGGTGGCGTGCCTGCTATGTGCGATGGTG
ZM4_MATCHED     CAAGGGAAGTTGGAGCCACAGTTCAAGTTGCTGGTGGAGTGCCTGCAATGTGCGATGGTG
ZM4_HR          CTCGTGAAGTTGGTGCTACAGTTCAAGTTGCTGGTGGTGTTCCTGCAATGTGTGATGGTG
ECOLI_NATIVE    C--ATGAAGCGAATGCGGTTGGTCAGGTTGCGGGCGGTGTTCCGGCGATGTGTGATGGTG
                *  ****   **    * ** ** ** ** **  ** ** ** ** ***** *******

ZM4_NATIVE      TGACCCAAGGTCAGCCGGGCATGGAAGAATCCCTGTTTAGCCGCGATGTTATCGCTTTGG
ZM4_MATCHED     TGACTCAGGGTCAACCTGGAATGGAAGAATCCCTATTTTCAAGGGATGTTATTGCATTAG
ZM4_HR          TTACTCAAGGTCAACCAGGTATGGAAGAATCTTTGTTTTCCAGAGATGTAATTGCTTTGG
ECOLI_NATIVE    TCACCCAGGGGCAGGATGGAATGGAATTGTCGCTGCTAAGCCGCGAAGTGATAGCGATGT
                * ** ** **  **  * ** ** ** ***   **     *  ** * **  ** ** *

ZM4_NATIVE      CTACCAGCGTTTCTTTGTCTCATGGTATGTTTGAAGGGGCTGCCCTTCTCGGTATCTGTG
ZM4_MATCHED     CAACTTCAGTTTCATTATCACATGGTATGTTTGAAGGGGCAGCTCTACTCGGTATATGTG
ZM4_HR          CTACATCTGTTTCATTGTCTCACGGAATGTTTGAAGGTGCTGCATTGTTGGGAATTTGTG
ECOLI_NATIVE    CTGCGGCGGTGGGGCTGTCCCATAACATGTTTGATGGTGCTCTGTTCCTCGGTGTGTGCG
                * *   *  **     * *  **  ********  ** **      *   ** * ** *

ZM4_NATIVE      ACAAGATTGTCCCTGGTCTGTTGATGGGCGCTCTGCGCTTTGGTCACCTGCCGACCATTC
ZM4_MATCHED     ACAAGATTGTTCCTGGTCTACTAATGGGAGCACTAAGGTTTGGTCACCTACCTACTATTC
ZM4_HR          ATAAAATTGTTCCAGGTTTGTTGATGGGTGCTTTGAGGTTCGGTCATTTGCCAACTATTT
ECOLI_NATIVE    ACAAGATTGTCCCGGGTCTGACGATGGCAGCCCTGTCGTTTGGTCATTTGCCTGCGGTGT
                * ** ***** **  ***     ****   **  **   ** *****  * **   *  *
```

FIG. 6C

```
ZM4_NATIVE       TGGTCCCATCAGGCCCGATGACGACTGGTATCCCGAACAAAGAAAAAATCCGTATCCGTC
ZM4_MATCHED      TAGTTCCCAGTGGACCTATGACAACGGGTATACCTAACAAAGAAAAAATTAGGATTAGGC
ZM4_HR           TGGTTCCATCTGGTCCAATGACTACTGGAATCCCAAATAAAGAAAAGATTAGAATTAGAC
ECOLI_NATIVE     TTGTGCCGTCTGGACCGATGGCAAGCGGTTTGCCAAATAAAGAAAAAGTGCGTATTCGCC
                  *  **  **       **  ***  *  * *  **  *    *  **  ** *   **

ZM4_NATIVE       AGCTCTATGCTCAGGGTAAAATCGGCCAGAAAGAACTTCTGGATATGGAAGCGGCTTGCT
ZM4_MATCHED      AACTCTATGCACAAGGTAAAATTGGACAAAAAGAACTACTAGATATGGAAGCCGCATGCT
ZM4_HR           AATTGTATGCTCAAGGAAAAATTGGTCAAAAGGAATTGTTGGATATGGAAGCTGCCTGTT
ECOLI_NATIVE     AGCTTTATGCCGAAGGTAAAGTGGACCGCATGGCCTTACTGGAGTCAGAAGCCGCGTCTT
                 *  * ***** *  ** ***     **  *  *  *    *    *    *****  **    *

ZM4_NATIVE       ACCATGCTGAAGGTACCTGCACCTTCTATGGTACGGCAAACACCAACCAGATGGTTATGG
ZM4_MATCHED      ACCATGCAGAAGGTACTTGCACTTTCTATGGTACAGCCAACACTAACCAGATGGTTATGG
ZM4_HR           ATCATGCTGAAGGTACTTGTACTTTTTATGGTACTGCTAACACTAATCAGATGGTTATGG
ECOLI_NATIVE     ACCATGCGCCGGAACATGTACTTTCTACGGTACTGCCAACACCAACCAGATGGTGGTGG
                  * *****   *      ** ** **  ** *****  ** *****  ** ******** ***

ZM4_NATIVE       AAGTCCTCGGTCTTCATATGCCAGGTTCGGCATTTGTTACCCCGGGTACCCCGCTCCGCC
ZM4_MATCHED      AAGTTCTCGGTCTACATATGCCCGGTAGTGCCTTTGTTACTCCGGTACTCCTCTCAGGC
ZM4_HR           AAGTTTTGGGTTTGCACATGCCAGGTAGTGCATTCGTTACTCCAGGTACTCCACTGAGAC
ECOLI_NATIVE     AGTTTATGGGGATGCAGTTGCCAGGCTCTTCTTTTGTTCATCCGGATTCTCCGCTGCGCG
                 * *  *  *   *  ** *****  *  *     * *  * * **  **  **  *

ZM4_NATIVE       AGGCTCTGACCCGTGCTGCTGTGCATCGCGTTGCTGAATTGGGTTGGAAGGGCGACGATT
ZM4_MATCHED      AAGCACTAACTAGGGCAGCAGTGCATAGGGTTGCAGAATTAGGTTGGAAGGGAGACGATT
ZM4_HR           AGGCTTTGACTAGAGCTGCTGTTCATAGAGTTGCAGAGTTGGGTTGGAAAGGTGATGATT
ECOLI_NATIVE     ATGCTTTGACCGCCGCAGCTGCGCGTCAGGTTACACGCATGACCGGTAATGGTAATGAAT
                 * **  *  **      **  * **   *    **    *   *  ** **   * **

ZM4_NATIVE       ATCGTCCGCTTGGTAAAATCATTGACGAAAAATCAATCGTCAATGCTATTGTTGGTCTGT
ZM4_MATCHED      ATAGGCCTCTAGGTAAAATTATTGACGAAAAAGTATTGTTAATGCAATTGTTGGTCTAT
ZM4_HR           ATAGACCTTTGGGTAAAATTATTGATGAGAAATCTATTGTTAATGCTATTGTTGGTTTGT
ECOLI_NATIVE     GGATGCCGATCGGTAAGATGATCGATGAGAAGTGGTGGTGAACGGTATCGTTGCACTGC
                      **   *  *****  ** ** ** ***         *    *  ** ** ****    *

ZM4_NATIVE       TGGCAACCGGTGGTTCCACCAACCATACCATGCATATTCCGGCCATTGCTCGTGCTGCTG
ZM4_MATCHED      TAGCCACTGGTGGTAGTACTAACCATACGATGCATATTCCTGCTATTGCAAGGGCAGCAG
ZM4_HR           TAGCTACAGGTGGTTCTACAAATCATACAATGCATATTCCGGCCATAGCTAGAGCAGCAG
ECOLI_NATIVE     TGGCGACCGGTGGTTCCACTAACCACACCATGCACCTGGTGGCGATGGCGCGCGCGGCCG
                 * **  ** ******    **  ** ** ** *****   *    ** ** *   ** **  *

ZM4_NATIVE       GTGTTATCGTTAACTGGAATGACTTCCATGATCTTTCTGAAGTTGTTCCGTTGATTGCCC
ZM4_MATCHED      GTGTTATTGTTAACTGGAATGACTTCCATGATCTATCAGAAGTTGTTCCTTTAATTGCTA
ZM4_HR           GGGTTATAGTTAATTGGAATGATTTTCATGATTTGTCTGAAGTTGTTCCATTGATTGCTA
ECOLI_NATIVE     GTATTCAGATTAACTGGGATGACTTCTCTGACCTTTCTGATGTTGTACCGCTGATGGCAC
                 *  **     **** ***  *****  *  ***    *  *  * *****  ** *  **  **

ZM4_NATIVE       GCATTTACCCGAATGGCCCGCGCGACATCAATGAATTCCAGAATGCAGGCGGCATGGCTT
ZM4_MATCHED      GGATTTACCCTAATGGACCTAGGGACATTAACGAATTTCAAAATGCCGGAGGAATGGCAT
ZM4_HR           GAATTTATCCAAATGGTCCTAGAGATATAAATGAATTTCAAAATGCAGGAGGAATGGCTT
ECOLI_NATIVE     GTCTCTACCCGAACGGTCCGGCCGATATTAACCACTTCCAGGCGGCAGGTGGCGTACCGG
                     *   * ** ** **      ** **  ** **    **  *   *  ****   *

ZM4_NATIVE       ATGTCATCAAAGAACTGCTTTCTGCTAATCTGTTGAACCGTGATGTCACGACCATTGCCA
ZM4_MATCHED      ATGTTATTAAGGAACTACTATCAGCAAATCTACTAAACAGGGATGTTACAACTATTGCTA
ZM4_HR           ATGTAATTAAAGAATTGTTGAGTGCGAATTTGTTAAATAGAGATGTTACTACTATTGCTA
ECOLI_NATIVE     TTCTGGTGCGTGAACTGCTCAAAGCAGGCCTGCTGCATGAAGATGTCAATACGGTGGCAG
                  *  *    * ***   *     **         *    **  *****  **  *  **
```

FIG. 6C (Cont. 1)

```
ZM4_NATIVE      AGGGCGGT--ATCGAAGAATACGCCAAGGCTCCGGCATTAAATGATGCTGGCGAATTGGT
ZM4_MATCHED     AGGGGAGGT--ATAGAAGAATACGCTAAGGCACCTGCCCTAAATGATGCAGGAGAATTAGT
ZM4_HR          AAGGAGGG--ATAGAAGAATATGCTAAAGCTCCAGCTCTGAACGATGCGGGTGAATTGGT
ECOLI_NATIVE    GTTTTGGTCTGTCTCGTTATACCCTTGAACCATGGC--TGAATAATG---GTGAACTGGA
                  **       *      ***  *   *    **  *  **   ***   * ***  *  *

ZM4_NATIVE      CTGG---AAGCCAGCTGGCGAACCTGGTGATGACACCATTCTGCGTCCGGTTTCTAAT--
ZM4_MATCHED     TTGG---AAGCCCGCAGGAGAACCTGGTGATGACACTATTCTAAGGCCTGTTTCAAAT--
ZM4_HR          GTGG---AAACCGGCTGGCGAACCTGGGGACGACACAATTTTGAGACCAGTATCTAAT--
ECOLI_NATIVE    CTGGCGGGAAGGGGCGGAAAAATCACTCGACAGCA--ATGTGATCGCTTCCTTCGAACAA
                 ***     *     **  *   ** *    *   **  **  **           ** **

ZM4_NATIVE      CCTTTCGCAAAAGATGGCGGTCTGCGTCTCTTGGAAGGTAACCTTGGCCGTGCAATGTAC
ZM4_MATCHED     CCTTTCGCCAAAGATGGAGGTCTAAGGCTCTTAGAAGGTAACCTAGGAAGGGCCATGTAC
ZM4_HR          CCATTTGCTAAAGATGGTGGTTTGCGTCTCTTGGAAGGTAATTTGGGTAGAGCAATGTAT
ECOLI_NATIVE    CCTTTCTCTCATCATGGTGGGACAAAAGTGTTAAGCGGTAACCTGGGCCGTGCCGGT-TAT
                ** **  *   * ****  **         *  **    *****  *  *  **  * **

ZM4_NATIVE      -AAGGCCAGTGCGGT--TGATCCTAAATTCTGGACCATTGAAGCACCGGTTCGCGTCTTC
ZM4_MATCHED     -AAGGCTAGCGCCGT--TGATCCTAAATTCTGGACTATTGAAGCCCCTGTTAGGGTTTTC
ZM4_HR          -AAGGCTTCTGCTGT--AGATCCAAAATTCTGGACTATTGAAGCTCCCGTTAGAGTTTTC
ECOLI_NATIVE    GAAAACCTCTGCCGTGCCGGTTGAGAA--CCAGGTGATTGAAGCGCCAGCGGTTGTTTTT
                 **    *  ** **   *   **  *  ** *   ******** **    **  ** **

ZM4_NATIVE      TCTGACCAAGACGATGTTCAGAAAGCCTTCAAGGCTGGCGAATTGAACAAAGACGTTATC
ZM4_MATCHED     TCAGACCAGGACGATGTTCAAAAAGCCTTCAAGGCAGGAGAACTAAACAAAGACGTTATT
ZM4_HR          TCTGATCAAGATGATGTTCAAAAGGCTTTTAAAGCAGGCGAGTTAAATAAAGATGTTATA
ECOLI_NATIVE    GAAAGCCAGCATGACGTTATGCCGGCCTTTGAAGCGGGTTTGCTGGACCGCGATTGTGTC
                   **  *  ** ***     **  **  **   *  *     *       **  *   *

ZM4_NATIVE      GTTGTTGTTCGTTTCCAGGGCCCGCGCGCAAACGGTATGCCTGAATTGCATAAGCTGACC
ZM4_MATCHED     GTTGTTGTTAGGTTCCAAGGACCTAGGGCCAACGGTATGCCTGAATTACATAAGCTAACT
ZM4_HR          GTTGTTGTTAGATTTCAAGGTCCTCGTGCTAATGGTATGCCTGAATTGCATAAGTTGACT
ECOLI_NATIVE    GTTGTTGTCCGTCATCAGGGGCCAAAAGCGAACGGAATGCCAGAATTACATAAACTCATG
                ********   *    ** **          **   **  **   ***** *****  *    *  *

ZM4_NATIVE      CCGGCTTTGGGTGTTCTGCAGGATAATGGCTACAAAGTTGCTTTGGTAACTGATGGTCGT
ZM4_MATCHED     CCTGCATTAGGTGTTCTACAAGATAATGGATACAAAGTTGCATTAGTGACGGATGGTAGG
ZM4_HR          CCTGCGCTAGGCGTATTGCAAGATAATGGTTATAAGGTTGCTTTAGTTACTGATGGTAGA
ECOLI_NATIVE    CCGCCACTTGGTGTATTATTGGACCGGTGTTTCAAAATTGCGTTAGTTACCGATGGACGA
                **  *   **  ** **  *  **     * *  ** ****     **  ** **    *

ZM4_NATIVE      ATGTCCGGTGCTACCGGTAAAGTTCCGGTTGCTTTGCATGTCAGCCCAGAAGCTCTTGGC
ZM4_MATCHED     ATGAGTGGTGCAACTGGTAAAGTTCCTGTTGCATTACATGTTTCACCCGAAGCACTAGGA
ZM4_HR          ATGTCTGGTGCAACTGGTAAAGTACCGGTGGCTCTGCATGTTTCACCAGAGGCTTTAGGA
ECOLI_NATIVE    CTCTCCGGCGCTTCAGGTAAAGTGCCGTCAGCTATCCACGTAACACCAGAAGCCTACGAT
                 *   ** **   * ********   *  ** *  * ** **    ** ***     *

ZM4_NATIVE      GGTGGTGCCATCGGTAAAT-TACGTGATGGCGATATCGTCCGTATCTCGGTTGAAGAAGG
ZM4_MATCHED     GGTGGTGCTATTGGTAAAC-TTAGGGATGGAGATATTGTTAGGATTAGTGTTGAAGAAGG
ZM4_HR          GGTGGGGCGATTGGCAAGT-TGAGAGATGGCGATATAGTTAGAATTTCTGTTGAAGAAGG
ECOLI_NATIVE    GGCGG-GCTGCTGGCAAAAGTGCGCGACGGGGACATCATTCGTGTGAATGGACAGACAGG
                ** ** **   ** **    *   ** **  **  * * *          *   *  ***

ZM4_NATIVE      CAAACTTGAAGCTTTGGTTCCAGCTGATGA-GTGGAA-----TGCTCG---TCCGCATG-
ZM4_MATCHED     AAAACTTGAAGCACTCGTTCCCGCAGATGA-GTGGAA-----TGCAAG---GCCTCATG-
ZM4_HR          TAAATTAGAGGCTCTTGTCCCCGCCGACGA-GTGGAA-----TGCTAG---ACCACATG-
ECOLI_NATIVE    CGAACT-GACGCTGCTG-----GTAGACGAAGCGGAACTGGCTGCTCGCGAACCGCACAT
                 ** **   * *   *     *  ** **  ** ** ****   ***  *   ** **
```

FIG. 6C (Cont. 2)

```
ZM4_NATIVE      --CTGAAAAACCGGCTTTCCGTCCGGGAACCGGACGCGAATTGTTTGATATCTTCCGTCA
ZM4_MATCHED     --CAGAAAAACCTGCATTCAGGCCTGGGACTGGGAGGGAATTATTTGATATTTTCAGGCA
ZM4_HR          --CTGAGAAGCCCGCTTTTAGACCTGGTACTGGGAGAGAATTGTTTGACATTTTTAGACA
ECOLI_NATIVE    TCCTGACCTGAGCGCGTCACGCGTGGGAACAGGACGTGAATTATTCAGCGCCTTGCGTGA
                  * **         ** **   *    ** ** **  * ***** **      ** *  *

ZM4_NATIVE      GAATGCTG-CTAAAGCTGAAGACGGTGCAGTCGCAATATATGCAGGTGCCGGTATC
ZM4_MATCHED     AAATGCAG-CAAAAGCAGAAGACGGTGCCGTTGCCATCTATGCCGGTGCTGGTATA
ZM4_HR          AAACGCTG-CTAAGGCTGAGGATGGTGCAGTTGCAATTTATGCTGGGGCAGGGATC
ECOLI_NATIVE    AAA-ACTGTCCGGTGCCGAACAGGG------CGCAACCTGTATCACTTTT------
                 **   * *    *    ** **   **          **   *   *

FIG. 6C (Cont. 3)
```

Protein Sequence Alignment for ZM4 Native, ZM4 Matched, ZM4 HR and E.coli Edd

```
ZM4_NATIVE    MTDLHSTVEKVTARVIERSRETRKAYLDLIQYEREKGVDRPNLSCSNLAHGFAAMN-GDK
ZM4_MATCHED   MTDLHSTVEKVTARVIERSRETRKAYLDLIQYEREKGVDRPNLSCSNLAHGFAAMN-GDK
ZM4_HR        MTDLHSTVEKVTARVIERSRETRKAYLDLIQYEREKGVDRPNLSCSNLAHGFAAMN-GDK
ECOLI_NATIVE  ---MNPQLLRVTNRIIERSRETRSAYLARIEQAKTSTVHRSQLACGNLAHGFAACQPEDK
                 :.  : :**  *;********.***  *:    :  .*.*:*:*.********  :  **

ZM4_NATIVE    PALRDFNRMNIGVVTSYNDMLSAHEPYYRYPEQMKVFAREVGATVQVAGGVPAMCDGVTQ
ZM4_MATCHED   PALRDFNRMNIGVVTSYNDMLSAHEPYYRYPEQMKVFAREVGATVQVAGGVPAMCDGVTQ
ZM4_HR        PALRDFNRMNIGVVTSYNDMLSAHEPYYRYPEQMKVFAREVGATVQVAGGVPAMCDGVTQ
ECOLI_NATIVE  ASLKSMLRNNIAIITSYNDMLSAHQPYEHYPEIIRKALHEANAVGQVAGGVPAMCDGVTQ
              .:*:.: * ** .::***********:** :***  ::    :*...*. **************

ZM4_NATIVE    GQPGMEESLFSRDVIALATSVSLSHGMFEGAALLGICDKIVPGLLMGALRFGHLPTILVP
ZM4_MATCHED   GQPGMEESLFSRDVIALATSVSLSHGMFEGAALLGICDKIVPGLLMGALRFGHLPTILVP
ZM4_HR        GQPGMEESLFSRDVIALATSVSLSHGMFEGAALLGICDKIVPGLLMGALRFGHLPTILVP
ECOLI_NATIVE  GQDGMELSLLSREVIAMSAAVGLSHNMFDGALFLGVCDKIVPGLTMAALSFGHLPAVFVP
              ** *** **:**:***.:::*.***.**:**.***:********* .** **** :::**

ZM4_NATIVE    SGPMTTGIPNKEKIRIRQLYAQGKIGQKELLDMEAACYHAEGTCTFYGTANTNQMVMEVL
ZM4_MATCHED   SGPMTTGIPNKEKIRIRQLYAQGKIGQKELLDMEAACYHAEGTCTFYGTANTNQMVMEVL
ZM4_HR        SGPMTTGIPNKEKIRIRQLYAQGKIGQKELLDMEAACYHAEGTCTFYGTANTNQMVMEVL
ECOLI_NATIVE  SGPMASGLPNKEKVRIRQLYAEGKVDRMALLESEAASYHAPGTCTFYGTANTNQMVVEFM
              ****: :*:*****:*******:**:   **: ***.*** **************:*.:

ZM4_NATIVE    GLHMPGSAFVTPGTPLRQALTRAAVHRVAELGWKGDDYRPLGKIIDEKSIVNAIVGLLAT
ZM4_MATCHED   GLHMPGSAFVTPGTPLRQALTRAAVHRVAELGWKGDDYRPLGKIIDEKSIVNAIVGLLAT
ZM4_HR        GLHMPGSAFVTPGTPLRQALTRAAVHRVAELGWKGDDYRPLGKIIDEKSIVNAIVGLLAT
ECOLI_NATIVE  GMQLPGSSFVHPDSPLRDALTAAAARQVTRMTGNGNEWMPIGKMIDEKVVVNGIVALLAT
              *:::***:** *.:***:*** ***  *  ..  :*:::**:*****.:**.**.****
```

FIG. 6D

```
ZM4_NATIVE      GGSTNHTMHIPAIARAAGVIVNWNDFHDLSEVVPLIARIYPNGPRDINEFQNAGGMAYVI
ZM4_MATCHED     GGSTNHTMHIPAIARAAGVIVNWNDFHDLSEVVPLIARIYPNGPRDINEFQNAGGMAYVI
ZM4_HR          GGSTNHTMHIPAIARAAGVIVNWNDFHDLSEVVPLIARIYPNGPRDINEFQNAGGMAYVI
ECOLI_NATIVE    GGSTNHTMHLVAMARAAGIQINWDDFSDLSDVVPLMARLYPNGPADINHFQAAGGVPVLV
                *********:.*:*****:.:**:** ***:****:**:***** ***.** ***:. ::

ZM4_NATIVE      KELLSANLLNRDVTTIAKGGIEEYAKAPALNDAGELVWKPAGEPG-DDTILRPVSNPFAK
ZM4_MATCHED     KELLSANLLNRDVTTIAKGGIEEYAKAPALNDAGELVWKPAGEPG-DDTILRPVSNPFAK
ZM4_HR          KELLSANLLNRDVTTIAKGGIEEYAKAPALNDAGELVWKPAGEPG-DDTILRPVSNPFAK
ECOLI_NATIVE    RELLKAGLLHEDVNTVAGFGLSRYTLEPWLNN-GELDWREGAEKSLDSNVIASFEQPFSH
                :***.*.**:.**.**.*:*   *:..*:   * **: *** *: ..* . *..:: ...:**::

ZM4_NATIVE      DGGLRLLEGNLGRAMYKASAVDPKFWTIEAPVRVFSDQDDVQKAFKAGELNKDVIVVVRF
ZM4_MATCHED     DGGLRLLEGNLGRAMYKASAVDPKFWTIEAPVRVFSDQDDVQKAFKAGELNKDVIVVVRF
ZM4_HR          DGGLRLLEGNLGRAMYKASAVDPKFWTIEAPVRVFSDQDDVQKAFKAGELNKDVIVVVRF
ECOLI_NATIVE    HGGTKVLSGNLGRAVMKTSAVPVENQVIEAPAVVFESQHDVMPAFEAGLLDRDCVVVVRH
                .**.::*.******:.*:*** :  *.****.**.**.*.** **:** *:::*.:****.

ZM4_NATIVE      QGPRANGMPELHKLTPALGVLQDNGYKVALVTDGRMSGATGKVPVALHVSPEALGGGAIG
ZM4_MATCHED     QGPRANGMPELHKLTPALGVLQDNGYKVALVTDGRMSGATGKVPVALHVSPEALGGGAIG
ZM4_HR          QGPRANGMPELHKLTPALGVLQDNGYKVALVTDGRMSGATGKVPVALHVSPEALGGGAIG
ECOLI_NATIVE    QGPKANGMPELHKLMPPLGVLLDRCFKIALVTDGRLSGASGKVPSAIHVTPEAYDGGLLA
                ***:**********:.****.*:. :*:*******:***:****.*:**:*** .** :.

ZM4_NATIVE      KLRDGDIVRISVEEGKLEALVPADEWNAR-PHA-EKPAFRPGTGRELFDIFRQNAAKAED
ZM4_MATCHED     KLRDGDIVRISVEEGKLEALVPADEWNAR-PHA-EKPAFRPGTGRELFDIFRQNAAKAED
ZM4_HR          KLRDGDIVRISVEEGKLEALVPADEWNAR-PHA-EKPAFRPGTGRELFDIFRQNAAKAED
ECOLI_NATIVE    KVRDGDIIRVNGQTGELTLLVDEAELAAREPHIPDLSASRVGTGRELFSALREKLSGAEQ
                *:*****:*:. :  *:* *** : :****   : *. * *.*******. :*:: : **:

ZM4_NATIVE      GAVAIYAGAGI
ZM4_MATCHED     GAVAIYAGAGI
ZM4_HR          GAVAIYAGAGI
ECOLI_NATIVE    GATCITF----
```

FIG. 6D (Cont.)

SEQUENCE LISTING

```
<160> NUMBER OF SEQ ID NOS: 685

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aactgactag taaaaaaatg cgtgatatcg attcc                             35

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtaactcga gctactaggc aacagcagcg cgcttg                            36

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aactgactag taaaaaaatg actgatctgc attcaacg                          38

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agtaactcga gctactagat accggcacct gcatatattg c                      41

<210> SEQ ID NO 5
<211> LENGTH: 46
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactgactag taaaaaaatg aaaaactgga aacaagtgc agaatc                    46

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtaactcga gctactacag cttagcgcct tctacagctt cacg                     44

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aactgactag taaaaaaatg aatccacaat tgttacgcgt aacaaatcg                49

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtaactcga gctactaaaa agtgatacag gttgcgccct gttcggcac                49

<210> SEQ ID NO 9
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgcatattcc gttcaatctt ataaagctgc catagatttt tacaccaagt cgttttaaga    60
gcttggtgag cgcta                                                     75

<210> SEQ ID NO 10
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttgccagtg aatgaccttt ggcattctca tggaaacttc agtttcatag tcgagttcaa    60
gagaaaaaaa aagaa                                                     75
```

```
<210> SEQ ID NO 11
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgactgtta ctactccttt tgtgaatggt acttcttatt gtaccgtcac tgcatattcc      60
gttcaatctt ataaa                                                      75

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaatcaact ctctttcttc caaccaaatg gtcagcaatg agtctggtag cttgccagtg      60
aatgaccttt ggcat                                                      75

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gactaactga actagtaaaa aaatgaccaa gccgcgcaca attaatcag                 49

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagtgagtaa ctcgagttat taaccgctgt tgcgaagtgc cgtcgc                    46

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgtctcatc atcatcatca tcataccaag ccgcgcacaa ttaatcagaa c              51

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gactaactga actagtaaaa aaatgtctca tcatcatcat catcatacca ag             52
```

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

```
atgtctcatc atcatcatca tcatatgacc aagccaagaa ctattaacca aaaccc        56
```

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 18

```
gactaactga actagtaaaa aaatgtctca tcatcatcat catcatatga ccaagccaag    60
```

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 19

```
aagtgagtaa ctcgagttat taaccggagt ttctcaaagc agtagcgata g             51
```

<210> SEQ ID NO 20
<211> LENGTH: 2679
<212> TYPE: DNA
<213> ORGANISM: Zymomonas mobilis

<400> SEQUENCE: 20

```
actagtaaaa aaatgaccaa gccgcgcaca attaatcaga acccagacct tcgctatttt    60
ggtaacctgc tcggtcaggt tattaaggaa caaggcggag agtctttatt caaccagatc   120
gagcaaattc gctctgccgc gattagacgc catcggggta ttgttgacag caccgagcta   180
agttctcgct tagccgatct cgaccttaat gacatgttct cttttgcaca tgccttttg    240
ctgttttcaa tgctggccaa tttggctgat gatcgtcagg gagatgccct tgatcctgat   300
gccaatatgg caagtgccct taaggacata aaagccaaag gcgtcagtca gcaggcgatc   360
attgatatga tcgacaaagc ctgcattgtg cctgttctga cagcacatcc gaccgaagtc   420
cgtcggaaaa gtatgcttga ccattataat cgcattgcag gtttaatgcg gttaaaagat   480
gctggacaaa cggtgaccga agatggtctt ccgatcgaag atgcgttaat ccagcaaatc   540
acgatattat ggcagactcg tccgctcatg ctgcaaaagc tgaccgtggc tgatgaaatc   600
gaaactgccc tgtctttctt aagagaaact tttctgcctg ttctgcccca gatttatgca   660
gaatgggaaa aattgcttgg tagttctatt ccaagcttta tcagacctgg taattggatt   720
ggtggtgacc gtgacggtaa ccccaatgtc aatgccgata cgatcatgct gtctttgaag   780
cgcagctcgg aaacggtatt gacggattat ctcaaccgtc ttgataaact gctttccaac   840
ctttcggtct caaccgatat ggtttcggta tccgatgata ttctacgtct agccgataaa   900
agtggtgacg atgctgcgat ccgtgcggat gaaccttatc gtcgtgcctt aaatggtatt   960
```

```
tatgaccgtt tagccgctac ctatcgtcag atcgccggtc gcaacccttc gcgcccagcc    1020
ttgcgttctg cagaagccta taaacggcct caagaattgc tggctgattt gaagaccttg    1080
gccgaaggct tgggtaaatt ggcagaaggt agttttaagg cattgatccg ttcggttgaa    1140
acctttggtt tccatttggc caccctcgat ctgcgtcaga attcgcaggt tcatgaaaga    1200
gttgtcaatg aactgctacg gacagccacc gttgaagccg attatttatc tctatcggaa    1260
gaagatcgcg ttaagctgtt aagacgggaa ttgtcgcagc gcggactct attcgttccg     1320 cgcgccgatt attccgaaga aacgcgttct gaacttgata ttattcaggc agcagcccgc    1380
gcccatgaaa ttttggccc tgaatccatt acgacttatt tgatttcgaa tggcgaaagc     1440
atttccgata ttctggaagt ctatttgctt ttgaaagaag cagggctgta tcaaggggt     1500 gctaagccaa aagcggcgat tgaagctgcg cctttattcg agacggtggc cgatcttgaa    1560
aatgcgccaa aggtcatgga ggaatggttc aagctgcctg aagcgcaagc cattgcaaag    1620
gcacatggcg ttcaggaagt gatggttggc tattctgact ccaataagga cggcggatat    1680
ctgacctcgg tttgggtct ttataaggct tgcctcgctt tggtgccgat ttttgagaaa     1740
gccggtgtac cgatccagtt tttccatgga cggggtggtt ccgttggtcg cggtggtggt    1800
tccaacttta atgccattct gtcgcagcca gccggagccg tcaaagggcg tatccgttat    1860
acagaacagg gtgaagtcgt ggcggccaaa tatggcaccc atgaaagcgc tattgcccat    1920
ctggatgagg ccgtagcggc gactttgatt acgtctttgg aagcaccgac cattgtcgag    1980
ccagagttta gtcgttaccg taaggccttg gatcagatct cagattcagc tttccaggcc    2040
tatcgccaat ggtctatgg aacgaagggc ttccgtaaat tctttagtga atttacgcct     2100
ttgccggaaa ttgccctgtt aaagatcggg tcacgcccac ctagccgcaa aaaatccgac    2160
cggattgaag atctacgcgc tattccttgg gtgtttagct ggtctcaagt tcgagtcatg    2220
ttacccggtt ggttcggttt cggtcaggct ttatatgact ttgaagatac cgagctgtta    2280
caggaaatgg caagccgttg gccgttttc cgcacgacta ttcggaatat ggaacaggtg      2340
atggcacgtt ccgatatgac gatcgccaag cattatctgg ccttggttga ggatcagaca    2400
aatggtgagg ctatctatga ttctatcgcg gatggctgga taaaggttg tgaaggtctg     2460 ttaaaggcaa cccagcagaa ttggctgttg aacgctttc cggcggttga taattcggtg     2520
cagatgcgtc ggcctatct ggaaccgctt aattacttac aggtcgaatt gctgaagaaa     2580
tggcggggag gtgataccaa cccgcatatc ctcgaatcta ttcagctgac aatcaatgcc    2640
attgcgacgg cacttcgcaa cagcggttaa taactcgag                           2679
```

<210> SEQ ID NO 21
<211> LENGTH: 2679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
actagtaaaa aaatgaccaa gccaagaact attaaccaaa acccagactt gagatacttc      60
ggtaacttgt tgggtcaagt tatcaaggaa caaggtggtg aatctttgtt caaccaaatt     120
gaacaaatca gatccgctgc tattagaaga cacagaggta tcgtcgactc taccgaattg     180
tcctctagat tggctgactt ggacttgaac gacatgttct ccttcgctca cgctttcttg    240
ttgttctcta tgttggctaa cttggctgac gacagacaag tgacgctttt ggacccagac    300
gctaacatgg cttccgcttt gaaggacatt aaggctaagg tgttctctca acaagctatc    360
```

```
attgacatga tcgacaaggc ttgtattgtc ccagttttga ctgctcaccc aaccgaagtc    420
agaagaaagt ccatgttgga ccactacaac agaatcgctg gtttgatgag attgaaggac    480
gctggtcaaa ctgttaccga agacggtttg ccaattgaag acgctttgat ccaacaaatt    540
actatcttgt ggcaaaccag accattgatg ttgcaaaagt tgactgtcgc tgacgaaatt    600
gaaaccgctt tgtctttctt gagagaaact tccttgccag ttttgccaca aatctacgct    660
gaatgggaaa agttgttggg ttcctctatt ccatccttca tcagaccagg taactggatt    720
ggtggtgaca gagacggtaa cccaaacgtc aacgctgaca ccatcatgtt gtctttgaag    780
agatcctctg aaactgtttt gaccgactac ttgaacagat tggacaagtt gttgtccaac    840
ttgtctgtct ccactgacat ggtttctgtc tccgacgaca ttttgagatt ggctgacaag    900
tctggtgacg acgctgctat cagagctgac gaaccataca gaagagcttt gaacggtatt    960
tacgacagat tggctgctac ctacagacaa atcgctggta aaacccatc cagaccagct    1020
ttgagatctg ctgaagctta caagagacca caagaattgt tggctgactt gaagactttg    1080
gctgaaggtt tgggtaagtt ggctgaaggt tccttcaagg ctttgattag atctgttgaa    1140
accttcggtt tccacttggc tactttggac ttgagacaaa actcccaagt ccacgaaaga    1200
gttgtcaacg aattgttgag aaccgctact gttgaagctg actacttgtc tttgtccgaa    1260
gaagacagag tcaagttgtt gagaagagaa ttgtctcaac caagaacctt gttcgttcca    1320
agagctgact actccgaaga aactagatct gaattggaca tcattcaagc tgctgctaga    1380
gctcacgaaa tcttcggtcc agaatccatt accacttact tgatctctaa cggtgaatcc    1440
atttctgaca tcttggaagt ctacttgttg ttgaaggaag ctggtttgta ccaaggtggt    1500
gctaagccaa aggctgctat tgaagctgct ccattgttcg aaaccgttgc tgacttggaa    1560
aacgctccaa aggtcatgga agaatggttc aagttgccag aagctcaagc tatcgctaag    1620
gctcacggtg ttcaagaagt catggttggt tactccgact ctaacaagga cggtggttac    1680
ttgacttccg tctggggttt gtacaaggct tgtttggctt tggttccaat tttcgaaaag    1740
gctggtgtcc caatccaatt cttccacggt agaggtggtt ctgttggtag aggtggtggt    1800
tccaacttca acgctatttt gtctcaacca gctggtgctg tcaagggtag aatcagatac    1860
accgaacaag gtgaagttgt cgctgctaag tacggtactc acgaatccgc tattgctcac    1920
ttggacgaag ctgttgctgc taccttgatc acttctttgg aagctccaac cattgtcgaa    1980
ccagaattct ccagatacag aaaggctttg gaccaaatct ctgactccgc tttccaagct    2040
tacagacaat tggtttacgg tactaagggt ttcagaaagt tcttctctga attcacccca    2100
ttgccagaaa ttgcttttgtt gaagatcggt tccagaccac catctagaaa gaagtccgac    2160
agaattgaag acttgagagc tatcccatgg gtcttctctt ggtcccaagt tagagtcatg    2220
ttgccaggtt ggttcggttt cggtcaagct ttgtacgact tcgaagacac tgaattgttg    2280
caagaaatgg cttctagatg gccattcttc agaaccacta ttagaaacat ggaacaagtt    2340
atggctagat ccgacatgac catcgctaag cactacttgg ctttggtcga agaccaaact    2400
aacggtgaag ctatttacga ctctatcgct gacggttgga acaagggttg tgaaggtttg    2460
ttgaaggcta cccaacaaaa ctggttgttg gaaagattcc cagctgttga caactccgtc    2520
caaatgagaa gaccatactt ggaaccattg aactacttgc aagttgaatt gttgaagaag    2580
tggagaggtg gtgacactaa cccacacatt ttggaatcta tccaattgac cattaacgct    2640
atcgctactg ctttgagaaa ctccggttaa taactcgag                          2679
```

<210> SEQ ID NO 22
<211> LENGTH: 1317
<212> TYPE: DNA
<213> ORGANISM: Ruminococcus flavefaciens

<400> SEQUENCE: 22

| | | | | | |
|---|---|---|---|---|---|
| atggaattt | tcagcaatat | cggtaaaatt | cagtatcagg | gaccaaaaag | tactgatcct | 60 |
| ctctcattta | agtactataa | ccctgaagaa | gtcatcaacg | gaaagacaat | gcgcgagcat | 120 |
| ctgaagttcg | ctctttcatg | gtggcacaca | atgggcggcg | acggaacaga | tatgttcggc | 180 |
| tgcggcacaa | cagacaagac | ctggggacag | tccgatcccg | ctgcaagagc | aaaggctaag | 240 |
| gttgacgcag | cattcgagat | catggataag | ctctccattg | actactattg | tttccacgat | 300 |
| cgcgatcttt | ctcccgagta | tggcagcctc | aaggctacca | cgatcagct | tgacatagtt | 360 |
| acagactata | tcaaggagaa | gcagggcgac | aagttcaagt | gcctctgggg | tacagcaaag | 420 |
| tgcttcgatc | atccaagatt | catgcacggt | gcaggtacat | ctccttctgc | tgatgtattc | 480 |
| gctttctcag | ctgctcagat | caagaaggct | ctggagtcaa | cagtaaagct | cggcggtaac | 540 |
| ggttacgttt | ctggggcgg | acgtgaaggc | tatgagacac | ttcttaatac | aaatatggga | 600 |
| ctcgaactcg | acaatatggc | tcgtcttatg | aagatggctg | ttgagtatgg | acgttcgatc | 660 |
| ggcttcaagg | gcgacttcta | tatcgagccc | aagcccaagg | agcccacaaa | gcatcagtac | 720 |
| gatttcgata | cagctactgt | tctgggattc | ctcagaaagt | acggtctcga | taaggatttc | 780 |
| aagatgaata | tcgaagctaa | ccacgctaca | cttgctcagc | atacattcca | gcatgagctc | 840 |
| cgtgttgcaa | gagacaatgg | tgtgttcggt | tctatcgacg | caaaccaggg | cgacgttctt | 900 |
| cttggatggg | atacagacca | gttccccaca | aatatctacg | atacaacaat | gtgtatgtat | 960 |
| gaagttatca | aggcaggcgg | cttcacaaac | ggcggtctca | acttcgacgc | taaggcacgc | 1020 |
| agagggagct | tcactcccga | ggatatcttc | tacagctata | tcgcaggtat | ggatgcattt | 1080 |
| gctctgggct | tcagagctgc | tctcaagctt | atcgaagacg | gacgtatcga | caagttcgtt | 1140 |
| gctgacagat | acgcttcatg | gaataccggt | atcggtgcag | acataatcgc | aggtaaggca | 1200 |
| gatttcgcat | ctcttgaaaa | gtatgctctt | gaaaagggcg | aggttacagc | ttcactctca | 1260 |
| agcggcagac | aggaaatgct | ggagtctatc | gtaaataacg | ttcttttcag | tctgtaa | 1317 |

<210> SEQ ID NO 23
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

| | | | | | |
|---|---|---|---|---|---|
| atggagttct | tttctaatat | aggtaaaatt | cagtatcaag | gtccaaaatc | tacagatcca | 60 |
| ttgtctttta | aatattataa | tccagaagaa | gttataaatg | gtaaaactat | gagagaacat | 120 |
| ttaaaatttg | ctttgtcttg | gtggcatact | atgggtggtg | atggtactga | tatgttcggt | 180 |
| tgtggtacta | ctgataaaac | ttggggtcaa | tctgatccag | ctgctagagc | aaaagccaaa | 240 |
| gtagatgcag | cctttgaaat | tatggataaa | ttgtctattg | attattattg | ttttcatgat | 300 |
| agagatttgt | ctcctgaata | tggttcttta | aaagcaacta | atgatcaatt | ggacattgtt | 360 |
| acggattata | ttaagagaaa | acaaggtgat | aaatttaaat | gtttgtgggg | cactgcgaaa | 420 |
| tgttttgatc | atccacgttt | tatgcatggt | gcggggacga | gtccttctgc | tgatgttttt | 480 |
| gcttttttctg | ccgctcaaat | taagaaggca | ttggaatcaa | ctgttaaatt | aggtgggaac | 540 |

-continued

```
gggtatgtat tctggggagg aagggaaggt tatgaaacat tattaaacac taatatgggt      600
ttggaattgg ataatatggc tagattgatg aaaatggctg tagaatacgg aaggtctatt      660
ggttttaagg gtgacttta tattgaacca aaacctaaag agcctactaa acatcaatat       720
gattttgata ctgctacagt tttgggattc ttgagaaaat atggtctgga taagattttt      780
aaaatgaata tagaagctaa tcatgcaaca ctcgcacaac atacttttca acatgaattg      840
agagttgcca gagataacgg agtttttgga tctatcgatg caaaccaggg agacgttttg      900
ctaggatggg atactgatca atttccaact aacatttatg atactactat gtgtatgtat      960
gaagtaatta aggcaggagg ctttactaat ggcggattaa actttgatgc gaaggctagg     1020
cgtggtagtt tcactccaga ggatatattc tattcttata ttgctggaat ggatgctttc     1080
gcgttaggtt tcagggcagc actaaaattg attgaagatg gtagaattga taagtttgta     1140
gctgatagat atgcttcttg gaatactgga ataggagcag atataatcgc tgggaaagcc     1200
gacttcgcca gtctggaaaa atatgcgctt gaaaaggag aagttactgc cagcttaagt      1260
tccggtcgtc aagaaatgtt ggaatctatt gtaaacaatg ttttatttc tctg           1314
```

<210> SEQ ID NO 24
<211> LENGTH: 1314
<212> TYPE: DNA
<213> ORGANISM: Piromyces sp.

<400> SEQUENCE: 24

```
atggctaagg aatatttccc acaaattcaa aagattaagt tcgaaggtaa ggattctaag       60
aatccattag ccttccacta ctacgatgct gaaaaggaag tcatgggtaa gaaaatgaag      120
gattggttac gtttcgccat ggcctggtgg cacactcttt gcgccgaagg tgctgaccaa      180
ttcggtggag gtacaaagtc tttcccatgg aacgaaggta ctgatgctat tgaaattgcc      240
aagcaaaagg ttgatgctgg tttcgaaatc atgcaaaagc ttggtattcc atactactgt      300
ttccacgatg ttgatcttgt ttccgaaggt aactctattg aagaatacga atccaacctt      360
aaggctgtcg ttgcttacct caaggaaaag caaaaggaaa ccggtattaa gcttctctgg      420
agtactgcta acgtcttcgg tcacaagcgt tacatgaacg gtgcctccac taacccagac      480
tttgatgttg tcgcccgtgc tattgttcaa attaagaacg ccatagacgc cggtattgaa      540
cttggtgctg aaaactacgt cttctggggt ggtcgtgaag gttacatgag tctccttaac      600
actgaccaaa agcgtgaaaa ggaacacatg gccactatgc ttaccatggc tcgtgactac      660
gctcgttcca agggattcaa gggtactttc ctcattgaac aaagccaat ggaaccaacc      720 aagcaccaat acgatgttga cactgaaacc gctattggtt ccttaaggc ccacaactta      780 gacaaggact caaggtcaa cattgaagtt aaccacgcta ctcttgctgg tcacactttc      840
gaacacgaac ttgcctgtgc tgttgatgct ggtatgctcg gttccattga tgctaaccgt      900
ggtgactacc aaaacggttg ggatactgat caattcccaa ttgatcaata cgaactcgtc      960
caagcttgga tggaaatcat ccgtggtggt ggtttcgtta ctggtggtac aacttcgat     1020 gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga gaaggaacg ttacgcttcc ttcgacagtg gtattggtaa ggactttgaa    1200
gatggtaagc tcacccgca acaagtttac gaatacggta agaagaacgg tgaaccaaag    1260
caaacttctg gtaagcaaga actctacgaa gctattgttg ccatgtacca ataa          1314
```

<210> SEQ ID NO 25

```
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggctaaag aatatttttcc acaaattcag aaaattaaat ttgaaggtaa agattctaaa      60
aatccattgg ctttccatta ttatgatgct gaaaagaag ttatgggtaa aaagatgaaa      120
gattggttga gattcgctat ggcttggtgg catactctat gtgctgaagg agctgatcaa      180
tttggaggag gtactaaatc ttttccttgg aatgaaggta ctgacgctat tgaaattgct      240
aagcagaaag tagacgcggg ttttgaaatt atgcaaaaat tgggaatacc atattattgt      300
tttcatgatg ttgatttggt atctgagggt aattctattg aagaatatga atctaattta      360
aaagctgttg ttgcttactt aaaagaaaaa caaaagaaa ctggaattaa attgttgtgg      420
tctacagcta atgttttcgg tcataaaaga tatatgaatg gtgcttctac aaatccagat      480
tttgatgttg tagctagagc tattgttcaa attaaaaatg ctatagatgc aggaattgaa      540
ttaggtgccg aaaattatgt tttctgggga ggtagagaag ttatatgtc tttgttaaat      600 actgatcaaa aacgtgaaaa ggaacacatg gcaactatgt tgacaatggc tagggattat      660
gctagatcta aaggttttaa aggtactttc ttgattgagc aaaacctat ggaaccaact      720 aaacatcaat atgacgttga cactgaaact gctattggtt tcttaaaagc tcataatttg      780
gataaagatt ttaaggttaa tatagaagtt aatcatgcta cactagctgg tcatactttt      840
gaacatgaat tagcttgtgc agttgatgcc ggtatgttag gttctatcga cgcaaataga      900
ggtgattatc aaaatggttg ggacacagat caatttccaa tagatcaata tgaattggtt      960
caagcatgga tggaaattat taggggtgga ggcttcgtta caggtggaac taattttgat     1020
gctaaaacta ggagaaattc tacagatctt gaagatataa ttattgctca tgtatctggt     1080
atggatgcga tggcccgtgc tttggaaaat gcagctaaat tacttcaaga atctccttat     1140
actaaaatga aaaaggaaag atatgcttct tttgattctg gaataggtaa ggattttgaa     1200
gatggtaaat tgacattgga acaagtttat gaatatggta agaagaatgg agaaccaaaa     1260
caaacttctg gtaaacaaga attatatgag gctatagtag ctatgtatca ataa         1314

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acttgactac tagtatggag ttcttttcta atataggtaa aatt                     44

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agtcaagtct cgagcagaga aaataaaaca ttgtttacaa taga                     44
```

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
agtcaagtct cgagctaatg atgatgatga tgatgcagag aaaataaaac attgtttac    59

<210> SEQ ID NO 29
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
atggaatttt tcagcaatat cggtaaaatt cagtatcagg gaccaaaaag tactgatcct      60
ctctcattta agtactataa ccctgaagaa gtcatcaacg aaagacaat  gcgcgagcat     120
ctgaagttcg ctctttcatg gtggcacaca atgggcggcg acggaacaga tatgttcggc    180
tgcggcacaa cagacaagac ctggggacag tccgatcccg ctgcaagagc aaaggctaag    240
gttgacgcag cattcgagat catggataag ctctccattg actactattg tttccacgat    300
cgcgatcttt ctcccgagta tggcagcctc aaggctacca acgatcagct tgacatagtt    360
acagactata tcaaggagaa gcagggcgac aagttcaagt gcctctgggg tacagcaaag    420
tgcttcgatc atccaagatt catgcacggt gcaggtacat ctccttctgc tgatgtattc    480
gctttctcag ctgctcagat caagaaggct ctggagtcaa cagtaaagct cggcggtaac    540
ggttacgttt tctggggcgg acgtgaaggc tatgagacac ttcttaatac aaatatggga    600
ctcgaactcg acaatatggc tcgtcttatg aagatggctg ttgagtatgg acgttcgatc    660
ggcttcaagg gcgacttcta tcgagcccc  aagcccaagg agcccacaaa gcatcagtac    720
gatttcgata cagctactgt tctgggattc tcagaaagt  acggtctcga taaggatttc    780
aagatgaata tcgaagctaa ccacgctaca cttgctcagc atacattcca gcatgagctc    840
cgtgttgcaa gagacaatgg tgtgttcggt tctatcgacg caaaccaggg cgacgttctt    900
cttggatggg atacagacca gttccccaca aatatctacg atacaacaat gtgtatgtat    960
gaagttatca aggcaggcgg cttcacaaac ggcggtctca acttcgacgc taaggcacgc   1020
agagggagct tcactcccga ggatatcttc tacagctata tcgcaggtat ggatgcattt   1080
gctctgggct tcagagctgc tctcaagctt atcgaagacg gacgtatcga caagttcgtt   1140
gctgacagat acgcttcatg gaataccggt atcggtgcag acataatcgc aggtaaggca   1200
gatttcgcat ctcttgaaaa gtatgctctt gaaaagggcg aggttacagc ttcactctca   1260
agcggcagac aggaaatgct ggagtctatc gtaaataacg ttcttttcag tctgtaa      1317
```

<210> SEQ ID NO 30
<211> LENGTH: 1317
<212> TYPE: DNA
<213> ORGANISM: Ruminococcus flavefaciens

<400> SEQUENCE: 30

```
atggaatttt tcagcaatat cggtaaaatt cagtatcagg gaccaaaaag tactgatcct      60
ctctcattta agtactataa ccctgaagaa gtcatcaacg aaagacaat  gcgcgagcat     120
ctgaagttcg ctctttcatg gtggcacaca atgggcggcg acggaacaga tatgttcggc    180
```

```
tgcggcacaa cagacaagac ctggggacag tccgatcccg ctgcaagagc aaaggctaag      240
gttgacgcag cattcgagat catggataag ctctccattg actactattg tttccacgat      300
cgcgatcttt ctcccgagta tggcagcctc aaggctacca acgatcagct tgacatagtt      360
acagactata tcaaggagaa gcagggcgac aagttcaagt gcctctgggg tacagcaaag      420
tgcttcgatc atccaagatt catgcacggt gcaggtacat ctccttctgc tgatgtattc      480
gctttctcag ctgctcagat caagaaggct ctcgagtcaa cagtaaagct cggcggtaac      540
ggttacgttt tctggggcgg acgtgaaggc tatgagacac ttcttaatac aaatatggga      600
ctcgaactcg acaatatggc tcgtcttatg aagatggctg ttgagtatgg acgttcgatc      660
ggcttcaagg gcgacttcta tatcgagccc aagcccaagg agcccacaaa gcatcagtac      720
gatttcgata cagctactgt tctgggattc ctcagaaagt acggtctcga taaggatttc      780
aagatgaata tcgaagctaa ccacgctaca cttgctcagc atacattcca gcatgagctc      840
cgtgttgcaa gagacaatgg tgtgttcggt tctatcgacg caaaccaggg cgacgttctt      900
cttggatggg atacagacca gttccccaca aatatctacg ataacaat gtgtatgtat       960 gaagttatca aggcaggcgg cttcacaaac ggcggtctca acttcgacgc taaggcacgc     1020
agagggagct tcactcccga ggatatcttc tacagctata tcgcaggtat ggatgcattt     1080
gctctgggct tcagagctgc tctcaagctt atcgaagacg acgtatcga caagttcgtt     1140 gctgacagat acgcttcatg aataccggt atcggtgcag acataatcgc aggtaaggca     1200
gatttcgcat ctcttgaaaa gtatgctctt gaaaagggcg aggttacagc ttcactctca     1260
agcggcagac aggaaatgct ggagtctatc gtaaataacg ttcttttcag tctgtaa       1317
```

<210> SEQ ID NO 31
<211> LENGTH: 438
<212> TYPE: PRT
<213> ORGANISM: Ruminococcus flavefaciens

<400> SEQUENCE: 31

```
Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125

Gly Asp Lys Phe Lys Cys Leu Trp Gly Thr Ala Lys Cys Phe Asp His
    130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175
```

```
Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
        195                 200                 205

Leu Met Lys Met Ala Val Glu Tyr Gly Arg Ser Ile Gly Phe Lys Gly
    210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
        275                 280                 285

Phe Gly Ser Ile Asp Ala Asn Gln Gly Asp Val Leu Leu Gly Trp Asp
    290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335

Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
        355                 360                 365

Lys Leu Ile Glu Asp Gly Arg Ile Asp Lys Phe Val Ala Asp Arg Tyr
    370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
        435

<210> SEQ ID NO 32
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggagttct tttctaatat aggtaaaatt cagtatcaag gtccaaaatc tacagatcca       60
ttgtctttta aatattataa tccagaagaa gttataaatg gtaaaactat gagagaacat      120
ttaaaatttg ctttgtcttg gtggcatact atgggtggtg atggtactga tatgttcggt      180
tgtggtacta ctgataaaac ttggggtcaa tctgatccag ctgctagagc aaaagccaaa      240
gtagatgcag cctttgaaat tatggataaa ttgtctattg attattattg ttttcatgat      300
agagatttgt ctcctgaata tggttcttta aaagcaacta atgatcaatt ggacattgtt      360
acggattata ttaagaaaaa acaaggtgat aaatttaaat gtttgtgggg cactgcgaaa      420
tgttttgatc atccacgttt tatgcatggt gcggggacga gtccttctgc tgatgttttt      480 gcttttttctg ccgctcaaat taagaaggca ttggaatcaa ctgttaaatt aggtgggaac      540
```

```
gggtatgtat tctggggagg aagggaaggt tatgaaacat tattaaacac taatatgggt      600
ttggaattgg ataatatggc tagattgatg aaaatggctg tagaatacgg aaggtctatt      660
ggttttaagg gtgactttta tattgaacca aaacctaaag agcctactaa acatcaatat      720
gattttgata ctgctacagt tttgggattc ttgagaaaat atggtctgga taaagatttt      780
aaaatgaata tagaagctaa tcatgcaaca ctcgcacaac atactttca acatgaattg       840 agagttgcca gagataacgg agttttttgga tctatcgatg caaaccaggg agacgttttg     900
ctaggatggg atactgatca atttccaact aacatttatg atactactat gtgtatgtat     960
gaagtaatta aggcaggagg ctttactaat ggcggattaa actttgatgc gaaggctagg    1020
cgtggtagtt tcactccaga ggatatattc tattcttata ttgctggaat ggatgctttc    1080
gcgttaggtt tcagggcagc actaaaattg attgaagatg gtagaattga taagtttgta    1140
gctgatagat atgcttcttg gaatactgga ataggagcag atataatcgc tgggaaagcc    1200
gacttcgcca gtctggaaaa atatgcgctt gaaaaaggag aagttactgc cagcttaagt    1260
tccggtcgtc aagaaatgtt ggaatctatt gtaaacaatg ttttatttc tctgtaa        1317
```

<210> SEQ ID NO 33
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggaattct tctctaacat tggtaagatc aataccaagg tccaaagtc caccgaccca       60 ttgtctttca agtactacaa cccagaagaa gttattaacg gtaagactat gagagaacac      120
ttgaagttcg ctttgtcctg gtggcacacc atgggtggtg acggtactga catgttcggt      180
tgtggtacca ctgacaagac ctggggtcaa tctgacccag ctgctagagc taaggctaag      240
gtcgacgctg ctttcgaaat catggacaag ttgtccattg actactactg tttccacgac      300
agagacttgt ctccagaata cggttccttg aaggctacta cgaccaatt ggacatcgtt       360 accgactaca ttaaggaaaa gcaaggtgac aagttcaagt gtttgtgggg tactgctaag      420
tgtttcgacc acccaagatt catgcacggt gctggtacct ctccatccgc tgacgtcttc      480
gctttctctg ctgctcaaat caagaaggct ttggaatcca ctgttaagtt gggtggtaac      540
ggttacgtct tctggggtgg tagagaaggt tacgaaacct tgttgaacac taacatgggt      600
ttggaattgg acaacatggc tagattgatg aagatggctg ttgaatacgg tagatctatt      660
ggtttcaagg gtgacttcta catcgaacca aagccaaagg aaccaaccaa gcaccaatac      720
gacttcgaca ctgctaccgt cttgggtttc ttgagaaagt acggtttgga caaggacttc      780
aagatgaaca ttgaagctaa ccacgctact ttggctcaac acaccttcca acacgaattg      840
agagttgcta gagacaacgg tgtcttcggt tccatcgacg ctaaccaagg tgacgttttg      900
ttgggttggg acactgacca attcccaacc aacatttacg acactaccat gtgtatgtac      960
gaagtcatca aggctggtgg tttcactaac ggtggtttga cttcgacgc taaggctaga     1020 agaggttctt tcaccccaga agacattttc tactcctaca tcgctggtat ggacgctttc    1080
gctttgggtt tcagagctgc tttgaagttg attgaagacg gtagaatcga caagttcgtt    1140
gctgacagat acgcttcttg gaacactggt attggtgctg acatcattgc tggtaaggct    1200
gacttcgctt ccttggaaaa gtacgctttg gaaaagggtg aagtcaccgc ttctttgtcc    1260
tctggtagac aagaaatgtt ggaatccatc gttaacaacg tcttgttctc tttgtaa       1317
```

<210> SEQ ID NO 34
<211> LENGTH: 1335
<212> TYPE: DNA
<213> ORGANISM: Piromyces sp.

<400> SEQUENCE: 34

```
actagtaaaa aaatggctaa ggaatatttc ccacaaattc aaaagattaa gttcgaaggt      60
aaggattcta agaatccatt agccttccac tactacgatg ctgaaaagga agtcatgggt     120
aagaaaatga aggattggtt acgtttcgcc atggcctggt ggcacactct ttgcgccgaa     180
ggtgctgacc aattcggtgg aggtacaaag tctttcccat ggaacgaagg tactgatgct     240
attgaaattg ccaagcaaaa ggttgatgct ggtttcgaaa tcatgcaaaa gcttggtatt     300
ccatactact gtttccacga tgttgatctt gtttccgaag taactctat tgaagaatac     360
gaatccaacc ttaaggctgt cgttgcttac ctcaaggaaa agcaaaagga accggtatt     420
aagcttctct ggagtactgc taacgtcttc ggtcacaagc gttacatgaa cggtgcctcc     480
actaacccag actttgatgt tgtcgcccgt gctattgttc aaattaagaa cgccatagac     540
gccggtattg aacttggtgc tgaaaactac gtcttctggg gtggtcgtga aggttacatg     600
agtctcctta acactgacca aaagcgtgaa aaggaacaca tggccactat gcttaccatg     660
gctcgtgact acgtcgttc aagggattc aagggtactt ccctcattga accaaagcca     720
atggaaccaa ccaagcacca atacgatgtt gacactgaaa ccgctattgg tttccttaag     780
gcccacaact tagacaagga cttcaaggtc aacattgaag ttaaccacgc tactcttgct     840
ggtcacactt tcgaacacga acttgcctgt gctgttgatg ctggtatgct cggttccatt     900
gatgctaacc gtggtgacta ccaaaacggt tgggatactg atcaattccc aattgatcaa     960
tacgaactcg tccaagcttg gatggaaatc atccgtggtg gtggtttcgt tactggtggt    1020
accaacttcg atgccaagac tcgtcgtaac tctactgacc tcgaagacat catcattgcc    1080
cacgtttctg gtatggatgc tatggctcgt gctcttgaaa acgctgccaa gctcctccaa    1140
gaatctccat acaccaagat gaagaaggaa cgttacgctt ccttcgacag tggtattggt    1200
aaggactttg aagatggtaa gctcacccct gaacaagttt acgaatacgg taagaagaac    1260
ggtgaaccaa gcaaacttc tggtaagcaa gaactctacg aagctattgt tgccatgtac    1320
caatagtagc tcgag                                                     1335
```

<210> SEQ ID NO 35
<211> LENGTH: 437
<212> TYPE: PRT
<213> ORGANISM: Piromyces sp.

<400> SEQUENCE: 35

```
Met Ala Lys Glu Tyr Phe Pro Gln Ile Gln Lys Ile Lys Phe Glu Gly
1               5                   10                  15
Lys Asp Ser Lys Asn Pro Leu Ala Phe His Tyr Tyr Asp Ala Glu Lys
            20                  25                  30
Glu Val Met Gly Lys Lys Met Lys Asp Trp Leu Arg Phe Ala Met Ala
        35                  40                  45
Trp Trp His Thr Leu Cys Ala Glu Gly Ala Asp Gln Phe Gly Gly Gly
    50                  55                  60
Thr Lys Ser Phe Pro Trp Asn Glu Gly Thr Asp Ala Ile Glu Ile Ala
65                  70                  75                  80
Lys Gln Lys Val Asp Ala Gly Phe Glu Ile Met Gln Lys Leu Gly Ile
                85                  90                  95
```

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 36
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agttaagtga gtaaactagt gaattccaga gaaaataaaa cattgtttac aataga        56

<210> SEQ ID NO 37
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agtcaagtct cgagtcaatg gtgatggtgg tgatgcagag aaaataaaac attgtttac        59

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
actagtatgg aattttcag caatatcggt aaaattc                                 37

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctcgagttac agactgaaaa gaacgttatt tacg                                   34

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
actagtatgg aattcttctc taacattgg                                         29

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcgagttac aaagagaaca agacgttgtt aacgatgg                               38

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
actagtaaaa aaatggctaa ggaatatttc ccacaaattc aaaag                       45

<210> SEQ ID NO 43

```
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atgactcgag ctactaatga tgatgatgat gatgttggta catggcaaca atagcttcg      59

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actagtaaaa aaatggaatt tttcagcaat atcggtaaaa ttc                      43

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
actagtaaaa aaatggctaa ggaatatttc agcaatatcg gtaaaattca g             51

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttcccacaaa ttcaaaaaat tcagtatcag ggaccaaaaa g                        41

<210> SEQ ID NO 47
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
actagtaaaa aaatggctaa ggaatatttc ccacaaattc aaaaaattca gtatcaggga    60
ccaaaaag                                                             68

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aagattaagt tcgaaggacc aaaaagtact gatcctctct c                        41

<210> SEQ ID NO 49
```

```
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttcccacaaa ttcaaaagat taagttcgaa ggaccaaaaa gtactgatcc tctctc          56

<210> SEQ ID NO 50
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
actagtaaaa aaatggctaa ggaatatttc ccacaaattc aaaagattaa gttc            54

<210> SEQ ID NO 51
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtaaggatt ctaaggatcc tctctcattt aagtactata accctg                    46

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caaaagatta agttcgaagg taaggattct aaggatcctc tcatttaa gtac              54

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctcgagttac agactgaaaa gaacgttatt tacg                                 34

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctcgagttac agactgaaaa gaacgttatt tacg                                 34

<210> SEQ ID NO 55
<211> LENGTH: 1329
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 55

```
aaaaaaatgg ctaaggaata tttcagcaat atcggtaaaa ttcagtatca gggaccaaaa      60
agtactgatc ctctctcatt taagtactat aaccctgaag aagtcatcaa cggaaagaca     120
atgcgcgagc atctgaagtt cgctctttca tggtggcaca caatgggcgg cgacggaaca     180
gatatgttcg gctgcggcac aacagacaag acctggggac agtccgatcc cgctgcaaga     240
gcaaaggcta aggttgacgc agcattcgag atcatggata agctctccat tgactactat     300
tgtttccacg atcgcgatct ttctcccgag tatggcagcc tcaaggctac caacgatcag     360
cttgacatag ttacagacta tatcaaggag aagcagggcg acaagttcaa gtgcctctgg     420
ggtacagcaa agtgcttcga tcatccaaga ttcatgcacg gtgcaggtac atctccttct     480
gctgatgtat tcgctttctc agctgctcag atcaagaagg ctctggagtc aacagtaaag     540
ctcggcggta acggttacgt tttctggggc ggacgtgaag ctatgagaca cttcttaat      600
acaaatatgg gactcgaact cgacaatatg gctcgtctta tgaagatggc tgttgagtat     660
ggacgttcga tcggcttcaa gggcgacttc tatatcgagc ccaagcccaa ggagcccaca     720
aagcatcagt acgatttcga tacagctact gttctgggat tcctcagaaa gtacggtctc     780
gataaggatt tcaagatgaa tatcgaagct aaccacgcta cacttgctca gcatacattc     840
cagcatgagc tccgtgttgc aagagacaat ggtgtgttcg gttctatcga cgcaaaccag     900
ggcgacgttc ttcttggatg ggatacagac cagttcccca caaatatcta cgatacaaca     960
atgtgtatgt atgaagttat caaggcaggc ggcttcacaa acggcggtct caacttcgac    1020
gctaaggcac gcagagggag cttcactccc gaggatatct tctacagcta tcgcaggt     1080
atggatgcat ttgctctggg cttcagagct gctctcaagc ttatcgaaga cggacgtatc    1140
gacaagttcg ttgctgacag atacgcttca tggaataccg gtatcggtgc agacataatc    1200
gcaggtaagg cagatttcgc atctcttgaa aagtatgctc ttgaaaaggg cgaggttaca    1260
gcttcactct caagcggcag acaggaaatg ctggagtcta tcgtaaataa cgttctttc     1320
agtctgtaa                                                            1329
```

<210> SEQ ID NO 56
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Met Ala Lys Glu Tyr Phe Ser Asn Ile Gly Lys Ile Gln Tyr Gln Gly
1               5                   10                  15

Pro Lys Ser Thr Asp Pro Leu Ser Phe Lys Tyr Tyr Asn Pro Glu Glu
            20                  25                  30

Val Ile Asn Gly Lys Thr Met Arg Glu His Leu Lys Phe Ala Leu Ser
        35                  40                  45

Trp Trp His Thr Met Gly Gly Asp Gly Thr Asp Met Phe Gly Cys Gly
    50                  55                  60

Thr Thr Asp Lys Thr Trp Gly Gln Ser Asp Pro Ala Ala Arg Ala Lys
65                  70                  75                  80

Ala Lys Val Asp Ala Ala Phe Glu Ile Met Asp Lys Leu Ser Ile Asp
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| Tyr | Tyr | Cys | Phe | His | Asp | Arg | Asp | Leu | Ser | Pro | Glu | Tyr | Gly | Ser | Leu |
|     |     |     | 100 |     |     |     |     | 105 |     |     |     |     | 110 |     |     |

Lys Ala Thr Asn Asp Gln Leu Asp Ile Val Thr Asp Tyr Ile Lys Glu
    115                 120                 125

Lys Gln Gly Asp Lys Phe Lys Cys Leu Trp Gly Thr Ala Lys Cys Phe
130                 135                 140

Asp His Pro Arg Phe Met His Gly Ala Gly Thr Ser Pro Ser Ala Asp
145                 150                 155                 160

Val Phe Ala Phe Ser Ala Ala Gln Ile Lys Lys Ala Leu Glu Ser Thr
                165                 170                 175

Val Lys Leu Gly Gly Asn Gly Tyr Val Phe Trp Gly Gly Arg Glu Gly
            180                 185                 190

Tyr Glu Thr Leu Leu Asn Thr Asn Met Gly Leu Glu Leu Asp Asn Met
        195                 200                 205

Ala Arg Leu Met Lys Met Ala Val Glu Tyr Gly Arg Ser Ile Gly Phe
    210                 215                 220

Lys Gly Asp Phe Tyr Ile Glu Pro Lys Pro Lys Glu Pro Thr Lys His
225                 230                 235                 240

Gln Tyr Asp Phe Asp Thr Ala Thr Val Leu Gly Phe Leu Arg Lys Tyr
                245                 250                 255

Gly Leu Asp Lys Asp Phe Lys Met Asn Ile Glu Ala Asn His Ala Thr
            260                 265                 270

Leu Ala Gln His Thr Phe Gln His Glu Leu Arg Val Ala Arg Asp Asn
        275                 280                 285

Gly Val Phe Gly Ser Ile Asp Ala Asn Gln Gly Asp Val Leu Leu Gly
    290                 295                 300

Trp Asp Thr Asp Gln Phe Pro Thr Asn Ile Tyr Asp Thr Thr Met Cys
305                 310                 315                 320

Met Tyr Glu Val Ile Lys Ala Gly Gly Phe Thr Asn Gly Gly Leu Asn
                325                 330                 335

Phe Asp Ala Lys Ala Arg Arg Gly Ser Phe Thr Pro Glu Asp Ile Phe
            340                 345                 350

Tyr Ser Tyr Ile Ala Gly Met Asp Ala Phe Ala Leu Gly Phe Arg Ala
        355                 360                 365

Ala Leu Lys Leu Ile Glu Asp Gly Arg Ile Asp Lys Phe Val Ala Asp
    370                 375                 380

Arg Tyr Ala Ser Trp Asn Thr Gly Ile Gly Ala Asp Ile Ile Ala Gly
385                 390                 395                 400

Lys Ala Asp Phe Ala Ser Leu Glu Lys Tyr Ala Leu Glu Lys Gly Glu
                405                 410                 415

Val Thr Ala Ser Leu Ser Ser Gly Arg Gln Glu Met Leu Glu Ser Ile
            420                 425                 430

Val Asn Asn Val Leu Phe Ser Leu
        435                 440

<210> SEQ ID NO 57
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
aaaaaaatgg ctaaggaata tttcccacaa attcaacagt atcagggacc aaaaagtact    60

-continued

```
gatcctctct catttaagta ctataaccct gaagaagtca tcaacggaaa gacaatgcgc    120
gagcatctga agttcgctct ttcatggtgg cacacaatgg gcggcgacgg aacagatatg    180
ttcggctgcg gcacaacaga caagacctgg ggacagtccg atcccgctgc aagagcaaag    240
gctaaggttg acgcagcatt cgagatcatg gataagctct ccattgacta ctattgtttc    300
cacgatcgcg atctttctcc cgagtatggc agcctcaagg ctaccaacga tcagcttgac    360
atagttacag actatatcaa ggagaagcag ggcgacaagt tcaagtgcct ctggggtaca    420
gcaaagtgct tcgatcatcc aagattcatg cacggtgcag gtacatctcc ttctgctgat    480
gtattcgctt tctcagctgc tcagatcaag aaggctctgg agtcaacagt aaagctcggc    540
ggtaacggtt acgttttctg gggcggacgt gaaggctatg agacacttct taatacaaat    600
atgggactcg aactcgacaa tatggctcgt cttatgaaga tggctgttga gtatggacgt    660
tcgatcggct tcaagggcga cttctatatc gagcccaagc ccaaggagcc cacaaagcat    720
cagtacgatt tcgatacagc tactgttctg ggattcctca gaaagtacgg tctcgataag    780
gatttcaaga tgaatatcga agctaaccac gctacacttg ctcagcatac attccagcat    840
gagctccgtg ttgcaagaga caatggtgtg ttcggttcta tcgacgcaaa ccagggcgac    900
gttcttcttg atgggatac agaccagttc cccacaaata tctacgatac aacaatgtgt    960
atgtatgaag ttatcaaggc aggcggcttc acaaacggcg tctcaacttc gacgctaag    1020 gcacgcagag ggagcttcac tcccgaggat atcttctaca gctatatcgc aggtatggat    1080
gcatttgctc tgggcttcag agctgctctc aagcttatcg aagacggacg tatcgacaag    1140
ttcgttgctg acagatacgc ttcatggaat accggtatcg gtgcagacat aatcgcaggt    1200
aaggcagatt tcgcatctct tgaaaagtat gctcttgaaa agggcgaggt tacagcttca    1260
ctctcaagcg gcagacagga aatgctggag tctatcgtaa ataacgttct tttcagtctg    1320
taa                                                                 1323
```

<210> SEQ ID NO 58
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Ala Lys Glu Tyr Phe Pro Gln Ile Gln Gln Tyr Gln Gly Pro Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125
```

```
Gly Asp Lys Phe Lys Cys Leu Trp Gly Thr Ala Lys Cys Phe Asp His
            130                 135                 140
Pro Arg Phe Met His Gly Ala Gly Thr Ser Pro Ser Ala Asp Val Phe
145                 150                 155                 160
Ala Phe Ser Ala Ala Gln Ile Lys Lys Ala Leu Glu Ser Thr Val Lys
                165                 170                 175
Leu Gly Gly Asn Gly Tyr Val Phe Trp Gly Arg Gly Tyr Glu
                180                 185                 190
Thr Leu Leu Asn Thr Asn Met Gly Leu Glu Leu Asp Asn Met Ala Arg
            195                 200                 205
Leu Met Lys Met Ala Val Glu Tyr Gly Arg Ser Ile Gly Phe Lys Gly
        210                 215                 220
Asp Phe Tyr Ile Glu Pro Lys Pro Lys Glu Pro Thr Lys His Gln Tyr
225                 230                 235                 240
Asp Phe Asp Thr Ala Thr Val Leu Gly Phe Leu Arg Lys Tyr Gly Leu
                245                 250                 255
Asp Lys Asp Phe Lys Met Asn Ile Glu Ala Asn His Ala Thr Leu Ala
            260                 265                 270
Gln His Thr Phe Gln His Glu Leu Arg Val Ala Arg Asp Asn Gly Val
        275                 280                 285
Phe Gly Ser Ile Asp Ala Asn Gln Gly Asp Val Leu Leu Gly Trp Asp
    290                 295                 300
Thr Asp Gln Phe Pro Thr Asn Ile Tyr Asp Thr Thr Met Cys Met Tyr
305                 310                 315                 320
Glu Val Ile Lys Ala Gly Gly Phe Thr Asn Gly Leu Asn Phe Asp
                325                 330                 335
Ala Lys Ala Arg Arg Gly Ser Phe Thr Pro Glu Asp Ile Phe Tyr Ser
            340                 345                 350
Tyr Ile Ala Gly Met Asp Ala Phe Ala Leu Gly Phe Arg Ala Ala Leu
        355                 360                 365
Lys Leu Ile Glu Asp Gly Arg Ile Asp Lys Phe Val Ala Asp Arg Tyr
    370                 375                 380
Ala Ser Trp Asn Thr Gly Ile Gly Ala Asp Ile Ile Ala Gly Lys Ala
385                 390                 395                 400
Asp Phe Ala Ser Leu Glu Lys Tyr Ala Leu Glu Lys Gly Glu Val Thr
                405                 410                 415
Ala Ser Leu Ser Ser Gly Arg Gln Glu Met Leu Glu Ser Ile Val Asn
            420                 425                 430
Asn Val Leu Phe Ser Leu
        435

<210> SEQ ID NO 59
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
aaaaaaatgg ctaaggaata tttcccacaa attcaaaaga ttaagttcga aaaaagtact    60
gatcctctct catttaagta ctataaccct gaagaagtca tcaacggaaa gacaatgcgc   120
gagcatctga agttcgctct ttcatggtgg cacacaatgg cggcgacgg aacagatatg   180 ttcggctgcg gcacaacaga caagacctgg ggacagtccg atcccgctgc aagagcaaag   240
gctaaggttg acgcagcatt cgagatcatg ataagctct ccattgacta ctattgtttc   300
```

-continued

```
cacgatcgcg atctttctcc cgagtatggc agcctcaagg ctaccaacga tcagcttgac    360
atagttacag actatatcaa ggagaagcag ggcgacaagt tcaagtgcct ctggggtaca    420
gcaaagtgct tcgatcatcc aagattcatg cacggtgcag gtacatctcc ttctgctgat    480
gtattcgctt tctcagctgc tcagatcaag aaggctctgg agtcaacagt aaagctcggc    540
ggtaacggtt acgttttctg gggcggacgt gaaggctatg agacacttct taatacaaat    600
atgggactcg aactcgacaa tatggctcgt cttatgaaga tggctgttga gtatggacgt    660
tcgatcggct tcaagggcga cttctatatc gagcccaagc ccaaggagcc acaaagcat     720 cagtacgatt tcgatacagc tactgttctg ggattcctca gaaagtacgg tctcgataag    780
gatttcaaga tgaatatcga agctaaccac gctacacttg ctcagcatac attccagcat    840
gagctccgtg ttgcaagaga caatggtgtg ttcggttcta tcgacgcaaa ccagggcgac    900
gttcttcttg gatgggatac agaccagttc cccacaaata tctacgatac aacaatgtgt    960
atgtatgaag ttatcaaggc aggcggcttc acaaacggcg gtctcaactt cgacgctaag   1020
gcacgcagag ggagcttcac tcccgaggat atcttctaca gctatatcgc aggtatggat   1080
gcatttgctc tgggcttcag agctgctctc aagcttatcg aagacggacg tatcgacaag   1140
ttcgttgctg acagatacgc ttcatggaat accggtatcg gtgcagacat aatcgcaggt   1200
aaggcagatt tcgcatctct tgaaaagtat gctcttgaaa agggcgaggt tacagcttca   1260
ctctcaagcg gcagacagga aatgctggag tctatcgtaa ataacgttct tttcagtctg   1320
taa                                                                 1323
```

<210> SEQ ID NO 60
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Ala Lys Glu Tyr Phe Pro Gln Ile Gln Lys Ile Lys Phe Glu Lys
1               5                   10                  15

Ser Thr Asp Pro Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125

Gly Asp Lys Phe Lys Cys Leu Trp Gly Thr Ala Lys Cys Phe Asp His
    130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175
```

```
Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
            195                 200             205

Leu Met Lys Met Ala Val Glu Tyr Gly Arg Ser Ile Gly Phe Lys Gly
210                 215                 220

Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
            260                 265                 270

Gln His Thr Phe Gln His Glu Leu Arg Val Ala Arg Asp Asn Gly Val
            275                 280                 285

Phe Gly Ser Ile Asp Ala Asn Gln Gly Asp Val Leu Leu Gly Trp Asp
290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Leu Asn Phe Asp
                325                 330                 335

Ala Lys Ala Arg Arg Gly Ser Phe Thr Pro Glu Asp Ile Phe Tyr Ser
            340                 345                 350

Tyr Ile Ala Gly Met Asp Ala Phe Ala Leu Gly Phe Arg Ala Ala Leu
                355                 360                 365

Lys Leu Ile Glu Asp Gly Arg Ile Asp Lys Phe Val Ala Asp Arg Tyr
370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
            420                 425                 430

Asn Val Leu Phe Ser Leu
            435
```

<210> SEQ ID NO 61
<211> LENGTH: 1322
<212> TYPE: DNA
<213> ORGANISM: Artificial Sequence
<220> FEATURE:
<223> OTHER INFORMATION: Description of Artificial Sequence: Synthetic
    polynucleotide <400> SEQUENCE: 61

```
aaaaaatggc taaggaatat ttcccacaaa ttcaaaagat taagttcgaa ggtaaggatt      60
ctaagctctc atttaagtac tataaccctg aagaagtcat caacggaaag acaatgcgcg     120
agcatctgaa gttcgctctt tcatggtggc acacaatggg cggcgacgga acagatatgt     180
tcggctgcgg cacaacagac aagacctggg acagtccga  tcccgctgca agagcaaagg     240
ctaaggttga cgcagcattc gagatcatgg ataagctctc cattgactac tattgtttcc     300
acgatcgcga tctttctccc gagtatcgga gcctcaaggc taccaacgat cagcttgaca     360
tagttacaga ctatatcaag gagaagcagg gcgacaagtt caagtgcctc tggggtacag     420
caaagtgctt cgatcatcca agattcatgc acgtgcagg  tacatctcct tctgctgatg     480
tattcgcttt ctcagctgct cagatcaaga aggctctgga gtcaacagta aagctcggcg     540
```

```
gtaacggtta cgttttctgg ggcggacgtg aaggctatga gacacttctt aatacaaata    600
tgggactcga actcgacaat atggctcgtc ttatgaagat ggctgttgag tatggacgtt    660
cgatcggctt caagggcgac ttctatatcg agcccaagcc caaggagccc acaaagcatc    720
agtacgattt cgatacagct actgttctgg gattcctcag aaagtacggt ctcgataagg    780
atttcaagat gaatatcgaa gctaaccacg ctacacttgc tcagcataca ttccagcatg    840
agctccgtgt tgcaagagac aatggtgtgt tcggttctat cgacgcaaac cagggcgacg    900
ttcttcttgg atgggataca gaccagttcc ccacaaatat ctacgataca acaatgtgta    960
tgtatgaagt tatcaaggca ggcggcttca caaacggcgg tctcaacttc gacgctaagg   1020
cacgcagagg gagcttcact cccgaggata tcttctacag ctatatcgca ggtatggatg   1080
catttgctct gggcttcaga gctgctctca agcttatcga agacggacgt atcgacaagt   1140
tcgttgctga cagatacgct tcatggaata ccggtatcgg tgcagacata atcgcaggta   1200
aggcagattt cgcatctctt gaaaagtatg ctcttgaaaa gggcgaggtt acagcttcac   1260
tctcaagcgg cagacaggaa atgctggagt ctatcgtaaa taacgttctt ttcagtctgt   1320
aa                                                                  1322
```

<210> SEQ ID NO 62
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Ala Lys Glu Tyr Phe Pro Gln Ile Gln Lys Ile Lys Phe Glu Gly
1               5                   10                  15

Lys Asp Ser Lys Leu Ser Phe Lys Tyr Tyr Asn Pro Glu Glu Val Ile
            20                  25                  30

Asn Gly Lys Thr Met Arg Glu His Leu Lys Phe Ala Leu Ser Trp Trp
        35                  40                  45

His Thr Met Gly Gly Asp Gly Thr Asp Met Phe Gly Cys Gly Thr Thr
    50                  55                  60

Asp Lys Thr Trp Gly Gln Ser Asp Pro Ala Ala Arg Ala Lys Ala Lys
65                  70                  75                  80

Val Asp Ala Ala Phe Glu Ile Met Asp Lys Leu Ser Ile Asp Tyr Tyr
                85                  90                  95

Cys Phe His Asp Arg Asp Leu Ser Pro Glu Tyr Gly Ser Leu Lys Ala
            100                 105                 110

Thr Asn Asp Gln Leu Asp Ile Val Thr Asp Tyr Ile Lys Glu Lys Gln
        115                 120                 125

Gly Asp Lys Phe Lys Cys Leu Trp Gly Thr Ala Lys Cys Phe Asp His
    130                 135                 140

Pro Arg Phe Met His Gly Ala Gly Thr Ser Pro Ser Ala Asp Val Phe
145                 150                 155                 160

Ala Phe Ser Ala Ala Gln Ile Lys Lys Ala Leu Glu Ser Thr Val Lys
                165                 170                 175

Leu Gly Gly Asn Gly Tyr Val Phe Trp Gly Gly Arg Glu Gly Tyr Glu
            180                 185                 190

Thr Leu Leu Asn Thr Asn Met Gly Leu Glu Leu Asp Asn Met Ala Arg
        195                 200                 205

Leu Met Lys Met Ala Val Glu Tyr Gly Arg Ser Ile Gly Phe Lys Gly
```

```
            210                 215                 220
Asp Phe Tyr Ile Glu Pro Lys Pro Lys Glu Pro Thr Lys His Gln Tyr
225                 230                 235                 240

Asp Phe Asp Thr Ala Thr Val Leu Gly Phe Leu Arg Lys Tyr Gly Leu
                245                 250                 255

Asp Lys Asp Phe Lys Met Asn Ile Glu Ala Asn His Ala Thr Leu Ala
                260                 265                 270

Gln His Thr Phe Gln His Glu Leu Arg Val Ala Arg Asp Asn Gly Val
                275                 280                 285

Phe Gly Ser Ile Asp Ala Asn Gln Gly Asp Val Leu Leu Gly Trp Asp
                290                 295                 300

Thr Asp Gln Phe Pro Thr Asn Ile Tyr Asp Thr Thr Met Cys Met Tyr
305                 310                 315                 320

Glu Val Ile Lys Ala Gly Gly Phe Thr Asn Gly Gly Leu Asn Phe Asp
                325                 330                 335

Ala Lys Ala Arg Arg Gly Ser Phe Thr Pro Glu Asp Ile Phe Tyr Ser
                340                 345                 350

Tyr Ile Ala Gly Met Asp Ala Phe Ala Leu Gly Phe Arg Ala Ala Leu
                355                 360                 365

Lys Leu Ile Glu Asp Gly Arg Ile Asp Lys Phe Val Ala Asp Arg Tyr
370                 375                 380

Ala Ser Trp Asn Thr Gly Ile Gly Ala Asp Ile Ile Ala Gly Lys Ala
385                 390                 395                 400

Asp Phe Ala Ser Leu Glu Lys Tyr Ala Leu Glu Lys Gly Glu Val Thr
                405                 410                 415

Ala Ser Leu Ser Ser Gly Arg Gln Glu Met Leu Glu Ser Ile Val Asn
                420                 425                 430

Asn Val Leu Phe Ser Leu
                435

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aactgaactg actagtaaaa aaatgcaccc tcgtgtgctc gaagt              45

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agtaaagtaa aagcttctac tagcgccagc cgttgaggct ct                 42

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
```

```
agtaaagtaa aagcttctac taatgatgat gatgatgatg gcgccagccg ttgaggctc      59
```

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

```
aactgaactg actagtaaaa aaatgcacaa ccttgaacag aagacc                    46
```

<210> SEQ ID NO 67
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
agtaaagtaa ctcgagctat tagtgtctgc ggtgctcggc gaa                       43
```

<210> SEQ ID NO 68
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
taaagtaact cgagctacta atgatgatga tgatgatggt gtctgcggtg ctcggcgaa      59
```

<210> SEQ ID NO 69
<211> LENGTH: 1830
<212> TYPE: DNA
<213> ORGANISM: Pseudomonas aeruginosa

<400> SEQUENCE: 69

```
atgcaccctc gtgtgctcga agtcacccgc cgcatccagg cccgtagcgc ggccactcgc      60
cagcgctacc tcgagatggt ccgggctgcg gccagcaagg ggccgcaccg cggcaccctg     120
ccgtgcggca acctcgccca cggggtcgcg gcctgtggcg aaagcgacaa gcagaccctg     180
cggctgatga accaggccaa cgtggccatc gtttccgcct acaacgacat gctctcgggcg    240
caccagccgt tcgagcgctt tccggggctg atcaagcagg cgctgcacga atcggttcg     300
gtcggccagt tcgccggcgg cgtgccggcc atgtgcgacg gggtgaccca gggcgagccg     360
ggcatggaac tgtcgctggc cagccgcgac gtgatcgcca tgtccaccgc catcgcgctg    420
tctcacaaca tgttcgatgc agcgctgtgc ctgggtgttt gcgacaagat cgtgccgggc    480
ctgctgatcg gctcgctgcg cttcggccac ctgcccaccg tgttcgtccc ggccgggccg    540
atgccgaccg gcatctccaa caggaaaag gccgcggtgc ccaactgtt cgccgaaggc     600
aaggccactc gcgaagagct gctggcctcg aaatggcct cctaccatgc acccggcacc    660
tgcaccttct atggcaccgc caataccaac cagttgctgg tggaggtgat gggcctgcac    720
ttgcccggtg cctccttcgt caacccgaac acccccctgc gcgacgaact cacccgcgaa    780
gcggcacgcc aggccagccg gctgacccc gagaacggca actacgtgcc gatggcggag    840
atcgtcgacg agaaggccat cgtcaactcg gtggtggcgc tgctcgccac cggcggctcg    900
```

-continued

```
accaaccaca ccctgcacct gctggcgatc gcccaggcgg cgggcatcca gttgacctgg   960
caggacatgt ccgagctgtc ccatgtggtg ccgaccctgg cgcgcatcta tccgaacggc  1020
caggccgaca tcaaccactt ccaggcggcc ggcggcatgt ccttcctgat ccgccaactg  1080
ctcgacggcg ggctgcttca cgaggacgta cagaccgtcg ccggcccggg cctgcgccgc  1140
tacacccgcg agccgttcct cgaggatggc cggctggtct ggcgcgaagg ccggaacgg   1200 agtctcgacg aagccatcct gcgtccgctg acaagccgt tctccgccga aggcggcttg   1260
cgcctgatgg agggcaacct cggtcgcggc gtgatgaagg tctcggcggt ggcgccggaa  1320
caccaggtgg tcgaggcgcc ggtacggatc ttccacgacc aggccagcct ggccgcgggcc  1380 ttcaaggccg gcgagctgga gcgcgacctg gtcgccgtgg tgcgtttcca gggcccgcgg  1440
gcgaacggca tgccggagct gcacaagctc acgccgttcc tcggggtcct gcaggatcgt  1500
ggcttcaagg tggcgctggt caccgacggg cgcatgtccg gggcgtcggg caaggtgccc  1560
gcggccatcc atgtgagtcc ggaagccatc gccggcggtc cgctggcgcg cctgcgcgac  1620
ggcgaccggg tgcgggtgga tggggtgaac ggcgagttgc gggtgctggt cgacgacgcc  1680
gaatggcagg cgcgcagcct ggagccggcg ccgcaggacg gcaatctcgg ttgcggccgc  1740
gagctgttcg ccttcatgcg caacgccatg agcagcgcgg aagagggcgc ctgcagcttt  1800
accgagagcc tcaacggctg gcgctagtag                                   1830
```

<210> SEQ ID NO 70
<211> LENGTH: 608
<212> TYPE: PRT
<213> ORGANISM: Pseudomonas aeruginosa

<400> SEQUENCE: 70

| Met | His | Pro | Arg | Val | Leu | Glu | Val | Thr | Arg | Arg | Ile | Gln | Ala | Arg | Ser |
|---|---|---|---|---|---|---|---|---|---|---|---|---|---|---|---|
| 1 | | | | 5 | | | | | 10 | | | | | 15 | |

| Ala | Ala | Thr | Arg | Gln | Arg | Tyr | Leu | Glu | Met | Val | Arg | Ala | Ala | Ser |
|---|---|---|---|---|---|---|---|---|---|---|---|---|---|---|
| | | 20 | | | | | 25 | | | | | 30 | | |

Lys Gly Pro His Arg Gly Thr Leu Pro Cys Gly Asn Leu Ala His Gly
          35                  40                  45

Val Ala Ala Cys Gly Glu Ser Asp Lys Gln Thr Leu Arg Leu Met Asn
      50                  55                  60

Gln Ala Asn Val Ala Ile Val Ser Ala Tyr Asn Asp Met Leu Ser Ala
65                  70                  75                  80

His Gln Pro Phe Glu Arg Phe Pro Gly Leu Ile Lys Gln Ala Leu His
                  85                  90                  95

Glu Ile Gly Ser Val Gly Gln Phe Ala Gly Gly Val Pro Ala Met Cys
              100                 105                 110

Asp Gly Val Thr Gln Gly Glu Pro Gly Met Glu Leu Ser Leu Ala Ser
          115                 120                 125

Arg Asp Val Ile Ala Met Ser Thr Ala Ile Ala Leu Ser His Asn Met
      130                 135                 140

Phe Asp Ala Ala Leu Cys Leu Gly Val Cys Asp Lys Ile Val Pro Gly
145                 150                 155                 160

Leu Leu Ile Gly Ser Leu Arg Phe Gly His Leu Pro Thr Val Phe Val
                  165                 170                 175

Pro Ala Gly Pro Met Pro Thr Gly Ile Ser Asn Lys Glu Lys Ala Ala
              180                 185                 190

Val Arg Gln Leu Phe Ala Glu Gly Lys Ala Thr Arg Glu Glu Leu Leu
          195                 200                 205

Ala Ser Glu Met Ala Ser Tyr His Ala Pro Gly Thr Cys Thr Phe Tyr

```
                210                 215                 220
Gly Thr Ala Asn Thr Asn Gln Leu Leu Val Glu Val Met Gly Leu His
225                 230                 235                 240

Leu Pro Gly Ala Ser Phe Val Asn Pro Asn Thr Pro Leu Arg Asp Glu
                245                 250                 255

Leu Thr Arg Glu Ala Ala Arg Gln Ala Ser Arg Leu Thr Pro Glu Asn
            260                 265                 270

Gly Asn Tyr Val Pro Met Ala Glu Ile Val Asp Glu Lys Ala Ile Val
        275                 280                 285

Asn Ser Val Val Ala Leu Leu Ala Thr Gly Gly Ser Thr Asn His Thr
290                 295                 300

Leu His Leu Leu Ala Ile Ala Gln Ala Ala Gly Ile Gln Leu Thr Trp
305                 310                 315                 320

Gln Asp Met Ser Glu Leu Ser His Val Val Pro Thr Leu Ala Arg Ile
                325                 330                 335

Tyr Pro Asn Gly Gln Ala Asp Ile Asn His Phe Gln Ala Ala Gly Gly
            340                 345                 350

Met Ser Phe Leu Ile Arg Gln Leu Leu Asp Gly Gly Leu Leu His Glu
        355                 360                 365

Asp Val Gln Thr Val Ala Gly Pro Gly Leu Arg Arg Tyr Thr Arg Glu
370                 375                 380

Pro Phe Leu Glu Asp Gly Arg Leu Val Trp Arg Glu Gly Pro Glu Arg
385                 390                 395                 400

Ser Leu Asp Glu Ala Ile Leu Arg Pro Leu Asp Lys Pro Phe Ser Ala
                405                 410                 415

Glu Gly Gly Leu Arg Leu Met Glu Gly Asn Leu Gly Arg Gly Val Met
            420                 425                 430

Lys Val Ser Ala Val Ala Pro Glu His Gln Val Val Glu Ala Pro Val
435                 440                 445

Arg Ile Phe His Asp Gln Ala Ser Leu Ala Ala Phe Lys Ala Gly
        450                 455                 460

Glu Leu Glu Arg Asp Leu Val Ala Val Arg Phe Gln Gly Pro Arg
465                 470                 475                 480

Ala Asn Gly Met Pro Glu Leu His Lys Leu Thr Pro Phe Leu Gly Val
                485                 490                 495

Leu Gln Asp Arg Gly Phe Lys Val Ala Leu Val Thr Asp Gly Arg Met
            500                 505                 510

Ser Gly Ala Ser Gly Lys Val Pro Ala Ala Ile His Val Ser Pro Glu
        515                 520                 525

Ala Ile Ala Gly Gly Pro Leu Ala Arg Leu Arg Asp Gly Asp Arg Val
530                 535                 540

Arg Val Asp Gly Val Asn Gly Glu Leu Arg Val Leu Val Asp Asp Ala
545                 550                 555                 560

Glu Trp Gln Ala Arg Ser Leu Gly Pro Ala Pro Gln Asp Gly Asn Leu
                565                 570                 575

Gly Cys Gly Arg Glu Leu Phe Ala Phe Met Arg Asn Ala Met Ser Ser
            580                 585                 590

Ala Glu Glu Gly Ala Cys Ser Phe Thr Glu Ser Leu Asn Gly Trp Arg
        595                 600                 605
```

<210> SEQ ID NO 71
<211> LENGTH: 666
<212> TYPE: DNA
<213> ORGANISM: Pseudomonas aeruginosa

```
<400> SEQUENCE: 71
atgcacaacc ttgaacagaa gaccgcccgc atcgacacgc tgtgccggga ggcgcgcatc      60
ctcccggtga tcaccatcga ccgcgaggcg gacatcctgc cgatggccga tgccctcgcc     120
gccggcggcc tgaccgccct ggagatcacc ctgcgcacgg cgcacgggct gaccgccatc     180
cggcgcctca gcgaggagcg cccgcacctg cgcatcggcg ccggcaccgt gctcgacccg     240
cggaccttcg ccgccgcgga aaaggccggg gcgagcttcg tggtcacccc gggttgcacc     300
gacgagttgc tgcgcttcgc cctggacagc gaagtcccgc tgttgccgg cgtggccagc      360 gcttccgaga tcatgctcgc ctaccgccat ggctaccgcc gcttcaagct gtttcccgcc     420
gaagtcagcg gcggcccggc ggcgctgaag gcgttctcgg gaccattccc cgatatccgc     480
ttctgcccca ccggaggcgt cagcctgaac aatctcgccg actacctggc ggtacccaac     540
gtgatgtgcg tcggcggcac ctggatgctg cccaaggccg tggtcgaccg cggcgactgg     600
gcccaggtcg agcgcctcag ccgcgaagcc ctggagcgct cgccgagca ccgcagacac      660 taatag                                                                666

<210> SEQ ID NO 72
<211> LENGTH: 220
<212> TYPE: PRT
<213> ORGANISM: Pseudomonas aeruginosa

<400> SEQUENCE: 72

Met His Asn Leu Glu Gln Lys Thr Ala Arg Ile Asp Thr Leu Cys Arg
1               5                   10                  15

Glu Ala Arg Ile Leu Pro Val Ile Thr Ile Asp Arg Glu Ala Asp Ile
                20                  25                  30

Leu Pro Met Ala Asp Ala Leu Ala Ala Gly Gly Leu Thr Ala Leu Glu
            35                  40                  45

Ile Thr Leu Arg Thr Ala His Gly Leu Thr Ala Ile Arg Arg Leu Ser
        50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220

<210> SEQ ID NO 73
<211> LENGTH: 43
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 73
gttcactgca ctagtaaaaa aatgcactca gtcgttcaat ctg                    43

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cttcgagatc tcgagttagt aaagttcatc gatggc                            36

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gttcactgca ctagtaaaaa aatgcttgag aataactggt c                      41

<210> SEQ ID NO 76
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cttcgagatc tcgagttaaa gtccgccaat cgcctc                            36

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gttcactgca ctagtaaaaa aatgtctctg aatcccgtcg tc                     42

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cttcgagatc tcgagttagt gaatgtcgtc gccaac                            36

<210> SEQ ID NO 79
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 79
gttcactgca ctagtaaaaa aatgatcgat actgccaaac tc                           42

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttcgagatc tcgagtcaga ccgtgaagag tgccgc                                  36

<210> SEQ ID NO 81
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gttcactgca ctagtaaaaa aatgagcgat aatttttct gcg                           43

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cttcgagatc tcgagctatt tcctgttgat gatagc                                  36

<210> SEQ ID NO 83
<211> LENGTH: 1827
<212> TYPE: DNA
<213> ORGANISM: Shewanella oneidensis

<400> SEQUENCE: 83
atgcactcag tcgttcaatc tgttactgac agaattattg cccgtagcaa agcatctcgt         60
gaagcatacc ttgctgcgtt aaacgatgcc cgtaaccatg gtgtacaccg aagttcctta        120
agttgcggta acttagccca cggttttgcg gcttgtaatc ccgatgacaa aaatgcattg        180
cgtcaattga cgaaggccaa tattgggatt atcaccgcat tcaacgatat gttatctgca        240
caccaaccct atgaaaccta tcctgatttg ctgaaaaaag cctgtcagga agtcggtagt        300
gttgcgcagg tggctggcgg tgttcccgcc atgtgtgacg gcgtgactca aggtcagccc        360
ggtatggaat tgagcttact gagccgtgaa gtgattgcga tggcaaccgc ggttggctta        420
tcacacaata tgtttgatgg agccttactc tcggtatttt gcgataaaat tgtaccgggt        480
ttactgattg gtgccttaag ttttggccat ttacctatgt tgtttgtgcc cgcaggccca        540
atgaaatcgg gtattcctaa taggaaaaaa gctcgcattc gtcagcaatt tgctcaaggt        600
aaggtcgata gagcacaact gctcgaagcg gaagcccagt cttaccacag tgcgggtact        660
tgtaccttct atggtaccgc taactcgaac caactgatgc tcgaagtgat ggggctgcaa        720
ttgccgggtt catctttgt gaatccagac gatccactgc gcgaagcctt aaacaaaatg        780
```

-continued

```
gcggccaagc aggtttgtcg tttaactgaa ctaggcactc aatacagtcc gattggtgaa      840
gtcgttaacg aaaaatcgat agtgaatggt attgttgcat tgctcgcgac gggtggttca      900
acaaacttaa ccatgcacat tgtggcggcg gcccgtgctg caggtattat cgtcaactgg      960
gatgactttt cggaattatc cgatgcggtg cctttgctgg cacgtgttta tccaaacggt     1020
catgcggata ttaaccattt ccacgctgcg ggtggtatgg ctttccttat caagaattac     1080
ctcgatgcag gtttgctgca tgaggatgtc aatactgtcg cgggttatgg tctgcgccgt     1140
tacacccaag agcctaaact gcttgatggc gagctgcgct gggtcgatgg cccaacagtg     1200
agtttagata ccgaagtatt aacctctgtg caacaccat tccaaaacaa cggtggttta      1260
aagctgctga agggtaactt aggccgcgct gtgattaaag tgtctgccgt tcagccacag     1320
caccgtgtgg tggaagcgcc cgcagtggtg attgacgatc aaaacaaact cgatgcgtta     1380
tttaaatccg gcgcattaga cagggattgt gtggtggtgg tgaaaggcca agggccgaaa     1440
gccaacggta tgccagagct gcataaacta acgccgctgt taggttcatt gcaggacaaa     1500
ggctttaaag tggcactgat gactgatggt cgtatgtcgg gcgcatcggg caaagtacct     1560
gcggcgattc atttaacccc tgaagcgatt gatggcgggt taattgcaaa ggtacaagac     1620
ggcgatttaa tccgagttga tgcactgacc ggcgagctga gtttattagt ctctgacacc     1680
gagcttgcca ccagaactgc cactgaaatt gatttacgcc attctcgtta tggcatgggg     1740
cgtgagttat ttggagtact gcgttcaaac ttaagcagtc ctgaaaccgg tgcgcgtagt     1800
actagcgcca tcgatgaact ttactaa                                          1827
```

<210> SEQ ID NO 84
<211> LENGTH: 608
<212> TYPE: PRT
<213> ORGANISM: Shewanella oneidensis

<400> SEQUENCE: 84

```
Met His Ser Val Val Gln Ser Val Thr Asp Arg Ile Ile Ala Arg Ser
1               5                   10                  15

Lys Ala Ser Arg Glu Ala Tyr Leu Ala Ala Leu Asn Asp Ala Arg Asn
            20                  25                  30

His Gly Val His Arg Ser Ser Leu Ser Cys Gly Asn Leu Ala His Gly
        35                  40                  45

Phe Ala Ala Cys Asn Pro Asp Asp Lys Asn Ala Leu Arg Gln Leu Thr
    50                  55                  60

Lys Ala Asn Ile Gly Ile Ile Thr Ala Phe Asn Asp Met Leu Ser Ala
65                  70                  75                  80

His Gln Pro Tyr Glu Thr Tyr Pro Asp Leu Leu Lys Lys Ala Cys Gln
                85                  90                  95

Glu Val Gly Ser Val Ala Gln Val Ala Gly Gly Val Pro Ala Met Cys
            100                 105                 110

Asp Gly Val Thr Gln Gly Gln Pro Gly Met Glu Leu Ser Leu Leu Ser
        115                 120                 125

Arg Glu Val Ile Ala Met Ala Thr Ala Val Gly Leu Ser His Asn Met
    130                 135                 140

Phe Asp Gly Ala Leu Leu Gly Ile Cys Asp Lys Ile Val Pro Gly
145                 150                 155                 160

Leu Leu Ile Gly Ala Leu Ser Phe Gly His Leu Pro Met Leu Phe Val
                165                 170                 175

Pro Ala Gly Pro Met Lys Ser Gly Ile Pro Asn Lys Glu Lys Ala Arg
            180                 185                 190
```

-continued

```
Ile Arg Gln Gln Phe Ala Gln Gly Lys Val Asp Arg Ala Gln Leu Leu
            195                 200                 205

Glu Ala Glu Ala Gln Ser Tyr His Ser Ala Gly Thr Cys Thr Phe Tyr
    210                 215                 220

Gly Thr Ala Asn Ser Asn Gln Leu Met Leu Glu Val Met Gly Leu Gln
225                 230                 235                 240

Leu Pro Gly Ser Ser Phe Val Asn Pro Asp Pro Leu Arg Glu Ala
                245                 250                 255

Leu Asn Lys Met Ala Ala Lys Gln Val Cys Arg Leu Thr Glu Leu Gly
            260                 265                 270

Thr Gln Tyr Ser Pro Ile Gly Glu Val Val Asn Glu Lys Ser Ile Val
            275                 280                 285

Asn Gly Ile Val Ala Leu Leu Ala Thr Gly Gly Ser Thr Asn Leu Thr
            290                 295                 300

Met His Ile Val Ala Ala Ala Arg Ala Ala Gly Ile Ile Val Asn Trp
305                 310                 315                 320

Asp Asp Phe Ser Glu Leu Ser Asp Ala Val Pro Leu Leu Ala Arg Val
                325                 330                 335

Tyr Pro Asn Gly His Ala Asp Ile Asn His Phe His Ala Ala Gly Gly
            340                 345                 350

Met Ala Phe Leu Ile Lys Glu Leu Leu Asp Ala Gly Leu Leu His Glu
            355                 360                 365

Asp Val Asn Thr Val Ala Gly Tyr Gly Leu Arg Arg Tyr Thr Gln Glu
            370                 375                 380

Pro Lys Leu Leu Asp Gly Glu Leu Arg Trp Val Asp Gly Pro Thr Val
385                 390                 395                 400

Ser Leu Asp Thr Glu Val Leu Thr Ser Val Ala Thr Pro Phe Gln Asn
                405                 410                 415

Asn Gly Gly Leu Lys Leu Leu Lys Gly Asn Leu Gly Arg Ala Val Ile
            420                 425                 430

Lys Val Ser Ala Val Gln Pro Gln His Arg Val Val Glu Ala Pro Ala
            435                 440                 445

Val Val Ile Asp Asp Gln Asn Lys Leu Asp Ala Leu Phe Lys Ser Gly
            450                 455                 460

Ala Leu Asp Arg Asp Cys Val Val Val Lys Gly Gln Gly Pro Lys
465                 470                 475                 480

Ala Asn Gly Met Pro Glu Leu His Lys Leu Thr Pro Leu Leu Gly Ser
                485                 490                 495

Leu Gln Asp Lys Gly Phe Lys Val Ala Leu Met Thr Asp Gly Arg Met
            500                 505                 510

Ser Gly Ala Ser Gly Lys Val Pro Ala Ala Ile His Leu Thr Pro Glu
            515                 520                 525

Ala Ile Asp Gly Gly Leu Ile Ala Lys Val Gln Asp Gly Asp Leu Ile
            530                 535                 540

Arg Val Asp Ala Leu Thr Gly Glu Leu Ser Leu Val Ser Asp Thr
545                 550                 555                 560

Glu Leu Ala Thr Arg Thr Ala Thr Glu Ile Asp Leu Arg His Ser Arg
                565                 570                 575

Tyr Gly Met Gly Arg Glu Leu Phe Gly Val Leu Arg Ser Asn Leu Ser
            580                 585                 590

Ser Pro Glu Thr Gly Ala Arg Ser Thr Ser Ala Ile Asp Glu Leu Tyr
            595                 600                 605

<210> SEQ ID NO 85
```

<211> LENGTH: 1848
<212> TYPE: DNA
<213> ORGANISM: Gluconobacter oxydans

<400> SEQUENCE: 85

```
atgtctctga atcccgtcgt cgagagcgtg actgcccgta tcatcgagcg ttcgaaagtc      60
tcccgtcgcc ggtatctcgc cctgatggag cgcaaccgcg ccaagggtgt gctccggccc     120
aagctggcct gcggtaatct ggcgcatgcc atcgcagcgt ccagcccgga caagccggat     180
ctgatgcgtc ccaccgggac caatatcggc gtgatcacga cctataacga catgctctcg     240
gcgcatcagc cgtatggccg ctatcccgag cagatcaagc tgttcgcccg tgaagtcggt     300
gcgacggccc aggttgcagg cggcgcacca gcaatgtgtg atggtgtgac gcaggggcag     360
gagggcatgg aactctccct gttctcccgt gacgtgatcg ccatgtccac ggcggtcggg     420
ctgagccacg gcatgtttga gggcgtggcg ctgctgggca tctgtgacaa gattgtgccg     480
ggccttctga tgggcgcgct gcgcttcggt catctcccgg ccatgctgat cccggcaggg     540
ccaatgccgt ccggtcttcc aaacaaggaa agcagcgca tccgccagct ctatgtgcag      600
ggcaaggtcg gcaggacga gctgatgaa gcggaaaacg cctcctatca gcccgggc        660
acctgcacgt tctatggcac ggccaatacg aaccagatga tggtcgaaat catgggtctg     720
atgatgccgg actcggcttt catcaatccc aacacgaagc tgcgtcaggc aatgacccgc     780
tcgggtattc accgtctggc cgaaatcggc ctgaacggcg aggatgtgcg cccgctcgct     840
cattgcgtag acgaaaaggc catcgtgaat gcggcggtcg ggttgctggc gacgggtggt     900
tcgaccaacc attcgatcca tcttcctgct atcgcccgtg ccgctggtat cctgatcgac     960
tgggaagaca tcagccgcct gtcgtccgcg gttccgctga tcacccgtgt ttatccgagc    1020
ggttccgagg acgtgaacgc gttcaaccgc gtgggtggta tgccgaccgt gatcgccgaa    1080
ctgacgcgcg ccgggatgct gcacaaggac attctgacgg tctctcgtgg cggtttctcc    1140
gattatgccc gtcgcgcatc gctggaaggc gatgagatcg tctacaccca cgcgaagccg    1200
tccacggaca ccgatatcct gcgcgatgtg ctacgccttt ccggcccga tggcggtatg     1260
cgcctgatga ctggtaatct gggccgcgcg atctacaaga gcagcgctat gcgcccgag    1320
cacctgaccg ttgaagcgcc ggcacgggtc ttccaggacc agcatgacgt cctcacggcc    1380
tatcagaatg tgagcttga gcgtgatgtt gtcgtggtcg tccggttcca gggaccggaa    1440
gccaacggca tgccggagct tcacaagctg accccgactc tgggcgtgct tcaggatcgc    1500
ggcttcaagg tggcccctgct gacgatgga cgcatgtccg gtgcgagcgg caaggtgccg    1560
gccgccattc atgtcggtcc gaagcgcag gttggcggtc cgatcgcccg cgtgcgggac    1620
ggcgacatga tccgtgtctg cgcggtgacg ggacagatcg aggctctggt ggatgccgcc    1680
gagtgggaga gccgcaagcc ggtcccgccg ccgctcccgg cattgggaac gggccgcgaa    1740
ctgttcgcgc tgatgcgttc ggtgcatgat ccggccgagg ctggcggatc cgcgatgctg    1800
gcccagatgg atcgcgtgat cgaagccgtt ggcgacgaca ttcactaa                  1848
```

<210> SEQ ID NO 86
<211> LENGTH: 615
<212> TYPE: PRT
<213> ORGANISM: Gluconobacter oxydans

<400> SEQUENCE: 86

```
Met Ser Leu Asn Pro Val Val Glu Ser Val Thr Ala Arg Ile Ile Glu
 1               5                  10                  15

Arg Ser Lys Val Ser Arg Arg Arg Tyr Leu Ala Leu Met Glu Arg Asn
```

```
                    20                  25                  30
Arg Ala Lys Gly Val Leu Arg Pro Lys Leu Ala Cys Gly Asn Leu Ala
                35                  40                  45

His Ala Ile Ala Ala Ser Ser Pro Asp Lys Pro Asp Leu Met Arg Pro
        50                  55                  60

Thr Gly Thr Asn Ile Gly Val Ile Thr Thr Tyr Asn Asp Met Leu Ser
65                  70                  75                  80

Ala His Gln Pro Tyr Gly Arg Tyr Pro Glu Gln Ile Lys Leu Phe Ala
                85                  90                  95

Arg Glu Val Gly Ala Thr Ala Gln Val Ala Gly Gly Ala Pro Ala Met
            100                 105                 110

Cys Asp Gly Val Thr Gln Gly Gln Glu Gly Met Glu Leu Ser Leu Phe
            115                 120                 125

Ser Arg Asp Val Ile Ala Met Ser Thr Ala Val Gly Leu Ser His Gly
        130                 135                 140

Met Phe Glu Gly Val Ala Leu Leu Gly Ile Cys Asp Lys Ile Val Pro
145                 150                 155                 160

Gly Leu Leu Met Gly Ala Leu Arg Phe Gly His Leu Pro Ala Met Leu
                165                 170                 175

Ile Pro Ala Gly Pro Met Pro Ser Gly Leu Pro Asn Lys Glu Lys Gln
            180                 185                 190

Arg Ile Arg Gln Leu Tyr Val Gln Gly Lys Val Gly Gln Asp Glu Leu
        195                 200                 205

Met Glu Ala Glu Asn Ala Ser Tyr His Ser Pro Gly Thr Cys Thr Phe
    210                 215                 220

Tyr Gly Thr Ala Asn Thr Asn Gln Met Met Val Glu Ile Met Gly Leu
225                 230                 235                 240

Met Met Pro Asp Ser Ala Phe Ile Asn Pro Asn Thr Lys Leu Arg Gln
                245                 250                 255

Ala Met Thr Arg Ser Gly Ile His Arg Leu Ala Glu Ile Gly Leu Asn
            260                 265                 270

Gly Glu Asp Val Arg Pro Leu Ala His Cys Val Asp Glu Lys Ala Ile
        275                 280                 285

Val Asn Ala Ala Val Gly Leu Leu Ala Thr Gly Gly Ser Thr Asn His
    290                 295                 300

Ser Ile His Leu Pro Ala Ile Ala Arg Ala Ala Gly Ile Leu Ile Asp
305                 310                 315                 320

Trp Glu Asp Ile Ser Arg Leu Ser Ser Ala Val Pro Leu Ile Thr Arg
                325                 330                 335

Val Tyr Pro Ser Gly Ser Glu Asp Val Asn Ala Phe Asn Arg Val Gly
            340                 345                 350

Gly Met Pro Thr Val Ile Ala Glu Leu Thr Arg Ala Gly Met Leu His
        355                 360                 365

Lys Asp Ile Leu Thr Val Ser Arg Gly Phe Ser Asp Tyr Ala Arg
    370                 375                 380

Arg Ala Ser Leu Glu Gly Asp Glu Ile Val Tyr Thr His Ala Lys Pro
385                 390                 395                 400

Ser Thr Asp Thr Asp Ile Leu Arg Asp Val Ala Thr Pro Phe Arg Pro
                405                 410                 415

Asp Gly Gly Met Arg Leu Met Thr Gly Asn Leu Gly Arg Ala Ile Tyr
            420                 425                 430

Lys Ser Ser Ala Ile Ala Pro Glu His Leu Thr Val Glu Ala Pro Ala
        435                 440                 445
```

```
Arg Val Phe Gln Asp Gln His Asp Val Leu Thr Ala Tyr Gln Asn Gly
    450                 455                 460

Glu Leu Glu Arg Asp Val Val Val Val Arg Phe Gln Gly Pro Glu
465                 470                 475                 480

Ala Asn Gly Met Pro Glu Leu His Lys Leu Thr Pro Thr Leu Gly Val
                485                 490                 495

Leu Gln Asp Arg Gly Phe Lys Val Ala Leu Leu Thr Asp Gly Arg Met
            500                 505                 510

Ser Gly Ala Ser Gly Lys Val Pro Ala Ala Ile His Val Gly Pro Glu
        515                 520                 525

Ala Gln Val Gly Gly Pro Ile Ala Arg Val Arg Asp Gly Asp Met Ile
    530                 535                 540

Arg Val Cys Ala Val Thr Gly Gln Ile Glu Ala Leu Val Asp Ala Ala
545                 550                 555                 560

Glu Trp Glu Ser Arg Lys Pro Val Pro Pro Leu Pro Ala Leu Gly
                565                 570                 575

Thr Gly Arg Glu Leu Phe Ala Leu Met Arg Ser Val His Asp Pro Ala
            580                 585                 590

Glu Ala Gly Gly Ser Ala Met Leu Ala Gln Met Asp Arg Val Ile Glu
        595                 600                 605

Ala Val Gly Asp Asp Ile His
    610                 615

<210> SEQ ID NO 87
<211> LENGTH: 1665
<212> TYPE: DNA
<213> ORGANISM: Ruminococcus flavefaciens

<400> SEQUENCE: 87
atgagcgata atttttttctg cgagggtgcg ataaagccc ctcagcgttc acttttcaat      60
gcactgggca tgactaaaga ggaaatgaag cgtcccctcg ttggtatcgt ttcttcctac     120
aatgagatcg ttcccggcca tatgaacatc gacaagctgg tcgaagccgt taagctgggt     180
gtagctatgg gcggcggcac tcctgttgtt ttccctgcta tcgctgtatg cgacggtatc     240
gctatgggtc acacaggcat gaagtacagc cttgttaccc gtgaccttat tgccgattct     300
acagagtgta tggctcttgc tcatcacttc gacgcactgg taatgatacc taactgcgac     360
aagaacgttc ccggcctgct tatggcggct gcacgtatca atgttcctac tgtattcgta     420
agcggcggcc ctatgcttgc aggccatgta aagggtaaga gacctctctc ttcatccatg     480
ttcgaggctg taggcgctta cacagcaggc aagatagacg aggctgaact tgacgaattc     540
gagaacaaga cctgccctac ctgcggttca tgttcgggta tgtataccgc taactccatg     600
aactgcctca ctgaggtact gggtatgggt ctcagaggca acggcactat ccctgctgtt     660
tactccgagc gtatcaagct tgcaaagcag gcaggtatgc aggttatgga actctacaga     720
aagaatatcc gccctctcga tatcatgaca gagaaggctt tccagaacgc tctcacagct     780
gatatggctc ttggatgttc cacaaacagt atgctccatc tccctgctat cgccaacgaa     840
tgcggcataa atatcaacct tgacatggct aacgagataa gcgccaagac tcctaacctc     900
tgccatcttg caccggcagg ccacacctac atggaagacc tcaacgaagc aggcggagtt     960
tatgcagttc tcaacgagct gagcaaaaag ggacttatca caccgactg catgactgtt    1020 acaggcaaga cgtaggcga gaatatcaag ggctgcatca accgtgaccc tgagactatc    1080
cgtcctatcg acaaccccata cagtgaaaca ggcggaatcg ccgtactcaa gggcaatctt    1140
gctcccgaca gatgtgttgt gaagagaagc gcagttgctc ccgaaatgct ggtacacaaa    1200
```

```
ggccctgcaa gagtattcga cagcgaggaa gaagctatca aggtcatcta tgagggcggt   1260
atcaaggcag gcgacgttgt tgttatccgt tacgaaggcc ctgcaggcgg ccccggcatg   1320
agagaaatgc tctctcctac atcagctata cagggtgcag gtctcggctc aactgttgct   1380
ctaatcactg acggacgttt cagcggcgct acccgtggtg cggctatcgg acacgtatcc   1440
cccgaagctg taaacggcgg tactatcgca tatgtcaagg acggcgatat tatctccatc   1500
gacataccga attactccat cactcttgaa gtatccgacg aggagcttgc agagcgcaaa   1560
aaggcaatgc ctatcaagcg caaggagaac atcacaggct atctgaagcg ctatgcacag   1620
caggtatcat ccgcagacaa gggcgctatc atcaacagga aatag                   1665
```

<210> SEQ ID NO 88
<211> LENGTH: 554
<212> TYPE: PRT
<213> ORGANISM: Ruminococcus flavefaciens

<400> SEQUENCE: 88

```
Met Ser Asp Asn Phe Phe Cys Glu Gly Ala Asp Lys Ala Pro Gln Arg
1               5                   10                  15

Ser Leu Phe Asn Ala Leu Gly Met Thr Lys Glu Glu Met Lys Arg Pro
            20                  25                  30

Leu Val Gly Ile Val Ser Ser Tyr Asn Glu Ile Val Pro Gly His Met
        35                  40                  45

Asn Ile Asp Lys Leu Val Glu Ala Val Lys Leu Gly Val Ala Met Gly
    50                  55                  60

Gly Gly Thr Pro Val Val Phe Pro Ala Ile Ala Val Cys Asp Gly Ile
65                  70                  75                  80

Ala Met Gly His Thr Gly Met Lys Tyr Ser Leu Val Thr Arg Asp Leu
                85                  90                  95

Ile Ala Asp Ser Thr Glu Cys Met Ala Leu Ala His His Phe Asp Ala
            100                 105                 110

Leu Val Met Ile Pro Asn Cys Asp Lys Asn Val Pro Gly Leu Leu Met
        115                 120                 125

Ala Ala Ala Arg Ile Asn Val Pro Thr Val Phe Val Ser Gly Gly Pro
    130                 135                 140

Met Leu Ala Gly His Val Lys Gly Lys Lys Thr Ser Leu Ser Ser Met
145                 150                 155                 160

Phe Glu Ala Val Gly Ala Tyr Thr Ala Gly Lys Ile Asp Glu Ala Glu
                165                 170                 175

Leu Asp Glu Phe Glu Asn Lys Thr Cys Pro Thr Cys Gly Ser Cys Ser
            180                 185                 190

Gly Met Tyr Thr Ala Asn Ser Met Asn Cys Leu Thr Glu Val Leu Gly
        195                 200                 205

Met Gly Leu Arg Gly Asn Gly Thr Ile Pro Ala Val Tyr Ser Glu Arg
    210                 215                 220

Ile Lys Leu Ala Lys Gln Ala Gly Met Gln Val Met Glu Leu Tyr Arg
225                 230                 235                 240

Lys Asn Ile Arg Pro Leu Asp Ile Met Thr Glu Lys Ala Phe Gln Asn
                245                 250                 255

Ala Leu Thr Ala Asp Met Ala Leu Gly Cys Ser Thr Asn Ser Met Leu
            260                 265                 270

His Leu Pro Ala Ile Ala Asn Glu Cys Gly Ile Asn Ile Asn Leu Asp
        275                 280                 285

Met Ala Asn Glu Ile Ser Ala Lys Thr Pro Asn Leu Cys His Leu Ala
```

```
                 290                 295                 300
Pro Ala Gly His Thr Tyr Met Glu Asp Leu Asn Glu Ala Gly Val
305                 310                 315                 320

Tyr Ala Val Leu Asn Glu Leu Ser Lys Lys Gly Leu Ile Asn Thr Asp
                325                 330                 335

Cys Met Thr Val Thr Gly Lys Thr Val Gly Glu Asn Ile Lys Gly Cys
                340                 345                 350

Ile Asn Arg Asp Pro Glu Thr Ile Arg Pro Ile Asp Asn Pro Tyr Ser
                355                 360                 365

Glu Thr Gly Gly Ile Ala Val Leu Lys Gly Asn Leu Ala Pro Asp Arg
                370                 375                 380

Cys Val Val Lys Arg Ser Ala Val Ala Pro Glu Met Leu Val His Lys
385                 390                 395                 400

Gly Pro Ala Arg Val Phe Asp Ser Glu Glu Glu Ala Ile Lys Val Ile
                        405                 410                 415

Tyr Glu Gly Gly Ile Lys Ala Gly Asp Val Val Val Ile Arg Tyr Glu
                420                 425                 430

Gly Pro Ala Gly Pro Gly Met Arg Glu Met Leu Ser Pro Thr Ser
                435                 440                 445

Ala Ile Gln Gly Ala Gly Leu Gly Ser Thr Val Ala Leu Ile Thr Asp
450                 455                 460

Gly Arg Phe Ser Gly Ala Thr Arg Gly Ala Ala Ile Gly His Val Ser
465                 470                 475                 480

Pro Glu Ala Val Asn Gly Gly Thr Ile Ala Tyr Val Lys Asp Gly Asp
                    485                 490                 495

Ile Ile Ser Ile Asp Ile Pro Asn Tyr Ser Ile Thr Leu Glu Val Ser
                500                 505                 510

Asp Glu Glu Leu Ala Glu Arg Lys Lys Ala Met Pro Ile Lys Arg Lys
                515                 520                 525

Glu Asn Ile Thr Gly Tyr Leu Arg Tyr Ala Gln Gln Val Ser Ser
                530                 535                 540

Ala Asp Lys Gly Ala Ile Ile Asn Arg Lys
545                 550

<210> SEQ ID NO 89
<211> LENGTH: 642
<212> TYPE: DNA
<213> ORGANISM: Shewanella oneidensis

<400> SEQUENCE: 89
atgcttgaga ataactggtc attacaacca caagatattt ttaaacgcag ccctattgtt     60
cctgttatgg tgattaacaa gattgaacat gcggtgccct tagctaaagc gctggttgcc    120
ggagggataa gcgtgttgga agtgacatta cgcacgccat gcgcccttga agctatcacc    180
aaaatcgcca aggaagtgcc tgaggcgctg gttggcgcgg ggactatttt aaatgaagcc    240
cagcttggac aggctatcgc cgctggtgcg caatttatta tcactccagg tgcgacagtt    300
gagctgctca aagcgggcat gcaaggaccg gtgccgttaa ttccgggcgt tgccagtatt    360
tccgaggtga tgacgggcat ggcgctgggc tacactcact ttaaattctt ccctgctgaa    420
gcgtcaggtg gcgttgatgc gcttaaggct ttctctgggc cgttagcaga tatccgcttc    480
tgcccaacag gtggaattac cccgagcagc tataaagatt acttagcgct gaagaatgtc    540
gattgtattg gtggcagctg gattgctcct accgatgcga tggagcaggg cgattgggat    600
cgtatcactc agctgtgtaa agaggcgatt ggcggacttt aa                       642
```

<210> SEQ ID NO 90
<211> LENGTH: 213
<212> TYPE: PRT
<213> ORGANISM: Shewanella oneidensis

<400> SEQUENCE: 90

```
Met Leu Glu Asn Asn Trp Ser Leu Gln Pro Gln Asp Ile Phe Lys Arg
1               5                   10                  15

Ser Pro Ile Val Pro Val Met Val Ile Asn Lys Ile Glu His Ala Val
            20                  25                  30

Pro Leu Ala Lys Ala Leu Val Ala Gly Gly Ile Ser Val Leu Glu Val
        35                  40                  45

Thr Leu Arg Thr Pro Cys Ala Leu Glu Ala Ile Thr Lys Ile Ala Lys
    50                  55                  60

Glu Val Pro Glu Ala Leu Val Gly Ala Gly Thr Ile Leu Asn Glu Ala
65                  70                  75                  80

Gln Leu Gly Gln Ala Ile Ala Ala Gly Ala Gln Phe Ile Ile Thr Pro
                85                  90                  95

Gly Ala Thr Val Glu Leu Leu Lys Ala Gly Met Gln Gly Pro Val Pro
            100                 105                 110

Leu Ile Pro Gly Val Ala Ser Ile Ser Glu Val Met Thr Gly Met Ala
        115                 120                 125

Leu Gly Tyr Thr His Phe Lys Phe Phe Pro Ala Glu Ala Ser Gly Gly
    130                 135                 140

Val Asp Ala Leu Lys Ala Phe Ser Gly Pro Leu Ala Asp Ile Arg Phe
145                 150                 155                 160

Cys Pro Thr Gly Gly Ile Thr Pro Ser Ser Tyr Lys Asp Tyr Leu Ala
                165                 170                 175

Leu Lys Asn Val Asp Cys Ile Gly Gly Ser Trp Ile Ala Pro Thr Asp
            180                 185                 190

Ala Met Glu Gln Gly Asp Trp Asp Arg Ile Thr Gln Leu Cys Lys Glu
        195                 200                 205

Ala Ile Gly Gly Leu
    210
```

<210> SEQ ID NO 91
<211> LENGTH: 624
<212> TYPE: DNA
<213> ORGANISM: Gluconobacter oxydans

<400> SEQUENCE: 91

```
atgatcgata ctgccaaact cgacgccgtc atgagccgtt gtccggtcat gccggtgctg      60
gtggtcaatg atgtggctct ggcccgcccg atggccgagg ctctggtggc gggtggactg     120
tccacgctgg aagtcacgct gcgcacgccc tgcgcccttg aagctattga ggaaatgtcg     180
aaagtaccag gcgcgctggt cggtgccggt acggtgctga atccgtccga catggaccgt     240
gccgtgaagg cgggtgcgcg cttcatcgtc agccccggcc tgaccgaggc gctggcaaag     300
gcgtcggttg agcatgacgt ccccttcctg ccaggcgttg ccaatgcggg tgacatcatg     360
cggggtctgg atctgggtct gtcacgcttc aagttcttcc cggctgtgac gaatggcggc     420
attcccgcgc tcaagagctt ggccagtgtt tttggcagca atgtccgttt ctgccccacg     480
ggcggcatta cggaagagag cgcaccggac tggctggcgc ttccctccgt ggcctgcgtc     540
ggcggatcct gggtgacggc cggcacgttc gatgcggaca aggtccgtca gcgcgccacg     600
gctgcggcac tcttcacggt ctga                                           624
```

<210> SEQ ID NO 92
<211> LENGTH: 207
<212> TYPE: PRT
<213> ORGANISM: Gluconobacter oxydans

<400> SEQUENCE: 92

Met Ile Asp Thr Ala Lys Leu Asp Ala Val Met Ser Arg Cys Pro Val
1               5                   10                  15

Met Pro Val Leu Val Val Asn Asp Val Ala Leu Ala Arg Pro Met Ala
            20                  25                  30

Glu Ala Leu Val Ala Gly Gly Leu Ser Thr Leu Glu Val Thr Leu Arg
        35                  40                  45

Thr Pro Cys Ala Leu Glu Ala Ile Glu Glu Met Ser Lys Val Pro Gly
    50                  55                  60

Ala Leu Val Gly Ala Gly Thr Val Leu Asn Pro Ser Asp Met Asp Arg
65                  70                  75                  80

Ala Val Lys Ala Gly Ala Arg Phe Ile Val Ser Pro Gly Leu Thr Glu
                85                  90                  95

Ala Leu Ala Lys Ala Ser Val Glu His Asp Val Pro Phe Leu Pro Gly
            100                 105                 110

Val Ala Asn Ala Gly Asp Ile Met Arg Gly Leu Asp Leu Gly Leu Ser
        115                 120                 125

Arg Phe Lys Phe Phe Pro Ala Val Thr Asn Gly Gly Ile Pro Ala Leu
    130                 135                 140

Lys Ser Leu Ala Ser Val Phe Gly Ser Asn Val Arg Phe Cys Pro Thr
145                 150                 155                 160

Gly Gly Ile Thr Glu Glu Ser Ala Pro Asp Trp Leu Ala Leu Pro Ser
                165                 170                 175

Val Ala Cys Val Gly Gly Ser Trp Val Thr Ala Gly Thr Phe Asp Ala
            180                 185                 190

Asp Lys Val Arg Gln Arg Ala Thr Ala Ala Leu Phe Thr Val
        195                 200                 205

<210> SEQ ID NO 93
<211> LENGTH: 459
<212> TYPE: DNA
<213> ORGANISM: Piromyces sp.

<400> SEQUENCE: 93
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt cgccgaaggt gctgaccaa      180 ttcggtggag gtacaaagtc tttcccatgg aacgaaggta ctgatgctat tgaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaac                            459

<210> SEQ ID NO 94
<211> LENGTH: 456
<212> TYPE: DNA
<213> ORGANISM: Escherichia coli

<400> SEQUENCE: 94
atgcaagcct attttgacca gctcgatcgc gttcgttatg aaggctcaaa atcctcaaac      60

-continued

```
ccgttagcat tccgtcacta caatcccgac gaactggtgt tgggtaagcg tatggaagag    120
cacttgcgtt ttgccgcctg ctactggcac accttctgct ggaacggggc ggatatgttt    180
ggtgtggggg cgtttaatcg tccgtggcag cagcctggtg aggcactggc gttggcgaag    240
cgtaaagcag atgtcgcatt tgagtttttc cacaagttac atgtgccatt ttattgcttc    300
cacgatgtgg atgtttcccc tgagggcgcg tcgttaaaag agtacatcaa taattttgcg    360
caaatggttg atgtcctggc aggcaagcaa gaagagagcg gcgtgaagct gctgtgggga    420
acggccaact gctttacaaa ccctcgctac ggcgcg                              456
```

<210> SEQ ID NO 95
<211> LENGTH: 456
<212> TYPE: DNA
<213> ORGANISM: Clostridium phytofermentans

<400> SEQUENCE: 95

```
atgaaaaatt actttccaaa tgttccagaa gtaaaatacg aaggcccaaa ttcaacgaat     60
ccatttgctt ttaaatatta tgacgcaaat aaagttgtag cgggtaaaac aatgaaagag    120
cactgtcgtt ttgcattatc ttggtggcat actctttgtg caggtggtgc tgatccattc    180
ggtgtaacaa ctatggatag aacctacgga aatatcacag atccaatgga acttgctaag    240
gcaaaagttg acgctggttt cgaattaatg actaaaattag gaattgaatt cttctgtttc    300
catgacgcag atattgctcc agaaggtgat acttttgaag agtcaaagaa gaatcttttt    360
gaaatcgttg attacatcaa agagaagatg gatcagactg gtatcaagtt attatggggt    420
actgctaata actttagtca tccaagattt atgcat                              456
```

<210> SEQ ID NO 96
<211> LENGTH: 459
<212> TYPE: DNA
<213> ORGANISM: Orpinomyces sp.

<400> SEQUENCE: 96

```
atgactaagg aatatttccc aactatcggc aagattagat tcgaaggtaa ggattctaag     60
aatccaatgg ccttccacta ctatgatgct gaaaaggaag tcatgggtaa gaaaatgaag    120
gattggttac gttcgccat ggcctggtgg cacactcttt cgccgatgg tgctgaccaa    180 ttcggtgttg gtactaagtc tttcccatgg aatgaaggta ctgacccaat tgctattgcc    240
aagcaaaagg ttgatgctgg ttttgaaatc atgaccaagc ttggtattga acactactgt    300
ttccacgatg ttgatcttgt ttctgaaggt aactctattg aagaatacga atccaacctc    360
aagcaagttg ttgcttacct taagcaaaag caacaagaaa ctggtattaa gcttctctgg    420
agtactgcca atgttttcgg taacccacgt tacatgaac                           459
```

<210> SEQ ID NO 97
<211> LENGTH: 453
<212> TYPE: DNA
<213> ORGANISM: Clostridium thermohydrosulfuricum

<400> SEQUENCE: 97

```
atggaatact tcaaaaatgt accacaaata aaatatgaag gaccaaaatc aaacaatcca     60
tatgcattta aattttacaa tccagatgaa ataatagacg gaaaacccttt aaaagaacac    120 ttgcgttttt cagtagcgta ctggcacaca tttacagcca atgggacaga tccatttgga    180
gcacccacaa tgcaaaggcc atgggaccat tttactgacc ctatggatat tgccaaagcg    240
agagtagaag cagcctttga actatttgaa aaactcgacg taccattttt ctgtttccat    300
```

```
gacagagata tagctccgga aggagagaca ttaagggaga cgaacaaaaa tttagataca    360
atagttgcaa tgataaaaga ctacttaaag acgagcaaaa caaaagtatt atggggcaca    420
gcgaaccttt tttcaaatcc gagatttgta cat                                 453
```

<210> SEQ ID NO 98
<211> LENGTH: 462
<212> TYPE: DNA
<213> ORGANISM: Bacteroides thetaiotaomicron

<400> SEQUENCE: 98

```
atggcaacaa agaatttttt tccgggaatt gaaaagatta aatttgaagg taaagatagt     60
aagaacccga tggcattccg ttattacgat gcagagaagg tgattaatgg taaaaagatg    120
aaggattggc tgagattcgc tatggcatgg tggcacacat tgtgcgctga aggtggtgat    180
cagttcggtg gcggaacaaa gcaattccca tggaatggta atgcagatgc tatacaggca    240 gcaaagata agatggatgc aggatttgaa ttcatgcaga gatgggtat cgaatactat     300 tgcttccatg acgtagactt ggtttcggaa ggtgccagtg tagaagaata cgaagctaac    360
ctgaaagaaa tcgtagctta tgcaaaacag aaacaggcag aaaccggtat caaactactg    420
tggggtactg ctaatgtatt cggtcacgcc cgctatatga ac                       462
```

<210> SEQ ID NO 99
<211> LENGTH: 450
<212> TYPE: DNA
<213> ORGANISM: Bacillus stearothermophilus

<400> SEQUENCE: 99

```
atggcttatt ttccgaatat cggcaagatt gcgtatgaag ggccggagtc gcgcaatccg     60
ttggcgttta agttttataa tccagaagaa aaagtcggcg acaaaacaat ggaggagcat    120
ttgcgctttt cagtgcccta ttggcatacg tttacggggg atgggtcgga tccgtttggc    180
gtcggcaata tgattcgtcc atggaataag tacagcggca tggatctggc gaaggcgcgc    240
gtcgaggcgg cgtttgagct gtttgaaaag ctgaacgttc cgttttttctg cttccatgac    300 gtcgacatcg cgccggaagg ggaaacgctc agcgagacgt acaaaaattt ggatgaaatt    360
gtcgatatga ttgaagaata catgaaaaca agcaaaacga agctgctttg gaatacggcg    420
aacttgttca gccatccgcg cttcgttcac                                     450
```

<210> SEQ ID NO 100
<211> LENGTH: 462
<212> TYPE: DNA
<213> ORGANISM: Bacillus uniformis

<400> SEQUENCE: 100

```
atggctacca aggaatactt cccaggtatt ggtaagatca aattcgaagg taaggaatcc     60
aagaacccaa tggccttcag atactacgat gctgacaagg ttatcatggg taagaagatg    120
tctgaatggt taaagttcgc tatggcttgg tggcatacct tgtgtgctga aggtggtgac    180
caattcggtg gtggtaccaa gaaattccca tggaacggta agctgacaa ggtccaagct     240 gctaagaaca agatggacgc tggttttcgaa tttatgcaaa agatgggtat tgaatactac    300
tgtttccacg atgttgactt gtgtgaagaa gctgaaacca tcgaagaata cgaagctaac    360
ttgaaggaaa ttgttgctta cgctaagcaa aagcaagctg aaactggtat caagctatta    420
tggggtactg ctaacgtctt tggtcatgcc agatacatga ac                       462
```

<210> SEQ ID NO 101
<211> LENGTH: 456
<212> TYPE: DNA
<213> ORGANISM: Clostridium cellulolyticum

<400> SEQUENCE: 101

```
atgtcagaag tatttagcgg tatttcaaac attaaatttg aaggaagcgg gtcagataat      60
ccattagctt ttaagtacta tgaccctaag gcagttatcg gcggaaagac aatggaagaa     120
catctgagat tcgcagttgc ctactggcat acttttgcag caccaggtgc tgacatgttc     180
ggtgcaggat catatgtaag accttggaat acaatgtccg atcctctgga aattgcaaaa     240
tacaaagttg aagcaaactt tgaattcatt gaaaagctgg gagcaccttt cttcgctttc     300
catgacaggg atattgctcc tgaaggcgac acactcgctg aaacaaataa aaaccttgat     360
acaatagttt cagtaattaa agatagaatg aaatccagtc cggtaaagtt attatgggga     420
actacaaatg ctttcggaaa cccaagattt atgcat                               456
```

<210> SEQ ID NO 102
<211> LENGTH: 450
<212> TYPE: DNA
<213> ORGANISM: Ruminococcus flavefaciens

<400> SEQUENCE: 102

```
atggaatttt tcaagaacat aagcaagatc ccttacgagg gcaaggacag cacaaatcct      60
ctcgcattca agtactacaa tcctgatgag gtaattgacg gcaagaagat gcgtgacatt     120
atgaagtttg ctctctcatg gtggcataca atgggcggcg acggaacaga tatgttcggc     180
tgcggtacag ctgacaagac atggggcgaa aatgatcctg ctgcaagagc taaggctaag     240
gttgacgcag ctttcgagat catgcagaag ctctctatcg attacttctg tttccacgac     300
cgtgatcttt ctcctgagta cggctcactg aaggacacaa acgctcagct ggacatcgtt     360
acagattaca tcaaggctaa gcaggctgag acaggtctca gtgcctctg gggtacagct     420 aagtgcttcg atcacccaag attcatgcac                                     450
```

<210> SEQ ID NO 103
<211> LENGTH: 456
<212> TYPE: DNA
<213> ORGANISM: Ruminococcus flavefaciens

<400> SEQUENCE: 103

```
atgagcgaat tttttacagg catttcaaag atcccctttg agggaaaggc atccaacaat      60
cccatggcgt tcaagtacta caacccggat gaggtcgtag gcggcaagac catgcgggag     120
cagctgaagt ttgcgctgtc ctggtggcat actatggggg gagacggtac ggacatgttt     180
ggtgtgggta ccaccaacaa gaagttcggc ggaaccgatc ccatggacat tgctaagaga     240
aaggtaaacg ctgcgtttga gctgatggac aagctgtcca tcgattattt ctgtttccac     300
gaccgggatc tggcgccgga ggctgataat ctgaaggaaa ccaaccagcg tctggatgaa     360
atcaccgagt atattgcaca gatgatgcag ctgaacccgg acaagaaggt tctgtggggt     420
actgcaaatt gcttcggcaa tccccggtat atgcat                               456
```

<210> SEQ ID NO 104
<211> LENGTH: 453
<212> TYPE: DNA
<213> ORGANISM: Clostriales sp.

<400> SEQUENCE: 104

```
atgaaatttt ttgaaaatgt ccctaaggta aaatatgagg gaagcaagtc taccaacccg      60
```

| | |
|---|---|
| tttgcattta agtattacaa tcctgaagcg gtgattgccg gtaaaaaaat gaaggatcac | 120 |
| ctgaaattcg cgatgtcctg gtggcacacc atgacgcga ccgggcaaga ccagttcggt | 180 |
| tcggggacga tgagccgaat atatgacggg caaactgaac cgctggcctt ggccaaagcc | 240 |
| cgagtggatg cggctttcga tttcatggaa aaattaaata tcgaatattt ttgttttcat | 300 |
| gatgccgact tggctccaga aggtaacagt ttgcaggaac gcaacgaaaa tttgcaggaa | 360 |
| atggtgtctt acctgaaaca aaagatggcc ggaacttcga ttaagctttt atggggaacc | 420 |
| tcgaattgtt tcagcaaccc tcgttttatg cac | 453 |

<210> SEQ ID NO 105
<211> LENGTH: 463
<212> TYPE: DNA
<213> ORGANISM: Bacillus stercoris

<400> SEQUENCE: 105

| | |
|---|---|
| atggcaacaa aagagtattt tcccggaata ggaaaaatca aattcgaagg caaagaaagt | 60 |
| aagaatccta tggcattccg ctactacgat gcggaaaaag taatcatggg caagaagatg | 120 |
| aaagattggt tgaagttctc tatggcatgg tggcatacac tctgtgcaga gggtggtgac | 180 |
| cagttcggcg gcggaacgaa acatttcccc tggaacggtg atgccgataa actgcaggct | 240 |
| gccaagaaca aaatggatgc tggtttcgag ttcatgcaga aaatgggcat cgaatattac | 300 |
| tgcttccacg atgttgacct tgcgacgag gccgatacaa tcgaagagta cgaagcaaac | 360 |
| ctgaaagcca tcgttgcata cgccaagcaa agcaggagg aaacaggtat caaactgttg | 420 |
| tggggtactg ccaacgtatt cggtcatgca cgttacatga acg | 463 |

<210> SEQ ID NO 106
<211> LENGTH: 300
<212> TYPE: DNA
<213> ORGANISM: Thermus thermophilus

<400> SEQUENCE: 106

| | |
|---|---|
| atgtacgagc ccaaaccgga gcacaggttt acctttggcc tttggactgt gggcaatgtg | 60 |
| ggccgtgatc ccttcgggga cgcggttcgg gagaggctgg acccggttta cgtggttcat | 120 |
| aagctggcgg agcttggggc ctacggggta aaccttcacg acgaggacct gatcccgcgg | 180 |
| ggcacgcctc ctcaggagcg ggaccagatc gtgaggcgct tcaagaaggc tctcgatgaa | 240 |
| accggcctca ggtccccat ggtcaccgcc aacctcttct ccgaccctgc tttcaaggac | 300 |

<210> SEQ ID NO 107
<211> LENGTH: 1320
<212> TYPE: DNA
<213> ORGANISM: Ruminococcus flavefaciens

<400> SEQUENCE: 107

| | |
|---|---|
| atggaatttt tcaagaacat aagcaagatc ccttacgagg gcaaggacag cacaaatcct | 60 |
| ctcgcattca gtactacaa tcctgatgag gtaattgacg gcaagaagat gcgtgacatt | 120 |
| atgaagtttg ctctctcatg gtggcataca atgggcggcg acggaacaga tatgttcggc | 180 |
| tgcggtacag ctgacaagac atggggcgaa aatgatcctg ctgcaagagc taaggctaag | 240 |
| gttgacgcag ctttcgagat catgcagaag ctctctatcg attacttctg tttccacgac | 300 |
| cgtgatcttt ctcctgagta cggctcactg aaggacacaa acgctcagct ggacatcgtt | 360 |
| acagattaca tcaaggctaa gcaggctgag acaggtctca gtgcctctg gggtacagct | 420 |
| aagtgcttcg atcacccaag attcatgcac ggtgcaggta cttcaccatc cgcagacgta | 480 |

```
ttcgctttct cagctgcaca gatcaagaag gctctcgagt ctactgtaaa gctcggcggt    540
acaggctacg tattctgggg cggacgtgag ggttatgaga ctctcctcaa cacaaacatg    600
ggccttgagc ttgacaacat ggctcgtctc atgaagatgg ctgttgagta cggacgttct    660
atcggcttca agggcgattt ctacatcgag cctaagccaa aggagccaac aaagcaccag    720
tacgatttcg atactgctac tgttctcggc ttcctcagaa agtacggtct cgacaaggat    780
ttcaagatga acatcgaagc taaccacgct acactggctc agcacacatt ccagcacgag    840
ctctgcgtag caagaacaaa cggtgctttc ggttcaatcg acgcaaacca gggcgatcct    900
ctcctcggat gggatacaga ccagttcccg acaaatatct atgacacaac aatgtgtatg    960
tacgaagtta tcaaggctgg cggcttcaca acggcggtc tcaacttcga tgcaaaggca   1020
agacgtggaa gcttcacacc tgaggatatc ttctacagct acattgcagg tatggatgca   1080
ttcgctctcg gctacaaggc tgcaagcaag ctcatcgctg acggacgtat cgacagcttc   1140
atttccgacc gctacgcttc atggagcgag ggaatcggtc tcgacatcat ctcaggcaag   1200
gctgatatgg ctgctcttga gaagtatgct ctcgaaaagg gcgaggttac agactctatt   1260
tccagcggca gacaggaact cctcgagtct atcgtaaaca cgttatatt caatctttga   1320
```

<210> SEQ ID NO 108
<211> LENGTH: 1326
<212> TYPE: DNA
<213> ORGANISM: Ruminococcus flavefaciens

<400> SEQUENCE: 108

```
atgagcgaat tttttacagg catttcaaag atcccctttg agggaaaggc atccaacaat    60
cccatggcgt tcaagtacta caacccggat gaggtcgtag gcggcaagac catgcgggag   120
cagctgaagt ttgcgctgtc ctggtggcat actatggggg agacggtac ggacatgttt   180 ggtgtgggta ccaccaacaa gaagttcggc ggaaccgatc ccatggacat tgctaagaga   240
aaggtaaacg ctgcgtttga gctgatggac aagctgtcca tcgattattt ctgtttccac   300
gaccgggatc tggcgccgga ggctgataat ctgaaggaaa ccaaccagcg tctggatgaa   360
atcaccgagt atattgcaca gatgatgcag ctgaacccgg acaagaaggt tctgtggggt   420
actgcaaatt gcttcggcaa tccccggtat atgcatggtg ccggcactgc gcccaatgcg   480
gacgtgtttg catttgcagc tgcgcagatc aaaaaggcaa ttgagatcac cgtaaagctg   540
ggtggcaagg gctatgtatt ctggggcggc agagagggct acgaaacgct gctgaacacc   600
aatatgggtc tggaactgga taatatggca cggctgctgc atatggcagt ggactatgca   660
agaagcatcg gctttaccgg cgacttctac atcgagccca gcccaaggga gcctaccaag   720
catcagtatg attttgatac cgcaaccgtg atcggcttcc tgcgcaagta taatctggac   780
aaggacttca agatgaacat cgaagccaac cacgcaaccc ttgcacagca caccttccag   840
catgaactgc gggtagcacg ggagaacggc ttctttggct ccatcgatgc taaccagggt   900
gacaccctgc tgggctggga tacggatcag ttccccacta ataccatgac cgcagcactg   960
tgtatgtacg aggtactcaa ggctggcggt tttaccaatg gcggtctgaa ctttgactcc  1020
aaggcacggc gtggatcctt tgagatggag gatatcttcc acagctacat tgccggtatg  1080 gacaccttg cactgggtct gaagattcgc agaagatga tcgatgacgg acggatcgac  1140
cagttcgtgg ctgatcggta tgcaagctgg aacaccggca tcggtgcgga tatcattcc  1200 ggcaaggcaa ccatgcgaga tttggaggct acgcactga gcaagggcga tgtgaccgca  1260
tccctcaaga gcggtcgtca ggaattgctg gaaagcatcc tgaacaatat tatgttcaat  1320
``` ctttaa                                                          1326

<210> SEQ ID NO 109
<211> LENGTH: 1323
<212> TYPE: DNA
<213> ORGANISM: Clostridiales sp.

<400> SEQUENCE: 109

```
atgaaatttt ttgaaaatgt ccctaaggta aaatatgagg gaagcaagtc taccaacccg    60
tttgcattta agtattacaa tcctgaagcg gtgattgccg gtaaaaaaat gaaggatcac   120
ctgaaattcg cgatgtcctg gtggcacacc atgacggcga ccgggcaaga ccagttcggt   180
tcggggacga tgagccgaat atatgacggg caaactgaac cgctggcctt ggccaaagcc   240
cgagtggatg cggctttcga tttcatggaa aaattaaata tcgaatattt ttgttttcat   300
gatgccgact ggctccaga aggtaacagt ttgcaggaac gcaacgaaaa tttgcaggaa   360
atggtgtctt acctgaaaca aaagatggcc ggaacttcga ttaagctttt atggggaacc   420
tcgaattgtt tcagcaaccc tcgttttatg cacggggcag ccacatcttg cgaagcggat   480
gtgtttgctt ggaccgccac tcagttgaaa aatgccatcg atgctaccat cgcgcttggc   540
ggtaaaggct atgttttctg gggcggccgg gaaggctatg aaaccttgct gaacactgat   600
gtcggcctgg agatggataa ttatgcaaga atgctgaaaa tggcggttgc atatgcgcat   660
tctaaaggtt atacgggtga cttttatatt gaacctaagc caaagaaacc cactaaacat   720
caatatgatt tcgatgtcgc cacttgcgtt gctttccttg aaaaatacga tttgatgcgt   780
gattttaaag taaacattga ggctaatcac gctactttgg ccggtcatac tttccaacat   840
gagttacgca tggcgcgtac cttcgggta ttcggctcgg ttgatgccaa tcagggcgac   900
agcaatctgg gctgggatac cgatcagttc ccgggcaata tttatgatac gactttggcc   960
atgtatgaga ttttgaaggc cggtggattt accaacggag gcttgaactt tgatgctaaa  1020
gtgcgtcgtc cgtcatttac cccggaagat attgcttatg cttatatttt gggcatggat  1080
acgtttgcct taggcttgat taaggcgcaa cagctgattg aggatggcag aattgatcgt  1140
ttcgtagcgg aaaaatatgc tagttataag tcgggcatcg gtgctgaaat cttgagtggt  1200
aaaaccggtt tgccggaatt ggaggcttac gcattgaaga aaggcgagcc taagttgtat  1260
agtgggcggc aggaatatct tgaaagtgtc gttaataacg taattttcaa cggaaatctt  1320
tga                                                              1323
```

<210> SEQ ID NO 110
<211> LENGTH: 439
<212> TYPE: PRT
<213> ORGANISM: Ruminococcus flavefaciens

<400> SEQUENCE: 110

```
Met Glu Phe Phe Lys Asn Ile Ser Lys Ile Pro Tyr Glu Gly Lys Asp
1               5                   10                  15

Ser Thr Asn Pro Leu Ala Phe Lys Tyr Tyr Asn Pro Asp Glu Val Ile
            20                  25                  30

Asp Gly Lys Lys Met Arg Asp Ile Met Lys Phe Ala Leu Ser Trp Trp
        35                  40                  45

His Thr Met Gly Gly Asp Gly Thr Asp Met Phe Gly Cys Gly Thr Ala
    50                  55                  60

Asp Lys Thr Trp Gly Glu Asn Asp Pro Ala Ala Arg Ala Lys Ala Lys
65                  70                  75                  80
```

```
Val Asp Ala Ala Phe Glu Ile Met Gln Lys Leu Ser Ile Asp Tyr Phe
            85                  90                  95

Cys Phe His Asp Arg Asp Leu Ser Pro Glu Tyr Gly Ser Leu Lys Asp
            100                 105                 110

Thr Asn Ala Gln Leu Asp Ile Val Thr Asp Tyr Ile Lys Ala Lys Gln
            115                 120                 125

Ala Glu Thr Gly Leu Lys Cys Leu Trp Gly Thr Ala Lys Cys Phe Asp
            130                 135                 140

His Pro Arg Phe Met His Gly Ala Gly Thr Ser Pro Ser Ala Asp Val
145                 150                 155                 160

Phe Ala Phe Ser Ala Ala Gln Ile Lys Lys Ala Leu Glu Ser Thr Val
            165                 170                 175

Lys Leu Gly Gly Thr Gly Tyr Val Phe Trp Gly Gly Arg Glu Gly Tyr
            180                 185                 190

Glu Thr Leu Leu Asn Thr Asn Met Gly Leu Glu Leu Asp Asn Met Ala
            195                 200                 205

Arg Leu Met Lys Met Ala Val Glu Tyr Gly Arg Ser Ile Gly Phe Lys
            210                 215                 220

Gly Asp Phe Tyr Ile Glu Pro Lys Pro Lys Glu Pro Thr Lys His Gln
225                 230                 235                 240

Tyr Asp Phe Asp Thr Ala Thr Val Leu Gly Phe Leu Arg Lys Tyr Gly
            245                 250                 255

Leu Asp Lys Asp Phe Lys Met Asn Ile Glu Ala Asn His Ala Thr Leu
            260                 265                 270

Ala Gln His Thr Phe Gln His Glu Leu Cys Val Ala Arg Thr Asn Gly
            275                 280                 285

Ala Phe Gly Ser Ile Asp Ala Asn Gln Gly Asp Pro Leu Leu Gly Trp
            290                 295                 300

Asp Thr Asp Gln Phe Pro Thr Asn Ile Tyr Asp Thr Thr Met Cys Met
305                 310                 315                 320

Tyr Glu Val Ile Lys Ala Gly Gly Phe Thr Asn Gly Gly Leu Asn Phe
            325                 330                 335

Asp Ala Lys Ala Arg Arg Gly Ser Phe Thr Pro Glu Asp Ile Phe Tyr
            340                 345                 350

Ser Tyr Ile Ala Gly Met Asp Ala Phe Ala Leu Gly Tyr Lys Ala Ala
            355                 360                 365

Ser Lys Leu Ile Ala Asp Gly Arg Ile Asp Ser Phe Ile Ser Asp Arg
            370                 375                 380

Tyr Ala Ser Trp Ser Glu Gly Ile Gly Leu Asp Ile Ile Ser Gly Lys
385                 390                 395                 400

Ala Asp Met Ala Ala Leu Glu Lys Tyr Ala Leu Glu Lys Gly Glu Val
            405                 410                 415

Thr Asp Ser Ile Ser Ser Gly Arg Gln Glu Leu Leu Glu Ser Ile Val
            420                 425                 430

Asn Asn Val Ile Phe Asn Leu
            435

<210> SEQ ID NO 111
<211> LENGTH: 440
<212> TYPE: PRT
<213> ORGANISM: Ruminococcus flavefaciens

<400> SEQUENCE: 111

Met Ser Glu Phe Phe Thr Gly Ile Ser Lys Ile Pro Phe Glu Gly Lys
1               5                   10                  15
```

```
Ala Ser Asn Asn Pro Met Ala Phe Lys Tyr Tyr Asn Pro Asp Glu Val
            20                  25                  30

Val Gly Gly Lys Thr Met Arg Glu Gln Leu Lys Phe Ala Leu Ser Trp
         35                  40                  45

Trp His Thr Met Gly Gly Asp Gly Thr Asp Met Phe Gly Val Gly Thr
 50                  55                  60

Thr Asn Lys Lys Phe Gly Gly Thr Asp Pro Met Asp Ile Ala Lys Arg
 65                  70                  75                  80

Lys Val Asn Ala Ala Phe Glu Leu Met Asp Lys Leu Ser Ile Asp Tyr
                 85                  90                  95

Phe Cys Phe His Asp Arg Asp Leu Ala Pro Glu Ala Asp Asn Leu Lys
            100                 105                 110

Glu Thr Asn Gln Arg Leu Asp Glu Ile Thr Glu Tyr Ile Ala Gln Met
        115                 120                 125

Met Gln Leu Asn Pro Asp Lys Lys Val Leu Trp Gly Thr Ala Asn Cys
130                 135                 140

Phe Gly Asn Pro Arg Tyr Met His Gly Ala Gly Thr Ala Pro Asn Ala
145                 150                 155                 160

Asp Val Phe Ala Phe Ala Ala Gln Ile Lys Lys Ala Ile Glu Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Leu His Met Ala Val Asp Tyr Ala Arg Ser Ile Gly
210                 215                 220

Phe Thr Gly Asp Phe Tyr Ile Glu Pro Lys Pro Lys Glu Pro Thr Lys
225                 230                 235                 240

His Gln Tyr Asp Phe Asp Thr Ala Thr Val Ile Gly Phe Leu Arg Lys
                245                 250                 255

Tyr Asn Leu Asp Lys Asp Phe Lys Met Asn Ile Glu Ala Asn His Ala
            260                 265                 270

Thr Leu Ala Gln His Thr Phe Gln His Glu Leu Arg Val Ala Arg Glu
        275                 280                 285

Asn Gly Phe Phe Gly Ser Ile Asp Ala Asn Gln Gly Asp Thr Leu Leu
290                 295                 300

Gly Trp Asp Thr Asp Gln Phe Pro Thr Asn Thr Tyr Asp Ala Ala Leu
305                 310                 315                 320

Cys Met Tyr Glu Val Leu Lys Ala Gly Gly Phe Thr Asn Gly Gly Leu
                325                 330                 335

Asn Phe Asp Ser Lys Ala Arg Arg Gly Ser Phe Glu Met Glu Asp Ile
            340                 345                 350

Phe His Ser Tyr Ile Ala Gly Met Asp Thr Phe Ala Leu Gly Leu Lys
        355                 360                 365

Ile Ala Gln Lys Met Ile Asp Asp Gly Arg Ile Asp Gln Phe Val Ala
370                 375                 380

Asp Arg Tyr Ala Ser Trp Asn Thr Gly Ile Gly Ala Asp Ile Ile Ser
385                 390                 395                 400

Gly Lys Ala Thr Met Ala Asp Leu Glu Ala Tyr Ala Leu Ser Lys Gly
                405                 410                 415

Asp Val Thr Ala Ser Leu Lys Ser Gly Arg Gln Glu Leu Leu Glu Ser
            420                 425                 430

Ile Leu Asn Asn Ile Met Phe Asn
        435                 440
```

```
<210> SEQ ID NO 112
<211> LENGTH: 440
<212> TYPE: PRT
<213> ORGANISM: Clostridiales sp.

<400> SEQUENCE: 112

Met Lys Phe Phe Glu Asn Val Pro Lys Val Lys Tyr Glu Gly Ser Lys
1               5                   10                  15

Ser Thr Asn Pro Phe Ala Phe Lys Tyr Tyr Asn Pro Glu Ala Val Ile
            20                  25                  30

Ala Gly Lys Lys Met Lys Asp His Leu Lys Phe Ala Met Ser Trp Trp
        35                  40                  45

His Thr Met Thr Ala Thr Gly Gln Asp Gln Phe Gly Ser Gly Thr Met
50                  55                  60

Ser Arg Ile Tyr Asp Gly Gln Thr Glu Pro Leu Ala Leu Ala Lys Ala
65                  70                  75                  80

Arg Val Asp Ala Ala Phe Asp Phe Met Glu Lys Leu Asn Ile Glu Tyr
                85                  90                  95

Phe Cys Phe His Asp Ala Asp Leu Ala Pro Glu Gly Asn Ser Leu Gln
            100                 105                 110

Glu Arg Asn Glu Asn Leu Gln Glu Met Val Ser Tyr Leu Lys Gln Lys
        115                 120                 125

Met Ala Gly Thr Ser Ile Lys Leu Leu Trp Gly Thr Ser Asn Cys Phe
130                 135                 140

Ser Asn Pro Arg Phe Met His Gly Ala Ala Thr Ser Cys Glu Ala Asp
145                 150                 155                 160

Val Phe Ala Trp Thr Ala Thr Gln Leu Lys Asn Ala Ile Asp Ala Thr
                165                 170                 175

Ile Ala Leu Gly Gly Lys Gly Tyr Val Phe Trp Gly Gly Arg Glu Gly
            180                 185                 190

Tyr Glu Thr Leu Leu Asn Thr Asp Val Gly Leu Glu Met Asp Asn Tyr
        195                 200                 205

Ala Arg Met Leu Lys Met Ala Val Ala Tyr Ala His Ser Lys Gly Tyr
210                 215                 220

Thr Gly Asp Phe Tyr Ile Glu Pro Lys Pro Lys Glu Pro Thr Lys His
225                 230                 235                 240

Gln Tyr Asp Phe Asp Val Ala Thr Cys Val Ala Phe Leu Glu Lys Tyr
                245                 250                 255

Asp Leu Met Arg Asp Phe Lys Val Asn Ile Glu Ala Asn His Ala Thr
            260                 265                 270

Leu Ala Gly His Thr Phe Gln His Glu Leu Arg Met Ala Arg Thr Phe
        275                 280                 285

Gly Val Phe Gly Ser Val Asp Ala Asn Gln Gly Asp Ser Asn Leu Gly
290                 295                 300

Trp Asp Thr Asp Gln Phe Pro Gly Asn Ile Tyr Asp Thr Thr Leu Ala
305                 310                 315                 320

Met Tyr Glu Ile Leu Lys Ala Gly Gly Phe Thr Asn Gly Gly Leu Asn
                325                 330                 335

Phe Asp Ala Lys Val Arg Arg Pro Ser Phe Thr Pro Glu Asp Ile Ala
            340                 345                 350

Tyr Ala Tyr Ile Leu Gly Met Asp Thr Phe Ala Leu Gly Leu Ile Lys
        355                 360                 365

Ala Gln Gln Leu Ile Glu Asp Gly Arg Ile Asp Arg Phe Val Ala Glu
370                 375                 380
```

```
Lys Tyr Ala Ser Tyr Lys Ser Gly Ile Gly Ala Glu Ile Leu Ser Gly
385                 390                 395                 400

Lys Thr Gly Leu Pro Glu Leu Glu Ala Tyr Ala Leu Lys Lys Gly Glu
            405                 410                 415

Pro Lys Leu Tyr Ser Gly Arg Gln Glu Tyr Leu Glu Ser Val Val Asn
            420                 425                 430

Asn Val Ile Phe Asn Gly Asn Leu
        435                 440

<210> SEQ ID NO 113
<211> LENGTH: 1665
<212> TYPE: DNA
<213> ORGANISM: Debaryomyces hansenii

<400> SEQUENCE: 113
atgtctcaag aagaatatag ttctggggta caaaccccag tttctaacca ttctggttta      60
gagaaagaag agcaacacaa gttagacggt ttagatgagg atgaaattgt cgatcaatta     120
ccttctttac cagaaaaatc agctaaggat tatttattaa tttctttctt ctgtgtatta     180
gttgcatttg gtggttttgt tttcggtttc gatactggta ctatctcagg tttcgttaac     240
atgagtgatt acttggaaag attcggtgag cttaatgcag atggtgaata tttcttatct     300
aatgttagaa ctggtttgat tgttgctatt tttaatgttg ttgtgctgtc ggtggtatt      360
ttcttatcta agattgctga tgtttatggt agaagaattg gtcttatgtt ttccatgatt     420
atttatgtga ttggtataat tgttcaaatc tcagcttctg acaagtggta tcaaatcgtt     480
gttggtagag ctattgcagg tttagctgtt ggtaccgttt ctgtcttatc cccattattc     540
attggtgaat cagcacctaa aaccttaaga ggtactttag tgtgttgttt ccaattatgt     600
attaccttag gtatcttctt aggttactgt actacatatg gtactaaaac ctacaccgac     660
tctagacaat ggagaattcc attaggttta tgttttgttt gggctatcat gttggttatt     720
ggtatggttt gcatgccaga atcaccaaga tacttagttg tcaagaacaa gattgaagaa     780
gctaagaaat cgattggtag atccaacaag gtttcaccag aagatcctgc tgtttacacc     840
gaagtccaat tgattcaagc aggtattgaa agagaaagtt tagctggttc tgcctcttgg     900
accgaattgg ttactggtaa gccaagaatc tttcgtagag tcattatggg tattatgtta     960
caatctttac aacaattgac tggtgacaac tatttcttct actatggtac tactattttc    1020
caagctgtcg gtatgactga ttccttccaa acatctattg tttttaggtgt tgttaacttt    1080
gcatctacat ttctcggtat ctacacaatt gaaagattcg gtagaagatt atgtttgtta    1140
actggttctg tctgtatgtt cgtttgtttc atcattact ccattttggg tgttacaaac    1200
ttatatattg atggctacga tggtccaact tcggttccaa ccggtgatgc gatgattttc    1260
attactacct tatacatttt cttcttcgca tccacctggg ctggtggtgt ctactgtatc    1320
gtttccgaaa cataccccatt gagaattaga tctaaggcca tgtccgttgc caccgctgct    1380
aactggattt ggggtttctt gatctctttc ttcactccat tcatcacctc ggctatccac    1440
ttctactacg gtttcgtttt cacaggatgt tgttattct cgttcttta cgtttacttc    1500
tttgttgttg aaactaaggg attaacttta gaagaagttg atgaattgta tgcccaaggt    1560
gttgccccat ggaagtcatc gaatgggtt ccaccaacca aggaagaaat ggcccattct    1620
tcaggatatg ctgctgaagc caaacctcac gatcaacaag tataa                    1665

<210> SEQ ID NO 114
<211> LENGTH: 1725
```

<212> TYPE: DNA
<213> ORGANISM: Saccharomyces cerevisiae

<400> SEQUENCE: 114

```
atggcagttg aggagaacaa tatgcctgtt gtttcacagc aaccccaagc tggtgaagac      60
gtgatctctt cactcagtaa agattcccat ttaagcgcac aatctcaaaa gtattctaat     120
gatgaattga agccggtga gtcagggtct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg ggtttgttgt ccaaacagac     300
ttttttgagaa ggtttggtat gaaacataag gatggtaccc actatttgtc aaacgtcaga     360
acaggtttaa tcgtcgccat tttcaatatt ggctgtgcct ttggtggtat tatactttcc     420
aaaggtggag atatgtatgg ccgtaaaaag ggtctttcga ttgtcgtctc ggtttatata     480
gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatcttttt gggctactg tactaattac ggtacaaaga gctattcgaa ctcagttcaa     720
tggagagttc cattagggct atgtttcgct tggtcattat ttatgattgg cgctttgacg     780
ttagttcctg aatccccacg ttatttatgt gaggtagata aggtagaaga cgccaagcgt     840
tccattgcta agtctaacaa ggtgtcacca gaggatcctg ccgtccaggc agagttagat     900
ctgatcatgg ccgtatagaa agctgaaaaa ctggctggca atgcgtcctg ggggaatta     960
ttttccacca agaccaaagt atttcaacgt tgttgatgg gtgtgtttgt tcaaatgttc    1020
caacaattaa ccgtaacaa ttattttttc tactacggta ccgttatttt caagtcagtt    1080
ggcctggatg attcctttga acatccatt gtcattggtg tagtcaactt tgcctccact    1140
ttctttagtt tgtggactgt cgaaaacttg ggacatcgta aatgtttact tttgggcgct    1200
gccactatga tggcttgtat ggtcatctac gcctctgttg gtgttactag attatatcct    1260
cacggtaaaa gccagccatc ttctaaaggt gccggtaact gtatgattgt cttaccctgt    1320
tttatatttt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                    1725
```

<210> SEQ ID NO 115
<211> LENGTH: 750
<212> TYPE: DNA
<213> ORGANISM: Saccharomyces cerevisiae

<400> SEQUENCE: 115

```
atggtgacag tcggtgtgtt ttctgagagg gctagtttga cccatcaatt gggggaattc      60
atcgtcaaga aacaagatga ggcgctgcaa aagaagtcag actttaaagt ttccgttagc     120
ggtggctctt tgatcgatgc tctgtatgaa agtttagtag cggacgaatc actatcttct     180
cgagtgcaat ggtctaaatg gcaaatctac ttctctgatg aaagaattgt gccactgacg     240
gacgctgaca gcaattatgg tgccttcaag agagctgttc tagataaatt accctcgact     300
```

```
agtcagccaa acgtttatcc catggacgag tccttgattg gcagcgatgc tgaatctaac    360
aacaaaattg ctgcagagta cgagcgtatc gtacctcaag tgcttgattt ggtactgttg    420
ggctgtggtc ctgatggaca cacttgttcc ttattccctg agaaacacat aggtacttg     480 ctgaacgaaa caaccaaaag agttgcttgg tgccacgatt ctcccaagcc tccaagtgac    540
agaatcacct tcactctgcc tgtgttgaaa gacgccaaag ccctgtgttt tgtggctgag    600
ggcagttcca acaaaatat aatgcatgag atctttgact gaaaaacga tcaattgcca     660 accgcattgg ttaacaaatt atttggtgaa aaaacatcct ggttcgttaa tgaggaagct    720
tttggaaaag ttcaaacgaa aacttttag                                     750
```

<210> SEQ ID NO 116
<211> LENGTH: 1518
<212> TYPE: DNA
<213> ORGANISM: Saccharomyces cerevisiae

<400> SEQUENCE: 116

```
atgagtgaag cccccgtcaa attcgaaaaa aataccgtca tatctgtctt tggtgcgtca    60
ggtgatctgg caagaagaa gacttttccc gccttatttg gcttttcag agaaggttac     120 cttgatccat ctaccaagat cttcggttat gcccggtcca aattgtccat ggaggaggac    180
ctgaagtccc gtgtcctacc ccacttgaaa aaacctcacg tgaagccga tgactctaag    240 gtcgaacagt tcttcaagat ggtcagctac atttcgggaa attacgacac agatgaaggc    300
ttcgacgaat taagaacgca gatcgagaaa ttcgagaaaa gtgccaacgt cgatgtccca    360
caccgtctct tctatctggc cttgccgcca agcgtttttt tgacggtggc caagcagatc    420
aagagtcgtg tgtacgcaga gaatggcatc acccgtgtaa tcgtagagaa acctttcggc    480
cacgacctgg cctctgccag ggagctgcaa aaaaacctgg ggcccctctt taagaagaa    540 gagttgtaca gaattgacca ttacttgggt aaagagttgg tcaagaatct tttagtcttg    600
aggttcggta ccagtttttt gaatgcctcg tggaatagag acaacattca aagcgttcag    660
atttcgttta agagaggtt cggcaccgaa ggccgtggcg ctatttcga ctctataggc    720 ataatcagag acgtgatgca gaaccatctg ttacaaatca tgactctctt gactatggaa    780
agaccggtgt cttttgaccc ggaatctatt cgtgacgaaa aggttaaggt tctaaaggcc    840
gtggccccca tcgacacgga cgacgtcctc ttgggccagt acggtaaatc tgaggacggg    900
tctaagcccg cctacgtgga tgatgacact gtagacaagg actctaaatg tgtcactttt    960
gcagcaatga ctttcaacat cgaaaacgag cgttgggagg gcgtccccat catgatgcgt    1020
gccggtaagg ctttgaatga gtccaaggtg gagatcagac tgcagtacaa agcggtcgca    1080
tcgggtgtct tcaaagacat tccaaataac gaactggtca tcagagtgca gcccgatgcc    1140
gctgtgtacc taaagtttaa tgctaagacc cctggtctgt caaatgctac ccaagtcaca    1200
gatctgaatc taacttacgc aagcaggtac caagactttt ggattccaga ggcttacgag    1260
gtgttgataa gagacgccct actgggtgac cattccaact ttgtcagaga tgacgaattg    1320
gatatcagtt gggcatatt cacccccatta ctgaagcaca tagagcgtcc ggacggtcca    1380
acaccggaaa tttaccccta cggatcaaga ggtccaaagg gattgaagga atatatgcaa    1440
aaacacaagt atgttatgcc cgaaaagcac ccttacgctt ggcccgtgac taagccagaa    1500
gatacgaagg ataattag                                                 1518
```

<210> SEQ ID NO 117
<211> LENGTH: 554

```
<212> TYPE: PRT
<213> ORGANISM: Debaryomyces hansenii

<400> SEQUENCE: 117
```

| | | | | | | | | | | | | | | |
|---|---|---|---|---|---|---|---|---|---|---|---|---|---|---|
| Met | Ser | Gln | Glu | Glu | Tyr | Ser | Ser | Gly | Val | Gln | Thr | Pro | Val | Ser | Asn |
| 1 | | | | 5 | | | | | 10 | | | | | 15 | |
| His | Ser | Gly | Leu | Glu | Lys | Glu | Gln | His | Lys | Leu | Asp | Gly | Leu | Asp |
| | | | 20 | | | | | 25 | | | | | 30 | |
| Glu | Asp | Glu | Ile | Val | Asp | Gln | Leu | Pro | Ser | Leu | Pro | Glu | Lys | Ser | Ala |
| | | 35 | | | | | 40 | | | | | 45 | | | |
| Lys | Asp | Tyr | Leu | Leu | Ile | Ser | Phe | Phe | Cys | Val | Leu | Ala | Phe | Gly |
| | 50 | | | | | 55 | | | | | 60 | | | | |
| Gly | Phe | Val | Phe | Gly | Phe | Asp | Thr | Gly | Thr | Ile | Ser | Gly | Phe | Val | Asn |
| 65 | | | | | 70 | | | | | 75 | | | | | 80 |
| Met | Ser | Asp | Tyr | Leu | Glu | Arg | Phe | Gly | Glu | Leu | Asn | Ala | Asp | Gly | Glu |
| | | | | 85 | | | | | 90 | | | | | 95 | |
| Tyr | Phe | Leu | Ser | Asn | Val | Arg | Thr | Gly | Leu | Ile | Val | Ala | Ile | Phe | Asn |
| | | | 100 | | | | | 105 | | | | | 110 | | |
| Val | Gly | Cys | Ala | Val | Gly | Gly | Ile | Phe | Leu | Ser | Lys | Ile | Ala | Asp | Val |
| | 115 | | | | | 120 | | | | | 125 | | | | |
| Tyr | Gly | Arg | Arg | Ile | Gly | Leu | Met | Phe | Ser | Met | Ile | Ile | Tyr | Val | Ile |
| 130 | | | | | 135 | | | | | 140 | | | | | |
| Gly | Ile | Ile | Val | Gln | Ile | Ser | Ala | Ser | Asp | Lys | Trp | Tyr | Gln | Ile | Val |
| 145 | | | | | 150 | | | | | 155 | | | | | 160 |
| Val | Gly | Arg | Ala | Ile | Ala | Gly | Leu | Ala | Val | Gly | Thr | Val | Ser | Val | Leu |
| | | | | 165 | | | | | 170 | | | | | 175 | |
| Ser | Pro | Leu | Phe | Ile | Gly | Glu | Ser | Ala | Pro | Lys | Thr | Leu | Arg | Gly | Thr |
| | | | 180 | | | | | 185 | | | | | 190 | | |
| Leu | Val | Cys | Cys | Phe | Gln | Leu | Cys | Ile | Thr | Leu | Gly | Ile | Phe | Leu | Gly |
| | 195 | | | | | 200 | | | | | 205 | | | | |
| Tyr | Cys | Thr | Thr | Tyr | Gly | Thr | Lys | Thr | Tyr | Thr | Asp | Ser | Arg | Gln | Trp |
| 210 | | | | | 215 | | | | | 220 | | | | | |
| Arg | Ile | Pro | Leu | Gly | Leu | Cys | Phe | Val | Trp | Ala | Ile | Met | Leu | Val | Ile |
| 225 | | | | | 230 | | | | | 235 | | | | | 240 |
| Gly | Met | Val | Cys | Met | Pro | Glu | Ser | Pro | Arg | Tyr | Leu | Val | Lys | Asn |
| | | | | 245 | | | | | 250 | | | | | 255 | |
| Lys | Ile | Glu | Glu | Ala | Lys | Lys | Ser | Ile | Gly | Arg | Ser | Asn | Lys | Val | Ser |
| | | | 260 | | | | | 265 | | | | | 270 | | |
| Pro | Glu | Asp | Pro | Ala | Val | Tyr | Thr | Glu | Val | Gln | Leu | Ile | Gln | Ala | Gly |
| | | 275 | | | | | 280 | | | | | 285 | | | |
| Ile | Glu | Arg | Glu | Ser | Leu | Ala | Gly | Ser | Ala | Ser | Trp | Thr | Glu | Leu | Val |
| | 290 | | | | | 295 | | | | | 300 | | | | |
| Thr | Gly | Lys | Pro | Arg | Ile | Phe | Arg | Arg | Val | Ile | Met | Gly | Ile | Met | Leu |
| 305 | | | | | 310 | | | | | 315 | | | | | 320 |
| Gln | Ser | Leu | Gln | Gln | Leu | Thr | Gly | Asp | Asn | Tyr | Phe | Phe | Tyr | Tyr | Gly |
| | | | | 325 | | | | | 330 | | | | | 335 | |
| Thr | Thr | Ile | Phe | Gln | Ala | Val | Gly | Met | Thr | Asp | Ser | Phe | Gln | Thr | Ser |
| | | | 340 | | | | | 345 | | | | | 350 | | |
| Ile | Val | Leu | Gly | Val | Val | Asn | Phe | Ala | Ser | Thr | Phe | Leu | Gly | Ile | Tyr |
| | 355 | | | | | 360 | | | | | 365 | | | | |
| Thr | Ile | Glu | Arg | Phe | Gly | Arg | Arg | Leu | Cys | Leu | Leu | Thr | Gly | Ser | Val |
| 370 | | | | | 375 | | | | | 380 | | | | | |
| Cys | Met | Phe | Val | Cys | Phe | Ile | Ile | Tyr | Ser | Ile | Leu | Gly | Val | Thr | Asn |
| 385 | | | | | 390 | | | | | 395 | | | | | 400 |

```
Leu Tyr Ile Asp Gly Tyr Asp Gly Pro Thr Ser Val Pro Thr Gly Asp
                405                 410                 415

Ala Met Ile Phe Ile Thr Thr Leu Tyr Ile Phe Phe Ala Ser Thr
            420                 425                 430

Trp Ala Gly Gly Val Tyr Cys Ile Val Ser Glu Thr Tyr Pro Leu Arg
        435                 440                 445

Ile Arg Ser Lys Ala Met Ser Val Ala Thr Ala Ala Asn Trp Ile Trp
450                 455                 460

Gly Phe Leu Ile Ser Phe Phe Thr Pro Phe Ile Thr Ser Ala Ile His
465                 470                 475                 480

Phe Tyr Tyr Gly Phe Val Phe Thr Gly Cys Leu Leu Ser Phe Phe
                485                 490                 495

Tyr Val Tyr Phe Phe Val Val Glu Thr Lys Gly Leu Thr Leu Glu Glu
                500                 505                 510

Val Asp Glu Leu Tyr Ala Gln Gly Val Ala Pro Trp Lys Ser Ser Lys
            515                 520                 525

Trp Val Pro Pro Thr Lys Glu Glu Met Ala His Ser Ser Gly Tyr Ala
        530                 535                 540

Ala Glu Ala Lys Pro His Asp Gln Gln Val
545                 550

<210> SEQ ID NO 118
<211> LENGTH: 574
<212> TYPE: PRT
<213> ORGANISM: Saccharomyces cerevisiae

<400> SEQUENCE: 118

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
210                 215                 220
```

```
Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
            245                 250                 255

Gly Ala Leu Thr Leu Val Pro Glu Ser Pro Arg Tyr Leu Cys Glu Val
        260                 265                 270

Asn Lys Val Glu Asp Ala Lys Arg Ser Ile Ala Lys Ser Asn Lys Val
    275                 280                 285

Ser Pro Glu Asp Pro Ala Val Gln Ala Glu Leu Asp Leu Ile Met Ala
290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
            325                 330                 335

Val Gln Met Phe Gln Gln Leu Thr Gly Asn Asn Tyr Phe Phe Tyr Tyr
        340                 345                 350

Gly Thr Val Ile Phe Lys Ser Val Gly Leu Asp Asp Ser Phe Glu Thr
    355                 360                 365

Ser Ile Val Ile Gly Val Val Asn Phe Ala Ser Thr Phe Phe Ser Leu
370                 375                 380

Trp Thr Val Glu Asn Leu Gly His Arg Lys Cys Leu Leu Leu Gly Ala
385                 390                 395                 400

Ala Thr Met Met Ala Cys Met Val Ile Tyr Ala Ser Val Gly Val Thr
            405                 410                 415

Arg Leu Tyr Pro His Gly Lys Ser Gln Pro Ser Ser Lys Gly Ala Gly
        420                 425                 430

Asn Cys Met Ile Val Phe Thr Cys Phe Tyr Ile Phe Cys Tyr Ala Thr
    435                 440                 445

Thr Trp Ala Pro Val Ala Trp Val Ile Thr Ala Glu Ser Phe Pro Leu
450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
            485                 490                 495

Asn Phe Tyr Tyr Gly Tyr Val Phe Met Gly Cys Leu Val Ala Met Phe
        500                 505                 510

Phe Tyr Val Phe Phe Phe Val Pro Glu Thr Lys Gly Leu Ser Leu Glu
    515                 520                 525

Glu Ile Gln Glu Leu Trp Glu Glu Gly Val Leu Pro Trp Lys Ser Glu
530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
                565                 570

<210> SEQ ID NO 119
<211> LENGTH: 505
<212> TYPE: PRT
<213> ORGANISM: Saccharomyces cerevisiae

<400> SEQUENCE: 119

Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30
```

-continued

```
Phe Gly Leu Phe Arg Glu Gly Tyr Leu Asp Pro Ser Thr Lys Ile Phe
         35                  40                  45
Gly Tyr Ala Arg Ser Lys Leu Ser Met Glu Glu Asp Leu Lys Ser Arg
 50                  55                  60
Val Leu Pro His Leu Lys Lys Pro His Gly Glu Ala Asp Asp Ser Lys
 65                  70                  75                  80
Val Glu Gln Phe Phe Lys Met Val Ser Tyr Ile Ser Gly Asn Tyr Asp
                 85                  90                  95
Thr Asp Glu Gly Phe Asp Glu Leu Arg Thr Gln Ile Glu Lys Phe Glu
                100                 105                 110
Lys Ser Ala Asn Val Asp Val Pro His Arg Leu Phe Tyr Leu Ala Leu
            115                 120                 125
Pro Pro Ser Val Phe Leu Thr Val Ala Lys Gln Ile Lys Ser Arg Val
130                 135                 140
Tyr Ala Glu Asn Gly Ile Thr Arg Val Ile Val Glu Lys Pro Phe Gly
145                 150                 155                 160
His Asp Leu Ala Ser Ala Arg Glu Leu Gln Lys Asn Leu Gly Pro Leu
                165                 170                 175
Phe Lys Glu Glu Glu Leu Tyr Arg Ile Asp His Tyr Leu Gly Lys Glu
            180                 185                 190
Leu Val Lys Asn Leu Leu Val Leu Arg Phe Gly Asn Gln Phe Leu Asn
            195                 200                 205
Ala Ser Trp Asn Arg Asp Asn Ile Gln Ser Val Gln Ile Ser Phe Lys
210                 215                 220
Glu Arg Phe Gly Thr Glu Gly Arg Gly Gly Tyr Phe Asp Ser Ile Gly
225                 230                 235                 240
Ile Ile Arg Asp Val Met Gln Asn His Leu Leu Gln Ile Met Thr Leu
                245                 250                 255
Leu Thr Met Glu Arg Pro Val Ser Phe Asp Pro Glu Ser Ile Arg Asp
            260                 265                 270
Glu Lys Val Lys Val Leu Lys Ala Val Ala Pro Ile Asp Thr Asp Asp
            275                 280                 285
Val Leu Leu Gly Gln Tyr Gly Lys Ser Glu Asp Gly Ser Lys Pro Ala
290                 295                 300
Tyr Val Asp Asp Asp Thr Val Asp Lys Asp Ser Lys Cys Val Thr Phe
305                 310                 315                 320
Ala Ala Met Thr Phe Asn Ile Glu Asn Glu Arg Trp Glu Gly Val Pro
                325                 330                 335
Ile Met Met Arg Ala Gly Lys Ala Leu Asn Glu Ser Lys Val Glu Ile
            340                 345                 350
Arg Leu Gln Tyr Lys Ala Val Ala Ser Gly Val Phe Lys Asp Ile Pro
            355                 360                 365
Asn Asn Glu Leu Val Ile Arg Val Gln Pro Asp Ala Ala Val Tyr Leu
370                 375                 380
Lys Phe Asn Ala Lys Thr Pro Gly Leu Ser Asn Ala Thr Gln Val Thr
385                 390                 395                 400
Asp Leu Asn Leu Thr Tyr Ala Ser Arg Tyr Gln Asp Phe Trp Ile Pro
                405                 410                 415
Glu Ala Tyr Glu Val Leu Ile Arg Asp Ala Leu Leu Gly Asp His Ser
            420                 425                 430
Asn Phe Val Arg Asp Asp Glu Leu Asp Ile Ser Trp Gly Ile Phe Thr
            435                 440                 445
Pro Leu Leu Lys His Ile Glu Arg Pro Asp Gly Pro Thr Pro Glu Ile
450                 455                 460
```

```
Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
            500                 505

<210> SEQ ID NO 120
<211> LENGTH: 249
<212> TYPE: PRT
<213> ORGANISM: Saccharomyces cerevisiae

<400> SEQUENCE: 120

Met Val Thr Val Gly Val Phe Ser Glu Arg Ala Ser Leu Thr His Gln
1               5                   10                  15

Leu Gly Glu Phe Ile Val Lys Lys Gln Asp Glu Ala Leu Gln Lys Lys
            20                  25                  30

Ser Asp Phe Lys Val Ser Val Ser Gly Gly Ser Leu Ile Asp Ala Leu
        35                  40                  45

Tyr Glu Ser Leu Val Ala Asp Glu Ser Leu Ser Ser Arg Val Gln Trp
    50                  55                  60

Ser Lys Trp Gln Ile Tyr Phe Ser Asp Glu Arg Ile Val Pro Leu Thr
65              70                  75                  80

Asp Ala Asp Ser Asn Tyr Gly Ala Phe Lys Arg Ala Val Leu Asp Lys
                85                  90                  95

Leu Pro Ser Thr Ser Gln Pro Asn Val Tyr Pro Met Asp Glu Ser Leu
            100                 105                 110

Ile Gly Ser Asp Ala Glu Ser Asn Asn Lys Ile Ala Ala Glu Tyr Glu
        115                 120                 125

Arg Ile Val Pro Gln Val Leu Asp Leu Val Leu Leu Gly Cys Gly Pro
    130                 135                 140

Asp Gly His Thr Cys Ser Leu Phe Pro Gly Glu Thr His Arg Tyr Leu
145                 150                 155                 160

Leu Asn Glu Thr Thr Lys Arg Val Ala Trp Cys His Asp Ser Pro Lys
                165                 170                 175

Pro Pro Ser Asp Arg Ile Thr Phe Thr Leu Pro Val Leu Lys Asp Ala
            180                 185                 190

Lys Ala Leu Cys Phe Val Ala Glu Gly Ser Ser Lys Gln Asn Ile Met
        195                 200                 205

His Glu Ile Phe Asp Leu Lys Asn Asp Gln Leu Pro Thr Ala Leu Val
    210                 215                 220

Asn Lys Leu Phe Gly Glu Lys Thr Ser Trp Phe Val Asn Glu Glu Ala
225                 230                 235                 240

Phe Gly Lys Val Gln Thr Lys Thr Phe
                245

<210> SEQ ID NO 121
<211> LENGTH: 2880
<212> TYPE: DNA
<213> ORGANISM: Saccharomyces cerevisiae

<400> SEQUENCE: 121
atgactgtta ctactccttt tgtgaatggt acttcttatt gtaccgtcac tgcatattcc      60
gttcaatctt ataaagctgc catagatttt tacaccaagt ttttgtcatt agaaaaccgc     120
tcttctccag atgaaaactc cactttattg tctaacgatt ccatctcttt gaagatcctt     180
```

```
ctacgtcctg atgaaaaaat caataaaaat gttgaggctc atttgaagga attgaacagt    240
attaccaaga ctcaagactg gagatcacat gccacccaat ccttggtatt taacacttcc    300
gacatcttgg cagtcaagga cactctaaat gctatgaacg ctcctcttca aggctaccca    360
acagaactat ttccaatgca gttgtacact ttgacccat taggtaacgt tgttggtgtt     420
acttctacta agaacgcagt ttcaaccaag ccaactccac caccagcacc agaagcttct    480
gctgagtctg tcttttcctc taaagttcac tcttacactg atttggctta ccgtatgaaa    540
accaccgaca cctatccatc tctgccaaag ccattgaaca ggcctcaaaa ggcaattgcc    600
gtcatgactt ccggtggtga tgctccaggt atgaactcta acgttagagc catcgtgcgt    660
tccgctatct tcaaaggttg tcgtgccttt gttgtcatgg aaggttatga aggtttggtt    720
cgtggtggtc cagaatacat caaggaattc cactgggaag acgtccgtgg ttggtctgct    780
gaaggtggta ccaacattgg tactgcccgt tgtatggaat caagaagcg cgaaggtaga    840
ttattgggtg cccaacattt gattgaggcc ggtgtcgatg ctttgatcgt tgtggtggt    900
gacggttctt tgactggtgc tgatctgttt agatcagaat ggccttcttt gatcgaggaa    960
ttgttgaaaa caaacagaat ttccaacgaa caatacgaaa gaatgaagca tttgaatatt   1020
tgcggtactg tcggttctat tgataacgat atgtccacca cggatgctac tattggtgct   1080
tactctgcct tggacagaat ctgtaaggcc atcgattacg ttgaagccac tgccaactct   1140
cactcaagag ctttcgttgt tgaagttatg ggtagaaact gtggttggtt agctttatta   1200
gctggtatcg ccacttccgc tgactatatc tttattccag agaagccagc cacttccagc   1260
gaatggcaag atcaaatgtg tgacattgtc tccaagcaca gatcaagggg taagagaacc   1320
accattgttg ttgttgcaga aggtgctatc gctgctgact tgaccccaat ttctccaagc   1380
gacgtccaca aagttctagt tgacagatta ggtttggata caagaattac taccttaggt   1440
cacgttcaaa gaggtggtac tgctgttgct tacgaccgta tcttggctac tttacaaggt   1500
cttgaggccg ttaatgccgt tttggaatcc actccagaca ccccatcacc attgattgct   1560
gttaacgaaa acaaaattgt tcgtaaacca ttaatggaat ccgtcaagtt gaccaaagca   1620
gttgcagaag ccattcaagc taaggatttc aagagagcta tgtctttaag agacactgag   1680
ttcattgaac atttaaacaa tttcatggct atcaactctg ctgaccacaa cgaaccaaag   1740
ctaccaaagg acaagagact gaagattgcc attgttaatg tcggtgctcc agctggtggt   1800
atcaactctg ccgtctactc gatggctact tactgtatgt cccaaggtca cagaccatac   1860
gctatctaca atggttggtc tggttttgca agacatgaaa gtgttcgttc tttgaactgg   1920
aaggatatgt tgggttggca atcccgtggt ggttctgaaa tcggtactaa cagagtcact   1980
ccagaagaag cagatctagg tatgattgct tactattcc aaaagtacga atttgatggt    2040
ttgatcatcg ttggtggttt cgaagctttt gaatctttac atcaattaga gagagcaaga   2100
gaaagttatc cagctttcag aatcccaatg gtcttgatac cagctacttt gtctaacaat   2160
gttccaggta ctgaatactc tttgggttct gataccgctt tgaatgctct aatggaatac   2220
tgtgatgttg ttaaacaatc cgcttcttca accagaggta gagccttcgt tgtcgattgt   2280
caaggtggta actcaggcta tttggccact tacgcttctt tggctgttgg tgctcaagtc   2340
tcttatgtcc cagaagaagg tatttctttg gagcaattgt ccgaggatat tgaatactta   2400
gctcaatctt ttgaaaaggc agaaggtaga ggtagatttg gtaaattgat tttgaagagt   2460
acaaacgctt ctaaggcttt atcagccact aaattggctg aagttattac tgctgaagcc   2520
gatggcagat ttgacgctaa gccagcttat ccaggtcatg tacaacaagg tggtttgcca   2580
```

```
tctccaattg atagaacaag agccactaga atggccatta aagctgtcgg cttcatcaaa    2640
gacaaccaag ctgccattgc tgaagctcgt gctgccgaag aaaacttcaa cgctgatgac    2700
aagaccattt ctgacactgc tgctgtcgtt ggtgttaagg gttcacatgt cgtttacaac    2760
tccattagac aattgtatga ctatgaaact gaagtttcca tgagaatgcc aaaggtcatt    2820
cactggcaag ctaccagact cattgctgac catttggttg gaagaaagag agttgattaa    2880
```

<210> SEQ ID NO 122
<211> LENGTH: 4179
<212> TYPE: DNA
<213> ORGANISM: Saccharomyces cerevisiae

<400> SEQUENCE: 122

```
atgactaacg aaaaggtctg gatagagaag ttggataatc caactctttc agtgttacca      60
catgactttt tacgcccaca caagaacct tatacgaaac aagctacata ttcgttacag     120
ctacctcagc tcgatgtgcc tcatgatagt ttttctaaca aatacgctgt cgctttgagt     180
gtatgggctg cattgatata tagagtaacc ggtgacgatg atattgttct ttatattgcg     240
aataacaaaa tcttaagatt caatattcaa ccaacgtggt catttaatga gctgtattct     300
acaattaaca atgagttgaa caagctcaat tctattgagg ccaattttc ctttgacgag      360 ctagctgaaa aaattcaaag ttgccaagat ctggaaagga cccctcagtt gttccgtttg     420 gccttttgg aaaaccaaga tttcaaatta gacgagttca agcatcattt agtggacttt     480
gctttgaatt tggataccag taataatgcg catgttttga acttaattta taacagctta     540
ctgtattcga atgaaagagt aaccattgtt gcggaccaat ttactcaata tttgactgct     600
gcgctaagcg atccatccaa ttgcataact aaaatctctc tgatcaccgc atcatccaag     660
gatagtttac ctgatccaac taagaacttg gctggtgcg atttcgtggg gtgtattcac      720
gacattttcc aggacaatgc tgaagccttc ccagagagaa cctgtgttgt ggagactcca     780
acactaaatt ccgacaagtc ccgttctttc acttatcgcg acatcaaccg cacttctaac     840
atagttgccc attatttgat taaaacaggt atcaaaagag gtgatgtagt gatgatctat     900
tcttctaggg gtgtggattt gatggtatgt gtgatgggtg tcttgaaagc cggcgcaacc     960
ttttcagtta tcgaccctgc atatccccca gccagacaaa ccatttactt aggtgttgct    1020
aaaccacgtg ggttgattgt tattagagct gctggacaat tggatcaact agtagaagat    1080
tacatcaatg atgaattgga gattgtttca agaatcaatt ccatcgctat tcaagaaaat    1140
ggtaccattg aaggtggcaa attggacaat ggcgaggatg ttttggctcc atatgatcac    1200
tacaaagaca ccagaacagg tgttgtagtt ggaccagatt ccaacccaac cctatctttc    1260
acatctggtt ccgaaggtat tcctaagggt gttcttggta acatttttc cttggcttat    1320 tatttcaatt ggatgtccaa aaggttcaac ttaacagaaa atgataaatt cacaatgctg    1380
agcggtattg cacatgatcc aattcaaaga gatatgttta caccattatt tttaggtgcc    1440
caattgtatg tccctactca agatgatatt ggtacaccgg ccgtttagc ggaatggatg     1500 agtaagtatg gttgcacagt tacccattta acacctgcca tgggtcaatt acttactgcc    1560
caagctacta caccattccc taagttacat catgcgttct tgtgggtgga cattttaaca    1620
aaacgtgatt gtctgaggtt acaaaccttg gcagaaaatt gccgtattgt taatatgtac    1680
ggtaccactg aaacacagcg tgcagtttct tatttcgaag ttaaatcaaa aaatgacgat    1740
ccaaactttt tgaaaaaatt gaaagatgtc atgcctgctg gtaaaggtat gttgaacgtt    1800
cagctactag ttgttaacag gaacgatcgt actcaaatat gtggtattgg cgaaataggt    1860
```

```
gagatttatg ttcgtgcagg tggtttggcc gaaggttata gaggattacc agaattgaat    1920
aaagaaaaat ttgtgaacaa ctggtttgtt gaaaaagatc actggaatta tttggataag    1980
gataatggtg aaccttggag acaattctgg ttaggtccaa gagatagatt gtacagaacg    2040
ggtgatttag gtcgttatct accaaacggt gactgtgaat gttgcggtag ggctgatgat    2100
caagttaaaa ttcgtgggtt cagaatcgaa ttaggagaaa tagatacgca catttcccaa    2160
catccattgg taagagaaaa cattacttta gttcgcaaaa atgccgacaa tgagccaaca    2220
ttgatcacat ttatggtccc aagatttgac aagccagatg acttgtctaa gttccaaagt    2280
gatgttccaa aggaggttga aactgaccct atagttaagg gcttaatcgg ttaccatctt    2340
ttatccaagg acatcaggac tttcttaaag aaaagattgg ctagctatgc tatgccttcc    2400
ttgattgtgg ttatggataa actaccattg aatccaaatg gtaaagttga taagcctaaa    2460
cttcaattcc caactcccaa gcaattaaat ttggtagctg aaaatacagt ttctgaaact    2520
gacgactctc agtttaccaa tgttgagcgc gaggttagag acttatggtt aagtatatta    2580
cctaccaagc cagcatctgt atcaccagat gattcgtttt tcgatttagg tggtcattct    2640
atcttggcta ccaaaaatgat ttttacctta agaaaaagc tgcaagttga tttaccattg    2700
ggcacaattt tcaagtatcc aacgataaag gcctttgccg cggaaattga cagaattaaa    2760
tcatcgggtg gatcatctca aggtgaggtc gtcgaaaatg tcactgcaaa ttatgcggaa    2820
gacgccaaga aattggttga gacgctacca agttcgtacc cctctcgaga atattttgtt    2880
gaacctaata gtgccgaagg aaaaacaaca attaatgtgt ttgttaccgg tgtcacagga    2940
tttctgggct cctacatcct tgcagatttg ttaggacgtt ctccaaagaa ctacagtttc    3000
aaagtgtttg cccacgtcag ggccaaggat gaagaagctg catttgcaag attcaaaaag    3060
gcaggtatca cctatggtac ttggaacgaa aaatttgcct caaatattaa agttgtatta    3120
ggcgatttat ctaaaagcca atttggtctt tcagatgaga agtggatgga tttggcaaac    3180
acagttgata taattatcca taatggtgcg ttagttcact gggtttatcc atatgccaaa    3240
ttgagggatc aaatgttat ttcaactatc aatgttatga gcttagccgc cgtcggcaag    3300
ccaaagttct ttgactttgt ttcctccact tctactcttg acactgaata ctactttaat    3360
ttgtcagata aacttgttag cgaagggaag ccaggcattt tagaatcaga cgatttaatg    3420
aactctgcaa gcgggctcac tggtggatat ggtcagtcca atgggctgc tgagtacatc    3480
attgacgtg caggtgaaag gggcctacgt gggtgtattg tcagaccagg ttacgtaaca    3540
ggtgcctctg ccaatggttc ttcaaacaca gatgatttct tattgagatt tttgaaaggt    3600
tcagtccaat taggtaagat tccagatatc gaaaattccg tgaatatggt tccagtagat    3660
catgttgctc gtgttgttgt tgctacgtct ttgaatcctc ccaaagaaaa tgaattggcc    3720
gttgctcaag taacgggtca cccaagaata ttattcaaag actacttgta tactttacac    3780
gattatggtt acgatgtcga aatcgaaagc tattctaaat ggaagaaatc attggaggcg    3840
tctgttattg acaggaatga agaaaatgcg ttgtatcctt tgctacacat ggtcttagac    3900
aacttacctg aaagtaccaa agctccggaa ctagacgata ggaacgccgt ggcatcttta    3960
aagaaagaca ccgcatggac aggtgttgat tggtctaatg gaataggtgt tactccagaa    4020
gaggttggta tatatattgc atttttaaac aaggttggat ttttacctcc accaactcat    4080
aatgacaaac ttccactgcc aagtatagaa ctaactcaag cgcaaataag tctagttgct    4140
tcaggtgctg gtgctcgtgg aagctccgca gcagcttaa                          4179
```

<210> SEQ ID NO 123

```
<211> LENGTH: 505
<212> TYPE: PRT
<213> ORGANISM: Pseudomonas fluorescens

<400> SEQUENCE: 123

Met Thr Thr Thr Arg Lys Lys Ser Lys Ala Leu Pro Ala Pro Pro Thr
1               5                   10                  15

Thr Leu Phe Leu Phe Gly Ala Arg Gly Asp Leu Val Lys Arg Leu Leu
            20                  25                  30

Met Pro Ala Leu Tyr Asn Leu Ser Arg Asp Gly Leu Leu Asp Glu Gly
        35                  40                  45

Leu Arg Ile Val Gly Val Asp His Asn Ala Val Ser Asp Ala Glu Phe
    50                  55                  60

Ala Thr Leu Leu Glu Asp Phe Leu Arg Asp Glu Val Leu Asn Lys Gln
65                  70                  75                  80

Gly Gln Gly Ala Ala Val Asp Ala Ala Val Trp Ala Arg Leu Thr Arg
                85                  90                  95

Gly Ile Asn Tyr Val Gln Gly Asp Phe Leu Asp Asp Ser Thr Tyr Ala
            100                 105                 110

Glu Leu Ala Ala Arg Ile Ala Ala Ser Gly Thr Gly Asn Ala Val Phe
        115                 120                 125

Tyr Leu Ala Thr Ala Pro Arg Phe Phe Ser Glu Val Val Arg Arg Leu
    130                 135                 140

Gly Ser Ala Gly Leu Leu Glu Glu Gly Pro Gln Ala Phe Arg Arg Val
145                 150                 155                 160

Val Ile Glu Lys Pro Phe Gly Ser Asp Leu Gln Thr Ala Glu Ala Leu
                165                 170                 175

Asn Gly Cys Leu Leu Lys Val Met Ser Glu Lys Gln Ile Tyr Arg Ile
            180                 185                 190

Asp His Tyr Leu Gly Lys Glu Thr Val Gln Asn Ile Leu Val Ser Arg
        195                 200                 205

Phe Ser Asn Ser Leu Phe Glu Ala Phe Trp Asn Asn His Tyr Ile Asp
    210                 215                 220

His Val Gln Ile Thr Ala Ala Glu Thr Val Gly Val Glu Thr Arg Gly
225                 230                 235                 240

Ser Phe Tyr Glu His Thr Gly Ala Leu Arg Asp Met Val Pro Asn His
                245                 250                 255

Leu Phe Gln Leu Leu Ala Met Val Ala Met Glu Pro Pro Ala Ala Phe
            260                 265                 270

Gly Ala Asp Ala Val Arg Gly Glu Lys Ala Lys Val Val Gly Ala Ile
        275                 280                 285

Arg Pro Trp Ser Val Glu Glu Ala Arg Ala Asn Ser Val Arg Gly Gln
    290                 295                 300

Tyr Ser Ala Gly Glu Val Ala Gly Lys Ala Leu Ala Gly Tyr Arg Glu
305                 310                 315                 320

Glu Ala Asn Val Ala Pro Asp Ser Ser Thr Glu Thr Tyr Val Ala Leu
                325                 330                 335

Lys Val Met Ile Asp Asn Trp Arg Trp Val Gly Val Pro Phe Tyr Leu
            340                 345                 350

Arg Thr Gly Lys Arg Met Ser Val Arg Asp Thr Glu Ile Val Ile Cys
        355                 360                 365

Phe Lys Pro Ala Pro Tyr Ala Gln Phe Arg Asp Thr Glu Val Glu Arg
    370                 375                 380

Leu Leu Pro Thr Tyr Leu Arg Ile Gln Ile Gln Pro Asn Glu Gly Met
385                 390                 395                 400
```

```
Trp Phe Asp Leu Leu Ala Lys Lys Pro Gly Pro Ser Leu Asp Met Ala
            405                 410                 415

Asn Ile Glu Leu Gly Phe Ala Tyr Arg Asp Phe Phe Glu Met Gln Pro
            420                 425                 430

Ser Thr Gly Tyr Glu Thr Leu Ile Tyr Asp Cys Leu Ile Gly Asp Gln
            435                 440                 445

Thr Leu Phe Gln Arg Ala Asp Asn Ile Glu Asn Gly Trp Arg Ala Val
        450                 455                 460

Gln Pro Phe Leu Asp Ala Trp Gln Gln Asp Ala Ser Leu Gln Asn Tyr
465                 470                 475                 480

Pro Ala Gly Val Asp Gly Pro Ala Ala Gly Asp Glu Leu Leu Ala Arg
                485                 490                 495

Asp Gly Arg Val Trp Arg Pro Leu Gly
            500                 505

<210> SEQ ID NO 124
<211> LENGTH: 1518
<212> TYPE: DNA
<213> ORGANISM: Pseudomonas fluorescens

<400> SEQUENCE: 124
atgaccacca cgcgaaagaa gtccaaggcg ttgccggcgc cgccgaccac gctgttcctg      60
ttcggcgccc gcggtgatct ggtcaagcgc ctgctgatgc cggcgctgta caacctcagc     120
cgcgacggtt tgctggatga ggggctgcgc attgtcggcg tcgaccacaa cgcggtgagc     180
gacgccgagt tcgccacgct gctggaagac ttccttcgcg atgaagtgct caacaagcaa     240 ggccagggg cggcggtgga tgccgccgtc tgggcccgcc tgaccgggg catcaactat       300 gtccagggcg attttctcga cgactccacc tatgccgaac tggcggcgcg gattgccgcc     360
agcggcaccg gcaacgcggt gttctacctg gccaccgcac cgcgcttctt cagtgaagtg     420
gtgcgccgcc tgggcagcgc cggggttgctg gaggaggggc cgcaggcttt tcgccgggtg   480
gtgatcgaaa acccttcgg ctccgacctg cagaccgccg aagccctcaa cggctgcctg      540
ctcaaggtca tgagcgagaa gcagatctat cgcatcgacc attacctggg caaggaaacg     600
gtccagaaca tcctggtcag ccgttttttcc aacagcctgt tcgaggcatt ctggaacaac    660
cattacatcg accacgtgca gatcaccgcg gcggaaaccg tcggcgtgga aacccgtggc     720
agcttttatg aacacaccgg tgccctgcgg gacatggtgc ccaaccacct gttccagttg     780
ctggcgatgg tggccatgga ccgccccgct gcctttggcg ccgatgcggt acgtggcgaa     840
aaggccaagg tggtgggggc tatccgcccc tggtccgtgg aagaggcccg ggccaactcg     900
gtgcgcggcc agtacagcgc cggtgaagtg ccggcaagg ccctggcggg ctaccgcgag      960
gaagccaacg tggcgccgga cagcagcacc gaaacctacg ttgcgctgaa ggtgatgatc    1020
gacaactggc gctgggtcgg ggtgccgttc tacctgcgca ccggcaagcg catgagtgtg    1080
cgcgacaccg agatcgtcat ctgcttcaag ccggcgccct atgcacagtt ccgcgatacc    1140
gaggtcgagc gcctgttgcc gacctacctg cggatccaga tccagcccaa cgaaggcatg    1200
tggttcgacc tgctggcgaa aaagcccggg ccgagcctgg acatggccaa catcgaactg    1260
ggttttgcct accgcgactt tttcgagatg cagcccccca ccggctacga aaccctgatc    1320
tacgactgcc tgatcggcga ccagaccctg ttccagcgcg ccgacaacat cgagaacggc    1380
tggcgcgcgg tgcaaccctt cctcgatgcc tggcaacagg acgccagctt gcagaactac    1440
ccggcgggcg tggatggccc ggcagccggg gatgaactgc tggcccggga tggccgcgta    1500
```

-continued tggcgacccc tgggggtga                                           1518

<210> SEQ ID NO 125
<211> LENGTH: 489
<212> TYPE: PRT
<213> ORGANISM: Pseudomonas fluorescens

<400> SEQUENCE: 125

Met Pro Ser Ile Thr Val Glu Pro Cys Thr Phe Ala Leu Phe Gly Ala
1               5                   10                  15

Leu Gly Asp Leu Ala Leu Arg Lys Leu Phe Pro Ala Leu Tyr Gln Leu
            20                  25                  30

Asp Ala Ala Gly Leu Leu His Asp Thr Arg Ile Leu Ala Leu Ala
        35                  40                  45

Arg Glu Pro Gly Ser Glu Gln Glu His Leu Ala Asn Ile Glu Thr Glu
50                  55                  60

Leu His Lys Tyr Val Gly Asp Lys Asp Ile Asp Ser Gln Val Leu Gln
65                  70                  75                  80

Arg Phe Leu Val Arg Leu Ser Tyr Leu His Val Asp Phe Leu Lys Ala
                85                  90                  95

Glu Asp Tyr Val Ala Leu Ala Glu Arg Val Gly Ser Glu Gln Arg Leu
            100                 105                 110

Ile Ala Tyr Phe Ala Thr Pro Ala Ala Val Tyr Gly Ala Ile Cys Glu
        115                 120                 125

Asn Leu Ser Arg Val Gly Leu Asn Gln His Thr Arg Val Val Leu Glu
130                 135                 140

Lys Pro Ile Gly Ser Asp Leu Asp Ser Ser Arg Lys Val Asn Asp Ala
145                 150                 155                 160

Val Ala Gln Phe Phe Pro Glu Thr Arg Ile Tyr Arg Ile Asp His Tyr
                165                 170                 175

Leu Gly Lys Glu Thr Val Gln Asn Leu Ile Ala Leu Arg Phe Ala Asn
            180                 185                 190

Ser Leu Phe Glu Thr Gln Trp Asn Gln Asn Tyr Ile Ser His Val Glu
        195                 200                 205

Ile Thr Val Ala Glu Lys Val Gly Ile Glu Gly Arg Trp Gly Tyr Phe
210                 215                 220

Asp Lys Ala Gly Gln Leu Arg Asp Met Ile Gln Asn His Leu Leu Gln
225                 230                 235                 240

Leu Leu Cys Leu Ile Ala Met Asp Pro Pro Ala Asp Leu Ser Ala Asp
                245                 250                 255

Ser Ile Arg Asp Glu Lys Val Lys Val Leu Lys Ala Leu Ala Pro Ile
            260                 265                 270

Ser Pro Glu Gly Leu Thr Thr Gln Val Val Arg Gly Gln Tyr Ile Ala
        275                 280                 285

Gly His Ser Glu Gly Gln Ser Val Pro Gly Tyr Leu Glu Glu Glu Asn
290                 295                 300

Ser Asn Thr Gln Ser Asp Thr Glu Thr Phe Val Ala Leu Arg Ala Asp
305                 310                 315                 320

Ile Arg Asn Trp Arg Trp Ala Gly Val Pro Phe Tyr Leu Arg Thr Gly
                325                 330                 335

Lys Arg Met Pro Gln Lys Leu Ser Gln Ile Val Ile His Phe Lys Glu
            340                 345                 350

Pro Ser His Tyr Ile Phe Ala Pro Glu Gln Arg Leu Gln Ile Ser Asn
        355                 360                 365

Lys Leu Ile Ile Arg Leu Gln Pro Asp Glu Gly Ile Ser Leu Arg Val

```
                370              375              380
Met Thr Lys Glu Gln Gly Leu Asp Lys Gly Met Gln Leu Arg Ser Gly
385              390                  395                  400

Pro Leu Gln Leu Asn Phe Ser Asp Thr Tyr Arg Ser Ala Arg Ile Pro
                405                  410                  415

Asp Ala Tyr Glu Arg Leu Leu Leu Glu Val Met Arg Gly Asn Gln Asn
                420                  425                  430

Leu Phe Val Arg Lys Asp Glu Ile Glu Ala Ala Trp Lys Trp Cys Asp
                435                  440                  445

Gln Leu Ile Ala Gly Trp Lys Lys Ser Gly Asp Ala Pro Lys Pro Tyr
            450                  455                  460

Ala Ala Gly Ser Trp Gly Pro Met Ser Ser Ile Ala Leu Ile Thr Arg
465                  470                  475                  480

Asp Gly Arg Ser Trp Tyr Gly Asp Ile
                485

<210> SEQ ID NO 126
<211> LENGTH: 1470
<212> TYPE: DNA
<213> ORGANISM: Pseudomonas fluorescens

<400> SEQUENCE: 126
```

| | | | | | |
|---|---|---|---|---|---|
| atgccttcga | taacggttga | accctgcacc | tttgccttgt | tggcgcgct | gggcgatctg | 60 |
| gcgctgcgta | agctgtttcc | tgccctgtac | caactcgatg | ccgccggttt | gctgcatgac | 120 |
| gacacgcgca | tcctggccct | ggcccgcgag | cctggcagcg | agcaggaaca | cctggcgaat | 180 |
| atcgaaaccg | agctgcacaa | gtatgtcggc | gacaaggata | tcgatagcca | ggtcctgcag | 240 |
| cgttttctcg | tccgcctgag | ctacctgcat | gtggacttcc | tcaaggccga | ggactacgtc | 300 |
| gccctggccg | aacgtgtcgg | cagcgagcag | cgcctgattg | cctacttcgc | cacgccggcg | 360 |
| gcggtgtatg | gcgcgatctg | cgaaaacctc | tcccgggtcg | gctcaaccca | gcacacccgt | 420 |
| gtggtcctgg | aaaaacccat | cggctcggac | ctggattcat | cacgcaaggt | caacgacgcg | 480 |
| gtggcgcagt | tcttcccgga | aacccgcatc | taccggatcg | accactacct | gggcaaggaa | 540 |
| acggtgcaga | acctgattgc | cctgcgtttc | gccaacagcc | tgttcgaaac | ccagtggaac | 600 |
| cagaactaca | tctcccacgt | ggaaatcacc | gtggccgaga | aggtcggcat | cgaaggtcgc | 660 |
| tggggctatt | tcgacaaggc | cggccaactg | cgggacatga | tccagaacca | cttgctgcaa | 720 |
| ctgctctgcc | tgatcgcgat | ggacccgccg | ccgaccttt | cggccgacag | catccgcgac | 780 |
| gagaaggtca | aggtgctcaa | ggccctggcg | cccatcagcc | cggaaggcct | gaccacccag | 840 |
| gtggtgcgcg | ccagtacat | cgccggccac | agcgaaggcc | agtcggtgcc | gggctacctg | 900 |
| gaggaagaaa | actccaacac | ccagagcgac | accgagacct | tcgtcgccct | gcgcgccgat | 960 |
| atccgcaact | ggcgctgggc | cggtgtgcct | ttctacctgc | gcaccggcaa | gcgcatgcca | 1020 |
| cagaagctgt | cgcagatcgt | catccacttc | aaggaaccct | cgcactacat | cttcgccccc | 1080 |
| gagcagcgcc | tgcagatcag | caacaagctg | atcatccgcc | tgcagccgga | cgaaggtatc | 1140 |
| tcgttgcggg | tgatgaccaa | ggagcagggc | ctggacaagg | gcatgcaact | cgcagcggt | 1200 |
| ccgttgcagc | tgaattttc | cgataccat | cgcagtgcac | ggatccccga | tgcctacgag | 1260 |
| cggttgttgc | tggaagtgat | gcgcggcaat | cagaacctgt | tgtgcgcaa | agatgaaatc | 1320 |
| gaagccgcgt | ggaagtggtg | tgaccagttg | attgccgggt | ggaagaaatc | cggcgatgcg | 1380 |
| cccaagccgt | acgcggccgg | gtcctgggg | ccgatgagct | ccattgcact | gatcacgcg | 1440 |
| gatgggaggt | cttggtatgg | cgatatctaa | | | | 1470 |

<210> SEQ ID NO 127
<211> LENGTH: 489
<212> TYPE: PRT
<213> ORGANISM: Pseudomonas aeruginosa

<400> SEQUENCE: 127

```
Met Pro Asp Val Arg Val Leu Pro Cys Thr Leu Ala Leu Phe Gly Ala
1               5                   10                  15

Leu Gly Asp Leu Ala Leu Arg Lys Leu Phe Pro Ala Leu Tyr Gln Leu
                20                  25                  30

Asp Arg Glu Asn Leu Leu His Arg Asp Thr Arg Val Leu Ala Leu Ala
            35                  40                  45

Arg Asp Glu Gly Ala Pro Ala Glu His Leu Ala Thr Leu Glu Gln Arg
        50                  55                  60

Leu Arg Leu Ala Val Pro Ala Lys Glu Trp Asp Asp Val Val Trp Gln
65                  70                  75                  80

Arg Phe Arg Glu Arg Leu Asp Tyr Leu Ser Met Asp Phe Leu Asp Pro
                85                  90                  95

Gln Ala Tyr Val Gly Leu Arg Glu Ala Val Asp Asp Glu Leu Pro Leu
            100                 105                 110

Val Ala Tyr Phe Ala Thr Pro Ala Ser Val Phe Gly Gly Ile Cys Glu
        115                 120                 125

Asn Leu Ala Ala Ala Gly Leu Ala Glu Arg Thr Arg Val Val Leu Glu
130                 135                 140

Lys Pro Ile Gly His Asp Leu Gly Ser Ser Arg Glu Val Asn Glu Ala
145                 150                 155                 160

Val Ala Arg Phe Phe Pro Glu Ser Arg Ile Tyr Arg Ile Asp His Tyr
                165                 170                 175

Leu Gly Lys Glu Thr Val Gln Asn Leu Ile Ala Leu Arg Phe Ala Asn
            180                 185                 190

Ser Leu Phe Glu Thr Gln Trp Asn Gln Asn His Ile Ser His Val Glu
        195                 200                 205

Ile Thr Val Ala Glu Lys Val Gly Ile Glu Gly Arg Trp Gly Tyr Phe
    210                 215                 220

Asp Gln Ala Gly Gln Leu Arg Asp Met Val Gln Asn His Leu Leu Gln
225                 230                 235                 240

Leu Leu Cys Leu Ile Ala Met Asp Pro Pro Ser Asp Leu Ser Ala Asp
                245                 250                 255

Ser Ile Arg Asp Glu Lys Val Lys Val Leu Arg Ala Leu Glu Pro Ile
            260                 265                 270

Pro Ala Glu Gln Leu Ala Ser Arg Val Val Arg Gly Gln Tyr Thr Ala
        275                 280                 285

Gly Phe Ser Asp Gly Lys Ala Val Pro Gly Tyr Leu Glu Glu Glu His
    290                 295                 300

Ala Asn Arg Asp Ser Asp Ala Glu Thr Phe Val Ala Leu Arg Val Asp
305                 310                 315                 320

Ile Arg Asn Trp Arg Trp Ser Gly Val Pro Phe Tyr Leu Arg Thr Gly
                325                 330                 335

Lys Arg Met Pro Gln Lys Leu Ser Gln Ile Val Ile His Phe Lys Glu
            340                 345                 350

Pro Pro His Tyr Ile Phe Ala Pro Glu Gln Arg Ser Leu Ile Ser Asn
        355                 360                 365

Arg Leu Ile Ile Arg Leu Gln Pro Asp Glu Gly Ile Ser Leu Gln Val
    370                 375                 380
```

```
Met Thr Lys Asp Gln Gly Leu Gly Lys Gly Met Gln Leu Arg Thr Gly
385                 390                 395                 400

Pro Leu Gln Leu Ser Phe Ser Glu Thr Tyr His Ala Ala Arg Ile Pro
            405                 410                 415

Asp Ala Tyr Glu Arg Leu Leu Leu Glu Val Thr Gln Gly Asn Gln Tyr
        420                 425                 430

Leu Phe Val Arg Lys Asp Glu Val Glu Phe Ala Trp Lys Trp Cys Asp
    435                 440                 445

Gln Leu Ile Ala Gly Trp Glu Arg Leu Ser Glu Ala Pro Lys Pro Tyr
450                 455                 460

Pro Ala Gly Ser Trp Gly Pro Val Ala Ser Val Ala Leu Val Ala Arg
465                 470                 475                 480

Asp Gly Arg Ser Trp Tyr Gly Asp Phe
                485

<210> SEQ ID NO 128
<211> LENGTH: 1470
<212> TYPE: DNA
<213> ORGANISM: Pseudomonas aeruginosa

<400> SEQUENCE: 128
atgcctgatg tccgcgttct gccttgcacg ttagcgctgt tcggtgcgct gggcgatctc      60
gccttgcgca agctgttccc ggcgctctac caactcgatc gtgagaacct gctgcaccgc     120
gatacccgcg tcctggccct ggcccgtgac gaaggcgctc cgccgaaca cctggcgacg      180
ctggagcagc gcctgcgcct ggcagtgccg gcgaaggagt gggacgacgt ggtctggcag     240
cgtttccgcg aacgcctcga ctacctgagc atggacttcc tcgacccgca ggcctatgtc     300
ggcttgcgcg aggcggtgga tgacgaactg ccgctggtcg cctacttcgc cacgccggcc     360
tcggtgttcg gcggcatctg cgagaacctc gccgccgccg tctcgccga gcgcacccgg      420
gtggtgctgg agaagcccat cggtcatgac ctggagtcgt cccgcgaggt caacgaggca     480
gtcgcccggt tcttcccgga aagccgcatc taccggatcg accattacct gggcaaggag     540
acggtgcaga acctgatcgc cctgcgcttc gccaacagcc tcttcgagac ccagtggaac     600
cagaaccaca tctcccacgt ggagatcacc gtggccgaga aggtcggcat cgaaggccgc     660
tggggctact cgaccaggc cgggcaactg cgcgacatgg tgcagaacca cctgctgcaa      720
ctgctctgcc tgatcgccat ggatccgccc agcgaccttt cggcggacag cattcgcgac     780
gagaaggtca aggtcctccg cgccctcgag ccgattcccg cagaacaact ggcttcgcgc     840
gtggtgcgtg gcagtacac cgccggtttc agcgacggca aggcagtgcc gggctacctg      900
gaggaggaac atgcgaatcg cgacagcgac gcggaaacct cgtcgccct cgcgtggac       960
atccgcaact ggcgctggtc gggcgtgccg ttctacctgc gcaccggcaa gcgcatgccg    1020
cagaagctgt cgcagatcgt catccacttc aaggagccgc cgcactacat cttcgctccc    1080
gagcagcgtt cgctgatcag caaccggctg atcatccgcc tgcagccgga cgaaggtatc    1140
tccctgcaag tgatgaccaa ggaccagggc ctgggcaagg catgcaatt gcgtaccggc     1200
ccgctgcaac tgagtttttc cgagacctac cacgcggcgc ggattcccga tgcctacgag    1260
cgtctgctgc tggaggtcac ccagggcaac cagtacctgt tcgtgcgcaa ggacgaggtg    1320
gagttcgcct ggaagtggtg cgaccagctg atcgctggct gggaacgcct gagcgaagcg    1380
cccaagccgt atccgcggg gagttggggg ccggtggcct cggtggccct ggtggcccgc    1440
gatgggagga gttggtatgg cgatttctga                                     1470
```

```
<210> SEQ ID NO 129
<211> LENGTH: 485
<212> TYPE: PRT
<213> ORGANISM: Zymomonas mobilis

<400> SEQUENCE: 129

Met Thr Asn Thr Val Ser Thr Met Ile Leu Phe Gly Ser Thr Gly Asp
1               5                   10                  15

Leu Ser Gln Arg Met Leu Leu Pro Ser Leu Tyr Gly Leu Asp Ala Asp
            20                  25                  30

Gly Leu Leu Ala Asp Asp Leu Arg Ile Val Cys Thr Ser Arg Ser Glu
        35                  40                  45

Tyr Asp Thr Asp Gly Phe Arg Asp Phe Ala Glu Lys Ala Leu Asp Arg
    50                  55                  60

Phe Val Ala Ser Asp Arg Leu Asn Asp Asp Ala Lys Ala Lys Phe Leu
65                  70                  75                  80

Asn Lys Leu Phe Tyr Ala Thr Val Asp Ile Thr Asp Pro Thr Gln Phe
                85                  90                  95

Gly Lys Leu Ala Asp Leu Cys Gly Pro Val Glu Lys Gly Ile Ala Ile
            100                 105                 110

Tyr Leu Ser Thr Ala Pro Ser Leu Phe Glu Gly Ala Ile Ala Gly Leu
        115                 120                 125

Lys Gln Ala Gly Leu Ala Gly Pro Thr Ser Arg Leu Ala Leu Glu Lys
    130                 135                 140

Pro Leu Gly Gln Asp Leu Ala Ser Ser Asp His Ile Asn Asp Ala Val
145                 150                 155                 160

Leu Lys Val Phe Ser Glu Lys Gln Val Tyr Arg Ile Asp His Tyr Leu
                165                 170                 175

Gly Lys Glu Thr Val Gln Asn Leu Leu Thr Leu Arg Phe Gly Asn Ala
            180                 185                 190

Leu Phe Glu Pro Leu Trp Asn Ser Lys Gly Ile Asp His Val Gln Ile
        195                 200                 205

Ser Val Ala Glu Thr Val Gly Leu Glu Gly Arg Ile Gly Tyr Phe Asp
    210                 215                 220

Gly Ser Gly Ser Leu Arg Asp Met Val Gln Ser His Ile Leu Gln Leu
225                 230                 235                 240

Val Ala Leu Val Ala Met Glu Pro Pro Ala His Met Glu Ala Asn Ala
                245                 250                 255

Val Arg Asp Glu Lys Val Lys Val Phe Arg Ala Leu Arg Pro Ile Asn
            260                 265                 270

Asn Asp Thr Val Phe Thr His Thr Val Thr Gly Gln Tyr Gly Ala Gly
        275                 280                 285

Val Ser Gly Gly Lys Glu Val Ala Gly Tyr Ile Asp Glu Leu Gly Gln
    290                 295                 300

Pro Ser Asp Thr Glu Thr Phe Val Ala Ile Lys Ala His Val Asp Asn
305                 310                 315                 320

Trp Arg Trp Gln Gly Val Pro Phe Tyr Ile Arg Thr Gly Lys Arg Leu
                325                 330                 335

Pro Ala Arg Arg Ser Glu Ile Val Val Gln Phe Lys Pro Val Pro His
            340                 345                 350

Ser Ile Phe Ser Ser Gly Gly Ile Leu Gln Pro Asn Lys Leu Arg
        355                 360                 365

Ile Val Leu Gln Pro Asp Glu Thr Ile Gln Ile Ser Met Met Val Lys
    370                 375                 380
```

```
Glu Pro Gly Leu Asp Arg Asn Gly Ala His Met Arg Glu Val Trp Leu
385                 390                 395                 400

Asp Leu Ser Leu Thr Asp Val Phe Lys Asp Arg Lys Arg Arg Ile Ala
            405                 410                 415

Tyr Glu Arg Leu Met Leu Asp Leu Ile Glu Gly Asp Ala Thr Leu Phe
        420                 425                 430

Val Arg Arg Asp Glu Val Glu Ala Gln Trp Val Trp Ile Asp Gly Ile
    435                 440                 445

Arg Glu Gly Trp Lys Ala Asn Ser Met Lys Pro Lys Thr Tyr Val Ser
    450                 455                 460

Gly Thr Trp Gly Pro Ser Thr Ala Ile Ala Leu Ala Glu Arg Asp Gly
465                 470                 475                 480

Val Thr Trp Tyr Asp
            485

<210> SEQ ID NO 130
<211> LENGTH: 1458
<212> TYPE: DNA
<213> ORGANISM: Zymomonas mobilis

<400> SEQUENCE: 130
atgacaaata ccgtttcgac gatgatattg tttggctcga ctggcgacct ttcacagcgt      60
atgctgttgc cgtcgcttta tggtcttgat gccgatggtt tgcttgcaga tgatctgcgt     120
atcgtctgca cctctcgtag cgaatacgac acagatggtt ccgtgatttt gcagaaaaa     180
gctttagatc gctttgtcgc ttctgaccgg ttaaatgatg acgctaaagc taaattcctt     240
aacaagcttt tctacgcgac ggtcgatatt acggatccga cccaattcgg aaaattagct     300
gacctttgtg gcccggtcga aaaggtatc gccatttatc tttcgactgc gccttctttg     360
tttgaagggg caatcgctgg cctgaaacag gctggtctgg ctggtccaac ttctcgcctg     420
gcgcttgaaa aacctttagg tcaagatctt gcttcttccg atcatattaa tgatgcggtt     480
ttgaaagttt tctctgaaaa gcaagtttat cgtattgacc attatctggg taaagaaacg     540
gttcagaatc ttctgaccct gcgttttggt aatgctttgt ttgaaccgct ttggaattca     600
aaaggcattg accacgttca gatcagcgtt gctgaaacgg ttggtcttga aggtcgtatc     660
ggttatttcg acggttctgg cagcttgcgc gatatggttc aaagccatat ccttcagttg     720
gtcgctttgg ttgcaatgga accaccggct catatggaag ccaacgctgt tcgtgacgaa     780
aaggtaaaag ttttccgcgc tctgcgtccg atcaataacg acaccgtctt tacgcatacc     840
gttaccggtc aatatggtgc cggtgtttct ggtggtaaag aagttgccgg ttacattgac     900
gaactgggtc agccttccga taccgaaacc tttgttgcta tcaaagcgca tgttgataac     960
tggcgttggc agggtgttcc gttctatatc cgcactggta agcgtttacc tgcacgtcgt    1020
tctgaaatcg tggttcagtt taaacctgtt ccgcattcga ttttctcttc ttcaggtggt    1080
atcttgcagc cgaacaagct gcgtattgtc ttacagcctg atgaaaccat ccagatttct    1140
atgatggtga agaaccgggt cttgaccgt aacggtgcgc atatgcgtga agtttggctg    1200
gatctttccc tcacggatgt gtttaaagac cgtaaacgtc gtatcgctta tgaacgcctg    1260
atgcttgatc ttatcgaagg cgatgctact ttatttgtgc gtcgtgacga agttgaggcg    1320
cagtgggttt ggattgacgg aattcgtgaa ggctggaaag ccaacagtat gaagccaaaa    1380
acctatgtct ctggtacatg ggggccttca actgctatag ctctggccga acgtgatgga    1440
gtaacttggt atgactga                                                 1458
```

```
<210> SEQ ID NO 131
<211> LENGTH: 750
<212> TYPE: DNA
<213> ORGANISM: Saccharomyces cerevisiae

<400> SEQUENCE: 131
atggtgacag tcggtgtgtt ttctgagagg gctagtttga cccatcaatt ggggaattc      60 atcgtcaaga aacaagatga ggcgctgcaa aagaagtcag actttaaagt ttccgttagc    120
ggtggctctt tgatcgatgc tctgtatgaa agtttagtag cggacgaatc actatcttct    180
cgagtgcaat ggtctaaatg caaatctac ttctctgatg aaagaattgt gccactgacg     240
gacgctgaca gcaattatgg tgccttcaag agagctgttc tagataaatt accctcgact    300
agtcagccaa acgtttatcc catggacgag tccttgattg gcagcgatgc tgaatctaac    360
aacaaaattg ctgcagagta cgagcgtatc gtacctcaag tgcttgattt ggtactgttg    420
ggctgtggtc ctgatggaca cacttgttcc ttattccctg agaaacaca taggtacttg     480 ctgaacgaaa caaccaaaag agttgcttgg tgccacgatt ctcccaagcc tccaagtgac    540
agaatcacct tcactctgcc tgtgttgaaa gacgccaaag ccctgtgttt tgtggctgag    600
ggcagttcca aacaaaatat aatgcatgag atctttgact tgaaaaacga tcaattgcca    660
accgcattgg ttaacaaatt atttggtgaa aaaacatcct ggttcgttaa tgaggaagct    720
tttggaaaag ttcaaacgaa aacttttag                                      750

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      FLAG tag

<400> SEQUENCE: 132

Asp Tyr Lys Asp Asp Asp Asp Lys Gly
1               5

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      V5 tag

<400> SEQUENCE: 133

Gly Lys Pro Ile Pro Asn Pro Leu Leu Gly Leu Asp Ser Thr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      c-MYC tag

<400> SEQUENCE: 134

Glu Gln Lys Leu Ile Ser Glu Glu Asp Leu
1               5                   10

<210> SEQ ID NO 135
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      HSV tag

<400> SEQUENCE: 135

Gln Pro Glu Leu Ala Pro Glu Asp Pro Glu Asp
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      HA tag

<400> SEQUENCE: 136

Tyr Pro Tyr Asp Val Pro Asp Tyr Ala
1               5

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      VSV-G tag

<400> SEQUENCE: 137

Tyr Thr Asp Ile Glu Met Asn Arg Leu Gly Lys
1               5                   10

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 138

His His His His His His
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any amino acid
<220> FEATURE:
<221> NAME/KEY: misc_feature
<222> LOCATION: (3)..(5)
<223> OTHER INFORMATION: /note=This region may encompass 1 to 3 residues

<400> SEQUENCE: 139

Cys Cys Xaa Xaa Xaa Cys Cys
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 140

Cys Cys Pro Gly Cys Cys
1               5

<210> SEQ ID NO 141
<211> LENGTH: 6
<212> TYPE: PRT
<213> ORGANISM: Unknown
<220> FEATURE:
<223> OTHER INFORMATION: Description of Unknown: Thrombin cleavage
      site peptide

<400> SEQUENCE: 141

Leu Val Pro Arg Gly Ser
1               5

<210> SEQ ID NO 142
<211> LENGTH: 5
<212> TYPE: PRT
<213> ORGANISM: Unknown
<220> FEATURE:
<223> OTHER INFORMATION: Description of Unknown: Enterokinase cleavage
      site peptide

<400> SEQUENCE: 142

Asp Asp Asp Asp Lys
1               5

<210> SEQ ID NO 143
<211> LENGTH: 7
<212> TYPE: PRT
<213> ORGANISM: Unknown
<220> FEATURE:
<223> OTHER INFORMATION: Description of Unknown: TEV protease cleavage
      site peptide

<400> SEQUENCE: 143

Glu Asn Leu Tyr Phe Gln Gly
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Glu Val Leu Phe Gln Gly Pro
1               5

<210> SEQ ID NO 145
<211> LENGTH: 627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
atgagagaca ttgattctgt tatgagattg gctccagtta tgccagtctt ggttatagaa      60
gatatagctg atgctaagcc aattgctgag gctttggttg ctggtggttt aaatgttttg     120
gaagttacat tgagaactcc atgtgctttg gaagctatta aaattatgaa ggaagttcca     180

| | |
|---|---|
| ggtgctgttg ttggtgctgg tactgtttta aacgctaaaa tgttggatca agctcaagaa | 240 |
| gctggttgtg agttctttgt ataccaggt ttgactgctg atttgggaaa acatgctgtt | 300 |
| gctcaaaaag cggctcttct accagggggtt gctaatgctg ctgatgttat gttgggattg | 360 |
| gatttgggtt tggatagatt taaattcttc ccagctgaaa atataggtgg tttgccagct | 420 |
| ttaaaatcta tggcttctgt ttttagacaa gttagatttt gtccaactgg aggaattact | 480 |
| ccgacttctg ctccaaaata tttggaaaat ccatctattt tgtgtgttgg tggttcttgg | 540 |
| gttgttccag cgggtaaacc agatgttgcg aaaattactg ctttggctaa agaggcttca | 600 |
| gcttttaaaa gagctgctgt ggcgtag | 627 |

<210> SEQ ID NO 146
<211> LENGTH: 1824
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

| | |
|---|---|
| atgacggatt tgcattcaac tgttgagaaa gtaactgcta gagtaattga agatcaagg | 60 |
| gaaactagaa aggcttattt ggatttgata caatatgaga gggaaaaagg tgttgataga | 120 |
| ccaaatttgt cttgttctaa tttggctcat ggttttgctg ctatgaatgg tgataaacca | 180 |
| gctttgagag attttaatag aatgaatata ggtgtagtta cttcttataa tgatatgttg | 240 |
| tctgctcatg aaccatatta tagatatcca gaacaaatga aggttttgc tcgtgaagtt | 300 |
| ggtgctacag ttcaagttgc tggtggtgtt cctgcaatgt gtgatggtgt tactcaaggt | 360 |
| caaccaggta tggaagaatc tttgtttcc agagatgtaa ttgctttggc tacatctgtt | 420 |
| tcattgtctc acggaatgtt tgaaggtgct gcattgttgg aatttgtga taaaattgtt | 480 |
| ccaggttttgt tgatgggtgc tttgaggttc ggtcatttgc caactatttt ggttccatct | 540 |
| ggtccaatga ctactggaat cccaaataaa gaaaagatta aattagaca attgtatgct | 600 |
| caaggaaaaa ttggtcaaaa ggaattgttg gatatggaag ctgcctgtta tcatgctgaa | 660 |
| ggtacttgta ctttttatgg tactgctaac actaatcaga tggttatgga gttttgggt | 720 |
| ttgcacatgc caggtagtgc attcgttact ccaggtactc cactgagaca ggctttgact | 780 |
| agagctgctg ttcatagagt tgcagagttg ggttggaaag gtgatgatta tagacctttg | 840 |
| ggtaaaatta ttgatgagaa atctattgtt aatgctattg ttggtttgtt agctacaggt | 900 |
| ggttctacaa atcatacaat gcatattccg gccatagcta agcagcagg ggttatagtt | 960 |
| aattggaatg atttcatga tttgtctgaa gttgttccat tgattgctag aatttatcca | 1020 |
| aatggtccta gagatataaa tgaatttcaa aatgcaggag gaatggctta tgtaattaaa | 1080 |
| gaattgttga gtcgaatttt gttaaataga gatgttacta ctattgctaa aggagggata | 1140 |
| gaagaatatg ctaaagctcc agctctgaac gatgcgggtg aattggtgtg gaaaccggct | 1200 |
| ggcgaacctg gggacgacac aattttgaga ccagtatcta atccatttgc taaagatggt | 1260 |
| ggtttgcgtc tcttggaagg taatttgggt agagcaatgt ataaggcttc tgctgtagat | 1320 |
| ccaaaattct ggactattga agctcccgtt agagttttct ctgatcaaga tgatgttcaa | 1380 |
| aaggctttta agcaggcga gttaaataaa gatgttatag ttgttgttag atttcaaggt | 1440 |
| cctcgtgcta atggtatgcc tgaattgcat aagttgactc ctgcgctagg cgtattgcaa | 1500 |
| gataatggtt ataaggttgc tttagttact gatggtagaa tgtctggtgc aactggtaaa | 1560 |
| gtaccggtgg ctctgcatgt ttcaccagag gctttaggag gtggggcgat tggcaagttg | 1620 |

```
agagatggcg atatagttag aatttctgtt gaagaaggta aattagaggc tcttgtcccc    1680
gccgacgagt ggaatgctag accacatgct gagaagcccg cttttagacc tggtactggg    1740
agagaattgt ttgacatttt tagacaaaac gctgctaagg ctgaggatgg tgcagttgca    1800
atttatgctg gggcagggat ctag                                           1824

<210> SEQ ID NO 147
<211> LENGTH: 627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
atgagggata ttgatagtgt gatgaggtta gcccctgtta tgcctgttct cgttattgaa      60
gatattgcag atgccaaacc tattgccgaa gcactcgttg caggtggtct aaacgttcta     120
gaagtgacac taaggactcc ttgtgcacta gaagctatta agattatgaa ggaagttcct     180
ggtgctgttg ttggtgctgg tacagttcta aacgccaaaa tgctcgacca ggcacaagaa     240
gcaggttgcg aattttctcg ttcacctggt ctaactgccg acctcggaaa gcacgcagtt     300
gctcaaaaag ccgcattact acccggtgtt gcaaatgcag cagatgtgat gctaggtcta     360
gacctaggtc tagataggtt caagttcttc cctgccgaaa acattggtgg tctacctgct     420
ctaaagagta tggcatcagt tttcaggcaa gttaggttct gccctactgg aggtataact     480
cctacaagtg cacctaaata tctagaaaac cctagtattc tatgcgttgg tggttcatgg     540
gttgttcctg ccggaaaacc cgatgttgcc aaaattacag ccctcgcaaa agaagcaagt     600
gcattcaaga gggcagcagt tgcttag                                         627

<210> SEQ ID NO 148
<211> LENGTH: 1824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
atgacggatc tacatagtac agtggagaag gttactgcca gggttattga aaggagtagg      60
gaaactagga aggcatatct agatttaatt caatatgaga gggaaaaagg agtggacagg     120
cccaacctaa gttgtagcaa cctagcacat ggattcgccg caatgaatgg tgacaagccc     180
gcattaaggg acttcaacag gatgaatatt ggagttgtga cgagttacaa cgatatgtta     240
agtgcacatg aaccctatta taggtatcct gagcaaatga aggtgtttgc aagggaagtt     300
ggagccacag ttcaagttgc tggtggagtg cctgcaatgt gcgatggtgt gactcagggt     360
caacctggaa tggaagaatc cctattttca agggatgtta ttgcattagc aacttcagtt     420
tcattatcac atggtatgtt gaaggggca gctctactcg gtatatgtga caagattgtt     480
cctggtctac taatgggagc actaaggttt ggtcacctac ctactattct agttcccagt     540
ggacctatga caacgggtat acctaacaaa gaaaaaatta ggattaggca actctatgca     600
caaggtaaaa ttggacaaaa agaactacta gatatggaag ccgcatgcta ccatgcagaa     660
ggtacttgca ctttctatgg tacagccaac actaaccaga tggttatgga agttctcggt     720
ctacatatgc ccggtagtgc ctttgttact cctggtactc ctctcaggca agcactaact     780
agggcagcag tgcataggt tgcagaatta ggttggaagg gagacgatta taggcctcta     840
```

```
ggtaaaatta ttgacgaaaa aagtattgtt aatgcaattg ttggtctatt agccactggt    900
ggtagtacta accatacgat gcatattcct gctattgcaa gggcagcagg tgttattgtt    960
aactggaatg acttccatga tctatcagaa gttgttcctt taattgctag gatttaccct   1020
aatggaccta gggacattaa cgaatttcaa aatgccggag aatggcata tgttattaag    1080 gaactactat cagcaaatct actaaacagg gatgttacaa ctattgctaa gggaggtata   1140
gaagaatacg ctaaggcacc tgccctaaat gatgcaggag aattagtttg gaagcccgca   1200
ggagaacctg gtgatgacac tattctaagg cctgtttcaa atcctttcgc caaagatgga   1260
ggtctaaggc tcttagaagg taacctagga agggccatgt acaaggctag cgccgttgat   1320
cctaaattct ggactattga agccctgtt agggttttct cagaccagga cgatgttcaa    1380
aaagccttca aggcaggaga actaaacaaa gacgttattg ttgttgttag gttccaagga   1440
cctagggcca acggtatgcc tgaattacat aagctaactc ctgcattagg tgttctacaa   1500
gataatggat acaaagttgc attagtgacg gatggtagga tgagtggtgc aactggtaaa   1560
gttcctgttg cattacatgt ttcacccgaa gcactaggag gtggtgctat tggtaaactt   1620
agggatggag atattgttag gattagtgtt gaagaaggaa aacttgaagc actcgttccc   1680
gcagatgagt ggaatgcaag gcctcatgca gaaaaacctg cattcaggcc tgggactggg   1740
agggaattat ttgatatttt caggcaaaat gcagcaaaag cagaagacgg tgccgttgcc   1800
atctatgccg gtgctggtat atag                                          1824

<210> SEQ ID NO 149
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
actagtatgg ctaaggaata tttcccacaa attcaaaag                            39

<210> SEQ ID NO 150
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ctcgagctac tattggtaca tggcaacaat agc                                  33

<210> SEQ ID NO 151
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ctcgagctac taatgatgat gatgatgatg ttggtacatg gcaacaatag cttcg          55

<210> SEQ ID NO 152
<211> LENGTH: 36
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 152
actagtatgg ctaaagaata ttttccacaa attcag                                    36

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ctcgagttat tgatacatag ctactatagc ctc                                       33

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ctcgagttaa tgatgatgat gatgatgttg atacatagct actatagcct cattgtttac          60

<210> SEQ ID NO 155
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
aatcgatcaa agcttctaaa tacaagacgt gcgatgacga ctatactgga c                   51

<210> SEQ ID NO 156
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
taccgtacta cccgggtata tagtcttttt gccctggtgt tccttaataa tttc                54

<210> SEQ ID NO 157
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgctaatgac ccgggaattc cacttgcaat tacataaaaa attccggcgg                     50

<210> SEQ ID NO 158
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
atgatcattg agctcagctt cgcaagtatt cattttagac ccatggtgg                49

<210> SEQ ID NO 159
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tgctaatgag agctctcatt ttttggtgcg atatgttttt ggttgatg                 48

<210> SEQ ID NO 160
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
aatgatcatg agctcgtcaa caagaactaa aaaattgttc aaaaatgc                 48

<210> SEQ ID NO 161
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ctaaatacaa gacgtgcgat gacgactata ctgg                                34

<210> SEQ ID NO 162
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gtcaacaaga actaaaaaat tgttcaaaaa tgcaattgtc                          40

<210> SEQ ID NO 163
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
atggagttct tttctaatat aggtaaaatt cagtatcaag gtc                      43

<210> SEQ ID NO 164
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

```
aatggatctg tagattttgg accttgatac tgaatttta                        39
```

<210> SEQ ID NO 165
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
caaaatctac agatccattg tcttttaaat attataatcc aga                   43
```

<210> SEQ ID NO 166
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166

```
gttttaccat ttataacttc ttctggatta taatatttaa aagac                 45
```

<210> SEQ ID NO 167
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

```
agaagttata aatggtaaaa ctatgagaga acatttaaaa ttt                   43
```

<210> SEQ ID NO 168
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
atagtatgcc accaagacaa agcaaatttt aaatgttctc tcata                 45
```

<210> SEQ ID NO 169
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

```
gctttgtctt ggtggcatac tatgggtggt gatggtactg atatg                 45
```

<210> SEQ ID NO 170
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

```
ttatcagtag taccacaacc gaacatatca gtaccatcac caccc                 45
```

<210> SEQ ID NO 171
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
ttcggttgtg gtactactga taaaacttgg ggtcaatctg atc                43

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
ggcttttgct ctagcagctg gatcagattg accccaagtt                   40

<210> SEQ ID NO 173
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
cagctgctag agcaaaagcc aaagtagatg cagcctttga aat                43

<210> SEQ ID NO 174
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
atcaatagac aatttatcca taatttcaaa ggctgcatct acttt              45

<210> SEQ ID NO 175
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
tatggataaa ttgtctattg attattattg ttttcatgat agaga              45

<210> SEQ ID NO 176
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 176
agaaccatat tcaggagaca aatctctatc atgaaaacaa taata              45

```
<210> SEQ ID NO 177
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
tttgtctcct gaatatggtt ctttaaaagc aactaatgat caa            43

<210> SEQ ID NO 178
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aatataatcc gtaacaatgt ccaattgatc attagttgct tttaa          45

<210> SEQ ID NO 179
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ttggacattg ttacggatta tattaaagaa aaacaaggtg ataaa          45

<210> SEQ ID NO 180
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cgcagtgccc cacaaacatt taaatttatc accttgtttt tcttt          45

<210> SEQ ID NO 181
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tttaaatgtt tgtggggcac tgcgaaatgt tttgatcatc cacgt          45

<210> SEQ ID NO 182
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
actcgtcccc gcaccatgca taaaacgtgg atgatcaaaa cattt          45

<210> SEQ ID NO 183
<211> LENGTH: 45
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
tttatgcatg gtgcggggac gagtccttct gctgatgttt ttgct            45

<210> SEQ ID NO 184
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cttcttaatt tgagcggcag aaaaagcaaa acatcagca gaagg             45

<210> SEQ ID NO 185
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttttctgccg ctcaaattaa gaaggcattg gaatcaactg ttaaa            45

<210> SEQ ID NO 186
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gaatacatac ccgttcccac ctaatttaac agttgattcc aatgc            45

<210> SEQ ID NO 187
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ttaggtggga acgggtatgt attctgggga ggaagggaag gttat            45

<210> SEQ ID NO 188
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
catattagtg tttaataatg tttcataacc ttcccttcct cccca            45

<210> SEQ ID NO 189
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 189
gaaacattat taaacactaa tatgggtttg gaattggata atatg            45

<210> SEQ ID NO 190
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tacagccatt ttcatcaatc tagccatatt atccaattcc aaacc            45

<210> SEQ ID NO 191
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gctagattga tgaaaatggc tgtagaatac ggaaggtcta ttggt            45

<210> SEQ ID NO 192
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ttcaatataa aagtcaccct taaaaccaat agaccttccg tattc            45

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tttaagggtg acttttatat tgaaccaaaa cctaaagagc ctact            45

<210> SEQ ID NO 194
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
agtatcaaaa tcatattgat gtttagtagg ctctttaggt tttgg            45

<210> SEQ ID NO 195
<211> LENGTH: 45
<212> TYPE: DNA
<213> ORGANISM: Artificial Sequence
<220> FEATURE:
<223> OTHER INFORMATION: Description of Artificial Sequence: Synthetic
```

```
                             oligonucleotide

<400> SEQUENCE: 195
aaacatcaat atgattttga tactgctaca gttttgggat tcttg              45

<210> SEQ ID NO 196
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
atctttatcc agaccatatt ttctcaagaa tcccaaaact gtagc              45

<210> SEQ ID NO 197
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
agaaaatatg gtctggataa agattttaaa atgaatatag aagct              45

<210> SEQ ID NO 198
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
atgttgtgcg agtgttgcat gattagcttc tatattcatt ttaaa              45

<210> SEQ ID NO 199
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aatcatgcaa cactcgcaca acatactttt caacatgaat tgaga              45

<210> SEQ ID NO 200
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
aaaaactccg ttatctctgg caactctcaa ttcatgttga aaagt              45

<210> SEQ ID NO 201
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 201
gttgccagag ataacggagt ttttggatct atcgatgcaa accag              45

<210> SEQ ID NO 202
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
atcccatcct agcaaaacgt ctccctggtt tgcatcgata gatcc              45

<210> SEQ ID NO 203
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggagacgttt tgctaggatg ggatactgat caatttccaa ctaac              45

<210> SEQ ID NO 204
<211> LENGTH: 45
<212> TYPE: DNA
<213> ORGANISM: Artificial Sequence
<220> FEATURE:
<221> NAME/KEY: source
<223> OTHER INFORMATION: /note=Description of Artificial Sequence:
      Synthetic oligonucleotide

<400> SEQUENCE: 204
catacacata gtagtatcat aaatgttagt tggaaattga tcagt              45

<210> SEQ ID NO 205
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
atttatgata ctactatgtg tatgtatgaa gtaattaagg cagga              45

<210> SEQ ID NO 206
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gtttaatccg ccattagtaa agcctcctgc cttaattact tcata              45

<210> SEQ ID NO 207
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
```

```
ggctttacta atggcggatt aaactttgat gcgaaggcta ggcgt            45
```

<210> SEQ ID NO 208
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208

```
tatatcctct ggagtgaaac taccacgcct agccttcgca tcaaa            45
```

<210> SEQ ID NO 209
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209

```
ggtagtttca ctccagagga tatattctat tcttatattg ctgga            45
```

<210> SEQ ID NO 210
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210

```
gaaacctaac gcgaaagcat ccattccagc aatataagaa tagaa            45
```

<210> SEQ ID NO 211
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

```
atggatgctt tcgcgttagg tttcagggca gcactaaaat tgatt            45
```

<210> SEQ ID NO 212
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212

```
cttatcaatt ctaccatctt caatcaattt tagtgctgcc ct               42
```

<210> SEQ ID NO 213
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213

```
gaagatggta gaattgataa gtttgtagct gatagatatg cttct            45
```

<210> SEQ ID NO 214
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tgctcctatt ccagtattcc aagaagcata tctatcagct acaaa            45

<210> SEQ ID NO 215
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tggaatactg gaataggagc agatataatc gctgggaaag ccgac            45

<210> SEQ ID NO 216
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
atatttttcc agactggcga agtcggcttt cccagcgatt atatc            45

<210> SEQ ID NO 217
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ttcgccagtc tggaaaaata tgcgcttgaa aaaggagaag ttact            45

<210> SEQ ID NO 218
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
acgaccggaa cttaagctgg cagtaacttc tccttttca agcgc            45

<210> SEQ ID NO 219
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gccagcttaa gttccggtcg tcaagaaatg ttggaatcta t                41

```
<210> SEQ ID NO 220
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
cagagaaaat aaaacattgt ttacaataga ttccaacatt tcttg             45

<210> SEQ ID NO 221
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
acttgactaa ctgaagcttc atatgatgga gttcttttct aatataggta aaatt     55

<210> SEQ ID NO 222
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
acttgactac tagtatggag ttcttttcta atataggtaa aatt                 44

<210> SEQ ID NO 223
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
acttgactaa ctgaagcttc atatgttgga cattgttacg gattatatta aagaa     55

<210> SEQ ID NO 224
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
acttgactaa ctgaagcttc atatgaaaca tcaatatgat tttgatactg ctaca     55

<210> SEQ ID NO 225
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
agttaagtga gtaaactagt gaattccaga gaaaataaaa cattgtttac aataga     56

<210> SEQ ID NO 226
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
agtcaagtct cgagctacag agaaaataaa acattgttta caataga                    47

<210> SEQ ID NO 227
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
agttaagtga gtaaactagt gaattccata ttagtgttta ataatgtttc ataacc          56

<210> SEQ ID NO 228
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
agttaagtga gtaaactagt gaattccata cacatagtag tatcataaat gttagt          56

<210> SEQ ID NO 229
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ggcgacaagt tcaagtgcct cttcggtaca gcaaag                                36

<210> SEQ ID NO 230
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ctttgctgta ccgaagaggc acttgaactt gtcgcc                                36

<210> SEQ ID NO 231
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
tcggcggtaa cggttacgtt agctggggcg gac                                   33

<210> SEQ ID NO 232
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 232
gtccgcccca gctaacgtaa ccgttaccgc cga                                      33

<210> SEQ ID NO 233
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
aacagtaaag ctcggcgcta acggttacgt tttct                                   35

<210> SEQ ID NO 234
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
agaaaacgta accgttagcg ccgagcttta ctgtt                                   35

<210> SEQ ID NO 235
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
aacagtaaag ctcggcgcta acggttacgt tagctggggc ggac                         44

<210> SEQ ID NO 236
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gtccgcccca gctaacgtaa ccgttagcgc cga                                     33

<210> SEQ ID NO 237
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gctaaggttg acgcagcaat ggagatcatg gataagctc                               39

<210> SEQ ID NO 238
<211> LENGTH: 39
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 238
gagcttatcc atgatctcca ttgctgcgtc aaccttagc                                    39

<210> SEQ ID NO 239
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ctaaggttga cgcagcatta gagatcatgg ataagctc                                     38

<210> SEQ ID NO 240
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
gagcttatcc atgatctcta atgctgcgtc aaccttag                                     38

<210> SEQ ID NO 241
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
agctaaccac gctacacttg ctacgcatac attccagcat g                                 41

<210> SEQ ID NO 242
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
catgctggaa tgtatgcgta gcaagtgtag cgtggttagc t                                 41

<210> SEQ ID NO 243
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gcgacaagtt caagtgcctc ataggtacag caaagtgctt cga                               43

<210> SEQ ID NO 244
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
tcgaagcact ttgctgtacc tatgaggcac ttgaacttgt cgc        43

<210> SEQ ID NO 245
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gcgacaagtt caagtgcctc tcgggtacag caa        33

<210> SEQ ID NO 246
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ttgctgtacc cgagaggcac ttgaacttgt cgc        33

<210> SEQ ID NO 247
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
gctaaccacg ctacacttgc tggtcataca ttccagcat        39

<210> SEQ ID NO 248
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
atgctggaat gtatgaccag caagtgtagc gtggttagc        39

<210> SEQ ID NO 249
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
cctcagaaag tacggtctcg ctaaggattt caagatgaat a        41

<210> SEQ ID NO 250
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tattcatctt gaaatcctta gcgagaccgt actttctgag g     41

<210> SEQ ID NO 251
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
cctcagaaag tacggtctcg agaaggattt caagatgaat atc     43

<210> SEQ ID NO 252
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gatattcatc ttgaaatcct tctcgagacc gtactttctg agg     43

<210> SEQ ID NO 253
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
gtcttatgaa gatggctggt gagtatggac gttcgat     37

<210> SEQ ID NO 254
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
atcgaacgtc catactcacc agccatcttc ataagac     37

<210> SEQ ID NO 255
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gtcaacagta aagctcggca gtaacggtta cgttagctgg     40

<210> SEQ ID NO 256
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ccagctaacg taaccgttac tgccgagctt tactgttgac     40

```
<210> SEQ ID NO 257
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ctagaactag taaaaaaatg gctaaggaat attattctaa tataggtaaa attcagtat        59

<210> SEQ ID NO 258
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
actatgagag aacatttaaa atttgctatg tcttggtggc atactwt                    47

<210> SEQ ID NO 259
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
agagaacatt taaaatttgc tttggcttgg tggcatactw tgkgtg                     46

<210> SEQ ID NO 260
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
actatgagag aacatttaaa atttgctatg gcttggtggc atactwtgkg tg              52

<210> SEQ ID NO 261
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ttgctttgtc ttggtggcat actttgkgtg stgatg                                36

<210> SEQ ID NO 262
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
cttggtggca tactatgtgt gstgatggta ctgats                                36

<210> SEQ ID NO 263
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gtggcatact atgggtgctg atggtactga tatgt                               35

<210> SEQ ID NO 264
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gtggcatact wtgkgtgctg atggtactga tcaat                               35

<210> SEQ ID NO 265
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gcatactwtg kgtgstgatg gtactgatca attcggttgt ggtact                   46

<210> SEQ ID NO 266
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gcaaaagcca aagtagatgc agccwtggaa attatggata aattgtctat tg            52

<210> SEQ ID NO 267
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ttatggataa attgtctatt gattattatt gttttcatga tgttgatttg tctcctgaat    60
atggttcttt aaaag                                                     75

<210> SEQ ID NO 268
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ttatggataa attgtctatt gattattatt gttttcatga tgttgatttg tctcctgaag    60
gtggttcttt aaaag                                                     75
```

<210> SEQ ID NO 269
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 269
gttttcatga tagagatttg tctcctgaag gtggttcttt aaaagcaact aatg    54

<210> SEQ ID NO 270
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 270
gttctttaaa agcaactaat gatcaattgg acattgttgt tgattatatt aaagaaaaac    60
aaggtgataa atttaaatg    79

<210> SEQ ID NO 271
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 271
gttctttaaa agcaactaat gatcaattgg acattgttgt tgattatatt aaagaaaaac    60
aaggtgatgg ttttaaatg    79

<210> SEQ ID NO 272
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 272
cggattatat taaagaaaaa caaggtgatg gttttaaatg tttgtkkggc actgcgaawt    60

<210> SEQ ID NO 273
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 273
ttatattaaa gaaaacaag gtgataaatt taaatgtttg tttggcactg cgaawtgttt    60
tgat    64

<210> SEQ ID NO 274
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

```
<400> SEQUENCE: 274
gtttgtgggg cactgcgaat tgttttgatc atcc                                    34

<210> SEQ ID NO 275
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ttttgatcat ccacgttata tgcatggtgc gggga                                   35

<210> SEQ ID NO 276
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggaatcaact gttaaattag gtagaaacgg gtatgtattc tgggga                       46

<210> SEQ ID NO 277
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gaatcaactg ttaaattagg tgctaacggg tatgtattct ggggag                       46

<210> SEQ ID NO 278
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ggaatcaact gttaaattag gtagaaacgg gtatgtatct tgggga                       46

<210> SEQ ID NO 279
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gaatcaactg ttaaattagg tgctaacggg tatgtatctt ggggag                       46

<210> SEQ ID NO 280
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
```

```
aaattaggtg ggaacgggta tgtatcttgg ggaggaaggg                    40
```

<210> SEQ ID NO 281
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281

```
cactaatatg ggtttggaat tggaaaatat ggctagattg atgaaaatg          49
```

<210> SEQ ID NO 282
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282

```
ggataatatg gctagattga tgaaaatggc tagagaatac ggaaggtcta         50
```

<210> SEQ ID NO 283
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283

```
gctagattga tgaaaatggc tggtgaatac ggaaggtcta ttggtt             46
```

<210> SEQ ID NO 284
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284

```
cagttttggg attcttgaga aaatatggtt tggctaaaga ttttaaaatg aatatagaag    60
cta                                                                 63
```

<210> SEQ ID NO 285
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285

```
agttttggga ttcttgagaa aatatggttt ggaaaaagat tttaaaatga atatagaagc    60
taa                                                                 63
```

<210> SEQ ID NO 286
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 286
atagaagcta atcatgcaac actcgcattt catactttc aacatgaatt gagagtt      57

<210> SEQ ID NO 287
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
atagaagcta atcatgcaac actcgcaact catactttc aacatgaatt gagagtt      57

<210> SEQ ID NO 288
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
agaagctaat catgcaacac tcgcaggtca tactttcaa catgaattga gag           53

<210> SEQ ID NO 289
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
taacggagtt tttggatctg ttgatgcaaa ccagggagac g                      41

<210> SEQ ID NO 290
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
taacggagtt tttggatctg ttgatgcaaa cagaggagac g                      41

<210> SEQ ID NO 291
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ttttggatct atcgatgcaa acagaggaga cgttttgcta ggatggg                47

<210> SEQ ID NO 292
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
```
aaggctaggc gtggtagttt cgatccagag gatatattct attc           44

<210> SEQ ID NO 293
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
cgaaggctag gcgtggtagt ttcgaaccag aggatatatt ctattctta     49

<210> SEQ ID NO 294
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cagggcagca ctaaaattga ttgaagaagg tagaattgat aagtttg       47

<210> SEQ ID NO 295
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tgggaaagcc gacttcgcca gtttggaaaa atatg                    35

<210> SEQ ID NO 296
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
atactgaatt ttacctatat tagaataata ttccttagcc atttttttac tagttctag  59

<210> SEQ ID NO 297
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
awagtatgcc accaagacat agcaaatttt aaatgttctc tcatagt       47

<210> SEQ ID NO 298
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
cacmcawagt atgccaccaa gccaaagcaa attttaaatg ttctct        46

```
<210> SEQ ID NO 299
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
cacmcawagt atgccaccaa gccatagcaa attttaaatg ttctctcata gt            52

<210> SEQ ID NO 300
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
catcascacm caaagtatgc caccaagaca aagcaa                              36

<210> SEQ ID NO 301
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
satcagtacc atcascacac atagtatgcc accaag                              36

<210> SEQ ID NO 302
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
acatatcagt accatcagca cccatagtat gccac                               35

<210> SEQ ID NO 303
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
attgatcagt accatcagca cmcawagtat gccac                               35

<210> SEQ ID NO 304
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
agtaccacaa ccgaattgat cagtaccatc ascacmcawa gtatgc                   46

<210> SEQ ID NO 305
```

```
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
caatagacaa tttatccata atttccawgg ctgcatctac tttggctttt gc            52

<210> SEQ ID NO 306
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
cttttaaaga accatattca ggagacaaat caacatcatg aaaacaataa taatcaatag    60
acaatttatc cataa                                                     75

<210> SEQ ID NO 307
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cttttaaaga accaccttca ggagacaaat caacatcatg aaaacaataa taatcaatag    60
acaatttatc cataa                                                     75

<210> SEQ ID NO 308
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
cattagttgc ttttaaagaa ccaccttcag gagacaaatc tctatcatga aaac          54

<210> SEQ ID NO 309
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
catttaaatt tatcaccttg tttttcttta atataatcaa caacaatgtc caattgatca    60
ttagttgctt ttaaagaac                                                 79

<210> SEQ ID NO 310
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
```

```
catttaaaac catcaccttg tttttcttta atataatcaa caacaatgtc caattgatca    60
ttagttgctt ttaaagaac                                                 79

<210> SEQ ID NO 311
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
awttcgcagt gccmmacaaa catttaaaac catcaccttg tttttcttta atataatccg    60

<210> SEQ ID NO 312
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
atcaaaacaw ttcgcagtgc caaacaaaca tttaaattta tccttgtt tttctttaat     60 ataa                                                                 64

<210> SEQ ID NO 313
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggatgatcaa aacaattcgc agtgccccac aaac                                34

<210> SEQ ID NO 314
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tccccgcacc atgcatataa cgtggatgat caaaa                               35

<210> SEQ ID NO 315
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tccccagaat acatacccgt ttctacctaa tttaacagtt gattcc                   46

<210> SEQ ID NO 316
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 316
ctccccagaa tacatacccg ttagcaccta atttaacagt tgattc            46

<210> SEQ ID NO 317
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tccccaagat acatacccgt ttctacctaa tttaacagtt gattcc            46

<210> SEQ ID NO 318
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
ctccccaaga tacatacccg ttagcaccta atttaacagt tgattc            46

<210> SEQ ID NO 319
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
cccttcctcc ccaagataca tacccgttcc cacctaattt            40

<210> SEQ ID NO 320
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cattttcatc aatctagcca tattttccaa ttccaaaccc atattagtg         49

<210> SEQ ID NO 321
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tagaccttcc gtattctcta gccattttca tcaatctagc catattatcc        50

<210> SEQ ID NO 322
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
```

```
aaccaataga ccttccgtat tcaccagcca ttttcatcaa tctagc                    46
```

<210> SEQ ID NO 323
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323

```
tagcttctat attcatttta aaatctttag ccaaaccata ttttctcaag aatcccaaaa    60
ctg                                                                   63
```

<210> SEQ ID NO 324
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324

```
ttagcttcta tattcatttt aaaatctttt tccaaaccat attttctcaa gaatcccaaa    60
act                                                                   63
```

<210> SEQ ID NO 325
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325

```
aactctcaat tcatgttgaa aagtatgaaa tgcgagtgtt gcatgattag cttctat       57
```

<210> SEQ ID NO 326
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326

```
aactctcaat tcatgttgaa aagtatgagt tgcgagtgtt gcatgattag cttctat       57
```

<210> SEQ ID NO 327
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327

```
ctctcaattc atgttgaaaa gtatgacctg cgagtgttgc atgattagct tct           53
```

<210> SEQ ID NO 328
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 328
cgtctccctg gtttgcatca acagatccaa aaactccgtt a                      41

<210> SEQ ID NO 329
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
cgtctcctct gtttgcatca acagatccaa aaactccgtt a                      41

<210> SEQ ID NO 330
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
cccatcctag caaaacgtct cctctgtttg catcgataga tccaaaa                 47

<210> SEQ ID NO 331
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gaatagaata tatcctctgg atcgaaacta ccacgcctag cctt                    44

<210> SEQ ID NO 332
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
taagaataga atatatcctc tggttcgaaa ctaccacgcc tagccttcg               49

<210> SEQ ID NO 333
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
caaacttatc aattctacct tcttcaatca attttagtgc tgccctg                 47

<210> SEQ ID NO 334
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
``` catattttc caaactggcg aagtcggctt tccca         35

<210> SEQ ID NO 335
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
cctgaaatta ttcccctact tgact         25

<210> SEQ ID NO 336
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ccttctcaag caaggttttc agtat         25

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
taaaacgacg gccagtgaat         20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tgcaggtcga ctctagagga t         21

<210> SEQ ID NO 339
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gtgtgcgtgt atgtgtacac ctgtatttaa tttccttact cgcgggtttt tctaaaacga         60
cggccagtga at         72

<210> SEQ ID NO 340
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340

```
tgtaccagtc tagaattcta ccaacaaatg gggaaatcaa agtaacttgg gctgcaggtc    60
gactctagag ga                                                       72

<210> SEQ ID NO 341
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gtcgactgga aatctggaag gttggt                                        26

<210> SEQ ID NO 342
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
gtcgacgctt tgctgcaagg attcat                                        26

<210> SEQ ID NO 343
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
actagtatga ctgttactac tccttttgtg aatggtac                           38

<210> SEQ ID NO 344
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
ctcgagttaa tcaactctct ttcttccaac caaatggtc                          39

<210> SEQ ID NO 345
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
aagcttttaa ttaatataac gctatgacgg tagttgaatg ttaaaaac                48

<210> SEQ ID NO 346
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
```
gaattcttaa ttaaagagaa caaagtattt aacgcacatg tataaatatt g            51

<210> SEQ ID NO 347
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
ggatccgcat gcggccggcc agcttttaat caaggaagta ataaataaag gac          53

<210> SEQ ID NO 348
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
ggatccgagc tcgcggccgc agcttttgaa caatgaattt tttgttcctt tc           52

<210> SEQ ID NO 349
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gcggccgcag cttcgcaagt attcatttta gacccatg                           38

<210> SEQ ID NO 350
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ggccggccgg taccaattcc acttgcaatt acataaaaaa ttcc                    44

<210> SEQ ID NO 351
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
ggatccgttt atcattatca atactcgcca tttcaaag                           38

<210> SEQ ID NO 352
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
catatgttgg gtaccggccg caaattaaag ccttcgagcg                         40

```
<210> SEQ ID NO 353
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
ggattcagtc agatcatatg ggtaccccccg ggttaattaa ggcgcgccag atctg          55

<210> SEQ ID NO 354
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
gtcgacaggc ctactgtacg gctagcgaat tcgagctcgt tttcgacact ggatggcggc     60

<210> SEQ ID NO 355
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
tctagactcg agtaataagc gaatttctta tgatttatg                            39

<210> SEQ ID NO 356
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
aagcttaggc ctggagcgat ttgcaggcat ttgc                                 34

<210> SEQ ID NO 357
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
ggatccgcta gcaccgcgaa tccttacatc acaccc                               36

<210> SEQ ID NO 358
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
tctagactcg agtaataagc gaatttctta tgatttatg                            39

<210> SEQ ID NO 359
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
gattgtactg agagtgcaca atatgcggtg tgaaatacc                             39

<210> SEQ ID NO 360
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
ggtatttcac accgcatatt gtgcactctc agtacaatc                             39

<210> SEQ ID NO 361
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
actagtaaaa aatgaaaaat tactttccaa atgttccaga agtacagtat cagggaccaa      60
aaag                                                                  64

<210> SEQ ID NO 362
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
actagtaaaa aatgactaag gaatatttcc caactatcgg caagattcag tatcagggac      60
caaaaag                                                               67

<210> SEQ ID NO 363
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
actagtaaaa aatggaatac ttcaaaaatg taccacaaat aaaacagtat cagggaccaa      60
aaag                                                                  64

<210> SEQ ID NO 364
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
```

```
actagtaaaa aatggcaaca aaagaattt ttccgggaat tgaaaagatt cagtatcagg      60
gaccaaaaag                                                            70
```

<210> SEQ ID NO 365
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365

```
actagtaaaa aatggcttat tttccgaata tcggcaagat tcagtatcag ggaccaaaaa     60
g                                                                     61
```

<210> SEQ ID NO 366
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366

```
actagtaaaa aatggctacc aaggaatact tcccaggtat tggtaagatc cagtatcagg     60
gaccaaaaag                                                            70
```

<210> SEQ ID NO 367
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367

```
actagtaaaa aatgtcagaa gtatttagcg gtatttcaaa cattcagtat cagggaccaa     60
aaag                                                                  64
```

<210> SEQ ID NO 368
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368

```
actagtaaaa aatggaattt ttcaagaaca taagcaagat ccagtatcag ggaccaaaaa     60
g                                                                     61
```

<210> SEQ ID NO 369
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369

```
actagtaaaa aatgagcgaa tttttacag gcatttcaaa gatccagtat cagggaccaa      60
aaag                                                                  64
```

```
<210> SEQ ID NO 370
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
actagtaaaa aatgaaattt tttgaaaatg tccctaaggt acagtatcag ggaccaaaaa      60
g                                                                     61

<210> SEQ ID NO 371
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
cctattttga ccagctcgat cgcgttcagt atcagggacc aaaaagtact gatcctctc      59

<210> SEQ ID NO 372
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
actagtaaaa aaatgcaagc ctattttgac cagctcgatc gcgttcagta tcagg          55

<210> SEQ ID NO 373
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ctcgagttac agactgaaaa gaacgttatt tacg                                 34

<210> SEQ ID NO 374
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ctcgagttag tgatggtggt ggtgatgcag actgaaaaga acgttattta cg             52

<210> SEQ ID NO 375
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gtgcgtcagg tgatctgggt aagaagaaga cttttccc                             38
```

```
<210> SEQ ID NO 376
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gggaaaagtc ttcttcttac ccagatcacc tgacgcac                              38

<210> SEQ ID NO 377
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gtgatctggg taagaagaag ggttttcccg ccttatttgg                            40

<210> SEQ ID NO 378
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ccaaataagg cgggaaaacc cttcttctta cccagatcac                            40

<210> SEQ ID NO 379
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ccttgatcca tctaccaaga tcttcggtta taatcggtcc aaattgtcca t               51

<210> SEQ ID NO 380
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
atggacaatt tggaccgatt ataaccgaag atcttggtag atggatcaag g               51

<210> SEQ ID NO 381
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
atctaccaag atcttcggtt atgatcggtc caaattgtcc atg                        43

<210> SEQ ID NO 382
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
catggacaat ttggaccgat cataaccgaa gatcttggta gat                    43

<210> SEQ ID NO 383
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ggtgatctgg caaagaagaa gttttttccc gccttatttg gg                     42

<210> SEQ ID NO 384
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cccaaataag gcgggaaaaa acttcttctt tgccagatca cc                     42

<210> SEQ ID NO 385
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
taccttgatc catctaccag aatcttcggt tatgcccggt                        40

<210> SEQ ID NO 386
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
accgggcata accgaagatt ctggtagatg gatcaaggta                        40

<210> SEQ ID NO 387
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gggcttttca gagaaggttt gcttgatcca tctaccaaga                        40

<210> SEQ ID NO 388
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 388
tcttggtaga tggatcaagc aaaccttctc tgaaaagccc                                40

<210> SEQ ID NO 389
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gaagaagact tttcccgcct tatacgggct tttcagagaa g                              41

<210> SEQ ID NO 390
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
cttctctgaa aagcccgtat aaggcgggaa aagtcttctt c                              41

<210> SEQ ID NO 391
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gtcaggtgat ctggcaaaga agaagttgtt tcccgcctta tttgg                          45

<210> SEQ ID NO 392
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ccaaataagg cgggaaacaa cttcttcttt gccagatcac ctgac                          45

<210> SEQ ID NO 393
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
cgaaaaaaat accgtcatat ctttgtttgg tgcgtcaggt gatctg                         46

<210> SEQ ID NO 394
<211> LENGTH: 46
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 394
cagatcacct gacgcaccaa acaaagatat gacggtattt ttttcg            46

<210> SEQ ID NO 395
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gacctgaagt cccgtgtcga accccacttg aaaaaacc                     38

<210> SEQ ID NO 396
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396 ggtttttca agtggggttc gacacgggac ttcaggtc                      38

<210> SEQ ID NO 397
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gtgcgtcagg tgatctgggt aagaagaaga cttttccc                     38

<210> SEQ ID NO 398
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gggaaaagtc ttcttcttac ccagatcacc tgacgcac                     38

<210> SEQ ID NO 399
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gtgcgtcagg tgatctgggt aagaagaaga cttttccc                     38

<210> SEQ ID NO 400
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 400
gggaaaagtc ttcttcttac ccagatcacc tgacgcac                                  38

<210> SEQ ID NO 401
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
accaagatct tcggttatgc cgattccaaa ttgtccatgg aggag                          45

<210> SEQ ID NO 402
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
ctcctccatg gacaatttgg aatcggcata accgaagatc ttggt                          45

<210> SEQ ID NO 403
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tccatctacc aagatcttcg gttatgatgc ttccaaattg tccatggagg aggac              55

<210> SEQ ID NO 404
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gtcctcctcc atggacaatt tggaagcatc ataaccgaag atcttggtag atgga              55

<210> SEQ ID NO 405
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
tccatctacc aagatcttcg gttatgatgc ttccaaattg tccatggagg aggac              55

<210> SEQ ID NO 406
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
```

```
gtcctcctcc atggacaatt tggaagcatc ataaccgaag atcttggtag atgga        55
```

<210> SEQ ID NO 407
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407

```
tccatctacc aagatcttcg gttatgatgc ttccaaattg tccatggagg aggac        55
```

<210> SEQ ID NO 408
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408

```
gtcctcctcc atggacaatt tggaagcatc ataaccgaag atcttggtag atgga        55
```

<210> SEQ ID NO 409
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409

```
aagatcttcg gttatgatca ttccaaattg tccatggagg                        40
```

<210> SEQ ID NO 410
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410

```
cctccatgga caatttggaa tgatcataac cgaagatctt                        40
```

<210> SEQ ID NO 411
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411

```
aagatcttcg gttatgccca ttccaaattg tccatggagg                        40
```

<210> SEQ ID NO 412
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412

```
cctccatgga caatttggaa tgggcataac cgaagatctt                        40
```

<210> SEQ ID NO 413
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
gctagcatgg tgacagtcgg tgtgttttct gag         33

<210> SEQ ID NO 414
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 414
gtcgacctaa aaagttttcg tttgaactttt tcc         33

<210> SEQ ID NO 415
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 415
ccaacactaa gaaataattt cgccatttct tg         32

<210> SEQ ID NO 416
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 416
gccaacaatt aaatccaagt tcacctattc tg         32

<210> SEQ ID NO 417
<211> LENGTH: 777
<212> TYPE: DNA
<213> ORGANISM: Saccharomyces cerevisiae

<400> SEQUENCE: 417
atggctgccg gtgtcccaaa aattgatgcg ttagaatctt tgggcaatcc tttggaggat         60
gccaagagag ctgcagcata cagagcagtt gatgaaaatt taaaatttga tgatcacaaa        120
attattggaa ttggtagtgg tagcacagtg gtttatgttg ccgaaagaat tggacaatat        180
ttgcatgacc ctaaatttta tgaagtagcg tctaaattca tttgcattcc aacaggattc        240
caatcaagaa acttgatttt ggataacaag ttgcaattag ctccattga acagtatcct        300 cgcattgata tagcgtttga cggtgctgat gaagtggatg agaatttaca attaattaaa        360
ggtggtggtg cttgtctatt tcaagaaaaa ttggttagta ctagtgctaa aaccttcatt        420
gtcgttgctg attcaagaaa aaagtcacca aaacatttag gtaagaactg gaggcaaggt        480
gttcccattg aaattgtacc ttcctcatac gtgagggtca agaatgatct attagaacaa        540
ttgcatgctg aaaaagttga catcagacaa ggaggttctg ctaaagcagg tcctgttgta        600

```
actgacaata ataacttcat tatcgatgcg gatttcggtg aaatttccga tccaagaaaa      660
ttgcatagag aaatcaaact gttagtgggc gtggtggaaa caggtttatt catcgacaac      720
gcttcaaaag cctacttcgg taattctgac ggtagtgttg aagttaccga aaagtga        777
```

<210> SEQ ID NO 418
<211> LENGTH: 258
<212> TYPE: PRT
<213> ORGANISM: Saccharomyces cerevisiae

<400> SEQUENCE: 418

```
Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
                20                  25                  30

Asn Leu Lys Phe Asp Asp His Lys Ile Ile Gly Ile Gly Ser Gly Ser
            35                  40                  45

Thr Val Val Tyr Val Ala Glu Arg Ile Gly Gln Tyr Leu His Asp Pro
        50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
                100                 105                 110

Asp Glu Asn Leu Gln Leu Ile Lys Gly Gly Gly Ala Cys Leu Phe Gln
            115                 120                 125

Glu Lys Leu Val Ser Thr Ser Ala Lys Thr Phe Ile Val Val Ala Asp
        130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255

Glu Lys
```

<210> SEQ ID NO 419
<211> LENGTH: 717
<212> TYPE: DNA
<213> ORGANISM: Saccharomyces cerevisiae

<400> SEQUENCE: 419

```
atggtcaaac caattatagc tcccagtatc cttgcttctg acttcgccaa cttgggttgc      60
gaatgtcata aggtcatcaa cgccggcgca gattggttac atatcgatgt catggacggc     120
cattttgttc caaacattac tctgggccaa ccaattgtta cctccctacg tcgttctgtg     180
ccacgccctg gcgatgctag caacacagaa aagaagccca ctgcgttctt cgattgtcac     240
```

```
atgatggttg aaaatcctga aaaatgggtc gacgattttg ctaaatgtgg tgctgaccaa      300
tttacgttcc actacgaggc cacacaagac cctttgcatt tagttaagtt gattaagtct      360
aagggcatca aagctgcatg cgccatcaaa cctggtactt ctgttgacgt tttatttgaa      420
ctagctcctc atttggatat ggctcttgtt atgactgtgg aacctgggtt tggaggccaa      480
aaattcatgg aagacatgat gccaaaagtg aaactttga gagccaagtt ccccccatttg      540 aatatccaag tcgatggtgg tttgggcaag agaccatcc cgaaagccgc caaagccggt       600
gccaacgtta ttgtcgctgg taccagtgtt tcactgcag ctgacccgca cgatgttatc       660
tccttcatga agaagaagt ctcgaaggaa ttgcgttcta gagatttgct agattag          717
```

<210> SEQ ID NO 420
<211> LENGTH: 238
<212> TYPE: PRT
<213> ORGANISM: Saccharomyces cerevisiae

<400> SEQUENCE: 420

```
Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
    210                 215                 220

Glu Glu Val Ser Lys Glu Leu Arg Ser Arg Asp Leu Leu Asp
225                 230                 235
```

<210> SEQ ID NO 421
<211> LENGTH: 1803
<212> TYPE: DNA
<213> ORGANISM: Saccharomyces cerevisiae

<400> SEQUENCE: 421

```
atgttgtgtt cagtaattca gagacagaca agagaggttt ccaacacaat gtctttagac      60
tcatactatc ttgggtttga tctttcgacc caacaactga aatgtctcgc cattaaccag     120
```

```
gacctaaaaa ttgtccattc agaaacagtg gaatttgaaa aggatcttcc gcattatcac      180
acaaagaagg gtgtctatat acacggcgac actatcgaat gtcccgtagc catgtggtta      240
gaggctctag atctggttct ctcgaaatat cgcgaggcta aatttccatt gaacaaagtt      300
atggccgtct cagggtcctg ccagcagcac gggtctgtct actggtcctc ccaagccgaa      360
tctctgttag agcaattgaa taagaaaccg gaaaaagatt tattgcacta cgtgagctct      420
gtagcatttg caaggcaaac cgcccccaat tggcaagacc acagtactgc aaagcaatgt      480
caagagtttg aagagtgcat aggtgggcct gaaaaaatgg ctcaattaac agggtccaga      540
gcccatttta gatttactgg tcctcaaatt ctgaaaattg cacaattaga accagaagct      600
tacgaaaaaa caaagaccat ttctttagtg tctaattttt tgacttctat cttagtgggc      660
catcttgttg aattagagga ggcagatgcc tgtggtatga acctttatga tatacgtgaa      720
agaaaattca gtgatgagct actacatcta attgatagtt cttctaagga taaaactatc      780
agacaaaaat taatgagagc acccatgaaa aatttgatag cgggtaccat ctgtaaatat      840
tttattgaga agtacggttt caatacaaac tgcaaggtct ctcccatgac tggggataat      900
ttagccacta tatgttcttt accccctgcgg aagaatgacg ttctcgtttc cctaggaaca      960
agtactacag ttcttctggt caccgataag tatcacccct ctccgaacta tcatcttttc     1020
attcatccaa ctctgccaaa ccattatatg ggtatgattt gttattgtaa tggttctttg     1080
gcaagggaga ggataagaga cgagttaaac aaagaacggg aaaataatta tgagaagact     1140
aacgattgga ctctttttaa tcaagctgtg ctagatgact cagaaagtag tgaaaatgaa     1200
ttaggtgtat attttcctct gggggagatc gttcctagcg taaaagccat aaacaaagg      1260 gttatcttca atccaaaaac gggtatgatt gaaagagagg tggccaagtt caaagacaag     1320
aggcacgatg ccaaaaatat tgtagaatca caggctttaa gttgcagggt aagaatatct     1380
cccctgcttt cggattcaaa cgcaagctca aacagagac tgaacgaaga tacaatcgtg      1440
aagtttgatt acgatgaatc tccgctgcgg gactacctaa ataaaaggcc agaaaggact     1500 tttttttgtag gtggggcttc taaaaacgat gctattgtga agaagtttgc tcaagtcatt     1560
ggtgctacaa agggtaattt taggctagaa acaccaaact catgtgccct tggtggttgt     1620
tataaggcca tgtggtcatt gttatatgac tctaataaaa ttgcagttcc ttttgataaa     1680
tttctgaatg acaattttcc atggcatgta atggaaagca tatccgatgt ggataatgaa     1740
aattgggatc gctataattc caagattgtc cccttaagcg aactggaaaa gactctcatc     1800
taa                                                                   1803
```

<210> SEQ ID NO 422
<211> LENGTH: 600
<212> TYPE: PRT
<213> ORGANISM: Saccharomyces cerevisiae

<400> SEQUENCE: 422

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
```

```
             65                  70                  75                  80
Glu Ala Leu Asp Leu Val Leu Ser Lys Tyr Arg Glu Ala Lys Phe Pro
                     85                  90                  95
Leu Asn Lys Val Met Ala Val Ser Gly Ser Cys Gln Gln His Gly Ser
                    100                 105                 110
Val Tyr Trp Ser Ser Gln Ala Glu Ser Leu Leu Glu Gln Leu Asn Lys
                115                 120                 125
Lys Pro Glu Lys Asp Leu Leu His Tyr Val Ser Ser Val Ala Phe Ala
130                 135                 140
Arg Gln Thr Ala Pro Asn Trp Gln Asp His Ser Thr Ala Lys Gln Cys
145                 150                 155                 160
Gln Glu Phe Glu Glu Cys Ile Gly Gly Pro Glu Lys Met Ala Gln Leu
                165                 170                 175
Thr Gly Ser Arg Ala His Phe Arg Phe Thr Gly Pro Gln Ile Leu Lys
                180                 185                 190
Ile Ala Gln Leu Glu Pro Glu Ala Tyr Glu Lys Thr Lys Thr Ile Ser
                195                 200                 205
Leu Val Ser Asn Phe Leu Thr Ser Ile Leu Val Gly His Leu Val Glu
210                 215                 220
Leu Glu Glu Ala Asp Ala Cys Gly Met Asn Leu Tyr Asp Ile Arg Glu
225                 230                 235                 240
Arg Lys Phe Ser Asp Glu Leu Leu His Leu Ile Asp Ser Ser Ser Lys
                245                 250                 255
Asp Lys Thr Ile Arg Gln Lys Leu Met Arg Ala Pro Met Lys Asn Leu
                260                 265                 270
Ile Ala Gly Thr Ile Cys Lys Tyr Phe Ile Glu Lys Tyr Gly Phe Asn
                275                 280                 285
Thr Asn Cys Lys Val Ser Pro Met Thr Gly Asp Asn Leu Ala Thr Ile
                290                 295                 300
Cys Ser Leu Pro Leu Arg Lys Asn Asp Val Leu Val Ser Leu Gly Thr
305                 310                 315                 320
Ser Thr Thr Val Leu Leu Val Thr Asp Lys Tyr His Pro Ser Pro Asn
                325                 330                 335
Tyr His Leu Phe Ile His Pro Thr Leu Pro Asn His Tyr Met Gly Met
                340                 345                 350
Ile Cys Tyr Cys Asn Gly Ser Leu Ala Arg Glu Arg Ile Arg Asp Glu
                355                 360                 365
Leu Asn Lys Glu Arg Glu Asn Asn Tyr Glu Lys Thr Asn Asp Trp Thr
                370                 375                 380
Leu Phe Asn Gln Ala Val Leu Asp Asp Ser Glu Ser Ser Glu Asn Glu
385                 390                 395                 400
Leu Gly Val Tyr Phe Pro Leu Gly Glu Ile Val Pro Ser Val Lys Ala
                405                 410                 415
Ile Asn Lys Arg Val Ile Phe Asn Pro Lys Thr Gly Met Ile Glu Arg
                420                 425                 430
Glu Val Ala Lys Phe Lys Asp Lys Arg His Asp Ala Lys Asn Ile Val
                435                 440                 445
Glu Ser Gln Ala Leu Ser Cys Arg Val Arg Ile Ser Pro Leu Leu Ser
                450                 455                 460
Asp Ser Asn Ala Ser Ser Gln Gln Arg Leu Asn Glu Asp Thr Ile Val
465                 470                 475                 480
Lys Phe Asp Tyr Asp Glu Ser Pro Leu Arg Asp Tyr Leu Asn Lys Arg
                485                 490                 495
```

-continued

```
Pro Glu Arg Thr Phe Phe Val Gly Gly Ala Ser Lys Asn Asp Ala Ile
                500                 505                 510
Val Lys Lys Phe Ala Gln Val Ile Gly Ala Thr Lys Gly Asn Phe Arg
            515                 520                 525
Leu Glu Thr Pro Asn Ser Cys Ala Leu Gly Gly Cys Tyr Lys Ala Met
        530                 535                 540
Trp Ser Leu Leu Tyr Asp Ser Asn Lys Ile Ala Val Pro Phe Asp Lys
545                 550                 555                 560
Phe Leu Asn Asp Asn Phe Pro Trp His Val Met Glu Ser Ile Ser Asp
                565                 570                 575
Val Asp Asn Glu Asn Trp Asp Arg Tyr Asn Ser Lys Ile Val Pro Leu
            580                 585                 590
Ser Glu Leu Glu Lys Thr Leu Ile
        595                 600
```

<210> SEQ ID NO 423
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
actagtatgt ctgacaagga acaaacgagc                                30

<210> SEQ ID NO 424
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
ctcgagttaa aagattaccc tttcagtaga tggtaatg                       38

<210> SEQ ID NO 425
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
caagcctttg gtggtaccca gaatccaggg ttagctcc                       38

<210> SEQ ID NO 426
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
ggagctaacc ctggattctg ggtaccacca aaggcttg                       38

<210> SEQ ID NO 427
<211> LENGTH: 37
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 427
ggtacaacgc atatgcagat gttgctacaa agcagaa          37

<210> SEQ ID NO 428
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
ttctgctttg tagcaacatc tgcatatgcg ttgtacc          37

<210> SEQ ID NO 429
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
gacgacgtct agaaaagaat actggagaaa tgaaaagaaa ac          42

<210> SEQ ID NO 430
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
gcatgcttaa ttaatgcgag gcatatttat ggtgaagg          38

<210> SEQ ID NO 431
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
ggccggccag atctgcggcc gcggccagca aaactaaaaa actgtattat aag          53

<210> SEQ ID NO 432
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
gcggccgcag atctggccgg ccgatttatc ttcgtttcct gcaggttttt g          51

<210> SEQ ID NO 433
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 433
gaattcttaa ttaactttg ttccactact ttttggaact cttg                    44

<210> SEQ ID NO 434
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
gcatgcgcgg ccgcacgtcg gcaggcccg                                    29

<210> SEQ ID NO 435
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
cgaaggacgc gcgaccaagt ttatcattat caatactcgc catttc                 46

<210> SEQ ID NO 436
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
gaaatggcga gtattgataa tgataaactt ggtcgcgcgt ccttcg                 46

<210> SEQ ID NO 437
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 437
gtcgacccgc aaattaaagc cttcgagc                                     28

<210> SEQ ID NO 438
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
gtcgacgtac ccccgggtta attaaggcg                                    29

<210> SEQ ID NO 439
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
```
gtcgaaaacg agctcgaatt cgacgtcggc aggcccg            37

<210> SEQ ID NO 440
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
cgggcctgcc gacgtcgaat tcgagctcgt tttcgac            37

<210> SEQ ID NO 441
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
ggatccgcgg ccgctggtcg cgcgtccttc g            31

<210> SEQ ID NO 442
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
gagggcacag ttaagccgct aaagg            25

<210> SEQ ID NO 443
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
gtcaacagta cccttagtat attctccagt agctagggag            40

<210> SEQ ID NO 444
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
cgttacccaa ttgaacacgg tattgtcac            29

<210> SEQ ID NO 445
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
gaagattgag cagcggtttg catttc            26

<210> SEQ ID NO 446
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
gagtcaaacg acgttgaaat tgaggctact gc                                    32

<210> SEQ ID NO 447
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
gattactgct gctgttccag cccatatcca ac                                    32

<210> SEQ ID NO 448
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
ggcaatcaaa ttgggaacga acaatg                                           26

<210> SEQ ID NO 449
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
ctcaaggtat cctcatggcc aagcaatac                                        29

<210> SEQ ID NO 450
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
gggtctacaa actgttgttg tcgaagaaga tg                                    32

<210> SEQ ID NO 451
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
cattcagttc caatgattta ttgacagtgc ac                                    32

<210> SEQ ID NO 452

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
cctacccgcc tcggatccca gctacc                                          26

<210> SEQ ID NO 453
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
ggtagctggg atccgaggcg ggtagg                                          26

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
cctcccggca cagcgtgtcg atgc                                            24

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
cgaagccctg gagcgcttcg c                                               21

<210> SEQ ID NO 456
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
gtggtcagga ttgattctgc acttgttttc cag                                  33

<210> SEQ ID NO 457
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
cgcgtgaagc tgtagaaggc gctaag                                          26

<210> SEQ ID NO 458
<211> LENGTH: 29
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 458
gagctcggcc gcaaattaaa gccttcgag                                         29

<210> SEQ ID NO 459
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
ggccggccgt ttatcattat caatactcgc catttcaaag aatacg                      46

<210> SEQ ID NO 460
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
gttcactgca ctagtaaaaa aatggtattg tcacacatcg aag                         43

<210> SEQ ID NO 461
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
cttcgagatc tcgagttact gttttgctgc ttcaacaaat tg                          42

<210> SEQ ID NO 462
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
gttcactgca ctagtaaaaa aatggagtcc aaagtcgttg aaaacc                      46

<210> SEQ ID NO 463
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
cttcgagatc tcgagttaca cttggaaaac agcctgcaaa tcc                         43

<210> SEQ ID NO 464
<211> LENGTH: 42
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 464
gttcactgca ctagtaaaaa aatgacaaac ctcgccccga cc                        42

<210> SEQ ID NO 465
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
cttcgagatc tcgagtcagt ccagcagggc cagg                                 34

<210> SEQ ID NO 466
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
gttcactgca ctagtaaaaa aatgacacag aacgaaaata atcagccgc                 49

<210> SEQ ID NO 467
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
cttcgagatc tcgagtcagt caaacagcgc cagcgc                               36

<210> SEQ ID NO 468
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
gttcactgca ctagtaaaaa aatggctatt acaaaagaat ttttagctcc ag             52

<210> SEQ ID NO 469
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
cttcgagatc tcgagttagc tagaaatttt agcggtagtt gcc                       43

<210> SEQ ID NO 470
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
gttcactgca ctagtaaaaa aatgacgatt gcccagaccc ag                42

<210> SEQ ID NO 471
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
cttcgagatc tcgagtcagc ccgcccgcac c                            31

<210> SEQ ID NO 472
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
gttcactgcc atatgaatcc acaattgtta cgcgtaacaa atcgaatcat tg      52

<210> SEQ ID NO 473
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
cttcgagatc tcgagttaaa aagtgataca ggttgcgccc tgttcggc          48

<210> SEQ ID NO 474
<211> LENGTH: 630
<212> TYPE: DNA
<213> ORGANISM: Saccharophagus degradans

<400> SEQUENCE: 474
atggctatta caaagaatt tttagctcca gttggcgtaa tgcctgttgt ggttgtggat     60
cgtgtagaag atgcggtgcc tattacaaac gcattaaaag ccggcggtat taaagcagtt   120
gagattactt tacgtactcc tgcggcactg gatgctattc gcgctattaa agctgagtgt   180
gaagacatcc tggtgggggt aggtacggtt attaaccatc aaaaccttaa agatattgct   240
gcaattggtg ttgatttcgc cgtatctcct ggttacaccc caacattgct gaagcaagcg   300
caagatttgg gcgtagaaat gttgcctggt gtaacttcgc cttctgaagt tatgcttggt   360
atggagctag gtttgtcttg cttcaagcta ttccctgcgg ttgcagtagg tggtttgcca   420
ttacttaagt ctattggtgg cccattacca caggtttcct tctgtccaac aggcggtttg   480
actatcgata cttctaccga cttcttggca ttgcctaacg ttgcttgtgt gggtggtact   540
tggttggtgc ctgcagatgc tgttgcagct aaaaaactggc aagctattac tgatattgcg   600
gcggcaacta ccgctaaaat ttctagctaa                                    630

<210> SEQ ID NO 475
<211> LENGTH: 209
<212> TYPE: PRT
<213> ORGANISM: Saccharophagus degradans

<400> SEQUENCE: 475

```
Met Ala Ile Thr Lys Glu Phe Leu Ala Pro Val Gly Val Met Pro Val
1               5                   10                  15

Val Val Val Asp Arg Val Glu Asp Ala Val Pro Ile Thr Asn Ala Leu
            20                  25                  30

Lys Ala Gly Gly Ile Lys Ala Val Glu Ile Thr Leu Arg Thr Pro Ala
        35                  40                  45

Ala Leu Asp Ala Ile Arg Ala Ile Lys Ala Glu Cys Glu Asp Ile Leu
    50                  55                  60

Val Gly Val Gly Thr Val Ile Asn His Gln Asn Leu Lys Asp Ile Ala
65                  70                  75                  80

Ala Ile Gly Val Asp Phe Ala Val Ser Pro Gly Tyr Thr Pro Thr Leu
                85                  90                  95

Leu Lys Gln Ala Gln Asp Leu Gly Val Glu Met Leu Pro Gly Val Thr
            100                 105                 110

Ser Pro Ser Glu Val Met Leu Gly Met Glu Leu Gly Leu Ser Cys Phe
        115                 120                 125

Lys Leu Phe Pro Ala Val Ala Val Gly Gly Leu Pro Leu Leu Lys Ser
    130                 135                 140

Ile Gly Gly Pro Leu Pro Gln Val Ser Phe Cys Pro Thr Gly Gly Leu
145                 150                 155                 160

Thr Ile Asp Thr Phe Thr Asp Phe Leu Ala Leu Pro Asn Val Ala Cys
                165                 170                 175

Val Gly Gly Thr Trp Leu Val Pro Ala Asp Ala Val Ala Ala Lys Asn
            180                 185                 190

Trp Gln Ala Ile Thr Asp Ile Ala Ala Ala Thr Thr Ala Lys Ile Ser
        195                 200                 205

Ser
```

<210> SEQ ID NO 476
<211> LENGTH: 660
<212> TYPE: DNA
<213> ORGANISM: Xanthomonas axonopodis

<400> SEQUENCE: 476

```
atgacgattg cccagaccca gaacaccgcc gaacagttgc tgcgcgatgc cggcatcttg      60
cccgtggtca ccgtggacac gctggatcag gcgcgccgcg tcgccgatgc gttgctcgaa     120
ggcggcctgc ccgcgatcga gctgaccctt cgcacgccag tggcgatcga cgcgctggcg     180
atgctcaagc gcgagcttcc taacatcttg atcggtgccg gcaccgtgct gagcgaattg     240
cagctgcgtc agtcggtgga tgccggtgca gacttcctgg tgaccccggg cacgccggcg     300
ccgctggcgc gcctgctggc ggatgcgccg atcccggccg ttcccggcgc ggccactccg     360
accgagctgc tgaccttgat gggtcttggc tttcgcgtct gcaagctgtt cccggccacc     420
gccgtgggcg gtctgcagat gctcaggggc ctggccggcc cgctgtccga gctcaagctg     480
tgccccaccg gcggcatcag cgaggccaac gccgccgagt tcctgtcgca gccgaacgtg     540
ctgtgcatcg gcggttcgtg gatggtcccc aaggattggc tggcgcacgg ccaatgggac     600
aaggtcaagg aaagctcggc caaggcggcg gcgatcgtgc ggcaggtgcg ggcgggctga     660
```

<210> SEQ ID NO 477
<211> LENGTH: 219
<212> TYPE: PRT
<213> ORGANISM: Xanthomonas axonopodis

<400> SEQUENCE: 477

Met Thr Ile Ala Gln Thr Gln Asn Thr Ala Glu Gln Leu Leu Arg Asp
1               5                   10                  15

Ala Gly Ile Leu Pro Val Val Thr Val Asp Thr Leu Asp Gln Ala Arg
            20                  25                  30

Arg Val Ala Asp Ala Leu Leu Glu Gly Gly Leu Pro Ala Ile Glu Leu
        35                  40                  45

Thr Leu Arg Thr Pro Val Ala Ile Asp Ala Leu Ala Met Leu Lys Arg
50                  55                  60

Glu Leu Pro Asn Ile Leu Ile Gly Ala Gly Thr Val Leu Ser Glu Leu
65                  70                  75                  80

Gln Leu Arg Gln Ser Val Asp Ala Gly Ala Asp Phe Leu Val Thr Pro
                85                  90                  95

Gly Thr Pro Ala Pro Leu Ala Arg Leu Leu Ala Asp Ala Pro Ile Pro
            100                 105                 110

Ala Val Pro Gly Ala Ala Thr Pro Thr Glu Leu Leu Thr Leu Met Gly
        115                 120                 125

Leu Gly Phe Arg Val Cys Lys Leu Phe Pro Ala Thr Ala Val Gly Gly
130                 135                 140

Leu Gln Met Leu Arg Gly Leu Ala Gly Pro Leu Ser Glu Leu Lys Leu
145                 150                 155                 160

Cys Pro Thr Gly Gly Ile Ser Glu Ala Asn Ala Ala Glu Phe Leu Ser
                165                 170                 175

Gln Pro Asn Val Leu Cys Ile Gly Gly Ser Trp Met Val Pro Lys Asp
            180                 185                 190

Trp Leu Ala His Gly Gln Trp Asp Lys Val Lys Glu Ser Ser Ala Lys
        195                 200                 205

Ala Ala Ala Ile Val Arg Gln Val Arg Ala Gly
    210                 215

<210> SEQ ID NO 478
<211> LENGTH: 675
<212> TYPE: DNA
<213> ORGANISM: Pseudomonas syringiae

<400> SEQUENCE: 478
atgacacaga acgaaaataa tcagccgctc accagcatgg cgaacaagat tgcccggatc        60
gacgaactct gcgccaaggc aaagattctg ccggtcatca ccattgcccg tgatcaggac       120
gtattgccac tggccgacgc gctggccgct ggtggcatga cggctctgga aatcaccctg       180
cgctcggcgt tcggactgag tgcgatccgc attttgcgcg agcagcgccc agagctgtgc       240
actggcgccg ggaccattct ggaccgcaag atgctggccg acgccgaggc ggcgggctcg       300
caattcattg tgaccccggg cagcacgcag gaactgttgc aggcggcgct cgacagcccg       360
ttgcccctgt tgccaggcgt cagcagcgcg tcggaaatca tgatcggcta tgccttgggt       420
tatcgccgct tcaagctgtt cccggcagaa atcagcggcg gtgtggcagc gatcaaggcc       480
ttgggcgggc ctttcaacga ggtgcgtttc tgcccgacgg gcggcgtcaa cgagcagaac       540
ctcaagaact acatggcctt gcccaacgtc atgtgcgtcg gcgggacatg gatgattgat       600
aacgcctggg tcaagaatgg cgactggggc cgcattcagg aagccacggc acaggcgctg       660
gcgctgtttg actga                                                       675

<210> SEQ ID NO 479
<211> LENGTH: 224
<212> TYPE: PRT
<213> ORGANISM: Pseudomonas syringiae

<400> SEQUENCE: 479

```
Met Thr Gln Asn Glu Asn Asn Gln Pro Leu Thr Ser Met Ala Asn Lys
1               5                   10                  15
Ile Ala Arg Ile Asp Glu Leu Cys Ala Lys Ala Lys Ile Leu Pro Val
            20                  25                  30
Ile Thr Ile Ala Arg Asp Gln Asp Val Leu Pro Leu Ala Asp Ala Leu
        35                  40                  45
Ala Ala Gly Gly Met Thr Ala Leu Glu Ile Thr Leu Arg Ser Ala Phe
    50                  55                  60
Gly Leu Ser Ala Ile Arg Ile Leu Arg Glu Gln Arg Pro Glu Leu Cys
65                  70                  75                  80
Thr Gly Ala Gly Thr Ile Leu Asp Arg Lys Met Leu Ala Asp Ala Glu
                85                  90                  95
Ala Ala Gly Ser Gln Phe Ile Val Thr Pro Gly Ser Thr Gln Glu Leu
            100                 105                 110
Leu Gln Ala Ala Leu Asp Ser Pro Leu Pro Leu Pro Gly Val Ser
        115                 120                 125
Ser Ala Ser Glu Ile Met Ile Gly Tyr Ala Leu Gly Tyr Arg Arg Phe
    130                 135                 140
Lys Leu Phe Pro Ala Glu Ile Ser Gly Gly Val Ala Ala Ile Lys Ala
145                 150                 155                 160
Leu Gly Gly Pro Phe Asn Glu Val Arg Phe Cys Pro Thr Gly Val
                165                 170                 175
Asn Glu Gln Asn Leu Lys Asn Tyr Met Ala Leu Pro Asn Val Met Cys
            180                 185                 190
Val Gly Gly Thr Trp Met Ile Asp Asn Ala Trp Val Lys Asn Gly Asp
        195                 200                 205
Trp Gly Arg Ile Gln Glu Ala Thr Ala Gln Ala Leu Ala Leu Phe Asp
    210                 215                 220
```

<210> SEQ ID NO 480
<211> LENGTH: 666
<212> TYPE: DNA
<213> ORGANISM: Pseudomonas fluorescens

<400> SEQUENCE: 480

```
atgacaaacc tcgccccgac cgtttccatg gcggacaaag ttgccctgat cgacagcctc    60
tgcgccaagg cgcggatcct gccggtgatc accattgccc gcgagcagga tgtcctgccg   120
ctggccgatg ccctggcggc cggcggcctg accgccctgg aagtgaccct gcgttcgcag   180
ttcggcctca aggcgatcca gatcctgcgc aacagcgcc cggagctggt gaccggtgcc    240
ggcaccgtgc tcgacccgca gatgctggtg gcggcggaag cggcaggttc gcagttcatc   300
gtcaccccgg gcatcacccg cgacctgctg caagccagcg tggccagccc gattcccctg   360
ctgccgggga tcagcaatgc ctccgggatc atggagggtt atgccctggg ctaccgccgc   420
ttcaagctgt tcccggcgga agtcagtggt ggcgtggcgg cgatcaaggc cctgggcggg   480
ccgttcggcg aggtcaagtt ctgccctacc ggcggcgtcg gccggccaa tatcaagagc   540
tacatggcgc tcaagaatgt gatgtgtgtc ggcggtagct ggatgctcga tcccgagtgg   600
atcaagaacg gcgactgggc acggatccag gagtgcacgg ccgaggccct ggccctgctg   660
gactga                                                              666
```

<210> SEQ ID NO 481
<211> LENGTH: 221

```
<212> TYPE: PRT
<213> ORGANISM: Pseudomonas fluorescens

<400> SEQUENCE: 481

Met Thr Asn Leu Ala Pro Thr Val Ser Met Ala Asp Lys Val Ala Leu
1               5                   10                  15

Ile Asp Ser Leu Cys Ala Lys Ala Arg Ile Leu Pro Val Ile Thr Ile
            20                  25                  30

Ala Arg Glu Gln Asp Val Leu Pro Leu Ala Asp Ala Leu Ala Ala Gly
        35                  40                  45

Gly Leu Thr Ala Leu Glu Val Thr Leu Arg Ser Gln Phe Gly Leu Lys
    50                  55                  60

Ala Ile Gln Ile Leu Arg Glu Gln Arg Pro Glu Leu Val Thr Gly Ala
65                  70                  75                  80

Gly Thr Val Leu Asp Pro Gln Met Leu Val Ala Glu Ala Ala Gly
                85                  90                  95

Ser Gln Phe Ile Val Thr Pro Gly Ile Thr Arg Asp Leu Leu Gln Ala
            100                 105                 110

Ser Val Ala Ser Pro Ile Pro Leu Leu Pro Gly Ile Ser Asn Ala Ser
        115                 120                 125

Gly Ile Met Glu Gly Tyr Ala Leu Gly Tyr Arg Arg Phe Lys Leu Phe
    130                 135                 140

Pro Ala Glu Val Ser Gly Gly Val Ala Ala Ile Lys Ala Leu Gly Gly
145                 150                 155                 160

Pro Phe Gly Glu Val Lys Phe Cys Pro Thr Gly Gly Val Gly Pro Ala
                165                 170                 175

Asn Ile Lys Ser Tyr Met Ala Leu Lys Asn Val Met Cys Val Gly Gly
            180                 185                 190

Ser Trp Met Leu Asp Pro Glu Trp Ile Lys Asn Gly Asp Trp Ala Arg
        195                 200                 205

Ile Gln Glu Cys Thr Ala Glu Ala Leu Ala Leu Asp
    210                 215                 220

<210> SEQ ID NO 482
<211> LENGTH: 591
<212> TYPE: DNA
<213> ORGANISM: Bacillus subtilis

<400> SEQUENCE: 482
atggagtcca aagtcgttga aaaccgtctg aaagaagcaa agctgattgc agtcattcgt      60
tcaaaggata agcaggaggc ctgtcagcag attgagagtt tattagataa agggattcgt     120
gcagttgaag tgacgtatac gaccccccggg gcatcagata ttatcgaatc cttccgtaat     180
agggaagata ttttaattgg cgcgggtacg gtcatcagcg cgcagcaagc tggggaagct     240
gctaaggctg gcgcgcagtt tattgtcagt ccgggttttt cagctgatct tgctgaacat     300
ctatcttttg taaagacaca ttatatcccc ggcgtcttga ctccgagcga aattatggaa     360
gcgctgacat tcggttttac gacattaaag ctgttcccaa gcggtgtgtt tggcattccg     420
tttatgaaaa atttagcggg tcctttcccg caggtgacct ttattccgac aggcgggata     480
catccgtctg aagtgcctga ttggcttaga gccggagctg gcgccgtcgg agtcggcagc     540
cagttgggca gctgttcaaa agaggatttg caggctgttt tccaagtgta a              591

<210> SEQ ID NO 483
<211> LENGTH: 196
<212> TYPE: PRT
<213> ORGANISM: Bacillus subtilis
```

<400> SEQUENCE: 483

```
Met Glu Ser Lys Val Glu Asn Arg Leu Lys Glu Ala Lys Leu Ile
1               5                   10                  15

Ala Val Ile Arg Ser Lys Asp Lys Gln Glu Ala Cys Gln Gln Ile Glu
            20                  25                  30

Ser Leu Leu Asp Lys Gly Ile Arg Ala Val Glu Val Thr Tyr Thr Thr
        35                  40                  45

Pro Gly Ala Ser Asp Ile Ile Glu Ser Phe Arg Asn Arg Glu Asp Ile
    50                  55                  60

Leu Ile Gly Ala Gly Thr Val Ile Ser Ala Gln Gln Ala Gly Glu Ala
65                  70                  75                  80

Ala Lys Ala Gly Ala Gln Phe Ile Val Ser Pro Gly Phe Ser Ala Asp
                85                  90                  95

Leu Ala Glu His Leu Ser Phe Val Lys Thr His Tyr Ile Pro Gly Val
            100                 105                 110

Leu Thr Pro Ser Glu Ile Met Glu Ala Leu Thr Phe Gly Phe Thr Thr
        115                 120                 125

Leu Lys Leu Phe Pro Ser Gly Val Phe Gly Ile Pro Phe Met Lys Asn
    130                 135                 140

Leu Ala Gly Pro Phe Pro Gln Val Thr Phe Ile Pro Thr Gly Gly Ile
145                 150                 155                 160

His Pro Ser Glu Val Pro Asp Trp Leu Arg Ala Gly Ala Gly Ala Val
                165                 170                 175

Gly Val Gly Ser Gln Leu Gly Ser Cys Ser Lys Glu Asp Leu Gln Ala
            180                 185                 190

Val Phe Gln Val
        195
```

<210> SEQ ID NO 484
<211> LENGTH: 624
<212> TYPE: DNA
<213> ORGANISM: Bacillus licheniformis

<400> SEQUENCE: 484

```
atggtattgt cacacatcga agaacaaaaa ctgattgcga tcatccgcgg atacaatccg      60
gaggaggcag tgagcattgc cggcgcctta aaagcgggcg gcatcaggct tgtggagatt    120
acgcttaatt cccctcaagc gatcaaagcg attgaagcgg tttcagagca ttttggggac    180
gaaatgcttg tcggagcggg aaccgtactt gatcccgaat ctgcgagagc ggcgctttta    240
gccggcgcgc ggtttatcct gtctccgacc gtcaatgaag agacgatcaa gctgacaaaa    300
cggtatggag cggtcagcat tccaggcgct tttaccccga ctgaaatatt gacggcgtat    360
gaaagcgggg gagacatcat caaggtattt cccggaacaa tggggcctgg ctatatcaag    420
gatatccacg gaccgcttcc gcatattccg ctgcttccga ctggaggagt cggattggaa    480
aaccttcacg agtttctgca ggccggtgcg gtcggagcgg gaatcggcgg ttcgcttgtt    540
cgggctaata agatgttaa tgacgcgttt ttagaagagc tgtccaaaaa agcaaagcaa    600
tttgttgaag cagcaaaaca gtaa                                          624
```

<210> SEQ ID NO 485
<211> LENGTH: 207
<212> TYPE: PRT
<213> ORGANISM: Bacillus licheniformis

<400> SEQUENCE: 485

```
Met Val Leu Ser His Ile Glu Glu Gln Lys Leu Ile Ala Ile Ile Arg
1               5                   10                  15

Gly Tyr Asn Pro Glu Glu Ala Val Ser Ile Ala Gly Ala Leu Lys Ala
            20                  25                  30

Gly Gly Ile Arg Leu Val Glu Ile Thr Leu Asn Ser Pro Gln Ala Ile
        35                  40                  45

Lys Ala Ile Glu Ala Val Ser Glu His Phe Gly Asp Glu Met Leu Val
50                  55                  60

Gly Ala Gly Thr Val Leu Asp Pro Glu Ser Ala Arg Ala Ala Leu Leu
65              70                  75                  80

Ala Gly Ala Arg Phe Ile Leu Ser Pro Thr Val Asn Glu Glu Thr Ile
            85                  90                  95

Lys Leu Thr Lys Arg Tyr Gly Ala Val Ser Ile Pro Gly Ala Phe Thr
            100                 105                 110

Pro Thr Glu Ile Leu Thr Ala Tyr Glu Ser Gly Gly Asp Ile Ile Lys
        115                 120                 125

Val Phe Pro Gly Thr Met Gly Pro Gly Tyr Ile Lys Asp Ile His Gly
        130                 135                 140

Pro Leu Pro His Ile Pro Leu Leu Pro Thr Gly Gly Val Gly Leu Glu
145             150                 155                 160

Asn Leu His Glu Phe Leu Gln Ala Gly Ala Val Gly Ala Gly Ile Gly
            165                 170                 175

Gly Ser Leu Val Arg Ala Asn Lys Asp Val Asn Asp Ala Phe Leu Glu
        180                 185                 190

Glu Leu Ser Lys Lys Ala Lys Gln Phe Val Glu Ala Ala Lys Gln
        195                 200                 205

<210> SEQ ID NO 486
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 486
atgaaaaact ggaaaacaag tgcagaatca atcctgacca ccggcccggt tgtaccggtt      60
atcgtggtaa aaaaactgga acacgcggtg ccgatggcaa aagcgttggt tgctggtggg     120
gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
gcagaagtca ctgaagcggg tgcacagttc gcaattagcc cgggtctgac cgagccgctg     300
ctgaaagctg ctaccgaagg gactattcct ctgattccgg gatcagcac tgtttccgaa     360 ctgatgctgg gtatggacta cggtttgaaa gagttcaaat tcttcccggc tgaagctaac     420
ggcggcgtga aagccctgca ggcgatcgcg ggtccgttct cccaggtccg tttctgcccg     480
acgggtggta tttctccggc taactaccgt gactacctgg cgctgaaaag cgtgctgtgc     540
atcggtggtt cctggctggt tccggcagat gcgctggaag cgggcgatta cgaccgcatt     600
actaagctgg cgcgtgaagc tgtagaaggc gctaagctgt aa                         642

<210> SEQ ID NO 487
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 487

```
Met Lys Asn Trp Lys Thr Ser Ala Glu Ser Ile Leu Thr Thr Gly Pro
1               5                   10                  15
Val Val Pro Val Ile Val Val Lys Lys Leu Glu His Ala Val Pro Met
            20                  25                  30
Ala Lys Ala Leu Val Ala Gly Gly Val Arg Val Leu Glu Val Thr Leu
        35                  40                  45
Arg Thr Glu Cys Ala Val Asp Ala Ile Arg Ala Ile Ala Lys Glu Val
    50                  55                  60
Pro Glu Ala Ile Val Gly Ala Gly Thr Val Leu Asn Pro Gln Gln Leu
65                  70                  75                  80
Ala Glu Val Thr Glu Ala Gly Ala Gln Phe Ala Ile Ser Pro Gly Leu
                85                  90                  95
Thr Glu Pro Leu Leu Lys Ala Ala Thr Glu Gly Thr Ile Pro Leu Ile
            100                 105                 110
Pro Gly Ile Ser Thr Val Ser Glu Leu Met Leu Gly Met Asp Tyr Gly
        115                 120                 125
Leu Lys Glu Phe Lys Phe Phe Pro Ala Glu Ala Asn Gly Gly Val Lys
    130                 135                 140
Ala Leu Gln Ala Ile Ala Gly Pro Phe Ser Gln Val Arg Phe Cys Pro
145                 150                 155                 160
Thr Gly Gly Ile Ser Pro Ala Asn Tyr Arg Asp Tyr Leu Ala Leu Lys
                165                 170                 175
Ser Val Leu Cys Ile Gly Gly Ser Trp Leu Val Pro Ala Asp Ala Leu
            180                 185                 190
Glu Ala Gly Asp Tyr Asp Arg Ile Thr Lys Leu Ala Arg Glu Ala Val
        195                 200                 205
Glu Gly Ala Lys Leu
    210
```

<210> SEQ ID NO 488
<211> LENGTH: 682
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 488

```
atgaaaaact ggaaacagaa gaccgcccgc atcgacacgc tgtgccggga ggcgcgcatc      60
ctcccggtga tcaccatcga ccgcgaggcg gacatcctgc cgatggccga tgccctcgcc     120
gccggcggcc tgaccgccct ggagatcacc ctgcgcacgg cgcacgggct gaccgccatc     180
cggcgcctca gcgaggagcg cccgcacctg cgcatcggcg ccggcaccgt gctcgacccg     240
cggaccttcg ccgccgcgga aaaggccggg gcgagcttcg tggtcacccc gggttgcacc     300
gacgagttgc tgcgcttcgc cctggacagc gaagtcccgc tgttgcccgg cgtggccagc     360
gcttccgaga tcatgctcgc ctaccgccat ggctaccgcc gcttcaagct gtttcccgcc     420
gaagtcagcg gcggcccggc ggcgctgaag gcgttctcgg gaccattccc cgatatccgc     480
ttctgcccca ccgaggcgt cagcctgaac aatctcgccg actacctggc ggtacccaac     540
gtgatgtgcg tcggcggcac ctggatgctg cccaaggccg tggtcgaccg cggcgactgg     600
gcccaggtcg agcgcctcag ccgcgaagcc ctggagcgct cgccgagca ccgcagacac     660
taatagctcg agttacttta ct                                              682
```

<210> SEQ ID NO 489
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 489

Met Lys Asn Trp Lys Gln Lys Thr Ala Arg Ile Asp Thr Leu Cys Arg
1               5                   10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg His
    210                 215                 220

<210> SEQ ID NO 490
<211> LENGTH: 682
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 490
atgaaaaact ggaaaacaag tgcagaatca atcgacacgc tgtgccggga ggcgcgcatc      60
ctcccggtga tcaccatcga ccgcgaggcg acatcctgc cgatggccga tgccctcgcc     120
gccggcggcc tgaccgccct ggagatcacc ctgcgcacgg cgcacgggct gaccgccatc     180
cggcgcctca gcgaggagcg cccgcacctg cgcatcggcg ccggcaccgt gctcgacccg     240
cggaccttcg ccgccgcgga aaaggccggg gcgagcttcg tggtcacccc gggttgcacc     300
gacgagttgc tgcgcttcgc cctggacagc gaagtcccgc tgttgcccgg cgtggccagc     360
gcttccgaga tcatgctcgc ctaccgccat ggctaccgcc gcttcaagct gtttcccgcc     420
gaagtcagcg gcggcccggc ggcgctgaag gcgttctcgg gaccattccc cgatatccgc     480

```
ttctgcccca ccggaggcgt cagcctgaac aatctcgccg actacctggc ggtacccaac    540
gtgatgtgcg tcggcggcac ctggatgctg cccaaggccg tggtcgaccg cggcgactgg    600
gcccaggtcg agcgcctcag ccgcgaagcc ctggagcgct cgccgagca ccgcagacac    660 taatagctcg agttacttta ct                                             682
```

```
<210> SEQ ID NO 491
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Met Lys Asn Trp Lys Thr Ser Ala Glu Ser Ile Asp Thr Leu Cys Arg
1               5                   10                  15

Glu Ala Arg Ile Leu Pro Val Ile Thr Ile Asp Arg Glu Ala Asp Ile
                20                  25                  30

Leu Pro Met Ala Asp Ala Leu Ala Ala Gly Gly Leu Thr Ala Leu Glu
            35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220
```

```
<210> SEQ ID NO 492
<211> LENGTH: 682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 492
atgaaaaact ggaaaacaag tgcagaatca atcctgacca ccggccggga ggcgcgcatc    60
ctcccggtga tcaccatcga ccgcgaggcg gacatcctgc cgatggccga tgccctcgcc    120
gccggcggcc tgaccgccct ggagatcacc ctgcgcacgg cgcacgggct gaccgccatc    180
cggcgcctca gcgaggagcg cccgcacctg cgcatcggcg ccggcaccgt gctcgacccg    240
```

```
cggaccttcg ccgccgcgga aaaggccggg gcgagcttcg tggtcacccc gggttgcacc      300
gacgagttgc tgcgcttcgc cctggacagc gaagtcccgc tgttgcccgg cgtggccagc      360
gcttccgaga tcatgctcgc ctaccgccat ggctaccgcc gcttcaagct gtttcccgcc      420
gaagtcagcg gcgccccggc ggcgctgaag gcgttctcgg gaccattccc cgatatccgc      480
ttctgcccca ccggaggcgt cagcctgaac aatctcgccg actacctggc ggtacccaac      540
gtgatgtgcg tcgcggcac ctggatgctg cccaaggccg tggtcgaccg cggcgactgg      600
gcccaggtcg agcgcctcag ccgcgaagcc ctggagcgct cgccgagca ccgcagacac      660 taatagctcg agttacttta ct                                              682
```

<210> SEQ ID NO 493
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 493

```
Met Lys Asn Trp Lys Thr Ser Ala Glu Ser Ile Leu Thr Thr Gly Arg
1               5                   10                  15

Glu Ala Arg Ile Leu Pro Val Ile Thr Ile Asp Arg Glu Ala Asp Ile
            20                  25                  30

Leu Pro Met Ala Asp Ala Leu Ala Ala Gly Gly Leu Thr Ala Leu Glu
        35                  40                  45

Ile Thr Leu Arg Thr Ala His Gly Leu Thr Ala Ile Arg Arg Leu Ser
    50                  55                  60

Glu Glu Arg Pro His Leu Arg Ile Gly Ala Gly Thr Val Leu Asp Pro
65                  70                  75                  80

Arg Thr Phe Ala Ala Ala Glu Lys Ala Gly Ala Ser Phe Val Val Thr
                85                  90                  95

Pro Gly Cys Thr Asp Glu Leu Leu Arg Phe Ala Leu Asp Ser Glu Val
            100                 105                 110

Pro Leu Leu Pro Gly Val Ala Ser Ala Ser Glu Ile Met Leu Ala Tyr
        115                 120                 125

Arg His Gly Tyr Arg Arg Phe Lys Leu Phe Pro Ala Glu Val Ser Gly
    130                 135                 140

Gly Pro Ala Ala Leu Lys Ala Phe Ser Gly Pro Phe Pro Asp Ile Arg
145                 150                 155                 160

Phe Cys Pro Thr Gly Gly Val Ser Leu Asn Asn Leu Ala Asp Tyr Leu
                165                 170                 175

Ala Val Pro Asn Val Met Cys Val Gly Gly Thr Trp Met Leu Pro Lys
            180                 185                 190

Ala Val Val Asp Arg Gly Asp Trp Ala Gln Val Glu Arg Leu Ser Arg
        195                 200                 205

Glu Ala Leu Glu Arg Phe Ala Glu His Arg Arg His
    210                 215                 220
```

<210> SEQ ID NO 494
<211> LENGTH: 1665
<212> TYPE: DNA
<213> ORGANISM: Saccharomyces cerevisiae

<400> SEQUENCE: 494

```
atgtccaata actcattcac taacttcaaa ctggccactg aattgccagc ctggtctaag       60
ttgcaaaaaa tttatgaatc tcaaggtaag actttgtctg tcaagcaaga attccaaaaa      120
```

-continued

```
gatgccaagc gttttgaaaa attgaacaag actttcacca actatgatgg ttccaaaatc      180
ttgttcgact actcaaagaa cttggtcaac gatgaaatca ttgctgcatt gattgaactg      240
gccaaggagg ctaacgtcac cggtttgaga gatgctatgt tcaaaggtga acacatcaac      300
tccactgaag atcgtgctgt ctaccacgtc gcattgagaa acagagctaa caagccaatg      360
tacgttgatg tgtcaacgt tgctccagaa gtcgactctg tcttgaagca catgaaggag       420
ttctctgaac aagttcgttc tggtgaatgg aagggttata ccggtaagaa gatcaccgat      480
gttgttaaca tcggtattgg tggttccgat ttgggtccag tcatggtcac tgaggctttg      540
aagcactacg ctggtgtctt ggatgtccac ttcgtttcca acattgacgg tactcacatt      600
gctgaaacct tgaaggttgt tgacccagaa actactttgt ttttgattgc ttccaagact      660
ttcactaccg ctgaaactat cactaacgct aacactgcca agaactggtt cttgtcgaag      720
acaggtaatg atccatctca cattgctaag catttcgctg cttttgtccac taacgaaacc     780
gaagttgcca agtcggtat tgacaccaaa acatgtttg gtttcgaaag ttgggtcggt        840
ggtcgttact ctgtctggtc ggctattggt ttgtctgttg ccttgtacat tggctatgac     900
aactttgagg ctttcttgaa gggtgctgaa gccgtcgaca accacttcac ccaaaccccca    960
ttggaagaca cattccatt gttgggtggt ttgttgtctg tctggtacaa caacttctttg   1020
ggtgctcaaa cccatttggt tgctccattc gaccaatact gcacagatt cccagcctac    1080
ttgcaacaat tgtcaatgga atcaacggt aagtctgtta ccagaggtaa cgtgtttact    1140
gactactcta ctggttctat cttgtttggt gaaccagcta ccaacgctca acactctttc   1200
ttccaattgg ttcaccaagg taccaagttg attccatctg atttcatctt agctgctcaa   1260
tctcataacc caattgagaa caaattacat caaaagatgt tggcttcaaa cttcttttgct  1320
caagctgaag ctttaatggt tggtaaggat gaagaacaag ttaaggctga aggtgccact   1380
ggtggtttgg tcccacacaa ggtcttctca ggtaacagac caactacctc tatcttggct   1440
caaaagatta ctccagctac tttgggtgct ttgattgcct actacgaaca tgttactttc   1500
actgaaggtg ccatttggaa tatcaactct ttcgaccaat ggggtgttga attgggtaaa   1560
gtcttggcta aagtcatcgg caaggaattg gacaactcct ccaccatttc tacccacgat   1620
gcttctacca acggtttaat caatcaattc aaggaatgga tgtga                    1665
```

<210> SEQ ID NO 495
<211> LENGTH: 1470
<212> TYPE: DNA
<213> ORGANISM: Saccharomyces cerevisiae

<400> SEQUENCE: 495

```
atgtctgctg atttcggttt gattggtttg gccgtcatgg gtcaaaattt gatcttgaac       60
gctgctgacc acggtttcac tgtttgtgct tacaacagaa ctcaatccaa ggtcgaccat      120
ttcttggcca atgaagctaa gggcaaatct atcatcggtg ctacttccat tgaagatttc      180
atctccaaat tgaagagacc tagaaaggtc atgcttttgg ttaaagctgg tgctccagtt      240
gacgctttga tcaaccaaat cgtcccactt ttggaaaagg gtgatattat catcgatggt      300
ggtaactctc acttcccaga ttctaataga cgttacgaag aattgaagaa gaagggtatt      360
cttttcgttg gttctggtgt ctccggtggt gaggaaggtc ccgttacgg tccatctttg      420
atgccaggtg gttctgaaga agcttggcca catattaaga acatcttcca atccatctct      480
gctaaatccg acggtgaacc atgttgcgaa tgggttggcc cagccggtgc tggtcactac      540
gtcaagatgg ttcacaacgg tattgaatac ggtgatatgc aattgatttg tgaagcttat     600
```

```
gacatcatga agagattggg tgggtttacc gataaggaaa tcagtgacgt ttttgccaaa      660
tggaacaatg gtgtcttgga ttccttcttg gtcgaaatta ccagagatat tttgaaattc      720
gacgacgtcg acggtaagcc attagttgaa aaaatcatgg atactgctgg tcaaaagggt      780
actggtaagt ggactgccat caacgccttg gatttgggta tgccagttac tttgattggt      840
gaagctgtct ttgcccgttg tctatctgct ttgaagaacg agagaattag agcctccaag      900
gtcttaccag gcccagaagt tccaaaagac gccgtcaagg acagagaaca atttgtcgat      960
gatttggaac aagctttgta tgcttccaag attatttctt acgctcaagg tttcatgttg     1020
atccgtgaag ctgctgctac ttatggctgg aaactaaaca ccctgccat cgctttgatg      1080 tggagaggtg gttgtatcat tagatctgtt ttcttgggtc aaatcacaaa ggcctacaga     1140
gaagaaccag atttggaaaa cttgttgttc aacaagttct tcgctgatgc cgtcaccaag     1200
gctcaatctg gttggagaaa gtcaattgcg ttggctacca cctacggtat cccaacacca     1260
gccttttcca ccgctttgtc tttctacgat gggtacagat ctgaaagatt gccagccaac     1320
ttactacaag ctcaacgtga ctactttggt gctcacactt tcagagtgtt gccagaatgt     1380
gcttctgaca acttgccagt agacaaggat atccatatca actggactgg ccacggtggt     1440
aatgtttctt cctctacata ccaagcttaa                                      1470
```

<210> SEQ ID NO 496
<211> LENGTH: 1479
<212> TYPE: DNA
<213> ORGANISM: Saccharomyces cerevisiae

<400> SEQUENCE: 496

```
atgtcaaagg cagtaggtga tttaggctta gttggtttag ccgtgatggg tcaaaatttg       60
atcttaaacg cagcggatca cggatttacc gtggttgctt ataataggac gcaatcaaag      120
gtagataggt ttctagctaa tgaggcaaaa ggaaaatcaa taattggtgc aacttcaatt      180
gaggacttgg ttgcgaaact aaagaaacct agaaagatta tgcttttaat caaagccggt      240
gctccggtcg acactttaat aaaggaactt gtaccacatc ttgataaagg cgacattatt      300
atcgacggtg gtaactcaca tttcccggac actaacagac gctacgaaga gctaacaaag      360
caaggaattc ttttttgtggg ctctggtgtc tcaggcggtg aagatggtgc acgttttggt      420
ccatctttaa tgcctggtgg gtcagcagaa gcatggccgc acatcaagaa catctttcaa      480
tctattgccg ccaaatcaaa cggtgagcca tgctgcgaat gggtggggcc tgccggttct      540
ggtcactatg tgaagatggt acacaacggt atcgagtacg gtgatatgca gttgatttgc      600
gaggcttacg atatcatgaa acgaattggc cggtttacgg ataaagagat cagtgaagta      660
tttgacaagt ggaacactgg agttttggat tctttcttga ttgaaatcac gagggacatt      720
ttaaaattcg atgacgtcga cggtaagcca ttggtggaaa aaattatgga tactgccggt      780
caaaagggta ctggtaaatg gactgcaatc aacgccttgg atttaggaat gccagtcact      840
ttaattgggg aggctgtttt cgctcgttgt tgtcagcca taaaggacga acgtaaaaga      900
gcttcgaaac ttctggcagg accaacagta ccaaggatg caatacatga tagagaacaa      960
tttgtgtatg atttggaaca agcattatac gcttcaaaga ttatttcata tgctcaaggt     1020
ttcatgctga tccgcgaagc tgccagatca tacggctgga aattaaacaa cccagctatt     1080
gctctaatgt ggagaggtgg ctgtataatc agatctgtgt tcttagctga gattacgaag     1140
gcttataggg acgatccaga tttggaaaat ttattattca acgagttctt cgcttctgca     1200
gttactaagg cccaatccgg ttggagaaga actattgccc ttgctgctac ttacggtatt     1260
```

-continued

| | |
|---|---|
| ccaactccag ctttctctac tgctttagcg ttttacgacg gctatagatc tgagaggcta | 1320 |
| ccagcaaact tgttacaagc gcaacgtgat tattttggcg ctcatacatt tagaatttta | 1380 |
| cctgaatgtg cttctgccca tttgccagta gacaaggata ttcatatcaa ttggactggg | 1440 |
| cacggaggta atatatcttc ctcaacctac caagcttaa | 1479 |

<210> SEQ ID NO 497
<211> LENGTH: 1008
<212> TYPE: DNA
<213> ORGANISM: Saccharomyces cerevisiae

<400> SEQUENCE: 497

| | |
|---|---|
| atgtctgaac cagctcaaaa gaaacaaaag gttgctaaca actctctaga acaattgaaa | 60 |
| gcctccggca ctgtcgttgt tgccgacact ggtgatttcg gctctattgc caagtttcaa | 120 |
| cctcaagact ccacaactaa cccatcattg atcttggctg ctgccaagca accaacttac | 180 |
| gccaagttga tcgatgttgc cgtggaatac ggtaagaagc atggtaagac caccgaagaa | 240 |
| caagtcgaaa atgctgtgga cagattgtta gtcgaattcg gtaaggagat cttaaagatt | 300 |
| gttccaggca gagtctccac cgaagttgat gctagattgt cttttgacac tcaagctacc | 360 |
| attgaaaagg ctagacatat cattaaattg tttgaacaag aaggtgtctc caaggaaaga | 420 |
| gtccttatta aaattgcttc cacttgggaa ggtattcaag ctgccaaaga attggaagaa | 480 |
| aaggacggta tccactgtaa tttgactcta ttattctcct tcgttcaagc agttgcctgt | 540 |
| gccgaggccc aagttacttt gatttcccca tttgttggta gaattctaga ctggtacaaa | 600 |
| tccagcactg gtaagattca aagggtgaa gccgacccag gtgttatttc cgtcaagaaa | 660 |
| atctacaact actacaagaa gtacggttac aagactattg ttatgggtgc ttcttttcaga | 720 |
| agcactgacg aaatcaaaaa cttggctggt gttgactatc taacaatttc tccagcttta | 780 |
| ttggacaagt tgatgaacag tactgaacct ttcccaagag ttttggaccc tgtctccgct | 840 |
| aagaaggaag ccggcgacaa gatttcttac atcagcgacg aatctaaatt cagattcgac | 900 |
| ttgaatgaag acgctatggc cactgaaaaa ttgtccgaag gtatcagaaa attctctgcc | 960 |
| gatattgtta ctctattcga cttgattgaa aagaaagtta ccgcttaa | 1008 |

<210> SEQ ID NO 498
<211> LENGTH: 335
<212> TYPE: PRT
<213> ORGANISM: Saccharomyces cerevisiae

<400> SEQUENCE: 498

```
Met Ser Glu Pro Ala Gln Lys Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110
```

```
Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335

<210> SEQ ID NO 499
<211> LENGTH: 2043
<212> TYPE: DNA
<213> ORGANISM: Saccharomyces cerevisiae

<400> SEQUENCE: 499
atgactcaat tcactgacat tgataagcta gccgtctcca ccataagaat tttggctgtg      60
gacaccgtat ccaaggccaa ctcaggtcac ccaggtgctc cattgggtat ggcaccagct     120
gcacacgttc tatggagtca aatgcgcatg aacccaacca acccagactg atcaacaga      180 gatagatttg tcttgtctaa cggtcacgcg gtcgctttgt tgtattctat gctacatttg     240
actggttacg atctgtctat tgaagacttg aaacagttca gacagttggg ttccagaaca     300
ccaggtcatc tgaatttga gttgccaggt gttgaagtta ctaccggtcc attaggtcaa      360
ggtatctcca acgctgttgg tatggccatg gctcaagcta acctggctgc cacttacaac     420
aagccgggct ttaccttgtc tgacaactac acctatgttt tcttgggtga cggttgtttg     480
caagaaggta tttcttcaga agcttcctcc ttggctggtc atttgaaatt gggtaacttg     540
attgccatct acgatgacaa caagatcact atcgatggtg ctaccagtat ctcattcgat     600
gaagatgttg ctaagagata cgaagcctac ggttgggaag ttttgtacgt agaaaatggt     660
aacgaagatc tagccggtat tgccaaggct attgctcaag ctaagttatc caaggacaaa     720
ccaactttga tcaaaatgac cacaaccatt ggttacggtt ccttgcatgc cggctctcac     780
tctgtgcacg gtgccccatt gaagcagat gatgttaaac aactaaagag caaattcggt     840
ttcaacccag acaagtcctt tgttgttcca caagaagttt acgaccacta ccaaaagaca     900
```

-continued

```
attttaaagc caggtgtcga agccaacaac aagtggaaca agttgttcag cgaataccaa    960
aagaaattcc cagaattagg tgctgaattg gctagaagat tgagcggcca actacccgca   1020
aattgggaat ctaagttgcc aacttacacc gccaaggact ctgccgtggc cactagaaaa   1080
ttatcagaaa ctgttcttga ggatgtttac aatcaattgc cagagttgat tggtggttct   1140
gccgatttaa caccttctaa cttgaccaga tggaaggaag cccttgactt ccaacctcct   1200
tcttccggtt caggtaacta ctctggtaga tacattaggt acggtattag agaacacgct   1260
atgggtgcca taatgaacgg tatttcagct ttcggtgcca actacaaacc atacggtggt   1320
acttccttga acttcgtttc ttatgctgct ggtgccgtta gattgtccgc tttgtctggc   1380
cacccagtta tttgggttgc tacacatgac tctatcggtg tcggtgaaga tggtccaaca   1440
catcaaccta ttgaaacttt agcacacttc agatccctac aaacattca agtttggaga   1500
ccagctgatg gtaacgaagt ttctgccgcc tacaagaact ctttagaatc caagcatact   1560
ccaagtatca ttgctttgtc cagacaaaac ttgccacaat ggaaggtag ctctattgaa   1620
agcgcttcta agggtggtta cgtactacaa gatgttgcta acccagatat tattttagtg   1680
gctactggtt ccgaagtgtc tttgagtgtt gaagctgcta gactttggc cgcaaagaac   1740
atcaaggctc gtgttgtttc tctaccagat ttcttcactt ttgacaaaca ccccctagaa   1800
tacagactat cagtcttacc agacaacgtt ccaatcatgt ctgttgaagt tttggctacc   1860
acatgttggg gcaaatacgc tcatcaatcc ttcggtattg acagatttgg tgcctccggt   1920
aaggcaccag aagtcttcaa gttcttcggt ttcaccccag aaggtgttgc tgaaagagct   1980
caaaagacca ttgcattcta agggtgac aagctaattt ctcctttgaa aaagctttc   2040
taa                                                                  2043
```

<210> SEQ ID NO 500
<211> LENGTH: 680
<212> TYPE: PRT
<213> ORGANISM: Saccharomyces cerevisiae

<400> SEQUENCE: 500

```
Met Thr Gln Phe Thr Asp Ile Asp Lys Leu Ala Val Ser Thr Ile Arg
1               5                   10                  15
Ile Leu Ala Val Asp Thr Val Ser Lys Ala Asn Ser Gly His Pro Gly
            20                  25                  30
Ala Pro Leu Gly Met Ala Pro Ala Ala His Val Leu Trp Ser Gln Met
        35                  40                  45
Arg Met Asn Pro Thr Asn Pro Asp Trp Ile Asn Arg Asp Arg Phe Val
    50                  55                  60
Leu Ser Asn Gly His Ala Val Ala Leu Leu Tyr Ser Met Leu His Leu
65                  70                  75                  80
Thr Gly Tyr Asp Leu Ser Ile Glu Asp Leu Lys Gln Phe Arg Gln Leu
                85                  90                  95
Gly Ser Arg Thr Pro Gly His Pro Glu Phe Glu Leu Pro Gly Val Glu
            100                 105                 110
Val Thr Thr Gly Pro Leu Gly Gln Gly Ile Ser Asn Ala Val Gly Met
        115                 120                 125
Ala Met Ala Gln Ala Asn Leu Ala Ala Thr Tyr Asn Lys Pro Gly Phe
    130                 135                 140
Thr Leu Ser Asp Asn Tyr Thr Tyr Val Phe Leu Gly Asp Gly Cys Leu
145                 150                 155                 160
Gln Glu Gly Ile Ser Ser Glu Ala Ser Ser Leu Ala Gly His Leu Lys
                165                 170                 175
```

```
Leu Gly Asn Leu Ile Ala Ile Tyr Asp Asp Asn Lys Ile Thr Ile Asp
        180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
        210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Ile Gly Tyr Gly Ser Leu His
        245                 250                 255

Ala Gly Ser His Ser Val His Gly Ala Pro Leu Lys Ala Asp Asp Val
        260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
        290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
        340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
                420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
        450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
                500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
        530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
        580                 585                 590

Thr Phe Asp Lys Gln Pro Leu Glu Tyr Arg Leu Ser Val Leu Pro Asp
```

```
                    595                 600                 605
Asn Val Pro Ile Met Ser Val Glu Val Leu Ala Thr Thr Cys Trp Gly
        610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680

<210> SEQ ID NO 501
<211> LENGTH: 1830
<212> TYPE: DNA
<213> ORGANISM: Saccharophagus degradans

<400> SEQUENCE: 501
atgaatagcg taatcgaagc tgtaactcag cgaattattg agcgcagtcg acattctcgt      60
caggcgtatt tgaatttaat gcgcaacacc atggagcagc atcctcctaa aaagcgtcta     120
tcttgcggca atttggctca tgcctatgca gcatgtggtc aatccgataa gcaaacaatt     180
cgtttaatgc aaagtgcaaa cataagtatt actacggcat taacgatat gctttcggcg      240 catcagcctt tagaaacata ccctcaaata atcaagaaaa ctgcgcgtgc aatgggttca     300
actgctcaag ttgcaggcgg cgtgccggca catgtgatg tgtaactca aggccagccc       360 ggtatggagc tgagtttgtt tagccgcgaa gttgtagcaa tggctacagc agtaggcctt     420
tcgcacaata tgtttgatgg caatatgttt ttgggtgtat cgataaaat gttcctggc       480 atgctaattg gcgcgttgca gtttggtcat attcctgggg tgtttgtgcc tgccggacca     540
atgccttctg gtattcccaa caagaaaaa gcaaaagttc gtcagcaata tgcggcgggc     600
attgtggggg aagataagct tttagaaacc gagtcggctt cctatcacag tgcaggcacg     660 tgtactttt acggtacagc gaatacaaac caaatgatgg ttgaaatgtt gggtgttcag      720
ttgcctggct cgtcgtttgt ttaccccggt actgagttgc gtgatgcctt aacgagagct     780
gctgttgaaa gttggtaaa atcacagat tcagccggta actaccgtcc gctctacgaa       840
gtcattacgg aaaaatccat cgtcaattca ataattggtt tgttggctac cggcggttct     900
actaaccaca cgctacacat tgttgctgtg gctcgcgctg cgggtataga ggttacgtgg     960
gcagatatgg acgagctttc gcgtgctgtg ccattacttg cacgtgttta ccctaacggc    1020
gaagctgatg ttaaccaatt ccagcaggct ggcggcatgg cttatttagt aagagagctg    1080
cgcagcggcg gtttgctaaa tgaagatgtg gttactatta gggtgaggg cctcgaggcc    1140 tacgaaaaag agcccatgct taacgataag gggcaggctg aatgggtaaa tgatgtacct   1200
gttagccgcg acgataccgt tgtgcgtcca gttacctcgc ctttcgataa agagggtggg   1260
ttgcgtctac tcaagggtaa cttagggcag ggcgtaatca aaatttctgc ggtagcgcca   1320
gaaaatcgcg ttgttgaggc cccatgtatt gtattcgagg cccaagaaga gctaatagct   1380
gcgtttaagc gtggtgagct cgaaaaagac tttgttgcgg tagtgcgctt ccaagggcct   1440
tctgccaatg gcatgccaga acttcataaa atgaccccgc ctttaggtgt gcttcaagat   1500
aagggtttca aggtagcgtt agttaccgat ggcagaatgt ctggtgcatc tggtaaagtg   1560
ccggccgtta tacacttgtc gccagaagcg agtaagggtg gctgttgaa taagctgcgc    1620 acgggtgatg tgattcgctt cgatgccgaa gcgggcgtta ttcaagcgct tgttagtgat   1680
```

```
gaagagttag ctgcgcgtga gccagctgtg caaccggtcg tggagcagaa cctcggacgc    1740
tctctgtttg gtggtttgcg cgatttggct ggtgtatcgc tacaaggcgg aacagttttc    1800
gattttgaaa gagagtttgg cgaaaaatag                                     1830
```

<210> SEQ ID NO 502
<211> LENGTH: 609
<212> TYPE: PRT
<213> ORGANISM: Saccharophagus degradans

<400> SEQUENCE: 502

```
Met Asn Ser Val Ile Glu Ala Val Thr Gln Arg Ile Ile Glu Arg Ser
1               5                   10                  15

Arg His Ser Arg Gln Ala Tyr Leu Asn Leu Met Arg Asn Thr Met Glu
            20                  25                  30

Gln His Pro Lys Lys Arg Leu Ser Cys Gly Asn Leu Ala His Ala
        35                  40                  45

Tyr Ala Ala Cys Gly Gln Ser Asp Lys Gln Thr Ile Arg Leu Met Gln
    50                  55                  60

Ser Ala Asn Ile Ser Ile Thr Thr Ala Phe Asn Asp Met Leu Ser Ala
65                  70                  75                  80

His Gln Pro Leu Glu Thr Tyr Pro Gln Ile Ile Lys Glu Thr Ala Arg
                85                  90                  95

Ala Met Gly Ser Thr Ala Gln Val Ala Gly Val Pro Ala Met Cys
            100                 105                 110

Asp Gly Val Thr Gln Gly Gln Pro Gly Met Glu Leu Ser Leu Phe Ser
        115                 120                 125

Arg Glu Val Val Ala Met Ala Thr Ala Val Gly Leu Ser His Asn Met
    130                 135                 140

Phe Asp Gly Asn Met Phe Leu Gly Val Cys Asp Lys Ile Val Pro Gly
145                 150                 155                 160

Met Leu Ile Gly Ala Leu Gln Phe Gly His Ile Pro Gly Val Phe Val
                165                 170                 175

Pro Ala Gly Pro Met Pro Ser Gly Ile Pro Asn Lys Glu Lys Ala Lys
            180                 185                 190

Val Arg Gln Gln Tyr Ala Ala Gly Ile Val Gly Glu Asp Lys Leu Leu
        195                 200                 205

Glu Thr Glu Ser Ala Ser Tyr His Ser Ala Gly Thr Cys Thr Phe Tyr
    210                 215                 220

Gly Thr Ala Asn Thr Asn Gln Met Met Val Glu Met Leu Gly Val Gln
225                 230                 235                 240

Leu Pro Gly Ser Ser Phe Val Tyr Pro Gly Thr Glu Leu Arg Asp Ala
                245                 250                 255

Leu Thr Arg Ala Ala Val Glu Lys Leu Val Lys Ile Thr Asp Ser Ala
            260                 265                 270

Gly Asn Tyr Arg Pro Leu Tyr Glu Val Ile Thr Glu Lys Ser Ile Val
        275                 280                 285

Asn Ser Ile Ile Gly Leu Leu Ala Thr Gly Gly Ser Thr Asn His Thr
    290                 295                 300

Leu His Ile Val Ala Val Ala Arg Ala Ala Gly Ile Glu Val Thr Trp
305                 310                 315                 320

Ala Asp Met Asp Glu Leu Ser Arg Ala Val Pro Leu Leu Ala Arg Val
                325                 330                 335

Tyr Pro Asn Gly Glu Ala Asp Val Asn Gln Phe Gln Gln Ala Gly Gly
            340                 345                 350
```

Met Ala Tyr Leu Val Arg Glu Leu Arg Ser Gly Gly Leu Leu Asn Glu
355 360 365

Asp Val Val Thr Ile Met Gly Glu Gly Leu Glu Ala Tyr Glu Lys Glu
370 375 380

Pro Met Leu Asn Asp Lys Gly Gln Ala Glu Trp Val Asn Asp Val Pro
385 390 395 400

Val Ser Arg Asp Asp Thr Val Val Arg Pro Val Thr Ser Pro Phe Asp
405 410 415

Lys Glu Gly Gly Leu Arg Leu Leu Lys Gly Asn Leu Gly Gln Gly Val
420 425 430

Ile Lys Ile Ser Ala Val Ala Pro Glu Asn Arg Val Val Glu Ala Pro
435 440 445

Cys Ile Val Phe Glu Ala Gln Glu Glu Leu Ile Ala Ala Phe Lys Arg
450 455 460

Gly Glu Leu Glu Lys Asp Phe Val Ala Val Val Arg Phe Gln Gly Pro
465 470 475 480

Ser Ala Asn Gly Met Pro Glu Leu His Lys Met Thr Pro Pro Leu Gly
485 490 495

Val Leu Gln Asp Lys Gly Phe Lys Val Ala Leu Val Thr Asp Gly Arg
500 505 510

Met Ser Gly Ala Ser Gly Lys Val Pro Ala Gly Ile His Leu Ser Pro
515 520 525

Glu Ala Ser Lys Gly Gly Leu Leu Asn Lys Leu Arg Thr Gly Asp Val
530 535 540

Ile Arg Phe Asp Ala Glu Ala Gly Val Ile Gln Ala Leu Val Ser Asp
545 550 555 560

Glu Glu Leu Ala Ala Arg Glu Pro Ala Val Gln Pro Val Val Glu Gln
565 570 575

Asn Leu Gly Arg Ser Leu Phe Gly Gly Leu Arg Asp Leu Ala Gly Val
580 585 590

Ser Leu Gln Gly Gly Thr Val Phe Asp Phe Glu Arg Glu Phe Gly Glu
595 600 605

Lys

<210> SEQ ID NO 503
<211> LENGTH: 1917
<212> TYPE: DNA
<213> ORGANISM: Xanthomonas axonopodis

<400> SEQUENCE: 503
atgagcctgc atccgaatat ccaagccgtc accgaccgta tccgcaagcg cagtgctccc 60
tcgcgcgcgg cgtatctggc cggcctcgat gccgccctgc gtgagggccc gttccgtagc 120
cggttgagct gcggcaatct cgcgcatggc ttcgctgcgt ccgagccggg cgacaaatcg 180
cgcctgcgcg gtgcggccac gccgaacctg ggcatcatca ctgcctataa cgacatgttg 240
tcggcacatc agccgttcga gcactacccg cagctgatcc gcgaaaccgc gcgctcactt 300
ggcgccactg cgcaggtggc cggcggcgtg ccggcgatgt gtgacggcgt gacccagggc 360
cgcgccggca tggagctgtc gctgttctcg cgcgacaaca tcgctcaggc tgcggccatt 420
ggcctgagcc atgacatgtt cgacagcgtg gtgtacctgg gggtgtgcga caagatcgtg 480
ccgggtctgc tgatcggtgc gctggcgttt ggccatttgc cggcgatctt catgccggct 540
ggtccgatga ccccgggcat cccgaacaag cagaaagccg aagtccgcga acgctacgcc 600
gctggcgaag ccacccgcgc cgaattgctg gaggccgaat cctcgtctta tcactcgccc 660

```
ggcacctgca ccttttacgg cacggcgaac tccaaccagg tgttgctcga agcgatgggc    720
gtgcagttgc ccggcgcctc gttcgtcaat ccggagctgc cgctgcgcga tgcactgacc    780
cgcgaaggca ccgcacgcgc attggcgatc tccgcgctgg gcgatgactt ccgcccgttc    840
ggtcgtttga tcgacgaacg ggccatcgtc aatgccgtgg tcgcgctgat ggcgaccggc    900
ggttcgacca accacaccat ccactggatc gcagtggcgc gtgcggccgg catcgtgttg    960
acctgggacg acatggatct gatctcgcag accgtgccgc tgttgacacg catctacccg   1020
aacggcgaag ccgacgtgaa ccgcttccag gccgcaggcg gcacggcgtt cgtgttccgc   1080
gaattgatgg acgccggcta catgcacgac gacctgccga ccatcgtcga aggcggcatg   1140
cgcgcgtacg tcaacgaacc gcgcctgcag gacggcaagg tgacctacgt gcccggcacc   1200
gcgaccactg ccgacgacag cgtcgcgcgt ccggtcagcg atgcattcga atcacaaggc   1260
ggcctgcgcc tgctgcgcgg caacctcggc cgctcgttga tcaagctgtc ggcggtcaag   1320
ccgcagcacc gcagcatcca agcgccagcg gtggtgatcg acaccccgca agtgctcaac   1380
aaactgcatg cggcgggcgt actgccgcac gatttcgtgg tggtactgcg ctatcagggc   1440
ccacgcgcaa acggcatgcc ggagctgcat tcgatggcgc cgctactggg cctgctgcag   1500
aaccagggcc ggcgcgtggc gttggtcacc gacggccgtc tgtccggcgc ctcgggcaag   1560
ttcccggcgg cgatccacat gaccccggaa gccgcacgcg gcggcccgat cgggcgcgta   1620
cgcgaaggcg acatcgtgcg actggacggc gaagccggca ccttggaagt gctggtttcg   1680
gccgaagaat gggcatcgcg cgaggtcgca ccgaacactg cgttggccgg caacgacctg   1740
ggccgcaacc tgttcgccat caaccgccag gtggttggcc cggccgacca gggcgcgatt   1800
tccatttcct gcggcccgac ccatccggac ggtgcgctgt ggagctacga cgccgagtac   1860
gaactcggtg ccgatgcagc tgcagccgcc gcgccgcacg agtccaagga cgcctga      1917
```

<210> SEQ ID NO 504
<211> LENGTH: 638
<212> TYPE: PRT
<213> ORGANISM: Xanthomonas axonopodis

<400> SEQUENCE: 504

```
Met Ser Leu His Pro Asn Ile Gln Ala Val Thr Asp Arg Ile Arg Lys
1               5                   10                  15

Arg Ser Ala Pro Ser Arg Ala Ala Tyr Leu Ala Gly Ile Asp Ala Ala
            20                  25                  30

Leu Arg Glu Gly Pro Phe Arg Ser Arg Leu Ser Cys Gly Asn Leu Ala
        35                  40                  45

His Gly Phe Ala Ala Ser Glu Pro Thr Asp Lys Ser Arg Leu Arg Gly
    50                  55                  60

Ala Ala Thr Pro Asn Leu Gly Ile Ile Thr Ala Tyr Asn Asp Met Leu
65                  70                  75                  80

Ser Ala His Gln Pro Phe Glu His Tyr Pro Gln Leu Ile Arg Glu Thr
                85                  90                  95

Ala Arg Ser Leu Gly Ala Thr Ala Gln Val Ala Gly Gly Val Pro Ala
            100                 105                 110

Met Cys Asp Gly Val Thr Gln Gly Arg Ala Gly Met Glu Leu Ser Leu
        115                 120                 125

Phe Ser Arg Asp Asn Ile Ala Gln Ala Ala Ala Ile Gly Leu Ser His
    130                 135                 140

Asp Met Phe Asp Ser Val Val Tyr Leu Gly Val Cys Asp Lys Ile Val
145                 150                 155                 160
```

```
Pro Gly Leu Leu Ile Gly Ala Leu Ala Phe Gly His Leu Pro Ala Ile
            165                 170                 175

Phe Met Pro Ala Gly Pro Met Thr Pro Gly Ile Pro Asn Lys Gln Lys
            180                 185                 190

Ala Glu Val Arg Glu Arg Tyr Ala Ala Gly Glu Ala Thr Arg Ala Glu
            195                 200                 205

Leu Leu Glu Ala Glu Ser Ser Tyr His Ser Pro Gly Thr Cys Thr
            210                 215                 220

Phe Tyr Gly Thr Ala Asn Ser Asn Gln Val Leu Leu Glu Ala Met Gly
225                 230                 235                 240

Val Gln Leu Pro Gly Ala Ser Phe Val Asn Pro Glu Leu Pro Leu Arg
            245                 250                 255

Asp Ala Leu Thr Arg Glu Gly Thr Ala Arg Ala Leu Ala Ile Ser Ala
            260                 265                 270

Leu Gly Asp Asp Phe Arg Pro Phe Gly Arg Leu Ile Asp Glu Arg Ala
            275                 280                 285

Ile Val Asn Ala Val Val Ala Leu Met Ala Thr Gly Gly Ser Thr Asn
            290                 295                 300

His Thr Ile His Trp Ile Ala Val Ala Arg Ala Ala Gly Ile Val Leu
305                 310                 315                 320

Thr Trp Asp Asp Met Asp Leu Ile Ser Gln Thr Val Pro Leu Leu Thr
            325                 330                 335

Arg Ile Tyr Pro Asn Gly Glu Ala Asp Val Asn Arg Phe Gln Ala Ala
            340                 345                 350

Gly Gly Thr Ala Phe Val Phe Arg Glu Leu Met Asp Ala Gly Tyr Met
            355                 360                 365

His Asp Asp Leu Pro Thr Ile Val Glu Gly Gly Met Arg Ala Tyr Val
            370                 375                 380

Asn Glu Pro Arg Leu Gln Asp Gly Lys Val Thr Tyr Val Pro Gly Thr
385                 390                 395                 400

Ala Thr Thr Ala Asp Asp Ser Val Ala Arg Pro Val Ser Asp Ala Phe
            405                 410                 415

Glu Ser Gln Gly Gly Leu Arg Leu Leu Arg Gly Asn Leu Gly Arg Ser
            420                 425                 430

Leu Ile Lys Leu Ser Ala Val Lys Pro Gln His Arg Ser Ile Gln Ala
            435                 440                 445

Pro Ala Val Val Ile Asp Thr Pro Gln Val Leu Asn Lys Leu His Ala
450                 455                 460

Ala Gly Val Leu Pro His Asp Phe Val Val Leu Arg Tyr Gln Gly
465                 470                 475                 480

Pro Arg Ala Asn Gly Met Pro Glu Leu His Ser Met Ala Pro Leu Leu
            485                 490                 495

Gly Leu Leu Gln Asn Gln Gly Arg Arg Val Ala Leu Val Thr Asp Gly
            500                 505                 510

Arg Leu Ser Gly Ala Ser Gly Lys Phe Pro Ala Ala Ile His Met Thr
            515                 520                 525

Pro Glu Ala Ala Arg Gly Gly Pro Ile Gly Arg Val Arg Glu Gly Asp
            530                 535                 540

Ile Val Arg Leu Asp Gly Glu Ala Gly Thr Leu Glu Val Leu Val Ser
545                 550                 555                 560

Ala Glu Glu Trp Ala Ser Arg Glu Val Ala Pro Asn Thr Ala Leu Ala
            565                 570                 575

Gly Asn Asp Leu Gly Arg Asn Leu Phe Ala Ile Asn Arg Gln Val Val
```

|  |  |  |
|---|---|---|
| 580 | 585 | 590 |

Gly Pro Ala Asp Gln Gly Ala Ile Ser Ile Ser Cys Gly Pro Thr His
            595                            600                        605

Pro Asp Gly Ala Leu Trp Ser Tyr Asp Ala Glu Tyr Glu Leu Gly Ala
    610                           615                        620

Asp Ala Ala Ala Ala Ala Pro His Glu Ser Lys Asp Ala
625                         630                        635

<210> SEQ ID NO 505
<211> LENGTH: 1827
<212> TYPE: DNA
<213> ORGANISM: Pseudomonas syringae

<400> SEQUENCE: 505

| | |
|---|---|
| atgcatcccc gcgtccttga agtaaccgag cggctcattg ctcgcagtcg cgatacccgt | 60 |
| cagcgctacc ttcaattgat tcgaggcgca gcgagcgatg gcccgatgcg cggcaagctt | 120 |
| caatgtgcca actttgctca cggcgtcgcc gcctgcggac cggaggacaa gcaaagcctg | 180 |
| cgtttgatga acgccgccaa cgtggcaatc gtctcttcct acaatgaaat gctctcggcg | 240 |
| catcagccct acgagcactt tcctgcacag atcaaacagg cgttacgtga cattggttcg | 300 |
| gtcggtcagt tgccggcgg cgtgcctgcc atgtgcgatg cgtgactca gggtgagccg | 360 |
| ggcatggaac tggccattgc cagccgcgaa gtgattgcca tgtccacggc aattgccttg | 420 |
| tcacacaata tgttcgacgc cgccatgatg ctgggtatct gcgacaagat cgtccccggc | 480 |
| ctgatgatgg gggcgttgcg tttcggtcat ctgccgacca tcttcgtgcc gggcgggccg | 540 |
| atggtgtcag gtatctccaa caaggaaaaa gccgacgtac ggcagcgtta cgctgaaggc | 600 |
| aaggccagcc gtgaagagct gctggactcg gaaatgaagt cctatcacgg cccgggaacc | 660 |
| tgcacgttct acggcaccgc caacaccaat cagttggtga tggaagtcat gggcatgcac | 720 |
| cttcccggtg cctcgttcgt caatccctac acaccactgc gtgatgcgct gacagctgaa | 780 |
| gcggctcgtc aggtcacgcg tctgaccatg caaagcggca gtttcatgcc gattggtgaa | 840 |
| atcgtcgacg agcgctcgct ggtcaattcc atcgttgcgc tgcacgccac cggcggctcg | 900 |
| accaaccaca cgctgcacat gccggcgatt gctcaggctg cgggtattca gctgacctgg | 960 |
| caggacatgg ccgacctctc cgaagtggtg ccgaccctca gtcacgtcta ccccaacggc | 1020 |
| aaggccgaca tcaaccattt ccaggccgca ggcggcatgt cgttcctgat cgcgagctg | 1080 |
| ctggcagccg gtctgctgca cgaaaacgtt aacaccgtgg ccggttatgg cctgagccgc | 1140 |
| tacaccaaag agccattcct ggaggatggc aaactggtct ggcgtgaagg cccgctggac | 1200 |
| agcctggatg aaaacatcct gcgcccggtg gcgcgtccgt tctcccctga aggcggtttg | 1260 |
| cgggtcatgg aaggcaacct gggtcgcggt gtcatgaaag tatcggccgt tgcgctggag | 1320 |
| catcagattg tcgaagcgcc agcccgagtg tttcaggatc agaaggagct ggccgatgcg | 1380 |
| ttcaaggccg gcgagctgga atgtgatttc gtcgccgtca tgcgttttca gggcccgcgc | 1440 |
| tgcaacggca tgcccgaact gcacaagatg accccgtttc tgggcgtgct gcaggatcgt | 1500 |
| ggtttcaaag tggcgctggt caccgatgga cggatgtcgg gcgcctcagg caagattccg | 1560 |
| gcggcgattc acgtctgccc ggaagcgttc gatggtggcc cgttggcact ggtacgcgac | 1620 |
| ggcgatgtga tccgcgtgga tggcgtaaaa ggcacgttac aagtgctggt cgaagcgtca | 1680 |
| gaattggccg cccgagaacc ggccatcaac cagatcgaca acagtgtcgg ctgcggtcgc | 1740 |
| gagcttttg gattcatgcg catggccttc agctccgcag agcaaggcgc cagcgccttt | 1800 |
| acctctagtc tggagacgct caagtga | 1827 |

<210> SEQ ID NO 506
<211> LENGTH: 608
<212> TYPE: PRT
<213> ORGANISM: Pseudomonas syringae

<400> SEQUENCE: 506

Met His Pro Arg Val Leu Glu Val Thr Glu Arg Leu Ile Ala Arg Ser
1               5                   10                  15

Arg Asp Thr Arg Gln Arg Tyr Leu Gln Leu Ile Arg Gly Ala Ala Ser
            20                  25                  30

Asp Gly Pro Met Arg Gly Lys Leu Gln Cys Ala Asn Phe Ala His Gly
        35                  40                  45

Val Ala Ala Cys Gly Pro Glu Asp Lys Gln Ser Leu Arg Leu Met Asn
    50                  55                  60

Ala Ala Asn Val Ala Ile Val Ser Ser Tyr Asn Glu Met Leu Ser Ala
65                  70                  75                  80

His Gln Pro Tyr Glu His Phe Pro Ala Gln Ile Lys Gln Ala Leu Arg
                85                  90                  95

Asp Ile Gly Ser Val Gly Gln Phe Ala Gly Val Pro Ala Met Cys
            100                 105                 110

Asp Gly Val Thr Gln Gly Glu Pro Gly Met Glu Leu Ala Ile Ala Ser
        115                 120                 125

Arg Glu Val Ile Ala Met Ser Thr Ala Ile Ala Leu Ser His Asn Met
130                 135                 140

Phe Asp Ala Ala Met Met Leu Gly Ile Cys Asp Lys Ile Val Pro Gly
145                 150                 155                 160

Leu Met Met Gly Ala Leu Arg Phe Gly His Leu Pro Thr Ile Phe Val
                165                 170                 175

Pro Gly Gly Pro Met Val Ser Gly Ile Ser Asn Lys Glu Lys Ala Asp
            180                 185                 190

Val Arg Gln Arg Tyr Ala Glu Gly Lys Ala Ser Arg Glu Glu Leu Leu
        195                 200                 205

Asp Ser Glu Met Lys Ser Tyr His Gly Pro Gly Thr Cys Thr Phe Tyr
    210                 215                 220

Gly Thr Ala Asn Thr Asn Gln Leu Val Met Glu Val Met Gly Met His
225                 230                 235                 240

Leu Pro Gly Ala Ser Phe Val Asn Pro Tyr Thr Pro Leu Arg Asp Ala
                245                 250                 255

Leu Thr Ala Glu Ala Ala Arg Gln Val Thr Arg Leu Thr Met Gln Ser
            260                 265                 270

Gly Ser Phe Met Pro Ile Gly Glu Ile Val Asp Glu Arg Ser Leu Val
        275                 280                 285

Asn Ser Ile Val Ala Leu His Ala Thr Gly Gly Ser Thr Asn His Thr
    290                 295                 300

Leu His Met Pro Ala Ile Ala Gln Ala Ala Gly Ile Gln Leu Thr Trp
305                 310                 315                 320

Gln Asp Met Ala Asp Leu Ser Glu Val Val Pro Thr Leu Ser His Val
                325                 330                 335

Tyr Pro Asn Gly Lys Ala Asp Ile Asn His Phe Gln Ala Ala Gly Gly
            340                 345                 350

Met Ser Phe Leu Ile Arg Glu Leu Leu Ala Ala Gly Leu Leu His Glu
        355                 360                 365

Asn Val Asn Thr Val Ala Gly Tyr Gly Leu Ser Arg Tyr Thr Lys Glu
    370                 375                 380

```
Pro Phe Leu Glu Asp Gly Lys Leu Val Trp Arg Glu Gly Pro Leu Asp
385                 390                 395                 400

Ser Leu Asp Glu Asn Ile Leu Arg Pro Val Ala Arg Pro Phe Ser Pro
            405                 410                 415

Glu Gly Gly Leu Arg Val Met Glu Gly Asn Leu Gly Arg Gly Val Met
        420                 425                 430

Lys Val Ser Ala Val Ala Leu Glu His Gln Ile Val Glu Ala Pro Ala
    435                 440                 445

Arg Val Phe Gln Asp Gln Lys Glu Leu Ala Asp Ala Phe Lys Ala Gly
450                 455                 460

Glu Leu Glu Cys Asp Phe Val Ala Val Met Arg Phe Gln Gly Pro Arg
465                 470                 475                 480

Cys Asn Gly Met Pro Glu Leu His Lys Met Thr Pro Phe Leu Gly Val
                485                 490                 495

Leu Gln Asp Arg Gly Phe Lys Val Ala Leu Val Thr Asp Gly Arg Met
            500                 505                 510

Ser Gly Ala Ser Gly Lys Ile Pro Ala Ala Ile His Val Cys Pro Glu
    515                 520                 525

Ala Phe Asp Gly Gly Pro Leu Ala Leu Val Arg Asp Gly Asp Val Ile
530                 535                 540

Arg Val Asp Gly Val Lys Gly Thr Leu Gln Val Leu Glu Ala Ser
545                 550                 555                 560

Glu Leu Ala Ala Arg Glu Pro Ala Ile Asn Gln Ile Asp Asn Ser Val
                565                 570                 575

Gly Cys Gly Arg Glu Leu Phe Gly Phe Met Arg Met Ala Phe Ser Ser
            580                 585                 590

Ala Glu Gln Gly Ala Ser Ala Phe Thr Ser Ser Leu Glu Thr Leu Lys
        595                 600                 605

<210> SEQ ID NO 507
<211> LENGTH: 1827
<212> TYPE: DNA
<213> ORGANISM: Pseudomonas fluorescens

<400> SEQUENCE: 507
atgcatcccc gcgttcttga ggtcaccgaa cggcttatcg cccgtagtcg cgccactcgc      60
caggcctatc tcgcgctgat ccgcgatgcc gccagcgacg gcccgcagcg gggcaagctg     120
caatgtgcga acttcgccca cggcgtggcc ggttgcggca ccgacgacaa gcacaacctg     180
cggatgatga atgcggccaa cgtggcaatt gtttcgtcat ataacgacat gttgtcggcg     240
caccagcctt acgaggtgtt ccccgagcag atcaagcgcg ccctgcgcga gatcggctcg     300
gtgggccagt tcgccggcgg cacccggcc atgtgcgatg gcgtgaccca gggcgaggcc     360
ggtatggaac tgagcctgcc gagccgtgaa gtgatcgccc tgtctacggc ggtggccctc     420
tctcacaaca tgttcgatgc cgcgctgatg ctggggatct cgacaagat tgtcccgggg     480
ttgatgatgg gcgctctgcg cttcggtcac ctgccgacca tcttcgttcc gggcgggccc     540
atggtctcgg gcatttccaa caagcagaaa gccgacgtgc cagcgtta cgccgaaggc     600
aaggccagcc gcgaggaact gctggagtcg gaaatgaagt cctaccacag ccccggcacc     660
tgcactttct acggcaccgc caacaccaac cagttgctga tggaagtgat gggcctgcac     720
ctgccgggcg cctctttcgt caaccccaat acgccgctgc gcgacgccct gacccatgag     780
gcggcgcagc aggtcacgcg cctgaccaag cagagcgggg ccttcatgcc gattggcgag     840
atcgtcgacg agcgcgtgct ggtcaactcc atcgttgccc tgcacgccac gggcggctcc     900
```

```
accaaccaca ccctgcacat gccggccatc gcccaggcgg cgggcatcca gctgacctgg      960
caggacatgg ccgacctctc cgaggtggtg ccgaccctgt cccacgtcta tccaaacggc     1020
aaggccgata tcaaccactt ccaggcggcg ggcggcatgt ctttcctgat ccgcgagctg     1080
ctggaagccg gcctgctcca cgaagacgtc aataccgtgg ccggccgcgg cctgagccgc     1140
tatacccagg aacccttcct ggacaacggc aagctggtgt ggcgcgacgg cccgattgaa     1200
agcctggacg aaaacatcct cgcgccggtg gcccgggcgt tctctgcgga gggcggcttg     1260
cgggtcatgg aaggcaacct cggtcgcggc gtgatgaagg tttccgccgt ggccccggag     1320
caccagatcg tcgaggcccc ggccgtggtg ttccaggacc agcaggacct ggccgatgcc     1380
ttcaaggccg gcctgctgga aaggacttc gtcgcggtga tgcgcttcca gggcccgcgc     1440
tccaacggca tgcccgagct gcacaagatg accccttcc tcggggtgct gcaggaccgc     1500
ggcttcaagg tggcgctggt caccgacggg cgcatgtccg cgcttcggg caagattccg     1560 gcagcgatcc atgtcagccc cgaagcccag gtgggtggcg cgctggcccg ggtgctggac     1620
ggcgatatca tccgagtgga tggcgtcaag ggcaccctgg agcttaaggt agacgccgca     1680
gaattcgccg cccgggagcc ggccaagggc ctgctgggca acaacgttgg caccggccgc     1740
gaactcttcg ccttcatgcg catggccttc agctcggcag agcagggcgc cagcgccttt     1800
acctctgccc tggagacgct caagtga                                        1827
```

<210> SEQ ID NO 508
<211> LENGTH: 608
<212> TYPE: PRT
<213> ORGANISM: Pseudomonas fluorescens

<400> SEQUENCE: 508

```
Met His Pro Arg Val Leu Glu Val Thr Glu Arg Leu Ile Ala Arg Ser
1               5                   10                  15

Arg Ala Thr Arg Gln Ala Tyr Leu Ala Leu Ile Arg Asp Ala Ala Ser
            20                  25                  30

Asp Gly Pro Gln Arg Gly Lys Leu Gln Cys Ala Asn Phe Ala His Gly
        35                  40                  45

Val Ala Gly Cys Gly Thr Asp Asp Lys His Asn Leu Arg Met Met Asn
    50                  55                  60

Ala Ala Asn Val Ala Ile Val Ser Ser Tyr Asn Asp Met Leu Ser Ala
65                  70                  75                  80

His Gln Pro Tyr Glu Val Phe Pro Glu Gln Ile Lys Arg Ala Leu Arg
                85                  90                  95

Glu Ile Gly Ser Val Gly Gln Phe Ala Gly Gly Thr Pro Ala Met Cys
            100                 105                 110

Asp Gly Val Thr Gln Gly Glu Ala Gly Met Glu Leu Ser Leu Pro Ser
        115                 120                 125

Arg Glu Val Ile Ala Leu Ser Thr Ala Val Ala Leu Ser His Asn Met
    130                 135                 140

Phe Asp Ala Ala Leu Met Leu Gly Ile Cys Asp Lys Ile Val Pro Gly
145                 150                 155                 160

Leu Met Met Gly Ala Leu Arg Phe Gly His Leu Pro Thr Ile Phe Val
                165                 170                 175

Pro Gly Gly Pro Met Val Ser Gly Ile Ser Asn Lys Gln Lys Ala Asp
            180                 185                 190

Val Arg Gln Arg Tyr Ala Glu Gly Lys Ala Ser Arg Glu Glu Leu Leu
        195                 200                 205
```

```
Glu Ser Glu Met Lys Ser Tyr His Ser Pro Gly Thr Cys Thr Phe Tyr
    210                 215                 220

Gly Thr Ala Asn Thr Asn Gln Leu Leu Met Glu Val Met Gly Leu His
225                 230                 235                 240

Leu Pro Gly Ala Ser Phe Val Asn Pro Asn Thr Pro Leu Arg Asp Ala
                245                 250                 255

Leu Thr His Glu Ala Ala Gln Gln Val Thr Arg Leu Thr Lys Gln Ser
            260                 265                 270

Gly Ala Phe Met Pro Ile Gly Glu Ile Val Asp Glu Arg Val Leu Val
        275                 280                 285

Asn Ser Ile Val Ala Leu His Ala Thr Gly Gly Ser Thr Asn His Thr
290                 295                 300

Leu His Met Pro Ala Ile Ala Gln Ala Ala Gly Ile Gln Leu Thr Trp
305                 310                 315                 320

Gln Asp Met Ala Asp Leu Ser Glu Val Val Pro Thr Leu Ser His Val
                325                 330                 335

Tyr Pro Asn Gly Lys Ala Asp Ile Asn His Phe Gln Ala Ala Gly Gly
            340                 345                 350

Met Ser Phe Leu Ile Arg Glu Leu Leu Glu Ala Gly Leu Leu His Glu
        355                 360                 365

Asp Val Asn Thr Val Ala Gly Arg Gly Leu Ser Arg Tyr Thr Gln Glu
370                 375                 380

Pro Phe Leu Asp Asn Gly Lys Leu Val Trp Arg Asp Gly Pro Ile Glu
385                 390                 395                 400

Ser Leu Asp Glu Asn Ile Leu Arg Pro Val Ala Arg Ala Phe Ser Ala
                405                 410                 415

Glu Gly Gly Leu Arg Val Met Glu Gly Asn Leu Gly Arg Gly Val Met
            420                 425                 430

Lys Val Ser Ala Val Ala Pro Glu His Gln Ile Val Glu Ala Pro Ala
435                 440                 445

Val Val Phe Gln Asp Gln Gln Asp Leu Ala Asp Ala Phe Lys Ala Gly
        450                 455                 460

Leu Leu Glu Lys Asp Phe Val Ala Val Met Arg Phe Gln Gly Pro Arg
465                 470                 475                 480

Ser Asn Gly Met Pro Glu Leu His Lys Met Thr Pro Phe Leu Gly Val
                485                 490                 495

Leu Gln Asp Arg Gly Phe Lys Val Ala Leu Val Thr Asp Gly Arg Met
            500                 505                 510

Ser Gly Ala Ser Gly Lys Ile Pro Ala Ala Ile His Val Ser Pro Glu
        515                 520                 525

Ala Gln Val Gly Gly Ala Leu Ala Arg Val Leu Asp Gly Asp Ile Ile
530                 535                 540

Arg Val Asp Gly Val Lys Gly Thr Leu Glu Leu Lys Val Asp Ala Ala
545                 550                 555                 560

Glu Phe Ala Ala Arg Glu Pro Ala Lys Gly Leu Leu Gly Asn Asn Val
                565                 570                 575

Gly Thr Gly Arg Glu Leu Phe Ala Phe Met Arg Met Ala Phe Ser Ser
            580                 585                 590

Ala Glu Gln Gly Ala Ser Ala Phe Thr Ser Ala Leu Glu Thr Leu Lys
        595                 600                 605

<210> SEQ ID NO 509
<211> LENGTH: 1677
<212> TYPE: DNA
<213> ORGANISM: Bacillus subtilis
```

<400> SEQUENCE: 509

```
atggcagaat tacgcagtaa tatgatcaca caaggaatcg atagagctcc gcaccgcagt      60
ttgcttcgtg cagcaggggt aaaagaagag gatttcggca agccgtttat tgcggtgtgt     120
aattcataca ttgatatcgt tcccggtcat gttcacttgc aggagtttgg gaaaatcgta     180
aagaagcaa tcagagaagc aggggggcgtt ccgtttgaat ttaataccat tggggtagat     240
gatggcatcg caatggggca tatcggtatg agatattcgc tgccaagccg tgaaattatc     300
gcagactctg tggaaacggt tgtatccgca cactggtttg acggaatggt ctgtattccg     360
aactgcgaca aaatcacacc gggaatgctt atggcggcaa tgcgcatcaa cattccgacg     420
atttttgtca gcggcggacc gatggcggca ggaagaacaa gttacgggcg aaaaatctcc     480
ctttcctcag tattcgaagg ggtaggcgcc taccaagcag ggaaaatcaa cgaaaacgag     540
cttcaagaac tagagcagtt cggatgccca acgtgcgggt cttgctcagg catgtttacg     600
gcgaactcaa tgaactgtct gtcagaagca cttggtcttg ctttgccggg taatggaacc     660
attctggcaa catctccgga acgcaaagag tttgtgagaa aatcggctgc caattaatg      720
gaaacgattc gcaagatat caaaccgcgt gatattgtta cagtaaaagc gattgataac     780
gcgtttgcac tcgatatggc gctcggaggt tctacaaata ccgttcttca taccottgcc     840
cttgcaaacg aagccggcgt tgaatactct ttagaacgca ttaacgaagt cgctgagcgc     900
gtgccgcact ggctaagct ggcgcctgca tcggatgtgt ttattgaaga tcttcacgaa     960
gcgggcggcg tttcagcggc tctgaatgag ctttcgaaga aagaaggagc gcttcattta    1020
gatgcgctga ctgttacagg aaaaactctt ggagaaacca ttgccggaca tgaagtaaag    1080
gattatgacg tcattcaccc gctggatcaa ccattcactg aaaagggagg ccttgctgtt    1140
ttattcggta atctagctcc ggacggcgct atcattaaaa caggcggcgt acagaatggg    1200
attacaagac acgaagggcc ggctgtcgta ttcgattctc aggacgaggc gcttgacggc    1260
attatcaacc gaaaagtaaa agaaggcgac gttgtcatca tcagatacga agggccaaaa    1320
ggcggacctg gcatgccgga atgctggcg ccaacatccc aaatcgttgg aatgggactc    1380
gggccaaaag tggcattgat tacggacgga cgttttccg gagcctcccg tggcctctca    1440
atcggccacg tatcacctga ggccgctgag ggcgggccgc ttgcctttgt tgaaaacgga    1500
gaccatatta tcgttgatat tgaaaaacgc atcttggatg tacaagtgcc agaagaagag    1560
tgggaaaaac gaaaagcgaa ctggaaaggt tttgaaccga agtgaaaaac cggctacctg    1620
gcacgttatt ctaaacttgt gacaagtgcc aacaccggcg tattatgaa aatctag       1677
```

<210> SEQ ID NO 510
<211> LENGTH: 558
<212> TYPE: PRT
<213> ORGANISM: Bacillus subtilis

<400> SEQUENCE: 510

```
Met Ala Glu Leu Arg Ser Asn Met Ile Thr Gln Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
```

-continued

```
                65                  70                  75                  80
        Asp Gly Ile Ala Met Gly His Ile Gly Met Arg Tyr Ser Leu Pro Ser
                            85                  90                  95
        Arg Glu Ile Ile Ala Asp Ser Val Glu Thr Val Ser Ala His Trp
                            100                 105                 110
        Phe Asp Gly Met Val Cys Ile Pro Asn Cys Asp Lys Ile Thr Pro Gly
                            115                 120                 125
        Met Leu Met Ala Ala Met Arg Ile Asn Ile Pro Thr Ile Phe Val Ser
                            130                 135                 140
        Gly Gly Pro Met Ala Ala Gly Arg Thr Ser Tyr Gly Arg Lys Ile Ser
        145                 150                 155                 160
        Leu Ser Ser Val Phe Glu Gly Val Gly Ala Tyr Gln Ala Gly Lys Ile
                            165                 170                 175
        Asn Glu Asn Glu Leu Gln Glu Leu Glu Gln Phe Gly Cys Pro Thr Cys
                            180                 185                 190
        Gly Ser Cys Ser Gly Met Phe Thr Ala Asn Ser Met Asn Cys Leu Ser
                            195                 200                 205
        Glu Ala Leu Gly Leu Ala Leu Pro Gly Asn Gly Thr Ile Leu Ala Thr
                            210                 215                 220
        Ser Pro Glu Arg Lys Glu Phe Val Arg Lys Ser Ala Ala Gln Leu Met
        225                 230                 235                 240
        Glu Thr Ile Arg Lys Asp Ile Lys Pro Arg Asp Ile Val Thr Val Lys
                            245                 250                 255
        Ala Ile Asp Asn Ala Phe Ala Leu Asp Met Ala Leu Gly Gly Ser Thr
                            260                 265                 270
        Asn Thr Val Leu His Thr Leu Ala Leu Ala Asn Glu Ala Gly Val Glu
                            275                 280                 285
        Tyr Ser Leu Glu Arg Ile Asn Glu Val Ala Glu Arg Val Pro His Leu
                            290                 295                 300
        Ala Lys Leu Ala Pro Ala Ser Asp Val Phe Ile Glu Asp Leu His Glu
        305                 310                 315                 320
        Ala Gly Gly Val Ser Ala Ala Leu Asn Glu Leu Ser Lys Lys Glu Gly
                            325                 330                 335
        Ala Leu His Leu Asp Ala Leu Thr Val Thr Gly Lys Thr Leu Gly Glu
                            340                 345                 350
        Thr Ile Ala Gly His Glu Val Lys Asp Tyr Asp Val Ile His Pro Leu
                            355                 360                 365
        Asp Gln Pro Phe Thr Glu Lys Gly Gly Leu Ala Val Leu Phe Gly Asn
                            370                 375                 380
        Leu Ala Pro Asp Gly Ala Ile Ile Lys Thr Gly Gly Val Gln Asn Gly
        385                 390                 395                 400
        Ile Thr Arg His Glu Gly Pro Ala Val Val Phe Asp Ser Gln Asp Glu
                            405                 410                 415
        Ala Leu Asp Gly Ile Ile Asn Arg Lys Val Lys Glu Gly Asp Val Val
                            420                 425                 430
        Ile Ile Arg Tyr Glu Gly Pro Lys Gly Gly Pro Gly Met Pro Glu Met
                            435                 440                 445
        Leu Ala Pro Thr Ser Gln Ile Val Gly Met Gly Leu Gly Pro Lys Val
                            450                 455                 460
        Ala Leu Ile Thr Asp Gly Arg Phe Ser Gly Ala Ser Arg Gly Leu Ser
        465                 470                 475                 480
        Ile Gly His Val Ser Pro Glu Ala Ala Glu Gly Gly Pro Leu Ala Phe
                            485                 490                 495
```

```
Val Glu Asn Gly Asp His Ile Ile Val Asp Ile Glu Lys Arg Ile Leu
            500                 505                 510
Asp Val Gln Val Pro Glu Glu Trp Glu Lys Arg Lys Ala Asn Trp
        515                 520                 525
Lys Gly Phe Glu Pro Lys Val Lys Thr Gly Tyr Leu Ala Arg Tyr Ser
        530                 535                 540
Lys Leu Val Thr Ser Ala Asn Thr Gly Gly Ile Met Lys Ile
545                 550                 555
```

<210> SEQ ID NO 511
<211> LENGTH: 1677
<212> TYPE: DNA
<213> ORGANISM: Bacillus licheniformis

<400> SEQUENCE: 511

```
atgacaggtt tacgcagtga catgattaca aaagggatcg acagagcgcc gcaccgcagt      60
ttgctgcgcg cggctggggt aaaagaagag gacttcggca aaccgtttat tgccgtttgc     120
aactcataca tcgatatcgt accgggtcat gtccatttgc aggagtttgg aaaaatcgtc     180
aaagaggcga tcagagaggc cggcggtgtt ccgtttgaat ttaatacaat cggggtcgac     240
gacggaattg cgatggggca catcggaatg aggtattctc tcccgagccg cgaaatcatc     300
gcagattcag tggaaacggt tgtatcggcg cactggtttg acggaatggt atgtattcca     360
aactgtgata aaatcacacc gggcatgatc atggcggcaa tgcggatcaa cattccgacc     420
gtgtttgtca gcggggggcc gatggaagcg gaagaacga gcgacggacg aaaaatctcg     480
ctttcctctg tatttgaagg cgttggcgct tatcaatcag gcaaaatcga tgagaaagga     540
ctcgaggagc ttgaacagtt cggctgtccg acttgcggat catgctcggg catgtttacg     600
gcgaactcga tgaactgtct ttctgaagct cttggcatcg ccatgccggg caacggcacc     660
attttggcga catcgcccga ccgcagggaa tttgccaaac agtcggcccg ccagctgatg     720
gagctgatca agtcggatat caaaccgcgc gacatcgtga ccgaaaaagc gatcgacaac     780
gcgttcgctt tagacatggc gctcggcgga tcaacgaata cgatccttca tacgcttgcg     840
atcgccaatg aagcgggtgt agactattcg cttgaacgga tcaatgaggt agcggcaagg     900
gttccgcatt tatcgaagct tgcaccggct tccgatgtgt ttattgaaga tttgcatgaa     960
gcaggaggcg atcggcagt cttaaacgag ctgtcgaaaa agaaggcgc gcttcacttg    1020
gatacgctga ctgtaacggg gaaaacgctt ggcgaaaata ttgccggacg cgaagtgaaa    1080
gattacgagg tcattcatcc gatcgatcag ccgttttcag agcaaggcgg actcgccgtc    1140
ctgttcggca acctggctcc tgacggtgcg atcattaaaa cgggcggcgt ccaagacggg    1200
attacccgcc atgaaggacc tgcggttgtc tttgattcac aggaagaagc gcttgacggc    1260
atcatcaacc gtaaagtaaa agcgggagat gtcgtcatca tccgctatga aggccctaaa    1320
ggcggaccgg gaatgcctga aatgcttgcg ccgacttcac agatcgtcgg aatgggcctc    1380
ggcccgaaag tcgccttgat taccgacggc cgcttttcag agcctcccg cggtctttcg    1440
atcgccacg tttcaccgga agcagccgaa ggcggcccgc ttgctttcgt agaaaacggc    1500
gaccatatcg ttgtcgatat cgaaaagcgg attttaaaca tcgaaatctc cgatgaggaa    1560
tgggaaaaaa gaaagcaaa ctggcccggc tttgaaccga agtgaaaac gggctatctc    1620
gccaggtatt caaagcttgt gacatctgcc aataccggcg gcattatgaa aatctag     1677
```

<210> SEQ ID NO 512
<211> LENGTH: 558
<212> TYPE: PRT

<213> ORGANISM: Bacillus licheniformis

<400> SEQUENCE: 512

Met Thr Gly Leu Arg Ser Asp Met Ile Thr Lys Gly Ile Asp Arg Ala
1               5                   10                  15

Pro His Arg Ser Leu Leu Arg Ala Ala Gly Val Lys Glu Glu Asp Phe
            20                  25                  30

Gly Lys Pro Phe Ile Ala Val Cys Asn Ser Tyr Ile Asp Ile Val Pro
        35                  40                  45

Gly His Val His Leu Gln Glu Phe Gly Lys Ile Val Lys Glu Ala Ile
    50                  55                  60

Arg Glu Ala Gly Gly Val Pro Phe Glu Phe Asn Thr Ile Gly Val Asp
65                  70                  75                  80

Asp Gly Ile Ala Met Gly His Ile Gly Met Arg Tyr Ser Leu Pro Ser
                85                  90                  95

Arg Glu Ile Ile Ala Asp Ser Val Glu Thr Val Val Ser Ala His Trp
            100                 105                 110

Phe Asp Gly Met Val Cys Ile Pro Asn Cys Asp Lys Ile Thr Pro Gly
        115                 120                 125

Met Ile Met Ala Ala Met Arg Ile Asn Ile Pro Thr Val Phe Val Ser
    130                 135                 140

Gly Gly Pro Met Glu Ala Gly Arg Thr Ser Asp Gly Arg Lys Ile Ser
145                 150                 155                 160

Leu Ser Ser Val Phe Glu Gly Val Gly Ala Tyr Gln Ser Gly Lys Ile
                165                 170                 175

Asp Glu Lys Gly Leu Glu Glu Leu Glu Gln Phe Gly Cys Pro Thr Cys
            180                 185                 190

Gly Ser Cys Ser Gly Met Phe Thr Ala Asn Ser Met Asn Cys Leu Ser
        195                 200                 205

Glu Ala Leu Gly Ile Ala Met Pro Gly Asn Gly Thr Ile Leu Ala Thr
    210                 215                 220

Ser Pro Asp Arg Arg Glu Phe Ala Lys Gln Ser Ala Arg Gln Leu Met
225                 230                 235                 240

Glu Leu Ile Lys Ser Asp Ile Lys Pro Arg Asp Ile Val Thr Glu Lys
                245                 250                 255

Ala Ile Asp Asn Ala Phe Ala Leu Asp Met Ala Leu Gly Gly Ser Thr
            260                 265                 270

Asn Thr Ile Leu His Thr Leu Ala Ile Ala Asn Glu Ala Gly Val Asp
        275                 280                 285

Tyr Ser Leu Glu Arg Ile Asn Glu Val Ala Ala Arg Val Pro His Leu
    290                 295                 300

Ser Lys Leu Ala Pro Ala Ser Asp Val Phe Ile Glu Asp Leu His Glu
305                 310                 315                 320

Ala Gly Gly Val Ser Ala Val Leu Asn Glu Leu Ser Lys Lys Glu Gly
                325                 330                 335

Ala Leu His Leu Asp Thr Leu Thr Val Thr Gly Lys Thr Leu Gly Glu
            340                 345                 350

Asn Ile Ala Gly Arg Glu Val Lys Asp Tyr Glu Val Ile His Pro Ile
        355                 360                 365

Asp Gln Pro Phe Ser Glu Gln Gly Gly Leu Ala Val Leu Phe Gly Asn
    370                 375                 380

Leu Ala Pro Asp Gly Ala Ile Ile Lys Thr Gly Gly Val Gln Asp Gly
385                 390                 395                 400

Ile Thr Arg His Glu Gly Pro Ala Val Val Phe Asp Ser Gln Glu Glu

```
                405                 410                 415
Ala Leu Asp Gly Ile Ile Asn Arg Lys Val Lys Ala Gly Asp Val Val
        420                 425                 430

Ile Ile Arg Tyr Glu Gly Pro Lys Gly Gly Pro Gly Met Pro Glu Met
            435                 440                 445

Leu Ala Pro Thr Ser Gln Ile Val Gly Met Gly Leu Gly Pro Lys Val
        450                 455                 460

Ala Leu Ile Thr Asp Gly Arg Phe Ser Gly Ala Ser Arg Gly Leu Ser
465                 470                 475                 480

Ile Gly His Val Ser Pro Glu Ala Ala Glu Gly Gly Pro Leu Ala Phe
                485                 490                 495

Val Glu Asn Gly Asp His Ile Val Val Asp Ile Glu Lys Arg Ile Leu
            500                 505                 510

Asn Ile Glu Ile Ser Asp Glu Glu Trp Glu Lys Arg Lys Ala Asn Trp
        515                 520                 525

Pro Gly Phe Glu Pro Lys Val Lys Thr Gly Tyr Leu Ala Arg Tyr Ser
    530                 535                 540

Lys Leu Val Thr Ser Ala Asn Thr Gly Gly Ile Met Lys Ile
545                 550                 555
```

<210> SEQ ID NO 513
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 513
cacgcacgga ccgaccgtca ccggaccgtt tcgcgcgacg tgcgcgaggc tccgacacga    60
aagacgggcc ccctattgcg ctcatgtcgg ccgcacccct gcgtaaagtc agatacgtgc   120
gccacccgag ccgggaccgc cctgagcgca tggtccgggc ggcgtggcaa gcgcaggagg   180
gcgtgccccg ttcgctaggc a                                             201

<210> SEQ ID NO 514
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 514
acgtatgtcg gctgatcgta cacgccgacc agcgcagtcg gcgtactcag gcgttccgag    60
tagctcacat ctgtgggccc cggcgtacct tcggcagggt tatgcgacgg ggcggcaggc   120
ttgcgctggc gtcgggaatc accgcgaact tgacccgcgc cggttccgta tcggtccgct   180
gcggccgtgc tccgcagtcg a                                             201

<210> SEQ ID NO 515
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 515
tgcagtccgc ccagccggcc gtgtagcacg gccgactgca ggtgcgacgt gctaggggcc    60

```
agcacgcgag cggccctacc acgggtcgtg tggggcgcat gaccgccggc cgggtctcgg    120
cacggggcga cgcggtgctc ctaggctagc agggcctcac cgggtgatcc cccgtgtagc    180
gccgcacaac accccctgcg a                                              201
```

<210> SEQ ID NO 516
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 516

```
tgcccgcata ccgcccgccc actggggatc ctccggcgct gtcgcgctat gcgcgtccat     60
cctggtcgga cgggctcggg ccccggacca aaccgcagcg gccccctggca gcgactaagg   120 gcgccgtctc accctagact tcttaatcgg ggtgtcccgg taggccggga gtagcctcgg   180
cgggctagcc gcgtgactat a                                              201
```

<210> SEQ ID NO 517
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 517

```
gcgggttagt ccccgtcgga cgtcatgcat acagtcgggg ctggcgagac aggaggctac    60 aggggggcgcc cggaggaaca cacgtgggac taagacgtcg gtccgtgtgc ccccgaaccg   120
gcgtgctcat cgtaggactg ggaagtccgt accgcgtggc tcgtacctcg cggtctgagt   180
ccgacacccg ctgacgccgg a                                              201
```

<210> SEQ ID NO 518
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 518

```
ctgagacgac tcccgcacta cggatcgcga gcgtagactc agcccggact ctcacgcgac     60
ctcggacgcg gcctaatgtc tcgactcgcg gtccgctgaa ggtctcgggg cacgcgagac    120
gcggggtcag gccggggga tccccgcaca cactcagtcg cggcgaacgg agtcccgtgg    180
cctggctagg gatcgtgggt a                                              201
```

<210> SEQ ID NO 519
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 519

```
ggggcgtcca ctctggctcg gtagagcgct gggctccgcg cgactgcgcg cacccatcgg     60
tttggcgcga cgcaccgtgg actcctgggc tagagggcgg gtcccgcca taccccgttc    120 tcgtgccggc tgggtaggac cggagtgacg gctgtggccg gcgactcggg cgcgcactgt   180
```
agtcggatct gggcgggcag a                                              201

<210> SEQ ID NO 520
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 520
gtcgggcgcg cgtcagtcca cgcgttaaac actggccgac gacacgacgg gatccgggca    60
cgccccgaga gcgcgtgttc gcgcgagtcg atcgggaggc cgcagcgtgt cgagcccaga   120
ccccgctcta gcgtggccat cgcggtgcta agtggggcgg ccgggtccta tacacgctta   180
ccgatagtca agtttgcgtg a                                              201

<210> SEQ ID NO 521
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 521
gtcttagggc ccagggaccg cacgggtcga ccgcgcgact ggtcggagct tgcgcgtcta    60
cgccactcgg cggccccgac gggggatgcc gcggaatgtc cgccggcgta tgcggctcaa   120
gccggaccgt cggactgcga agcgccgtga gcacccctcg acctgaccgg acgcggcgca   180
cccgtccgag tatcgtcgcg a                                              201

<210> SEQ ID NO 522
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 522
tcgggtctcg cccggcgcta gtccagccgt agcgctctcc ggcgatcacc ccggagcact    60
ctggagccga gcggtcgggt ctgttgggcg cgccgcggct acggacggct cgactcactg   120
gcgctcgacc ccgtatcccc cgtctcggac gacgcaccgt tgcgcgggaa cgatcggcgg   180
cgctcacacg cacgatcgga a                                              201

<210> SEQ ID NO 523
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 523
cttaaggctg gcgcaccatg agggccgcgc cacgtccgac ccgcagcccg cgcgtagtag    60
cctagccggg cggggttcct cccgtgcgtc acctagcacg gggcctggca ccgaacgcga   120
gcccgtccgg tcaccgcggc gggtctgcgg acgtccccgg tcgctcggct cggagtcccc   180
gctggggatc gcgtcgggac a                                              201

<210> SEQ ID NO 524

```
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 524
cgacggcgta gcactcgcgg acctagggcg cgcgagtcgg gggagcccgc ggtgcgacgc    60
tcggggagga gctcgcatgc ccaaggcacg atctagggggg gggtacgggg ggcgtccgtc  120
cgagcgccgg gactgcgatc cggggccaca tgctaaccgg cggaaggggg gacctaaccg  180
gtgtggactc cgggtaatcc a                                             201

<210> SEQ ID NO 525
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 525 cgggggggctg acacgtctcg gatcgccccg tcagtcagcc ccctagtccc ggacaggacg   60
tcggaggtcg agtccgcact gtcgggcctg ctcgtgggca cggcaggacg cgtccccatg  120
gtcagccgcc gtgcgatacc tcgccacgac tctgagccgg gcgcgagcgt gagagcccga  180
gccgcggtac acggggcgtc a                                             201

<210> SEQ ID NO 526
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 526
gcgagctcgc tctcgactcc gggctcccgt gctgacacgg ggtgcgaccc cgcggcgatt   60
gtccgcacgc ctgtcggacg acgtcggccc gtcgtagtgc cggtcagagg cagggggggct 120 gctcgcgctg gccgcctcgt cgcgcgtgga ccctatgggg gatcacgcgt ggggtcggga  180
tcggggaccg cgcgacttgg a                                             201

<210> SEQ ID NO 527
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 527
cgcgccccgt aacggacgcg gtgagtcgag cttacgcggc tagggccgag tcgtgttagc   60
gtctcgcgta agcgaatgcc acgtccccg ccgcccgtcg cgcagctggc tacgcaacgc  120
ctccgcggcc tccgtagcga gtgcgtggga cgctggccgt ccgcgtgttc cgggacctgg 180
atgcgggagg gacctaaggc a                                             201

<210> SEQ ID NO 528
<211> LENGTH: 201
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 528
agaacgtgcg gtcgtcccca cgcacgggat gacggacggg gtagacgggc gtcgtgcgcg      60
cgggtagcgt aaccggttac agtccccgca acgctctagc tccggccctc gcttaggagt     120
tcgcggccga gacatgaggt ggtccggacg gcaggggtc gcggagaccg tggagccgat      180
tctgccggac gccacgtccc a                                               201

<210> SEQ ID NO 529
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 529
cgggacgccc cgtaccgtgt acgaagcccc ggtcggtcgg cggatcgtag atcccggagc      60
cgacgccttg aacccggctt tcccagcgac tcgcgccccc actgggtccc tcggaccccc     120 gctccccca gacgcataca gcccgcaagc gggggcagtc tcggaccgcc cggacactgg      180
ccttaggcac cgtgggctcg a                                               201

<210> SEQ ID NO 530
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 530
gtgtccgggg cgcatcggag ctgtccgacc gagttccggg gacggcgcac gttgtgccgg      60
cctcagacgg agcctgtagc ccccggacag tgtgtgcccg cccactacgg gttaggcacg     120
gggttggtcg gcacgcgtcc tccgcgtgtc acggaccgat gcagaccgct ggccgggagg     180 tcgcccccc aggggtgcac a                                                201

<210> SEQ ID NO 531
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 531
cgcgcagcac gcacgtccgg ggcacgcgcg gctcggaggg tccgggctgg gacgggaggt      60
ttggagtcgc gtgcgcgtag cagcgcaccc gcctggtcgc cgggtctagt agggctgggt     120
tacggaggac gtgcaggcga ccccaaccgt tgacgacggg tccgaccacg cctttagccg     180
tggcgtgtcc gtcgcgagcc a                                               201

<210> SEQ ID NO 532
<211> LENGTH: 12
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base

```
<222> LOCATION: (4)..(9)
<223> OTHER INFORMATION: a, c, t, g, unknown or other

<400> SEQUENCE: 532
tcrnnnnnna cg                                                     12

<210> SEQ ID NO 533
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(14)
<223> OTHER INFORMATION: a, c, t, g, unknown or other

<400> SEQUENCE: 533
cggnnnnnnn nnnnccg                                                17

<210> SEQ ID NO 534
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 534
gaannttcnn gaa                                                    13

<210> SEQ ID NO 535
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 535 tgatgtannt                                                        10

<210> SEQ ID NO 536
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other

<400> SEQUENCE: 536 ccnnnwwrgg                                                        10
```

```
<210> SEQ ID NO 537
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 537 wwwwsygggg                                                                10

<210> SEQ ID NO 538
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(9)
<223> OTHER INFORMATION: a, c, t, g, unknown or other

<400> SEQUENCE: 538
rmacccannc ayy                                                            13

<210> SEQ ID NO 539
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 539
tycgtnnrna rtgaya                                                         16

<210> SEQ ID NO 540
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 540
rrraararaa nanraraa                                                       18

<210> SEQ ID NO 541
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
```

```
<400> SEQUENCE: 541
gtgtgtgtgt gtgtg                                                        15

<210> SEQ ID NO 542
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 542
anagngagag agnggcag                                                     18

<210> SEQ ID NO 543
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 543
ytstysttnt tgytwtt                                                      17

<210> SEQ ID NO 544
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 544
tnnccwnttt ktttc                                                        15

<210> SEQ ID NO 545
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 545
gcatgaccat ccacg                                                        15
```

<210> SEQ ID NO 546
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 546
aaaaararaa aarma                                                       15

<210> SEQ ID NO 547
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 547
gsgayarmgg amaaaaa                                                     17

<210> SEQ ID NO 548
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(14)
<223> OTHER INFORMATION: a, c, t, g, unknown or other

<400> SEQUENCE: 548
ykytyttytt nnnnky                                                      16

<210> SEQ ID NO 549
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 549
trccgagryw nsssgcgs                                                    18

<210> SEQ ID NO 550
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 550
cgtccggcgc                                                             10

<210> SEQ ID NO 551
<211> LENGTH: 15
<212> TYPE: DNA
<213> ORGANISM: Artificial Sequence
<220> FEATURE:
<223> OTHER INFORMATION: Description of Artificial Sequence: Synthetic binding motif oligonucleotide

<400> SEQUENCE: 551
gaaaaagmaa aaaaa                                                    15

<210> SEQ ID NO 552
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other

<400> SEQUENCE: 552
aarwtsgarg nanncsaa                                                 18

<210> SEQ ID NO 553
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 553
ttttyyttyt tkyntynt                                                 18

<210> SEQ ID NO 554
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other

<400> SEQUENCE: 554
csnccaatgk nncs                                                     14

<210> SEQ ID NO 555
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 555

```
catkyttttt tkyty                                                15
```

<210> SEQ ID NO 556
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 556

```
gctnactaat                                                      10
```

<210> SEQ ID NO 557
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 557

```
cacgtgacya                                                      10
```

<210> SEQ ID NO 558
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 558

```
cannnacaca sana                                                 14
```

<210> SEQ ID NO 559
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 559

```
cayamrtgyn c                                                    11
```

<210> SEQ ID NO 560
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base

```
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 560
ggnanannar narggcn                                                  17

<210> SEQ ID NO 561
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 561 tsgygrgasa                                                          10

<210> SEQ ID NO 562
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 562
tttkytktty nytttkty                                                 18

<210> SEQ ID NO 563
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (6)..(8)
<223> OTHER INFORMATION: a, c, t, g, unknown or other

<400> SEQUENCE: 563
kncncnnnsc gctackgc                                                 18

<210> SEQ ID NO 564
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 564 wttktttty tttttnt                                                     17

<210> SEQ ID NO 565
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 565
srnggcmcgg cnssg                                                      15

<210> SEQ ID NO 566
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 566 ttktttttytt c                                                         11

<210> SEQ ID NO 567
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other

<400> SEQUENCE: 567
tacyacanca cawga                                                      15

<210> SEQ ID NO 568
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
```

```
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 568
aaannraang arraanar                                                18

<210> SEQ ID NO 569
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 569
ccytgnaytt cwncttc                                                 17

<210> SEQ ID NO 570
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 570
gtgmaknmgr angng                                                   15

<210> SEQ ID NO 571
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 571
nttwacaycc rtacayny                                                18

<210> SEQ ID NO 572
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 572
tttnctttky ttnytttt                                               18

<210> SEQ ID NO 573
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other

<400> SEQUENCE: 573
aawnrtaaay arg                                                    13

<210> SEQ ID NO 574
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 574
aaaranraaa naaarnaa                                               18

<210> SEQ ID NO 575
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other

<400> SEQUENCE: 575
```

```
ggnaawangt aaacaa                                                      16
```

<210> SEQ ID NO 576
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 576

```
cacacacaca cacacac                                                     17
```

<210> SEQ ID NO 577
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 577

```
sastkcwctc ktcgt                                                       15
```

<210> SEQ ID NO 578
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 578

```
ttgcttgaac gsatgcca                                                    18
```

<210> SEQ ID NO 579
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 579

```
yctttttttt yttyykg                                                     17
```

<210> SEQ ID NO 580
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(7)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(13)
<223> OTHER INFORMATION: a, c, t, g, unknown or other

<400> SEQUENCE: 580

```
cggmnnncwn ynnccccg                                                    17
```

```
<210> SEQ ID NO 581
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 581
rrsccgmcgm grcgcgcs                                                   18

<210> SEQ ID NO 582
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 582
rgargtsacg cakrttct                                                   18

<210> SEQ ID NO 583
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 583
aaanararnr aaaarrar                                                   18

<210> SEQ ID NO 584
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 584
ggaagctgaa acgymwrr                                                   18

<210> SEQ ID NO 585
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 585
ggagaggcat gatggggg                                                   18

<210> SEQ ID NO 586
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
```

<400> SEQUENCE: 586
aggtgatgga gtgctcag                                                        18

<210> SEQ ID NO 587
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 587 ctnccttct                                                                  10

<210> SEQ ID NO 588
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 588
gkctrrnrgg agangm                                                          16

<210> SEQ ID NO 589
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 589
gaaarraaaa aamrmara                                                        18

<210> SEQ ID NO 590
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 590
ngggsgntns ygtncga                                                    17

<210> SEQ ID NO 591
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other

<400> SEQUENCE: 591
gngccrsnnt m                                                          11

<210> SEQ ID NO 592
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 592
agnawgtttt tgwcaama                                                   18

<210> SEQ ID NO 593
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 593 tttttttyttt tynktttt                                                  18

<210> SEQ ID NO 594
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 594
kcksgcaggc wttkytct                                                   18

<210> SEQ ID NO 595
<211> LENGTH: 18
<212> TYPE: DNA
<213> ORGANISM: Artificial Sequence
<220> FEATURE:
<223> OTHER INFORMATION: Description of Artificial Sequence: Synthetic binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 595
yttcttttyt nyncnktn                                                 18

<210> SEQ ID NO 596
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 596
gnccsartng c                                                        11

<210> SEQ ID NO 597
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 597 tnsykcttttt cytty                                                   15

<210> SEQ ID NO 598
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(10)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 598
sgcgmgggnn ccngaccg                                                 18

```
<210> SEQ ID NO 599
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 599
sttnytttyn ttytyyyy                                                  18

<210> SEQ ID NO 600
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 600
yctnattsgn cngs                                                      14

<210> SEQ ID NO 601
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 601
ykntttwyyt c                                                         11

<210> SEQ ID NO 602
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
```

```
<220> FEATURE:
<221> NAME/KEY: modified_base
<222> LOCATION: (17)..(17)
<223> OTHER INFORMATION: a, c, t, g, unknown or other

<400> SEQUENCE: 602
tnttsmttny tttccknc                                              18

<210> SEQ ID NO 603
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 603
aaaananaar arnag                                                 15

<210> SEQ ID NO 604
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 604
ccacktksgs cctns                                                 15

<210> SEQ ID NO 605
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 605 waaaaagaa aanaaaar                                               18

<210> SEQ ID NO 606
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 606
crsgcywgkg c                                                     11
```

<210> SEQ ID NO 607
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 607
aaanggnara m                                                              11

<210> SEQ ID NO 608
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 608
naaraagcng ggcacnc                                                        17

<210> SEQ ID NO 609
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 609
tyttcyagaa nnttcy                                                         16

<210> SEQ ID NO 610
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 610
cacacacaca cacacaca                                                       18

<210> SEQ ID NO 611
<211> LENGTH: 11

-continued

```
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 611
tttycacatg c                                                              11

<210> SEQ ID NO 612
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 612
sckkcgckst ssttyaa                                                        17

<210> SEQ ID NO 613
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 613
gnngcatgtg aaaa                                                           14

<210> SEQ ID NO 614
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 614
gaaaanaaaa aaaarana                                                       18

<210> SEQ ID NO 615
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 615
ctttttttyy tsgcc                                                          15

<210> SEQ ID NO 616
<211> LENGTH: 15
<212> TYPE: DNA
<213> ORGANISM: Artificial Sequence
<220> FEATURE:
```

-continued

```
<223> OTHER INFORMATION: Description of Artificial Sequence: Synthetic
      binding motif oligonucleotide
<220> FEATURE:
<221> NAME/KEY: modified_base
<222> LOCATION: (13)..(13)
<223> OTHER INFORMATION: a, c, t, g, unknown or other

<400> SEQUENCE: 616
gaaaaaraar aanaa                                                     15

<210> SEQ ID NO 617
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(15)
<223> OTHER INFORMATION: a, c, t, g, unknown or other

<400> SEQUENCE: 617
gccggtmmcg sycnn                                                     15

<210> SEQ ID NO 618
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(7)
<223> OTHER INFORMATION: a, c, t, g, unknown or other

<400> SEQUENCE: 618
yttktnnttt ttytyttt                                                  18

<210> SEQ ID NO 619
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other

<400> SEQUENCE: 619 annttttyt tkygc                                                      15

<210> SEQ ID NO 620
<211> LENGTH: 10
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 620 gcagngcagg                                                           10
```

```
<210> SEQ ID NO 621
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 621
aaacntttat anataca                                                      17

<210> SEQ ID NO 622
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other

<400> SEQUENCE: 622
caatntctnc k                                                            11

<210> SEQ ID NO 623
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 623 tttytyktttt nyyttttt                                                    18

<210> SEQ ID NO 624
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
```

```
<222> LOCATION: (14)..(14)
<223> OTHER INFORMATION: a, c, t, g, unknown or other

<400> SEQUENCE: 624
gnrrnanacg cgtnr                                                    15

<210> SEQ ID NO 625
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 625
tttccnaawn rggaaa                                                   16

<210> SEQ ID NO 626
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 626
yttyyttytt ttytyttc                                                 18

<210> SEQ ID NO 627
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 627 mttttytyt yttc                                                      14

<210> SEQ ID NO 628
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (7)..(7)
<223> OTHER INFORMATION: a, c, t, g, unknown or other

<400> SEQUENCE: 628
tatacanagm krtatatg                                                 18

<210> SEQ ID NO 629
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
```

```
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 629
tmtttntync ttntttwk                                                 18

<210> SEQ ID NO 630
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 630
ktnnttwtta ttccnc                                                   16

<210> SEQ ID NO 631
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(3)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 631
rnnaaaanra naaraaat                                                 18

<210> SEQ ID NO 632
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 632 tttttttcw ctttkyc                                                   17

<210> SEQ ID NO 633
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 633
tttynytktt tynyttyt                                                  18

<210> SEQ ID NO 634
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 634
ttynnttytt nytttyyy                                                  18

<210> SEQ ID NO 635
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 635
tnygtgkryg tnyg                                                      14

<210> SEQ ID NO 636
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 636
ttyyyttttt yttttytt                                                  18

<210> SEQ ID NO 637
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide
```

-continued

```
<400> SEQUENCE: 637
gamaaaaaar aaaar                                                   15

<210> SEQ ID NO 638
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 638
cycgggaagc sammnccg                                                18

<210> SEQ ID NO 639
<211> LENGTH: 13
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 639
grtgyayggr tgy                                                     13

<210> SEQ ID NO 640
<211> LENGTH: 14
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 640
kmaaraaaaa raar                                                    14

<210> SEQ ID NO 641
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 641
aygraaaara raaaaraa                                                18

<210> SEQ ID NO 642
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other

<400> SEQUENCE: 642
ggaksccntt tyngmrta                                                18
```

```
<210> SEQ ID NO 643
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 643
ttttcnkttt yttttc                                                  17

<210> SEQ ID NO 644
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 644
araagmagaa arraa                                                   15

<210> SEQ ID NO 645
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 645
yttttctttt ynttttt                                                 17

<210> SEQ ID NO 646
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 646
arraraaagg n                                                       11

<210> SEQ ID NO 647
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(7)
```

```
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other

<400> SEQUENCE: 647
ystnykntyt tnctcccm                                                18

<210> SEQ ID NO 648
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other

<400> SEQUENCE: 648
garanaaaar nraaraaa                                                18

<210> SEQ ID NO 649
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(4)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other

<400> SEQUENCE: 649
cynnggssan c                                                       11

<210> SEQ ID NO 650
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 650
cacacacaca cacaya                                                  16

<210> SEQ ID NO 651
<211> LENGTH: 15
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 651
cttytwttkt tktsa                                                   15

<210> SEQ ID NO 652
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 652
yttyyytytt tytyyttt                                                   18

<210> SEQ ID NO 653
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 653
amaaaaaraa rwaranaa                                                   18

<210> SEQ ID NO 654
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 654
araaaarraa aaagnraa                                                   18

<210> SEQ ID NO 655
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 655
raaraaaaar cmrsraaa                                                   18

<210> SEQ ID NO 656
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 656
ttytktytyn tyyktttty                                                  18

<210> SEQ ID NO 657
<211> LENGTH: 18
<212> TYPE: DNA
<213> ORGANISM: Artificial Sequence
```

```
-continued

<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 657
gaaaamaana aaanaaa                                                 18

<210> SEQ ID NO 658
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 658
yaanaraara aaanaam                                                 18

<210> SEQ ID NO 659
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 659 tynttttty tttttntk                                                 18

<210> SEQ ID NO 660
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 660
```

-continued raaraaraaa naanrnaa                                             18

<210> SEQ ID NO 661
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (12)..(12)
<223> OTHER INFORMATION: a, c, t, g, unknown or other

<400> SEQUENCE: 661
raarrraaaa anaaamaa                                             18

<210> SEQ ID NO 662
<211> LENGTH: 11
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 662
gccagaccta c                                                    11

<210> SEQ ID NO 663
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 663
ttyttyttyt ttynytyt                                             18

<210> SEQ ID NO 664
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 664
yksgcgcgyc kcgkcggs                                             18

<210> SEQ ID NO 665
<211> LENGTH: 17
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 665
ttttyytttt yyyyktt                                              17

<210> SEQ ID NO 666
<211> LENGTH: 13
<212> TYPE: DNA

```
<213> ORGANISM: Artificial Sequence
<220> FEATURE:
<223> OTHER INFORMATION: Description of Artificial Sequence: Synthetic
      binding motif oligonucleotide

<400> SEQUENCE: 666
ttcttktyyt ttt                                                            13

<210> SEQ ID NO 667
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 667
ttyttttyty ytttyttt                                                       18

<210> SEQ ID NO 668
<211> LENGTH: 18
<212> TYPE: DNA
<213> ORGANISM: Artificial Sequence
<220> FEATURE:
<223> OTHER INFORMATION: Description of Artificial Sequence: Synthetic
      binding motif oligonucleotide

<400> SEQUENCE: 668
ttgcttgaac ggatgcca                                                       18

<210> SEQ ID NO 669
<211> LENGTH: 16
<212> TYPE: DNA
<213> ORGANISM: Artificial Sequence
<220> FEATURE:
<223> OTHER INFORMATION: Description of Artificial Sequence: Synthetic
      binding motif oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 669
mgnmcaaaaa taaaas                                                         16

<210> SEQ ID NO 670
<211> LENGTH: 624
<212> TYPE: DNA
<213> ORGANISM: Zymomonas mobilis

<400> SEQUENCE: 670
atgcgtgata tcgattccgt aatgcgtttg gcaccggtta tgccggtcct cgtcattgaa         60
gatattgctg atgcaaaacc tatcgcagaa gctttggttg ctggtggtct gaacgttctt        120
gaagtaacgc ttcgcacccc ttgtgctctt gaagccatca agatcatgaa agaagttccg        180
ggtgccgttg ttggtgccgg tacggttctg aacgcaaaaa tgctcgacca agctcaggaa        240
gctggttgcg aattttttcgt tagcccgggt ctgaccgctg acctcggcaa gcatgctgtt        300
gcccagaaag cagctttgct tccaggtgtt gctaatgctg ctgatgtgat gcttggtctt        360
gaccttggtc ttgatcgctt caaattcttc ccggctgaaa atatcggtgg tttacctgcc        420
ctgaagtcca tggcttctgt tttccgtcag gttcgtttct gcccgaccgg cggtatcacc        480
ccgacgtcag ctcctaaata tcttgaaaac ccgtccattc tttgcgtcgg tggtagctgg        540
gttgttccgg ctggcaaacc agatgtcgca aaaatcacgg cactcgctaa gaagcttct         600
```

```
gctttcaagc gcgctgctgt tgcc                                         624
```

<210> SEQ ID NO 671
<211> LENGTH: 624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 671

```
atgagggata ttgatagtgt gatgaggtta gcccctgtta tgcctgttct cgttattgaa     60
gatattgcag atgccaaacc tattgccgaa gcactcgttg caggtggtct aaacgttcta    120
gaagtgacac taaggactcc ttgtgcacta gaagctatta agattatgaa ggaagttcct    180
ggtgctgttg ttggtgctgg tacagttcta aacgccaaaa tgctcgacca ggcacaagaa    240
gcaggttgcg aatttttcgt ttcacctggt ctaactgccg acctcggaaa gcacgcagtt    300
gctcaaaaag ccgcattact acccggtgtt gcaaatgcag cagatgtgat gctaggtcta    360
gacctaggtc tagataggtt caagttcttc cctgccgaaa acattggtgg tctacctgct    420
ctaaagagta tggcatcagt tttcaggcaa gttaggttct gccctactgg aggtataact    480
cctacaagtg cacctaaata tctagaaaac cctagtattc tatgcgttgg tggttcatgg    540
gttgttcctg ccggaaaacc cgatgttgcc aaaattacag ccctcgcaaa agaagcaagt    600
gcattcaaga gggcagcagt tgct                                          624
```

<210> SEQ ID NO 672
<211> LENGTH: 624
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 672

```
atgagagaca ttgattctgt tatgagattg gctccagtta tgccagtctt ggttatagaa     60
gatatagctg atgctaagcc aattgctgag gctttggttg ctggtggttt aaatgttttg    120
gaagttacat tgagaactcc atgtgctttg gaagctatta aaattatgaa ggaagttcca    180
ggtgctgttg ttggtgctgg tactgtttta aacgctaaaa tgttggatca agctcaagaa    240
gctggttgtg agttctttgt atcaccaggt ttgactgctg atttgggaaa acatgctgtt    300
gctcaaaaag cggctcttct accagggggt gctaatgctg ctgatgttat gttgggattg    360
gatttgggtt tggatagatt taaattcttc ccagctgaaa atataggtgg tttgccagct    420
ttaaaatcta tggcttctgt ttttagacaa gttagatttt gtccaactgg aggaattact    480
ccgacttctg ctccaaaata tttggaaaat ccatctattt tgtgtgttgg tggttcttgg    540
gttgttccag cgggtaaacc agatgttgcg aaaattactg ctttggctaa agaggcttca    600
gcttttaaaa gagctgctgt ggcg                                          624
```

<210> SEQ ID NO 673
<211> LENGTH: 639
<212> TYPE: DNA
<213> ORGANISM: Escherichia coli

<400> SEQUENCE: 673

```
atgaaaaact ggaaaacaag tgcagaatca atcctgacca ccggcccggt tgtaccggtt     60
atcgtggtaa aaaaactgga acacgcggtg ccgatggcaa aagcgttggt tgctggtggg    120
```

```
gtgcgcgttc tggaagtgac tctgcgtacc gagtgtgcag ttgacgctat ccgtgctatc      180
gccaaagaag tgcctgaagc gattgtgggt gccggtacgg tgctgaatcc acagcagctg      240
gcagaagtca ctgaagcggg tgcacagttc gcaattagcc cgggtctgac cgagccgctg      300
ctgaaagctg ctaccgaagg gactattcct ctgattccgg ggatcagcac tgtttccgaa      360
ctgatgctgg gtatggacta cggtttgaaa gagttcaaat tcttcccggc tgaagctaac      420
ggcggcgtga aagccctgca ggcgatcgcg ggtccgttct cccaggtccg tttctgcccg      480
acgggtggta tttctccggc taactaccgt gactacctgg cgctgaaaag cgtgctgtgc      540
atcggtggtt cctggctggt tccggcagat gcgctggaag cgggcgatta cgaccgcatt      600
actaagctgg cgcgtgaagc tgtagaaggc gctaagctg                            639
```

<210> SEQ ID NO 674
<211> LENGTH: 208
<212> TYPE: PRT
<213> ORGANISM: Zymomonas mobilis

<400> SEQUENCE: 674

```
Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
            20                  25                  30

Val Ala Gly Gly Leu Asn Val Leu Glu Val Thr Leu Arg Thr Pro Cys
        35                  40                  45

Ala Leu Glu Ala Ile Lys Ile Met Lys Glu Val Pro Gly Ala Val Val
    50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Leu Leu Pro Gly Val Ala Asn
            100                 105                 110

Ala Ala Asp Val Met Leu Gly Leu Asp Leu Gly Leu Asp Arg Phe Lys
        115                 120                 125

Phe Phe Pro Ala Glu Asn Ile Gly Gly Leu Pro Ala Leu Lys Ser Met
    130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
            180                 185                 190

Thr Ala Leu Ala Lys Glu Ala Ser Ala Phe Lys Arg Ala Ala Val Ala
        195                 200                 205
```

<210> SEQ ID NO 675
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

```
Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
```

```
                        20                  25                  30
Val Ala Gly Gly Leu Asn Val Leu Glu Val Thr Leu Arg Thr Pro Cys
            35                  40                  45

Ala Leu Glu Ala Ile Lys Ile Met Lys Glu Val Pro Gly Ala Val Val
        50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Leu Leu Pro Gly Val Ala Asn
            100                 105                 110

Ala Ala Asp Val Met Leu Gly Leu Asp Leu Gly Leu Asp Arg Phe Lys
            115                 120                 125

Phe Phe Pro Ala Glu Asn Ile Gly Gly Leu Pro Ala Leu Lys Ser Met
            130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
                180                 185                 190

Thr Ala Leu Ala Lys Glu Ala Ser Ala Phe Lys Arg Ala Ala Val Ala
            195                 200                 205

<210> SEQ ID NO 676
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Met Arg Asp Ile Asp Ser Val Met Arg Leu Ala Pro Val Met Pro Val
1               5                   10                  15

Leu Val Ile Glu Asp Ile Ala Asp Ala Lys Pro Ile Ala Glu Ala Leu
            20                  25                  30

Val Ala Gly Gly Leu Asn Val Leu Glu Val Thr Leu Arg Thr Pro Cys
        35                  40                  45

Ala Leu Glu Ala Ile Lys Ile Met Lys Glu Val Pro Gly Ala Val Val
        50                  55                  60

Gly Ala Gly Thr Val Leu Asn Ala Lys Met Leu Asp Gln Ala Gln Glu
65                  70                  75                  80

Ala Gly Cys Glu Phe Phe Val Ser Pro Gly Leu Thr Ala Asp Leu Gly
                85                  90                  95

Lys His Ala Val Ala Gln Lys Ala Leu Leu Pro Gly Val Ala Asn
            100                 105                 110

Ala Ala Asp Val Met Leu Gly Leu Asp Leu Gly Leu Asp Arg Phe Lys
            115                 120                 125

Phe Phe Pro Ala Glu Asn Ile Gly Gly Leu Pro Ala Leu Lys Ser Met
            130                 135                 140

Ala Ser Val Phe Arg Gln Val Arg Phe Cys Pro Thr Gly Gly Ile Thr
145                 150                 155                 160

Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
```

180             185             190
Thr Ala Leu Ala Lys Glu Ala Ser Ala Phe Lys Arg Ala Ala Val Ala
        195                 200                 205

<210> SEQ ID NO 677
<211> LENGTH: 213
<212> TYPE: PRT
<213> ORGANISM: Escherichia coli

<400> SEQUENCE: 677

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
        210

<210> SEQ ID NO 678
<211> LENGTH: 1821
<212> TYPE: DNA
<213> ORGANISM: Zymomonas mobilis

<400> SEQUENCE: 678
atgactgatc tgcattcaac ggtagaaaag gttaccgcgc gcgttattga acgctcgcgg     60
gaaacccgta aggcttatct ggatttgatc cagtatgagc gggaaaaagg cgtagaccgt    120
ccaaacctgt cctgtagtaa ccttgctcat ggctttgcgg ctatgaatgg tgacaagcca    180
gctttgcgcg acttcaaccg catgaatatc ggcgtcgtga cttcctacaa cgatatgttg    240
tcggctcatg aaccatatta tcgctatccg agcagatgaa agtatttgc tcgcgaagtt    300 ggcgcaacgg ttcaggtcgc cggtggcgtg cctgctatgt gcgatggtgt gacccaaggt    360
cagccgggca tggaagaatc cctgtttagc cgcgatgtta tcgctttggc taccagcgtt    420
tctttgtctc atggtatgtt tgaagggggct gccttctcg gtatctgtga caagattgtc    480
cctggtctgt tgatgggcgc tctgcgcttt ggtcacctgc cgaccattct ggtcccatca    540

```
ggcccgatga cgactggtat cccgaacaaa gaaaaaatcc gtatccgtca gctctatgct    600
cagggtaaaa tcggccagaa agaacttctg gatatggaag cggcttgcta ccatgctgaa    660
ggtacctgca ccttctatgg tacggcaaac accaaccaga tggttatgga agtcctcggt    720
cttcatatgc caggttcggc atttgttacc ccgggtaccc cgctccgcca ggctctgacc    780
cgtgctgctg tgcatcgcgt tgctgaattg gttggaagg gcgacgatta tcgtccgctt    840
ggtaaaatca ttgacgaaaa atcaatcgtc aatgctattg ttggtctgtt ggcaaccggt    900
ggttccacca accataccat gcatattccg gccattgctc gtgctgctgg tgttatcgtt    960
aactggaatg acttccatga tctttctgaa gttgttccgt tgattgcccg catttacccg   1020
aatggcccgc gcgacatcaa tgaattccag aatgcaggcg gcatggctta tgtcatcaaa   1080
gaactgcttt ctgctaatct gttgaaccgt gatgtcacga ccattgccaa gggcggtatc   1140
gaagaatacg ccaaggctcc ggcattaaat gatgctggcg aattggtctg gaagccagct   1200
ggcgaacctg gtgatgacac cattctgcgt ccggtttcta atcctttcgc aaaagatggc   1260
ggtctgcgtc tcttggaagg taaccttggc cgtgcaatgt acaaggccag tgcggttgat   1320
cctaaattct ggaccattga agcaccggtt cgcgtcttct ctgaccaaga cgatgttcag   1380
aaagccttca aggctggcga attgaacaaa gacgttatcg ttgttgttcg tttccagggc   1440
ccgcgcgcaa acggtatgcc tgaattgcat aagctgaccc cggctttggg tgttctgcag   1500
gataatggct acaaagttgc tttggtaact gatggtcgta tgtccggtgc taccggtaaa   1560
gttccggttg ctttgcatgt cagcccgaaa gctcttggcg tggtgccat cggtaaatta   1620 cgtgatggcg atatcgtccg tatctcggtt gaagaaggca aacttgaagc tttggttcca   1680
gctgatgagt ggaatgctcg tccgcatgct gaaaaaccgg ctttccgtcc gggaaccgga   1740
cgcgaattgt ttgatatctt ccgtcagaat gctgctaaag ctgaagacgg tgcagtcgca   1800
atatatgcag gtgccggtat c                                             1821
```

<210> SEQ ID NO 679
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 679

```
atgacggatc tacatagtac agtggagaag gttactgcca gggttattga aaggagtagg     60
gaaactagga aggcatatct agatttaatt caatatgaga gggaaaaagg agtggacagg    120
cccaacctaa gttgtagcaa cctagcacat ggattcgccg caatgaatgg tgacaagccc    180
gcattaaggg acttcaacag gatgaatatt ggagttgtga cgagttacaa cgatatgtta    240
agtgcacatg aacccatta taggtatcct gagcaaatga aggtgtttgc aagggaagtt    300
ggagccacag ttcaagttgc tggtggagtg cctgcaatgt gcgatggtgt gactcagggt    360
caacctggaa tggaagaatc cctatttca agggatgtta ttgcattagc aacttcagtt    420
tcattatcac atggtatgtt tgaaggggca gctctactcg gtatatgtga caagattgtt    480
cctggtctac taatgggagc actaaggttt ggtcacctac ctactattct agttcccagt    540
ggacctatga caacgggtat acctaacaaa gaaaaaatta ggattaggca actctatgca    600
caaggtaaaa ttgacaaaaa agaactacta gatatggaag ccgcatgcta ccatgcagaa    660
ggtacttgca ctttctatgg tacagccaac actaaccaga tggttatgga agttctcggt    720
```

| | |
|---|---|
| ctacatatgc ccggtagtgc ctttgttact cctggtactc ctctcaggca agcactaact | 780 |
| agggcagcag tgcatagggt tgcagaatta ggttggaagg gagacgatta taggcctcta | 840 |
| ggtaaaatta ttgacgaaaa aagtattgtt aatgcaattg ttggtctatt agccactggt | 900 |
| ggtagtacta accatacgat gcatattcct gctattgcaa gggcagcagg tgttattgtt | 960 |
| aactggaatg acttccatga tctatcagaa gttgttcctt taattgctag gatttaccct | 1020 |
| aatggaccta gggacattaa cgaatttcaa atgccggag aatggcata tgttattaag | 1080 |
| gaactactat cagcaaatct actaaacagg gatgttacaa ctattgctaa gggaggtata | 1140 |
| gaagaatacg ctaaggcacc tgccctaaat gatgcaggag aattagtttg gaagcccgca | 1200 |
| ggagaacctg gtgatgacac tattctaagg cctgtttcaa atcctttcgc caagatgga | 1260 |
| ggtctaaggc tcttagaagg taacctagga agggccatgt acaaggctag cgccgttgat | 1320 |
| cctaaattct ggactattga agccctgtt agggttttct cagaccagga cgatgttcaa | 1380 |
| aaagccttca aggcaggaga actaaacaaa gacgttattg ttgttgttag gttccaagga | 1440 |
| cctagggcca acggtatgcc tgaattacat aagctaactc ctgcattagg tgttctacaa | 1500 |
| gataatggat acaaagttgc attagtgacg gatggtagga tgagtggtgc aactggtaaa | 1560 |
| gttcctgttg cattacatgt ttcacccgaa gcactaggag gtggtgctat tggtaaactt | 1620 |
| agggatggag atattgttag gattagtgtt gaagaaggaa aacttgaagc actcgttccc | 1680 |
| gcagatgagt ggaatgcaag gcctcatgca gaaaaacctg cattcaggcc tgggactggg | 1740 |
| agggaattat ttgatatttt caggcaaaat gcagcaaaag cagaagacgg tgccgttgcc | 1800 |
| atctatgccg gtgctggtat a | 1821 |

<210> SEQ ID NO 680
<211> LENGTH: 1821
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 680

| | |
|---|---|
| atgacggatt tgcattcaac tgttgagaaa gtaactgcta gagtaattga aagatcaagg | 60 |
| gaaactagaa aggcttattt ggatttgata caatatgaga gggaaaaagg tgttgataga | 120 |
| ccaaatttgt cttgttctaa tttggctcat ggttttgctg ctatgaatgg tgataaacca | 180 |
| gctttgagag atttttaatag aatgaatata ggtgtagtta cttcttataa tgatatgttg | 240 |
| tctgctcatg aaccatatta tagatatcca gaacaaatga aggttttgc tcgtgaagtt | 300 |
| ggtgctacag ttcaagttgc tggtggtgtt cctgcaatgt gtgatggtgt tactcaaggt | 360 |
| caaccaggta tggaagaatc tttgtttttcc agagatgtaa ttgctttggc tacatctgtt | 420 |
| tcattgtctc acggaatgtt tgaaggtgct gcattgttgg gaatttgtga taaaattgtt | 480 |
| ccaggttttgt tgatgggtgc tttgaggttc ggtcatttgc caactatttt ggttccatct | 540 |
| ggtccaatga ctactggaat cccaaataaa gaaaagatta gaattagaca attgtatgct | 600 |
| caaggaaaaa ttggtcaaaa ggaattgttg gatatggaag ctgcctgtta tcatgctgaa | 660 |
| ggtacttgta cttttatgg tactgctaac actaatcaga tggttatgga agttttgggt | 720 |
| ttgcacatgc caggtagtgc attcgttact ccaggtactc cactgagaca ggctttgact | 780 |
| agagctgctg ttcatagagt tgcagagttg ggttggaaag gtgatgatta tagacctttg | 840 |
| ggtaaaatta ttgatgagaa atctattgtt aatgctattg ttggtttgtt agctacaggt | 900 |
| ggttctacaa atcatacaat gcatattccg gccatagcta gagcagcagg ggttatagtt | 960 |

| | |
|---|---:|
| aattggaatg attttcatga tttgtctgaa gttgttccat tgattgctag aatttatcca | 1020 |
| aatggtccta gagatataaa tgaatttcaa aatgcaggag gaatggctta tgtaattaaa | 1080 |
| gaattgttga gtgcgaattt gttaaataga gatgttacta ctattgctaa aggagggata | 1140 |
| gaagaatatg ctaaagctcc agctctgaac gatgcgggtg aattggtgtg gaaaccggct | 1200 |
| ggcgaacctg gggacgacac aattttgaga ccagtatcta atccatttgc taaagatggt | 1260 |
| ggtttgcgtc tcttggaagg taatttgggt agagcaatgt ataaggcttc tgctgtagat | 1320 |
| ccaaaattct ggactattga agctcccgtt agagttttct ctgatcaaga tgatgttcaa | 1380 |
| aaggctttta aagcaggcga gttaaataaa gatgttatag ttgttgttag atttcaaggt | 1440 |
| cctcgtgcta atggtatgcc tgaattgcat aagttgactc ctgcgctagg cgtattgcaa | 1500 |
| gataatggtt ataaggttgc tttagttact gatggtagaa tgtctggtgc aactggtaaa | 1560 |
| gtaccggtgg ctctgcatgt ttcaccagag gctttaggag gtggggcgat tggcaagttg | 1620 |
| agagatggcg atatagttag aatttctgtt gaagaaggta aattagaggc tcttgtcccc | 1680 |
| gccgacgagt ggaatgctag accacatgct gagaagcccg cttttagacc tggtactggg | 1740 |
| agagaattgt ttgacatttt tagacaaaac gctgctaagg ctgaggatgg tgcagttgca | 1800 |
| atttatgctg gggcagggat c | 1821 |

<210> SEQ ID NO 681
<211> LENGTH: 1809
<212> TYPE: DNA
<213> ORGANISM: Escherichia coli

<400> SEQUENCE: 681

| | |
|---|---:|
| atgaatccac aattgttacg cgtaacaaat cgaatcattg aacgttcgcg cgagactcgc | 60 |
| tctgcttatc tcgcccggat agaacaagcg aaaacttcga ccgttcatcg ttcgcagttg | 120 |
| gcatgcggta acctggcaca cggtttcgct gcctgccagc cagaagacaa agcctctttg | 180 |
| aaaagcatgt tgcgtaacaa tatcgccatc atcacctcct ataacgacat gctctccgcg | 240 |
| caccagcctt atgaacacta tccagaaatc attcgtaaag ccctgcatga agcgaatgcg | 300 |
| gttggtcagg ttgcgggcgg tgttccggcg atgtgtgatg gtgtcaccca ggggcaggat | 360 |
| ggaatggaat gtcgctgct aagccgcgaa gtgatagcga tgtctgcggc ggtgggctg | 420 |
| tcccataaca tgtttgatgg tgctctgttc ctcggtgtgt gcgacaagat tgtcccgggt | 480 |
| ctgacgatgg cagccctgtc gtttggtcat ttgcctgcgg tgtttgtgcc gtctggaccg | 540 |
| atggcaagcg gtttgccaaa taagaaaaa gtgcgtattc gccagcttta tgccgaaggt | 600 |
| aaagtggacc gcatggcctt actggagtca gaagccgcgt cttaccatgc gccgggaaca | 660 |
| tgtactttct acggtactgc caacaccaac cagatggtgg tggagtttat ggggatgcag | 720 |
| ttgccaggct cttcttttgt tcatccggat tctccgctgc gcgatgcttt gaccgccgca | 780 |
| gctgcgcgtc aggttacacg catgaccggt aatggtaatg aatggatgcc gatcggtaag | 840 |
| atgatcgatg agaaagtggt ggtgaacggt atcgttgcac tgctggcgac cggtggttcc | 900 |
| actaaccaca ccatgcacct ggtggcgatg gcgcgcgcgg ccgtattcca gattaactgg | 960 |
| gatgacttct ctgacctttc tgatgttgta ccgctgatgg cacgtctcta cccgaacggt | 1020 |
| ccggccgata ttaaccactt ccaggcggca ggtggcgtac cggttctggt gcgtgaactg | 1080 |
| ctcaaagcag gcctgctgca tgaagatgtc aatacggtgg caggttttgg tctgtctcgt | 1140 |
| tatacccttg aaccatggct gaataatggt gaactggact ggcgggaagg ggcggaaaaa | 1200 |
| tcactcgaca gcaatgtgat cgcttccttc gaacaacctt tctctcatca tggtgggaca | 1260 |

```
aaagtgttaa gcggtaaccct gggccgtgcg gttatgaaaa cctctgccgt gccggttgag   1320
aaccaggtga ttgaagcgcc agcggttgtt tttgaaagcc agcatgacgt tatgccggcc   1380
tttgaagcgg gtttgctgga ccgcgattgt gtcgttgttg tccgtcatca ggggccaaaa   1440
gcgaacggaa tgccagaatt acataaactc atgccgccac ttggtgtatt attggaccgg   1500
tgtttcaaaa ttgcgttagt taccgatgga cgactctccg gcgcttcagg taaagtgccg   1560
tcagctatcc acgtaacacc agaagcctac gatggcgggc tgctggcaaa agtgcgcgac   1620
ggggacatca ttcgtgtgaa tggacagaca ggcgaactga cgctgctggt agacgaagcg   1680
gaactggctg ctcgcgaacc gcacattcct gacctgagcg cgtcacgcgt gggaacagga   1740
cgtgaattat tcagcgcctt gcgtgaaaaa ctgtccggtg ccgaacaggg cgcaacctgt   1800
atcactttt                                                            1809
```

<210> SEQ ID NO 682
<211> LENGTH: 607
<212> TYPE: PRT
<213> ORGANISM: Zymomonas mobilis

<400> SEQUENCE: 682

```
Met Thr Asp Leu His Ser Thr Val Glu Lys Val Thr Ala Arg Val Ile
1               5                   10                  15

Glu Arg Ser Arg Glu Thr Arg Lys Ala Tyr Leu Asp Leu Ile Gln Tyr
            20                  25                  30

Glu Arg Glu Lys Gly Val Asp Arg Pro Asn Leu Ser Cys Ser Asn Leu
        35                  40                  45

Ala His Gly Phe Ala Ala Met Asn Gly Asp Lys Pro Ala Leu Arg Asp
    50                  55                  60

Phe Asn Arg Met Asn Ile Gly Val Val Thr Ser Tyr Asn Asp Met Leu
65                  70                  75                  80

Ser Ala His Glu Pro Tyr Tyr Arg Tyr Pro Glu Gln Met Lys Val Phe
                85                  90                  95

Ala Arg Glu Val Gly Ala Thr Val Gln Val Ala Gly Gly Val Pro Ala
            100                 105                 110

Met Cys Asp Gly Val Thr Gln Gly Gln Pro Gly Met Glu Glu Ser Leu
        115                 120                 125

Phe Ser Arg Asp Val Ile Ala Leu Ala Thr Ser Val Ser Leu Ser His
    130                 135                 140

Gly Met Phe Glu Gly Ala Ala Leu Leu Gly Ile Cys Asp Lys Ile Val
145                 150                 155                 160

Pro Gly Leu Leu Met Gly Ala Leu Arg Phe Gly His Leu Pro Thr Ile
                165                 170                 175

Leu Val Pro Ser Gly Pro Met Thr Thr Gly Ile Pro Asn Lys Glu Lys
            180                 185                 190

Ile Arg Ile Arg Gln Leu Tyr Ala Gln Gly Lys Ile Gly Gln Lys Glu
        195                 200                 205

Leu Leu Asp Met Glu Ala Ala Cys Tyr His Ala Glu Gly Thr Cys Thr
    210                 215                 220

Phe Tyr Gly Thr Ala Asn Thr Asn Gln Met Val Met Glu Val Leu Gly
225                 230                 235                 240

Leu His Met Pro Gly Ser Ala Phe Val Thr Pro Gly Thr Pro Leu Arg
                245                 250                 255

Gln Ala Leu Thr Arg Ala Ala Val His Arg Val Ala Glu Leu Gly Trp
            260                 265                 270
```

```
Lys Gly Asp Asp Tyr Arg Pro Leu Gly Lys Ile Ile Asp Glu Lys Ser
            275                 280                 285

Ile Val Asn Ala Ile Val Gly Leu Leu Ala Thr Gly Gly Ser Thr Asn
        290                 295                 300

His Thr Met His Ile Pro Ala Ile Ala Arg Ala Ala Gly Val Ile Val
305                 310                 315                 320

Asn Trp Asn Asp Phe His Asp Leu Ser Glu Val Val Pro Leu Ile Ala
                325                 330                 335

Arg Ile Tyr Pro Asn Gly Pro Arg Asp Ile Asn Glu Phe Gln Asn Ala
            340                 345                 350

Gly Gly Met Ala Tyr Val Ile Lys Glu Leu Leu Ser Ala Asn Leu Leu
        355                 360                 365

Asn Arg Asp Val Thr Thr Ile Ala Lys Gly Gly Ile Glu Glu Tyr Ala
370                 375                 380

Lys Ala Pro Ala Leu Asn Asp Ala Gly Glu Leu Val Trp Lys Pro Ala
385                 390                 395                 400

Gly Glu Pro Gly Asp Asp Thr Ile Leu Arg Pro Val Ser Asn Pro Phe
                405                 410                 415

Ala Lys Asp Gly Gly Leu Arg Leu Leu Glu Gly Asn Leu Gly Arg Ala
            420                 425                 430

Met Tyr Lys Ala Ser Ala Val Asp Pro Lys Phe Trp Thr Ile Glu Ala
        435                 440                 445

Pro Val Arg Val Phe Ser Asp Gln Asp Val Gln Lys Ala Phe Lys
450                 455                 460

Ala Gly Glu Leu Asn Lys Asp Val Ile Val Val Arg Phe Gln Gly
465                 470                 475                 480

Pro Arg Ala Asn Gly Met Pro Glu Leu His Lys Leu Thr Pro Ala Leu
                485                 490                 495

Gly Val Leu Gln Asp Asn Gly Tyr Lys Val Ala Leu Val Thr Asp Gly
            500                 505                 510

Arg Met Ser Gly Ala Thr Gly Lys Val Pro Val Ala Leu His Val Ser
        515                 520                 525

Pro Glu Ala Leu Gly Gly Gly Ala Ile Gly Lys Leu Arg Asp Gly Asp
530                 535                 540

Ile Val Arg Ile Ser Val Glu Glu Gly Lys Leu Glu Ala Leu Val Pro
545                 550                 555                 560

Ala Asp Glu Trp Asn Ala Arg Pro His Ala Glu Lys Pro Ala Phe Arg
                565                 570                 575

Pro Gly Thr Gly Arg Glu Leu Phe Asp Ile Phe Arg Gln Asn Ala Ala
            580                 585                 590

Lys Ala Glu Asp Gly Ala Val Ala Ile Tyr Ala Gly Ala Gly Ile
        595                 600                 605

<210> SEQ ID NO 683
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Met Thr Asp Leu His Ser Thr Val Glu Lys Val Thr Ala Arg Val Ile
1               5                   10                  15

Glu Arg Ser Arg Glu Thr Arg Lys Ala Tyr Leu Asp Leu Ile Gln Tyr
            20                  25                  30
```

-continued

Glu Arg Glu Lys Gly Val Asp Arg Pro Asn Leu Ser Cys Ser Asn Leu
    35                  40                  45

Ala His Gly Phe Ala Ala Met Asn Gly Asp Lys Pro Ala Leu Arg Asp
50                  55                  60

Phe Asn Arg Met Asn Ile Gly Val Val Thr Ser Tyr Asn Asp Met Leu
65                  70                  75                  80

Ser Ala His Glu Pro Tyr Tyr Arg Tyr Pro Glu Gln Met Lys Val Phe
            85                  90                  95

Ala Arg Glu Val Gly Ala Thr Val Gln Val Ala Gly Gly Val Pro Ala
                100                 105                 110

Met Cys Asp Gly Val Thr Gln Gly Gln Pro Gly Met Glu Glu Ser Leu
            115                 120                 125

Phe Ser Arg Asp Val Ile Ala Leu Ala Thr Ser Val Ser Leu Ser His
130                 135                 140

Gly Met Phe Glu Gly Ala Ala Leu Leu Gly Ile Cys Asp Lys Ile Val
145                 150                 155                 160

Pro Gly Leu Leu Met Gly Ala Leu Arg Phe Gly His Leu Pro Thr Ile
                165                 170                 175

Leu Val Pro Ser Gly Pro Met Thr Thr Gly Ile Pro Asn Lys Glu Lys
            180                 185                 190

Ile Arg Ile Arg Gln Leu Tyr Ala Gln Gly Lys Ile Gly Gln Lys Glu
        195                 200                 205

Leu Leu Asp Met Glu Ala Ala Cys Tyr His Ala Glu Gly Thr Cys Thr
    210                 215                 220

Phe Tyr Gly Thr Ala Asn Thr Asn Gln Met Val Met Glu Val Leu Gly
225                 230                 235                 240

Leu His Met Pro Gly Ser Ala Phe Val Thr Pro Gly Thr Pro Leu Arg
                245                 250                 255

Gln Ala Leu Thr Arg Ala Ala Val His Arg Val Ala Glu Leu Gly Trp
            260                 265                 270

Lys Gly Asp Asp Tyr Arg Pro Leu Gly Lys Ile Ile Asp Glu Lys Ser
        275                 280                 285

Ile Val Asn Ala Ile Val Gly Leu Leu Ala Thr Gly Gly Ser Thr Asn
    290                 295                 300

His Thr Met His Ile Pro Ala Ile Ala Arg Ala Ala Gly Val Ile Val
305                 310                 315                 320

Asn Trp Asn Asp Phe His Asp Leu Ser Glu Val Val Pro Leu Ile Ala
                325                 330                 335

Arg Ile Tyr Pro Asn Gly Pro Arg Asp Ile Asn Glu Phe Gln Asn Ala
            340                 345                 350

Gly Gly Met Ala Tyr Val Ile Lys Glu Leu Leu Ser Ala Asn Leu Leu
        355                 360                 365

Asn Arg Asp Val Thr Thr Ile Ala Lys Gly Gly Ile Glu Glu Tyr Ala
    370                 375                 380

Lys Ala Pro Ala Leu Asn Asp Ala Gly Glu Leu Val Trp Lys Pro Ala
385                 390                 395                 400

Gly Glu Pro Gly Asp Asp Thr Ile Leu Arg Pro Val Ser Asn Pro Phe
                405                 410                 415

Ala Lys Asp Gly Gly Leu Arg Leu Leu Glu Gly Asn Leu Gly Arg Ala
            420                 425                 430

Met Tyr Lys Ala Ser Ala Val Asp Pro Lys Phe Trp Thr Ile Glu Ala
        435                 440                 445

Pro Val Arg Val Phe Ser Asp Gln Asp Val Gln Lys Ala Phe Lys
    450                 455                 460

Ala Gly Glu Leu Asn Lys Asp Val Ile Val Val Arg Phe Gln Gly
465                 470                 475                 480

Pro Arg Ala Asn Gly Met Pro Glu Leu His Lys Leu Thr Pro Ala Leu
            485                 490                 495

Gly Val Leu Gln Asp Asn Gly Tyr Lys Val Ala Leu Val Thr Asp Gly
            500                 505                 510

Arg Met Ser Gly Ala Thr Gly Lys Val Pro Val Ala Leu His Val Ser
            515                 520                 525

Pro Glu Ala Leu Gly Gly Ala Ile Gly Lys Leu Arg Asp Gly Asp
            530                 535                 540

Ile Val Arg Ile Ser Val Glu Glu Gly Lys Leu Glu Ala Leu Val Pro
545                 550                 555                 560

Ala Asp Glu Trp Asn Ala Arg Pro His Ala Glu Lys Pro Ala Phe Arg
                565                 570                 575

Pro Gly Thr Gly Arg Glu Leu Phe Asp Ile Phe Arg Gln Asn Ala Ala
            580                 585                 590

Lys Ala Glu Asp Gly Ala Val Ala Ile Tyr Ala Gly Ala Gly Ile
            595                 600                 605

<210> SEQ ID NO 684
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 684

Met Thr Asp Leu His Ser Thr Val Glu Lys Val Thr Ala Arg Val Ile
1               5                   10                  15

Glu Arg Ser Arg Glu Thr Arg Lys Ala Tyr Leu Asp Leu Ile Gln Tyr
            20                  25                  30

Glu Arg Glu Lys Gly Val Asp Arg Pro Asn Leu Ser Cys Ser Asn Leu
        35                  40                  45

Ala His Gly Phe Ala Ala Met Asn Gly Asp Lys Pro Ala Leu Arg Asp
    50                  55                  60

Phe Asn Arg Met Asn Ile Gly Val Val Thr Ser Tyr Asn Asp Met Leu
65                  70                  75                  80

Ser Ala His Glu Pro Tyr Tyr Arg Tyr Pro Glu Gln Met Lys Val Phe
                85                  90                  95

Ala Arg Glu Val Gly Ala Thr Val Gln Val Ala Gly Val Pro Ala
            100                 105                 110

Met Cys Asp Gly Val Thr Gln Gly Gln Pro Gly Met Glu Glu Ser Leu
            115                 120                 125

Phe Ser Arg Asp Val Ile Ala Leu Ala Thr Ser Val Ser Leu Ser His
    130                 135                 140

Gly Met Phe Glu Gly Ala Ala Leu Leu Gly Ile Cys Asp Lys Ile Val
145                 150                 155                 160

Pro Gly Leu Leu Met Gly Ala Leu Arg Phe Gly His Leu Pro Thr Ile
                165                 170                 175

Leu Val Pro Ser Gly Pro Met Thr Thr Gly Ile Pro Asn Lys Glu Lys
            180                 185                 190

Ile Arg Ile Arg Gln Leu Tyr Ala Gln Gly Lys Ile Gly Gln Lys Glu
        195                 200                 205

Leu Leu Asp Met Glu Ala Ala Cys Tyr His Ala Glu Gly Thr Cys Thr
    210                 215                 220

| | | | | | | | | | | | |
|---|---|---|---|---|---|---|---|---|---|---|---|
|Phe|Tyr|Gly|Thr|Ala|Asn|Thr|Asn|Gln|Met|Val|Met|Glu|Val|Leu|Gly|
|225| | | | |230| | | | |235| | | | |240|

Leu His Met Pro Gly Ser Ala Phe Val Thr Pro Gly Thr Pro Leu Arg
                245                 250                 255

Gln Ala Leu Thr Arg Ala Ala Val His Arg Val Ala Glu Leu Gly Trp
            260                 265                 270

Lys Gly Asp Asp Tyr Arg Pro Leu Gly Lys Ile Ile Asp Glu Lys Ser
        275                 280                 285

Ile Val Asn Ala Ile Val Gly Leu Leu Ala Thr Gly Gly Ser Thr Asn
290                 295                 300

His Thr Met His Ile Pro Ala Ile Ala Arg Ala Ala Gly Val Ile Val
305                 310                 315                 320

Asn Trp Asn Asp Phe His Asp Leu Ser Glu Val Val Pro Leu Ile Ala
                325                 330                 335

Arg Ile Tyr Pro Asn Gly Pro Arg Asp Ile Asn Glu Phe Gln Asn Ala
            340                 345                 350

Gly Gly Met Ala Tyr Val Ile Lys Glu Leu Leu Ser Ala Asn Leu Leu
        355                 360                 365

Asn Arg Asp Val Thr Thr Ile Ala Lys Gly Gly Ile Glu Glu Tyr Ala
370                 375                 380

Lys Ala Pro Ala Leu Asn Asp Ala Gly Glu Leu Val Trp Lys Pro Ala
385                 390                 395                 400

Gly Glu Pro Gly Asp Asp Thr Ile Leu Arg Pro Val Ser Asn Pro Phe
                405                 410                 415

Ala Lys Asp Gly Gly Leu Arg Leu Leu Glu Gly Asn Leu Gly Arg Ala
            420                 425                 430

Met Tyr Lys Ala Ser Ala Val Asp Pro Lys Phe Trp Thr Ile Glu Ala
        435                 440                 445

Pro Val Arg Val Phe Ser Asp Gln Asp Val Gln Lys Ala Phe Lys
450                 455                 460

Ala Gly Glu Leu Asn Lys Asp Val Ile Val Val Arg Phe Gln Gly
465                 470                 475                 480

Pro Arg Ala Asn Gly Met Pro Glu Leu His Lys Leu Thr Pro Ala Leu
                485                 490                 495

Gly Val Leu Gln Asp Asn Gly Tyr Lys Val Ala Leu Val Thr Asp Gly
            500                 505                 510

Arg Met Ser Gly Ala Thr Gly Lys Val Pro Val Ala Leu His Val Ser
        515                 520                 525

Pro Glu Ala Leu Gly Gly Gly Ala Ile Gly Lys Leu Arg Asp Gly Asp
530                 535                 540

Ile Val Arg Ile Ser Val Glu Glu Gly Lys Leu Glu Ala Leu Val Pro
545                 550                 555                 560

Ala Asp Glu Trp Asn Ala Arg Pro His Ala Glu Lys Pro Ala Phe Arg
                565                 570                 575

Pro Gly Thr Gly Arg Glu Leu Phe Asp Ile Phe Arg Gln Asn Ala Ala
            580                 585                 590

Lys Ala Glu Asp Gly Ala Val Ala Ile Tyr Ala Gly Ala Gly Ile
        595                 600                 605

<210> SEQ ID NO 685
<211> LENGTH: 603
<212> TYPE: PRT
<213> ORGANISM: Escherichia coli

<400> SEQUENCE: 685

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60

Arg Asn Asn Ile Ala Ile Ile Thr Ser Tyr Asn Asp Met Leu Ser Ala
65                  70                  75                  80

His Gln Pro Tyr Glu His Tyr Pro Glu Ile Ile Arg Lys Ala Leu His
                85                  90                  95

Glu Ala Asn Ala Val Gly Gln Val Ala Gly Val Pro Ala Met Cys
                100                 105                 110

Asp Gly Val Thr Gln Gly Gln Asp Gly Met Glu Leu Ser Leu Leu Ser
            115                 120                 125

Arg Glu Val Ile Ala Met Ser Ala Ala Val Gly Leu Ser His Asn Met
        130                 135                 140

Phe Asp Gly Ala Leu Phe Leu Gly Val Cys Asp Lys Ile Val Pro Gly
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190

Ile Arg Gln Leu Tyr Ala Glu Gly Lys Val Asp Arg Met Ala Leu Leu
        195                 200                 205

Glu Ser Glu Ala Ala Ser Tyr His Ala Pro Gly Thr Cys Thr Phe Tyr
        210                 215                 220

Gly Thr Ala Asn Thr Asn Gln Met Val Val Glu Phe Met Gly Met Gln
225                 230                 235                 240

Leu Pro Gly Ser Ser Phe Val His Pro Asp Ser Pro Leu Arg Asp Ala
                245                 250                 255

Leu Thr Ala Ala Ala Ala Arg Gln Val Thr Arg Met Thr Gly Asn Gly
            260                 265                 270

Asn Glu Trp Met Pro Ile Gly Lys Met Ile Asp Glu Lys Val Val Val
        275                 280                 285

Asn Gly Ile Val Ala Leu Leu Ala Thr Gly Gly Ser Thr Asn His Thr
        290                 295                 300

Met His Leu Val Ala Met Ala Arg Ala Ala Gly Ile Gln Ile Asn Trp
305                 310                 315                 320

Asp Asp Phe Ser Asp Leu Ser Asp Val Val Pro Leu Met Ala Arg Leu
                325                 330                 335

Tyr Pro Asn Gly Pro Ala Asp Ile Asn His Phe Gln Ala Ala Gly Gly
            340                 345                 350

Val Pro Val Leu Val Arg Glu Leu Leu Lys Ala Gly Leu Leu His Glu
        355                 360                 365

Asp Val Asn Thr Val Ala Gly Phe Gly Leu Ser Arg Tyr Thr Leu Glu
        370                 375                 380

Pro Trp Leu Asn Asn Gly Glu Leu Asp Trp Arg Glu Gly Ala Glu Lys
385                 390                 395                 400

Ser Leu Asp Ser Asn Val Ile Ala Ser Phe Glu Gln Pro Phe Ser His
                405                 410                 415

His Gly Gly Thr Lys Val Leu Ser Gly Asn Leu Gly Arg Ala Val Met

-continued

```
                        420                     425                     430
Lys Thr Ser Ala Val Pro Val Glu Asn Gln Val Ile Glu Ala Pro Ala
        435                     440                     445

Val Val Phe Glu Ser Gln His Asp Val Met Pro Ala Phe Glu Ala Gly
    450                     455                     460

Leu Leu Asp Arg Asp Cys Val Val Val Arg His Gln Gly Pro Lys
465                     470                     475                     480

Ala Asn Gly Met Pro Glu Leu His Lys Leu Met Pro Pro Leu Gly Val
                485                     490                     495

Leu Leu Asp Arg Cys Phe Lys Ile Ala Leu Val Thr Asp Gly Arg Leu
                500                     505                     510

Ser Gly Ala Ser Gly Lys Val Pro Ser Ala Ile His Val Thr Pro Glu
        515                     520                     525

Ala Tyr Asp Gly Gly Leu Leu Ala Lys Val Arg Asp Gly Asp Ile Ile
    530                     535                     540

Arg Val Asn Gly Gln Thr Gly Glu Leu Thr Leu Leu Val Asp Glu Ala
545                     550                     555                     560

Glu Leu Ala Ala Arg Glu Pro His Ile Pro Asp Leu Ser Ala Ser Arg
                565                     570                     575

Val Gly Thr Gly Arg Glu Leu Phe Ser Ala Leu Arg Glu Lys Leu Ser
                580                     585                     590

Gly Ala Glu Gln Gly Ala Thr Cys Ile Thr Phe
        595                     600
```

ENGINEERED MICROORGANISMS WITH ENHANCED FERMENTATION ACTIVITY

RELATED PATENT APPLICATION(S)

This patent application is a continuation application which claims the benefit of international patent application no. PCT/US2010/041618 filed on Jul. 9, 2010, entitled ENGINEERED MICROORGANISMS WITH ENHANCED FERMENTATION ACTIVITY, naming Stephen Picataggio, Kirsty Anne Lily Salmon and Jose Miguel LaPlaza as inventors, which claims the benefit of (i) U.S. provisional patent application No. 61/224,430 filed on Jul. 9, 2009, entitled ENGINEERED MICROORGANISMS WITH ENHANCED FERMENTATION ACTIVITY, naming Stephen Picataggio as inventor; (ii) U.S. provisional patent application No. 61/316,780 filed on Mar. 23, 2010, entitled ENGINEERED MICROORGANISMS WITH ENHANCED FERMENTATION ACTIVITY, naming Stephen Picataggio as inventor; and (iii) U.S. provisional patent application No. 61/334,097 filed on May 12, 2010, entitled ENGINEERED MICROORGANISMS WITH ENHANCED FERMENTATION ACTIVITY, naming Stephen Picataggio as inventor. The entire content of the foregoing patent applications is incorporated herein by reference, including, without limitation, all text, tables and drawings.

SEQUENCE LISTING

The instant application contains a Sequence Listing which has been submitted in ASCII format via EFS-Web and is hereby incorporated by reference in its entirety. Said ASCII copy, created on Feb. 23, 2011, is named VRD12CT2.txt and is 489,285 bytes in size.

FIELD

The technology relates in part to genetically modified microorganisms that have enhanced fermentation activity, and methods for making and using such microorganisms.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules utilized or secreted by the organism.

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Such genetic engineering can change the biological pathways within the host organism, causing it to produce a desired product. Microorganic industrial production can minimize the use of caustic chemicals and production of toxic byproducts, thus providing a "clean" source for certain products.

SUMMARY

Provided herein are engineered microorganisms having enhanced fermentation activity. In certain non-limiting embodiments, such microorganisms are capable of generating a target product with enhanced fermentation efficiency by, for example, (i) preferentially utilizing a particular glycolysis pathway, which increases yield of a target product, upon a change in fermentation conditions; (ii) reducing cell division rates upon a change in fermentation conditions, thereby diverting nutrients towards production of a target product; (iii) having the ability to readily metabolize five-carbon sugars; and/or (iv) having the ability to readily metabolize carbon dioxide; and combinations of the foregoing. In some embodiments, a target product is ethanol or succinic acid.

Thus, provided in certain embodiments are engineered microorganisms that comprise: (a) a functional Embden-Meyerhoff glycolysis pathway that metabolizes six-carbon sugars under aerobic fermentation conditions, and (b) a genetic modification that reduces an Embden-Meyerhoff glycolysis pathway member activity upon exposure of the engineered microorganism to anaerobic fermentation conditions, whereby the engineered microorganisms preferentially metabolize six-carbon sugars by the Enter-Doudoroff pathway under the anaerobic fermentation conditions. In some embodiments, the genetic modification is insertion of a promoter into genomic DNA in operable linkage with a polynucleotide that encodes the Embden-Meyerhoff glycolysis pathway member activity. In certain embodiments, the genetic modification is provision of a heterologous promoter polynucleotide in operable linkage with a polynucleotide that encodes the Embden-Meyerhoff glycolysis pathway member activity. In some embodiments, the genetic modification is a deletion or disruption of a polynucleotide that encodes, or regulates production of, the Embden-Meyerhoff glycolysis pathway member, and the microorganism comprises a heterologous nucleic acid that includes a polynucleotide encoding the Embden-Meyerhoff glycolysis pathway member operably linked to a polynucleotide that down-regulates production of the member under anaerobic fermentation conditions. In certain embodiments, the Embden-Meyerhoff glycolysis pathway member activity is a phosphofructokinase activity, a phosphoglucose isomerase activity, or a phosphofructokinase activity and a phosphoglucose isomerase activity. In some embodiments, the activity of one or more (e.g., 2, 3, 4, 5 or more) pathway members in an EM pathway is reduced or removed to undetectable levels. In certain embodiments, one or more activities in an EM pathway, not mentioned herein, also can be modified to further enhance production of a desired product (e.g., alcohol).

Also provided in some embodiments are engineered microorganisms that comprise a genetic modification that inhibits cell division upon exposure to a change in fermentation conditions, where: the genetic modification comprises introduction of a heterologous promoter operably linked to a polynucleotide encoding a polypeptide that regulates the cell cycle of the microorganism; and the promoter activity is altered by the change in fermentation conditions. Provided also in certain embodiments are engineered microorganisms that comprise a genetic modification that inhibits cell division and/or cell proliferation upon exposure of the microorganisms to a change in fermentation conditions. In certain embodiments, the genetic modification inhibits cell division, inhibits cell proliferation, inhibits the cell cycle and/or induces cell cycle arrest. In some embodiments, the change in fermentation conditions is a switch to anaerobic fermentation conditions, and in certain embodiments, the change in fermentation conditions is a switch to an elevated temperature. In some embodiments, the polypeptide that regulates the cell cycle has thymidylate synthase activity. In certain embodiments, the promoter activity is reduced by the change in fermentation conditions. In some embodiments, the genetic modification is a temperature sensitive mutation.

Provided also in some embodiments are methods for manufacturing a target product produced by an engineered microorganism, which comprise: (a) culturing an engineered microorganism described herein under aerobic conditions; and (b) culturing the engineered microorganism after (a) under anaerobic conditions, whereby the engineered microorganism produces the target product. Also provided in some embodiments are methods for producing a target product by an engineered microorganism, which comprise: (a) culturing an engineered microorganism described herein under a first set of fermentation conditions; and (b) culturing the engineered microorganism after (a) under a second set of fermentation conditions different than the first set of fermentation conditions, whereby the second set of fermentation conditions inhibits cell division and/or cell proliferation of the engineered microorganism. In certain embodiments, the target product is ethanol or succinic acid. In some embodiments, the host microorganism from which the engineered microorganism is produced does not produce a detectable amount of the target product. In certain embodiments, the culture conditions comprise fermentation conditions, comprise introduction of biomass, comprise introduction of a six-carbon sugar (e.g., glucose), and/or comprise introduction of a five-carbon sugar (e.g., xylulose, xylose); or combinations of the foregoing. In some embodiments, the target product is produced with a yield of greater than about 0.3 grams per gram of glucose added, and in certain embodiments, a method comprises purifying the target product from the cultured microorganisms. In some embodiments, a method comprises modifying the target product, thereby producing modified target product. In certain embodiments, a method comprises placing the cultured microorganisms, the target product or the modified target product in a container, and in certain embodiments, a method comprises shipping the container. In some embodiments, the second set of fermentation conditions comprises an elevated temperature as compared to the temperature in the first set of fermentation conditions. In certain embodiments, the genetic modification inhibits the cell cycle of the engineered microorganism upon exposure to the second set of fermentation conditions. In some embodiments, the genetic modification inhibits cell proliferation, inhibits cell division, inhibits the cell cycle and/or induces cell cycle arrest upon exposure to the second set of fermentation conditions. In certain embodiments, the genetic modification inhibits thymidylate synthase activity upon exposure to the change in fermentation conditions, and sometimes the genetic modification comprises a temperature sensitive mutation.

Also provided in certain embodiments are methods for manufacturing an engineered microorganism, which comprise: (a) introducing a genetic modification to a host microorganism that reduces an Embden-Meyerhoff glycolysis pathway member activity upon exposure of the engineered microorganism to anaerobic conditions; and (b) selecting for engineered microorganisms that (i) metabolize six-carbon sugars by the Embden-Meyerhoff glycolysis pathway under aerobic fermentation conditions, and (ii) preferentially metabolize six-carbon sugars by the Entner-Doudoroff pathway under the anaerobic fermentation conditions. In some embodiments, the genetic modification is insertion of a promoter into genomic DNA in operable linkage with a polynucleotide that encodes the Embden-Meyerhoff glycolysis pathway member activity. The genetic modification sometimes is provision of a heterologous promoter polynucleotide in operable linkage with a polynucleotide that encodes the Embden-Meyerhoff glycolysis pathway member activity. In certain embodiments, the genetic modification is a deletion or disruption of a polynucleotide that encodes, or regulates production of, the Embden-Meyerhoff glycolysis pathway member, and the microorganism comprises a heterologous nucleic acid that includes a polynucleotide encoding the Embden-Meyerhoff glycolysis pathway member operably linked to a polynucleotide that down-regulates production of the member under anaerobic fermentation conditions. In some embodiments, the Embden-Meyerhoff glycolysis pathway member activity is a phosphofructokinase activity, and in certain embodiments, the Embden-Meyerhoff glycolysis pathway member activity is a phosphoglucose isomerase activity. In some embodiments, the activity of one or more (e.g., 2, 3, 4, 5 or more) pathway members in an EM pathway is reduced or removed to undetectable levels.

Provided also in some embodiments are methods for manufacturing an engineered microorganism, which comprise: (a) introducing a genetic modification to a host microorganism that inhibits cell division upon exposure to a change in fermentation conditions, thereby producing engineered microorganisms; and (b) selecting for engineered microorganisms with inhibited cell division upon exposure of the engineered microorganisms to the change in fermentation conditions. In certain embodiments, the change in fermentation conditions comprises a change to anaerobic fermentation conditions. The change in fermentation conditions sometimes comprises a change to an elevated temperature. In some embodiments, the genetic modification inhibits the cell cycle of the engineered microorganism upon exposure to the change in fermentation conditions. The genetic modification sometimes inhibits cell division, inhibits the cell cycle, inhibits cell proliferation and/or induces cell cycle arrest upon exposure to the change in fermentation conditions. In some embodiments, the genetic modification inhibits thymidylate synthase activity upon exposure to the change in fermentation conditions, and in certain embodiments, the genetic modification comprises a temperature sensitive mutation.

In certain embodiments pertaining to engineered microorganisms, and methods of making or using such microorganisms, the microorganism comprises a genetic modification that adds or alters a five-carbon sugar metabolic activity. In some embodiments, the microorganism comprises a genetic alteration that adds or alters xylose isomerase activity. In certain embodiments, the microorganism comprises a genetic alteration that adds or alters a xylose reductase (XR) activity and a xylitol dehydrogenase (XD) activity. In some embodiments, the microorganism comprises a xylulokinase (XK) activity. In certain embodiments, the microorganism comprises a genetic alteration that adds or alters five-carbon sugar transporter activity, and sometimes the transporter activity is a transporter facilitator activity or an active transporter activity. In some embodiments, the microorganism comprises a genetic alteration that adds or alters carbon dioxide fixation activity, and sometimes the genetic alteration that adds or alters phosphoenolpyruvate (PEP) carboxylase activity. In certain embodiments, the microorganism comprises a genetic modification that reduces or removes an alcohol dehydrogenase 2 activity. In certain embodiments, the microorganism comprises a genetic alteration that adds or alters a 6-phosphogluconate dehydrogenase (decarboxylating) activity. In some embodiments the microorganism is an engineered yeast, such as a *Saccharomyces* yeast (e.g., *S. cerevisiae*), for example.

In some embodiments, provided are nucleic acids, comprising a polynucleotide that encodes a polypeptide from *Ruminococcus* possessing a xylose to xylulose xylose isomerase activity, or a polypeptide possessing xylose reductase activity and xylitol dehydrogenase activity. In certain embodiments, provided are nucleic acids, comprising a polynucleotide that encodes a polypeptide possessing xylulokinase activity. Also provided in certain embodiments are expression vectors comprising a polynucleotide that encodes a polypeptide from *Ruminococcus* possessing a xylose isomerase activity. Also provided in some embodiments are expression vectors comprising a polynucleotide that encodes a polypeptide possessing a xylose reductase activity and xylitol dehydrogenase activity. Also provided in some embodiments are expression vectors comprising a polynucleotide that encodes a polypeptide possessing a xylulokinase activity. The polynucleotide sometimes includes one or more substituted codons, and in some embodiments, the one or more substituted codons are yeast codons (e.g., some or all codons are optimized with yeast codons (e.g., *S. cerevisiae* codons).

The polynucleotide sometimes includes a nucleotide sequence of SEQ ID NO: 29, 30, 32 or 33, fragment thereof, or sequence having 50% identity or greater (e.g., about 55, 60, 65, 70, 75, 80, 85, 90, 95% identity or greater) to the foregoing, and in certain embodiments the polypeptide includes an amino acid sequence of SEQ ID NO: 31, fragment thereof, or sequence having 75% identity or greater (e.g., about 80, 85, 90, 95% identity or greater) to the foregoing. In certain embodiments, a stretch of contiguous nucleotides of the polynucleotide is from another organism, and sometimes the stretch of contiguous nucleotides from the other organism is from a nucleotide sequence that encodes a polypeptide possessing a xylose isomerase activity. The other organism sometimes is a fungus, such as a *Piromyces* fungus (e.g., *Piromyces* strain E2 or another *Piromyces* strain) for example, and at times the stretch of contiguous nucleotides from the other organism is from SEQ ID NO: 34, or sequence having 50% identity or greater (e.g., about 55, 60, 65, 70, 75, 80, 85, 90, 95% identity or greater) to the foregoing. In some embodiments, the stretch of contiguous nucleotides from the other organism encodes an amino acid sequence from SEQ ID NO: 35, or sequence having 75% identity or greater (e.g., about 80, 85, 90, 95% identity or greater) to the foregoing. The stretch of contiguous nucleotides from the other organism sometimes is about 1% to about 30% (e.g., about 2, 3, 4, 5, 6, 7, 8, 9, 10, 15, 20, 25%) of the total number of nucleotides in the polynucleotide that encodes the polypeptide possessing xylose isomerase activity. In some embodiments, about 30 contiguous nucleotides from the polynucleotide from *Ruminococcus* are replaced by about 10 to about 20 nucleotides from the other organism. Sometimes, the contiguous stretch of polynucleotides from the other organism is at the 5' end of the polynucleotide. In some embodiments, the polynucleotide includes a nucleotide sequence of SEQ ID NO: 55, 56, 57, 59 or 61, fragment thereof, or sequence having 50% identity or greater (e.g., about 55, 60, 65, 70, 75, 80, 85, 90, 95% identity or greater) to the foregoing. The polynucleotide sometimes encodes a polypeptide that includes an amino acid sequence of SEQ ID NO: 58, 60 or 62, fragment thereof, or sequence having 75% identity or greater (e.g., about 80, 85, 90, 95% identity or greater) to the foregoing. In some embodiments, the polynucleotide comprises one or more point mutations, and sometimes the point mutation is at a position corresponding to position 179 of the *R. flavefaciens* strain Siijpesteijn 1948 polypeptide having xylose isomerase activity (e.g., the point mutation is a glycine 179 to alanine point mutation). In certain embodiments, an expression vector includes a regulatory nucleotide sequence in operable linkage with the polynucleotide. A regulatory nucleotide sequence sometimes includes a promoter sequence (e.g., an inducible promoter sequence, constitutively active promoter sequence. In certain embodiments, provided are methods for preparing an expression vector of any one of embodiments H1 to H24, comprising: (i) providing a nucleic acid that contains a regulatory sequence, and (ii) inserting the polynucleotide into the nucleic acid in operable linkage with the regulatory sequence.

Thus, in some embodiments, provided are chimeric xylose isomerase enzymes, and polynucleotides that encode them, which include subsequences from two or more xylose isomerase donor sequences. The xylose isomerase donor sequences sometimes are naturally occurring native sequences from an organism, and sometimes are modified sequences. In certain embodiments, a subsequence from one donor may represent a majority of the chimeric xylose isomerase sequence (e.g., about 55% to about 99% of the chimeric xylose isomerase nucleotide or amino acid sequence (e.g., about 60, 65, 70, 75, 80, 81, 82, 83, 84, 85, 86, 87, 88, 89, 90, 91, 92, 93, 94, 95, 96, 97, 98%) or all but 30 or fewer nucleotides or amino acids of the chimeric sequence (e.g., all but about 25, 24, 23, 22, 21, 20, 19, 18, 17, 16, 15, 14, 13, 12, 11, 10, 9, 8, 7, 6, 5, 4, 3, 2 or 1 nucleotides or amino acids of the chimeric molecule). In some embodiments, a subsequence from one donor may represent a minority of the chimeric xylose isomerase sequence (e.g., about 1% to about 45% of the chimeric xylose isomerase nucleotide or amino acid sequence (e.g., about 40, 35, 30, 25, 24, 23, 22, 21, 20, 19, 18, 17, 16, 15, 14, 13, 12, 11, 10, 9, 8, 7, 6, 5, 4, 3, 2%) or about 1 to about 30 nucleotides or amino acids of the chimeric sequence (e.g., about 25, 24, 23, 22, 21, 20, 19, 18, 17, 16, 15, 14, 13, 12, 11, 10, 9, 8, 7, 6, 5, 4, 3, 2 or 1 nucleotides or amino acids of the chimeric molecule). In some embodiments, one or more donor sequences for a chimeric xylose isomerase molecule are from a xylose isomerase described in the following Table:

| Organism Name (XI Donor) | SEQ ID NO (nucleotide sequence/amino acid sequence) | Accession Number (nucleotide sequence/amino acid sequence) |
|---|---|---|
| Clostridiales_genomosp. BVAB3 str UPII9-5 | 104 and 109/112 | YP_003474614.1 |
| *Ruminococcus flavefaciens* | 22 and 30/31 | AJ132472/ CAB51938.1 |
| Ruminococcus_FD1 | 102 and 107/110 | ZP_06143883.1 |
| Ruminococcus_18P13 | 103 and 108/111 | CBL17278.1 |
| *Thermus thermophilus* | 106 | P26997.1 |
| *Bacillus stercoris* | 105 | ZP_02435145.1 |
| *Clostridium cellulolyticum* | 101 | YP_002507697.1 |
| *Bacillus uniformis* | 100 | ZP_02069286.1 |
| *Bacillus stearothermophilus* | 99 | ABI49954.1 |
| *Bacteroides thetaiotaomicron* | 98 | NP_809706.1 |
| *Clostridium thermohydrosulfuricum* | 97 | P22842.1 |
| *Orpinomyces* sp. ukk1 | 96 | ACA65427.1 |
| *Clostridium phytofermentans* | 95 | YP_001558336.1 |
| *Escherichia coli* | 94 | |
| *Piromyces* strain E2 | 24 and 34 and 93/35 | AJ249909/ CAB76571.1 | or a nucleotide sequence or amino acid sequence that is (a) about 80% or more identical to one of the foregoing sequences referenced in the Table (e.g., about 81, 82, 83, 84, 85, 86, 87, 88, 89, 90, 91, 92, 93, 94, 95, 96, 97, 98, 99% identical), and/or (b) has about 1 to about 20 nucleotide or amino acid modifications (e.g., substitutions, deletions or insertions) relative to one of the foregoing sequences referenced in the Table (e.g., about 2, 3, 4, 5, 6, 7, 8, 9, 10, 11, 12, 13, 14, 15, 16, 17, 18, 19 nucleotide or amino acid modifications). In certain embodiments, (a) the majority of a chimeric xylose isomerase molecule is from a *Ruminococcus* xylose isomerase described in the foregoing Table (e.g., about 80% or more of the nucleotides or amino acids of the chimeric molecule (e.g., about 81, 82, 83, 84, 85, 86, 87, 88, 89, 90, 91, 92, 93, 94, 95, 96, 97, 98, 99% of the nucleotides or amino acids) or all but about 30 of the nucleotides or amino acids in the chimeric molecule (e.g., all but about 25, 24, 23, 22, 21, 20, 19, 18, 17, 16, 15, 14, 13, 12, 11, 10, 9, 8, 7, 6, 5, 4, 3, 2 or 1 nucleotides or amino acids of the chimeric molecule)), and (b) a minority of the chimeric xylose isomerase is from a xylose isomerase of another organism (e.g., about 20% or fewer of the nucleotides or amino acids of the chimeric molecule (e.g., about 19, 18, 17, 16, 15, 14, 13, 12, 11, 10, 9, 8, 7, 6, 5, 4, 3, 2, 1% of the nucleotides or amino acids) or about 30 of the nucleotides or amino acids in the chimeric molecule (e.g., about 25, 24, 23, 22, 21, 20, 19, 18, 17, 16, 15, 14, 13, 12, 11, 10, 9, 8, 7, 6, 5, 4, 3, 2 or 1 nucleotides or amino acids of the chimeric molecule)). In the latter embodiments, the minority of the chimeric xylose isomerase sometimes is from a xylose isomerase referenced in the foregoing Table, such as a xylose isomerase from the *Piromyces* strain, for example. In some embodiments, a donor sequence includes one or more nucleotide or amino acid mutations, examples of which are described herein.

In some embodiments, provided are nucleic acids, including a polynucleotide that includes a first stretch of contiguous nucleic acids from a first organism and a second stretch of contiguous nucleic acids from a second organism, where the polynucleotide encodes a polypeptide possessing a xylose to xylulose xylose isomerase activity. In certain embodiments, an expression vector, comprising a polynucleotide that includes a first stretch of contiguous expression vectors from a first organism and a second stretch of contiguous expression vectors from a second organism, where the polynucleotide encodes a polypeptide possessing a xylose to xylulose, xylose isomerase activity. In some embodiments, the first organism and the second organism are the same, and in certain embodiments, the first organism and the second organism are different. In some embodiments, the first stretch of contiguous nucleotides and the second stretch of contiguous nucleotides independently are selected from nucleotide sequence that encodes a polypeptide having xylose isomerase activity. In certain embodiments, the first organism is a bacterium. In some embodiments, the bacterium is a *Ruminococcus* bacterium, and in certain embodiments, the bacterium is a *Ruminococcus flavefaciens* bacterium (e.g., *Ruminococcus flavefaciens* strain 17, *Ruminococcus flavefaciens* strain Siijpesteijn 1948, *Ruminococcus flavefaciens* strain FD1, *Ruminococcus flavefaciens* strain 18P13). In some embodiments, the stretch of contiguous nucleotides is from SEQ ID NO: 29, 30, 32, 33, or a sequence having 50% identity or greater (e.g., about 55, 60, 65, 70, 75, 80, 85, 90, 95% identity or greater) to the foregoing. In certain embodiments, the stretch of contiguous nucleotides from the other organism encodes an amino acid sequence from SEQ ID NO: 31, or a sequence having 75% identity or greater (e.g., about 80, 85, 90, 95% identity or greater) to the foregoing. In certain embodiments, the second organism is a fungus. In some embodiments, the fungus is a *Piromyces* fungus, and in some embodiments, the fungus is a *Piromyces* strain E2 fungus. In certain embodiments, the stretch of contiguous nucleotides is from SEQ ID NO: 34, or a sequence having 50% identity or greater (e.g., about 55, 60, 65, 70, 75, 80, 85, 90, 95% identity or greater) to the foregoing. In some embodiments, the stretch of contiguous nucleotides from the other organism encodes an amino acid sequence from SEQ ID NO: 35, or a sequence having 75% identity or greater (e.g., about 80, 85, 90, 95% identity or greater) to the foregoing. In certain embodiments, the polynucleotide includes one or more substituted codons. In some embodiments, the one or more substituted codons are yeast codons. In certain embodiments, the stretch of contiguous nucleotides from the first organism or second organism is about 1% to about 30% (e.g., about 2, 3, 4, 5, 6, 7, 8, 9, 10, 15, 20, 25%) of the total number of nucleotides in the polynucleotide that encodes the polypeptide possessing xylose isomerase activity. In some embodiments, the stretch of contiguous nucleotides from the second organism is about 1% to about 30% (e.g., about 2, 3, 4, 5, 6, 7, 8, 9, 10, 15, 20, 25) of the total number of nucleotides in the polynucleotide, the polynucleotide includes a nucleotide sequence of SEQ ID NO: 55, 56, 57, 59 or 61, fragment thereof, or sequence having 50% identity or greater (e.g., about 55, 60, 65, 70, 75, 80, 85, 90, 95% identity or greater) to the foregoing. In certain embodiments, the polynucleotide encodes a polypeptide that includes an amino acid sequence of SEQ ID NO: 58, 60 or 62, fragment thereof, or sequence having 75% identity or greater (e.g., about 80, 85, 90, 95% identity or greater) to the foregoing. In some embodiments, the expression vector can include one or more point mutations. In certain embodiments, the point mutation is at a position corresponding to position 179 of *R. flavefaciens* polypeptide having xylose isomerase activity. In some embodiments, the point mutation is a glycine 179 to alanine point mutation.

In certain embodiments, the microbes described herein can be used in fermentation methods. In some embodiments, a method includes, contacting a microbe described herein with a feedstock comprising a five carbon molecule under conditions for generating ethanol. In certain embodiments, the five carbon molecule includes xylose. In some embodiments, about 15 grams per liter of ethanol, or more, is generated within about 372 hours. In certain embodiments, about 2.0 grams per liter dry cell weight, or more, is generated within about 372 hours.

In some embodiments, provided are nucleic acids, including a polynucleotide that includes a first stretch of contiguous nucleic acids from a first organism and a second stretch of contiguous nucleic acids from a second organism, where the polynucleotide encodes a polypeptide possessing a phosphogluconate dehydratase activity. In certain embodiments, an expression vector, comprising a polynucleotide that includes a first stretch of contiguous expression vectors from a first organism and a second stretch of contiguous expression vectors from a second organism, where the polynucleotide encodes a polypeptide possessing a phosphogluconate dehydratase activity. In some embodiments, the first organism and the second organism are the same, and in certain embodiments, the first organism and the second organism are different. In some embodiments, the first stretch of contiguous nucleotides and the second stretch of contiguous nucleotides independently are selected from nucleotide sequence that encodes a polypeptide having a phosphogluconate dehydratase activity.

In some embodiments, provided are nucleic acids, including a polynucleotide that includes a first stretch of contiguous nucleic acids from a first organism and a second stretch of contiguous nucleic acids from a second organism, where the polynucleotide encodes a polypeptide possessing a 2-keto-3-deoxygluconate-6-phosphate aldolase activity. In certain embodiments, an expression vector, comprising a polynucleotide that includes a first stretch of contiguous expression vectors from a first organism and a second stretch of contiguous expression vectors from a second organism, where the polynucleotide encodes a polypeptide possessing a 2-keto-3-deoxygluconate-6-phosphate aldolase activity. In some embodiments, the first organism and the second organism are the same, and in certain embodiments, the first organism and the second organism are different. In some embodiments, the first stretch of contiguous nucleotides and the second stretch of contiguous nucleotides independently are selected from nucleotide sequence that encodes a polypeptide having a 2-keto-3-deoxygluconate-6-phosphate aldolase activity.

In certain embodiments, the expression vector includes a regulatory nucleotide sequence in operable linkage with the polynucleotide. In some embodiments, the regulatory nucleotide sequence comprises a promoter sequence. In certain embodiments, the promoter sequence is an inducible promoter sequence. In some embodiments, the promoter sequence is a constitutively active promoter sequence. In certain embodiments, a method for preparing an expression vector as described herein, includes (i) providing a nucleic acid that contains a regulatory sequence, and (ii) inserting the polynucleotide into the nucleic acid in operable linkage with the regulatory sequence. In some embodiments, a microbe as described herein includes the nucleic acid of anyone of the foregoing embodiments. In certain embodiments, a microbe includes an expression vector of any one of the foregoing embodiments. In some embodiments, the microbe is a yeast. In certain embodiments, the microbe is a *Saccharomyces* yeast, and in some embodiments, the microbe is a *Saccharomyces cerevisiae* yeast.

In various embodiments, provided herein is a nucleic acid comprising polynucleotide subsequences that encode a phosphogluconate dehydratase enzyme (e.g., EDD), a 2-keto-3-deoxygluconate-6-phosphate aldolase enzyme (e.g., EDA), a transaldolase enzyme (e.g., TAL1), a transketolase enzyme (e.g., TKL1, TKL2, or TKL1 and TKL2), a glucose-6-phosphate dehydrogenase enzyme (e.g., ZWF1), a 6-phosphogluconolactonase enzyme (e.g., SOL3, SOL4, or SOL3 and SOL4) and a xylose isomerase enzyme or a xylose reductase (XR) enzyme and a xylitol dehydrogenase (XD) enzyme, and a xylulokinase (XK) enzyme. In some embodiments, polynucleotide subsequences encoding the phosphogluconate dehydratase enzyme and the 3-deoxygluconate-6-phosphate aldolase enzyme independently are from an *Escherichia* spp. (e.g., *Escherichia coli*) or *Pseudomonas* spp. (e.g., *Pseudomonas aeruginosa*), and in certain embodiments, the polynucleotide encoding the phosphogluconate dehydratase enzyme and/or the 3-deoxygluconate-6-phosphate aldolase enzyme is a chimeric polynucleotide that includes part of such a sequence and part of another phosphogluconate dehydratase enzyme and the 3-deoxygluconate-6-phosphate aldolase enzyme sequence (e.g., from a different organism). In certain embodiments, the polynucleotide subsequence that encodes the xylose isomerase enzyme is from a *Ruminococcus* spp. (e.g., *Ruminococcus flavefaciens*), and in some embodiments, is a chimeric polynucleotide that includes part of such a sequence and part of another xylose isomerase sequence (e.g., from a *Piromyces* spp.). Non-limiting examples of xylose isomerase chimeric sequences are described herein. In some embodiments, a nucleic acid includes a polynucleotide subsequence that encodes a glucose-6-phosphate dehydrogenase enzyme (e.g., ZWF1) and/or a polynucleotide subsequence that encodes a 6-phosphogluconolactonase enzyme (e.g., SOL3/SOL4). In certain embodiments, the polynucleotide subsequences that encode the glucose-6-phosphate dehydrogenase enzyme and the 6-phosphogluconolactonase enzyme are from a yeast, non-limiting examples of which are *Saccharomyces* spp. (e.g., *Saccharomyces cerevisiae*). In some embodiments, a nucleic acid includes a polynucleotide subsequence that encodes a glucose transporter (e.g., GAL2, GXS1, GXF1, HXT7). In certain embodiments, the polynucleotide subsequence that encodes the glucose transporter is from a yeast, non-limiting examples of which are *Saccharomyces* spp. (e.g., *Saccharomyces cerevisiae*). In some embodiments, a nucleic acid includes a polynucleotide subsequence that alters the activity of 6-phosphogluconate dehydrogenase (decarboxylating) enzyme (e.g., GND1, GND2). In certain embodiments, the polynucleotide subsequences that alter the activity of 6-phosphogluconate dehydrogenase (decarboxylating) enzyme are from a yeast. In some embodiments, a nucleic acid includes a polynucleotide subsequence that decreases expression of, or disrupts, a 6-phosphogluconate dehydrogenase (decarboxylating) enzyme. In some embodiments, a nucleic acid includes a polynucleotide subsequence that disrupts a phosphoglucose isomerase enzyme (e.g., PGI1). In some embodiments, a nucleic acid includes a polynucleotide subsequence that decreases expression of, or disrupts, a phosphoglucose isomerase enzyme. In some embodiments, a nucleic acid includes a polynucleotide subsequence that encodes a transaldolase enzyme (e.g., TAL1). In certain embodiments, the polynucleotide subsequences that encode the transaldolase enzyme are from a yeast, non-limiting examples of which are *Kluyveromyces*, *Pichia*, *Escherichia*, *Bacillus*, *Ruminococcus*, *Schizosaccharomyces*, and *Candida*. In some embodiments, a nucleic acid includes a polynucleotide subsequence that decreases expression of, or disrupts, transaldolase enzyme. In some embodiments, a nucleic acid includes a polynucleotide subsequence that encodes a transketolase enzyme (e.g., TKL1, TKL2, or TKL1 and TKL2). In certain embodiments, the polynucleotide subsequences that encode the transketolase enzyme are from a yeast, non-limiting examples of which are *Kluyveromyces*, *Pichia*, *Escherichia*, *Bacillus*, *Ruminococcus*, *Schizosaccharomyces*, and *Candida*. In some embodiments, a nucleic acid includes a polynucleotide subsequence that decreases expression of, or disrupts, transketolase enzyme.

In some embodiments, a nucleic acid includes one or more promoters operable in a yeast (e.g., *Saccharomyces* spp. (e.g., *Saccharomyces cerevisiae*), and in operable connection with one or more polynucleotide subsequences described above. Such promoters often are constitutively active and sometimes are operable under anaerobic and aerobic conditions. Non-limiting examples of promoters include those that control glucose phosphate dehydrogenase (GPD), translation elongation factor (TEF-1), phosphoglucokinase (PGK-1) and triose phosphate dehydrogenase (TDH-1). A nucleic acid can be one or two nucleic acids in some embodiments, and each nucleic acid can include one or two or more of the polynucleotide subsequences and or promoters described above. A nucleic acid can be in circular (e.g., plasmid) or linear form, in some embodiments, and sometimes functions as an expression vector. In some embodiments, a nucleic acid functions as a tool for integrating the polynucleotide subsequences, and optionally promoter sequences, included in the nucleic acid, into genomic DNA of a host organism.

In some embodiments, provided herein is an engineered microbe comprising heterologous polynucleotide subsequences that encode a phosphogluconate dehydratase enzyme (e.g., EDD), a 2-keto-3-deoxygluconate-6-phosphate aldolase enzyme (e.g., EDA), a xylose isomerase enzyme or a xylose reductase (XR) enzyme and a xylitol dehydrogenase (XD) enzyme, and a xylulokinase (XK) enzyme. In certain embodiments, the microbe is a yeast, non-limiting examples of which are *Saccharomyces* spp. (e.g., *Saccharomyces cerevisiae*). In some embodiments, polynucleotide subsequences encoding the phosphogluconate dehydratase enzyme and the 3-deoxygluconate-6-phosphate aldolase enzyme independently are from an *Escherichia* spp. (e.g., *Escherichia coli*) or *Pseudomonas* spp. (e.g., *Pseudomonas aeruginosa*), and in certain embodiments, the polynucleotide encoding the phosphogluconate dehydratase enzyme and/or the 3-deoxygluconate-6-phosphate aldolase enzyme is a chimeric polynucleotide that includes part of such a sequence and part of another phosphogluconate dehydratase enzyme and the 3-deoxygluconate-6-phosphate aldolase enzyme sequence (e.g., from a different organism). In certain embodiments, the polynucleotide subsequence that encodes the xylose isomerase enzyme is from a *Ruminococcus* spp. (e.g., *Ruminococcus flavefaciens*), and in some embodiments, is a chimeric polynucleotide that includes part of such a sequence and part of another xylose isomerase sequence (e.g., from a *Piromyces* spp.). Non-limiting examples of xylose isomerase chimeric sequences are described herein. In some embodiments, the engineered microbe expresses a glucose-6-phosphate dehydrogenase enzyme (e.g., ZWF1) and/or a 6-phosphogluconolactonase enzyme (e.g., SOL3/SOL4). In certain embodiments, the polynucleotide subsequences that encode the glucose-6-phosphate dehydrogenase enzyme and the 6-phosphogluconolactonase enzyme are from a yeast, non-limiting examples of which are *Saccharomyces* spp. (e.g., *Saccharomyces cerevisiae*). In certain embodiments, the polynucleotide subsequences that disrupt the 6-phosphogluconate dehydrogenase (decarboxylating) enzyme are from a yeast. In some embodiments, a nucleic acid includes a polynucleotide subsequence that decreases expression of, or disrupts, a 6-phosphogluconate dehydrogenase (decarboxylating) enzyme.

Thus, an engineered microbe sometimes expresses higher-than-normal levels (e.g., over-express) of an endogenous glucose-6-ph6-phosphogluconolactonase enzyme glucose-6-phosphate dehydrogenase enzyme (e.g., under control of a constitutive promoter, or multiple copies of the nucleotide subsequences that encode such enzymes are inserted in the microbe). In some embodiments, the engineered microbe includes a polynucleotide subsequence that encodes a glucose transporter (e.g., GAL2, GSX1, GXF1, HXT7). In certain embodiments, the polynucleotide subsequence that encodes the glucose transporter is from a yeast, non-limiting examples of which are *Saccharomyces* spp. (e.g., *Saccharomyces cerevisiae*). Thus, an engineered microbe sometimes expresses higher-than-normal levels (e.g., over-express) of one or more endogenous glucose transport enzymes (e.g., under control of a constitutive promoter, or multiple copies of the nucleotide subsequences that encode such enzymes are inserted in the microbe). In some embodiments, the engineered microbe includes a genetic alteration that reduces the activity of an endogenous phosphofructokinase enzyme activity. In certain embodiments, a polynucleotide subsequence that encodes such an enzyme is altered such that enzyme activity is significantly reduced or not detectable in the engineered microbe. In some embodiments, a nucleic acid includes a polynucleotide subsequence that alters the activity of 6-phosphogluconate dehydrogenase (decarboxylating) enzyme (e.g., GND1, GND2). In certain embodiments, the polynucleotide subsequences that alter the activity of 6-phosphogluconate dehydrogenase (decarboxylating) enzyme are from a yeast. In some embodiments, a nucleic acid includes a polynucleotide subsequence that decreases expression of, or disrupts, a 6-phosphogluconate dehydrogenase (decarboxylating) enzyme. In some embodiments, a nucleic acid includes a polynucleotide subsequence that alters a phosphoglucose isomerase enzyme (e.g., PGI1) activity. In certain embodiments, the polynucleotide subsequences that alter the phosphoglucose isomerase enzyme are from a yeast. In some embodiments, a nucleic acid includes a polynucleotide subsequence that decreases expression of, or disrupts, a phosphoglucose isomerase enzyme. In some embodiments, a nucleic acid includes a polynucleotide subsequence that alters a transaldolase enzyme (e.g., TAL1). In certain embodiments, the polynucleotide subsequences that alter the transaldolase enzyme activity, increase the transaldolase activity, and in some embodiments the polynucleotide sequences are from a yeast, non-limiting examples of which are *Kluyveromyces, Pichia, Escherichia, Bacillus, Ruminococcus, Schizosaccharomyces*, and *Candida*. In certain embodiments, the polynucleotide subsequences that alter transaldolase enzyme activity, decrease the transaldolase activity. In some embodiments, a nucleic acid includes a polynucleotide subsequence that decreases expression of, or disrupts, transaldolase enzyme. In some embodiments, a nucleic acid includes a polynucleotide subsequence that alters a transketolase enzyme (e.g., TKL1, TKL2, or TKL1 and TKL2). In certain embodiments, the polynucleotide subsequences that alter the transketolase enzyme increase transketolase activity and in some embodiments, the polynucleotide sequences are from a yeast, non-limiting examples of which are *Kluyveromyces, Pichia, Escherichia, Bacillus, Ruminococcus, Schizosaccharomyces*, and *Candida*. In certain embodiments, the polynucleotide subsequences that alter transketolase enzyme activity, decrease the transketolase activity. In some embodiments, a nucleic acid includes a polynucleotide subsequence that decreases expression of, or disrupts, transketolase enzyme.

In some embodiments, the engineered microbe includes one or more promoters operable in a yeast (e.g., *Saccharomyces* spp. (e.g., *Saccharomyces cerevisiae*), and in operable connection with one or more polynucleotide subsequences described above. Such promoters often are constitutively active and sometimes are operable under anaerobic and aerobic conditions. Non-limiting examples of promoters include those that control glucose phosphate dehydrogenase (GPD), translation elongation factor (TEF-1), phosphoglucokinase (PGK-1) and triose phosphate dehydrogenase (TDH-1). The polynucleotide sequences and promoters described above sometimes are non-stably associated with the microbe (e.g., they are in a non-integrated nucleic acid (e.g., a plasmid), and in some embodiments, are integrated in genomic DNA of the microbe. In some embodiments, the polynucleotide sequences are integrated in a transposition integration event, a homologous recombination integration event or a transposition integration event and a homologous recombination integration event. In some embodiments, a transposition integration event includes transposition of an operon comprising two or more of the polynucleotide subsequences and/or promoters described above. In certain embodiments, a homologous recombination integration event includes homologous recombination of an operon comprising two or more of the polynucleotide subsequences and or promoters described above. In certain embodiments, provided are methods for producing xylulose and/or ethanol using an engineered microbe described above, which comprise contacting the engineered microbe with a medium (e.g., feedstock) under conditions in which the microbe synthesizes xylulose and/or ethanol. In some embodiments, the engineered microbe synthesizes xylulose and/or ethanol to about 85% to about 99% of theoretical yield (e.g., about 86%, 87%, 88%, 89%, 90%, 91%, 92%, 93%, 94%, 95%, 96%, 97%, 98% or 99% of theoretical xylulose and/or ethanol yield). In some embodiments, the medium (e.g., feedstock) contains a six-carbon sugar (e.g., hexose, glucose) and/or a five-carbon sugar (e.g., pentose, xylose). In certain embodiments, the ethanol is separated and/or recovered from the engineered microorganism.

Additional embodiments can be found in Example 42: Examples of the embodiments. Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

In FIG. 2 the activity of an enzyme in the Embden-Meyerhoff pathway, phosphofructokinase (e.g., PFK) is permanently or temporarily reduced or eliminated. The inactivation is shown as the "X" in FIG. 2. Disruption of the activity of PFK serves to inactivate the Embden-Meyerhoff pathway (EM pathway). To allow cells to survive with a non-functional PFK, two activities from the Entner-Doudoroff pathway (ED pathway) have been introduced into a host organism engineered with the reduced or non-functional EM pathway. The introduced activities allow survival with an inactivated EM pathway in addition to increased efficiency of ethanol production.

FIG. 6 shows DNA and amino acid sequence alignments for the nucleotide sequences of EDA (FIG. 6A, 6B) (SEQ ID NOS 670-677, respectively, in order of appearance) and EDD (FIG. 6C, 6D) (SEQ ID NOS 678-685, respectively, in order of appearance) genes from *Zymomonas mobilis* (native and optimized) and *Escherichia coli*.

Results are presented as percent activity over wild type (WT) activity. Experimental details and results of the kinetic assays are present in Example 12.

Figure 11:
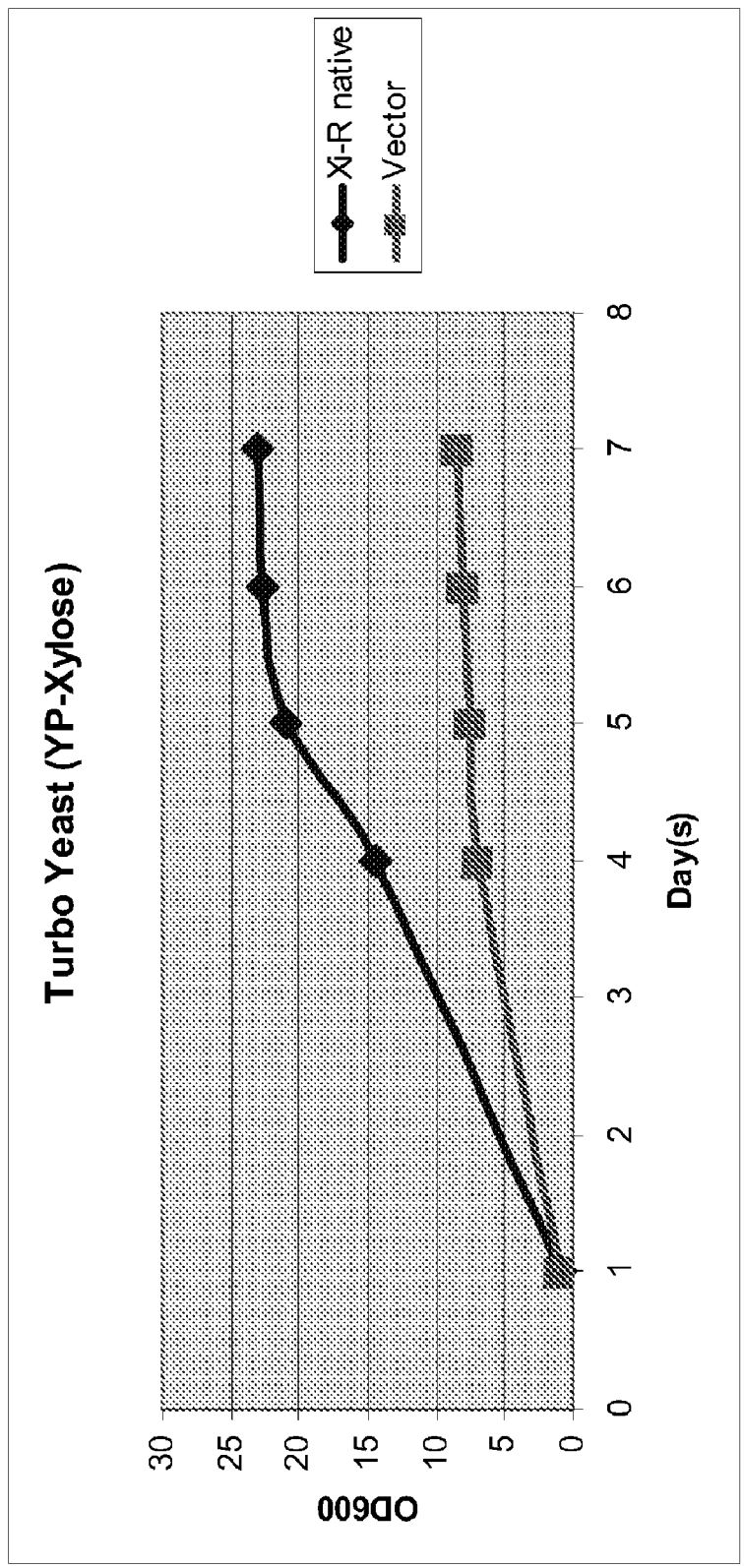

FIG. 11 illustrates comparative growth analysis results of yeast strains carrying vector only or a vector containing native *Ruminococcus* xylose isomerase, grown on media containing xylose. Experimental details and results of the growth assays are described in Example 13.

Figure 12:
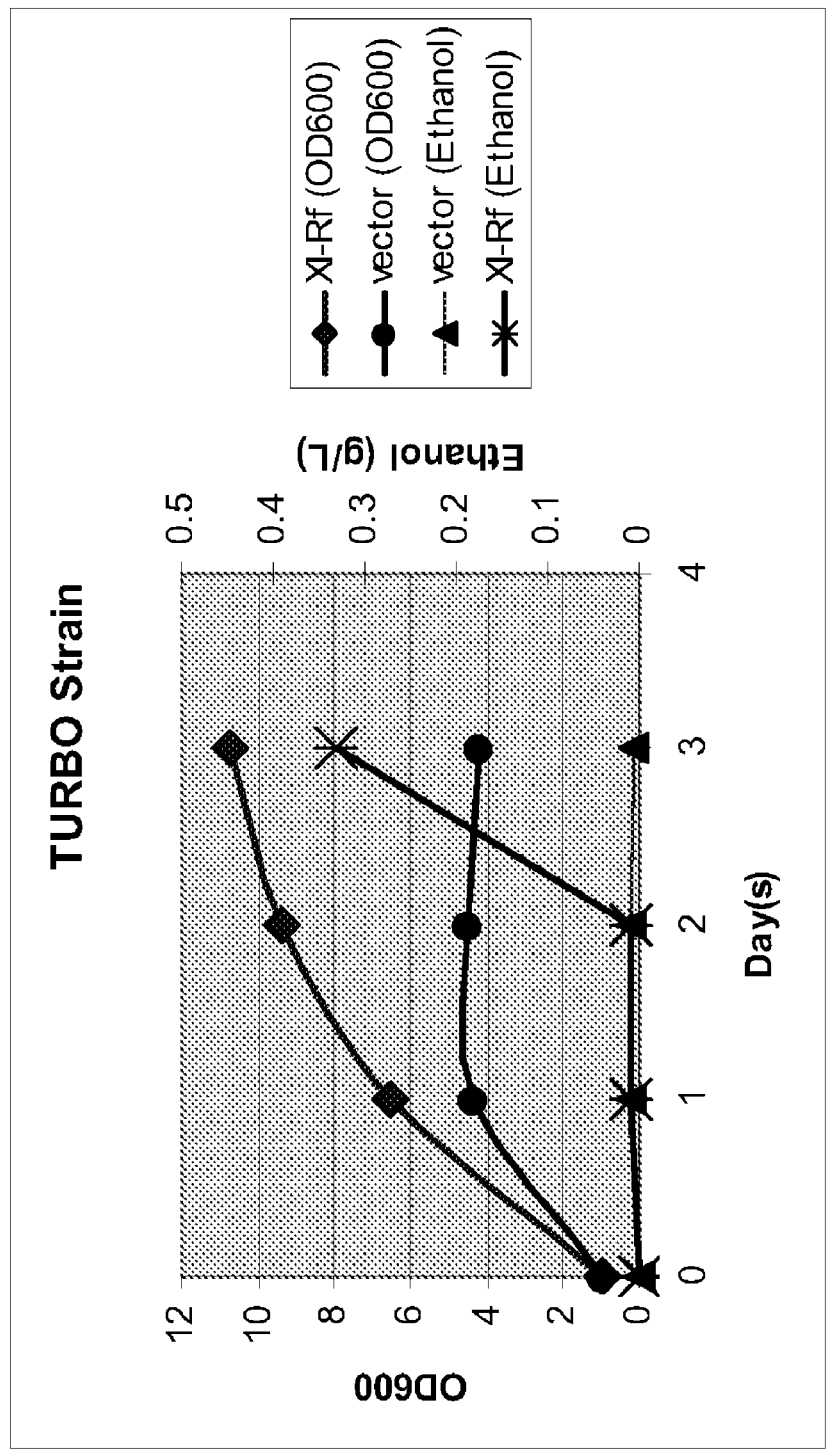

FIG. 12 illustrates comparative growth analysis results and measurement of ethanol production in yeast strains carrying vector only or a vector containing native *Ruminococcus* xylose isomerase. Growth of cells is shown by the lines connected by "diamonds" (vector with xylose isomerase) or "squares" (vector only). Ethanol production is shown by the lines connected by "x's" (vector with xylose isomerase) or "circles" (vector only). Experimental conditions and results are described in Example 13.

Figure 13A:
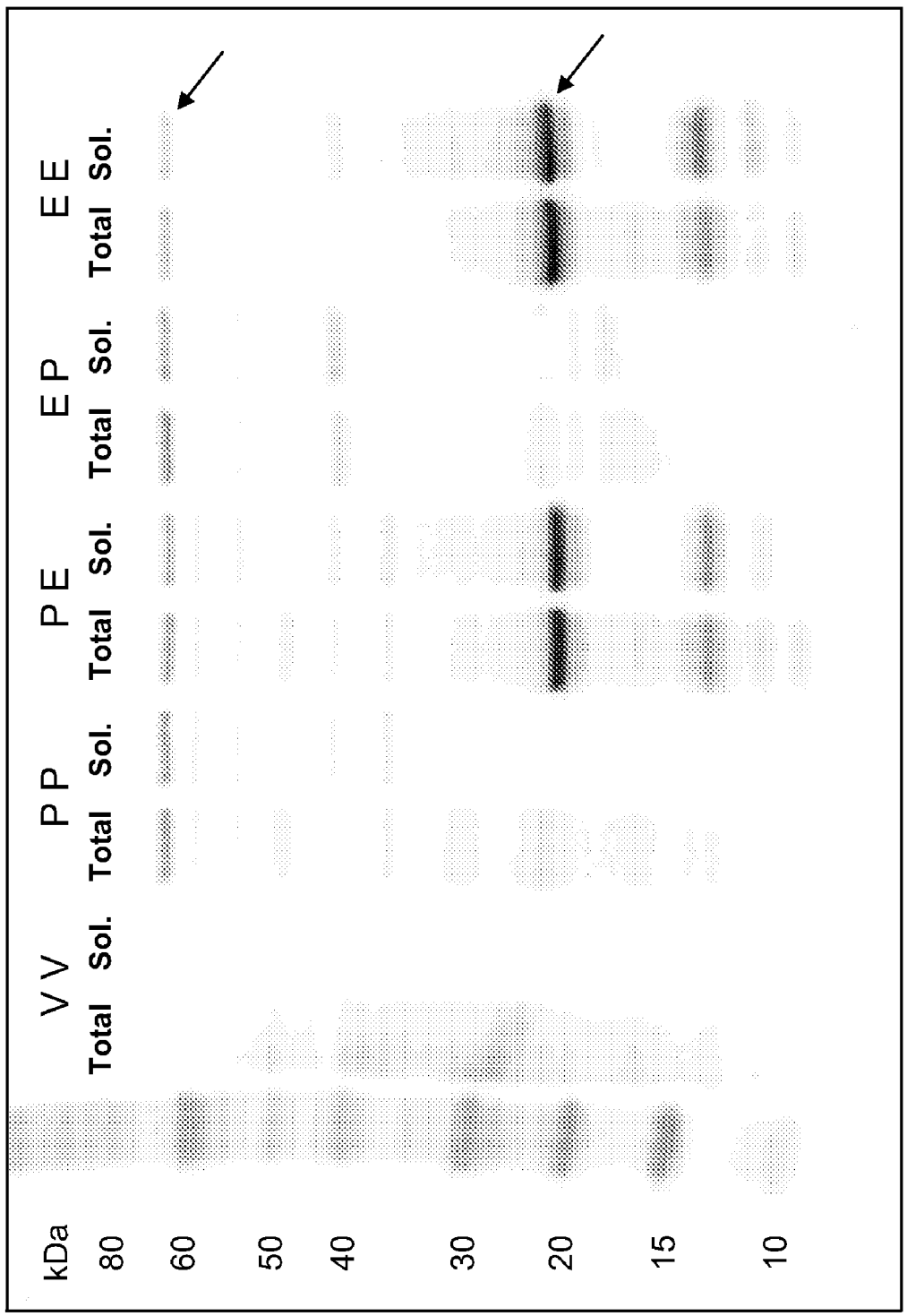
Figure 13B:
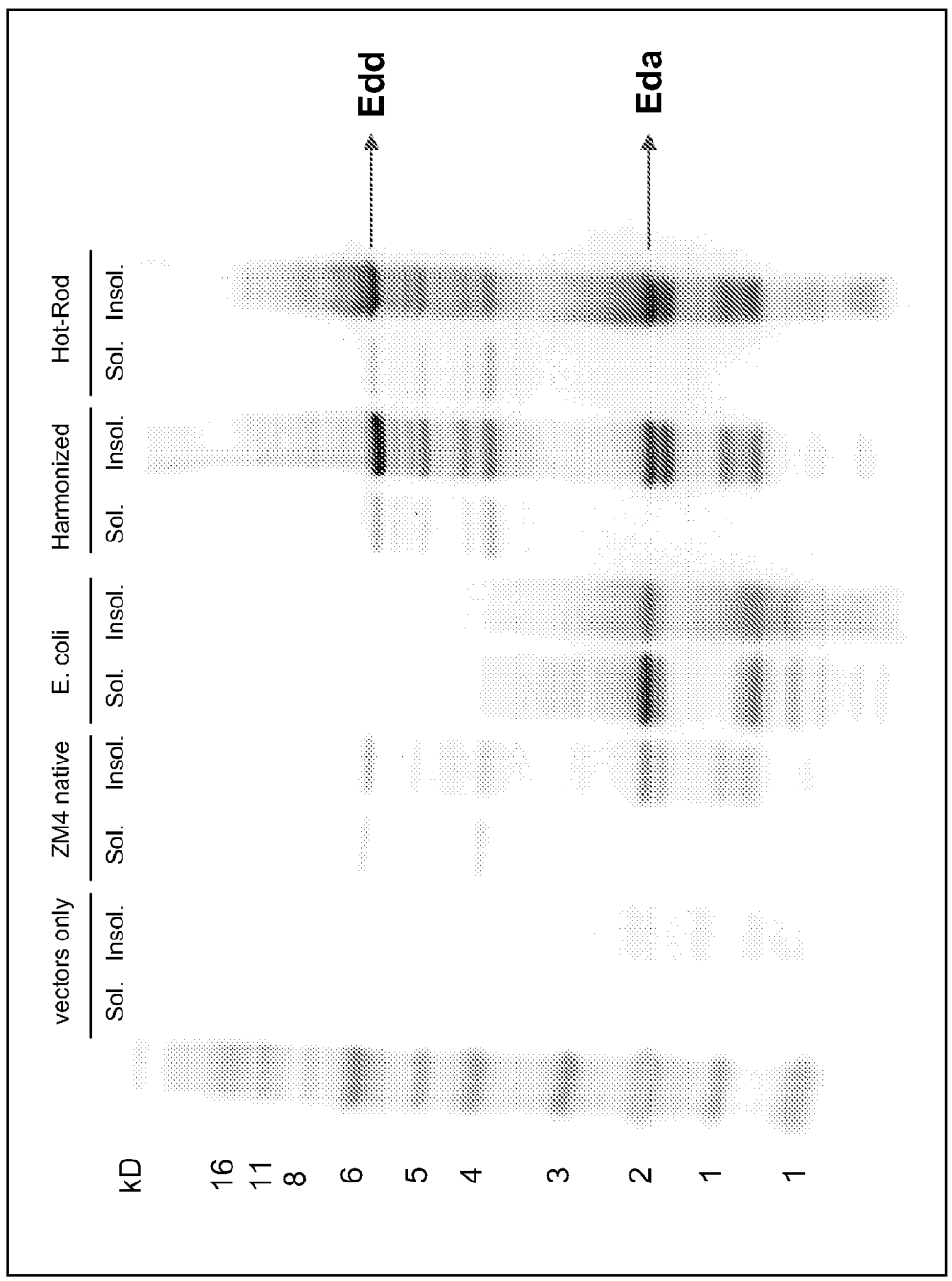

FIGS. 13A and 13B show representative Western blots used to detect levels of various exogenous EDD and EDA gene combinations expressed in a host organism. Experimental conditions and results are described in Example 17.

Figure 14:
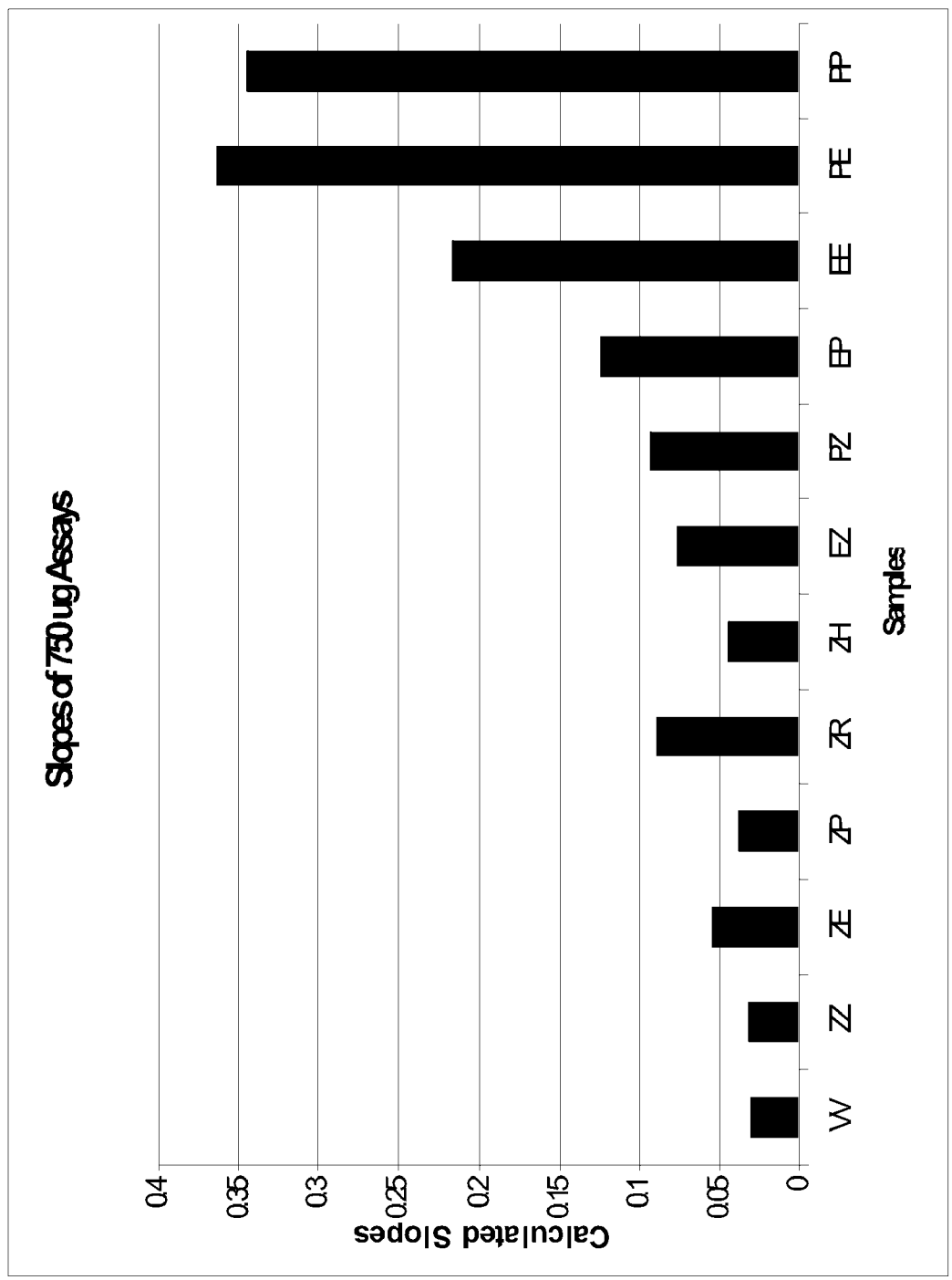

FIG. 14 graphically displays the relative activities of the various EDD/EDA combinations generated as described in Example 18.

Figure 15:
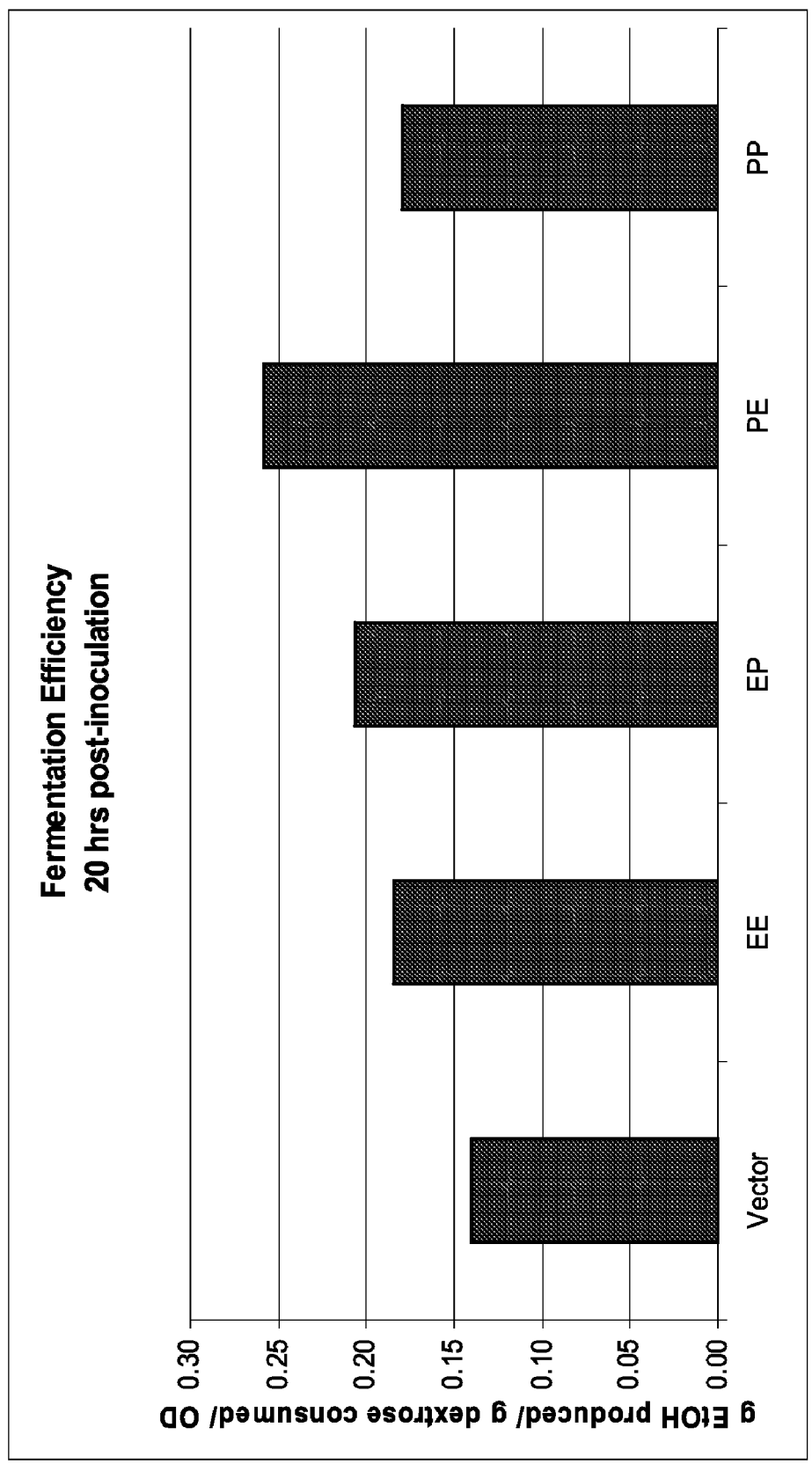

FIG. 15 graphically represents the fermentation efficiency of engineered yeast strains carrying exogenous EDD/EDA gene combinations. Vector=p426GPD/p425GPD; EE=EDD-*E. coli*/EDA-*E. coli*, EP=EDD-*E. coli*/EDA-PAO1; PE=EDD-PAO1/EDA-*E. coli*, PP=EDD-PAO1/EDA-PAO1. Experimental conditions and results are described in Example 19.

Figure 16A:
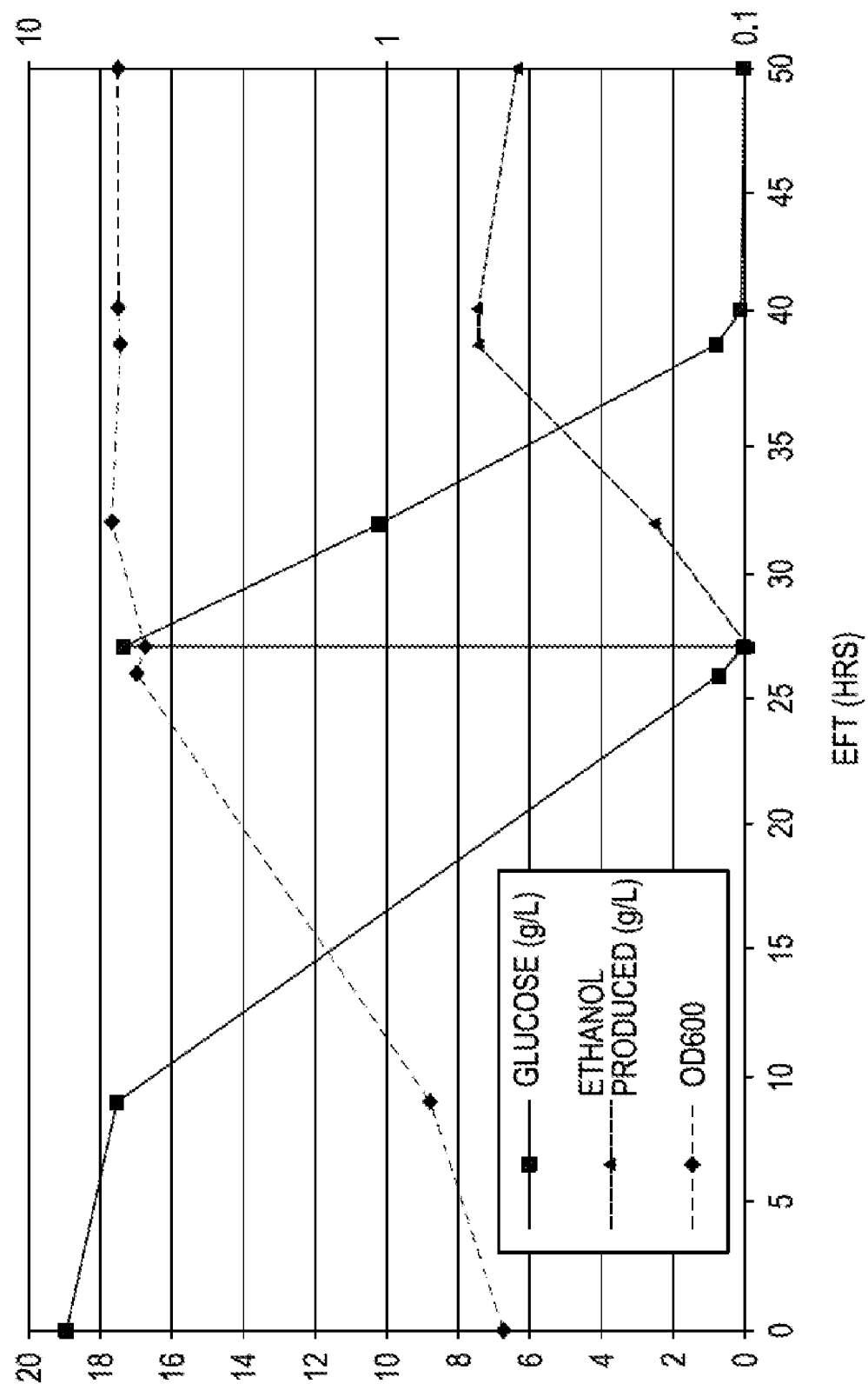
Figure 16B:
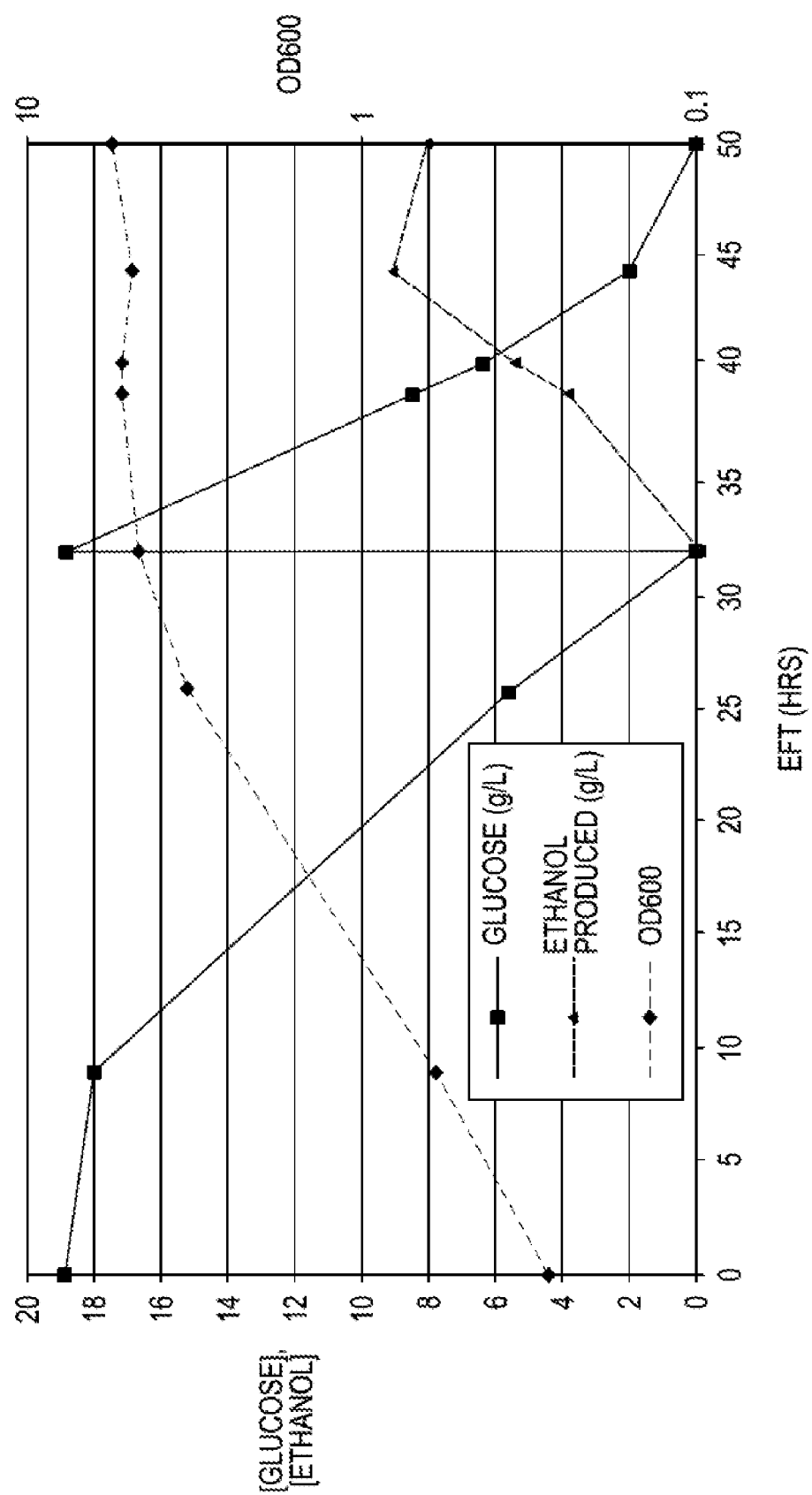

FIGS. 16A and 16B graphically illustrate fermentation data (e.g., cell growth, glucose usage and ethanol production) for engineered yeast strains generated as described herein. FIG. 16A illustrates the fermentation data for engineered strain BF428 (BY4742 with vector controls), and FIG. 16B illustrates the fermentation data for engineered strain BF591 (BY4742 with EDD-PAO1/EDA-PAO1). Experimental conditions and results are described in Example 20.

Figure 17A:
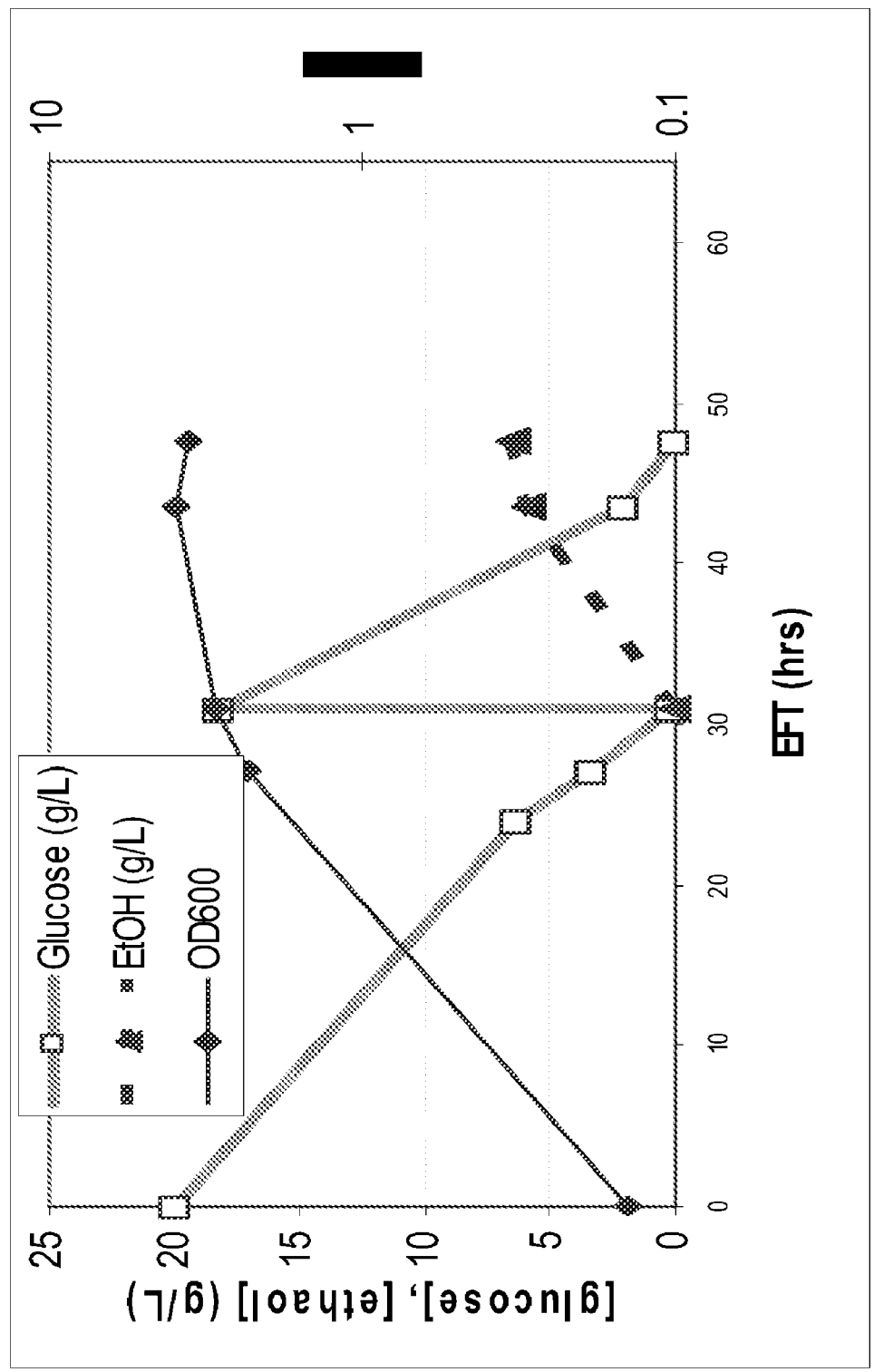
Figure 17B:
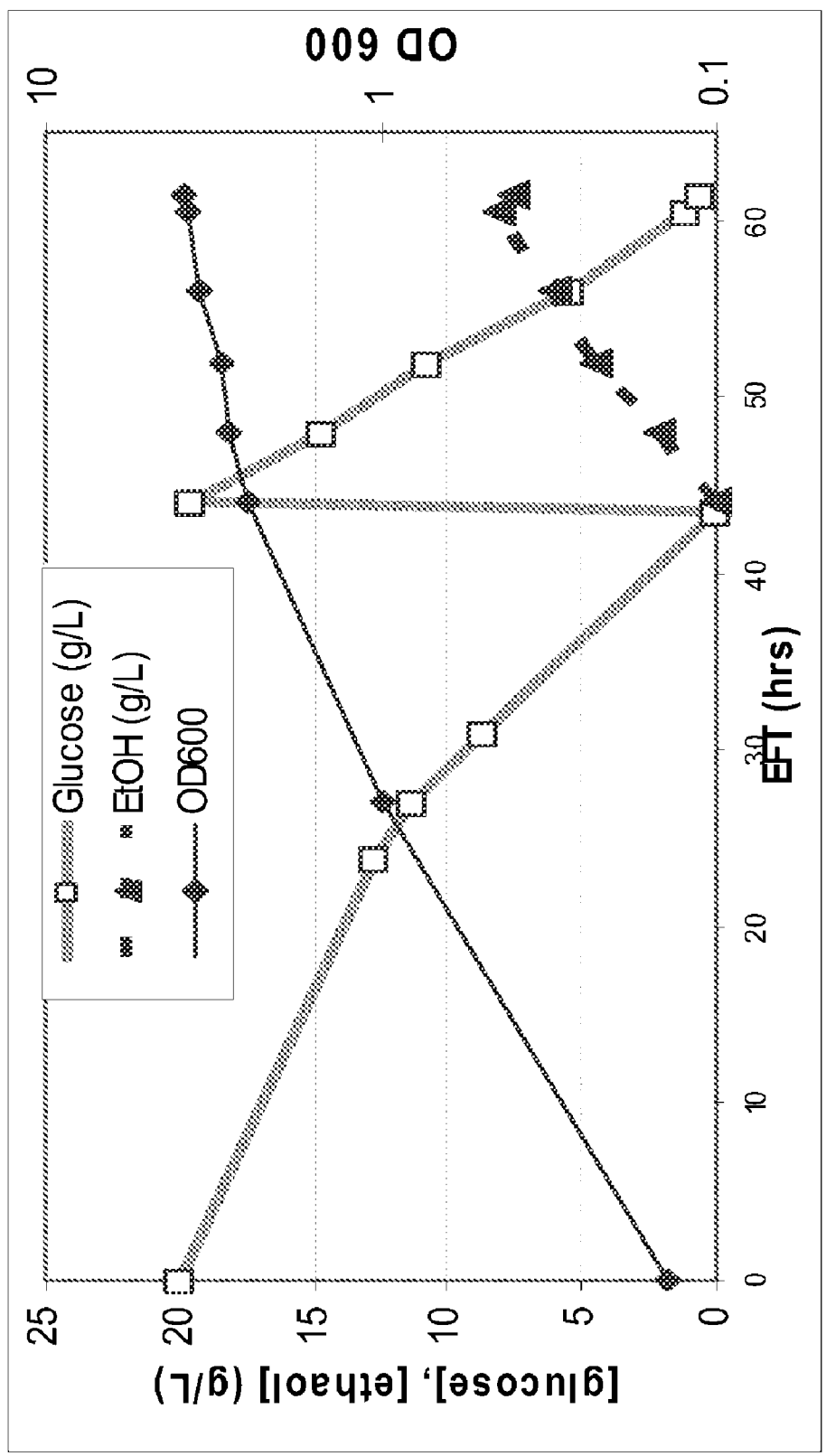

FIGS. 17A and 17B graphically illustrate fermentation data for engineered yeast strains described herein. FIG. 17A illustrates the fermentation data for engineered strain BF738 (BY4742 tal1 with vector controls p426GPD and p425GPD). FIG. 17B illustrates the fermentation data for engineered strain BF741 (BY4742 tal1 with plasmids pBF290 (EDD-PAO1) and pBF292 (EDA-PAO1). Experimental conditions and results are described in Example 21.

Figure 18A:
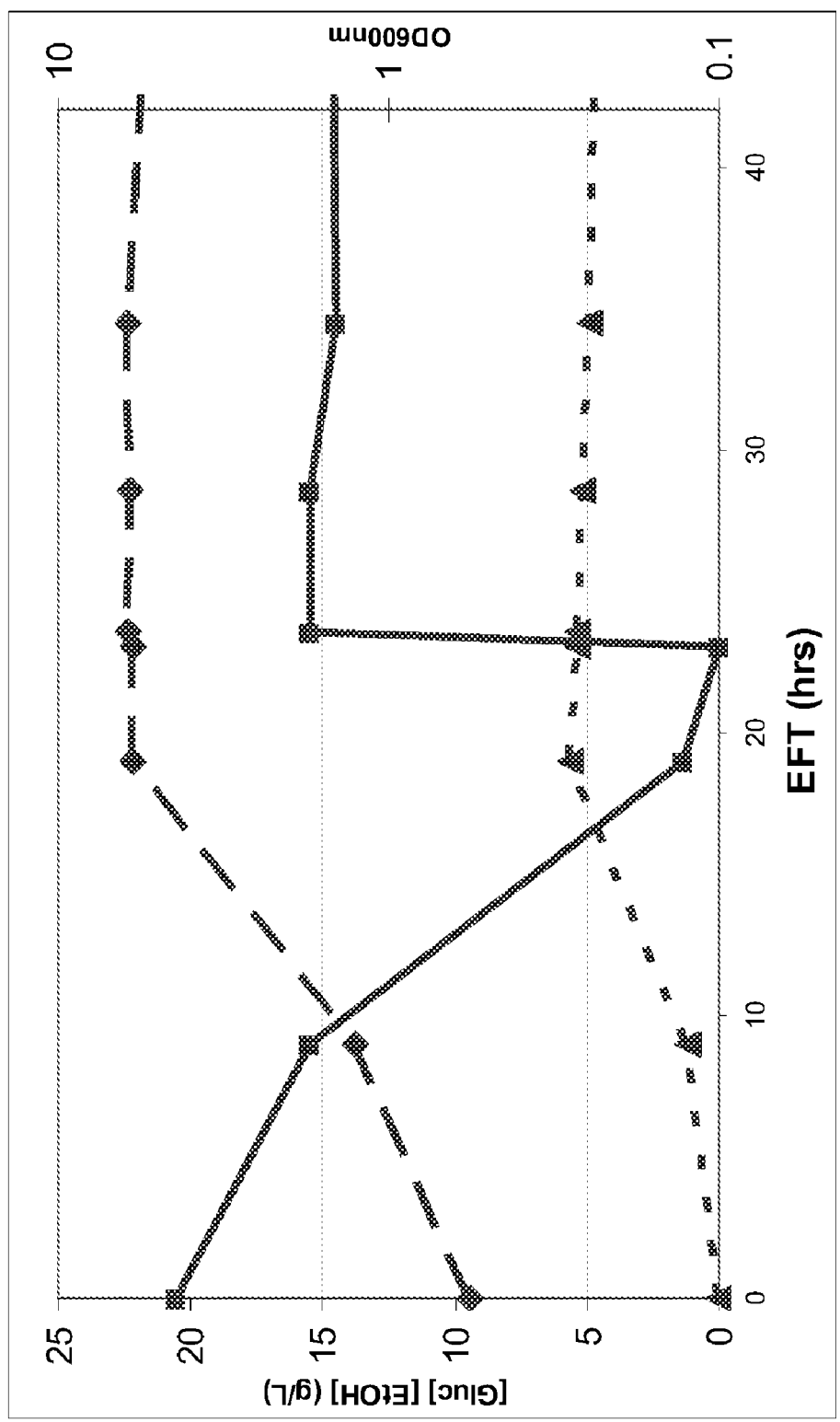
Figure 18B:
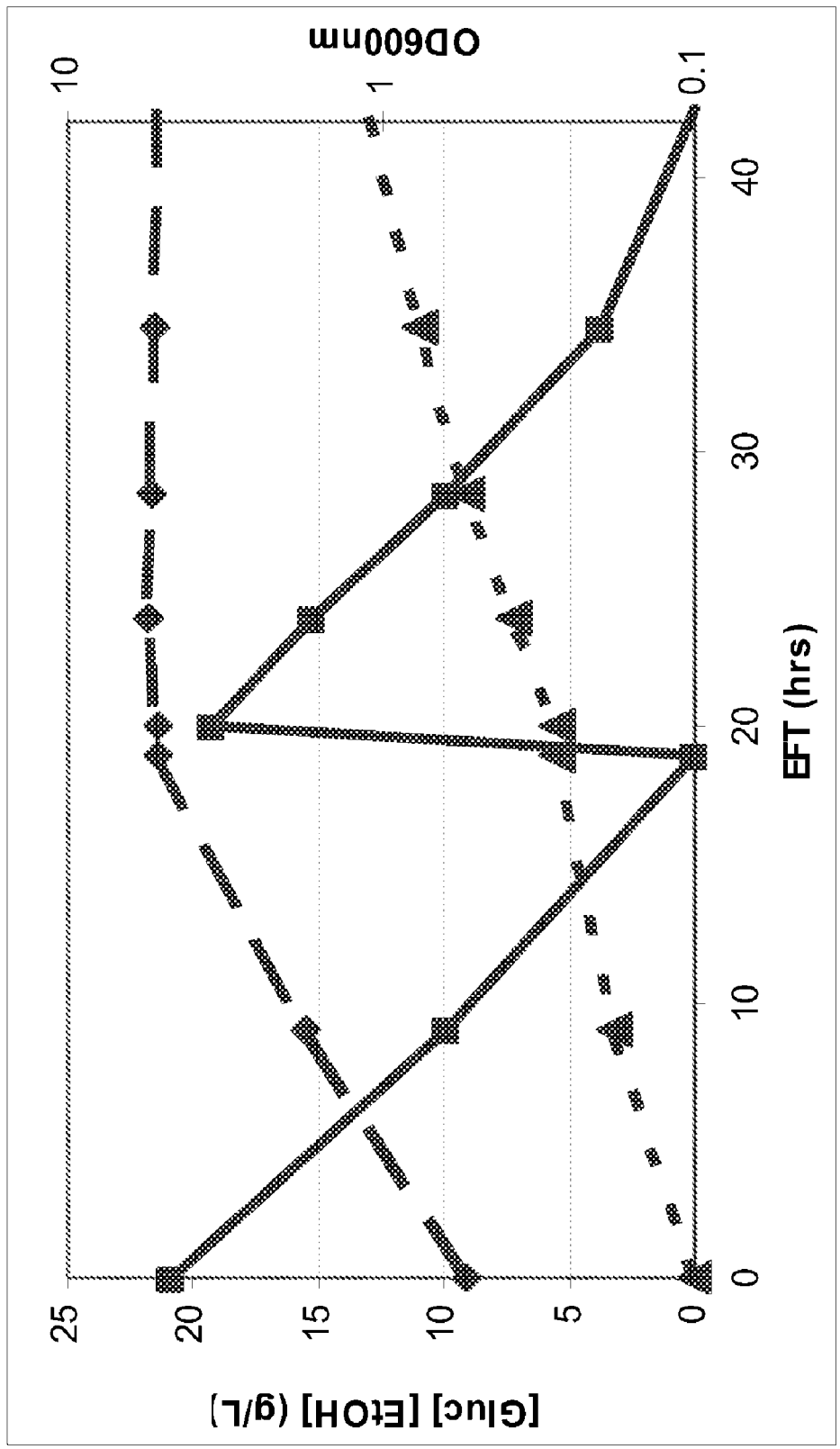

FIGS. 18A and 18B graphically illustrate fermentation data for engineered yeast strains as described herein. FIG. 18A illustrates the fermentation data for BF740 grown on 2% dextrose, and FIG. 18B illustrates the fermentation data for BF743 grown on 2% dextrose. Strain descriptions, experimental conditions and results are described in Example 22.

Figure 19:
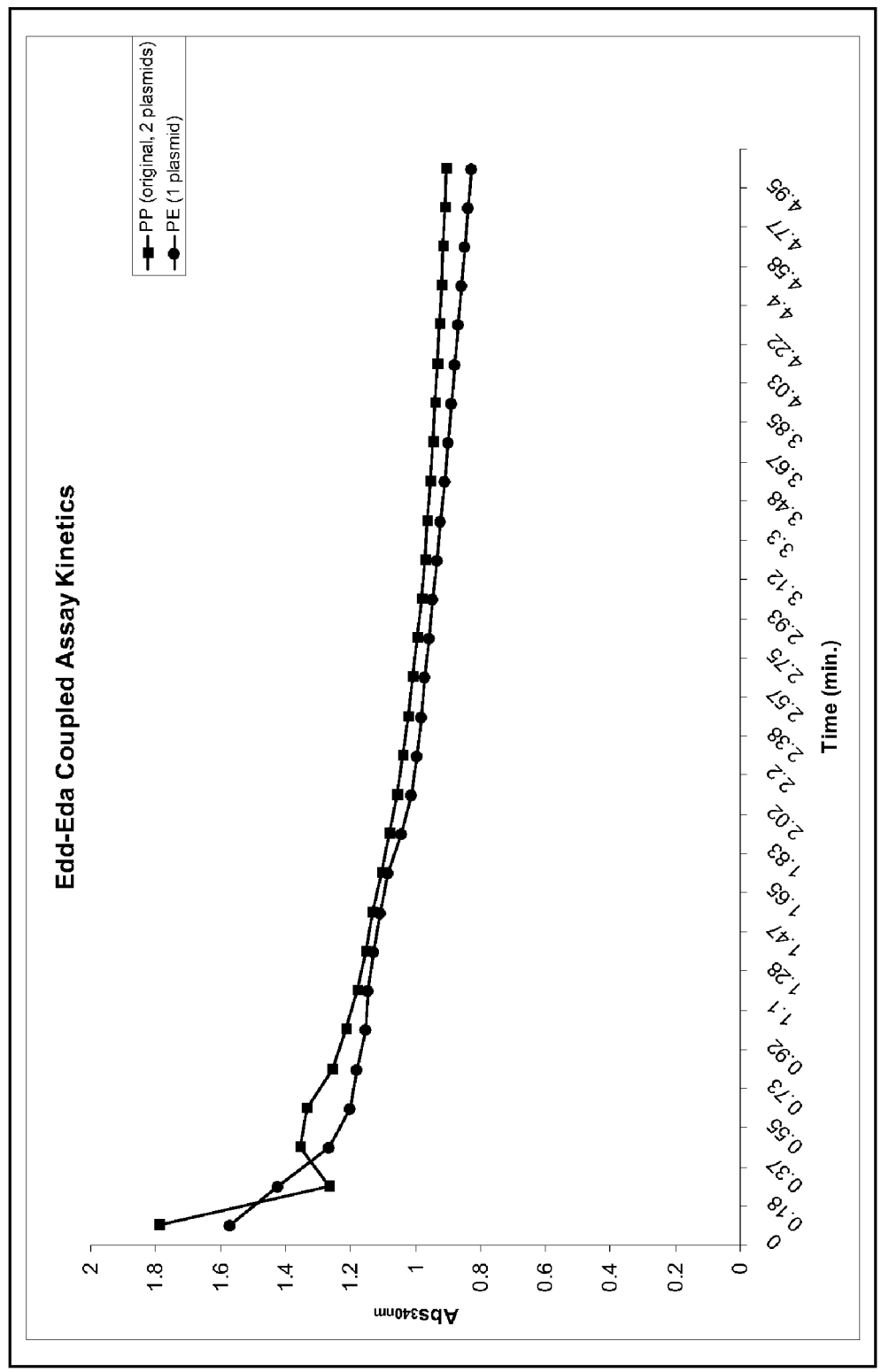

FIG. 19 graphically illustrates the results of coupled assay kinetics for single plasmid and two plasmid edd/eda expression vector systems. Vector construction and experimental conditions are described in Example 24.

Figure 2:
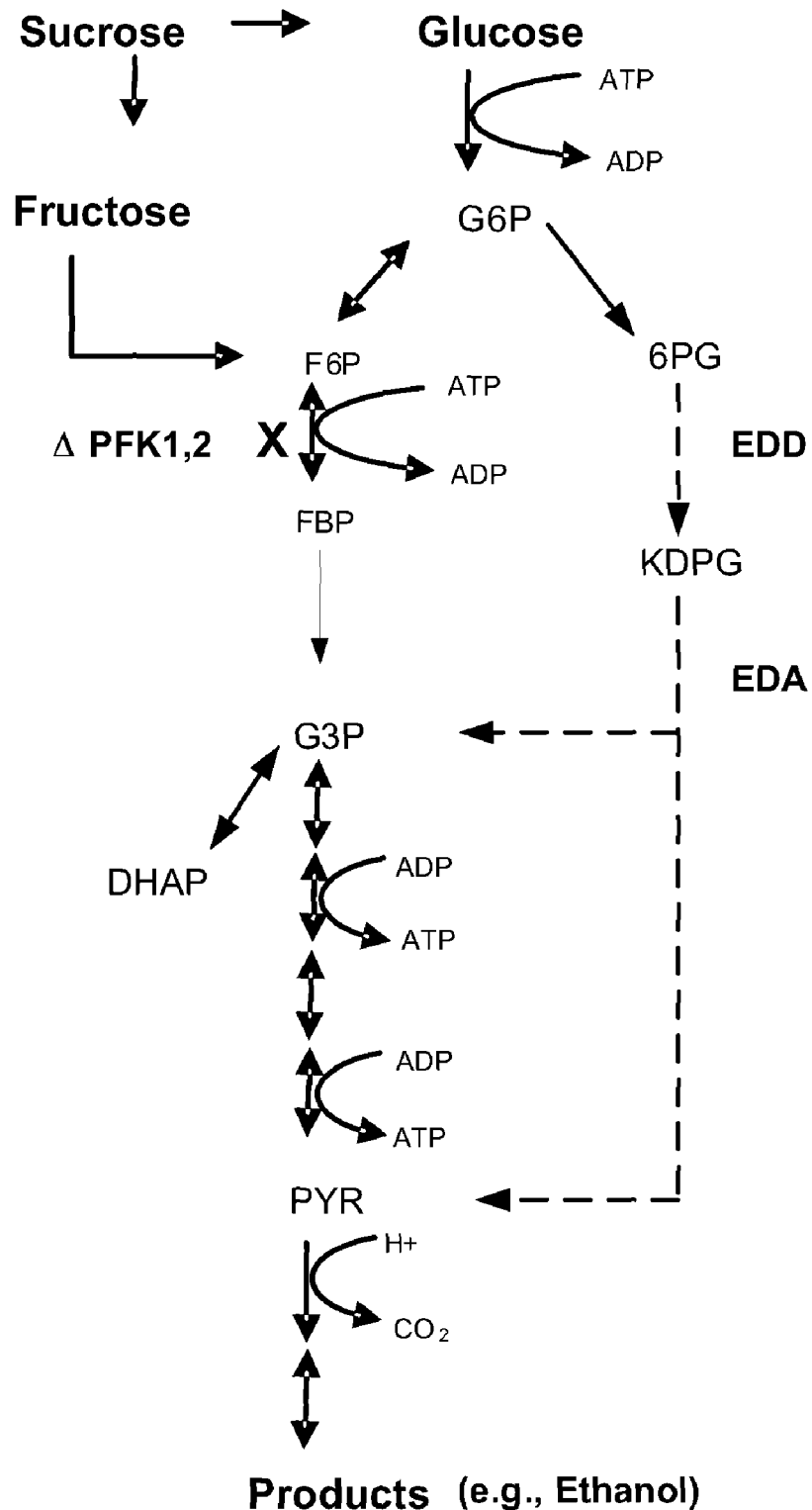
FIG. 2 depicts an engineered metabolic pathway that can be used to produce ethanol more efficiently in a host microorganism in which the pathway has been engineered. The solid lines in FIGS. 2-5 represent the metabolic pathway naturally found in a host organism (e.g., *Saccharomyces cerevisiae*, for example). The dashed lines in FIGS. 2-5 represent a novel activity or pathway engineered into a microorganism to allow increased ethanol production efficiency.
Figure 3:
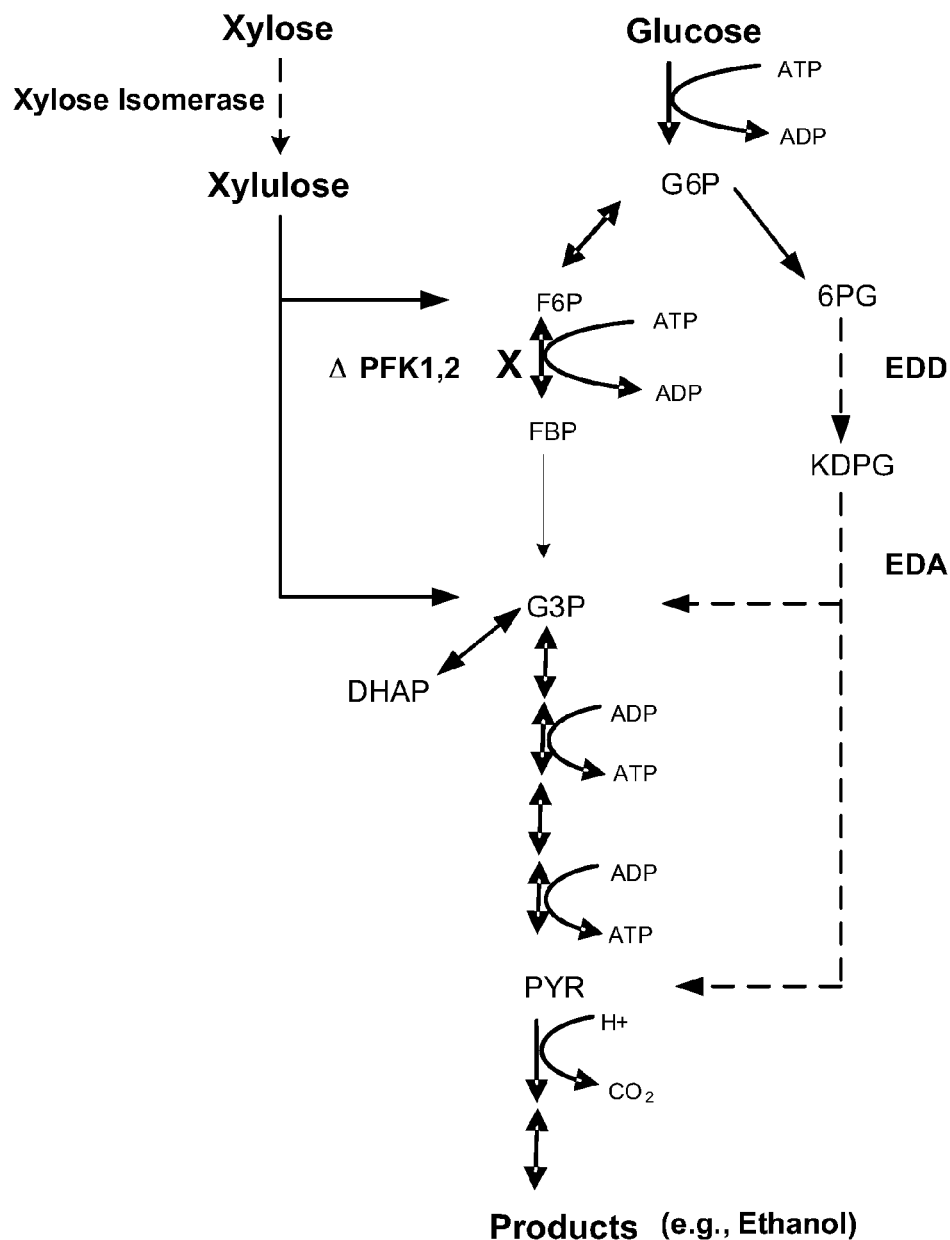
FIG. 3 depicts an engineered metabolic pathway that can be used to produce ethanol using xylose as a carbon source by introducing the activity into a microorganism. The engineered microorganism can convert xylose to xylulose in a single reaction using the introduced xylose isomerase activity. Xylose also can be metabolized by the combined activities of xylose reductase, and xylitol dehydrogenase, as depicted in FIG. 20. Xylulose then can be fermented to ethanol by entering the EM pathway. Engineered microorganisms also can use the increased efficiency of ethanol production associated with inactivation of the EM pathway and introduction of activities of the ED pathway, shown in FIG. 2 and discussed below. The ability to utilize xylose efficiently (e.g., concurrently with six-carbon sugars or prior to the depletion of six-carbon sugars) can be provided by the introduction of the novel activities, xylose isomerase, or xylose reductase and xylitol dehydrogenase.
Figure 20:
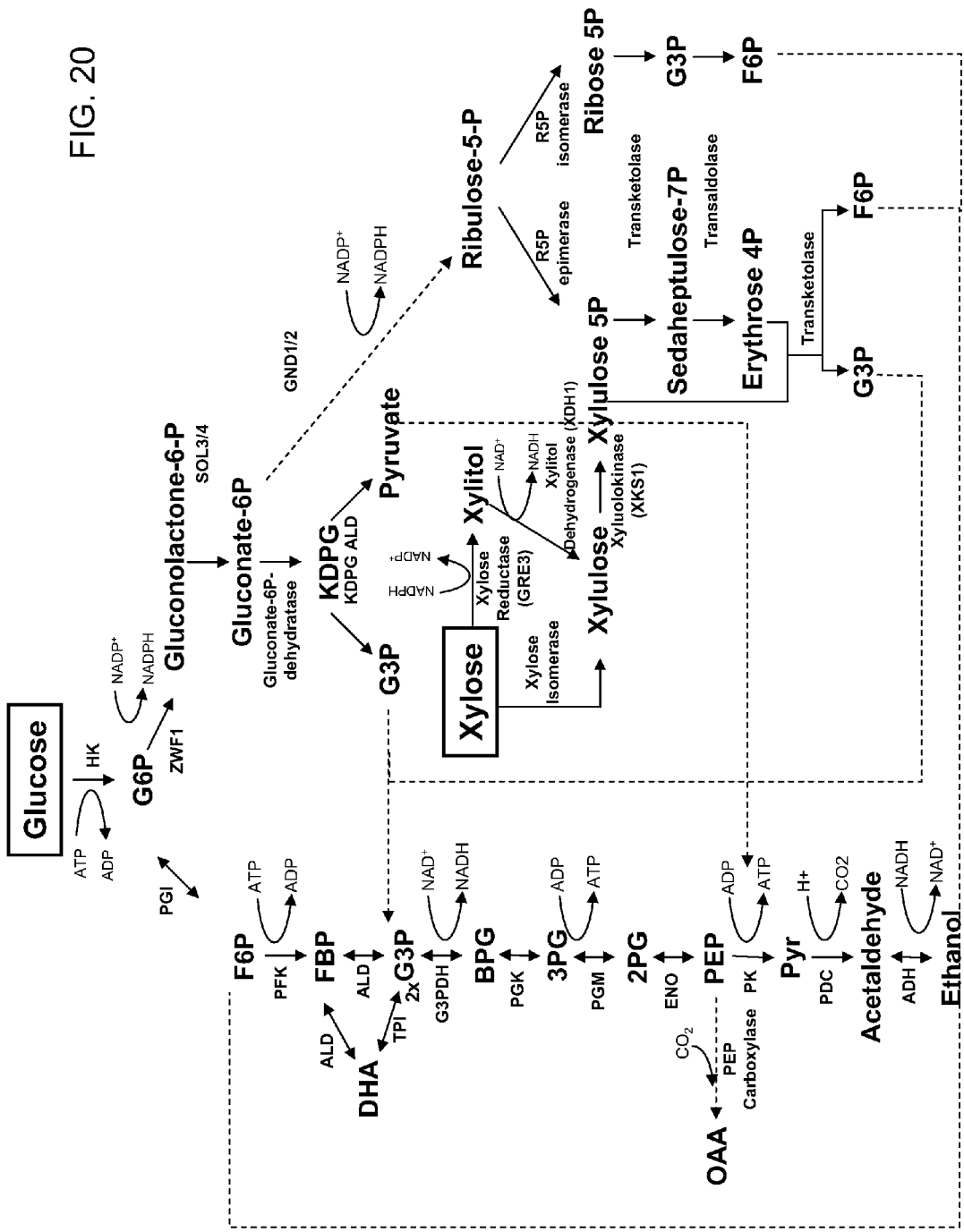

FIG. 20 depicts an engineered metabolic pathway that can be used to produce ethanol using xylose as a carbon source by introducing the activity into a microorganism. The engineered microorganism can convert xylose to xylulose by the activities of xylose reductase and xylitol dehydrogenase. Xylose also can be metabolized by the combined activities of xylose reductase, and xylitol dehydrogenase, as depicted in FIG. 20. Xylulose then can be fermented to ethanol by entering the EM pathway. Engineered microorganisms also can use the increased efficiency of ethanol production associated with inactivation of the EM pathway and introduction of activities of the ED pathway, shown in FIG. 2 and discussed below. The ability to utilize xylose efficiently (e.g., concurrently with six-carbon sugars or prior to the depletion of six-carbon sugars) can be provided by the introduction of the novel activities, xylose isomerase, or xylose reductase and xylitol dehydrogenase.

Figure 21:
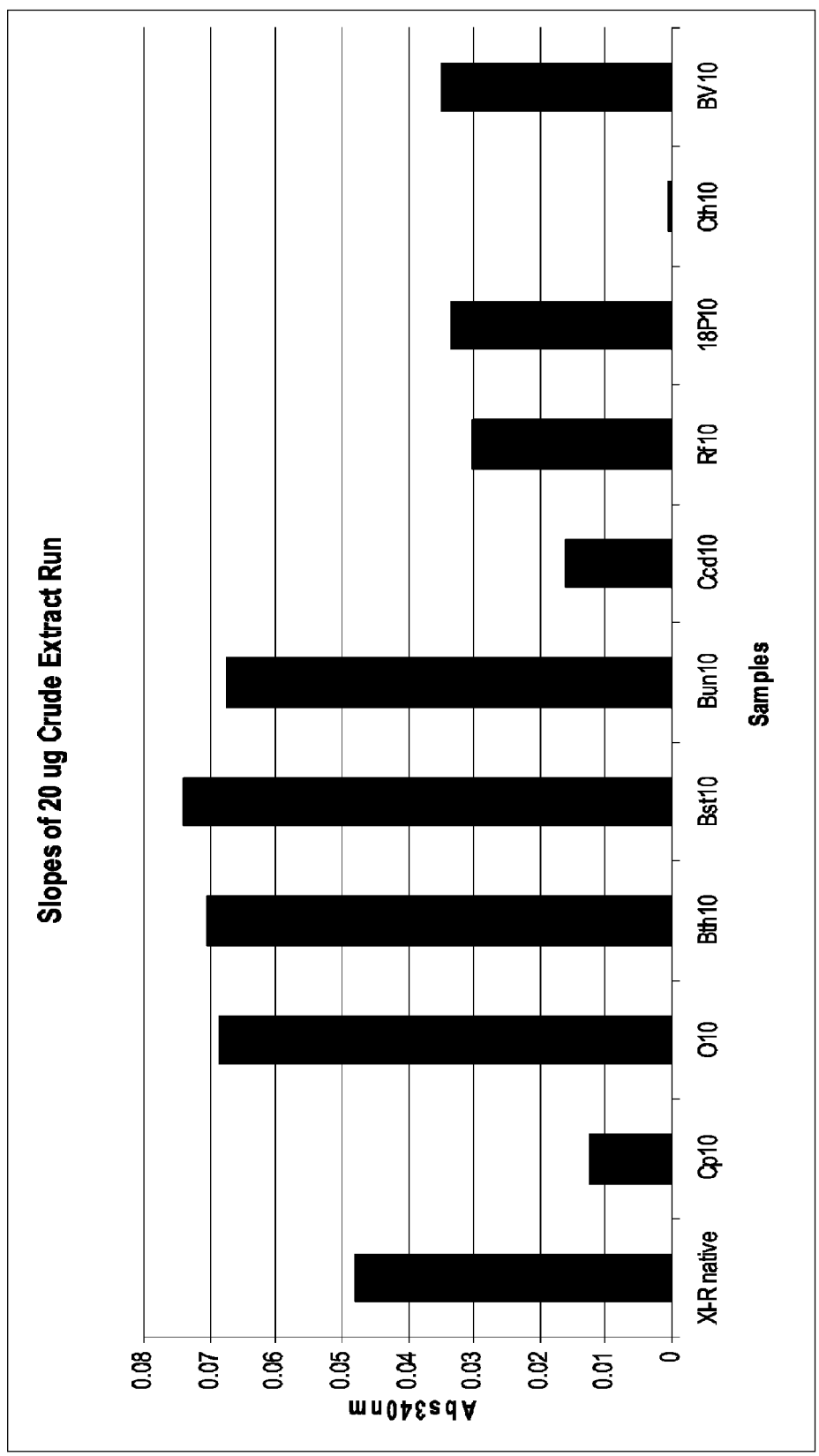

FIG. 21 graphically illustrates the results of xylose isomerase chimera generated with various 5' edge sequences. Experimental methods and results are described in Example 28.

Figure 22:
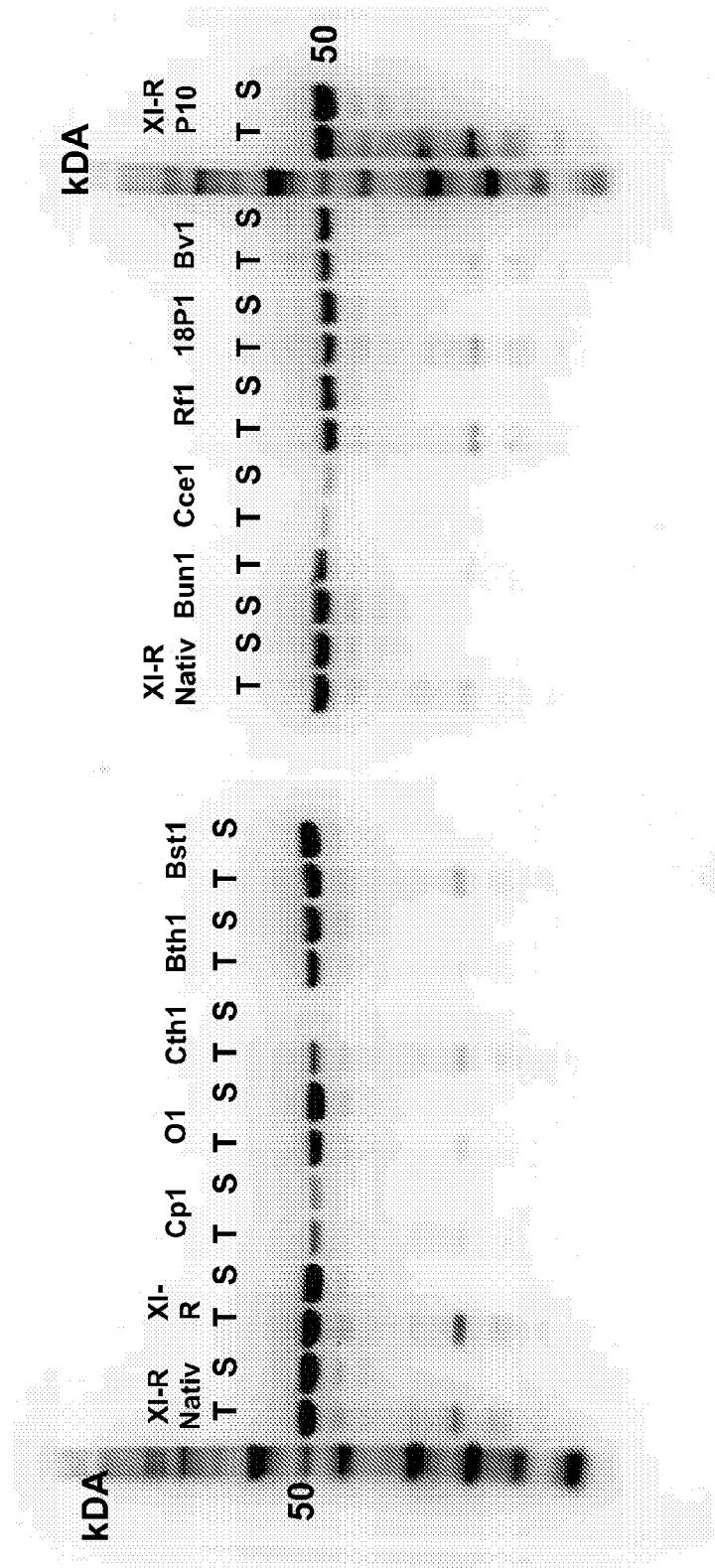

FIG. 22 shows the results of western blots performed on xylose isomerase chimera generated with various 5' edge sequences. Experimental methods and results are described in Example 28.

Figure 23:
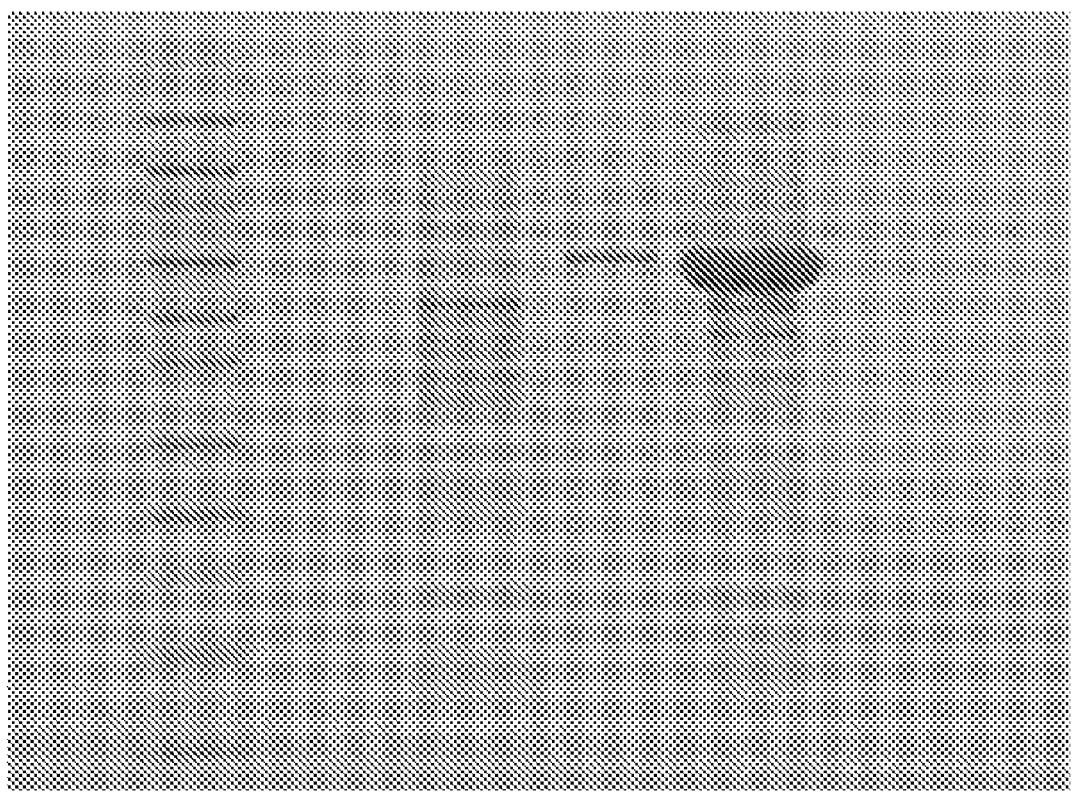

FIG. 23 shows a western blot of *E. coli* crude extract illustrated the presence of the EDD protein at the expected size. Lane 1 is a standard size ladder (Novex Sharp standard), Lane 2 is 1 µg BF1055 cell lysate, Lane 3 is 10 µg BF1055 cell lysate, Lane 4 is 1.5 µg BF1706 cell lysate, Lane 5 is 15 µg BF1706 cell lysate. Experimental methods and results are described in Example 34.

Figure 24:
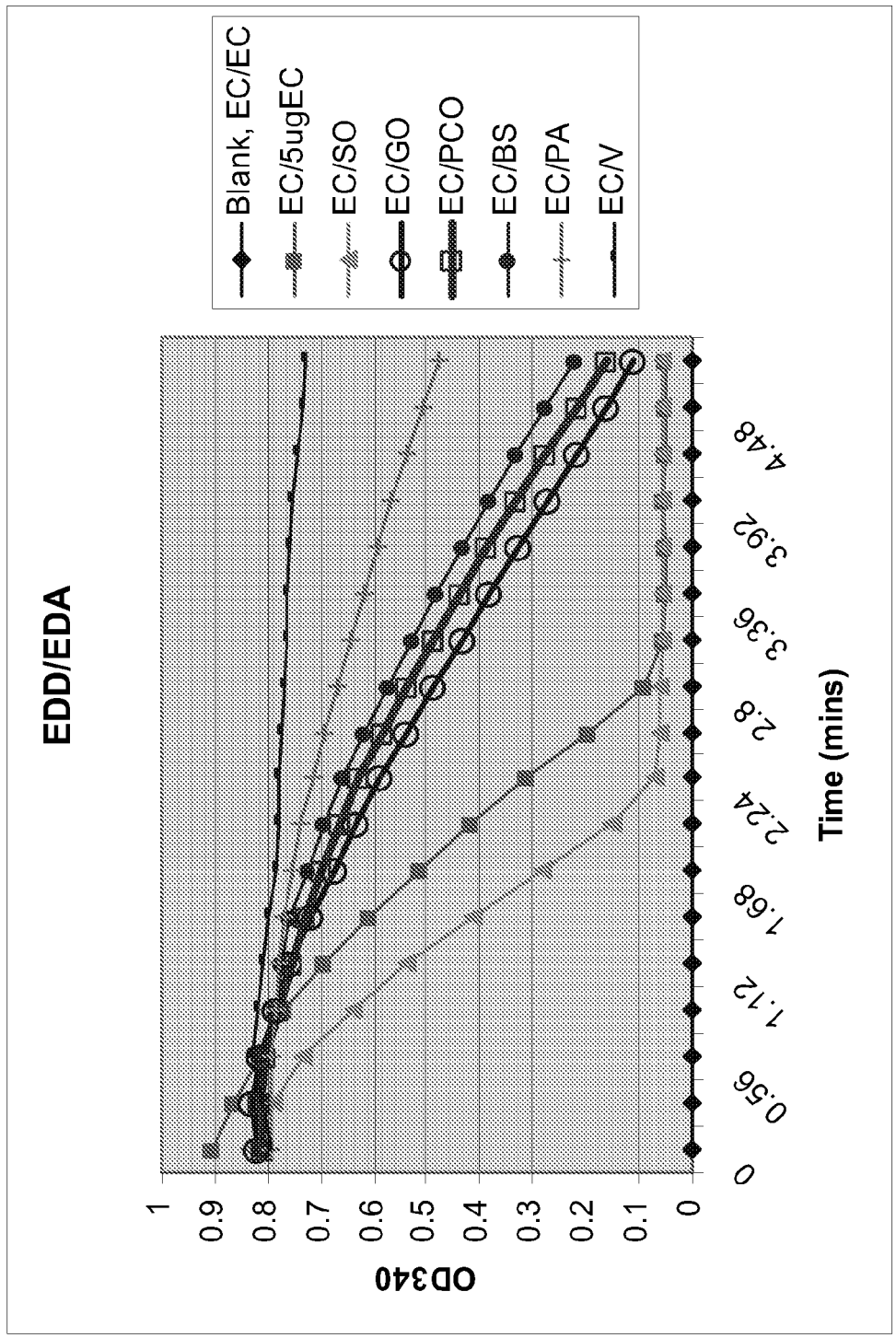

FIG. 24 graphically illustrates the results of activity evaluations of EDA genes expressed in yeast. Experimental methods and results are described in Example 34.

Figure 25:
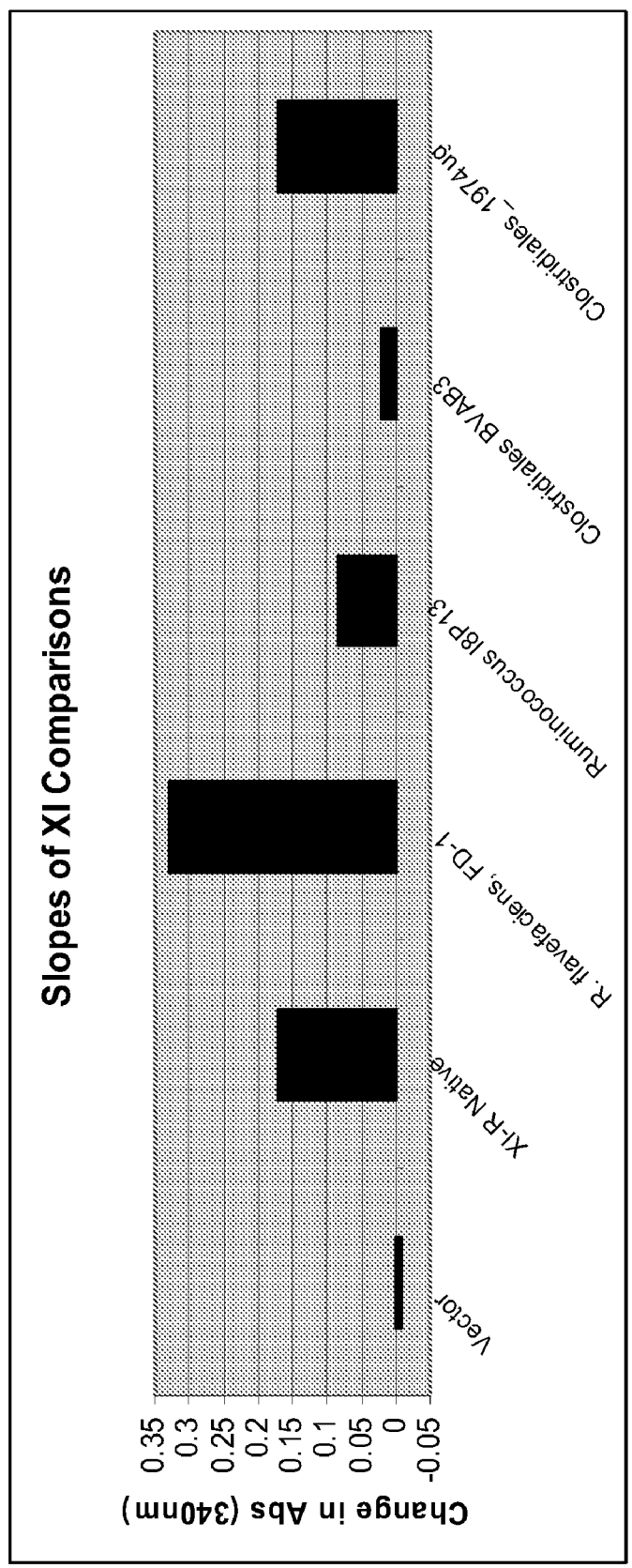

FIG. 25 graphically illustrates the specific activity of various xylose isomerase candidate activities. Experimental methods and results are described in Example 41.

DETAILED DESCRIPTION

Ethanol is a two carbon, straight chain, primary alcohol that can be produced from fermentation (e.g., cellular respiration processes) or as a by-product of petroleum refining. Ethanol has widespread use in medicine, consumables, and in industrial processes where it often is used as an essential solvent and a precursor, or feedstock, for the synthesis of other products (e.g., ethyl halides, ethyl esters, diethyl ether, acetic acid, ethyl amines and to a lesser extent butadiene, for example). The largest use of ethanol, worldwide, is as a motor fuel and fuel additive. Greater than 90% of the cars produced world wide can run efficiently on hydrous ethanol (e.g., 95% ethanol and 5% water). Ethanol also is commonly used for production of heat and light.

World production of ethanol exceeds 50 gigaliters (e.g., $1.3 \times 10^{10}$ US gallons), with 69% of the world supply coming from Brazil and the United States. The United States fuel ethanol industry is based largely on corn biomass. The use of corn biomass for ethanol production may not yield a positive net energy gain, and further has the potential of diverting land that could be used for food production into ethanol production. It is possible that cellulosic crops may displace corn as the main fuel crop for producing bio-ethanol. Non-limiting examples of cellulosic crops and waste materials include switchgrass and wood pulp waste from paper production and wood milling industries.

Biomass produced in the paper pulping and wood milling industries contains both 5 and six-carbon sugars. Use of this wasted biomass could allow production of significant amounts of bio-fuels and products, while reducing the use of land that could be used for food production. Predominant forms of sugars in the biomass produced in wood and paper pulping and wood milling industries are glucose and xylose.

Provided herein are methods for producing ethanol, ethanol derivatives and/or conjugates and other organic chemical intermediates (e.g., pyruvate, acetaldehyde, glyceraldehyde-3-phospate, and the like) using biological systems. Such production systems may have significantly less environmental impact and could be economically competitive with current manufacturing systems. Thus, provided herein are methods for manufacturing ethanol and other organic chemical intermediates by engineered microorganisms. In some embodiments microorganisms are engineered to contain at least one heterologous gene encoding an enzyme, where the enzyme is a member of a novel pathway engineered into the microorganism. In certain embodiments, an organism may be selected for elevated activity of a native enzyme.

Genetically engineered microorganisms described herein produce organic molecules for industrial uses. The organisms are designed to be "feedstock flexible" in that they can use five-carbon sugars (e.g., pentose sugars such as xylose, for example), six-carbon sugars (e.g., hexose sugars such as glucose or fructose, for example) or both as carbon sources. Further, the organisms described herein have been designed to be highly efficient in their use of hexose sugars to produce desired organic molecules. To that end, the microorganisms described herein are "pathway flexible" such that the microorganisms are able to direct hexose sugars primarily to either (i) the traditional glycolysis pathway (the Embden-Meyerhoff pathway) thereby generating ATP energy for cell growth and division at certain times, or (ii) a separate glycolytic pathway (the Entner-Doudoroff pathway) thereby producing significant levels of pyruvic acid, a key 3-carbon intermediate for producing many desired industrial organic molecules.

Pathway selection in the microorganism can be directed via one or more environmental switches such as a temperature change, oxygen level change, addition or subtraction of a component of the culture medium, or combinations thereof. The metabolic pathway flexibility of microorganisms described herein allow the microorganisms to efficiently use hexose sugars, which ultimately can lead to microorganisms capable of producing a greater amount of industrial chemical product per gram of feedstock as compared with conventional microorganisms (e.g., the organism from which the engineered organism was generated, for example). In some embodiments, the metabolic pathway flexibility of the engineered microorganisms described herein is generated by adding or increasing metabolic activities associated with the Entner-Doudoroff pathway. In certain embodiments the metabolic activities added are phosphogluconate dehydratase (e.g., EDD gene), 2-keto-3-deoxygluconate-6-phosphate aldolase (e.g., EDA gene) or both.

A number of industrially useful microorganisms (e.g., microorganisms used in fermentation processes, yeast for example), metabolize xylose inefficiently or are incapable of metabolizing xylose. Many organisms that can metabolize xylose do so only after all glucose and/or other six-carbon sugars have been depleted. The microorganisms described herein have been engineered to efficiently utilize five-carbon sugars (e.g., xylose, for example) as an alternative or additional source of carbon, concurrently with and/or prior to six-carbon sugar usage, by the incorporation of a heterologous nucleic acid (e.g., gene) encoding a xylose isomerase, in some embodiments, and in certain embodiments, by the incorporation of a heterologous nucleic acid encoding a xylose reductase and a xylitol dehydrogenase. Xylose isomerase converts the five-carbon sugar xylose to xylulose, in some embodiments. In certain embodiments, xylose reductase and xylitol dehydrogenase convert xylose to xylulose. Xylulose can ultimately be converted to pyruvic acid or to ethanol through metabolism via the Embden-Meyerhoff or Entner-Doudoroff pathways.

Many non-photosynthetic organisms are not capable of incorporating inorganic atmospheric carbon into organic carbon compounds, via carbon fixation pathways, to any appreciable degree, or at all. Often, microorganisms used in industrial fermentation process also are incapable of significant carbon fixation. The ability to incorporate atmospheric carbon dioxide, or carbon dioxide waste from respiration in fermentation processes, can increase the amount of industrial chemical product produced per gram of feedstock, in certain embodiments. Thus, the microorganisms described herein also can be modified to add or increase the ability to incorporate carbon from carbon dioxide into industrial chemical products, in some embodiments. In certain embodiments, the microorganisms described herein are engineered to express enzymes such as phosphoenolpyruvate carboxylase ("PEP" carboxylase) and/or ribulose 1,5-bis-phosphate carboxylase ("Rubisco"), thus allowing the use of carbon dioxide as an additional source of carbon.

A particularly useful industrial chemical product produced by fermentation is ethanol. Ethanol is an end product of cellular respiration and is produced from acetaldehyde by an alcohol dehydrogenase activity (e.g., by an enzyme like alcohol dehydrogenase 1 or ADH1, for example). However, ethanol can readily be converted back to acetaldehyde by the action of the enzyme alcohol dehydrogenase 2 (e.g., ADH2), thus lowering the yield of ethanol produced. In some embodiments, microorganisms described herein are modified to reduce or eliminate the activity of ADH2, to allow increased yields of ethanol. In certain embodiments, the engineered microorganisms described herein also are modified to have a higher tolerance to alcohol, thus enabling even higher yields of alcohol as a fermentation product without inhibition of cellular processes due to increased levels of alcohol in the growth medium.

Microorganisms

A microorganism selected often is suitable for genetic manipulation and often can be cultured at cell densities useful for industrial production of a target product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba).

Any suitable yeast may be selected as a host microorganism, engineered microorganism or source for a heterologous polynucleotide. Yeast include, but are not limited to, *Yarrowia* yeast (e.g., *Y. lipolytica* (formerly classified as *Candida lipolytica*)), *Candida* yeast (e.g., *C. revkaufi, C. pulcherrima,*

C. tropicalis, C. utilis), Rhodotorula yeast (e.g., R. glutinus, R. graminis), Rhodosporidium yeast (e.g., R. toruloides), Saccharomyces yeast (e.g., S. cerevisiae, S. bayanus, S. pastorianus, S. carlsbergensis), Cryptococcus yeast, Trichosporon yeast (e.g., T. pullans, T. cutaneum), Pichia yeast (e.g., P. pastoris) and Lipomyces yeast (e.g., L. starkeyii, L. lipoferus). In some embodiments, a yeast is a S. cerevisiae strain including, but not limited to, YGR240CBY4742 (ATCC accession number 4015893) and BY4742 (ATCC accession number 201389). In some embodiments, a yeast is a Y. lipolytica strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a C. tropicalis strain that includes, but is not limited to, ATCC20336, ATCC20913, SU-2 (ura3-/ura3-), ATCC20962, H5343 (beta oxidation blocked; U.S. Pat. No. 5,648,247) strains.

Any suitable fungus may be selected as a host microorganism, engineered microorganism or source for a heterologous polynucleotide. Non-limiting examples of fungi include, but are not limited to, Aspergillus fungi (e.g., A. parasiticus, A. nidulans), Thraustochytrium fungi, Schizochytrium fungi and Rhizopus fungi (e.g., R. arrhizus, R. oryzae, R. nigricans), Orpinomyces or Piromyces. In some embodiments, a fungus is an A. parasiticus strain that includes, but is not limited to, strain ATCC24690, and in certain embodiments, a fungus is an A. nidulans strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, Bacillus bacteria (e.g., B. subtilis, B. megaterium, B. stearothermophilus), Bacteroides bacteria (e.g., Bacteroides uniformis, Bacteroides thetaiotaomicron), Clostridium bacteria (e.g., C. phytofermentans, C. thermohydrosulfuricum, C. cellulyticum (H10)), Acinetobacter bacteria, Norcardia baceteria, Lactobacillus bacterial (e.g., Lactobacillus pentosus), Xanthobacter bacteria, Escherichia bacteria (e.g., E. coli (e.g., strains DH10B, Stb12, DH5-alpha, DB3, DB3.1), DB4, DB5, JDP682 and ccdA-over (e.g., U.S. application Ser. No. 09/518,188))), Streptomyces bacteria (e.g., Streptomyces rubiginosus, Streptomyces murinus), Erwinia bacteria, Klebsiella bacteria, Serratia bacteria (e.g., S. marcessans), Pseudomonas bacteria (e.g., P. aeruginosa), Salmonella bacteria (e.g., S. typhimurium, S. typhi), Thermus bacteria (e.g., Thermus thermophilus), and Thermotoga bacteria (e.g., Thermotoga maritiima, Thermotoga neopolitana) and Ruminococcus (e.g., Ruminococcus environmental samples, Ruminococcus albus, Ruminococcus bromii, Ruminococcus callidus, Ruminococcus flavefaciens, Ruminococcus gauvreauii, Ruminococcus gnavus, Ruminococcus lactaris, Ruminococcus obeum, Ruminococcus sp., Ruminococcus sp. 14531, Ruminococcus sp. 15975, Ruminococcus sp. 16442, Ruminococcus sp. 18P13, Ruminococcus sp. 25F6, Ruminococcus sp. 25F7, Ruminococcus sp. 25F8, Ruminococcus sp. 4_1_47FAA, Ruminococcus sp. 5, Ruminococcus sp. 5_1_39BFAA, Ruminococcus sp. 7L75, Ruminococcus sp. 8_1_37FAA, Ruminococcus sp. 9SE51, Ruminococcus sp. C36, Ruminococcus sp. CB10, Ruminococcus sp. CB3, Ruminococcus sp. CCUG 37327 A, Ruminococcus sp. CE2, Ruminococcus sp. CJ60, Ruminococcus sp. CJ63, Ruminococcus sp. CO1, Ruminococcus sp. CO12, Ruminococcus sp. CO22, Ruminococcus sp. CO27, Ruminococcus sp. CO28, Ruminococcus sp. CO34, Ruminococcus sp. CO41, Ruminococcus sp. CO47, Ruminococcus sp. CO7, Ruminococcus sp. CS1, Ruminococcus sp. CS6, Ruminococcus sp. DJF_VR52, Ruminococcus sp. DJF_VR66, Ruminococcus sp. DJF_VR67, Ruminococcus sp. DJF_VR70k1, Ruminococcus sp. DJF_VR87, Ruminococcus sp. Eg2, Ruminococcus sp. Egf, Ruminococcus sp. END-1, Ruminococcus sp. FD1, Ruminococcus sp. GM2/1, Ruminococcus sp. ID1, Ruminococcus sp. ID8, Ruminococcus sp. K-1, Ruminococcus sp. KKA Seq234, Ruminococcus sp. M-1, Ruminococcus sp. M10, Ruminococcus sp. M22, Ruminococcus sp. M23, Ruminococcus sp. M6, Ruminococcus sp. M73, Ruminococcus sp. M76, Ruminococcus sp. MLG080-3, Ruminococcus sp. NML 00-0124, Ruminococcus sp. Pei041, Ruminococcus sp. SC101, Ruminococcus sp. SC103, Ruminococcus sp. Siijpesteijn 1948, Ruminococcus sp. WAL 17306, Ruminococcus sp. YE281, Ruminococcus sp. YE58, Ruminococcus sp. YE71, Ruminococcus sp. ZS2-15, Ruminococcus torques). Bacteria also include, but are not limited to, photosynthetic bacteria (e.g., green non-sulfur bacteria (e.g., Choroflexus bacteria (e.g., C. aurantiacus), Chloronema bacteria (e.g., C. gigateum)), green sulfur bacteria (e.g., Chlorobium bacteria (e.g., C. limicola), Pelodictyon bacteria (e.g., P. lutecium), purple sulfur bacteria (e.g., Chromatium bacteria (e.g., C. okenii)), and purple non-sulfur bacteria (e.g., Rhodospirillum bacteria (e.g., R. rubrum), Rhodobacter bacteria (e.g., R. sphaeroides, R. capsulatus), and Rhodomicrobium bacteria (e.g., R. vanellii)).

Cells from non-microbial organisms can be utilized as a host microorganism, engineered microorganism or source for a heterologous polynucleotide. Examples of such cells, include, but are not limited to, insect cells (e.g., Drosophila (e.g., D. melanogaster), Spodoptera (e.g., S. frugiperda Sf9 or Sf21 cells) and Trichoplusa (e.g., High-Five cells); nematode cells (e.g., C. elegans cells); avian cells; amphibian cells (e.g., Xenopus laevis cells); reptilian cells; and mammalian cells (e.g., NIH3T3, 293, CHO, COS, VERO, C127, BHK, Per-C6, Bowes melanoma and HeLa cells).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Six-Carbon Sugar Metabolism and Activities

Six-carbon or hexose sugars can be metabolized using one of two pathways in many organisms. One pathway, the Embden-Meyerhoff pathway (EM pathway), operates primarily under aerobic (e.g., oxygen rich) conditions. The other pathway, the Entner-Doudoroff pathway (ED pathway), operates primarily under anaerobic (e.g., oxygen poor) conditions, producing pyruvate that can be converted to lactic acid. Lactic acid can be further metabolized upon a return to appropriate conditions. The EM pathway produces two ATP for each six-carbon sugar metabolized, as compared to one ATP produced for each six-carbon sugar metabolized in the ED pathway. Thus the ED pathway yields ethanol more efficiently than the EM pathway with respect to a given amount of input carbon, as seen by the lower net energy yield. However, yeast preferentially use the EM pathway for metabolism of six-carbon sugars, thereby preferentially using the pathway that yields more energy and less desired product.

The following steps and enzymatic activities metabolize six-carbon sugars via the EM pathway. Six-carbon sugars (glucose, sucrose, fructose, hexose and the like) are converted to glucose-6-phosphate by hexokinase or glucokinase (e.g., HXK or GLK, respectively). Glucose-6-phosphate can be converted to fructose-6-phosphate by phosphoglucoisomerase (e.g., PGI). Fructose-6-phosphate can be converted to fructose-1,6-bisphosphate by phosphofructokinase (e.g., PFK). Fructose-1,6-bisphosphate (F1,6BP) represents a key intermediate in the metabolism of six-carbon sugars, as the next enzymatic reaction converts the six-carbon sugar into two 3 carbon sugars. The reaction is catalyzed by fructose bisphosphate aldolase and yields a mixture of dihydroxyacetone phosphate (DHAP) and glyceraldehyde-3-phosphate (G-3-P). The mixture of the two 3 carbon sugars is preferentially converted to glyceraldehyde-3-phosphate by the action of triosephosphate isomerase. G-3-P is converted is converted to 1,3-diphosphoglycerate (1,3-DPG) by glyceraldehyde-3-phosphate dehydrogenase (GLD). 1,3-DPG is converted to 3-phosphoglycerate (3-P-G by phosphoglycerate kinase (PGK). 3-P-G is converted to 2-phosphoglycerate (2-P-G) by phophoglycero mutase (GPM). 2-P-G is converted to phosphoenolpyruvate (PEP) by enolase (ENO). PEP is converted to pyruvate (PYR) by pyruvate kinase (PYK). PYR is converted to acetaldehyde by pyruvate dicarboxylase (PDC). Acetaldehyde is converted to ethanol by alcohol dehydrogenase 1 (ADH1).

Many enzymes in the EM pathway are reversible. The enzymes in the EM pathway that are not reversible, and provide a useful activity with which to control six-carbon sugar metabolism, via the EM pathway, include, but are not limited to phosphofructokinase and alcohol dehydrogenase. In some embodiments, reducing or eliminating the activity of phosphofructokinase may inactivate the EM pathway. Engineering microorganisms with modified activities in PFK and/or ADH may yield increased product output as compared to organisms with the wild type activities, in certain embodiments. In some embodiments, modifying a reverse activity (e.g., the enzyme responsible for catalyzing the reverse activity of ADH, for example) may also yield an increase in product yield by reducing or eliminating the back conversion of products by the backwards reaction. The activity which catalyzes the conversion of ethanol to acetaldehyde is alcohol dehydrogenase 2 (ADH2). Reducing or eliminating the activity of ADH2 can increase the yield of ethanol per unit of carbon input due to the inactivation of the conversion of ethanol to acetaldehyde, in certain embodiments. In addition to enzyme activities that are not reversible, certain reversible activities also can be used to control six-carbon sugar metabolism via the EM pathway, in some embodiments. A non-limiting example of a reversible enzymatic activity that can be utilized to control six-carbon sugar metabolism includes phosphoglucose isomerase (PGI).

A microorganism may be engineered to include or regulate one or more activities in the Embden-Meyerhoff pathway, for example. In some embodiments, one or more of these activities may be altered such that the activity or activities can be increased or decreased according to a change in environmental conditions. In certain embodiments, one or more of the activities (e.g., PGI, PFK or ADH2) can be altered to allow regulated control and an alternative pathway for more efficient carbon metabolism can be provided (e.g., one or more activities from the ED pathway, for example). An engineered organism with the EM pathway under regulatable control and a novel or enhanced ED pathway would be useful for producing significantly more ethanol or other end product from a given amount of input feedstock. The term "activity" as used herein refers to the functioning of a microorganism's natural or engineered biological pathways to yield various products including ethanol and its precursors. Ethanol (or other product) producing activity can be provided by any non-mammalian source in certain embodiments. Such sources include, without limitation, eukaryotes such as yeast and fungi and prokaryotes such as bacteria. In some embodiments, the activity of one or more (e.g., 2, 3, 4, 5 or more) pathway members in an EM pathway is reduced or removed to undetectable levels.

An engineered microorganism may, in some embodiments, preferentially metabolize six-carbon sugars via the ED pathway as opposed to the EM pathway under certain conditions. Such engineered microorganisms may metabolize about 60% or more of the available six-carbon sugars via the ED pathway (e.g., about 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing), and such fraction of the available six-carbon sugars are not metabolized by the EM pathway, under certain conditions. A microorganism may metabolize six-carbon sugars substantially via the ED pathway, and not the EM pathway, in certain embodiments (e.g., 99% or greater, or 100%, of the available six-carbon sugars are metabolized via the ED pathway). A six-carbon sugar is deemed as being metabolized via a particular pathway when the sugar is converted to end metabolites of the pathway, and not intermediate metabolites only, of the particular pathway. A microorganism may preferentially metabolize certain sugars under the ED pathway after a certain time after the microorganism is exposed to a certain set of conditions (e.g., there may be a time delay after a microorganism is exposed to a certain set of conditions before the microorganism preferentially metabolizes sugars by the ED pathway).

Certain novel activities involved in the metabolism of six-carbon sugars by the ED pathway can be engineered into a desired yeast strain to increase the efficiency of ethanol (or other products) production. Yeast do not have an activity that converts 6-phophogluconate to 2-keto-3-deoxy-6-p-gluconate or an activity that converts 2-keto-3-deoxy-6-p-gluconate to pyruvate. Addition of these activities to engineered yeast can allow the engineered microorganisms to increase fermentation efficiency by allowing yeast to ferment ethanol under anaerobic condition without having to use the EM pathway and expend additional energy. Therefore, by providing novel activities associated with converting 6-phophogluconate to 2-keto-3-deoxy-6-p-gluconate and 2-keto-3-deoxy-6-p-gluconate to pyruvate, the engineered microorganism can benefit by producing ethanol more efficiently, with respect to a given amount of input carbon, than by using the native EM pathway.

Bacteria often have enzymatic activities that confer the ability to anaerobically metabolize six-carbon sugars to ethanol. These activities are associated with the ED pathway and include, but are not limited to, phosphogluconate dehydratase (e.g., the EDD gene, for example), and 2-keto-3-deoxygluconate-6-phosphate aldolase (e.g., the EDA gene, for example). Phosphogluconate dehydratase converts 6-phogluconate to 2-keto-3-deoxy-6-p-gluconate. 2-keto-3-deoxygluconate-6-phosphate aldolase converts 2-keto-3-deoxy-6-p-gluconate to pyruvate. In some embodiments, these activities can be introduced into a host organism to generate an engineered microorganism which gains the ability to use the ED pathway to produce ethanol more efficiently than the non-engineered starting organism, by virtue of the lower net energy yield by the ED pathway. A microorganism may be engineered to include or regulate one or more activities in the Entner-Doudoroff pathway. In some embodiments, one or more of these activities may be altered such that the activity or activities can be increased or decreased according to a change in environmental conditions. Nucleic acid sequences encoding Embden-Meyerhoff pathway and Entner-Doudoroff pathway activities can be obtained from any suitable organism (e.g., plants, bacteria, and other microorganisms, for example) and any of these activities can be used herein with the proviso that the nucleic acid sequence is naturally active in the chosen microorganism when expressed, or can be altered or modified to be active.

Yeast also can have endogenous or heterologous enzymatic activities that enable the organism to anaerobically metabolize six carbon sugars. Saccharomyces cerevisiae used in fermentation often convert glucose-6-phospate (G-6-P) to fructose-6-phosphate (F-6-P) via phosphoglucose isomerase (EC 5.3.1.9), up to 95% of G-6-P is converted to F-6-P in this manner for example. Only a minor proportion of G-6-P is converted to 6-phophoglucono-lactone (6-PGL) by an alternative enzyme, glucose-6-phosphate dehydrogenase (EC 1.1.1.49). Yeast engineered to carry both Entner-Doudoroff (ED) and Embden-Meyerhoff (EM) pathways often covert sugars to ethanol using the EM pathway preferentially. Inactivation of one or more activities in the EM pathway can result in conversion of sugars to ethanol using the ED pathway preferentially, in some embodiments.

Phosphoglucose isomerase (EC 5.3.1.9) catalyzes the reversible interconversion of glucose-6-phosphate and fructose-6-phosphate. Phosphoglucose isomerase is encoded by the PGI1 gene in S. cerevisiae. The proposed mechanism for sugar isomerization involves several steps and is thought to occur via general acid/base catalysis. Since glucose 6-phosphate and fructose 6-phosphate exist predominantly in their cyclic forms, PGI is believed to catalyze first the opening of the hexose ring to yield the straight chain form of the substrates. Glucose 6-phosphate and fructose 6-phosphate then undergo isomerization via formation of a cis-enediol intermediate with the double bond located between C-1 and C-2. Phosphoglucose isomerase sometimes also is referred to as glucose-6-phosphate isomerase or phosphohexose isomerase.

PGI is involved in different pathways in different organisms. In some higher organisms PGI is involved in glycolysis, and in mammals PGI also is involved in gluconeogenesis. In plants PGI is involved in carbohydrate biosynthesis, and in some bacteria PGI provides a gateway for fructose into the Entner-Doudoroff pathway. PGI also is known as neuroleukin (a neurotrophic factor that mediates the differentiation of neurons), autocrine motility factor (a tumor-secreted cytokine that regulates cell motility), differentiation and maturation mediator and myofibril-bound serine proteinase inhibitor, and has different roles inside and outside the cell. In the cytoplasm, PGI catalyses the second step in glycolysis, while outside the cell it serves as a nerve growth factor and cytokine. PGI activity is involved in cell cycle progression and completion of the gluconeogenic events of sporulation in S. cerevisiae.

In certain embodiments, phosphoglucose isomerase activity is altered in an engineered microorganism. In some embodiments phosphoglucose isomerase activity is decreased or disrupted in an engineered microorganism. In certain embodiments, decreasing or disrupting phosphoglucose isomerase activity may be desirable to decrease or eliminate the isomerization of glucose-6-phosphate to fructose-6-phosphate, thereby increasing the proportion of glucose-6-phosphate converted to gluconolactone-6-phosphate by the activity encoded by ZWF1 (e.g., glucose-6-phosphate dehydrogenase). Increased levels of gluconolactone-6-phosphate can be further metabolized and thereby improve fermentation of sugar to ethanol via activities in the Entner-Doudoroff pathway, even in the presence of the enzymes comprising the Embden-Meyerhoff pathway. Decreased or disrupted phosphoglucose isomerase (EC 5.3.1.9) activity in yeast may be achieved by any suitable method, or as described herein. Non-limiting examples of methods suitable for decreasing or disrupting the activity of phosphoglucose isomerase include use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologus gene with lower specific activity, the like or combinations thereof. In some embodiments, a gene used to knockout one activity can also introduce or increase another activity. PGI1 genes may be native to S. cerevisiae, or may be obtained from a heterologous source.

Glucose-6-phosphate dehydrogenase (EC 1.1.1.49) catalyzes the first step of the pentose phosphate pathway, and is encoded by the S. cerevisiae gene, zwf1. The reaction for the first step in the PPP pathway is;

This reaction is irreversible and rate-limiting for efficient fermentation of sugar via the Entner-Doudoroff pathway. The enzyme regenerates NADPH from NADP+ and is important both for maintaining cytosolic levels of NADPH and protecting yeast against oxidative stress. Zwf1p expression in yeast is constitutive, and the activity is inhibited by NADPH such that processes that decrease the cytosolic levels of NADPH stimulate the oxidative branch of the pentose phosphate pathway. Amplification of glucose-6-phosphate dehydrogenase activity in yeast may be desirable to increase the proportion of glucose-6-phosphate converted to 6-phosphoglucono-lactone and thereby improve fermentation of sugar to ethanol via the Entner-Doudoroff pathway, even in the presence of the enzymes comprising the Embden-Meyerhoff pathway.

Glucose-6-phosphate dehydrogenase (EC 1.1.1.49) activity in yeast may be amplified by over-expression of the zwf1 gene by any suitable method. Non-limiting examples of methods suitable to amplify or over express zwf1 include amplifying the number of ZWF1 genes in yeast following transformation with a high-copy number plasmid (e.g., such as one containing a 2 uM origin of replication), integration of multiple copies of ZWF1 into the yeast genome, over-expression of the ZWF1 gene directed by a strong promoter, the like or combinations thereof. The ZWF1 gene may be native to S. cerevisiae, or it may be obtained from a heterologous source.

6-phosphogluconolactonase (EC 3.1.1.31) catalyzes the second step of the ED (e.g., pentose phosphate pathway), and is encoded by S. cerevisiae genes SOL3 and SOL4. The reaction for the second step of the pentose phosphate pathway is;

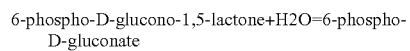

Amplification of 6-phosphogluconolactonase activity in yeast may be desirable to increase the proportion of 6-phospho-D-glucono-1,5-lactone converted to 6-phospho-D-gluconate and thereby improve fermentation of sugar to ethanol via the Entner-Doudoroff pathway, even in the presence of the enzymes comprising the Embden-Meyerhoff pathway. For example, over expression of SOL3 is known to increase the rate of carbon source utilization to result in faster growth on xylose than wild type.

The *Saccharomyces cerevisiae* SOL protein family includes Sol3p and Sol4p. Both localize predominantly in the cytosol, exhibit 6-phosphogluconolactonase activity and function in the pentose phosphate pathway. 6-phosphogluconolactonase (EC 3.1.1.31) activity in yeast may be amplified by over-expression of the SOL3 and/or SOL4 gene(s) by any suitable method. Non-limiting examples of methods to amplify or over express SOL3 and SOL4 include increasing the number of SOL3 and/or SOL4 genes in yeast by transformation with a high-copy number plasmid, integration of multiple copies of SOL3 and/or SOL4 gene(s) into the yeast genome, over-expression of the SOL3 and/or SOL4 gene(s) directed by a strong promoter, the like or combinations thereof. The SOL3 and/or SOL4 gene(s) may be native to *S. cerevisiae*, or may be obtained from a heterologous source. For example, Sol3p and Sol4p have similarity to each other, and to *Candida albicans* Sol1p, *Schizosaccharomyces pombe* Sol1p, human PGLS which is associated with 6-phosphogluconolactonase deficiency, and human H6PD which is associated with cortisone reductase deficiency. Sol3p and Sol4p are also similar to the 6-phosphogluconolactonases in bacteria (*Pseudomonas aeruginosa*) and eukaryotes (*Drosophila melanogaster, Arabidopsis thaliana*, and *Trypanosoma brucei*), to the glucose-6-phosphate dehydrogenase enzymes from bacteria (*Mycobacterium leprae*) and eukaryotes (*Plasmodium falciparum* and rabbit liver microsomes), and have regions of similarity to proteins of the Nag family, including human GNPI and *Escherichia coli* NagB.

Phosphogluconate dehydrogenase (EC:1.1.1.44) catalyzes the second oxidative reduction of NADP+ to NADPH in the cytosolic oxidative branch of the pentose phosphate pathway, and is encoded by the *S. cerevisiae* genes GND1 and GND2. GND1 encodes the major isoform of the enzyme accounting for up to 80% of phosphogluconate dehydrogenase activity, while GND2 encodes the minor isoform of the enzyme. Phosphogluconate dehydrogenase sometimes also is referred to as phosphogluconic acid dehydrogenase, 6-phosphogluconic dehydrogenase, 6-phosphogluconic carboxylase, 6-phosphogluconate dehydrogenase (decarboxylating), and 6-phospho-D-gluconate dehydrogenase. Phosphogluconate dehydrogenase belongs to the family of oxidoreductases, specifically those acting on the CH—OH group of donor with NAD$^+$ or NADP$^+$ as the acceptor. The reaction for the second oxidative reduction of NADP+ to NADPH in the cytosolic oxidative branch of the pentose phosphate pathway is;

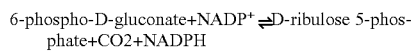

6-phospho-D-gluconate+NADP$^+$ ⇌ D-ribulose 5-phosphate+CO2+NADPH

Decreasing the level of 6-phosphogluconolactonase activity in yeast may be desirable to decrease the proportion of 6-phospho-D-gluconate converted to D-ribulose 5-phosphate thereby increasing the levels of the intermediate gluconate-6-phosphate available for conversion to 6-dehydro-3-deoxygluconate-6-phosphate, in some embodiments involving engineered microorganisms including increased EDA and EDD activities, thereby improving fermentation of sugar to ethanol via the Entner-Doudoroff pathway, even in the presence of the enzymes comprising the Embden-Meyerhoff pathway.

Decreasing or disrupting 6-phosphogluconolactonase activity in yeast may be achieved by any suitable method, or as described herein. Non-limiting examples of methods suitable for decreasing the activity of 6-phosphogluconate dehydrogenase include use of a regulated promoter, use of a weak constitutive promoter, disruption of one of the two copies of the gene in a diploid yeast (e.g., partial gene knockout), disrupting both copies of the gene in a diploid yeast (e.g., complete gene knockout) expression of an anti-sense nucleic acid, expression of an siRNA, over expression of a negative regulator of the endogenous promoter, alteration of the activity of an endogenous or heterologous gene, use of a heterologus gene with lower specific activity, the like or combinations thereof. In some embodiments, a gene used to knockout one activity can also introduce or increase another activity. GND1 and/or GND2 gene(s) may be native to *S. cerevisiae*, or may be obtained from a heterologous source. For example, *S. cerevisiae* GND1 and GND2 have similarity to each other, and to the phosphogluconate dehydrogenase nucleotide sequences of *Candida parapsilosis, Cryptococcus neoformans* and humans.

Five-Carbon Sugar Metabolism and Activities

As noted above, five-carbon sugars are the second most predominant form of sugars in lignocelluosic waste biomass produced in wood pulp and wood milling industries. Furthermore, xylose is the second most abundant carbohydrate in nature. However, the conversion of biomass to energy (e.g., ethanol, for example) has not proven economically attractive because many organisms cannot metabolize hemicellulose. Biomass and waste biomass contain both cellulose and hemicellulose. Many industrially applicable organisms can metabolize five-carbon sugars (e.g., xylose, pentose and the like), but may do so at low efficiency, or may not begin metabolizing five-carbon sugars until all six-carbon sugars have been depleted from the growth medium. Many yeast and fungus grow slowly on xylose and other five-carbon sugars. Some yeast, such as *S. cerevisiae* do not naturally use xylose, or do so only if there are no other carbon sources. An engineered microorganism (e.g., yeast, for example) that could grow rapidly on xylose and provide ethanol and/or other products as a result of fermentation of xylose can be useful due to the ability to use a feedstock source that is currently underutilized while also reducing the need for petrochemicals.

The pentose phosphate pathway (PPP), which is a biochemical route for xylose metabolism, is found in virtually all cellular organisms where it provides D-ribose for nucleic acid biosynthesis, D-erythrose 4-phosphate for the synthesis of aromatic amino acids and NADPH for anabolic reactions. The PPP is thought of as having two phases. The oxidative phase converts the hexose, D-glucose 6P, into the pentose, D-ribulose 5P, plus CO2 and NADPH. The non-oxidative phase converts D-ribulose 5P into D-ribose 5P, D-xylulose 5P, D-sedoheptulose 7P, D-erythrose 4P, D-fructose 6P and D-glyceraldehyde 3P. D-Xylose and L-arabinose enter the PPP through D-xylulose.

Certain organisms (e.g., yeast, filamentous fungus and other eukaryotes, for example) require two or more activities to convert xylose to a usable from that can be metabolized in the pentose phosphate pathway. The activities are a reduction and an oxidation carried out by xylose reductase (XR; XYL1) and xylitol dehydrogenase (XD; XYL2), respectively. Xylose reductase converts D-xylose to xylitol. Xylitol dehydrogenase converts xylitol to D-xylulose. The use of these activities sometimes can inhibit cellular function due to cofactor and metabolite imbalances.

In some embodiments, the xylose reductase activity and/or xylitol dehydrogenase activity selected for inclusion in an engineered organism can be chosen from an organism whose XR and/or XD activities utilize NADPH or NADH (e.g., co-factor flexible activities), thereby reducing or eliminating inhibition of cellular function due to cofactor and metabolite imbalances. Non-limiting examples of yeast whose xylose reductase enzyme and/or xylitol dehydrogenase enzyme can use NADP+/NADPH and/or NAD+/NADH include *C. shehatae, C. parapsilosis, P. segobiensis, P. stipitis,* and *Pachysolen tannophilus*. In certain embodiments, xylose reductase and/or xylitol dehydrogenase activities can be engineered to alter cofactor preference and/or specificity. Some organisms (e.g., certain bacteria, for example) require only one activity, xylose isomerase (xylA). Xylose isomerase converts xylose directly to xylulose.

Xylulose is converted to xylulose-5-phophate by the activity of a xylulokinase enzyme (EC 2.7.1.17). Xylulose kinase (e.g., XYK3, XYL3) catalyzes the chemical reaction,

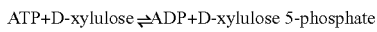
ATP+D-xylulose ⇌ ADP+D-xylulose 5-phosphate

Xylulokinase sometimes also is referred to as ATP:D-xylulose 5-phosphotransferase, xylulokinase (phosphorylating), and D-xylulokinase. Increasing the activity of xylose isomerase or xylose reductase and xylitol dehydrogenase may cause an increase of xylulose in an engineered microorganism. Therefore, increasing xylulokinase activity levels in embodiments involving increased levels of XI or XR and XD may be desirable to allow increased flux through the respective metabolic pathways. Xylulokinase activity levels can be increased using any suitable method. Non-limiting examples of methods suitable for increasing xylulokinase activity include increasing the number of xylulokinase genes in yeast by transformation with a high-copy number plasmid, integration of multiple copies of xylulokinase genes into the yeast genome, over-expression of the xylulokinase gene directed by a strong promoter, the like or combinations thereof. The xylulokinase gene may be native to *S. cerevisiae*, or may be obtained from a heterologous source.

Phosphorylation of xylulose by xylulokinase allows the five-carbon sugar to be further converted by transketolase (e.g., TKL1/TKL2) to enter the EM pathway for further metabolism at either fructose-6-phosphate or glyceraldehyde-3-phosphate. In some embodiments, where the EM pathway is inactivated, five-carbon sugars enter the EM pathway and are further converted for use by the ED pathway. Therefore, engineering a microorganism with xylose isomerase activity or co-factor flexible xylose reductase activity and xylitol dehydrogenase activity, along with increased xylulokinase activity may allow rapid growth on xylose when compared to the non-engineered microorganism, while avoiding cofactor and metabolite imbalances, in some embodiments. In certain embodiments, engineering a microorganism with co-factor flexible xylose reductase activity and xylitol dehydrogenase activity, may allow rapid growth on xylose when compared to the non-engineered microorganism, while avoiding cofactor and metabolite imbalances. The term "co-factor flexible" as used herein with respect to xylose reductase activity and xylose isomerase activity refers to the ability to use NADP+/NADPH and/or NAD+/NADH as a cofactor for electron transport.

A microorganism may be engineered to include or regulate one or more activities in a five-carbon sugar metabolism pathway (e.g., pentose phosphate pathway, for example). In some embodiments, an engineered microorganism can comprise a xylose isomerase activity. In some embodiments, the xylose isomerase activity may be altered such that the activity can be increased or decreased according to a change in environmental conditions. Nucleic acid sequences encoding xylose isomerase activities can be obtained from any suitable bacteria (e.g., *Piromyces, Orpinomyces, Bacteroides thetaiotaomicron, Clostridium phytofermentans, Thermus thermophilus* and *Ruminococcus* (e.g., *R. flavefaciens, R. flavefaciens* strain FD1, *R. Flavefaciens* strain 18P13) are non-limiting examples) and any of these activities can be used herein with the proviso that the nucleic acid sequence is naturally active in the chosen microorganism when expressed, or can be altered or modified to be active. In some embodiments, an engineered microorganism can comprise a xylose reductase activity and a xylitol dehydrogenase activity. In certain embodiments, an engineered microorganism can comprise a xylulokinase activity. In some embodiments, the xylose reductase activity, xylitol dehydrogenase activity and/or xylulokinase activity may be altered such that the activity can be increased or decreased according to a change in environmental conditions. Nucleic acid sequences encoding xylose reductase activity, xylitol dehydrogenase activity and/or xylulokinase activities can be obtained from any suitable organism, and any of these activities can be used herein with the proviso that the nucleic acid sequence is naturally active in the chosen microorganism when expressed, or can be altered or modified to be active.

Activities Linking 5-Carbon and 6-Carbon Sugar Metabolic Pathways

In some embodiments, an engineered microorganism includes one or more altered activities that function to link 5-carbon sugar and 6-carbon sugar metabolic pathways (e.g., provide intermediates that enter and/or are metabolized by the pentose phosphate pathway, the glycolytic pathway, or the pentose phosphate and glycolytic pathways). In certain embodiments, the altered linking activity is added, increased or amplified, with respect to a host or starting organism. In some embodiments, the altered activity is decreased or disrupted, with respect to a host or starting organism. Non-limiting examples of activities that function to reversibly link 5-carbon sugar and 6-carbon sugar metabolic pathways include transaldolase, transketolase, the like, or combinations thereof. Transketolase and transaldolase catalyze transfer of 2 carbon and 3 carbon molecular fragments respectively, in each case from a ketose donor to an aldose acceptor.

Transaldolase (EC:2.2.1.2) catalyses the reversible transfer of a three-carbon ketol unit from sedoheptulose 7-phosphate to glyceraldehyde 3-phosphate to form erythrose 4-phosphate and fructose 6-phosphate. The cofactor-less enzyme acts through a Schiff base intermediate (e.g., bound dihydroxyacetone). Transaldolase is encoded by the gene TAL1 in *S. cerevisiae*, and is an enzyme in the non-oxidative pentose phosphate pathway that provides a link between the pentose phosphate and the glycolytic pathways.

Transaldolase activity is thought to be found in substantially all organisms, and include 5 subfamilies. Three transaldolase subfamilies have demonstrated transaldolase activity, one subfamily comprises an activity of undetermined function and the remaining subfamily includes a fructose 6-phosphate aldolase activity. Transaldolase deficiency is well tolerated in many microorganisms, and without being limited by any theory, is thought to be involved in oxidative stress responses and apoptosis. Transaldolase sometimes also is referred to as dihydroxyacetone transferase, glycerone transferase, or dihydroxyacetonetransferase, sedoheptulose-7-phosphate:D-glyceraldehyde-3-phosphate glyceronetransferase, and catalyzes the reaction:

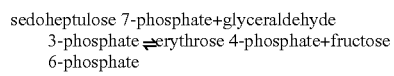
sedoheptulose 7-phosphate+glyceraldehyde
3-phosphate ⇌ erythrose 4-phosphate+fructose
6-phosphate In some embodiments, increasing or amplifying transaldolase activity in yeast may be desirable to increase the proportion of sedoheptulose 7-phosphate and glyceraldehyde 3-phosphate converted to fructose-6-phosphate and erythrose-4-phosphate, thereby increasing levels of fructose-6-phosphate. Increased levels of fructose-6-phosphate can be further metabolized and thereby improve fermentation of sugar to ethanol via activities in the Entner-Doudoroff pathway, even in the presence of the enzymes comprising the Embden-Meyerhoff pathway. Transaldolase (EC:2.2.1.2) activity in yeast may be amplified by over-expression of the TAL1 gene by any suitable method. Non-limiting examples of methods to amplify or over express TAL1 include increasing the number of TAL1 genes in yeast by transformation with a high-copy number plasmid, integration of multiple copies of TAL1 genes into the yeast genome, over-expression of TAL1 genes directed by a strong promoter, the like or combinations thereof. The TAL1 genes may be native to S. cerevisiae, or may be obtained from a heterologous source.

In certain embodiments, decreasing or disrupting transaldolase activity may be desirable to decrease the proportion of sedoheptulose-7-phosphate and glyceraldehyde-3-phosphate converted to fructose-6-phosphate and erythrose-4-phosphate, thereby increasing levels of glyceraldehyde-3-phosphate in the engineered microorganism. Increased levels of glyceraldehyde-3-phosphate can be further metabolized and thereby improve fermentation of sugar to ethanol via activities in the Entner-Doudoroff pathway, even in the presence of the enzymes comprising the Embden-Meyerhoff pathway. Decreased or disrupted transaldolase (EC:2.2.1.2) activity in yeast may be achieved by any suitable method, or as described herein. Non-limiting examples of methods suitable for decreasing or disrupting the activity of transaldolase include use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologus gene with lower specific activity, the like or combinations thereof. In some embodiments, a gene used to knockout one activity can also introduce or increase another activity.

Transketolase (EC:2.2.1.1) catalyzes the reversible transfer of a two-carbon ketol unit from a ketose (e.g., xylulose 5-phosphate, fructose 6-phosphate, sedoheptulose 7-phosphate) to an aldose receptor (e.g., ribose 5-phosphate, erythrose 4-phosphate, glyceraldehyde 3-phosphate). Transketolase is encoded by the TKL1 and TKL2 genes in S. cerevisiae. TKL1 encodes the major isoform of the enzyme and TKL2 encodes a minor isoform. Transketolase sometimes also is referred to as glycoaldehyde transferase, glycolaldehydetransferase, sedoheptulose-7-phosphate:D-glyceraldehyde-3-phosphate glycolaldehydetransferase, or fructose 6-phosphate:D-glyceraldehyde-3-phosphate glycolaldehydetransferase.

Transketolase double null mutants (e.g., tkl1/tkl2) are viable but are auxotrophic for aromatic amino acids, indicating the genes are involved in the synthesis of aromatic amino acids. Transketolase activity also is thought to be involved in the efficient use of fermentable carbon sources, and has been shown to catalyze a one-substrate reaction utilizing only xylulose 5-phosphate to produce glyceraldehyde 3-phosphate and erythrulose. Transketolase activity requires thiamine pyrophosphate as a cofactor, and has been purified as a homodimer of approximately 70 kilodalton subunits, from S. cerevisiae. Sequences from a variety of eukaryotic and prokaryotic sources indicate transketolase enzymes have been evolutionarily conserved. Tkl1p has similarity to S. cerevisiae Tkl2p, Escherichia coli transketolase, Rhodobacter sphaeroides transketolase, Streptococcus pneumoniae recP, Hansenula polymorpha dihydroxyacetone synthase, Kluyveromyces lactis TKL1, Pichia stipitis TKT, rabbit liver transketolase, rat TKT, mouse TKT, and human TKT. Tkl1p is also related to E. coli pyruvate dehydrogenase E1 subunit, which is another vitamin B1-dependent enzyme.

In some embodiments, increasing or amplifying transketolase activity in yeast may be desirable to increase the proportion of xylulose 5-phosphate converted to glyceraldehyde 3-phosphate, thereby increasing levels of glyceraldehyde 3-phosphate available for entry into a 6-carbon sugar metabolic pathway directly and/or conversion to fructose-6-phosphate. Increased levels of fructose-6-phosphate and/or glyceraldehyde 3-phosphate can be further metabolized and thereby improve fermentation of sugar to ethanol via activities in the Entner-Doudoroff pathway, even in the presence of the enzymes comprising the Embden-Meyerhoff pathway. Transketolase (EC 2.2.1.1) activity in yeast may be increased or amplified by over-expression of the TKL1 and/or TKL2 gene(s) by any suitable method. Non-limiting examples of methods to amplify or over express TKL1 and TKL2 include increasing the number of TKL1 and/or TKL2 gene(s) in yeast by transformation with a high-copy number plasmid, integration of multiple copies of TKL1 and/or TKL2 gene(s) into the yeast genome, over-expression of TKL1 and/or TKL2 gene(s) directed by a strong promoter, the like or combinations thereof.

In certain embodiments, decreasing or disrupting transketolase activity may be desirable to decrease the proportion of xylulose 5-phosphate converted to glyceraldehyde 3-phosphate, thereby increasing levels of xylulose 5-phosphate in the engineered microorganism. Increased levels of xylulose 5-phosphate can be further metabolized and thereby improve fermentation of sugar to ethanol via activities in the Entner-Doudoroff pathway, even in the presence of the enzymes comprising the Embden-Meyerhoff pathway. Decreased or disrupted transketolase (EC 2.2.1.1) activity in yeast may be achieved by any suitable method, or as described herein. Non-limiting examples of methods suitable for decreasing or disrupting the activity of transketolase include use of a regulated promoter, use of a weak constitutive promoter, disruption of one of the two copies of the gene in a diploid yeast, disruption of both copies of the gene in a diploid yeast, expression of an anti-sense nucleic acid, expression of an siRNA, over expression of a negative regulator of the endogenous promoter, alteration of the activity of an endogenous or heterologous gene, use of a heterologus gene with lower specific activity, the like or combinations thereof. In some embodiments, a gene used to knockout one activity can also introduce or increase another activity. TKL1 and/or TKL2 gene(s) may be native to S. cerevisiae, or may be obtained from a heterologous source.

Sugar Transport Activities

Sugar metabolized as a carbon source by organisms typically is transported from outside a cell into the cell for use as an energy source and/or a raw material for synthesis of cellular products. Sugar can be transported into the cell using active or passive transport mechanisms. Active transport systems frequently utilize energy to transport the sugar across the cell membrane. Sugars often are modified by phosphorylation, once transported inside the cell or organism, to prevent diffusion out of the cell. Sugar transport activities are thought also to act as sugar sensors and have high affinity and low affinity transporters. The rate of glucose utilization in yeast often is dictated by the activity and concentration of glucose transporters in the plasma membrane.

In yeast, sugar transporters have been found to be part of a multi-gene family. Some sugar transport systems transport certain sugars preferentially and other non-preferred sugars at a lower rate. Certain sugar transport systems transport one or more structurally similar sugars at substantially similar rates. Non-limiting examples of sugar transporters include high affinity glucose transporters (e.g., HXT (e.g., HXT1, HXT7}), glucose-xylose transporters (e.g., GXF1, GXS1), and high affinity galactose transporters (e.g., GAL2), the like and combinations thereof.

Galactose permease is a high affinity galactose transport enzyme activity that also can transport glucose. Galactose permease is encoded by the GAL2 gene, and sometimes also is referred to as a galactose/glucose (methylgalactoside) porter. Gal2p is an integral plasma membrane protein belonging to a super family of sugar transporters that are predicted to contain 12 transmembrane domains separated by charged residues. Structurally and functionally similar sugar transporters have been identified in bacteria, rat, and humans.

Glucose often is transported by high affinity glucose transporters. High affinity glucose transporters (e.g., HXT) are members of the major facilitator gene super family, and include the genes HXT6 (Hxt6p) and HXT7 (Hxt7p). HXT6 and HXT7 are substantially similar activities, and are expressed at high basal levels relative to other high affinity glucose transporters. Approximately 20 HXT genes have been identified. High affinity glucose transporters sometimes also are referred to as hexose transporters.

Certain sugar transport systems include high and low affinity transport activities that act on more than one sugar. A non-limiting example of such a sugar transport system includes the glucose/xylose transport system from *Candida* yeast. Glucose and xylose are transported into certain *Candida* by a high affinity xylose-proton symporter (e.g., GXS1) and a low affinity diffusion facilitator (e.g., GXF1). *S. cerevisiae* normally lacks an efficient transport system for xylose, although xylose can enter the cell at low efficiency via non-specific transport systems sometimes involving HXT activities. Addition of the *Candida* GSX1, GXF1 or GXS1 and GXF1 activities to *S. cerevisiae* engineered to metabolize xylose can further enhance the ability to ferment xylose to alcohol or other desired products.

In some embodiments, an engineered microorganism includes one or more sugar transport activities that has been genetically added or altered. In certain embodiments, the sugar transport activity is amplified or increased. Sugar transport activities can be added, amplified by over expression or increased by any suitable method. Non-limiting methods of adding, amplifying or increasing the activity of sugar transport systems include increasing the number of genes of a sugar transport activity (e.g., GAL2, GXF1, GXS1, HXT7) gene(s) in yeast by transformation with a high-copy number plasmid, integration of multiple copies of sugar transport activity (e.g., GAL2, GXF1, GXS1, HXT7) gene(s) into the yeast genome, over-expression of sugar transport activity gene(s) directed by a strong promoter, the like or combinations thereof. The sugar transport activity (e.g., GAL2, GXF1, GXS1, HXT7) gene(s) may be native to *S. cerevisiae*, or may be obtained from a heterologous source.

Carbon Dioxide Metabolism and Activities

Microorganisms grown in fermentors often are grown under anaerobic conditions, with limited or no gas exchange. Therefore the atmosphere inside fermentors sometimes is carbon dioxide rich. Unlike photosynthetic organisms, many microorganisms suitable for use in industrial fermentation processes do not incorporate atmospheric carbon (e.g., $CO_2$) to any significant degree, or at all. Thus, to ensure that increasing levels of carbon dioxide do not inhibit cell growth and the fermentation process, methods to remove carbon dioxide from the interior of fermentors can be useful.

Photosynthetic organisms make use of atmospheric carbon by incorporating the carbon available in carbon dioxide into organic carbon compounds by a process known as carbon fixation. The activities responsible for a photosynthetic organism's ability to fix carbon dioxide include phosphoenolpyruvate carboxylase (e.g., PEP carboxylase) or ribulose 1,5-bis-phosphate carboxylase (e.g., Rubisco). PEP carboxylase catalyzes the addition of carbon dioxide to phosphoenolpyruvate to generate the four-carbon compound oxaloacetate. Oxaloacetate can be used in other cellular processes or be further converted to yield several industrially useful products (e.g., malate, succinate, citrate and the like). Rubisco catalyzes the addition of carbon dioxide and ribulose-1,5-bisphosphate to generate 2 molecules of 3-phosphoglycerate. 3-phosphoglycerate can be further converted to ethanol via cellular fermentation or used to produce other commercially useful products. Nucleic acid sequences encoding PEP carboxylase and Rubisco activities can be obtained from any suitable organism (e.g., plants, bacteria, and other microorganisms, for example) and any of these activities can be used herein with the proviso that the nucleic acid sequence is either naturally active in the chosen microorganism when expressed, or can be altered or modified to be active.

Examples of Altered Activities

In some embodiments, engineered microorganisms can include modifications to one or more (e.g., 1, 2, 3, 4, 5, 6 or all) of the following activities: phosphofructokinase activity (PFK1 A subunit, PFK2 B subunit), phosphogluconate dehydratase activity (EDD), 2-keto-3-deoxygluconate-6-phosphate aldolase activity (EDA), xylose isomerase activity (xylA), xylose reductase activity (XYL1), xylitol dehydrogenase activity (XYL2), xylulokinase activity (XKS1, XYL3), phosphoenolpyruvate carboxylase activity (PEP carboxylase), alcohol dehydrogenase 2 activity (ADH2), thymidylate synthase activity, phosphoglucose isomerase activity (PGI1), transaldolase activity (TAL1), transketolase activity (TKL1, TKL2), 6-phosphogluconolactonase activity (SOL3, SOL4), Glucose-6-phosphate dehydrogenase activity (ZWF1), 6-phosphogluconate dehydrogenase (decarboxylating) activity (GND1, GND2), galactose permease activity (GAL2), high affinity glucose transport activity (HXT7), glucose/xylose transport activity (GXS1, GXF1) and combinations of the foregoing.

The term "phosphofructokinase activity" as used herein refers to conversion of fructose-6-phosphate to fructose-1,6-bisphosphate. Phosphofructokinase activity may be provided by an enzyme that includes one or two subunits (referred to hereafter as "subunit A" and/or "subunit B"). The term "inactivating the Embden-Meyerhoff pathway" as used herein refers to reducing or eliminating the activity of one or more activities in the Embden-Meyerhoff pathway, including but not limited to phosphofructokinase activity. In some embodiments, the phosphofructokinase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the phosphofructokinase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of phosphofructokinase activity can have sequences partially or substantially complementary to sequences described herein. Presence or absence of the amount of phosphofructokinase activity can be detected by any suitable method known in the art, including requiring a five-carbon sugar carbon source or a functional Entner-Doudoroff pathway for growth. Inactivation of the Embden-Meyerhoff pathway is described in further detail below. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

The term "phosphogluconate dehydratase activity" as used herein refers to conversion of 6-phophogluconate to 2-keto-3-deoxy-6-p-gluconate. The phosphogluconate dehydratase activity can be provided by a polypeptide. In some embodiments, the polypeptide is encoded by a heterologous nucleotide sequence introduced to a host microorganism. Nucleic acid sequences conferring phosphogluconate dehydratase activity can be obtained from a number of sources, including *Zymomonas mobilis* and *Escherichia coli*. Examples of an amino acid sequence of a polypeptide having phosphogluconate dehydratase activity, and a nucleotide sequence of a polynucleotide that encodes the polypeptide, are presented below in tables. Presence, absence or amount of phosphogluconate dehydratase activity can be detected by any suitable method known in the art, including western blot analysis.

The term "2-keto-3-deoxygluconate-6-phosphate aldolase activity" as used herein refers to conversion of 2-keto-3-deoxy-6-p-gluconate to pyruvate. The 2-keto-3-deoxygluconate-6-phosphate aldolase activity can be provided by a polypeptide. In some embodiments, the polypeptide is encoded by a heterologous nucleotide sequence introduced to a host microorganism. Nucleic acid sequences conferring 2-keto-3-deoxygluconate-6-phosphate aldolase activity can be obtained from a number of sources, including *Zymomonas mobilis* and *Escherichia coli*. Examples of an amino acid sequence of a polypeptide having 2-keto-3-deoxygluconate-6-phosphate aldolase activity, and a nucleotide sequence of a polynucleotide that encodes the polypeptide, are presented below in tables. Presence, absence or amount of 2-keto-3-deoxygluconate-6-phosphate aldolase activity can be detected by any suitable method known in the art, including western blot analysis.

The term "xylose isomerase activity" as used herein refers to conversion of xylose to xylulose. The xylose isomerase activity can be provided by a polypeptide. In some embodiments, the polypeptide is encoded by a heterologous nucleotide sequence introduced to a host microorganism. Nucleic acid sequences conferring xylose isomerase activity can be obtained from a number of sources, including *Piromyces*, *Orpinomyces*, *Bacteroides* (e.g., *B. thetaiotaomicron*, *B. uniformis*, *B. stercoris*), *Clostrialies* (e.g., *Clostrialies* BVAB3), *Clostridium* (e.g., *C. phytofermentans*, *C. thermohydrosulfuricum*, *C. cellulyticum*), *Thermus thermophilus*, *Escherichia coli*, *Streptomyces* (e.g., *S. rubiginosus*, *S. murinus*), *Bacillus stearothermophilus*, *Lactobacillus pentosus*, *Thermotoga* (e.g., *T. maritime*, *T. neopolitana*) and *Ruminococcus* (e.g., *Ruminococcus* environmental samples, *Ruminococcus albus*, *Ruminococcus bromii*, *Ruminococcus callidus*, *Ruminococcus flavefaciens*, *Ruminococcus gauvreauii*, *Ruminococcus gnavus*, *Ruminococcus lactaris*, *Ruminococcus obeum*, *Ruminococcus* sp., *Ruminococcus* sp. 14531, *Ruminococcus* sp. 15975, *Ruminococcus* sp. 16442, *Ruminococcus* sp. 18P13, *Ruminococcus* sp. 25F6, *Ruminococcus* sp. 25F7, *Ruminococcus* sp. 25F8, *Ruminococcus* sp. 4_1_47FAA, *Ruminococcus* sp. 5, *Ruminococcus* sp. 5_1_39BFAA, *Ruminococcus* sp. 7L75, *Ruminococcus* sp. 8_1_37FAA, *Ruminococcus* sp. 9SE51, *Ruminococcus* sp. C36, *Ruminococcus* sp. CB10, *Ruminococcus* sp. CB3, *Ruminococcus* sp. CCUG 37327 A, *Ruminococcus* sp. CE2, *Ruminococcus* sp. CJ60, *Ruminococcus* sp. CJ63, *Ruminococcus* sp. CO1, *Ruminococcus* sp. CO12, *Ruminococcus* sp. CO22, *Ruminococcus* sp. CO27, *Ruminococcus* sp. CO28, *Ruminococcus* sp. CO34, *Ruminococcus* sp. CO41, *Ruminococcus* sp. CO47, *Ruminococcus* sp. CO7, *Ruminococcus* sp. CS1, *Ruminococcus* sp. CS6, *Ruminococcus* sp. DJF_VR52, *Ruminococcus* sp. DJF_VR66, *Ruminococcus* sp. DJF_VR67, *Ruminococcus* sp. DJF_VR70k1, *Ruminococcus* sp. DJF_VR87, *Ruminococcus* sp. Eg2, *Ruminococcus* sp. Egf, *Ruminococcus* sp. END-1, *Ruminococcus* sp. FD1, *Ruminococcus* sp. GM2/1, *Ruminococcus* sp. ID1, *Ruminococcus* sp. ID8, *Ruminococcus* sp. K-1, *Ruminococcus* sp. KKA Seq234, *Ruminococcus* sp. M-1, *Ruminococcus* sp. M10, *Ruminococcus* sp. M22, *Ruminococcus* sp. M23, *Ruminococcus* sp. M6, *Ruminococcus* sp. M73, *Ruminococcus* sp. M76, *Ruminococcus* sp. MLGO80-3, *Ruminococcus* sp. NML 00-0124, *Ruminococcus* sp. Pei041, *Ruminococcus* sp. SC101, *Ruminococcus* sp. SC103, *Ruminococcus* sp. Siijpesteijn 1948, *Ruminococcus* sp. WAL 17306, *Ruminococcus* sp. YE281, *Ruminococcus* sp. YE58, *Ruminococcus* sp. YE71, *Ruminococcus* sp. ZS2-15, *Ruminococcus* torques). Examples of an amino acid sequence of a polypeptide having xylose isomerase activity, and a nucleotide sequence of a polynucleotide that encodes the polypeptide, are presented below in tables. Presence, absence or amount of xylose isomerase activity can be detected by any suitable method known in the art, including western blot analysis.

The term "phosphoenolpyruvate carboxylase activity" as used herein refers to the addition of carbon dioxide to phosphoenolpyruvate to generate the four-carbon compound oxaloacetate. The phosphoenolpyruvate carboxylase activity can be provided by a polypeptide. In some embodiments, the polypeptide is encoded by a heterologous nucleotide sequence introduced to a host microorganism. Nucleic acid sequences conferring phosphoenolpyruvate carboxylase activity can be obtained from a number of sources, including *Zymomonas mobilis*. Examples of an amino acid sequence of a polypeptide having phosphoenolpyruvate carboxylase activity, and a nucleotide sequence of a polynucleotide that encodes the polypeptide, are presented below in tables. Presence, absence or amount of xylose isomerase activity can be detected by any suitable method known in the art.

The term "alcohol dehydrogenase 2 activity" as used herein refers to conversion of ethanol to acetaldehyde, which is the reverse of the forward action catalyzed by alcohol dehydrogenase 1. The term "inactivation of the conversion of ethanol to acetaldehyde" refers to a reduction or elimination in the activity of alcohol dehydrogenase 2. Reducing or eliminating the activity of alcohol dehydrogenase 2 activity can lead to an increase in ethanol production. In some embodiments, the alcohol dehydrogenase 2 activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the alcohol dehydrogenase 2 activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a non-functional polypeptide or protein. Nucleic acid sequences that can be used to reduce or eliminate the activity of alcohol dehydrogenase 2 can have sequences partially or substantially complementary to nucleic acid sequences that encode alcohol dehydrogenase 2 activity. Presence or absence of the amount of alcohol dehydrogenase 2 activity can be detected by any suitable method known in the art, including inability to grown in media with ethanol as the sole carbon source.

The term "thymidylate synthase activity" as used herein refers to a reductive methylation, where deoxyuridine monophosphate (dUMP) and N5,N10-methylene tetrahydrofolate are together used to generate thymidine monophosphate (dTMP), yielding dihydrofolate as a secondary product. The term "temporarily inactivate thymidylate synthase activity" refers to a temporary reduction or elimination in the activity of thymidylate synthase when the modified organism is shifted to a non-permissive temperature. The activity can return to normal upon return to a permissive temperature. Temporarily inactivating thymidylate synthase uncouples cell growth from cell division while under the non permissive temperature. This inactivation in turn allows the cells to continue fermentation without producing biomass and dividing, thus increasing the yield of product produced during fermentation.

In some embodiments, the thymidylate synthase activity can be temporarily reduced or eliminated by genetic modification, as described below. In certain embodiments, the genetic modification renders the activity responsive to changes in the environment. Nucleic acid sequences conferring temperature sensitive thymidylate synthase activity can be obtained from S. cerevisiae strain 172066 (accession number 208583). The cdc21 mutation in S. cerevisiae strain 172066 has a point mutation at position G139S relative to the initiating methionine. Examples of nucleotide sequences used to PCR amplify the polynucleotide encoding the temperature sensitive polypeptide, are presented below in tables. Presence, absence or amount of thymidylate synthase activity can be detected by any suitable method known in the art, including growth arrest at the non-permissive temperature.

Thymidylate synthase is one of many polypeptides that regulate the cell cycle. The cell cycle may be inhibited in engineered microorganisms under certain conditions (e.g., temperature shift, dissolved oxygen shift), which can result in inhibited or reduced cell proliferation, inhibited or reduced cell division, and sometimes cell cycle arrest (collectively "cell cycle inhibition"). Upon exposure to triggering conditions, a microorganism may display cell cycle inhibition after a certain time after the microorganism is exposed to the triggering conditions (e.g., there may be a time delay after a microorganism is exposed to a certain set of conditions before the microorganism displays cell cycle inhibition). Where cell cycle inhibition results in reduced cell proliferation, cell proliferation rates may be reduced by about 50% or greater, for example (e.g., reduced by about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Where cell cycle inhibition results a reduced number of cells undergoing cell division, the rate of cell division may be reduced by about 50% or greater, for example (e.g., the number of cells undergoing division is reduced by about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Where cell cycle inhibition results in cell cycle arrest, cells may be arrested at any stage of the cell cycle (e.g., resting $G_0$ phase, interphase (e.g., $G_1$, S, $G_2$ phases), mitosis (e.g., prophase, prometaphase, metaphase, anaphase, telophase)) and different percentages of cells in a population can be arrested at different stages of the cell cycle.

The term "phosphoglucose isomerase activity" as used herein refers to the conversion of glucose-6-phosphate to fructose-6-phosphate. The term "inactivation of the conversion of glucose-6-phosphate to fructose-6-phosphate" refers to a reduction or elimination in the activity of phosphoglucose isomerase. Reducing or eliminating the activity of phosphoglucose isomerase activity can lead to an increase in ethanol production. In some embodiments, the phosphoglucose isomerase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the phosphoglucose isomerase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a non-functional polypeptide or protein. Nucleic acid sequences that can be used to reduce or eliminate the activity of phosphoglucose isomerase can have sequences partially or substantially complementary to nucleic acid sequences that encode phosphoglucose isomerase activity. Presence or absence of the amount of phosphoglucose isomerase activity can be detected by any suitable method known in the art, including nucleic acid based analysis and western blot analysis.

The term "glucose-6-phosphate dehydrogenase activity" as used herein refers to conversion of glucose-6-phosphate to gluconolactone-6-phosphate coupled with the generation of NADPH. The glucose-6-phosphate dehydrogenase aldolase activity can be provided by a polypeptide. In some embodiments, the polypeptide is encoded by a heterologous nucleotide sequence introduced to a host microorganism. Nucleic acid sequences conferring glucose-6-phosphate dehydrogenase activity can be obtained from a number of sources, including, but not limited to S. cerevisiae Examples of a nucleotide sequence of a polynucleotide that encodes the polypeptide, are presented below in tables. Presence, absence or amount of glucose-6-phosphate dehydrogenase activity can be detected by any suitable method known in the art, including western blot analysis.

The term "6-phosphogluconolactonase activity" as used herein refers to conversion of gluconolactone-6-phosphate to gluconate-6-phosphate. The 6-phosphogluconolactonase activity can be provided by a polypeptide. In some embodiments, the polypeptide is encoded by a heterologous nucleotide sequence introduced to a host microorganism. Nucleic acid sequences conferring 6-phosphogluconolactonase activity can be obtained from a number of sources, including, but not limited to *S. cerevisiae*. Examples of an amino acid sequence of a polypeptide having 6-phosphogluconolactonase activity, and a nucleotide sequence of a polynucleotide that encodes the polypeptide, are presented below in tables. Presence, absence or amount of 6-phosphogluconolactonase activity can be detected by any suitable method known in the art, including nucleic acid based analysis and western blot analysis.

The term "6-phosphogluconate dehydrogenase (decarboxylating) activity" as used herein refers to the conversion of gluconate-6-phosphate to ribulose-5-phosphate. The term "inactivation of the conversion of gluconate-6-phosphate to ribulose-5-phosphate" refers to a reduction or elimination in the activity of 6-phosphogluconate dehydrogenase. Reducing or eliminating the activity of 6-phosphogluconate dehydrogenase (decarboxylating) activity can lead to an increase in ethanol production. In some embodiments, the 6-phosphogluconate dehydrogenase (decarboxylating) activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the 6-phosphogluconate dehydrogenase (decarboxylating) activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of 6-phosphogluconate dehydrogenase (decarboxylating) can have sequences partially or substantially complementary to nucleic acid sequences that encode 6-phosphogluconate dehydrogenase (decarboxylating) activity. Presence or absence of the amount of 6-phosphogluconate dehydrogenase (decarboxylating) activity can be detected by any suitable method known in the art, including nucleic acid based analysis and western blot analysis.

The term "transketolase activity" as used herein refers to conversion of xylulose-5-phosphate and ribose-5-phosphate to sedoheptulose-7-phosphate and glyceraldehyde-3-phosphate. The transketolase activity can be provided by a polypeptide. In some embodiments, the polypeptide is encoded by a heterologous nucleotide sequence introduced to a host microorganism. Nucleic acid sequences conferring transketolase activity can be obtained from a number of sources, including, but not limited to *S. cerevisiae, Kluyveromyces, Pichia, Escherichia, Bacillus, Ruminococcus, Schizosaccharomyces*, and *Candida*. Examples of an amino acid sequence of a polypeptide having transketolase activity, and a nucleotide sequence of a polynucleotide that encodes the polypeptide, are presented below in the examples. The term "inactivation of the conversion of xylulose-5-phosphate and ribose-5-phosphate to sedoheptulose-7-phosphate and glyceraldehyde-3-phosphate" refers to a reduction or elimination in the activity of transketolase. Reducing or eliminating the activity of transketolase activity can lead to an increase in ethanol production. In some embodiments, the transketolase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the transketolase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of transketolase can have sequences partially or substantially complementary to nucleic acid sequences that encode transketolase activity. Presence, absence or amount of transketolase activity can be detected by any suitable method known in the art, including nucleic acid based analysis and western blot analysis.

The term "transaldolase activity" as used herein refers to conversion of sedoheptulose 7-phosphate and glyceraldehyde 3-phosphate to erythrose 4-phosphate and fructose 6-phosphate. The transaldolase activity can be provided by a polypeptide. In some embodiments, the polypeptide is encoded by a heterologous nucleotide sequence introduced to a host microorganism. Nucleic acid sequences conferring transaldolase activity can be obtained from a number of sources, including, but not limited to *S. cerevisiae, Kluyveromyces, Pichia, Escherichia, Bacillus, Ruminococcus, Schizosaccharomyces*, and *Candida*. Examples of an amino acid sequence of a polypeptide having transaldolase activity, and a nucleotide sequence of a polynucleotide that encodes the polypeptide, are presented below in the examples. The term "inactivation of the conversion of sedoheptulose 7-phosphate and glyceraldehyde 3-phosphate to erythrose 4-phosphate and fructose 6-phosphate" refers to a reduction or elimination in the activity of transaldolase. Reducing or eliminating the activity of transaldolase activity can lead to an increase in ethanol production. In some embodiments, the transaldolase activity can be reduced or eliminated by introduction of an untranslated RNA molecule (e.g., antisense RNA, RNAi, and the like, for example). In certain embodiments, the untranslated RNA is encoded by a heterologous nucleotide sequence introduced to a host microorganism.

In some embodiments, the transaldolase activity can be temporarily or permanently reduced or eliminated by genetic modification, as described below. In certain embodiments, the genetic modification renders the activity responsive to changes in the environment. In some embodiments, the genetic modification disrupts synthesis of a functional nucleic acid encoding the activity or produces a nonfunctional polypeptide or protein. Nucleic acid sequences that can be used to reduce or eliminate the activity of transaldolase can have sequences partially or substantially complementary to nucleic acid sequences that encode transaldolase activity. Presence, absence or amount of transaldolase activity can be detected by any suitable method known in the art, including nucleic acid based analysis and western blot analysis.

The term "galactose permease activity" as used herein refers to the import of galactose into a cell or organism by an activity that transports galactose across cell membranes. The galactose permease activity can be provided by a polypeptide. In some embodiments, the polypeptide is encoded by a heterologous nucleotide sequence introduced to a host microorganism. Nucleic acid sequences conferring galactose permease activity can be obtained from a number of sources, including, but not limited to *S. cerevisiae, Candida albicans, Debaryomyces hansenii, Schizosaccharomyces pombe, Arabidopsis thaliana*, and *Colwellia psychrerythraea*. Examples of an amino acid sequence of a polypeptide having galactose permease activity, and a nucleotide sequence of a polynucleotide that encodes the polypeptide, are presented below in the Examples. Presence, absence or amount of galactose permease activity can be detected by any suitable method known in the art, including nucleic acid based analysis and western blot analysis.

The term "glucose/xylose transport activity" as used herein refers to the import of glucose and/or xylose into a cell or organism by an activity that transports glucose and/or xylose across cell membranes. The glucose/xylose transport activity can be provided by a polypeptide. In some embodiments, the polypeptide is encoded by a heterologous nucleotide sequence introduced to a host microorganism. Nucleic acid sequences conferring glucose/xylose transport activity can be obtained from a number of sources, including, but not limited to *Pichia yeast, S. cerevisiae, Candida albicans, Debaryomyces hansenii, Schizosaccharomyces pombe, Arabidopsis thaliana*, and *Colwellia psychrerythraea*. Examples of an amino acid sequence of a polypeptide having glucose/xylose transport activity, and a nucleotide sequence of a polynucleotide that encodes the polypeptide, are presented below in the Examples. Presence, absence or amount of glucose/xylose transport activity can be detected by any suitable method known in the art, including nucleic acid based analysis and western blot analysis.

The terms "high affinity glucose transport activity" and "hexose transport activity" as used herein refer to the import of glucose and other hexose sugars into a cell or organism by an activity that transports glucose and other hexose sugars across cell membranes. The high affinity glucose transport activity or hexose transport activity can be provided by a polypeptide. In some embodiments, the polypeptide is encoded by a heterologous nucleotide sequence introduced to a host microorganism. Nucleic acid sequences conferring high affinity glucose transport activity or hexose transport activity can be obtained from a number of sources, including, but not limited to *S. cerevisiae, Candida albicans, Debaryomyces hansenii, Schizosaccharomyces pombe, Arabidopsis thaliana*, and *Colwellia psychrerythraea*. Presence, absence or amount of glucose/xylose transport activity can be detected by any suitable method known in the art, including nucleic acid based analysis and western blot analysis.

The term "xylose reductase activity" as used herein refers to the conversion of xylose to xylitol. In some embodiments, the polypeptide is encoded by a heterologous nucleotide sequence introduced to a host microorganism. Nucleic acid sequences conferring xylose reductase activity can be obtained from a number of sources. Presence, absence or amount of xylose reductase activity can be detected by any suitable method known in the art, including activity assays, nucleic acid based analysis and western blot analysis.

The term "xylitol dehydrogenase activity" as used herein refers to the conversion of xylitol to xylulose. In some embodiments, the polypeptide is encoded by a heterologous nucleotide sequence introduced to a host microorganism. Nucleic acid sequences conferring xylitol dehydrogenase activity can be obtained from a number of sources. Presence, absence or amount of xylitol dehydrogenase activity can be detected by any suitable method known in the art, including activity assays, nucleic acid based analysis and western blot analysis.

The term "xylulokinase activity" as used herein refers to the conversion of xylulose to xylulose-5-phosphate. In some embodiments, the polypeptide is encoded by a heterologous nucleotide sequence introduced to a host microorganism. Nucleic acid sequences conferring xylulokinase activity can be obtained from a number of sources. Presence, absence or amount of xylulokinase activity can be detected by any suitable method known in the art, including activity assays, nucleic acid based analysis and western blot analysis.

Activities described herein can be modified to generate microorganisms engineered to allow a method of independently regulating or controlling (e.g., ability to independently turn on or off, or increase or decrease, for example) six-carbon sugar metabolism, five-carbon sugar metabolism, atmospheric carbon metabolism (e.g., carbon dioxide fixation) or combinations thereof. In some embodiments, regulated control of a desired activity can be the result of a genetic modification. In certain embodiments, the genetic modification can be modification of a promoter sequence. In some embodiments the modification can increase of decrease an activity encoded by a gene operably linked to the promoter element. In certain embodiments, the modification to the promoter element can add or remove a regulatory sequence. In some embodiments the regulatory sequence can respond to a change in environmental or culture conditions. Non-limiting examples of culture conditions that could be used to regulate an activity in this manner include, temperature, light, oxygen, salt, metals and the like. Additional methods for altering an activity by modification of a promoter element are given below.

In some embodiments, the genetic modification can be to an ORF. In certain embodiments, the modification of the ORF can increase or decrease expression of the ORF. In some embodiments modification of the ORF can alter the efficiency of translation of the ORF. In certain embodiments, modification of the ORF can alter the activity of the polypeptide or protein encoded by the ORF. Additional methods for altering an activity by modification of an ORF are given below.

In some embodiments, the genetic modification can be to an activity associated with cell division (e.g., cell division cycle or CDC activity, for example). In certain embodiments the cell division cycle activity can be thymidylate synthase activity. In certain embodiments, regulated control of cell division can be the result of a genetic modification. In some embodiments, the genetic modification can be to a nucleic acid sequence that encodes thymidylate synthase. In certain embodiments, the genetic modification can temporarily inactivate thymidylate synthase activity by rendering the activity temperature sensitive (e.g., heat resistant, heat sensitive, cold resistant, cold sensitive and the like).

In some embodiments, the genetic modification can modify a promoter sequence operably linked to a gene encoding an activity involved in control of cell division. In some embodiments the modification can increase of decrease an activity encoded by a gene operably linked to the promoter element. In certain embodiments, the modification to the promoter element can add or remove a regulatory sequence. In some embodiments the regulatory sequence can respond to a change in environmental or culture conditions. Non-limiting examples of culture conditions that could be used to regulate an activity in this manner include, temperature, light, oxygen, salt, metals and the like. In some embodiments, an engineered microorganism comprising one or more activities described above or below can be used in to produce ethanol by inhibiting cell growth and cell division by use of a temperature sensitive cell division control activity while allowing cellular fermentation to proceed, thereby producing a significant increase in ethanol yield when compared to the native organism.

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like). The terms "amplify", "amplification", "amplification reaction", or "amplifying" as used herein refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3'direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments.

A promoter often interacts with a RNA polymerase. A polymerase is an enzyme that catalyses synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein. The term "operably linked" as used herein with respect to promoters refers to a nucleic acid sequence (e.g., a coding sequence) present on the same nucleic acid molecule as a promoter element and whose expression is under the control of said promoter element.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a 6th order Markov background model and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate on that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 70% or more identical to the foregoing (or to the complementary sequences). That is, a nucleotide sequence that is at least 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As use herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

As noted above, nucleic acid reagents may also comprise one or more 5' UTR's, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, -35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews 0004.1-0001.10 (2002); Gallie, Nucleic Acids Research 30: 3401-3411 (2002); Shaloiko et al., http address www.interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide or protein of interest, and may be a ribonucleotide sequence or a deoxyribonucleotide sequence.

A target nucleic acid sometimes can comprise a chimeric nucleic acid (or chimeric nucleotide sequence), which can encode a chimeric protein (or chimeric amino acid sequence). The term "chimeric" as used herein refers to a nucleic acid or nucleotide sequence, or encoded product thereof, containing sequences from two or more different sources. Any suitable source can be selected, including, but not limited to, a sequence from a nucleic acid, nucleotide sequence, ribosomal nucleic acid, RNA, DNA, regulatory nucleotide sequence (e.g., promoter, URL, enhancer, repressor and the like), coding nucleic acid, gene, nucleic acid linker, nucleic acid tag, amino acid sequence, peptide, polypeptide, protein, chromosome, and organism. A chimeric molecule can include a sequence of contiguous nucleotides or amino acids from a source including, but not limited to, a virus, prokaryote, eukaryote, genus, species, homolog, ortholog, paralog and isozyme, nucleic acid linkers, nucleic acid tags, the like and combinations thereof). A chimeric molecule can be generated by placing in juxtaposition fragments of related or unrelated nucleic acids, nucleotide sequences or DNA segments, in some embodiments. In certain embodiments the nucleic acids, nucleotide sequences or DNA segments can be native or wild type sequences, mutant sequences or engineered sequences (completely engineered or engineered to a point, for example).

In some embodiments, a chimera includes about 1, 2, 3, 4 or 5 sequences (e.g., contiguous nucleotides, contiguous amino acids) from one organism and 1, 2, 3, 4 or 5 sequences (e.g., contiguous nucleotides, contiguous amino acids) from another organism. The organisms sometimes are a microbe, such as a bacterium (e.g., gram positive, gram negative), yeast or fungus (e.g., aerobic fungus, anaerobic fungus), for example. In some embodiments, the organisms are bacteria, the organisms are yeast or the organisms are fungi (e.g., different species), and sometimes one organism is a bacterium or yeast and another is a fungus. A chimeric molecule may contain up to about 99% of sequences from one organism (e.g., about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99%) and the balance percentage from one or more other organisms. In certain embodiments, a chimeric molecule includes altered codons (in the case of a chimeric nucleic acid) and one or more mutations (e.g., point mutations, nucleotide substitutions, amino acid substitutions). In some embodiments, the chimera comprises a portion of a xylose isomerase from one bacteria species and a portion of a xylose isomerase from another bacteria species. In still other embodiments, the chimera comprises a portion of a xylose isomerase from one species of fungus and another portion of a xylose isomerase from another species of fungus. In still other embodiments, the chimera comprises one portion of a xylose isomerase from a plant, and another portion of a xylose isomerase from a non-plant (such as a bacteria or fungus).

In other embodiments, the chimera comprises one portion of a xylose isomerase from a plant, another portion of a xylose isomerase from a bacteria, and yet another portion of a xylose isomerase from a fungus.

In specific embodiments, a gene encoding a xylose isomerase protein is chimeric, and includes a portion of a xylose isomerase encoding sequence from one organism (e.g. a fungus (e.g., *Piromyces, Orpinomyces, Neocallimastix, Caecomyces, Ruminomyces*, and the like)) and a portion of a xylose isomerase encoding sequence from another organism (e.g., bacterium (e.g., *Ruminococcus, Thermotoga, Clostridium*)). Sometimes a fungal sequence is located at the N-terminal portion of the encoded xylose isomerase polypeptide and the bacterial sequence is located at the C-terminal portion of the polypeptide. In some embodiments one contiguous fungal xylose isomerase sequence is about 1% to about 30% of overall sequence (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29%) and the remaining sequence is a contiguous bacterial xylose isomerase sequence. In certain embodiments, a chimeric xylose isomerase includes one or more point mutations.

A chimera sometimes is the result of recombination between two or more nucleic acids, nucleotide sequences or genes, and sometimes is the result of genetic manipulation (e.g., designed and/or generated by the hand of a human being). Any suitable nucleic acid or nucleotide sequence and method for combining nucleic acids or nucleotide sequences can be used to generate a chimeric nucleic acid or nucleotide sequence. Non-limiting examples of nucleic acid and nucleotide sequence sources and methods for generating chimeric nucleic acids and nucleotide sequences are presented herein.

In some embodiments, fragments used to generate a chimera can be juxtaposed as units (e.g., nucleic acid from the sources are combined end to end and not interspersed. In embodiments where a chimera includes one stretch of contiguous nucleotides for each organism, nucleotide sequence combinations can be noted as DNA source 1 DNA source 2 or DNA source 1/DNA source 2/DNA source 3, the like and combinations thereof, for example. In certain embodiments, fragments used to generate a chimera can be juxtaposed such that one or more fragments from one or more sources can be interspersed with other fragments used to generate the chimera (e.g., DNA source 1/DNA source 2/DNA source 1/DNA source 3/DNA source 2/DNA source 1). In some embodiments, the nucleotide sequence length of the fragments used to generate a chimera can be in the range from about 5 base pairs to about 5,000 base pairs (e.g., about 5 base pairs (bp), about 10 bp, about 15 bp, about 20 bp, about 25 bp, about 30 bp, about 35 bp, about 40 bp, about 45 bp, about 50 bp, about 55 bp, about 60 bp, about bp, about 65 bp, about 70 bp, about 75 bp, about 80 bp, about 85 bp, about 90 bp, about 95 bp, about 100 bp, about 125 bp, about 150 bp, about 175 bp, about 200 bp, about 250 bp, about 300 bp, about 350 bp, about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1500 bp, about 2000 bp, about 2500 bp, about 3000 bp, about 3500 bp, about 4000 bp, about 4500 bp, or about 5000 bp).

In certain embodiments, a chimeric nucleic acid or nucleotide sequence encodes the same activity as the activity encoded by the source nucleic acids or nucleotide sequences. In some embodiments, a chimeric nucleic acid or nucleotide sequence has a similar or the same activity, but the amount of the activity, or kinetics of the activity, are altered (e.g., increased, decreased). In certain embodiments, a chimeric nucleic acid or nucleotide sequence encodes a different activity, and in some embodiments a chimeric nucleic acid or nucleotide sequences encodes a chimeric activity (e.g., a combination of two or more activities).

A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a person of ordinary skill in the art. Representative proteins include enzymes (e.g., phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed hereafter. The term "protein" as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG) (SEQ ID NO: 132), V5 (e.g., GKPIPNPLLGLDST) (SEQ ID NO: 133), c-MYC (e.g., EQKLISEEDL) (SEQ ID NO: 134), HSV (e.g., QPELAPEDPED) (SEQ ID NO: 135), influenza hemaglutinin, HA (e.g., YPYDVPDYA) (SEQ ID NO: 136), VSV-G (e.g., YTDIEMNRLGK) (SEQ ID NO: 137), bacterial glutathione-5-transferase, maltose binding protein, a streptavidin- or avidin-binding tag (e.g., pcDNA™6 BioEase™ Gateway® Biotinylation System (Invitrogen)), thioredoxin, 6-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6) (SEQ ID NO: 138) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 139), wherein X is any amino acid and n is 1 to 3, and the cysteine-rich sequence sometimes is CCPGCC (SEQ ID NO: 140). In certain embodiments, the tag comprises a cysteine-rich element and a polyhistidine element (e.g., CCPGCC (SEQ ID NO: 140) and His6 (SEQ ID NO: 138)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS) (SEQ ID NO: 141), enterokinase (e.g., recognition site DDDDK) (SEQ ID NO: 142), TEV protease (e.g., recognition site ENLYFQG) (SEQ ID NO: 143) or PreScission™ protease (e.g., recognition site LEVLFQGP) (SEQ ID NO: 144), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, gIT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rpIL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address vvww.invitrogen.com/content/sfs/manuals/tagondemand_supernatant_man.pdf; Tag-On-Demand™ Gateway® Vector Instruction Manual, Version B, 20 Jun., 2003 at http address www.invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described hereafter. In some embodiments, a cloning strategy can be combined with genetic manipulation such as recombination (e.g., recombination of a nucleic acid reagent with a nucleic acid sequence of interest into the genome of the organism to be modified, as described further below). In some embodiments, the cloned ORF(s) can produce (directly or indirectly) a desire product, by engineering a microorganism with one or more ORFs of interest, which microorganism comprises one or more altered activities selected from the group consisting of phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity, sugar transport activity, phosphoglucoisomerase activity, transaldolase activity, transketolase activity, glucose-6-phosphate dehydrogenase activity, 6-phosphogluconolactonase activity, 6-phosphogluconate dehydrogenase (decarboxylating) activity, xylose reductase activity, xylitol dehydrogenase activity, xylulokinase activity and thymidylate synthase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the ura3 gene (e.g., for *S. cerevisiae* and *C. albicans*, for example) or ura4 and ura5 genes (e.g., for *S. pombe*, for example) and toxicity of the nucleotide analogue 5-Fluoroorotic acid (5-FOA). The ura3 or ura4 and ura5 genes encode orotine-5'-monophosphate (OMP) dicarboxylase. Yeast with an active ura3 or ura4 and ura5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisiae*), flanked on either side by the same nucleotide sequence in the same orientation. The ura3 cassette comprises a promoter, the ura3 gene and a functional transcription terminator. Target sequences which direct the construct to a particular nucleic acid region of interest in the organism to be engineered are added such that the target sequences are adjacent to and abut the flanking sequences on either side of the ura3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the ura3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner. Further detail will be described below in the engineering section and in the example section.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T) CCTT-PO4-TOPO, a complex of the topoisomerase covalently bound to the 3' phosphate via a tyrosine in the topoisomerase (e.g., Shuman, J. Biol. Chem. 266:11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., http address www.invitrogen.com/downloads/F-13512_Topo_Flyer.pdf; http address at world wide web uniform resource locator invitrogen.com/content/sfs/brochures/710_021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address world wide web uniform resource locator devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include, deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) Molecular Cloning: a Laboratory Manual; Cold Spring Harbor Laboratory, Cold Spring Harbor, N.Y.

The term "genetic modification" as used herein refers to any suitable nucleic acid addition, removal or alteration that facilitates production of a target product (e.g., phosphogluconate dehydratase activity, 2-keto-3-deoxygluconate-6-phosphate aldolase activity, xylose isomerase activity, or phosphoenolpyruvate carboxylase activity, for example). in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

The term "altered activity" as used herein refers to an activity in an engineered microorganism that is added or modified relative to the host microorganism (e.g., added, increased, reduced, inhibited or removed activity). An activity can be altered by introducing a genetic modification to a host microorganism that yields an engineered microorganism having added, increased, reduced, inhibited or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences).

An AU-rich element (ARE, e.g., AUUUA repeats) and/or splicing junction that follows a non-sense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce or potentially reduce translation efficiency are present in the elements, and adding, removing or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. For example, the codon usage, and therefore the codon triplets encoded by a nucleic acid sequence from bacteria may be different from the preferred codon usage in eukaryotes like yeast or plants. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiment, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like) can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., C. tropicalis and C. maltosa) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either *Candida* yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter and the like). A modification sometimes is made that can add or enhance binding of a feedback regulator and sometimes a modification is made that can reduce, inhibit or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins or other desired products (e.g., adipic acid, for example). A modification sometimes can be made that can alter, add or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding or removing sequences involved in the expression of an anti-sense RNA, RNAi, siRNA, ribozyme and the like. The methods described above can be used to modify expression of anti-sense RNA, RNAi, siRNA, ribozyme and the like.

Engineered microorganisms can be prepared by altering, introducing or removing nucleotide sequences in the host genome or in stably maintained epigenetic nucleic acid reagents, as noted above. The nucleic acid reagents use to alter, introduce or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures available in Maniatis, T., E. F. Fritsch and J. Sambrook (1982) Molecular Cloning: a Laboratory Manual; Cold Spring Harbor Laboratory, Cold Spring Harbor, N.Y. or with commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR(RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification and the like, for example). Standard cloning procedures (e.g., enzymic digestion, ligation, and the like) are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some embodiments, nucleic acid sequences prepared by isolation or amplification can be used, without any further modification, to add an activity to a microorganism and thereby generate a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., E. coli, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophoretic procedures. A modification of this method uses linear amplification methods and a pair of mutagenic primers that amplify the entire plasmid. The procedure takes advantage of the E. coli Dam methylase system which causes DNA replicated in vivo to be sensitive to the restriction endonucleases Dpnl. PCR synthesized DNA is not methylated and is therefore resistant to Dpnl. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both server to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to "pop out" the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes in to the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis, and allows counter selection for recombination out of the LYS2 gene using alpha-amino adipate (α-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 kan$^r$, Cm$^r$, Hyg$^r$, CUP1, and DHFR. Tn903 kan$^r$ encodes an activity involved in kanamycin antibiotic resistance (e.g., typically neomycin phosphotransferase II or NPTII, for example). Cm$^r$ encodes an activity involved in chloramphenicol antibiotic resistance (e.g., typically chloramphenicol acetyl transferase or CAT, for example). Hyg$^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamde compounds.

In contrast to site-directed or specific mutagenesis, random mutagenesis does not require any sequence information and can be accomplished by a number of widely different methods. Random mutagenesis often is used to generate mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1, 2, 7, 8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organisms DNA replication and repair mechanisms to incorporate and replicate the mutagenized base or bases. Another type of chemical mutagenesis involves the use of base-analogs. The use of base-analogs cause incorrect base pairing which in the following round of replication is corrected to a mismatched nucleotide when compared to the starting sequence. Base analog mutagenesis introduces a small amount of non-randomness to random mutagenesis, because specific base analogs can be chose which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultra violet (UV) induced mutagenesis is caused by the formation of thymidine dimers when UV light irradiates chemical bonds between two adjacent thymine residues. Excision repair mechanism of the host organism correct the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 kan$^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL strategene.com and World Wide Web URL clontech.com, respectively, for example). Rolling circle error-prone PCR is a variant of error-prone PCR in which wild-type sequence is first cloned into a plasmid, the whole plasmid is then amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods available to one of skill in the art can be found in Maniatis, T., E. F. Fritsch and J. Sambrook (1982) Molecular Cloning: a Laboratory Manual; Cold Spring Harbor Laboratory, Cold Spring Harbor, N.Y.

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

Culture, Production and Process Methods

Engineered microorganisms often are cultured under conditions that optimize yield of a target molecule. A non-limiting example of such a target molecule is ethanol. Culture conditions often can alter (e.g., add, optimize, reduce or eliminate, for example) activity of one or more of the following activities: phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activities. In general, conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

The term "fermentation conditions" as used herein refers to any culture conditions suitable for maintaining a microorganism (e.g., in a static or proliferative state). Fermentation conditions can include several parameters, including without limitation, temperature, oxygen content, nutrient content (e.g., glucose content), pH, agitation level (e.g., revolutions per minute), gas flow rate (e.g., air, oxygen, nitrogen gas), redox potential, cell density (e.g., optical density), cell viability and the like. A change in fermentation conditions (e.g., switching fermentation conditions) is an alteration, modification or shift of one or more fermentation parameters. For example, one can change fermentation conditions by increasing or decreasing temperature, increasing or decreasing pH (e.g., adding or removing an acid, a base or carbon dioxide), increasing or decreasing oxygen content (e.g., introducing air, oxygen, carbon dioxide, nitrogen) and/or adding or removing a nutrient (e.g., one or more sugars or sources of sugar, biomass, vitamin and the like), or combinations of the foregoing. Examples of fermentation conditions are described herein. Aerobic conditions often comprise greater than about 50% dissolved oxygen (e.g., about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Anaerobic conditions often comprise less than about 50% dissolved oxygen (e.g., about 1%, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48%, or less than any one of the foregoing).

Culture media generally contain a suitable carbon source. Carbon sources may include, but are not limited to, monosaccharides (e.g., glucose, fructose, xylose), disaccharides (e.g., lactose, sucrose), oligosaccharides, polysaccharides (e.g., starch, cellulose, hemicellulose, other lignocellulosic materials or mixtures thereof), sugar alcohols (e.g., glycerol), and renewable feedstocks (e.g., cheese whey permeate, cornsteep liquor, sugar beet molasses, barley malt). Carbon sources also can be selected from one or more of the following non-limiting examples: linear or branched alkanes (e.g., hexane), linear or branched alcohols (e.g., hexanol), fatty acids (e.g., about 10 carbons to about 22 carbons), esters of fatty acids, monoglycerides, diglycerides, triglycerides, phospholipids and various commercial sources of fatty acids including vegetable oils (e.g., soybean oil) and animal fats. A carbon source may include one-carbon sources (e.g., carbon dioxide, methanol, formaldehyde, formate and carbon-containing amines) from which metabolic conversion into key biochemical intermediates can occur. It is expected that the source of carbon utilized may encompass a wide variety of carbon-containing sources and will only be limited by the choice of the engineered microorganism(s).

Nitrogen may be supplied from an inorganic (e.g., (NH.sub.4).sub.2SO.sub.4) or organic source (e.g., urea or glutamate). In addition to appropriate carbon and nitrogen sources, culture media also can contain suitable minerals, salts, cofactors, buffers, vitamins, metal ions (e.g., Mn.sup.+2, Co.sup.+2, Zn.sup.+2, Mg.sup.+2) and other components suitable for culture of microorganisms. Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known.

A variety of host organisms can be selected for the production of engineered microorganisms. Non-limiting examples include yeast and fungi. In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L NaNO$_3$, 10.4 g/L KCl, 10.4 g/L MgSO$_4$.7 H$_2$O), 1 mL/L 1000× Trace Elements (22 g/L ZnSO$_4$.7 H$_2$O, 11 g/L H$_3$BO$_3$, 5 g/L MnCl$_2$.7 H$_2$O, 5 g/L FeSO$_4$.7 H$_2$O, 1.7 g/L CoCl$_2$.6 H$_2$O, 1.6 g/L CuSO$_4$.5 H$_2$O, 1.5 g/L Na$_2$MoO$_4$.2 H$_2$O, and 50 g/L Na$_4$EDTA), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Culturing may be conducted under aerobic or anaerobic conditions, where microaerobic conditions sometimes are maintained. A two-stage process may be utilized, where one stage promotes microorganism proliferation and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions).

A variety of fermentation processes may be applied for commercial biological production of a target product. In some embodiments, commercial production of a target product from a recombinant microbial host is conducted using a batch, fed-batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die. A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen and the partial pressure of waste gases (e.g., $CO_2$).

Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In various embodiments ethanol may be purified from the culture media or extracted from the engineered microorganisms. Culture media may be tested for ethanol concentration and drawn off when the concentration reaches a predetermined level. Detection methods are known in the art, including but not limited to the use of a hydrometer and infrared measurement of vibrational frequency of dissolved ethanol using the CH band at 2900 $cm^{-1}$. Ethanol may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to methods known in the art.

In certain embodiments, target product is extracted from the cultured engineered microorganisms. The microorganism cells may be concentrated through centrifugation at speed sufficient to shear the cell membranes. In some embodiments, the cells may be physically disrupted (e.g., shear force, sonication) or chemically disrupted (e.g., contacted with detergent or other lysing agent). The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, ethanol may be derivatized or further processed to produce ethyl halides, ethyl esters, diethyl ether, acetic acid, ethyl amines, butadiene, solvents, food flavorings, distilled spirits and the like.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free.

In some embodiments target product or modified target product purified from microbes is provided, and target product sometimes is provided in substantially pure form. In certain embodiments, ethanol can be provided in anhydrous or hydrous forms. Ethanol may be transported in a variety of containers including pints, quarts, liters, gallons, drums (e.g., 10 gallon or 55 gallon, for example) and the like.

In certain embodiments, a target product (e.g., ethanol, succinic acid) is produced with a yield of about 0.30 grams of target product, or greater, per gram of glucose added during a fermentation process (e.g., about 0.31 grams of target product per gram of glucose added, or greater; about 0.32 grams of target product per gram of glucose added, or greater; about 0.33 grams of target product per gram of glucose added, or greater; about 0.34 grams of target product per gram of glucose added, or greater; about 0.35 grams of target product per gram of glucose added, or greater; about 0.36 grams of target product per gram of glucose added, or greater; about 0.37 grams of target product per gram of glucose added, or greater; about 0.38 grams of target product per gram of glucose added, or greater; about 0.39 grams of target product per gram of glucose added, or greater; about 0.40 grams of target product per gram of glucose added, or greater; about 0.41 grams of target product per gram of glucose added, or greater; 0.42 grams of target product per gram of glucose added, or greater; 0.43 grams of target product per gram of glucose added, or greater; 0.44 grams of target product per gram of glucose added, or greater; 0.45 grams of target product per gram of glucose added, or greater; 0.46 grams of target product per gram of glucose added, or greater; 0.47 grams of target product per gram of glucose added, or greater; 0.48 grams of target product per gram of glucose added, or greater; 0.49 grams of target product per gram of glucose added, or greater; 0.50 grams of target product per gram of glucose added, or greater; 0.51 grams of target product per gram of glucose added, or greater; 0.52 grams of target product per gram of glucose added, or greater; 0.53 grams of target product per gram of glucose added, or greater; 0.54 grams of target product per gram of glucose added, or greater; 0.55 grams of target product per gram of glucose added, or greater; 0.56 grams of target product per gram of glucose added, or greater; 0.57 grams of target product per gram of glucose added, or greater; 0.58 grams of target product per gram of glucose added, or greater; 0.59 grams of target product per gram of glucose added, or greater; 0.60 grams of target product per gram of glucose added, or greater; 0.61 grams of target product per gram of glucose added, or greater; 0.62 grams of target product per gram of glucose added, or greater; 0.63 grams of target product per gram of glucose added, or greater; 0.64 grams of target product per gram of glucose added, or greater; 0.65 grams of target product per gram of glucose added, or greater; 0.66 grams of target product per gram of glucose added, or greater; 0.67 grams of target product per gram of glucose added, or greater; 0.68 grams of target product per gram of glucose added, or greater; 0.69 or 0.70 grams of target product per gram of glucose added or greater). In some embodiments, 0.45 grams of target product per gram of glucose added, or greater, is produced during the fermentation process.

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) *Molecular Cloning: a Laboratory Manual*; Cold Spring Harbor Laboratory, Cold Spring Harbor, N.Y. DNA mutagenesis can be accomplished using the Stratagene (San Diego, Calif.) "QuickChange" kit according to the manufacturer's instructions, or by one of the other types of mutagenesis described above.

Example 1

Activation of the Entner-Doudoroff Pathway in Yeast Cells

Genomic DNA from *Zymomonas mobilis* (ZM4) was obtained from the American Type Culture Collection (ATCC accession number 31821 D-5). The genes encoding phosphogluconate dehydratase EC 4.2.1.12 (referred to as "edd") and 2-keto-3-deoxygluconate-6-phosphate aldolase EC 4.2.1.14 (referred to as "eda") were isolated from the ZM4 genomic DNA using the following oligonucleotides:

The ZM4 eda gene:

```
                                          (SEQ ID No: 1)
5'-aactgactagtaaaaaaatgcgtgatatcgattcc-3'

(SEQ ID No: 2)
5'-agtaactcgagctactaggcaacagcagcgcgcttg-3'
```

The ZM4 edd gene:

```
                                          (SEQ ID NO: 3)
5'-aactgactagtaaaaaaatgactgatctgcattcaacg-3'

(SEQ ID NO: 4)
5'-agtaactcgagctactagataccggcacctgcatatattgc-3'
```

*E. coli* genomic DNA was prepared using Qiagen DNeasy blood and tissue kit according to the manufacture's protocol. The *E. coli* edd and eda constructs were isolated from *E. coli* genomic DNA using the following oligonucleotides:

The *E. coli* eda gene:

```
                                          (SEQ ID NO: 5)
5'-aactgactagtaaaaaaatgaaaaactggaaaacaagtgcagaatc-
3'

(SEQ ID NO: 6)
5'-agtaactcgagctactacagcttagcgccttctacagcttcacg-3'
```

The *E. coli* edd gene:

```
                                          (SEQ ID NO: 7)
5'-aactgactagtaaaaaaatgaatccacaattgttacgcgtaacaa
atcg-3'

(SEQ ID NO: 8)
5'agtaactcgagctactaaaaagtgatacaggttgcgccctgttcg
gcac-3'
```

All oligonucleotides set forth above were purchased from Integrated DNA technologies ("IDT", Coralville, Iowa). These oligonucleotides were designed to incorporate a SpeI restriction endonuclease cleavage site upstream and a XhoI restriction endonuclease cleavage site downstream of the edd and eda gene constructs such that these sites could be used to clone these genes into yeast expression vectors p426GPD (ATCC accession number 87361) and p425GPD (ATCC accession number 87359). In addition to incorporating restriction endonuclease cleavage sites, the forward oligonucleotides were designed to incorporate six consecutive AAAAAA nucleotides immediately upstream of the ATG initiation codon. This ensured that there was a conserved kozak sequence important for efficient translation initiation in yeast.

Cloning the edd and eda genes from ZM4 and *E. coli* genomic DNA was accomplished using the following procedure: About 100 ng of ZM4 or *E. coli* genomic DNA, 1 µM of the oligonucleotide primer set listed above, 2.5 U of PfuUltra High-Fidelity DNA polymerase (Stratagene), 300 µM dNTPs (Roche), and 1×PfuUltra reaction buffer was mixed in a final reaction volume of 50 µl. A BIORAD DNA Engine Tetrad 2

Peltier thermal cycler was used for the PCR reactions and the following cycle conditions were used: 5 min denaturation step at 95° C., followed by 30 cycles of 20 sec at 95° C., 20 sec at 55° C., and 1 min at 72° C., and a final step of 5 min at 72° C.

In an attempt to maximize expression of the ZM4 edd and eda genes in yeast, two different approaches were undertaken to optimize the ZM4 edd and eda genes. The first approach was to remove translational pauses from the polynucleotide sequence by designing the gene to incorporate only codons that are preferred in yeast. This optimization is referred to as the "hot rod" optimization. In the second approach, translational pauses which are present in the native organism gene sequence are matched in the heterologous expression host organism by substituting the codon usage pattern of that host organism. This optimization is referred to as the "matched" optimization. The final gene and protein sequences for edd and eda from the ZM4 native, hot rod (HR) and matched versions, as well as the *E. coli* native are shown in FIG. 6. Certain sequences in FIG. 6 are presented at the end of this Example 1. The matched version of ZM4 edd and ZM4 eda genes were synthesized by IDT, and the hot rod version was constructed using methods described in Larsen et al. (*Int. J. Bioinform. Res. Appl;* 2008:4[3]; 324-336).

Each version of each edd and eda gene was inserted into the yeast expression vector p426GPD (GPD promoter, 2 micron, URA3) (ATCC accession number 87361) between the SpeI and XhoI cloning sites. Each version of the eda gene was also inserted into the SpeI and XhoI sites of the yeast expression vector p425GPD (GPD promoter, 2 micron, LEU3) (ATCC accession number 87359). For each edd and eda version, 3' His tagged and non tagged p426 GPD constructs were made. Please refer to table 1 for all oligonucleotides used for PCR amplification of edd and eda constructs for cloning into p425 and p426 GPD vectors. All cloning procedures were conducted according to standard cloning procedures described by Maniatis et al.

Each edd and eda p426GPD construct was transformed into *Saccharomyces cerevisiae* strain BY4742 (MATalpha his3delta1 leu2delta0 lys2delta0 ura3delta0) (ATCC accession number 201389). This strain has a deletion of the his3 gene, an imidazoleglycerol-phosphate dehydratase which catalyzes the sixth step in histidine biosynthesis; a deletion of leu2 gene, a beta-isopropylmalate dehydrogenase which catalyzes the third step in the leucine biosynthesis pathway; a deletion of the lys2 gene, an alpha aminoadipate reductase which catalyzes the fifth step in biosynthesis of lysine; and a deletion of the ura3 gene, an orotidine-5'-phosphate decarboxylase which catalyzes the sixth enzymatic step in the de novo biosynthesis of pyrimidines. The genotype of BY4742 makes it an auxotroph for histidine, leucine, lysine and uracil.

Transformation of the p426GPD plasmids containing an edd or an eda variant gene into yeast strain BY4742 was accomplished using the Zymo Research frozen-EZ yeast transformation II kit according to the manufacturer's protocol. The transformed BY4742 cells were selected by growth on a synthetic dextrose medium (SD) (0.67% yeast nitrogen base-2% dextrose) containing complete amino acids minus uracil (Krackeler Scientific Inc). Plates were incubated at about 30° C. for about 48 hours. Transformant colonies for each edd and eda variant were inoculated onto 5 ml of SD minus uracil medium and cells were grown at about 30° C. and shaken at about 250 rpm for about 24 hours. Cells were harvested by centrifugation at 1000×g for about 5 minutes, after which protein crude extract was prepared with Y-PER Plus (Thermo Scientific) according to the manufacturer's instructions. Whole cell extract protein concentrations were determined using the Coomassie Plus Protein Assay (Thermo Scientific) according to the manufacturer's directions. For each edd and eda variant His-tagged construct, about 10 µg of soluble and insoluble fractions were loaded on 4-12% NuPAGE Novex Bis-Tris protein gels (Invitrogen) and proteins were analyzed by western using anti-(H is)$_6$ (SEQ ID NO: 138) mouse monoclonal antibody (Abcam) and HRP-conjugated secondary antibody (Abcam). Supersignal West Pico Chemiluminescent substrate (Thermo Scientific) was used for western detection according to manufacturer's instructions. All edd variants showed expression in both soluble and insoluble fractions whereas only the *E. coli* eda variant showed expression in the soluble fraction.

In order to confirm that edd and eda variants were functional in yeast, the combined edd and eda activities were assayed by the formation of pyruvate, coupled to the NADH-dependent activity of lactate dehydrogenase. Transformation of combined edd (in p426GPD) and edd (in p425GPD) constructs was accomplished with the Zymo Research frozen-EZ yeast transformation II kit based on manufacturer's protocol. As a negative control, p425GPD and p426GPD vectors were also transformed into BY4742. Transformants (16 different combinations total including the variant edd and eda combinations plus vector controls) were selected on synthetic dextrose medium (SD) (0.67% yeast nitrogen base-2% dextrose) containing complete amino acids minus uracil and leucine. Transformants of edd and eda variant combinations were inoculated onto 5 ml of SD minus uracil and leucine and cells were grown at about 30° C. in shaker flasks at about 250 rpm for about 24 hours. Fresh overnight culture was used to inoculate about 100 ml of (SD media minus uracil and leucine containing about 0.01 g ergosterol /L and about 400 µl of Tween80) to an initial inoculum $OD_{600nm}$ of about 0.1 and grown anaerobically at about 30° C. for approximately 14 hours until cells reached an $OD_{600nm}$ of 3-4. The cells were centrifuged at about 3000 g for about 10 minutes. The cells were then washed with 25 ml deionized $H_2O$ and centrifuged at 3000 g for 10 min. the cells were resuspended at about 2 ml/g of cell pellet) in lysis buffer (50 mM TrisCl pH7, mM $MgCl_2$, 1× Calbiochem protease inhibitor cocktail set III). Approximately 900 µl of glass beads were added and cells were lysed by vortexing at maximum speed for 4×30 seconds. Cell lysate was removed from the glass beads, placed into fresh tubes and spun at about 10,000 g for about 10 minutes at about 4° C. The supernatant containing whole cell extract (WCE) was transferred to a fresh tube. WCE protein concentrations were measured using the Coomassie Plus Protein Assay (Thermo Scientific) according to the manufacturer's directions. A total of about 750 µg of WCE was used for the edd and eda coupled assay. For this assay, about 750 µg of WCE was mixed with about 2 mM 6-phosphogluconate and about 4.5 U lactate dehydrogenase in a final volume of about 400 µl. A total of about 100 µl of NADH was added to this reaction to a final molarity of about 0.3 mM, and NADH oxidation was monitored for about 10 minutes at about 340 nM using a DU800 spectrophotometer.

ZM4 HR EDA GENE (SEQ ID NO: 145)
ATGAGAGACATTGATTCTGTTATGAGATTGGCTCCAGTTATGCCAGTCT

TGGTTATAGAAGATATAGCTGATGCTAAGCCAATTGCTGAGGCTTTGGT

TGCTGGTGGTTTAAATGTTTTGGAAGTTACATTGAGAACTCCATGTGCT

TTGGAAGCTATTAAAATTATGAAGGAAGTTCCAGGTGCTGTTGTTGGTG

CTGGTACTGTTTTAAACGCTAAAATGTTGGATCAAGCTCAAGAAGCTGG

TTGTGAGTTCTTTGTATCACCAGGTTTGACTGCTGATTTGGGAAAACAT

GCTGTTGCTCAAAAAGCGGCTCTTCTACCAGGGGTTGCTAATGCTGCTG

ATGTTATGTTGGGATTGGATTTGGGTTGGATAGATTTAAATTCTTCCC

AGCTGAAAATATAGGTGGTTTGCCAGCTTTAAAATCTATGGCTTCTGTT

TTTAGACAAGTTAGATTTTGTCCAACTGGAGGAATTACTCCGACTTCTG

GCTCCAAAATATTTGAAAATCCATCTATTTTGTGTGTTGGTGGTTCTTG

GGTTGTTCCAGCGGGTAAACCAGATGTTGCGAAAATTACTGCTTTGGCT

AAAGAGGCTTCAGCTTTTAAAAGAGCTGCTGTGGCGTAG

ZM4 HR EDD GENE (SEQ ID NO: 146)
ATGACGGATTTGCATTCAACTGTTGAGAAAGTAACTGCTAGAGTAATTG

AAAGATCAAGGGAAACTAGAAAGGCTTATTTGGATTTGATACAATATGA

GAGGGAAAAAGGTGTTGATAGACCAAATTTGTCTTGTTCTAATTTGGCT

CATGGTTTTGCTGCTATGAATGGTGATAAACCAGCTTTGAGAGATTTTA

ATAGAATGAATATAGGTGTAGTTACTTCTTATAATGATATGTTGTCTGC

TCATGAACCATATTATAGATATCCAGAACAAATGAAGGTTTTTGCTCGT

GAAGTTGGTGCTACAGTTCAAGTTGCTGGTGGTGTTCCTGCAATGTGTG

ATGGTGTTACTCAAGGTCAACCAGGTATGGAAGAATCTTTGTTTTCCAG

AGATGTAATTGCTTTGGCTACATCTGTTTCATTGTCTCACGGAATGTTT

GAAGGTGCTGCATTGTTGGGAATTTGTGATAAAATTGTTCCAGGTTTGT

TGATGGGTGCTTTGAGGTTCGGTCATTTGCCAACTATTTTGGTTCCATC

TGGTCCAATGACTACTGGAATCCCAAATAAAGAAAAGATTAGAATTAGA

CAATTGTATGCTCAAGGAAAAATTGGTCAAAAGGAATTGTTGGATATGG

AAGCTGCCTGTTATCATGCTGAAGGTACTTGTACTTTTTATGGTACTGC

TAACACTAATCAGATGGTTATGGAAGTTTTGGGTTTGCACATGCCAGGT

AGTGCATTCGTTACTCCAGGTACTCCACTGAGACAGGCTTTGACTAGAG

CTGCTGTTCATAGAGTTGCAGAGTTGGGTTGGAAAGGTGATGATTATAG

ACCTTTGGGTAAAATTATTGATGAGAAATCTATTGTTAATGCTATTGTT

GGTTTGTTAGCTACAGGTGGTTCTACAAATCATACAATGCATATTCCGG

CCATAGCTAGAGCAGCAGGGGTTATAGTTAATTGGAATGATTTTCATGA

TTTGTCTGAAGTTGTTCCATTGATTGCTAGAATTTATCCAAATGGTCCT

AGAGATATAAATGAATTTCAAAATGCAGGAGGAATGGCTTATGTAATTA

AAGAATTGTTGAGTGCGAATTTGTTAAATAGAGATGTTACTACTATTGC

TAAAGGAGGGATAGAAGAATATGCTAAAGCTCCAGCTCTGAACGATGCG

GGTGAATTGGTGTGGAAACGGCTGGCGAACCTGGGGACGACACAATTT

TGAGACCAGTATCTAATCCATTTGCTAAAGATGGTGGTTTGCGTCTCTT

GGAAGGTAATTTGGGTAGAGCAATGTATAAGGCTTCTGCTGTAGATCCA

AAATTCTGGACTATTGAAGCTCCCGTTAGAGTTTTCTCTGATCAAGATG

ATGTTCAAAAGGCTTTTAAAGCAGGCGAGTTAAATAAAGATGTTATAGT

TGTTGTTAGATTTCAAGGTCCTCGTGCTAATGGTATGCCTGAATTGCAT

AAGTTGACTCCTGCGCTAGGCGTATTGCAAGATAATGGTTATAAGGTTG

CTTTAGTTACTGATGGTAGAATGTCTGGTGCAACTGGTAAAGTACCGGT

GGCTCTGCATGTTTCACCAGAGGCTTTAGGAGGTGGGGCGATTGGCAAG

TTGAGAGATGGCGATATAGTTAGAATTTCTGTTGAAGAAGGTAAATTAG

AGGCTCTTGTCCCCGCCGACGAGTGGAATGCTAGACCACATGCTGAGAA

GCCCGCTTTTAGACCTGGTACTGGGAGAGAATTGTTTGACATTTTTAGA

CAAAACGCTGCTAAGGCTGAGGATGGTGCAGTTGCAATTTATGCTGGGG

CAGGGATCTAG

ZM4 MATCHED EDA GENE (SEQ ID NO: 147)
ATGAGGGATATTGATAGTGTGATGAGGTTAGCCCCTGTTATGCCTGTTC

TCGTTATTGAAGATATTGCAGATGCCAAACCTATTGCCGAAGCACTCGT

TGCAGGTGGTCTAAACGTTCTAGAAGTGACACTAAGGACTCCTTGTGCA

CTAGAAGCTATTAAGATTATGAAGGAAGTTCCTGGTGCTGTTGTTGGTG

CTGGTACAGTTCTAAACGCCAAAATGCTCGACCAGGCACAAGAAGCAGG

TTGCGAATTTTTCGTTTCACCTGGTCTAACTGCCGACCTCGGAAAGCAC

GCAGTTGCTCAAAAAGCCGCATTACTACCCGGTGTTGCAAATGCAGCAG

ATGTGATGCTAGGTCTAGACCTAGGTCTAGATAGGTTCAAGTTCTTCCC

TGCCGAAAACATTGGTGGTCTACCTGCTCTAAAGAGTATGGCATCAGTT

ATTCAGGCAGTTAGGTTCTGCCCTACTGGAGGTATAACTCCTACAAGTG

GCACCTAAATATCTAAAAACCCTAGTATTCTATGCGTTGGTGGTTCATG

GGTTGTTCCTGCCGGAAAACCCGATGTTGCCAAAATTACAGCCCTCGCA

AAAGAAGCAAGTGCATTCAAGAGGGCAGCAGTTGCTTAG

ZM4 MATCHED EDD GENE (SEQ ID NO: 148)
ATGACGGATCTACATAGTACAGTGGAGAAGGTTACTGCCAGGGTTATTG

AAAGGAGTAGGGAAACTAGGAAGGCATATCTAGATTTAATTCAATATGA

GAGGGAAAAAGGAGTGGACAGGCCCAACCTAAGTTGTAGCAACCTAGCA

CATGGATTCGCCGCAATGAATGGTGACAAGCCCGCATTAAGGGACTTCA

ACAGGATGAATATTGGAGTTGTGACGAGTTACAACGATATGTTAAGTGC

ACATGAACCCTATTATAGGTATCCTGAGCAAATGAAGGTGTTTGCAAGG

GAAGTTGGAGCCACAGTTCAAGTTGCTGGTGGAGTGCCTGCAATGTGCG

ATGGTGTGACTCAGGGTCAACCTGGAATGGAAGAATCCCTATTTTCAAG

GGATGTTATTGCATTAGCAACTTCAGTTTCATTATCACATGGTATGTTT

GAAGGGGCAGCTCTACTCGGTATATGTGACAAGATTGTTCCTGGTCTAC

TAATGGGAGCACTAAGGTTTGGTCACCTACCTACTATTCTAGTTCCCAG

ATGGACCTATGACAACGGGTATCCTAACAAAGAAAAAATTAGGATTAGG

CAACTCTATGCACAAGGTAAAATTGGACAAAAAGAACTACTAGATATGG

AAGCCGCATGCTACCATGCAGAAGGTACTTGCACTTTCTATGGTACAGC

CAACACTAACCAGATGGTTATGGAAGTTCTCGGTCTACATATGCCCGGT

AGTGCCTTTGTTACTCCTGGTACTCCTCTCAGGCAAGCACTAACTAGGG

CAGCAGTGCATAGGGTTGCAGAATTAGGTTGGAAGGGAGACGATTATAG

GCCTCTAGGTAAAATTATTGACGAAAAAAGTATTGTTAATGCAATTGTT

-continued
GGTCTATTAGCCACTGGTGGTAGTACTAACCATACGATGCATATTCCTG

CTATTGCAAGGGCAGCAGGTGTTATTGTTAACTGGAATGACTTCCATGA

TCTATCAGAAGTTGTTCCTTTAATTGCTAGGATTTACCCTAATGGACCT

AGGGACATTAACGAATTTCAAAATGCCGGAGGAATGGCATATGTTATTA

CAGGAACTACTATCAGCAAATCTACTAAACAGGGATGTTACAATATTGC

TAAGGGAGGTATAGAAGAATACGCTAAGGCACCTGCCCTAAATGATGCA

GGAGAATTAGTTTGGAAGCCCGCAGGAGAACCTGGTGATGACACTATTC

TAAGGCCTGTTTCAAATCCTTTCGCCAAAGATGGAGGTCTAAGGCTCTT

GAGAAGGTAACCTAGAAGGGCCATGTACAAGGCTAGCGCCGTTGATCCT

AAATTCTGGACTATTGAAGCCCCTGTTAGGGTTTTCTCAGACCAGGACG

AATGTTCAAAAAGCCTTCAAGGCAGGAGACTAAACAAAGACGTTATTGT

TGTTGTTAGGTTCCAAGGACCTAGGGCCAACGGTATGCCTGAATTACAT

AAGCTAACTCCTGCATTAGGTGTTCTACAAGATAATGGATACAAAGTTG

CATTAGTGACGGATGGTAGGATGAGTGGTGCAACTGGTAAAGTTCCTGT

TGCATTACATGTTTCACCCGAAGCACTAGGAGGTGGTGCTATTGGTAAA

CTTAGGGATGGAGATATTGTTAGGATTAGTGTTGAAGAAGGAAAACTTG

AAGCACTCGTTCCCGCAGATGAGTGGAATGCAAGGCCTCATGCAGAAAA

ACCTGCATTCAGGCCTGGGACTGGGAGGGAATTATTTGATATTTTCAGG

CAAAATGCAGCAAAAGCAGAAGACGGTGCCGTTGCCATCTATGCCGGTG

CTGGTATATAG

Example 2

Inactivation of the Embden-Meyerhof Pathway in Yeast

*Saccharomyces cerevisiae* strain YGR240CBY4742 was obtained from the ATCC (accession number 4015893). This strain is genetically identical to *S. cerevisiae* strain BY4742, except that YGR420C, the gene encoding the PFK1 enzyme, which is the alpha subunit of heterooctameric phosphofructokinase, has been deleted. A DNA construct designed to delete the gene encoding the PFK2 enzyme via homologous recombination was prepared. This construct substituted the gene encoding HIS3 (imidazoleglycerol-phosphate dehydratase, an enzyme required for synthesis of histidine) for the PFK2 gene. The DNA construct comprised, in the 5' to 3' direction, 100 bases of the 5' end of the open reading frame of PFK2, followed by the HIS3 promoter, HIS3 open reading frame, HIS3 terminator, and 100 bp of the 3' end of the PFK2 open reading frame.

This construct was prepared by two rounds of PCR. In the first round, about 100 ng of BY4742 genomic DNA was used as a template. The genomic DNA was prepared from cells using the Zymo Research Yeastar kit according to the manufacturer's instructions. PCR was performed using the following primers:

(SEQ ID NO: 9)
5'-tgcatattccgttcaatcttataaagctgccatagatttttacacc aagtcgttttaagagcttggtgagcgcta-3'

(SEQ ID NO: 10)
5'-cttgccagtgaatgacctttggcattctcatggaaacttcagttt catagtcgagttcaagagaaaaaaaagaa-3'

The PCR reaction conditions were the same as those set forth in Example 1 for preparing the edd and eda genes.

For the second round of PCR, approximately 1 µl of the first PCR product was used as a template. The second round of PCR reaction was performed with the following primer set:

(SEQ ID NO: 11)
5'-atgactgttactactccttttgtgaatggtacttcttattgtaccgt cactgcatattccgttcaatcttataaa-3'

(SEQ ID NO: 12)
5'-ttaatcaactctctttcttccaaccaaatggtcagcaatgagtctg gtagcttgccagtgaatgacctttggcat-3'

PCR conditions for this reaction were the same as for the first reaction immediately above. The final PCR product was separated by agarose gel electrophoresis, excised, and purified using MP Biomedicals Geneclean II kit according to the manufacturer's instructions.

Approximately 2 µg of the purified DNA was used for transformation of the yeast strain YGR240CBY4742 by lithium acetate procedure as described by Shiestl and Gietz with an additional recovery step added after the heat shock step. Essentially after heat shock, cells were centrifuged at 500×g for 2 min and resuspended in 1 ml of YP-Ethanol (1% yeast extract-2% peptone-2% ethanol) and incubated at 30° C. for 2 hours prior to plating on selective media containing SC-Ethanol (0.67% yeast nitrogen base-2% ethanol) containing complete amino acids minus histidine. The engineered transformant strain referred to as YGR420CBY4742ΔPFK2 has PFK1 and PFK2 genes deleted and is an auxotroph for leucine, uracil and lysine.

The YGR420CBY4742ΔPFK2 strain was used for transformation of the combination of edd-p426 GPD (edd variants in p426 GPD) and eda-p425 GPD (eda variants in p425 GPD) variant constructs. A total of 16 combinations of edd-p426 GPD and eda-p425 GPD variant constructs were tested. Each combination was transformed into YGR420CBY4742ΔPFK2. For all transformation, 1 µg of edd-p426 GPD and 1 µg of eda-p425 GPD was used. All transformants from each edd-p426 GPD and eda-p425 GPD construct combination were selected on SC-Ethanol (0.67% yeast nitrogen base-2% ethanol) containing complete amino acids minus uracil and leucine.

To confirm that the edd and eda variants are functional in yeast, a complementation test for growth of YGR420CBY4742ΔPFK2 strain on YPD (1% yeast extract-2% peptone-2% dextrose) and YPGluconate (1% yeast extract-2% peptone-2% gluconate) was performed. Viable colonies of edd-p426 GPD and eda-p425 GPD variant construct combinations grown on SC-Ethanol minus uracil and leucine were patched to plates containing SC-ethanol minus uracil and leucine and incubated at 30° C. for 48 hrs. These patches were used to inoculate 5 ml of YPD media to an initial inoculum $OD_{600nm}$ of 0.1 and the cells were grown anaerobically at 30° C. for 3 to 7 days.

Example 3

Preparation of Carbon Dioxide Fixing Yeast Cells

Total genomic DNA from *Zymomonas mobilis* was obtained from ATCC (ATCC Number 31821). The *Z. mobilis* gene encoding the enzyme phosphoenolpyruvate carboxylase ("PEP carboxylase") was isolated from this genomic DNA and cloned using PCR amplification. PCR was performed in a total volume of about 50 micro-liters in the presence of about 20 nanograms of Z. mobilis genomic DNA, about 0.2 mM of 5' forward primer, about 0.2 mM of 3' reverse primer, about 0.2 mM of dNTP, about 1 micro-liter of pfu Ultra II DNA polymerase (Stratagene, La Jolla, Calif.), and 1×PCR buffer (Stratagene, La Jolla, Calif.). PCR was carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed by Step Three "72° C. for 5 minutes" for 1 cycle, and then Step Four "4° C. Hold" to stop the reaction. The primers for the PCR reaction were:

(SEQ ID NO: 13)
5'GACTAACTGAACTAGTAAAAAAATGACCAAGCCGCGCACAATTAATC

AG-3'

(SEQ ID NO: 14)
5'AAGTGAGTAACTCGAGTTATTAACCGCTGTTGCGAAGTGCCGTCGC-
3'

The DNA sequence of native Z. Mobilis PEP carboxylase is set forth as SEQ ID NO:20.

The cloned gene was inserted into the vector pGPD426 (ATCC Number: 87361) in between the SpeI and XhoI sites. The final plasmid containing the PEP carboxylase gene was named pGPD426 PEPC.

Separately, a similar plasmid, referred to as pGPD426 N-his PEPC was constructed to insert a six-histidine tag (SEQ ID NO: 138) at the N-terminus of the PEPC sequence for protein expression verification in yeast. This plasmid was constructed using two rounds of PCR to extend the 5' end of the PEPC gene to incorporate a six-histidine tag (SEQ ID NO: 138) at the N-terminus of the PEPC protein. The two 5' forward primers used sequentially were:

(SEQ ID NO: 15)
5'ATGTCTCATCATCATCATCATCATACCAAGCCGCGCACAATTAATCA

GAAC-3'
and (SEQ ID NO: 16)
5'GACTAACTGAACTAGTAAAAAAATGTCTCATCATCATCATCATCATA

CCAAG-3'

The same 3' primer was used as described above. The PCR was performed in a total volume of about 50 micro-liters in the presence of about 20 nanograms of Z. Mobilis PEP carboxylase polynucleotide, about 0.2 mM of 5' forward primer, about 0.2 mM of 3' reverse primer, about 0.2 mM of dNTP, about 1 micro-liter of pfu Ultra II DNA polymerase (Stratagene, La Jolla, Calif.), and 1×PCR buffer (Stratagene, La Jolla, Calif.). The PCR was carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed Step Three "72° C. for 5 minutes" for 1 cycle, and then Step Four "4° C. Hold" to stop the reaction.

To increase protein expression level of Z. Mobilis PEP carboxylase in yeast, the PEPC coding sequence was optimized to incorporate frequently used codons obtained from yeast glycolytic genes. The resulting PEP carboxylase amino acid sequence remains identical to the wild type.

The codon optimized PEP carboxylase DNA sequence was ordered from IDT and was inserted into the vector pGPD426 at the SpeI and XhoI site. The final plasmid containing the codon optimized PEP carboxylase gene was named pGPD426 PEPC_opti. A similar plasmid, named pGPD426 N-his PEPC_opti was constructed to insert a six-histidine tag (SEQ ID NO: 138) at the N-terminus of the optimized PEPC gene for protein expression verification in yeast.

To construct pGPD426 N-his PEPC_opti, two rounds of PCR were performed to extend the 5' end of the codon optimized PEPC gene to incorporate the six-histidine tag (SEQ ID NO: 138) at the N-terminus of the PEPC protein. Two 5' forward primers used in sequential order were:

(SEQ ID NO: 17)
5'ATGTCTCATCATCATCATCATCATATGACCAAGCCAAGAACTATTAAC

CAAAACCC-3'
and (SEQ ID NO: 18)
5'GACTAACTGAACTAGTAAAAAAATGTCTCATCATCATCATCATCATAT

GACCAAGCCAAG 3'

The 3' reverse primer sequence used for both PCR reactions was:

(SEQ ID NO: 19)
5'AAGTGAGTAACTCGAGTTATTAACCGGAGTTTCTCAAAGCAGTAGCGA

TAG3'

Both PCR reactions were performed in a total volume of about 50 micro-liters in the presence of about 20 nanograms of the codon optimized PEP carboxylase polynucleotide, about 0.2 mM of 5' forward primer, about 0.2 mM of 3' reverse primer, about 0.2 mM of dNTP, about 1 micro-liter of pfu UltraII DNA polymerase (Stratagene, La Jolla, Calif.), and 1×PCR buffer (Stratagene, La Jolla, Calif.). PCR reactions were carried out in a thermocycler using the following program: Step One "95° C. for 10 minutes" for 1 cycle, followed by Step Two "95° C. for 20 seconds, 65° C. for 30 seconds, and 72° C. for 45 seconds" for 35 cycles, followed Step Three "72° C. for 5 minutes" for 1 cycle, and then Step Four "4° C. Hold" to stop the reaction.

Saccharomyces cerevisiae strain BY4742 was cultured in YPD medium to an OD of about 1.0, and then prepared for transformation using the Frozen-EZ Yeast Transformation II kit (Zymo Research, Orange, Calif.) and following the manufacturer's instructions. Approximately 500 micrograms of each plasmid was added to the cells, and transformation was accomplished by addition of PEG solution ("Solution 3" in the Frozen-EZ Yeast Transformation II kit) and incubation at about 30° C. for an hour. After transformation, the cells were plated on synthetic complete medium (described in Example IV below) minus uracil (sc-ura) medium, grown for about 48 hours at about 30° C., and transformants were selected based on auxotrophic complementation.

Following a similar procedure, the same plasmids were individually transformed using the procedure described above into the following yeast mutant strains: YKR097W (ATCC Number 4016013, ΔPCK, in the phosphoenolpyruvate carboxykinase gene is deleted), YGL062W (ATCC Number 4014429, ΔPYC1, in which the pyruvate carboxylase 1 gene is deleted), and YBR218c (ATCC Number 4013358, ΔPYC2, in which the pyruvate carboxylase 2 gene is deleted).

The transformed yeast cells were grown aerobically in a shake flask in synthetic complete medium minus uracil (see Example IV) containing 1% glucose to mid-log phase (an OD of 2.0). The mid-log phase cultures were then used to inoculate a fresh culture (in sc-ura medium with 1% glucose) to an initial OD of 0.1 at which time the cultures were then grown anaerobically in a serum bottle. Culture samples were drawn periodically to monitor the level of glucose consumption and ethanol production.

DNA sequence of the native Z. mobilis PEP carboxylase gene (SEQ ID NO:20):

ACTAGTAAAAAAATGACCAAGCCGCGCACAATTAATCAGAACCCAGACCT
TCGCTATTTTGGTAACCTGCTCGGTCAGGTTATTAAGGAACAAGGCGGA
GAGTCTTTATTCAACCAGATCGAGCAAATTCGCTCTGCCGCGATTAGAC
GCCATCGGGGTATTGTTGACAGCACCGAGCTAAGTTCTCGCTTAGCCGA
TCTCGACCTTAATGACATGTTCTCTTTTGCACATGCCTTTTTGCTGTTT
TCAATGCTGGCCAATTTGGCTGATGATCGTCAGGGAGATGCCCTTGATC
CTGATGCCAATATGGCAAGTGCCCTTAAGGACATAAAAGCCAAAGGCGT
CAGTCAGCAGGCGATCATTGATATGATCGACAAAGCCTGCATTGTGCCT
GTTCTGACAGCACATCCGACCGAAGTCCGTCGGAAAAGTATGCTTGACC
ATTATAATCGCATTGCAGGTTTAATGCGGTTAAAAGATGCTGGACAAAC
GGTGACCGAAGATGGTCTTCCGATCGAAGATGCGTTAATCCAGCAAATC
ACGATATTATGGCAGACTCGTCCGCTCATGCTGCAAAAGCTGACCGTGG
CTGATGAAATCGAAACTGCCCTGTCTTTCTTAAGAGAAACTTTTCTGCC
TGTTCTGCCCCAGATTTATGCAGAATGGGAAAAATTGCTTGGTAGTTCT
ATTCCAAGCTTTATCAGACCTGGTAATTGGATTGGTGGTGACCGTGACG
GTAACCCCAATGTCAATGCCGATACGATCATGCTGTCTTTGAAGCGCAG
CTCGGAAACGGTATTGACGGATTATCTCAACCGTCTTGATAAACTGCTT
TCCAACCTTTCGGTCTCAACCGATATGGTTTCGGTATCCGATGATATTC
TACGTCTAGCCGATAAAGTGGTGACGATGCTGCGATCCGTGCGGATGA
ACCTTATCGTCGTGCCTTAAATGGTATTTATGACCGTTTAGCCGCTACC
TATCGTCAGATCGCCGGTCGCAACCCTTCGCGCCCAGCCTTGCGTTCTG
CAGAAGCCTATAAACGGCCTCAAGAATTGCTGGCTGATTTGAAGACCTT
GGCCGAAGGCTTGGGTAAATTGGCAGAAGGTAGTTTTAAGGCATTGATC
CGTTCGGTTGAAACCTTTGGTTTCCATTTGGCCACCCTCGATCTGCGTC
AGAATTCGCAGGTTCATGAAAGAGTTGTCAATGAACTGCTACGGACAGC
CACCGTTGAAGCCGATTATTTATCTCTATCGGAAGAAGATCGCGTTAAG
CTGTTAAGACGGGAATTGTCGCAGCCGCGGACTCTATTCGTTCCGCGCG
CCGATTATTCCGAAGAAACGCGTTCTGAACTTGATATTATTCAGGCAGC
AGCCCGCGCCCATGAAATTTTGGCCCTGAATCCATTACGACTTATTTG
ATTTCGAATGGCGAAAGCATTTCCGATATTCTGGAAGTCTATTTGCTTT
TGAAAGAAGCAGGGCTGTATCAAGGGGGTGCTAAGCCAAAAGCGGCGAT
TGAAGCTGCGCCTTTATTCGAGACGGTGGCCGATCTTGAAAATGCGCCA
AAGGTCATGGAGGAATGGTTCAAGCTGCCTGAAGCGCAAGCCATTGCAA
AGGCACATGGCGTTCAGGAAGTGATGGTTGGCTATTCTGACTCCAATAA
GGACGGCGGATATCTGACCTCGGTTTGGGGTCTTTATAAGGCTTGCCTC
GCTTTGGTGCCGATTTTTGAGAAAGCCGGTGTACCGATCCAGTTTTTCC
ATGGACGGGGTGGTTCCGTTGGTCGCGGTGGTGGTTCCAACTTTAATGC
CATTCTGTCGCAGCCAGCCGGAGCCGTCAAAGGGCGTATCCGTTATACA
GAACAGGGTGAAGTCGTGGCGGCCAAATATGGCACCCATGAAAGCGCTA
TTGCCCATCTGGATGAGGCCGTAGCGGCGACTTTGATTACGTCTTTGGA
AGCACCGACCATTGTCGAGCCAGAGTTTAGTCGTTACCGTAAGGCCTTG
GATCAGATCTCAGATTCAGCTTTCCAGGCCTATCGCCAATTGGTCTATG
GAACGAAGGGCTTCCGTAAATTCTTTAGTGAATTTACGCCTTTGCCGGA
AATTGCCCTGTTAAAGATCGGGTCACGCCCACCTAGCCGCAAAAAATCC
GACCGGATTGAAGATCTACGCGCTATTCCTTGGGTGTTTAGCTGGTCTC
AAGTTCGAGTCATGTTACCCGGTTGGTTCGGTTTCGGTCAGGCTTTATA
TGACTTTGAAGATACCGAGCTGTTACAGGAAATGGCAAGCCGTTGGCCG
TTTTTCCGCACGACTATTCGGAATATGGAACAGGTGATGGCACGTTCCG
ATATGACGATCGCCAAGCATTATCTGGCCTTGGTTGAGGATCAGACAAA
TGGTGAGGCTATCTATGATTCTATCGCGGATGGCTGGAATAAAGGTTGT
GAAGGTCTGTTAAAGGCAACCCAGCAGAATTGGCTGTTGGAACGCTTTC
CGGCGGTTGATAATTCGGTGCAGATCGTCGGCCTTATCTGGAACCGCT
TAATTACTTACAGGTCGAATTGCTGAAGAAATGGCGGGGAGGTGATACC
AACCCGCATATCCTCGAATCTATTCAGCTGACAATCAATGCCATTGCGA
CGGCACTTCGCAACAGCGGTTAATAACTCGAG

DNA sequence of the codon optimized PEP carboxylase gene (SEQ ID NO:21):

ACTAGTAAAAAAATGACCAAGCCAAGAACTATTAACCAAAACCCAGACT
TGAGATACTTCGGTAACTTGTTGGGTCAAGTTATCAAGGAACAAGGTGG
TGAATCTTTGTTCAACCAAATTGAACAAATCAGATCCGCTGCTATTAGA
AGACACAGAGGTATCGTCGACTCTACCGAATTGTCCTCTAGATTGGCTG
ACTTGGACTTGAACGACATGTTCTCCTTCGCTCACGCTTTCTTGTTGTT
CTCTATGTTGGCTAACTTGGCTGACGACAGACAAGGTGACGCTTTGGAC
CCAGACGCTAACATGGCTTCCGCTTTGAAGGACATTAAGGCTAAGGGTG
TTTCTCAACAAGCTATCATTGACATGATCGACAAGGCTTGTATTGTCCC
AGTTTTGACTGCTCACCCAACCGAAGTCAGAAGAAAGTCCATGTTGGAC
CACTACAACAGAATCGCTGGTTTGATGAGATTGAAGGACGCTGGTCAAA
CTGTTACCGAAGACGGTTTGCCAATTGAAGACGCTTTGATCCAACAAAT
TACTATCTTGTGGCAAACCAGACCATTGATGTTGCAAAAGTTGACTGTC
GCTGACGAAATTGAAACCGCTTTGTCTTTCTTGAGAGAAACTTTCTTGC
CAGTTTTGCCACAAATCTACGCTGAATGGGAAAAGTTGTTGGGTTCCTC
TTATTCCATCCTCATCAGACCAGGTAACTGGATTGGTGGTGACAGAGAC
GGTAACCCAAACGTCAACGCTGACACCATCATGTTGTCTTTGAAGAGAT

```
CCTCTGAAACTGTTTTGACCGACTACTTGAACAGATTGGACAAGTTGTT

GTCCAACTTGTCTGTCTCCACTGACATGGTTTCTGTCTCCGACGACATT

TTGAGATTGGCTGACAAGTCTGGTGACGACGCTGCTATCAGAGCTGACG

AACCATACAGAAGAGCTTTGAACGGTATTTACGACAGATTGGCTGCTAC

CTACAGACAAATCGCTGGTAGAAACCCATCCAGACCAGCTTTGAGATCT

GCTGAAGCTTACAAGAGACCACAAGAATTGTTGGCTGACTTGAAGCTT

TGGCTGAAGGTTTGGGTAAGTTGGCTGAAGGTTCCTTCAAGGCTTTGAT

TAGATCTGTTGAAACCTTCGGTTTCCACTTGGCTACTTTGGACTTGAGA

CAAAACTCCCAAGTCCACGAAAGAGTTGTCAACGAATTGTTGAGAACCG

CTACTGTTGAAGCTGACTACTTGTCTTTGTCCGAAGAAGACAGAGTCAA

GTTGTTGAGAAGAGAATTGTCTCAACCAAGAACCTTGTTCGTTCCAAGA

GCTGACTACTCCGAAGAAACTAGATCTGAATTGGACATCATTCAAGCTG

CTGCTAGAGCTCACGAAATCTTCGGTCCAGAATCCATTACCACTTACTT

GATCTCTAACGGTGAATCCATTTCTGACATCTTGGAAGTCTACTTGTTG

TTGAAGGAAGCTGGTTTGTACCAAGGTGGTGCTAAGCCAAAGGCTGCTA

TTGAAGCTGCTCCATTGTTCGAAACCGTTGCTGACTTGGAAAACGCTCC

AAAGGTCATGGAAGAATGGTTCAAGTTGCCAGAAGCTCAAGCTATCGCT

AAGGCTCACGGTGTTCAAGAAGTCATGGTTGGTTACTCCGACTCTAACA

AGGACGGTGGTTACTTGACTTCCGTCTGGGGTTTGTACAAGGCTTGTTT

GGCTTTGGTTCCAATTTTCGAAAAGGCTGGTGTCCCAATCCAATTCTTC

CACGGTAGAGGTGGTTCTGTTGGTAGAGGTGGTGGTTCCAACTTCAACG

CTATTTTGTCTCAACCAGCTGGTGCTGTCAAGGGTAGAATCAGATACAC

CGAACAAGGTGAAGTTGTCGCTGCTAAGTACGGTACTCACGAATCCGCT

ATTGCTCACTTGGACGAAGCTGTTGCTGCTACCTTGATCACTTCTTTGG

AAGCTCCAACCATTGTCGAACCAGAATTCTCCAGATACAGAAAGGCTTT

GGACCAAATCTCTGACTCCGCTTTCCAAGCTTACAGACAATTGGTTTAC

GGTACTAAGGGTTTCAGAAAGTTCTTCTCTGAATTCACCCCATTGCCAG

AAATTGCTTTGTTGAAGATCGGTTCCAGACCACCATCTAGAAAGAAGTC

CGACAGAATTGAAGACTTGAGAGCTATCCCATGGGTCTTCTCTTGGTCC

CAAGTTAGAGTCATGTTGCCAGGTTGGTTCGGTTTCGGTCAAGCTTTGT

ACGACTTCGAAGACACTGAATTGTTGCAAGAAATGGCTTCTAGATGGCC

ATTCTTCAGAACCACTATTAGAAACATGGAACAAGTTATGGCTAGATCC

GACATGACCATCGCTAAGCACTACTTGGCTTTGGTCGAAGACCAAACTA

ACGGTGAAGCTATTTACGACTCTATCGCTGACGGTTGGAACAAGGGTTG

TGAAGGTTTGTTGAAGGCTACCCAACAAAACTGGTTGTTGGAAAGATTC

CCAGCTGTTGACAACTCCGTCCAAATGAGAAGACCATACTTGGAACCAT

TGAACTACTTGCAAGTTGAATTGTTGAAGAAGTGGAGAGGTGGTGACAC

TAACCCACACATTTTGGAATCTATCCAATTGACCATTAACGCTATCGCT

ACTGCTTTGAGAAACTCCGGTTAATAACTCGAG
```

Example 4

Production of Pentose Sugar Utilizing Yeast Cells

The full length gene encoding the enzyme xylose isomerase from *Ruminococcus flavefaciens* strain 17 (also known as *Ruminococcus flavefaciens* strain Siijpesteijn 1948) with a substitution at position 513 (in which cytidine was replaced by guanidine) was synthesized by Integrated DNA Technologies, Inc. ("IDT", Coralville, Iowa; www.idtdna.com). The sequence of this gene is set forth below as SEQ ID NO:22.

SEQ ID NO: 22

```
atggaatttttcagcaatatcggtaaaattcagtatcagggaccaaaaagtactgatcctctctcatttaagtactataaccctgaagaagtca tcaacggaaagacaatgcgcgagcatctgaagttcgctcttcatggtggcacacaatgggcggcgacggaacagatatgttcggctgc ggcacaacagacaagacctggggacagtccgatcccgctgcaagagcaaaggctaaggttgacgcagcattcgagatcatggataa gctctccattgactactattgtttccacgatcgcgatctttctcccgagtatggcagcctcaaggctaccaacgatcagcttgacatagttacag actatatcaaggagaagcagggcgacaagttcaagtgcctctggggtacagcaaagtgcttcgatcatccaagattcatgcacggtgca ggtacatctccttctgctgatgtattcgcttctcagctgctcagatcaagaaggctctGgagtcaacagtaaagctcggcggtaacggttac gttttctggggcggacgtgaaggctatgagacacttcttaatacaaatatgggactcgaactcgacaatatggctcgtcttatgaagatggct gttgagtatggacgttcgatcggcttcaagggcgacttctatatcgagcccaagcccaaggagcccacaaagcatcagtacgatttcgata cagctactgttctgggattcctcagaaagtacggtctcgataaggatttcaagatgaatatcgaagctaaccacgctacacttgctcagcata cattccagcatgagctccgtgttgcaagagacaatggtgtgttcggttctatcgacgcaaaccagggcgacgttcttcttggatgggataca gaccagttcccacacaaatatctacgatacaacaatgtgtatgtatgaagttatcaaggcaggcggcttcacaaacggcggtctcaacttcg acgctaaggcacgcagagggagcttcactcccgaggatatcttctacagctatatcgcaggtatggatgcatttgctctgggcttcagagct gctctcaagcttatcgaagacggacgtatcgacaagttcgttgctgacagatacgcttcatggaataccggtatcggtgcagacataatcgc aggtaaggcagatttcgcatctcttgaaaagtatgctcttgaaaagggcgaggttacagcttcactctcaagcggcagacaggaaatgctg gagtctatcgtaaataacgttcttttcagtctgtaa
```

Separately, PCR was conducted to add a DNA sequence encoding 6 histidines (SEQ ID NO: 138) to the 3' terminus of this gene.

Two variants designed to remove the translational pauses in the gene were prepared using the DNA self-assembly method of Larsen et al., supra. One variant contained DNA sequence encoding a 6-hisitidine tag (SEQ ID NO: 138) at the 5' terminus, and the other version did not. The annealing temperature for the self assembly reactions was about 48 degrees Celsius. This gene variant is referred to as a "Hot Rod" or "HR" gene variant. The sequence of this HR gene is set forth below as SEQ ID NO: 23:

```
                                            SEQ ID NO: 23
ATGGAGTTCTTTTCTAATATAGGTAAAATTCAGTATCAAGGTCCAAAATC

TACAGATCCATTGTCTTTTAAATATTATAATCCAGAAGAAGTTATAAATG

GTAAAACTATGAGAGAACATTTAAAATTTGCTTTGTCTTGGTGGCATACT

ATGGGTGGTGATGGTACTGATATGTTCGGTTGTGGTACTACTGATAAAAC

TTGGGGTCAATCTGATCCAGCTGCTAGAGCAAAAGCCAAAGTAGATGCAG

CCTTTGAAATTATGGATAAATTGTCTATTGATTATTATTGTTTTCATGAT

AGAGATTTGTCTCCTGAATATGGTTCTTTAAAAGCAACTAATGATCAATT

GGACATTGTTACGGATTATATTAAAGAAAAACAAGGTGATAAATTTAAAT

GTTTGTGGGCACTGCGAAATGTTTTGATCATCCACGTTTTATGCATGGT

GCGGGGACGAGTCCTTCTGCTGATGTTTTTGCTTTTTCTGCCGCTCAAAT

TAAGAAGGCATTGGAATCAACTGTTAAATTAGGTGGGAACGGGTATGTAT

TCTGGGGAGGAAGGGAAGGTTATGAAACATTATTAAACACTAATATGGGT

TTGGAATTGGATAATATGGCTAGATTGATGAAAATGGCTGTAGAATACGG

AAGGTCTATTGGTTTTAAGGGTGACTTTTATATTGAACCAAAACCTAAAG

AGCCTACTAAACATCAATATGATTTTGATACTGCTACAGTTTTGGGATTC

TTGAGAAAATATGGTCTGGATAAAGATTTTAAAATGAATATAGAAGCTAA

TCATGCAACACTCGCACAACATACTTTTCAACATGAATTGAGAGTTGCCA

GAGATAACGGAGTTTTTGGATCTATCGATGCAAACCAGGGAGACGTTTTG

CTAGGATGGGATACTGATCAATTTCCAACTAACATTTATGATACTACTAT

GTGTATGTATGAAGTAATTAAGGCAGGAGGCTTTACTAATGGCGGATTAA
```

-continued

```
ACTTTGATGCGAAGGCTAGGCGTGGTAGTTTCACTCCAGAGGATATATTC

TATTCTTATATTGCTGGAATGGATGCTTTCGCGTTAGGTTTCAGGGCAGC

ACTAAAATTGATTGAAGATGGTAGAATTGATAAGTTTGTAGCTGATAGAT

ATGCTTCTTGGAATACTGGAATAGGAGCAGATATAATCGCTGGGAAAGCC

GACTTCGCCAGTCTGGAAAAATATGCGCTTGAAAAAGGAGAAGTTACTGC

CAGCTTAAGTTCCGGTCGTCAAGAAATGTTGGAATCTATTGTAAACAATG

TTTTATTTTCTCTG
```

For cloning purposes, PCR was used to engineer a unique SpeI restriction site into the 5' end of each of the xylose isomerase genes, and to engineer a unique XhoI restriction site at the 3' end. In addition, a version of each gene was created that contained a 6-HIS tag (SEQ ID NO: 138) at the 3' end of each gene to enable detection of the proteins using Western analysis.

PCR amplifications were performed in about 50 μl reactions containing 1×PfuII Ultra reaction buffer (Stratagene, San Diego, Calif.), 0.2 mM dNTPs, 0.2 μM specific 5' and 3' primers, and 1 U PfuUltra II polymerase (Stratagene, San Diego, Calif.). The reactions were cycled at 95° C. for 10 minutes, followed by 30 rounds of amplification (95° C. for 30 seconds, 62° C. for 30 seconds, 72° C. for 30 seconds) and a final extension incubation at 72° C. for 5 minutes. Amplified PCR products were cloned into pCR Blunt II TOPO (Life Sciences, Carlsbad, Calif.) and confirmed by sequencing (GeneWiz, La Jolla, Calif.). The PCR primers for these reactions were:

(SEQ ID NO: 26)
5'ACTTGACTACTAGTATGGAGTTCTTTTCTAATATAGGTAAAATT

3' (without the His tag):
(SEQ ID NO: 27)
AGTCAAGTCTCGAGCAGAGAAAATAAAACATTGTTTACAATAGA 3' (with the His tag):
(SEQ ID NO: 28)
AGTCAAGTCTCGAGCTAATGATGATGATGATGCAGAGAAAATAAAAC
ATTGTTTAC Separately, the xylose isomerase gene from *Piromyces*, strain E2 (Harhangi et al., *Arch. Microbiol.*, 180(2): 134-141 (2003)) was synthesized by IDT. The sequence of this gene is set forth below as

```
  1 atggctaagg aatatttccc acaaattcaa aagattaagt tcgaaggtaa ggattctaag 61 aatccattag ccttccacta ctacgatgct gaaaaggaag tcatgggtaa gaaaatgaag 121 gattggttac gtttcgccat ggcctggtgg cacactcttt gcgccgaagg tgctgaccaa 181 ttcggtggag gtacaaagtc tttcccatgg aacgaaggta ctgatgctat tgaaattgcc 241 aagcaaaagg ttgatgctgg tttcgaaatc atgcaaaagc ttggtattcc atactactgt 301 ttccacgatg ttgatcttgt ttccgaaggt aactctattg aagaatacga atccaacctt 361 aaggctgtcg ttgcttacct caaggaaaag caaaaggaaa ccggtattaa gcttctctgg 421 agtactgcta acgtcttcgg tcacaagcgt tacatgaacg gtgcctccac taacccagac 481 tttgatgttg tcgcccgtgc tattgttcaa attaagaacg ccatagacgc cggtattgaa 541 cttggtgctg aaaactacgt cttctggggt ggtcgtgaag gttacatgag tctccttaac 601 actgaccaaa agcgtgaaaa ggaacacatg gccactatgc ttaccatggc tcgtgactac
```

-continued

```
 661 gctcgttcca agggattcaa gggtactttc ctcattgaac caaagccaat ggaaccaacc 721 aagcaccaat acgatgttga cactgaaacc gctattggtt tccttaaggc ccacaactta 781 gacaaggact tcaaggtcaa cattgaagtt aaccacgcta ctcttgctgg tcacactttc 841 gaacacgaac ttgcctgtgc tgttgatgct ggtatgctcg gttccattga tgctaaccgt 901 ggtgactacc aaaacggttg ggatactgat caattcccaa ttgatcaata cgaactcgtc 961 caagcttgga tggaaatcat ccgtggtggt ggtttcgtta ctggtggtac caacttcgat 1021 gccaagactc gtcgtaactc tactgacctc gaagacatca tcattgccca cgtttctggt 1081 atggatgcta tggctcgtgc tcttgaaaac gctgccaagc tcctccaaga atctccatac 1141 accaagatga agaaggaacg ttacgcttcc ttcgacagtg gtattggtaa ggactttgaa 1201 gatggtaagc tcaccctcga acaagtttac gaatacggta agaagaacgg tgaaccaaag 1261 caaacttctg gtaagcaaga actctacgaa gctattgttg ccatgtacca ataa
```

Two hot rod ("HR") versions of the *Piromyces* xylose isomerase gene were prepared using the method of Larsen et al., supra. One version contained DNA sequence encoding a 6-histidine tag (SEQ ID NO: 138) at the 5' terminus and the other did not. The annealing temperature for the self-assembling oligonucleotides was about 48 degrees Celsius. The sequence of this gene is set forth below as

SEQ ID NO: 25

```
ATGGCTAAAGAATATTTTCCACAAATTCAGAAAATTAAATTTGAAGGTAAAGATTCTAAAAATCCATTGGCTTTCCATTA
TTATGATGCTGAAAAAGAAGTTATGGGTAAAAAGATGAAAGATTGGTTGAGATTCGCTATGGCTTGGTGGCATACTCTAT
GTGCTGAAGGAGCTGATCAATTTGGAGGAGGTACTAAATCTTTTCCTTGGAATGAAGGTACTGACGCTATTGAAATTGCT
AAGCAGAAAGTAGACGCGGGTTTTGAAATTATGCAAAAATTGGGAATACCATATTATTGTTTTCATGATGTTGATTTGGT
ATCTGAGGGTAATTCTATTGAAGAATATGAATCTAATTTAAAAGCTGTTGTTGCTTACTTAAAAGAAAAACAAAAGAAA
CTGGAATTAAATTGTTGTGGTCTACAGCTAATGTTTTCGGTCATAAAAGATATATGAATGGTGCTTCTACAAATCCAGAT
TTTGATGTTGTAGCTAGAGCTATTGTTCAAATTAAAAATGCTATAGATGCAGGAATTGAATTAGGTGCCGAAAATTATGT
TTTCTGGGGAGGTAGAGAAGGTTATATGTCTTTGTTAAATACTGATCAAAAACGTGAAAAGGAACACATGGCAACTATGT
TGACAATGGCTAGGGATTATGCTAGATCTAAAGGTTTTAAAGGTACTTTCTTGATTGAGCCAAAACCTATGGAACCAACT
AAACATCAATATGACGTTGACACTGAAACTGCTATTGGTTTCTTAAAAGCTCATAATTTGGATAAAGATTTTAAGGTTAA
TATAGAAGTTAATCATGCTACACTAGCTGGTCATACTTTTGAACATGAATTAGCTTGTGCAGTTGATGCCGGTATGTTAG
GTTCTATCGACGCAAATAGAGGTGATTATCAAAATGGTTGGGACACAGATCAATTTCCAATAGATCAATATGAATTGGTT
CAAGCATGGATGGAAATTATTAGGGGTGGAGGCTTCGTTACAGGTGGAACTAATTTTGATGCTAAAACTAGGAGAAATTC
TACAGATCTTGAAGATATAATTATTGCTCATGTATCTGGTATGGATGCGATGGCCCGTGCTTTGGAAAATGCAGCTAAAT
TACTTCAAGAATCTCCTTATACTAAAATGAAAAAGGAAAGATATGCTTCTTTTGATTCTGGAATAGGTAAGGATTTTGAA
GATGGTAAATTGACATTGGAACAAGTTTATGAATATGGTAAGAAGAATGGAGAACCAAAACAAACTTCTGGTAAACAAGA
ATTATATGAGGCTATAGTAGCTATGTATCAAtaa.
```

For cloning purposes, a unique SpeI restriction site was engineered at the 5' end of each of the XI genes, and a unique XhoI restriction site was engineered at the 3' end. When needed, a 6-HIS tag (SEQ ID NO: 138) was engineered at the 3' end of each gene sequence to enable detection of the proteins using Western analysis. The primers are listed in Table X. PCR amplifications were performed in 50 μl reactions containing 1×PfuII Ultra reaction buffer (Stratagene, San Diego, Calif.), 0.2 mM dNTPs, 0.2 μM specific 5' and 3' primers, and 1 U PfuUltra II polymerase (Stratagene, San Diego, Calif.). The reactions were cycled at 95° C. for 10 minutes, followed by 30 rounds of amplification (95° C. for 30 seconds, 62° C. for 30 seconds, 72° C. for 30 seconds) and a final extension incubation at 72° C. for 5 minutes. Amplified PCR products were cloned into pCR Blunt II TOPO (Life Sciences, Carlsbad, Calif.) and confirmed by sequencing (GeneWiz, La Jolla, Calif.).

The primers used for PCR were:

5' (native gene)
(SEQ ID NO: 149)
ACTAGTATGGCTAAGGAATATTTCCCACAAATTCAAAAG

3' (native gene)
(SEQ ID NO: 150)
CTCGAGCTACTATTGGTACATGGCAACAATAGC

3' (native gene plus His tag)
(SEQ ID NO: 151)
CTCGAGCTACTAATGATGATGATGATGATGTTGGTACATGGCAACAATAG
CTTCG 5' (hot rod gene)
(SEQ ID NO: 152)
ACTAGTATGGCTAAAGAATATTTTCCACAAATTCAG 3' (hot rod gene)
(SEQ ID NO: 153)
CTCGAGTTATTGATACATAGCTACTATAGCCTC 3' (hot rod gene plus His tag)
(SEQ ID NO: 154)
CTCGAGTTAATGATGATGATGATGATGTTGATACATAGCTACTATAGCCT
CATTGTTTAC The genes encoding the native and HR versions of xylose isomerase were separately inserted into the vector p426GDP (ATCC catalog number 87361).

*Saccharomyces cerevisiae* strain BY4742 cells (ATCC catalog number 201389) were cultured in YPD media (10 g Yeast Extract, 20 g Bacto-Peptone, 20 g Glucose, 1 L total) at about 30° C. Separate aliquots of the cells were transformed with the plasmid constructs containing the various xylose isomerase constructs or with the vector alone. Transformation was accomplished using the Zymo kit (Catalog number T2001; Zymo Research Corp., Orange, Calif. 92867) using about 1 µg plasmid DNA and cultured on SC media (set forth below) containing glucose but no uracil (20 g glucose; 2.21 g SC dry mix, 6.7 g Yeast Nitrogen Base, 1 L total) for 2-3 days at about 30° C.

Synthetic Complete Medium mix (minus uracil) contained:

| | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 2.63 g | Leucine |
| 0.9 g | Lysine |
| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 1.2 g | Valine |

Figure 7:
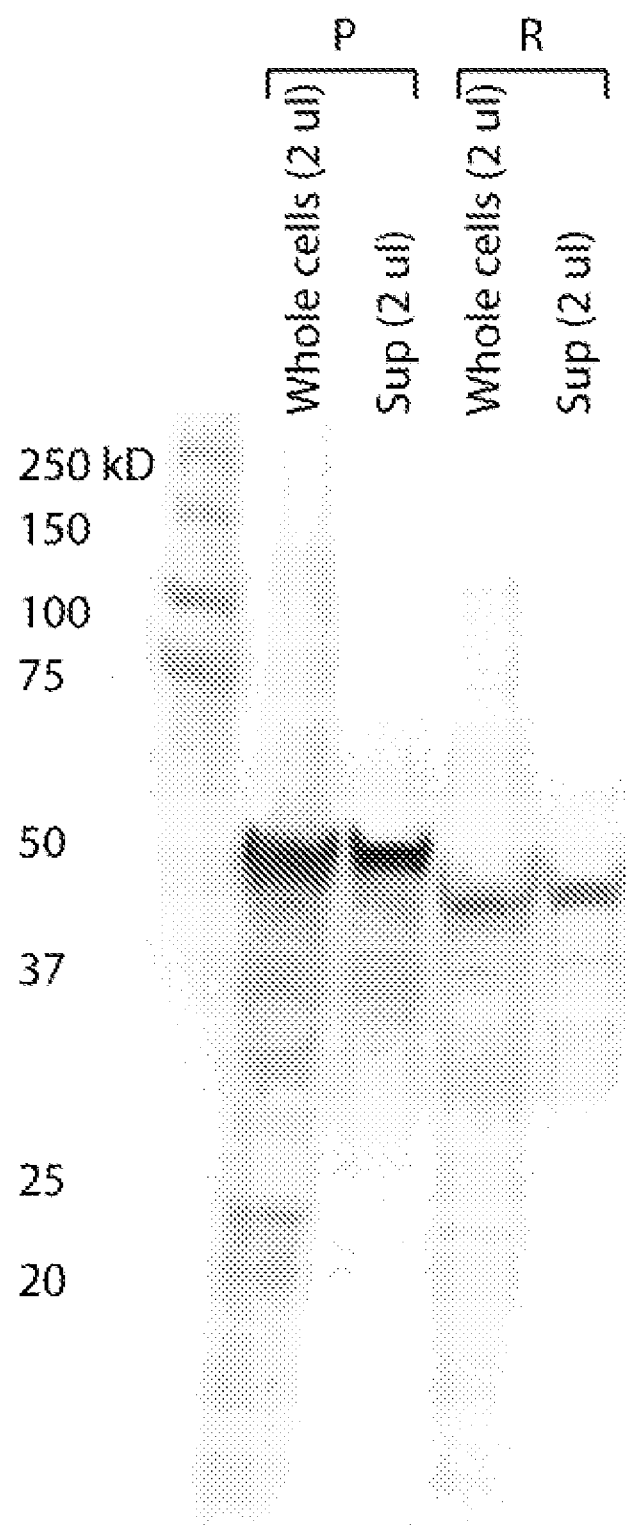
FIG. 7 shows a representative western blot used to detect the presence of an enzyme associated with an activity described herein.

For expression and activity analysis, transformed cells containing the various xylose isomerase constructs were selected from the cultures and grown in about 100 ml of SC-Dextrose (minus uracil) to an $OD_{600}$ of about 4.0. The *S. cerevisiae* cultures that were transformed with the various xylose isomerase-histidine constructs were then lysed using YPER-Plus reagent (Thermo Scientific, catalog number 78999) according to the manufacturer's directions. Protein quantitation of the lysates was performed using the Coomassie-Plus kit (Thermo Scientific, catalog number 23236) as directed by the manufacturer. Denaturing and native Western blot analyses were then conducted. To detect his-tagged xylose isomerase polypeptides Western analysis was employed. Gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with the 1:5000 dilution of primary antibody (Ms mAB to 6×His Tag (SEQ ID NO: 138), AbCam, Cambridge, Mass.) in 0.3% BSA (Fraction V, EMD, San Diego, Calif.) dissolved in 1×PBS and 0.05% Tween-20 with gentle shaking. Incubation was allowed to proceed for about 1 hour with gentle shaking. The membrane was then washed three times for 5 minutes each with 1×PBS and 0.05% Tween-20 with gentle shaking. The secondary antibody [Dnk pAb to Ms IgG (HRP), AbCam, Cambridge, Mass.] was used at 1:15000 dilution in 0.3% BSA and allowed to incubate for about 90 minutes at room temperature with gentle shaking. The membrane was washed three times for about 5 minutes using 1×PBS and 0.05% Tween-20 with gentle shaking. The membrane was then incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds. The results are shown in FIG. 7. As can be seen, both *Piromyces* ("P" in FIG. 7) and *Ruminococcus* ("R" in FIG. 7) xylose isomerases are expressed in both the soluble and insoluble fractions of the yeast cells.

To measure activity of the various xylose isomerase constructs, assays were performed according to Kuyper et al. (*FEMS Yeast Res.*, 4:69 [2003]). About 20 µg of soluble whole cell extract was incubated in the presence of 100 mM Tris, pH 7.5, 10 mM $MgCl_2$, 0.15 mM NADH (Sigma, St. Louis, Mo.), and about 2 U sorbitol dehydrogenase (Roche) at about 30° C. To start the reaction, about 100 µl of xylose was added at various final concentrations of 40-500 mM. A Beckman DU-800 was utilized with an Enzyme Mechanism software package (Beckman Coulter, Inc.), and the change in the $A_{340}$ was monitored for 2-3 minutes.

Example 5

Preparation of Selective Growth Yeast

The yeast gene cdc21 encodes thymidylate synthase, which is required for de novo synthesis of pyrimidine deoxyribonucleotides. A cdc 21 mutant, strain 17206, (ATCC accession number 208583) has a point mutation G139S relative to the initiating methionine. The restrictive temperature of this temperature sensitive mutant is 37° C., which arrests cell division at S phase, so that little or no cell growth and division occurs at or above this temperature.

*Saccharomyces cerevisiae* strain YGR420CBY4742ΔPFK2 was used as the starting cell line to create the cdc21 growth sensitive mutant. A construct for homologous recombination was prepared to replace the wild type thymidylate synthase YGR420CBY4742ΔPFK2 for the cdc21 mutant. This construct was made in various steps. First, the cdc21 mutant region from *Saccharomyces cerevisiae* strain 17206 was PCR amplified using the following primers:

CDC21_fwd:
(SEQ ID NO: 155)
5'-aatcgatcaaagcttctaaatacaagacgtgcgatgacgactata ctggac-3'
CDC21_rev:
(SEQ ID NO: 156)
5'-taccgtactacccgggtatatagtcttttttgccctggtgttcctt aataatttc-3'

For this PCR amplification reaction *Saccharomyces cerevisiae* 17206 genomic DNA was used. The genomic DNA was extracted using Zymo research YeaStar Genomic DNA kit according to instructions. In the PCR amplification reaction 100 ng of 17206 genomic DNA, 1 μM of the oligonucleotide primer set listed above, 2.5 U of PfuUltra High-Fidelity DNA polymerase (Stratagene), 300 μM dNTPs (Roche), and 1×PfuUltra reaction buffer was mixed in a final reaction volume of 50 μl. Using a BIORAD DNA Engine Tetrad 2 Peltier thermal cycler the following cycle conditions were used: 5 min denaturation step at 95° C., followed by 30 cycles of 20 sec at 95° C., 20 sec at 50° C., and 1 min at 72° C., and a final step of 5 min at 72° C. This PCR product was digested with HindIII and XmaI restriction endonucleases and cloned in the HindIII and XmaI sites of PUC19 (NEB) according to standard cloning procedures described by Maniatis in Molecular Cloning.

The genomic DNA of BR214-4a (ATTC accession number 208600) was extracted using Zymo research YeaStar Genomic DNA kit according to instructions. The lys2 gene with promoter and terminator regions was PCR amplified from BR214-4a genomic DNA using the following primers:

Lys2Fwd:
(SEQ ID NO: 157)
5'-tgctaatgacccgggaattccacttgcaattacataaaaaattcc ggcgg-3'
Lys2Rev:
(SEQ ID NO: 158)
5'-atgatcattgagctcagcttcgcaagtattcattttagacccatg gtgg-3'.

The PCR cycle was identical to that just described above but with genomic DNA of BR214-4a instead. XmaI and SacI restriction sites were designed to flank this DNA construct to clone it into the XmaI and SacI sites of the PUC19-cdc21 vector according to standard cloning procedures described by Maniatis in Molecular Cloning. The new construct with the cdc21 mutation with a lys2 directly downstream of that will be referred to as PUC19-cdc21-lys2.

The final step involved the cloning of the downstream region of thymidylate synthase into the PUC19-cdc21-lys2 vector immediately downstream of the lys2 gene. The downstream region of the thymidylate synthase was amplified from BY4742 genomic DNA (ATCC accession number 201389D-5 using the following primers:

ThymidylateSynthase_DownFwd:
(SEQ ID NO: 159)
5'-tgctaatgagagctctcatttttttggtgcgatatgttttttggttg atg-3'
and ThymidylateSynthatse_DownRev:
(SEQ ID NO: 160)
5'-aatgatcatgagctcgtcaacaagaactaaaaaattgttcaaaa atgc-3'.

This final construct is referred as PUC19-cdc21-lys2-ThymidylateSynthase_down. The sequence is set forth in the tables. A final PCR amplification reaction of this construct was performed using the following PCR primers:

ThymidylateSynthase::cdc21 fwd:
(SEQ ID NO: 161)
5'-ctaaatacaagacgtgcgatgacgactatactgg-3'
and ThymidylateSynthase::cdc21 rev:
(SEQ ID NO: 162)
5'-gtcaacaagaactaaaaaattgttcaaaaatgcaattgtc-3'.

The PCR reaction was identical to that described above but using 100 ng of the PUC19-cdc2'-lys2-ThymidylateSynthase_down construct as a template.

The final PCR product was separated by agarose gel electrophoresis, excised, and purified using MP Biomedicals Geneclean II kit as recommended. Homologous recombination of YGR420CBY4742ΔPFK2 to replace the wt thymidylate synthase for the cdc21 mutant was accomplished using 10 μg of the purified PCR product to transform YGR420CBY4742ΔPFK2 strain using same transformation protocol described above. Transformants were selected by culturing the cells on selective media containing SC-Ethanol (0.67% yeast nitrogen base-2% ethanol) containing complete amino acids minus lysine.

The genome of this final engineered strain contains the mutated cdc21 gene, and has both the PFK1 and PFK2 genes deleted. This final engineered strain will be transformed with the best combination of edd-p426 GPD and eda -p425 GPD variant constructs. Ethanol and glucose measurements will be monitored during aerobic and anaerobic growth conditions using Roche ethanol and glucose kits according to instructions.

Example 6

Examples of Polynucleotide Regulators

Provided in the tables hereafter are non-limiting examples of regulator polynucleotides that can be utilized in embodiments herein. Such polynucleotides may be utilized in native form or may be modified for use herein. Examples of regulatory polynucleotides include those that are regulated by oxygen levels in a system (e.g., up-regulated or down-regulated by relatively high oxygen levels or relatively low oxygen levels)

| Regulated Yeast Promoters - Up-regulated by oxygen | | | | |
|---|---|---|---|---|
| ORF name | Gene name | Relative mRNA level (Aerobic) | Relative mRNA level (Anaerobic) | Ratio |
| YPL275W | | 4389 | 30 | 219.5 |
| YPL276W | | 2368 | 30 | 118.4 |

| Regulated Yeast Promoters - Up-regulated by oxygen | | | | |
|---|---|---|---|---|
| ORF name | Gene name | Relative mRNA level (Aerobic) | Relative mRNA level (Anaerobic) | Ratio |
| YDR256C | CTA1 | 2076 | 30 | 103.8 |
| YHR096C | HXT5 | 1846 | 30 | 72.4 |
| YDL218W | | 1189 | 30 | 59.4 |
| YCR010C | | 1489 | 30 | 48.8 |
| YOR161C | | 599 | 30 | 29.9 |
| YPL200W | | 589 | 30 | 29.5 |
| YGR110W | | 1497 | 30 | 27 |
| YNL237W | YTP1 | 505 | 30 | 25.2 |
| YBR116C | | 458 | 30 | 22.9 |
| YOR348C | PUT4 | 451 | 30 | 22.6 |
| YBR117C | TKL2 | 418 | 30 | 20.9 |
| YLL052C | | 635 | 30 | 20 |
| YNL195C | | 1578 | 30 | 19.4 |
| YPR193C | | 697 | 30 | 15.7 |
| YDL222C | | 301 | 30 | 15 |
| YNL335W | | 294 | 30 | 14.6 |
| YPL036W | PMA2 | 487 | 30 | 12.8 |
| YML122C | | 206 | 30 | 10.3 |
| YGR067C | | 236 | 30 | 10.2 |
| YPR192W | | 204 | 30 | 10.2 |
| YNL014W | | 828 | 30 | 9.8 |
| YFL061W | | 256 | 30 | 9.1 |
| YNR056C | | 163 | 30 | 8.1 |
| YOR186W | | 153 | 30 | 7.6 |
| YDR222W | | 196 | 30 | 6.5 |
| YOR338W | | 240 | 30 | 6.3 |
| YPR200C | | 113 | 30 | 5.7 |
| YMR018W | | 778 | 30 | 5.2 |
| YOR364W | | 123 | 30 | 5.1 |
| YNL234W | | 93 | 30 | 4.7 |
| YNR064C | | 85 | 30 | 4.2 |
| YGR213C | RTA1 | 104 | 30 | 4 |
| YCL064C | CHA1 | 80 | 30 | 4 |
| YOL154W | | 302 | 30 | 3.9 |
| YPR150W | | 79 | 30 | 3.9 |
| YPR196W | MAL63 | 30 | 30 | 3.6 |
| YDR420W | HKR1 | 221 | 30 | 3.5 |
| YJL216C | | 115 | 30 | 3.5 |
| YNL270C | ALP1 | 67 | 30 | 3.3 |
| YHL016C | DUR3 | 224 | 30 | 3.2 |
| YOL131W | | 230 | 30 | 3 |
| YOR077W | RTS2 | 210 | 30 | 3 |
| YDR536W | STL1 | 55 | 30 | 2.7 |
| YNL150W | | 78 | 30 | 2.6 |
| YHR212C | | 149 | 30 | 2.4 |
| YJL108C | | 106 | 30 | 2.4 |
| YGR069W | | 49 | 30 | 2.4 |
| YDR106W | | 60 | 30 | 2.3 |
| YNR034W | SOL1 | 197 | 30 | 2.2 |
| YEL073C | | 104 | 30 | 2.1 |
| YOL141W | | 81 | 30 | 1.8 |

Figure 1:
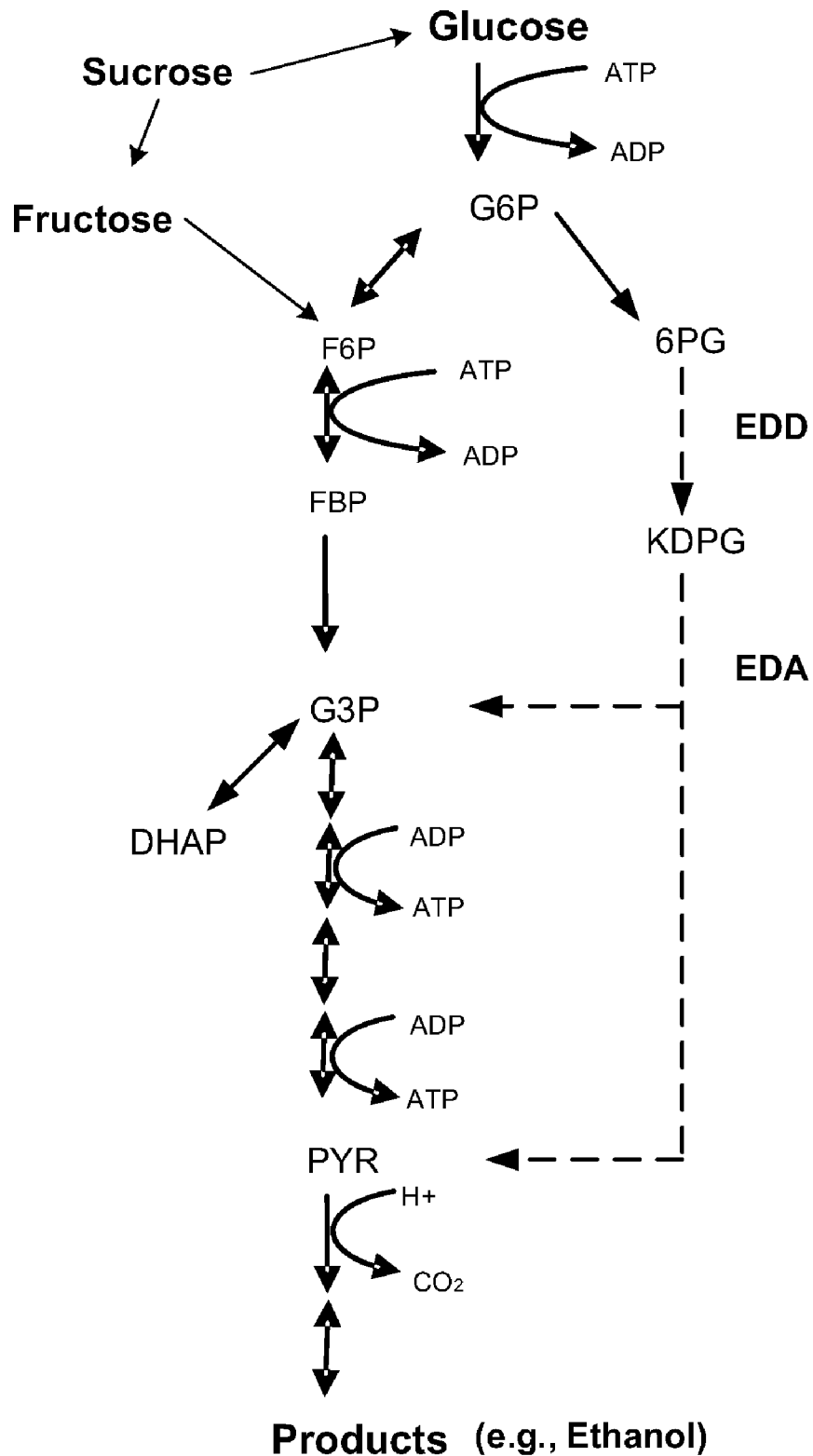
FIG. 1 depicts a metabolic pathway that produces ethanol as by product of cellular respiration. The solid lines represent activities present in the Embden-Meyerhoff pathway (e.g., aerobic respiration). Dashed lines represent activities associated with the Entner-Doudoroff pathway (e.g., anaerobic respiration). One or both pathways often can be operational in a microorganism. The level of activity of each pathway can vary from organism to organism. The arrow from FBP (e.g., Fructose-1,6-bisphosphate, also referred to as F-1,6-BP) to G3P (e.g., glceraldehyde-3-phosphate), illustrates wild type levels of conversion of FBP to two molecules of G3P. In the embodiments shown in FIGS. 2, 3 and 5 a smaller arrow from FBP to G3P is illustrated, indicating reduced or no conversion of FBP to G3P. The reduction in conversion of FBP to G3P illustrated in FIGS. 2, 3 and 5 is a result of the reduction or elimination of the previous activity that converts fructose-6-phosphate (F6P) to FBP (e.g., the activity of PFK).

| Regulated Yeast Promoters - Down-regulated by oxygen | | | | |
|---|---|---|---|---|
| ORF name | Gene name | Relative mRNA level (Aerobic) | Relative mRNA level (Anaerobic) | Ratio |
| YJR047C | ANB1 | 30 | 4901 | 231.1 |
| YMR319C | FET4 | 30 | 1159 | 58 |
| YPR194C | | 30 | 982 | 49.1 |
| YIR019C | STA1 | 30 | 981 | 22.8 |
| YHL042W | | 30 | 608 | 12 |
| YHR210C | | 30 | 552 | 27.6 |
| YHR079B | SAE3 | 30 | 401 | 2.7 |
| YGL162W | STO1 | 30 | 371 | 9.6 |
| YHL044W | | 30 | 334 | 16.7 |
| YOL015W | | 30 | 320 | 6.1 |
| YCLX07W | | 30 | 292 | 4.2 |
| YIL013C | PDR11 | 30 | 266 | 10.6 |
| YDR046C | | 30 | 263 | 13.2 |
| YBR040W | FIG1 | 30 | 257 | 12.8 |
| YLR040C | | 30 | 234 | 2.9 |
| YOR255W | | 30 | 231 | 11.6 |
| YOL014W | | 30 | 229 | 11.4 |
| YAR028W | | 30 | 212 | 7.5 |
| YER089C | | 30 | 201 | 6.2 |
| YFL012W | | 30 | 193 | 9.7 |
| YDR539W | | 30 | 187 | 3.4 |
| YHL043W | | 30 | 179 | 8.9 |
| YJR162C | | 30 | 173 | 6 |
| YMR165C | SMP2 | 30 | 147 | 3.5 |
| YER106W | | 30 | 145 | 7.3 |
| YDR541C | | 30 | 140 | 7 |
| YCRX07W | | 30 | 138 | 3.3 |
| YHR048W | | 30 | 137 | 6.9 |
| YCL021W | | 30 | 136 | 6.8 |
| YOL160W | | 30 | 136 | 6.8 |
| YCRX08W | | 30 | 132 | 6.6 |
| YMR057C | | 30 | 109 | 5.5 |
| YDR540C | | 30 | 83 | 4.2 |
| YOR378W | | 30 | 78 | 3.9 |
| YBR085W | AAC3 | 45 | 1281 | 28.3 |
| YER188W | | 47 | 746 | 15.8 |
| YLL065W | GIN11 | 50 | 175 | 3.5 |
| YDL241W | | 58 | 645 | 11.1 |
| YBR238C | | 59 | 274 | 4.6 |
| YCR048W | ARE1 | 60 | 527 | 8.7 |
| YOL165C | | 60 | 306 | 5.1 |
| YNR075W | | 60 | 251 | 4.2 |
| YJL213W | | 60 | 250 | 4.2 |
| YPL265W | DIP5 | 61 | 772 | 12.7 |
| YDL093W | PMT5 | 62 | 353 | 5.7 |
| YKR034W | DAL80 | 63 | 345 | 5.4 |
| YKR053C | | 66 | 1268 | 19.3 |
| YJR147W | | 68 | 281 | 4.1 |

| Known and putative DNA binding motifs | |
|---|---|
| Regulator | Known Consensus Motif |
| Abf1 | TCRNNNNNNACG (SEQ ID NO: 532) |
| Cbf1 | RTCACRTG |
| Gal4 | CGGNNNNNNNNNNNCCG (SEQ ID NO: 533) |
| Gcn4 | TGACTCA |

-continued

| | Known and putative DNA binding motifs | |
|---|---|---|
| | Gcr1 | CTTCC |
| | Hap2 | CCAATNA |
| | Hap3 | CCAATNA |
| | Hap4 | CCAATNA |
| | Hsf1 | GAANNTTCNNGAA (SEQ ID NO: 534) |
| | Ino2 | ATGTGAAA |
| | Mata(A1) | TGATGTANNT (SEQ ID NO: 535) |
| | Mcm1 | CCNNNWWRGG (SEQ ID NO: 536) |
| | Mig1 | WWWWSYGGGG (SEQ ID NO: 537) |
| | Pho4 | CACGTG |
| | Rap1 | RMACCCANNCAYY (SEQ ID NO: 538) |
| | Reb1 | CGGGTRR |
| | Ste12 | TGAAACA |
| | Swi4 | CACGAAA |
| | Swi6 | CACGAAA |
| | Yap1 | TTACTAA |

| Putative DNA Binding Motifs Regulator | Best Motif (scored by E-value) | Best Motif (scored by Hypergeometric) |
|---|---|---|
| Abf1 | TYCGT--R-ARTGAYA (SEQ ID NO: 539) | TYCGT--R-ARTGAYA (SEQ ID NO: 539) |
| Ace2 | RRRAARARAA-A-RARAA (SEQ ID NO: 540) | GTGTGTGTGTGTGTG (SEQ ID NO: 541) |
| Adr1 | A-AG-GAGAGAG-GGCAG (SEQ ID NO: 542) | YTSTYSTT-TTGYTWTT (SEQ ID NO: 543) |
| Arg80 | T--CCW-TTTKTTTC (SEQ ID NO: 544) | GCATGACCATCCACG (SEQ ID NO: 545) |
| Arg81 | AAAAARARAAAARMA (SEQ ID NO: 546) | GSGAYARMGGAMAAAAA (SEQ ID NO: 547) |
| Aro80 | YKYTYTTYTT----KY (SEQ ID NO: 548) | TRCCGAGRYW-SSSGCGS (SEQ ID NO: 549) |
| Ash1 | CGTCCGGCGC (SEQ ID NO: 550) | CGTCCGGCGC (SEQ ID NO: 550) |
| Azf1 | GAAAAAGMAAAAAAA (SEQ ID NO: 551) | AARWTSGARG-A--CSAA (SEQ ID NO: 552) |
| Bas1 | TTTTYYTTYTTKY-TY-T (SEQ ID NO: 553) | CS-CCAATGK--CS (SEQ ID NO: 554) |
| Cad1 | CATKYTTTTTKYTY (SEQ ID NO: 555) | GCT-ACTAAT (SEQ ID NO: 556) |
| Cbf1 | CACGTGACYA (SEQ ID NO: 557) | CACGTGACYA (SEQ ID NO: 557) |
| Cha4 | CA---ACACASA-A (SEQ ID NO: 558) | CAYAMRTGY-C (SEQ ID NO: 559) |

-continued

| | Known and putative DNA binding motifs | |
|---|---|---|
| Cin5 | none | none |
| Crz1 | GG-A-A--AR-ARGGC- (SEQ ID NO: 560) | TSGYGRGASA (SEQ ID NO: 561) |
| Cup9 | TTTKYTKTTY-YTTTKTY (SEQ ID NO: 562) | K-C-C---SCGCTACKGC (SEQ ID NO: 563) |
| Dal81 | WTTKTTTTYTTTT-T (SEQ ID NO: 564) | SR-GGCMCGGC-SSG (SEQ ID NO: 565) |
| Dal82 | TTKTTTTYTTC (SEQ ID NO: 566) | TACYACA-CACAWGA (SEQ ID NO: 567) |
| Dig1 | AAA--RAA-GARRAA-AR (SEQ ID NO: 568) | CCYTG-AYTTCW-CTTC (SEQ ID NO: 569) |
| Dot6 | GTGMAK-MGRA-G-G (SEQ ID NO: 570) | GTGMAK-MGRA-G-G (SEQ ID NO: 570) |
| Fhl1 | -TTWACAYCCRTACAY-Y (SEQ ID NO: 571) | -TTWACAYCCRTACAY-Y (SEQ ID NO: 571) |
| Fkh1 | TTT-CTTTKYTT-YTTTT (SEQ ID NO: 572) | AAW-RTAAAYARG (SEQ ID NO: 573) |
| Fkh2 | AAARA-RAAA-AAAR-AA (SEQ ID NO: 574) | GG-AAWA-GTAAACAA (SEQ ID NO: 575) |
| Fzf1 | CACACACACACACACAC (SEQ ID NO: 576) | SASTKCWCTCKTCGT (SEQ ID NO: 577) |
| Gal4 | TTGCTTGAACGSATGCCA (SEQ ID NO: 578) | TTGCTTGAACGSATGCCA (SEQ ID NO: 578) |
| Gal4 (Gal) | YCTTTTTTTYTTYYKG (SEQ ID NO: 579) | CGGM---CW-Y--CCCG (SEQ ID NO: 580) |
| Gat1 | none | none |
| Gat3 | RRSCCGMCGMGRCGCGCS (SEQ ID NO: 581) | RGARGTSACGCAKRTTCT (SEQ ID NO: 582) |
| Gcn4 | AAA-ARAR-RAAAARRAR (SEQ ID NO: 583) | TGAGTCAY |
| Gcr1 | GGAAGCTGAAACGYMWRR (SEQ ID NO: 584) | GGAAGCTGAAACGYMWRR (SEQ ID NO: 584) |
| Gcr2 | GGAGAGGCATGATGGGGG (SEQ ID NO: 585) | AGGTGATGGAGTGCTCAG (SEQ ID NO: 586) |
| Gln3 | CT-CCTTTCT (SEQ ID NO: 587) | GKCTRR-RGGAGA-GM (SEQ ID NO: 588) |
| Grf10 | GAAARRAAAAAMRMARA (SEQ ID NO: 589) | -GGGSG-T-SYGT-CGA (SEQ ID NO: 590) |
| Gts1 | G-GCCRS--TM (SEQ ID NO: 591) | AG-AWGTTTTTGWCAAMA (SEQ ID NO: 592) |
| Haa1 | none | none |
| Hal9 | TTTTTTYTTTTY-KTTTT (SEQ ID NO: 593) | KCKSGCAGGCWTTKYTCT (SEQ ID NO: 594) |
| Hap2 | YTTCTTTTYT-Y-C-KT- (SEQ ID NO: 595) | G-CCSART-GC (SEQ ID NO: 596) |
| Hap3 | T-SYKCTTTTCYTTY (SEQ ID NO: 597) | SGCGMGGG--CC-GACCG (SEQ ID NO: 598) |
| Hap4 | STT-YTTTY-TTYTYYYY (SEQ ID NO: 599) | YCT-ATTSG-C-GS (SEQ ID NO: 600) |
| Hap5 | YK-TTTWYYTC (SEQ ID NO: 601) | T-TTSMTT-YTTTCCK-C (SEQ ID NO: 602) |

-continued

| | Known and putative DNA binding motifs | |
|---|---|---|
| Hir1 | AAAA-A-AARAR-AG (SEQ ID NO: 603) | CCACKTKSGSCCT-S (SEQ ID NO: 604) |
| Hir2 | WAAAAAAGAAAA-AAAAR (SEQ ID NO: 605) | CRSGCYWGKGC (SEQ ID NO: 606) |
| Hms1 | AAA-GG-ARAM (SEQ ID NO: 607) | -AARAAGC-GGGCAC-C (SEQ ID NO: 608) |
| Hsf1 | TYTTCYAGAA--TTCY (SEQ ID NO: 609) | TYTTCYAGAA--TTCY (SEQ ID NO: 609) |
| Ime4 | CACACACACACACACACA (SEQ ID NO: 610) | CACACACACACACACACA (SEQ ID NO: 610) |
| Ino2 | TTTYCACATGC (SEQ ID NO: 611) | SCKKCGCKSTSSTTYAA (SEQ ID NO: 612) |
| Ino4 | G--GCATGTGAAAA (SEQ ID NO: 613) | G--GCATGTGAAAA (SEQ ID NO: 613) |
| Ixr1 | GAAAA-AAAAAAARA-A (SEQ ID NO: 614) | CTTTTTTTYYTSGCC (SEQ ID NO: 615) |
| Leu3 | GAAAAARAARAA-AA (SEQ ID NO: 616) | GCCGGTMMCGSYC-- (SEQ ID NO: 617) |
| Mac1 | YTTKT--TTTTTYTYTTT (SEQ ID NO: 618) | A--TTTTTYTTKYGC (SEQ ID NO: 619) |
| Mal13 | GCAG-GCAGG (SEQ ID NO: 620) | AAAC-TTTATA-ATACA (SEQ ID NO: 621) |
| Mal33 | none | none |
| Mata1 | GCCC-C | CAAT-TCT-CK (SEQ ID NO: 622) |
| Mbp1 | TTTYTYKTTT-YYTTTTT (SEQ ID NO: 623) | G-RR-A-ACGCGT-R (SEQ ID NO: 624) |
| Mcm1 | TTTCC-AAW-RGGAAA (SEQ ID NO: 625) | TTTCC-AAW-RGGAAA (SEQ ID NO: 625) |
| Met31 | YTTYYTTYTTTTYTYTTC (SEQ ID NO: 626) | |
| Met4 | MTTTTTYTYTYTTC (SEQ ID NO: 627) | |
| Mig1 | TATACA-AGMKRTATATG (SEQ ID NO: 628) | |
| Mot3 | TMTTT-TY-CTT-TTTWK (SEQ ID NO: 629) | |
| Msn1 | KT--TTWTTATTCC-C (SEQ ID NO: 630) | |
| Msn2 | ACCACC | |
| Msn4 | R--AAAA-RA-AARAAAT (SEQ ID NO: 631) | |
| Mss11 | TTTTTTTTCWCTTTKYC (SEQ ID NO: 632) | |
| Ndd1 | TTTY-YTKTTTY-YTTYT (SEQ ID NO: 633) | |
| Nrg1 | TTY--TTYTT-YTTTYYY (SEQ ID NO: 634) | |
| Pdr1 | T-YGTGKRYGT-YG (SEQ ID NO: 635) | |
| Phd1 | TTYYYTTTTTYTTTYTT (SEQ ID NO: 636) | |

-continued

Known and putative DNA binding motifs

| | |
|---|---|
| Pho4 | GAMAAAAARAAAAR (SEQ ID NO: 637) |
| Put3 | CYCGGGAAGCSAMM-CCG (SEQ ID NO: 638) |
| Rap1 | GRTGYAYGGRTGY (SEQ ID NO: 639) |
| Rcs1 | KMAARAAAARAAR (SEQ ID NO: 640) |
| Reb1 | RTTACCCGS |
| Rfx1 | AYGRAAAARARAAAARAA (SEQ ID NO: 641) |
| Rgm1 | GGAKSCC-TTTY-GMRTA (SEQ ID NO: 642) |
| Rgt1 | CCCTCC |
| Rim101 | GCGCCGC |
| Rlm1 | TTTTC-KTTTYTTTTC (SEQ ID NO: 643) |
| Rme1 | ARAAGMAGAAARRAA (SEQ ID NO: 644) |
| Rox1 | YTTTTCTTTTY-TTTTT (SEQ ID NO: 645) |
| Rph1 | ARRARAAAGG-(SEQ ID NO: 646) |
| Rtg1 | YST-YK-TYTT-CTCCCM (SEQ ID NO: 647) |
| Rtg3 | GARA-AAAAR-RAARAAA (SEQ ID NO: 648) |
| Sfl1 | CY--GGSSA-C (SEQ ID NO: 649) |
| Sfp1 | CACACACACACACAYA (SEQ ID NO: 650) |
| Sip4 | CTTYTWTTKTTKTSA (SEQ ID NO: 651) |
| Skn7 | YTTYYYTYTTTYTYYTTT (SEQ ID NO: 652) |
| Sko1 | none |
| Smp1 | AMAAAAARAARWARA-AA (SEQ ID NO: 653) |
| Sok2 | ARAAAARRAAAAAG-RAA (SEQ ID NO: 654) |
| Stb1 | RAARAAAARCMRSRAAA (SEQ ID NO: 655) |
| Ste12 | TTYTKTYTY-TYYKTTTY (SEQ ID NO: 656) |
| Stp1 | GAAAAMAA-AAAAA-AAA (SEQ ID NO: 657) |
| Stp2 | YAA-ARAARAAAAA-AAM (SEQ ID NO: 658) |
| Sum1 | TY-TTTTTYTTTTT-TK (SEQ ID NO: 659) |

| Known and putative DNA binding motifs | |
|---|---|
| Swi4 | RAARAARAAA-AA-R-AA (SEQ ID NO: 660) |
| Swi5 | CACACACACACACACACA (SEQ ID NO: 610) |
| Swi6 | RAARRRAAAAA-AAAMAA (SEQ ID NO: 661) |
| Thi2 | GCCAGACCTAC (SEQ ID NO: 662) |
| Uga3 | GG-GGCT |
| Yap1 | TTYTTYTTYTTTY-YTYT (SEQ ID NO: 663) |
| Yap3 | none |
| Yap5 | YKSGCGCGYCKCGKCGGS (SEQ ID NO: 664) |
| Yap6 | TTTTYYTTTTYYYYKTT (SEQ ID NO: 665) |
| Yap7 | none |
| Yfl044c | TTCTTKTYYTTTT (SEQ ID NO: 666) |
| Yjl206c | TTYTTTTYTYYTTTYTTT (SEQ ID NO: 667) |
| Zap1 | TTGCTTGAACGGATGCCA (SEQ ID NO: 668) |
| Zms1 | MG-MCAAAAATAAAAS (SEQ ID NO: 669) |

| Transcriptional repressors | |
|---|---|
| Associated Gene(s) | Description(s) |
| WHI5 | Repressor of G1 transcription that binds to SCB binding factor (SBF) at SCB target promoters in early G1; phosphorylation of Whi5p by the CDK, Cln3p/Cdc28p relieves repression and promoter binding by Whi5; periodically expressed in G1 |
| TUP1 | General repressor of transcription, forms complex with Cyc8p, involved in the establishment of repressive chromatin structure through interactions with histones H3 and H4, appears to enhance expression of some genes |
| ROX1 | Heme-dependent repressor of hypoxic genes; contains an HMG domain that is responsible for DNA bending activity |
| SFL1 | Transcriptional repressor and activator; involved in repression of flocculation-related genes, and activation of stress responsive genes; negatively regulated by cAMP-dependent protein kinase A subunit Tpk2p |
| RIM101 | Transcriptional repressor involved in response to pH and in cell wall construction; required for alkaline pH-stimulated haploid invasive growth and sporulation; activated by proteolytic processing; similar to *A. nidulans* PacC |
| RDR1 | Transcriptional repressor involved in the control of multidrug resistance; negatively regulates expression of the PDR5 gene; member of the Gal4p family of zinc cluster proteins |
| SUM1 | Transcriptional repressor required for mitotic repression of middle sporulation-specific genes; also acts as general replication initiation factor; involved in telomere maintenance, chromatin silencing; regulated by pachytene checkpoint |
| XBP1 | Transcriptional repressor that binds to promoter sequences of the cyclin genes, CYS3, and SMF2; expression is induced by stress or starvation during mitosis, and late in meiosis; member of the Swi4p/Mbp1p family; potential Cdc28p substrate |

-continued

| Transcriptional repressors | |
|---|---|
| Associated Gene(s) | Description(s) |
| NRG2 | Transcriptional repressor that mediates glucose repression and negatively regulates filamentous growth; has similarity to Nrg1p |
| NRG1 | Transcriptional repressor that recruits the Cyc8p-Tup1p complex to promoters; mediates glucose repression and negatively regulates a variety of processes including filamentous growth and alkaline pH response |
| CUP9 | Homeodomain-containing transcriptional repressor of PTR2, which encodes a major peptide transporter; imported peptides activate ubiquitin-dependent proteolysis, resulting in degradation of Cup9p and de-repression of PTR2 transcription |
| YOX1 | Homeodomain-containing transcriptional repressor, binds to Mcm1p and to early cell cycle boxes (ECBs) in the promoters of cell cycle-regulated genes expressed in M/G1 phase; expression is cell cycle-regulated; potential Cdc28p substrate |
| RFX1 | Major transcriptional repressor of DNA-damage-regulated genes, recruits repressors Tup1p and Cyc8p to their promoters; involved in DNA damage and replication checkpoint pathway; similar to a family of mammalian DNA binding RFX1-4 proteins |
| MIG3 | Probable transcriptional repressor involved in response to toxic agents such as hydroxyurea that inhibit ribonucleotide reductase; phosphorylation by Snf1p or the Mec1p pathway inactivates Mig3p, allowing induction of damage response genes |
| RGM1 | Putative transcriptional repressor with proline-rich zinc fingers; overproduction impairs cell growth |
| YHP1 | One of two homeobox transcriptional repressors (see also Yox1p), that bind to Mcm1p and to early cell cycle box (ECB) elements of cell cycle regulated genes, thereby restricting ECB-mediated transcription to the M/G1 interval |
| HOS4 | Subunit of the Set3 complex, which is a meiotic-specific repressor of sporulation specific genes that contains deacetylase activity; potential Cdc28p substrate |
| CAF20 | Phosphoprotein of the mRNA cap-binding complex involved in translational control, repressor of cap-dependent translation initiation, competes with eIF4G for binding to eIF4E |
| SAP1 | Putative ATPase of the AAA family, interacts with the Sin1p transcriptional repressor in the two-hybrid system |
| SET3 | Defining member of the SET3 histone deacetylase complex which is a meiosis-specific repressor of sporulation genes; necessary for efficient transcription by RNAPII; one of two yeast proteins that contains both SET and PHD domains |
| RPH1 | JmjC domain-containing histone demethylase which can specifically demethylate H3K36 tri- and dimethyl modification states; transcriptional repressor of PHR1; Roh1p phosphorylation during DNA damage is under control of the MEC1-RAD53 pathway |
| YMR181C | Protein of unknown function; mRNA transcribed as part of a bicistronic transcript with a predicted transcriptional repressor RGM1/YMR182C; mRNA is destroyed by nonsense-mediated decay (NMD); YMR181C is not an essential gene |
| YLR345W | Similar to 6-phosphofructo-2-kinase/fructose-2,6-bisphosphatase enzymes responsible for the metabolism of fructoso-2,6-bisphosphate; mRNA expression is repressed by the Rfx1p-Tup1p-Ssn6p repressor complex; YLR345W is not an essential gene |
| MCM1 | Transcription factor involved in cell-type-specific transcription and pheromone response; plays a central role in the formation of both repressor and activator complexes |
| PHR1 | DNA photolyase involved in photoreactivation, repairs pyrimidine dimers in the presence of visible light; induced by DNA damage; regulated by transcriptional repressor Rph1p |
| HOS2 | Histone deacetylase required for gene activation via specific deacetylation of lysines in H3 and H4 histone tails; subunit of the Set3 complex, a meiotic-specific repressor of sporulation specific genes that contains deacetylase activity |
| RGT1 | Glucose-responsive transcription factor that regulates expression of several glucose transporter (HXT) genes in response to glucose; binds to promoters and acts both as a transcriptional activator and repressor |
| SRB7 | Subunit of the RNA polymerase II mediator complex; associates with core polymerase subunits to form the RNA polymerase II holoenzyme; essential for transcriptional regulation; target of the global repressor Tup1p |
| GAL11 | Subunit of the RNA polymerase II mediator complex; associates with core polymerase subunits to form the RNA polymerase II holoenzyme; affects transcription by acting as target of activators and repressors |

| Associated Gene(s) | Description(s) |
|---|---|
| | Transcriptional activators |
| SKT5 | Activator of Chs3p (chitin synthase III), recruits Chs3p to the bud neck via interaction with Bni4p; has similarity to Shc1p, which activates Chs3p during sporulation |
| MSA1 | Activator of G1-specific transcription factors, MBF and SBF, that regulates both the timing of G1-specific gene transcription, and cell cycle initiation; potential Cdc28p substrate |
| AMA1 | Activator of meiotic anaphase promoting complex (APC/C); Cdc20p family member; required for initiation of spore wall assembly; required for Clb1p degradation during meiosis |
| STB5 | Activator of multidrug resistance genes, forms a heterodimer with Pdr1p; contains a Zn(II)2Cys6 zinc finger domain that interacts with a PDRE (pleotropic drug resistance element) in vitro; binds Sin3p in a two-hybrid assay |
| RRD2 | Activator of the phosphotyrosyl phosphatase activity of PP2A, peptidyl-prolyl cis/trans-isomerase; regulates G1 phase progression, the osmoresponse, microtubule dynamics; subunit of the Tap42p-Pph21p-Rrd2p complex |
| BLM10 | Proteasome activator subunit; found in association with core particles, with and without the 19S regulatory particle; required for resistance to bleomycin, may be involved in protecting against oxidative damage; similar to mammalian PA200 |
| SHC1 | Sporulation-specific activator of Chs3p (chitin synthase III), required for the synthesis of the chitosan layer of ascospores; has similarity to Skt5p, which activates Chs3p during vegetative growth; transcriptionally induced at alkaline pH |
| NDD1 | Transcriptional activator essential for nuclear division; localized to the nucleus; essential component of the mechanism that activates the expression of a set of late-S-phase-specific genes |
| IMP2' | Transcriptional activator involved in maintenance of ion homeostasis and protection against DNA damage caused by bleomycin and other oxidants, contains a C-terminal leucine-rich repeat |
| LYS14 | Transcriptional activator involved in regulation of genes of the lysine biosynthesis pathway; requires 2-aminoadipate semialdehyde as co-inducer |
| MSN1 | Transcriptional activator involved in regulation of invertase and glucoamylase expression, invasive growth and pseudohyphal differentiation, iron uptake, chromium accumulation, and response to osmotic stress; localizes to the nucleus |
| HAA1 | Transcriptional activator involved in the transcription of TPO2, YRO2, and other genes putatively encoding membrane stress proteins; involved in adaptation to weak acid stress |
| UGA3 | Transcriptional activator necessary for gamma-aminobutyrate (GABA)-dependent induction of GABA genes (such as UGA1, UGA2, UGA4); zinc-finger transcription factor of the Zn(2)-Cys(6) binuclear cluster domain type; localized to the nucleus |
| GCR1 | Transcriptional activator of genes involved in glycolysis; DNA-binding protein that interacts and functions with the transcriptional activator Gcr2p |
| GCR2 | Transcriptional activator of genes involved in glycolysis; interacts and functions with the DNA-binding protein Gcr1p |
| GAT1 | Transcriptional activator of genes involved in nitrogen catabolite repression; contains a GATA-1-type zinc finger DNA-binding motif; activity and localization regulated by nitrogen limitation and Ure2p |
| GLN3 | Transcriptional activator of genes regulated by nitrogen catabolite repression (NCR), localization and activity regulated by quality of nitrogen source |
| PUT3 | Transcriptional activator of proline utilization genes, constitutively binds PUT1 and PUT2 promoter sequences and undergoes a conformational change to form the active state; has a Zn(2)-Cys(6) binuclear cluster domain |
| ARR1 | Transcriptional activator of the basic leucine zipper (bZIP) family, required for transcription of genes involved in resistance to arsenic compounds |
| PDR3 | Transcriptional activator of the pleiotropic drug resistance network, regulates expression of ATP-binding cassette (ABC) transporters through binding to cis-acting sites known as PDREs (PDR responsive elements) |
| MSN4 | Transcriptional activator related to Msn2p; activated in stress conditions, which results in translocation from the cytoplasm to the nucleus; binds DNA at stress response elements of responsive genes, inducing gene expression |
| MSN2 | Transcriptional activator related to Msn4p; activated in stress conditions, which results in translocation from the cytoplasm to the nucleus; binds DNA at stress response elements of responsive genes, inducing gene expression |

Transcriptional activators

| Associated Gene(s) | Description(s) |
|---|---|
| PHD1 | Transcriptional activator that enhances pseudohyphal growth; regulates expression of FLO11, an adhesin required for pseudohyphal filament formation; similar to StuA, an *A. nidulans* developmental regulator; potential Cdc28p substrate |
| FHL1 | Transcriptional activator with similarity to DNA-binding domain of Drosophila forkhead but unable to bind DNA in vitro; required for rRNA processing; isolated as a suppressor of splicing factor prp4 |
| VHR1 | Transcriptional activator, required for the vitamin H-responsive element (VHRE) mediated induction of VHT1 (Vitamin H transporter) and BIO5 (biotin biosynthesis intermediate transporter) in response to low biotin concentrations |
| CDC20 | Cell-cycle regulated activator of anaphase-promoting complex/cyclosome (APC/C), which is required for metaphase/anaphase transition; directs ubiquitination of mitotic cyclins, Pds1p, and other anaphase inhibitors; potential Cdc28p substrate |
| CDH1 | Cell-cycle regulated activator of the anaphase-promoting complex/cyclosome (APC/C), which directs ubiquitination of cyclins resulting in mitotic exit; targets the APC/C to specific substrates including Cdc20p, Ase1p, Cin8p and Fin1p |
| AFT2 | Iron-regulated transcriptional activator; activates genes involved in intracellular iron use and required for iron homeostasis and resistance to oxidative stress; similar to Aft1p |
| MET4 | Leucine-zipper transcriptional activator, responsible for the regulation of the sulfur amino acid pathway, requires different combinations of the auxiliary factors Cbf1p, Met28p, Met31p and Met32p |
| CBS2 | Mitochondrial translational activator of the COB mRNA; interacts with translating ribosomes, acts on the COB mRNA 5'-untranslated leader |
| CBS1 | Mitochondrial translational activator of the COB mRNA; membrane protein that interacts with translating ribosomes, acts on the COB mRNA 5'-untranslated leader |
| CBP6 | Mitochondrial translational activator of the COB mRNA; phosphorylated |
| PET111 | Mitochondrial translational activator specific for the COX2 mRNA; located in the mitochondrial inner membrane |
| PET494 | Mitochondrial translational activator specific for the COX3 mRNA, acts together with Pet54p and Pet122p; located in the mitochondrial inner membrane |
| PET122 | Mitochondrial translational activator specific for the COX3 mRNA, acts together with Pet54p and Pet494p; located in the mitochondrial inner membrane |
| RRD1 | Peptidyl-prolyl cis/trans-isomerase, activator of the phosphotyrosyl phosphatase activity of PP2A; involved in G1 phase progression, microtubule dynamics, bud morphogenesis and DNA repair; subunit of the Tap42p-Sit4p-Rrd1p complex |
| YPR196W | Putative maltose activator |
| POG1 | Putative transcriptional activator that promotes recovery from pheromone induced arrest; inhibits both alpha-factor induced G1 arrest and repression of CLN1 and CLN2 via SCB/MCB promoter elements; potential Cdc28p substrate; SBF regulated |
| MSA2 | Putative transcriptional activator, that interacts with G1-specific transcription factor, MBF and G1-specific promoters; ortholog of Msa2p, an MBF and SBF activator that regulates G1-specific transcription and cell cycle initiation |
| PET309 | Specific translational activator for the COX1 mRNA, also influences stability of intron-containing COX1 primary transcripts; localizes to the mitochondrial inner membrane; contains seven pentatricopeptide repeats (PPRs) |
| TEA1 | Ty1 enhancer activator required for full levels of Ty enhancer-mediated transcription; C6 zinc cluster DNA-binding protein |
| PIP2 | Autoregulatory oleate-specific transcriptional activator of peroxisome proliferation, contains Zn(2)-Cys(6) cluster domain, forms heterodimer with Oaf1p, binds oleate response elements (OREs), activates beta-oxidation genes |
| CHA4 | DNA binding transcriptional activator, mediates serine/threonine activation of the catabolic L-serine (L-threonine) deaminase (CHA1); Zinc-finger protein with Zn[2]-Cys[6] fungal-type binuclear cluster domain |
| SFL1 | Transcriptional repressor and activator; involved in repression of flocculation-related genes, and activation of stress responsive genes; negatively regulated by cAMP-dependent protein kinase A subunit Tpk2p |
| RDS2 | Zinc cluster transcriptional activator involved in conferring resistance to ketoconazole |
| CAT8 | Zinc cluster transcriptional activator necessary for derepression of a variety of genes under non-fermentative growth conditions, active after |

Transcriptional activators

| Associated Gene(s) | Description(s) |
|---|---|
| | diauxic shift, binds carbon source responsive elements |
| ARO80 | Zinc finger transcriptional activator of the Zn2Cys6 family; activates transcription of aromatic amino acid catabolic genes in the presence of aromatic amino acids |
| SIP4 | C6 zinc cluster transcriptional activator that binds to the carbon source-responsive element (CSRE) of gluconeogenic genes; involved in the positive regulation of gluconeogenesis; regulated by Snf1p protein kinase; localized to the nucleus |
| SPT10 | Putative histone acetylase, sequence-specific activator of histone genes, binds specifically and highly cooperatively to pairs of UAS elements in core histone promoters, functions at or near the TATA box |
| MET28 | Basic leucine zipper (bZIP) transcriptional activator in the Cbf1p-Met4p-Met28p complex, participates in the regulation of sulfur metabolism |
| GCN4 | Basic leucine zipper (bZIP) transcriptional activator of amino acid biosynthetic genes in response to amino acid starvation; expression is tightly regulated at both the transcriptional and translational levels |
| CAD1 | AP-1-like basic leucine zipper (bZIP) transcriptional activator involved in stress responses, iron metabolism, and pleiotropic drug resistance; controls a set of genes involved in stabilizing proteins; binds consensus sequence TTACTAA |
| INO2 | Component of the heteromeric Ino2p/Ino4p basic helix-loop-helix transcription activator that binds inositol/choline-responsive elements (ICREs), required for derepression of phospholipid biosynthetic genes in response to inositol depletion |
| THI2 | Zinc finger protein of the Zn(II)2Cys6 type, probable transcriptional activator of thiamine biosynthetic genes |
| SWI4 | DNA binding component of the SBF complex (Swi4p-Swi6p), a transcriptional activator that in concert with MBF (Mbp1-Swi6p) regulates late G1-specific transcription of targets including cyclins and genes required for DNA synthesis and repair |
| HAP5 | Subunit of the heme-activated, glucose-repressed Hap2/3/4/5 CCAAT-binding complex, a transcriptional activator and global regulator of respiratory gene expression; required for assembly and DNA binding activity of the complex |
| HAP3 | Subunit of the heme-activated, glucose-repressed Hap2p/3p/4p/5p CCAAT-binding complex, a transcriptional activator and global regulator of respiratory gene expression; contains sequences contributing to both complex assembly and DNA binding |
| HAP2 | Subunit of the heme-activated, glucose-repressed Hap2p/3p/4p/5p CCAAT-binding complex, a transcriptional activator and global regulator of respiratory gene expression; contains sequences sufficient for both complex assembly and DNA binding |
| HAP4 | Subunit of the heme-activated, glucose-repressed Hap2p/3p/4p/5p CCAAT-binding complex, a transcriptional activator and global regulator of respiratory gene expression; provides the principal activation function of the complex |
| YML037C | Putative protein of unknown function with some characteristics of a transcriptional activator; may be a target of Dbf2p-Mob1p kinase; GFP-fusion protein co-localizes with clathrin-coated vesicles; YML037C is not an essential gene |
| TRA1 | Subunit of SAGA and NuA4 histone acetyltransferase complexes; interacts with acidic activators (e.g., Gal4p) which leads to transcription activation; similar to human TRRAP, which is a cofactor for c-Myc mediated oncogenic transformation |
| YLL054C | Putative protein of unknown function with similarity to Pip2p, an oleate-specific transcriptional activator of peroxisome proliferation; YLL054C is not an essential gene |
| RTG2 | Sensor of mitochondrial dysfunction; regulates the subcellular location of Rtg1p and Rtg3p, transcriptional activators of the retrograde (RTG) and TOR pathways; Rtg2p is inhibited by the phosphorylated form of Mks1p |
| YBR012C | Dubious open reading frame, unlikely to encode a functional protein; expression induced by iron-regulated transcriptional activator Aft2p |
| JEN1 | Lactate transporter, required for uptake of lactate and pyruvate; phosphorylated; expression is derepressed by transcriptional activator Cat8p during respiratory growth, and repressed in the presence of glucose, fructose, and mannose |
| MRP1 | Mitochondrial ribosomal protein of the small subunit; MRP1 exhibits genetic interactions with PET122, encoding a COX3-specific translational activator, and with PET123, encoding a small subunit mitochondrial ribosomal protein |
| MRP17 | Mitochondrial ribosomal protein of the small subunit; MRP17 exhibits genetic interactions with PET122, encoding a COX3-specific translational activator |

Transcriptional activators

Figure 4:
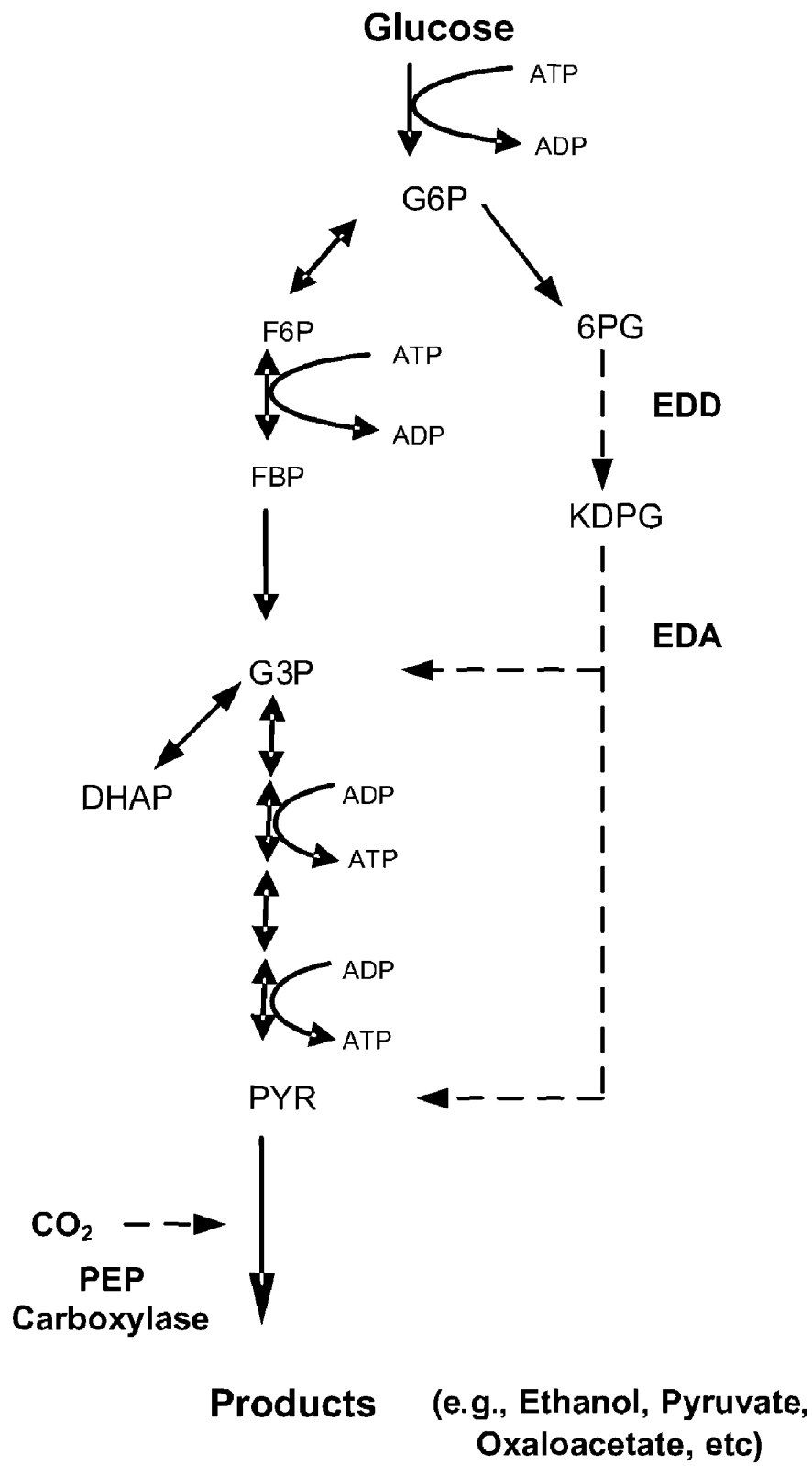
FIG. 4 depicts an engineered metabolic pathway that can be used to increase the efficiency of ethanol production (and other products) by introducing the ability to fix atmospheric carbon dioxide into a microorganism. The engineered microorganism can incorporate or fix atmospheric carbon dioxide into organic molecules using the introduced phosphoenolpyruvate carboxylase activity. Carbon dioxide incorporated in this manner can be used as an additional carbon source that can increase production of many organic molecules, including ethanol. Non-limiting examples of other products whose production can benefit from carbon fixation include; pyruvate, oxaloacetate, glyceraldehyde-3-phosphate and the like. The pathway depicted in FIG. 4 illustrates the introduction of the novel carbon dioxide fixation activity in the background of a fully functional EM pathway, and an introduced ED pathway. It is understood the introduction of the carbon fixation activity can benefit microorganisms that have no other modifications to any metabolic pathways. It also is understood that microorganism modified in one, or multiple, other metabolic pathways can benefit from the introduction of a carbon fixation activity.
Figure 5:
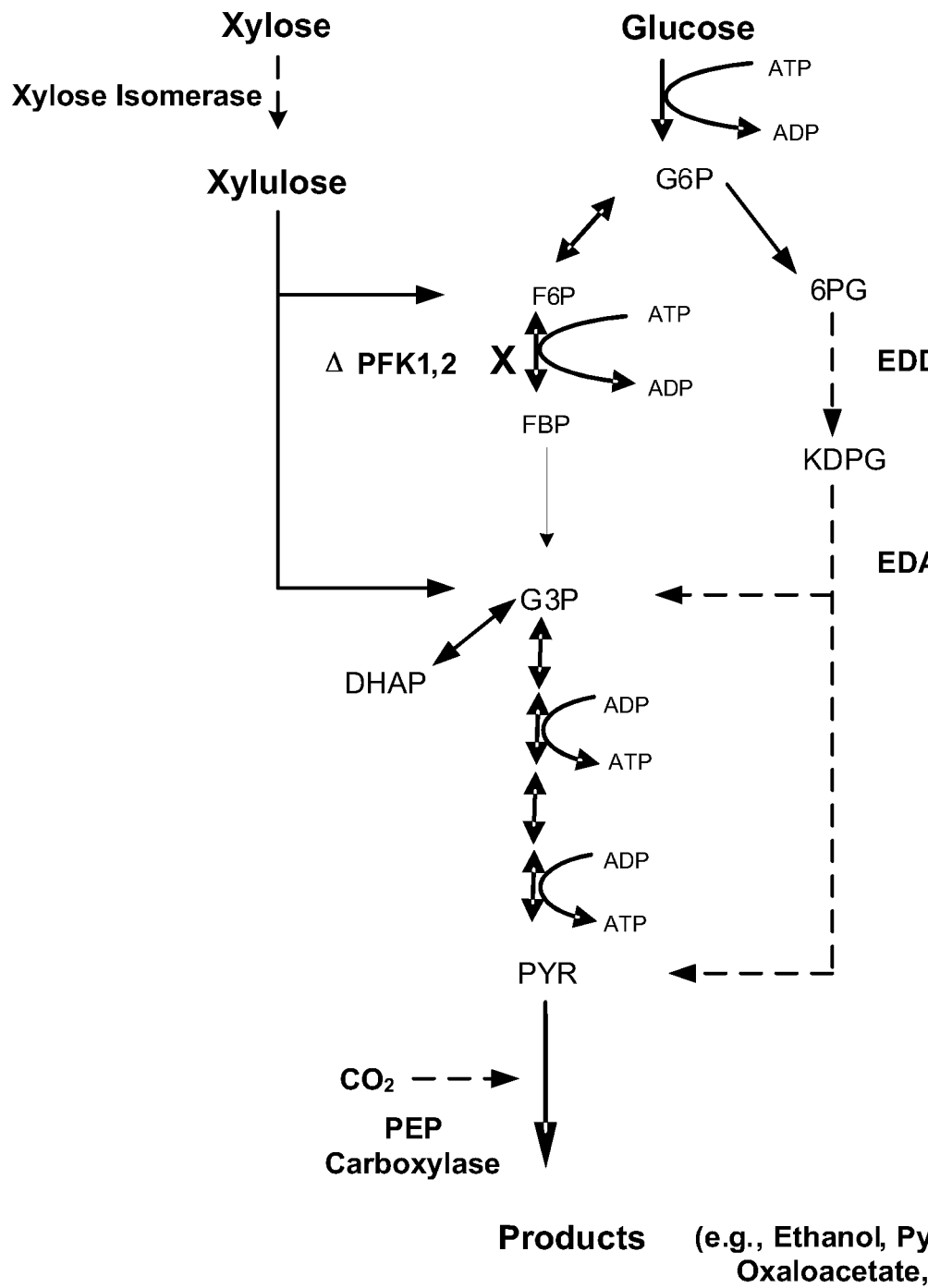
FIG. 5 shows a combination of some engineered metabolic pathways described herein. The combination of engineered metabolic pathways shown in FIG. 5 can provide significant increases in the production of ethanol (or other products) when compared to the wild type organism or organisms lacking one, two, three or more of the modifications. Other combinations of engineered metabolic pathways not shown in FIG. 5 are possible, including but not limited to, combinations including increased alcohol tolerance, modified alcohol dehydrogenase 2 activity and/or modified thymidylate synthase activity, as described herein. Therefore, FIG. 5 also illustrates an embodiment of a method for generating an engineered microorganism with the ability to produce a greater amount of target product comprising expressing one or more genetically modified activities, described herein, in a host organism that produces the desired target (e.g., ethanol, pyruvate, oxaloacetate and the like, for example) via one or more metabolic pathways. In some embodiments, the combination of metabolic pathways includes those depicted in FIG. 5 in addition to combinations including one, two or three of the following activities; increased alcohol tolerance, modified alcohol dehydrogenase 2 activity and modified thymidylate synthase activity.

| Associated Gene(s) | Description(s) |
|---|---|
| TPI1 | Triose phosphate isomerase, abundant glycolytic enzyme; mRNA half-life is regulated by iron availability; transcription is controlled by activators Reb1p, Gcr1p, and Rap1p through binding sites in the 5' non-coding region |
| PKH3 | Protein kinase with similarity to mammalian phosphoinositide-dependent kinase 1 (PDK1) and yeast Pkh1p and Pkh2p, two redundant upstream activators of Pkc1p; identified as a multicopy suppressor of a pkh1 pkh2 double mutant |
| YGL079W | Putative protein of unknown function; green fluorescent protein (GFP)-fusion protein localizes to the endosome; identified as a transcriptional activator in a high-throughput yeast one-hybrid assay |
| TFB1 | Subunit of TFIIH and nucleotide excision repair factor 3 complexes, required for nucleotide excision repair, target for transcriptional activators |
| PET123 | Mitochondrial ribosomal protein of the small subunit; PET123 exhibits genetic interactions with PET122, which encodes a COX3 mRNA-specific translational activator |
| MHR1 | Protein involved in homologous recombination in mitochondria and in transcription regulation in nucleus; binds to activation domains of acidic activators; required for recombination-dependent mtDNA partitioning |
| MCM1 | Transcription factor involved in cell-type-specific transcription and pheromone response; plays a central role in the formation of both repressor and activator complexes |
| EGD1 | Subunit beta1 of the nascent polypeptide-associated complex (NAC) involved in protein targeting, associated with cytoplasmic ribosomes; enhances DNA binding of the Gal4p activator; homolog of human BTF3b |
| STE5 | Pheromone-response scaffold protein; binds Ste11p, Ste7p, and Fus3p kinases, forming a MAPK cascade complex that interacts with the plasma membrane and Ste4p-Ste18p; allosteric activator of Fus3p that facilitates Ste7p-mediated activation |
| RGT1 | Glucose-responsive transcription factor that regulates expression of several glucose transporter (HXT) genes in response to glucose; binds to promoters and acts both as a transcriptional activator and repressor |
| TYE7 | Serine-rich protein that contains a basic-helix-loop-helix (bHLH) DNA binding motif; binds E-boxes of glycolytic genes and contributes to their activation; may function as a transcriptional activator in Ty1-mediated gene expression |
| VMA13 | Subunit H of the eight-subunit V1 peripheral membrane domain of the vacuolar H+-ATPase (V-ATPase), an electrogenic proton pump found throughout the endomembrane system; serves as an activator or a structural stabilizer of the V-ATPase |
| GAL11 | Subunit of the RNA polymerase II mediator complex; associates with core polymerase subunits to form the RNA polymerase II holoenzyme; affects transcription by acting as target of activators and repressors |
| VAC14 | Protein involved in regulated synthesis of PtdIns(3,5)P(2), in control of trafficking of some proteins to the vacuole lumen via the MVB, and in maintenance of vacuole size and acidity; interacts with Fig4p; activator of Fab1p |

Example 7

Heterologous Xylose Isomerase Expression in Yeast

Provided hereafter are non-limiting examples of certain organisms from which nucleic acids that encode a polypeptide having xylose isomerase activity can be obtained. Certain nucleic acid encoded polypeptides having active xylose isomerase activity can be expressed in an engineered yeast (*S. cerevisiae*).

| Donor Organism | Active? (yes/no) | Xylose isomerase type (Type 1/Type 2) |
|---|---|---|
| *Piromyces* | Yes | Type 2 |
| *Orpinomyces* | Yes | |
| *Bacteroides thetaiotaomicron* | Yes | |
| *Clostridium phytofermentans* | Yes | |
| *Thermus thermophilus* | Yes | Type 1 |
| *Ruminococcus flavefaciens* | Yes | |
| *Escherichia coli* | No | |
| *Bacillus subtilis* | No | |
| *Lactobacillus pentoses* | No | |
| *Leifsoria xyli* subsp. *Cynodontis* | No | |
| *Clostridium thermosulfurogenes* | No | |
| *Bacillus licheniformis* | No | |
| *Burkholderia xenovorans* | No | |
| *Psudomonas savastanoi* | No | |
| *Robiginitalea biformata* | No | |
| *Saccharophagus degradans* | No | |
| *Staphylococcus xylosus* | No | |
| *Streptomyces diastaticus* subsp *diastaticus* | No | |
| *Xanthomonas campestris* | No | |

-continued

| Donor Organism | Active? (yes/no) | Xylose isomerase type (Type 1/Type 2) |
|---|---|---|
| Salmonella enterica serovar Typhimurium | No | |
| Agrobacterium tumefaciens | No | |
| Arabidopsis thaliana | No | |
| Pseudomonas syringae | No | |
| Actinoplanes missouriensis | No | |
| Streptomyces rubiginosus | No | |
| Epilopiscium | No | |

Example 8

Examples of Nucleic Acid and Amino Acid Sequences

Provided hereafter and non-limiting examples of certain nucleic acid sequences.

| Gene Name | Organism/ ATCC identifier | Nucleic acid Accession No. or other identifier | Nucleotide Sequence |
|---|---|---|---|
| Xylose Isomerase (XI-RF Native) | Ruminococcus flavefaciens strain 17 | AJ132472 | atggaatttt tcagcaatat cggtaaaatt cagtatcagg gaccaaaaag tactgatcct ctctcattta agtactataa ccctgaagaa gtcatcaacg gaagacaat gcgcgacgt ctgaagttcg ctcttcatg gtgcacaca atggcgggcg acgaacaga tatgttcggc tgcgcacaa cagacaagac ctgggacag tcgatcccg ctgaagagc aaggtcaag gttgacgcag cattcgagat catggataag ctctccattg actactattg tttccacgat cgcgactctt ctcccgagta tgcagcctc aaggtcaca acgatcagct tgcacatagt acagactata tcaaggagaa gcaggcgac aagtcaagt gcctctggg tacacaaag tgcttcgatc atccaagatt catgcacggt gcagtacat ctccttctgc tgatgattc gtttccag ctgctcagat caagaaggct ccgagtcaa cagtaaaagct cggcggtaac ggtacgttt tctgggacgg tatggacgcg tcttcaatgc ttcttaatac aaatatggga ctcgaaccg acaatatggc tcgtcttatg aagatggtg ttgatatgg acgttcgatc ggcttcaagg gcgacttcta tatcgagccc aagcccaaga agccacaaa gcatcagtac gattcgata cagctactgt tctcgggattc actcgtcga taaggatttc aagatgata tcgaagctaa ccacgctaca cttgctcagc atacattcca gcatgagctc cggttgcaa gagagaccg tgtgtcgt tctatcgagc caaccaggg cgacgttctt cttggatgggg atacagacca gttcccaca aatatctacg atacaacaat gtgtatgtat gaagtatca aggcaggcgg cttcacaaac ggcgtctca acttcgacgc taaggcacgc agagggagct tcactcccga ggatatcttc tacagctata tcgcaggtat ggatgcattt gcctcgggct tcagagctgc tctcaagctc atcgaagacg gacgtatcga caagtcgtt gctgacagat acgcttcatg gaataccgt atcgtgcag acataatcgc agtaaggca gattcccat ctctgaaaa gtatgctctt gaaaaggggc aggttacgac ttcacctcta agcggcgac aggaaatgct ggagtctatc gtaataacg ttcttttcag tctgtaa (SEQ ID NO: 30) |
| Xylose isomerase (point mutation) | Based on Ruminococcus flavefaciens strain 17 | | atggaattttcagcaatatcgtaaaattcagtatcaggaccaaaagtactgatcctctcattaagtactgatcctcattaagtactataacc ctgaagaagtcatcaacggaaagacaatgcgcgagcctgaagttcgctcttcatggtgcaccaatggcggc gacgaacagatatgttcggctgcgcaacagacaagacctgggacagtcgatcccgctgaagacgcaa gctaaggttgacgcagcattcgagatcatggataagctctccatattgttccacgatcgcgatcttctccc gagtatgcagcctcaaggctaccaacgatcagcttgcatatagtacagactatatcaaggagaaggcaca agttcgcttctcagtgctgcagaaggctcaacagtaagtgctcgacagctcaacaatatgctggctcttatga agcatcagtacgatttcgatacagctactgttctcgggattcctcagacatatccagcatgagctccgtgttgcag gttctatcgaagactgtgggcttctggggatatcccagatacttccaggatgccaagatagaatgtgtttcg aatgtgtatgatgttcactcccgaggatatcttctacagcagtatatcgcaggatgatgcatttgccttcagagctgcta gcttatcgaagacgacagtcgcttacaggttcgtgcgacatacgctcatggaataccgtatcgtgctgctagacata atcgcaggtaagactatcttcgcatcttgaaagtctcttgaaaaggggccaggttacgactcactccaagcg gcagacaggaaatgctggagtctatcgtaaataacgttctttcagtctgtaa (SEQ ID NO: 29) |
| Xylose isomerase (XI-RF_HR) | | | atggagttctttctaatatagtaaattcagtatcaaggtccaaaatc tacagatccattgctctttaaatatataatccagaagaagttataaatg gtaaactacatgagagaacatttaaaattgcttgtctggtgcatct atggtggtagtcgatgtccgttgtgttactactgataaac ttgggggtcaatcgatccagctgctagcaaacgcaaagtagatgcag cctttgaaattatgagtaaatgtctattgatttattgtttttcatgat |

-continued

| Gene Name | Organism/ ATCC identifier | Nucleic acid Accession No. or other identifier | Nucleotide Sequence |
|---|---|---|---|
| | | | agagattgtctcctgaatatggttcttaaagcaactaatgatcaatt ggacattgttacggattatattaagaaaaacaaggtgataaatttaaat gttgtgggcactgcgaaatgttttgatcatccacgttttatgcatggt gcgggacgagtccctcgctgatgttttgctgttttctgccgctcaaat taagaaggcaattggaatcaactgtaaattaggtgggaacggtatgtat tctgggaggaaggaaggttatgaacattattaaacactaatatggt ttgaatgtgataatatgcgtgatgaaatggctgtagaatacgg aagtccattgtttaaggtgtacttttatattgaaccaaaacctaaag agcctactaaaacatcaatatgattttgataactgctacagtttgggattc ttgagaaaatatggtctggataaagattttaaaatgaatatagaagtaa tcatgcaactcgcaacactcttttcaactgaatgagagttgcca gaataacggagttttggatctatcgatgcaaccaggagacgtttg ctagatgggaactgatcaatttccaactaacattatgataactact acttgatgcgaaggctaggcgtgctagtttcactccgaggatatattc tattcttatattgcgaatgatgctagaatgataagttgtagctagagt actaaaattgattgaagatgtaagatgcagatataacgctgggaagcc atgctctttggaatactggaataggacagaatatatacgctgggaaagcc gactcgccagtctgaaaatatgccttgaaaagaaggaagtatcgc cagcttaagttcggtctgtcaagaaatgttgaatctcattgtaacaatg ttttatttcctg (SEQ ID NO: 23) |
| Xylose isomerase (XI-P Native) | Piromyces sp. E2 | AJ249909 | atggctaagg aatattccc acaaattcaa aagattaagt tcgaagtcaa ggattctaag aatccattag ccttccacta ctacgatgct gaaaaggaag tcatgggtaa gaaaatgaag gattggtac gttcgccat ggcctggtgg cacactcttt ggccgaagg tgctgaccaa ttcggtgag gtacaaagtc tttcccatgg aacgaagta ctgatgctat tgaaattgcc agcaaaagg ttgatgctgg tttccgaaatc atgcaaaagc ttggtattcc atactactgt ttccacgatg tgatctgt ttccgaagt aactctattg aagatacca atccaacctt aaggctgcg tgcttacct caaggaaag caaaaggaaa ccgtattaa gcttcctcgg agtactgta acgtctccgg tcacaagcgt tacatgaac gtgcctccac taaccagac ttgatgtg tcgcccgtgc tattgttcaa attaagaaac ccatagacgc cggtattgaa cttggtgtg aaaactgct ccttctgggt ggtcatgag gtacatcgag tctccttaac actgaccaa agcgtgaaaa ggaacacatg gccactatgc tacctgc tcgtgactac gctcgtccca aggattcaa ggtacttct ctcattgtt tccttaagc caacactttc aagcaccaat acgatgttga cactgaaacc cattgaagct aacccgcta ctcctgctg gttccattga tgctaaccgt gacaaggact tcaaggtt caaggaagtt ctttgggt gtcatgctg gtacactttc gaacacgaac ttgcctgc tgtgatgtct tgtgatgtg caatcccaa gttccattga tgatcaata cgaactgcc gttgactacc aaaacggttg ggatactgat ccgtggtggt caattttcgta ctggtggtc cgttttcggt caagctgga gtgactaactc tactgacctc gaagcatca cattgcccca cgtttggt gccaagact gtcgtaactc tgctgcaagc gctgacagtg tcctccaaga actccatac atggatgcta tggctcctgc tcttgaaac gctgcaagc ttcgacagtg gtattgtaa ggacttggt accaagatga ageaagaacg ttacgcttcc ttcgacagtg gtattgtaa gaagaacgt tgatgtaagc tcacctcga acaagttac gaataacgta gctacctac tcctccaga actccatac atggatgcta caaacttctg gtaagcaaga acctctacgaa gctactgtg ccatgtcc gaatgaagt ataaSeQ ID NO: 24) |
| Xylose Isomerase (XI-P-HR1) | Based on Piromyces sp. E2 | | ATGGCTAAGAATATTTTCCACAAATTCAAGAAATTTAAATTTGAAGTAAGATTC TAAAAATCCATTGGCTTTCCATTATTATGATGCTGAAAAAGAAGTTATGGGTAAAA AGATGAAAGATTGGTTGAGATTCGCTATGGCTTGGTGGCATACTCTATGTCTG AAGGAGCTGATCAATTGGAGGAGGTACTAAATCTTTTCCTTGAATGAAGGTA |

-continued

| Gene Name | Organism/ ATCC identifier | Nucleic acid Accession No. or other identifier | Nucleotide Sequence |
|---|---|---|---|
| | | | CTGACGCTATTGAAATGCTAAGCAGAAAGTAGACGCGGGTTTTGAAATTATGC<br>AAAAATTGGAATACCATATTATTGTTTTCATGATGTTGATTTGGTATCTGAGGGT<br>AATTCTATTGAAGAATATGGAATTAATTAAAAGCTGTTGTTGCTTACTTAAAGA<br>AAAACAAAAAGAAACTGGAATTAAATTGTTGGTCTACAGCTAATGTTTTCGGT<br>CATAAAAGATATATGAATTGTGCTTCTACAAATCCAGATTTTGATGTTGTAGCTA<br>GAGCTATTGTTCAAATTAAAAATGTGCAGAAATTGAATTAGGTGCCGA<br>AAATTATGTTTTCTGGGAGGTAGAGAAGGTTATATGTCTTTGTTAAATACTGAT<br>CAAAAACGTGAAAAGGAACACATGGCAACTATGTTGACAATGGCTAGGGATTAT<br>GCTAGATCTAAAGGTTTTAAAGGTACTTTCTTGATTGAGCCAAAACTATGGAAC<br>CAACTAAAAACATCAATATGACGTTGACACTGCTATGGTTTCTTAAAGC<br>TCATAAATTGGATAAAGATTTTAAGGTTAATATAGAAGTTAATCATGCTACACTAG<br>CTGGTCATACTTTTGAACATGAGGTTGATTATCAAAATGGTTGGGACACAGATCAATTT<br>TTCTATCGACGCAAATAGAGGTGATTATCAAGCATGGATGGAAATTATTAGGGGTGA<br>CCAATAGATCAATATGAATTGGTTCAAGCATGGATGGAAATTATTAGGGGTGA<br>GGCTTCGTTACAGGTGGACTAATTTTGATGCTAAAACTAGGAGAAATTCTACAG<br>AICTTGAAGATAATAATTATTGCTCATGTATCTGGTATGCGATGCCCGTGC<br>TTTGGAAAATGCAGCTAAATTACTTCAAGAATCTCCTATACTAAAATGAAAAAGG<br>AAAGATATGCTTCTTTTGATTCTGGAATAGGTAAGGATTTTGAAGATGGTAAATT<br>GACATTGGAACAAGTTTATGAATATGGTAAGAGAATGGAGAACCAAAACAAACT<br>TCTGGTAAACAAGAATTATATGAGGCTATAGTAGCTATGTATCAAta (SEQ ID NO: 25) |
| PEP Carboxylase (PEPC-Native) | Zymomonas mobilis | ATCC 31821 | ACTAGTAAAAAATGACCAAGCCGCGCACAATTAATCAGAACCCAGACCTTCGC<br>TATTTTGGTAACCTGCTCGGTCAGGTTATTAAGGAACAAGGCGGAGAGTCTTTAT<br>TCAACCAGATCGAGCCAAATTCGCTTCGCTTAGCCGATCTCGACCTTAATGACATGT<br>TGACAGCACCGAGCTAAGTTCTCGCTTAGCCGATCTCGACCTTAATGACATGT<br>TCTCTTTTGCACATGCCCTTTTGCTGTTTTCAATGCTGGCCAATTTGGCTGATGA<br>TCGTCAGGGAGATGCCCTTGTCTGATCTGATGCCAATATGCAAGTGCCCTTAAGGA<br>CATAAAAGCCAAAGGCGTCAGTTCAGGTCAGGCGATCATTGATATGATCGACAAAGC<br>CTGCATTGTGCCTGTTCTGACAGCACATCCAGGTTTAATGCGGTTAAAGATGCTGGACAA<br>ACGGTGACCAAGATGGTCTTCCGATCGAAGATGCGTTAATCCAGCAATCACG<br>ATATTATGGCAGACTCGTCCGTCCGCTCATGCTGCAAAAGCTGACCGTGCTGATGAA<br>ATCGAAACTGCCCTGCTTCTGTCTTTCTTAAGGAAACTTTCTGCCTGTTCTGCCCCAGA<br>TTTATGCAGAATGGGAAAAATTGCTTGGTAGTTCTATTCCAAGCTTTATCAGACC<br>TGGTAATTGGATTGGTGAACGTGACGGTAACCCCAATGTCAATGCCGATAC<br>GATCATGCTGTCTTTGAAGCGCAGCTCGGAAACGTATTGACCGATTATCTCAA<br>CCGTCTTGATAAACTGCTTTCAGCCGATATTCGGTCAACCTTTCGGTCAACCGATATGCTGCCATCCGT<br>TCCGATGATATTTCACGTCTAGCCGATAAAAGTGGTGACGATGCTGCCGATCCGT<br>GCGGATGAACCTTATCGTCGTGCCTAAAATGGTATTTATGACCGTTTAGCCGCTA<br>CCTATCGTCAGATCGCCGTGCAATCGCCAACCCTTCGCGCGTCCAGCCTTGCGTTCTGCA<br>GAAGCCTATAAACGGCTTCAAGAATTGCTGGCTAGTTTTAAGGACCCTTGGCGAA<br>GGTTGGGTAAATTGGCAGAAGGTAGTTTTAAGGCATTGATCCGTTCGGTTGAA<br>ACCTTTGGTTTCCATTGGCCACCCTGATCTGCGTCAGAATTCGCAGGTTCAT<br>GAAAGAGTTGTCAATGAACTGCTACGGACAGCCACCGTTGAAGCCGATTATTA<br>TCTCTATCGGAAGAGATCGCCGTTAAGCTGTTAAGACGGGAATTGTCGCAGCCG<br>CGGACTCTATTCGTTCGCGCGCCGATTATTCCGAAGAAACGCGTTCGAACTT<br>GATATTATTCAGGCAGCAGCCCCGGCCATGAAGCATTATTCCGATAATCCATT<br>ACGACTTATTTGATTTCGAATGGCGAAAGCATTTCGATATTCTGAAGTTCTATT |

| Gene Name | Organism/ ATCC identifier | Nucleic acid Accession No. or other identifier | Nucleotide Sequence |
|---|---|---|---|
| | | | TGCTTTTGAAAGAAGCAGGGCTGTATCAAGGGGTGTAAGCCAAAGCGGCG<br>ATTGAAGCTGCGCCTTTATTCGAGACTGGCCGATCTTGAAAATGCGCCAAAG<br>GTCATGGAGGAATGGTTCAAGCTGCCTGAAGCCAAGCCAATCTTCAAAGGCACA<br>TGGCGTTCAGGAAGTGATGGTTGGCTATTCTGACTCCAATAAGGACGGCGATA<br>TCTGACCTCGGTTTGGGGTCTTTATAAGGCTTGCCTCGCTTTGGTGCCGATTTT<br>GAGAAAGCCGGTGTACCCAGTTTTTCCATGGACGGGGTGGTTCCGTTGG<br>TCGCGTGGTGGTTCCAACTTTAATGCCATTCTGTCGCAGCCAGCCGAGCCG<br>TCAAAGGGCGTATCCGTTATACAGAACCAGGGTGAAGTCGTGGCGGCCAAATAT<br>GGCACCCATGAAAGCGTATTGCCCATCTGGATGAGGCCTGGCGGCGACTTT<br>GATTACGTCTTTGAAGCACCGACCATTGTCGAGCCAGAGTTTAGTCGTTACCG<br>TAAGGCCTTGGATCAGAATTCAGCTTCCAGCCTATCGCCAATTGT<br>CTATGGAACGAAGGGCTTCCGTAAATTCTTTAGTGAATTACCGCTTTGCCGGAA<br>ATTGCCCTGTTAAAGATCGGGTCACGCCCACCTAGCCGCAAAAATCGACCG<br>GATTGAAGATCTACGGCTATTCCTTGGGTGTTTAGCTGGTCTCAAGTTCGACT<br>CATGTTACCCGGTGGTTCGGTTCAGGCTTTATATGACTTTGAAGATACC<br>GAGCTGTTTACAGGAAATGGCAAGCCGTTGGCCGTTTTTCCGCACGACTATTCG<br>AATATGGAACAGGTGATGGCACGTTCCGATATGACGATCGCCAAGCATTATCTG<br>GCCTTGGTTGAGGATCAGCAAATGGTGAGGCTATCTATGATTCTATCGCGGAT<br>GGCTGGAATAAAGGTTGTGAAGGTCTGTTAAAGGCAACCCAGCAGAATTGGCTG<br>TTGGAACGCTTTCCGGCGGTTGATAATTCGGTGCAGATGCGTCGGCCTTATCTG<br>GAACCGCTTAATTACTTACAGGTCGAATTGCTGAAGAAATGCTGAAGGAGGTGAT<br>ACCAACCCGCATATCCTCGAATCTATTCAGCTGACAATCAATGCCATTGCGACG<br>GCACTTCCAACGCGGTTAATAACTCGAG (SEQ ID NO: 20) |
| PEP Carboxylase (PEPC-HR) | Based on Zymomonas mobilis | | ACTAGTAAAAAAATGACCAAGCCAAGACTATTAACCAAAACCCAGACTTGAGAT<br>ACTTCGGTAACTTGTTGGTCAAGTTATCAAGGAACAAGGTGTGAATCTTTGTT<br>CAACCAAATTGAACAAATCAGATCCGCTGCTATTAGAGACAACAGAGGTATCGT<br>CGACTTCTACCGAATGTCCTCTAGATTGGCTGGACTTGAACGACATGTT<br>CTCCTTCGCTCACGCTTTCTTGTTCTCTATGTTGGCTAACTTGGCTGACGAC<br>AGACAAGGTGACCGTTTGGACCCAGACGCTAACATGGCTCCGCTTTGAAGGA<br>CATTAAGGCTAAGGCTGGTTTTCTGACAAGCTATCATTGACATTGATCGACAAGGCT<br>TGTATTGTCCAGTTTTGACTGCTGACTCACCCAACCGAAGTCAGAAGAAAGTCCATG<br>TTGGACCACTACAACAGAATCGCTGGTTTGATGAGATTGAAGGACGCTGGTCAA<br>ACTGTTACCGGAAGACGGTTTGCCAATTGAACGACGCTTTGATCCAACAAATTACTA<br>TCTTGTGCAAACCAGACCATTGATGTTGCAAAAGTTGACTGTCGCTGACGAAA<br>TTGAAACCGCTTGTCTTCTTGAGAGAACTTCTGACGCTTGCCAGTTTGCCACAAAT<br>CTACGCTGAATGGGAAAAGTTGTTGGGTTCCTCTATTCCATCCTCATCAGACCA<br>GGTAACTGGATTGGTGGTGACAGAGAGATCCTGAAACTGTTTTGACGTACTTGAAC<br>CATCATGTTGTCTTTGAAGAGATCCTTGAAGCTGACTTTGTCTCCACTGACGTTTCTGTCT<br>AGATTGGACAAGTTGTCAACTTGTCTGTCTCCACTGACGTTCTGTGTCT<br>CCGACGACATTTTGAGATTGGCTGACAAGTCTGGTGACGACGTCTATCAGAG<br>CTGACGAACCATACAGAAGAGCTTTGAACGGTATTACGACAGATTGGCTGCTA<br>CCTACAGACAAATCGCTGGTAGAACATCCATCCAGACCAGCTTTGAGATCTGCTG<br>AAGCTTACAAGAGACCACAAGAATTGTTGCTGACTTGAAGACTTGGCTGAAG<br>GTTTGGGTAAGTTGGCTGAAGGTTCCTTCAAGCTTTGATTAGATCTGTTGAAAC<br>CTTCGGTTTCCACTTGGCTACTTTGGACTTGAGACAAAACTCCCAAGTCCACGA<br>AAGAGTTGTCAACGAATTGTTGAGAACCGCTACTGTTGAAGAGAATTCTCAACCAGA<br>TTGTCCGAAGAAGCAGAGTCAAGTTGTTGAGAAGAGAATTGCTCGAATTGGAC<br>ACCTTGTTCGTTCAAGACTGACTACTCCGAAGAAACTAGATCTGAATTGGAC |

-continued

| Gene Name | Organism/ATCC identifier | Nucleic acid Accession No. or other identifier | Nucleotide Sequence |
|---|---|---|---|
| | | | ATCATTCAAGCTGCTGCTAGAGCTCAGTCCAGAATCTTCGTCAGAATCATTACCA<br>CTTACTTGATCTGAATCCGTGTAACGGTGAATCCATTCTGACATCTTGGAAGTCTACTTGTT<br>GTTGAAGGAAGCTGGTTTGTACAAGGTGTGTAAGCAAGGCTGTATTGA<br>AGCTGCTCCATTGTTCGAAACCGTTGCTGACTTGGAAAACGCTCCAAAGGTCAT<br>GAAGAATGGTTCAAGTTGCCAGAAGCTCAAGCTATCCGTAAGGCTCACGGTGT<br>TCAAGAAGTCATGGTTGTACTTCCGACTGTTGGCTTTGGTTCCAATTTCGAAAAG<br>TTCCGTCTGGGGTTGTACAAGGCTGTTGGCTTTGGTTCCAATTTCGAAAAG<br>GCTGGTGTCCCAATCCAATTCTTCCACGGTAGAGGTGGTTCTGTTGTGTAGAGGT<br>GGTGGTTCCAACTTCAACGCTATTTTTGTCTCAACCACTGGTGCTGTCAAGGGT<br>AGAATCAGATACACCGAACAAGGTGAAGTTGTCGCTGCTAAGTACGTACTCAC<br>GAATCCGCTATTGCTCACTTGGACGAAGCTGTTGCTGCTACCTGATCACTTCTT<br>TGGAAGCTCCAACCATTGTCGAACCAGAATTCTCCAGATACAGAAAGGCTTTGG<br>ACCAAATCTCTGACTCCGCTTTCCAAGCTTACACCCCATTGTTTACGGTACTAA<br>GGGTTTCAGAAAGTTCTTCTCTGAATTCACCCCATTGCCAGAATTGCTTTGTTG<br>AAGATCGGTTCCGACACCACATCGCTAAGACTACTACTGGCTTTGCTGTCGAAG<br>AGAGCTATCCATGGGCTTCTTCTTGGTCCCAAGTTAGAGTCATGTTCCAGGT<br>TGGTTCGTTTCGGTCAAGCTTTGTGAAGGCTACCGAAGACACTGAATTGTTGCAA<br>GAAATGGCTTCTAGATGCCATTCTTCAGAACCACTATTAGAAACATGGAACAAG<br>TTATGGCTGATCGACATGACCATCGCTAAGACTACTACTGGCTTTGCTGTCGAAG<br>ACCAAACTAACGGTGAAGCTATTTACGACTCCACCAACAAACTGGTTGTTGGAACAAGG<br>GTTGTGAAGGTTTGTGACAACTCCGTCAACTAGCACCATATTGAACCATTGAACT<br>CAGCTGTTGACAACTCCGTCCAACTAGCACCATATTGAACCATTGAACT<br>ACTTGCAGTTGAATTGTTGAAGAAGTGCAGAGGTGGTGACACTAACCACACA<br>TTTTGGAATCTATCCAATTGACCATTAACGCTATCGCTATCGCTACTGTTTGAGAAACTC<br>CGGTTAATAACTCGAG (SEQ ID NO: 21) |
| EDA Primers | Zymomonas mobilis (ZM4) | 31821D-5 | 5'-aactgactagtaaaaaatgcgtgatatcgattcc-3' (SEQ ID NO: 1)<br>5'-agtaactcgagctactaggcaacagcagcgcgcttg-3' (SEQ ID NO: 2) |
| EDD Primers | Zymomonas mobilis (ZM4) | 31821D-5 | 5'-aactgactagtaaaaaatgactgatctgcattcaacg-3' (SEQ ID NO: 3)<br>5'-agtaactcgagctactagatccgcacctgcatatattgc-3' (SEQ ID NO: 4) |
| EDA Primers | Escherichia coli | | 5'-aactgactagtaaaaaatgaaaactgaaaacaagtgcagaatc-3' (SEQ ID NO: 5)<br>5'-agtaactcgagctactacagcttagcgccttctcagcttcacg-3' (SEQ ID NO: 6) |
| EDD Primers | Escherichia coli | | 5'-aactgactagtaaaaaatgaatccacaattgtacgctaacaaatg-3' (SEQ ID NO: 7)<br>5'-agtaactcgagctactacagcttaaaaagtgataacaggttgcgccccgttcggcac-3' (SEQ ID NO: 8) |
| PFK primers | Saccharomyces cerevisiae YGR240CBY4742 | 4015893 | 5'-tgcatattccgttcaatcttataagctgccataagatttttaccaccaagtcgttttaagagctgttggtgagcgcta-3' (SEQ ID NO: 9)<br>5'-cttgccagtgaatgacctttggcattctcatgtttcatagtcgagttcaagagaaaaagaa-3' (SEQ ID NO: 10)<br>5'-atgactgtactactccttttgtgaatggtacttcttattgtaccgtcactgtagctttgccagtgaatgacctttggcat-3' (SEQ ID NO: 11)<br>5'-ttaatcaactctcttttcttccaaccaaatggtcagcaatgagtcgtgatgacgactatggac-3' (SEQ ID NO: 12) |
| Thymidilate synthase | Saccharomyces cerevisiae strain | 208583 | CDC21_fwd: 5'-aactgatcaaagcttctaaatacaagacgtgcgatgacgactatggac-3' (SEQ ID NO: 155) |

| Gene Name | Organism/ ATCC identifier | Nucleic acid Accession No. or other identifier | Nucleotide Sequence |
|---|---|---|---|
| Primers (cdc21) | 17206 | | CDC21_rev: 5'-taccgtactacccgggtatatgtcttttgcctgtgttcttaataattc-3' (SEQ ID NO: 156)<br>ThymidylateSynthase::cdc21 fwd: 5'-ctaaatacaagacgtgcgatgacgactatactgg-3' (SEQ ID NO: 161)<br>ThymidylateSynthase::cdc21 rev: 5'-gtcaacaagaactaaaaaatgttcaaaaatgcaattgtc-3' (SEQ ID NO: 162). |
| LYS2 | BR214-4a | 208600 | Lys2Fwd: 5'-tgctaatgacccgggaattccacttgcaattacataaaaattccggcgg-3' (SEQ ID NO: 157)<br>Lys2Rev: 5'-atgatcattgagctcagctcgcaagtattcattttagacccatggtgg-3' (SEQ ID NO: 158). |
| PEPC Primers | Zymomonas mobilis | | 5' forward (5'-GACTAACTGAACTAGTAAAAAAAATGACCAAGCCGGCACACAATTAATCAG-3') (SEQ ID NO: 13)<br>3' reverse (5'-AAGTGAGTAACTCGAGTTATTAACCGCTGTTGCGAAGTGCCGTCGC-3') (SEQ ID NO: 14). |

Provided hereafter are non-limiting examples of certain amino acid sequences.

| Gene Name | Organism/ ATCC identifier | Amino acid Accession No. or other identifier | Amino Acid Sequence |
|---|---|---|---|
| Xylose Isomerase (XI-RF Native) | *Ruminococcus flavefaciens* strain 17 | CAB51938.1 | MEFFSNIGKIQYQGPKSTDPLSFKYYNPEEVINGKTMREHLKFALSWWHTMGGDGTDM FGCGTTDKTWGQSDPAARAKAKVDAAFEIMDKLSIDYYCFHDRDLSPEYGSLKATNDQL DIVTDYIKEKQGDKFKCLWGTAKCFDHPRFMHGAGTSPSADVFAFSAAQIKKALESTVKL GGNGYVFWGGREGYETLLNTNMGLELDNMARLMKMAVEYGRSIGFKGDFYIEPKPKEP TKHQYDFDTATVLGFLRKYGLDKDFKMNIEANHATLAQHTFQHELRVARDNGVFGSIDA NQGDVLLGWDTDQFPTNIYDTTMCMYEVIKAGGFTNGGLNFDAKARRGSFTPEDIFYSY IAGMDAFALGFRAALKLIEDGRIDKFVADRYASWNTGIGADIIAGKADFASLEKYALEKGE VTASLSSGRQEMLESIVNNVLFSL (SEQ ID NO: 31) |
| Xylose isomerase (XI-P Native) | *Piromyces* sp. E2 | CAB76571.1 | MAKEYFPQIQKIKFEGKDSKNPLAFHYYDAEKEVMGKKMKDWLR FAMAWWHTLCAEGADQFGGGTKSFPWNEGTDAIEIAKQKVDAGFEIMQKLGIPYYCFH DVDLVSEGNSIEEYESNLKAVVAYLKEKQKETGIKLLWSTANVFGHKRYMNGASTNPD FDVVARAIVQIKNAIDAGIELGAENYVFWGGREGYMSLLNTDQKREKEHMATMLTMAR DYARSKGFKGTFLIEPKPMEPTKHQYDVDTETAIGFLKAHNLDKDFKVNIEVNHATLA GHTFEHELACAVDAGMLGSIDANRGDYQNGWDTDQFPIDQYELVQAWMEIIRGGGFVT GGTNFDAKTRRNSTDLEDIIIAHVSGMDAMARALENAAKLLQESPYTKMKKERYASFDS GIGKDFEDGKLTLEQVYEYGKKNGEPKQTSGKQELYEAIVAMYQ (SEQ ID NO: 35) |

Example 9

Preparation and Expression of Xylose Isomerase Genes

A full length native gene encoding a xylose isomerase from *Ruminococcus flavefaciens* was synthesized by IDT DNA, Inc. (Coralville, Iowa), with a single silent point mutation (a "C" to a "G") at position 513. The sequence of this gene is set forth as SEQ ID NO: 29 the point mutation is indicated as the larger bold capital letter "G".

```
                                       SEQ ID NO: 29
ATGGAATTTTTCAGCAATATCGGTAAAATTCAGTATCAGGGACCAAAA

AGTACTGATCCTCTCTCATTTAAGTACTATAACCCTGAAGAAGTCATC

AACGGAAAGACAATGCGCGAGCATCTGAAGTTCGCTCTTTCATGGT

GGCACACAATGGGCGGCGACGGAACAGATATGTTCGGCTGCGGCA

CAACAGACAAGACCTGGGGACAGTCCGATCCCGCTGCAAGAGCAA

AGGCTAAGGTTGACGCAGCATTCGAGATCATGGATAAGCTCTCCAT

TGACTACTATTGTTTCCACGATCGCGATCTTTCTCCCGAGTATGGCA

GCCTCAAGGCTACCAACGATCAGCTTGACATAGTTACAGACTATAT

CAAGGAGAAGCAGGGCGACAAGTTCAAGTGCCTCTGGGGTACAGC

AAAGTGCTTCGATCATCCAAGATTCATGCACGGTGCAGGTACATCT

CCTTCTGCTGATGTATTCGCTTTCTCAGCTGCTCAGATCAAGAAGG

CTCTGGAGTCAACAGTAAAGCTCGGCGGTAACGGTTACGTTTTCT

GGGGCGGACGTGAAGGCTATGAGACACTTCTTAATACAAATATGG

GACTCGAACTCGACAATATGGCTCGTCTTATGAAGATGGCTGTTGA

GTATGGACGTTCGATCGGCTTCAAGGGCGACTTCTATATCGAGC

CCAAGCCCAAGGAGCCCACAAAGCATCAGTACGATTTCGATAC

AGCTACTGTTCTGGGATTCCTCAGAAAGTACGGTCTCGATAAGG

ATTTCAAGATGAATATCGAAGCTAACCACGCTACACTTGCTCAG
```

-continued

```
CATACATTCCAGCATGAGCTCCGTGTTGCAAGAGACAATGGTGTG

TTCGGTTCTATCGACGCAAACCAGGGCGACGTTCTTCTTGGATGG

GATACAGACCAGTTCCCCACAAATATCTACGATACAACAATGTGT

ATGTATGAAGTTATCAAGGCAGGCGGCTTCACAAACGGCGGTCT

CAACTTCGACGCTAAGGCACGCAGAGGGAGCTTCACTCCCGAG

GATATCTTCTACAGCTATATCGCAGGTATGGATGCATTTGCTCTG

GGCTTCAGAGCTGCTCTCAAGCTTATCGAAGACGGACGTATCG

ACAAGTTCGTTGCTGACAGATACGCTTCATGGAATACCGGTATC

GGTGCAGACATAATCGCAGGTAAGGCAGATTTCGCATCTCTTGA

AAAGTATGCTCTTGAAAAGGGCGAGGTTACAGCTTCACTCTCA

AGCGGCAGACAGGAAATGCTGGAGTCTATCGTAAATAACGTT

CTTTTCAGTCTGTAA
```

The nucleotide sequence of the native gene is set forth as SEQ ID NO. 30 and in Gen Bank as accession number AJ132472 (CAB51938.1).

```
                                       SEQ ID NO. 30
ATGGAATTTTTCAGCAATATCGGTAAAATTCAGTATCAGGGACCAAAA

GTACTGATCCTCTCTCATTTAAGTACTATAACCCTGAAGAAGTCATCAA

CGGAAAGACAATGCGCGAGCATCTGAAGTTCGCTCTTTCATGGTGGCA

CACAATGGGCGGCGACGGAACAGATATGTTCGGCTGCGGCACAACAG

ACAAGACCTGGGGACAGTCCGATCCCGCTGCAAGAGCAAAGGCTAA

GGTTGACGCAGCATTCGAGATCATGGATAAGCTCTCCATTGACTACTA

TTGTTTCCACGATCGCGATCTTTCTCCCGAGTATGGCAGCCTCAAGG

CTACCAACGATCAGCTTGACATAGTTACAGACTATATCAAGGAGAAG

CAGGGCGACAAGTTCAAGTGCCTCTGGGGTACAGCAAAGTGCTTCG

ATCATCCAAGATTCATGCACGGTGCAGGTACATCTCCTTCTGCTGATG
```

-continued

TATTCGCTTTCTCAGCTGCTCAGATCAAGAAGGCTCTCGAGTCAACAG

TAAAGCTCGGCGGTAACGGTTACGTTTTCTGGGGCGGACGTGAAGGC

TATGAGACACTTCTTAATACAAATATGGGACTCGAACTCGACAATATG

GCTCGTCTTATGAAGATGGCTGTTGAGTATGGACGTTCGATCGGCTTC

AAGGGCGACTTCTATATCGAGCCCAAGCCCAAGGAGCCCACAAAGC

ATCAGTACGATTTCGATACAGCTACTGTTCTGGGATTCCTCAGAAAG

TACGGTCTCGATAAGGATTTCAAGATGAATATCGAAGCTAACCACGC

TACACTTGCTCAGCATACATTCCAGCATGAGCTCCGTGTTGCAAGA

GACAATGGTGTGTTCGGTTCTATCGACGCAAACCAGGGCGACGTTC

TTCTTGGATGGGATACAGACCAGTTCCCCACAAATATCTACGATACA

ACAATGTGTATGTATGAAGTTATCAAGGCAGGCGGCTTCACAAACGGC

GGTCTCAACTTCGACGCTAAGGCACGCAGAGGGAGCTTCACTCCC

GAGGATATCTTCTACAGCTATATCGCAGGTATGGATGCATTTGCTCT

GGGCTTCAGAGCTGCTCTCAAGCTTATCGAAGACGGACGTATCGAC

AAGTTCGTTGCTGACAGATACGCTTCATGGAATACCGGTATCGGTGC

AGACATAATCGCAGGTAAGGCAGATTTCGCATCTCTTGAAAAGTATG

CTCTTGAAAAGGGCGAGGTTACAGCTTCACTCTCAAGCGGCAGACA

GGAAATGCTGGAGTCTATCGTAAATAACGTTCTTTTCAGTCTGTAA

The corresponding amino acid sequence of the native *Ruminococcus flavefaciens* is set forth in SEQ ID NO: 31.

SEQ ID NO: 31
MEFFSNIGKIQYQGPKSTDPLSFKYYNPEEVINGKTMREHLKFALSWW

HTMGGDGTDMFGCGTTDKTWGQSDPAARAKAKVDAAFEIMDKLSID

YYCFHDRDLSPEYGSLKATNDQLDIVTDYIKEKQGDKFKCLWGTAKC

FDHPRFMHGAGTSPSADVFAFSAAQIKKALESTVKLGGNGYVFWGG

REGYETLLNTNMGLELDNMARLMKMAVEYGRSIGFKGDFYIEPKPKE

PTKHQYDFDTATVLGFLRKYGLDKDFKMNIEANHATLAQHTFQHELR

VARDNGVFGSIDANQGDVLLGWDTDQFPTNIYDTTMCMYEVIKAGG

FTNGGLNFDAKARRGSFTPEDIFYSYIAGMDAFALGFRAALKLIEDG

RIDKFVADRYASWNTGIGADIIAGKADFASLEKYALEKGEVTASLSS

GRQEMLESIVNNVLFSL

An additional nucleic acid variant of the native *Ruminococcus* xylose isomerase gene was designed to eliminate over-represented codon pairs, improve codon preferences, and reduce mRNA secondary structures. The amino acid sequence of the hot rod xylose isomerase gene is substantially identical to the wild type. This sequence variant, referred to as the "hot rod" variant, is set forth in SEQ ID NO: 32.

SEQ ID NO: 32
ATGGAGTTCTTTTCTAATATAGGTAAAATTCAGTATCAAGGTCCAAAA

TCTACAGATCCATTGTCTTTTAAATATTATAATCCAGAAGAAGTTATAA

ATGGTAAAACTATGAGAGAACATTTAAAATTTGCTTTGTCTTGGTGGC

ATACTATGGGTGGTGATGGTACTGATATGTTCGGTTGTGGTACTACTG

ATAAAACTTGGGGTCAATCTGATCCAGCTGCTAGAGCAAAAGCCAA

AGTAGATGCAGCCTTTGAAATTATGGATAAATTGTCTATTGATTATTAT

TGTTTTCATGATAGAGATTTGTCTCCTGAATATGGTTCTTTAAAAGCAA

CTAATGATCAATTGGACATTGTTACGGATTATATTAAAGAAAAACAAG

GTGATAAATTTAAATGTTTGTGGGGCACTGCGAAATGTTTTGATCATC

CACGTTTTATGCATGGTGCGGGGACGAGTCCTTCTGCTGATGTTTTT

GCTTTTTCTGCCGCTCAAATTAAGAAGGCATTGGAATCAACTGTTAA

ATTAGGTGGGAACGGGTATGTATTCTGGGGAGGAAGGGAAGGTTAT

GAAACATTATTAAACACTAATATGGGTTTGGAATTGGATAATATGGC

TAGATTGATGAAAATGGCTGTAGAATACGGAAGGTCTATTGGTTTTA

AGGGTGACTTTTATATTGAACCAAAACCTAAAGAGCCTACTAAACA

TCAATATGATTTTGATACTGCTACAGTTTTGGGATTCTTGAGAAAAT

ATGGTCTGGATAAAGATTTTAAAATGAATATAGAAGCTAATCATGC

AACACTCGCACAACATACTTTTCAACATGAATTGAGAGTTGCCAGA

GATAACGGAGTTTTTGGATCTATCGATGCAAACCAGGGAGACGTTT

TGCTAGGATGGGATACTGATCAATTTCCAACTAACATTTATGATACT

ACTATGTGTATGTATGAAGTAATTAAGGCAGGAGGCTTTACTAATGG

CGGATTAAACTTTGATGCGAAGGCTAGGCGTGGTAGTTTCACTCC

AGAGGATATATTCTATTCTTATATTGCTGGAATGGATGCTTTCGCGT

TAGGTTTCAGGGCAGCACTAAAATTGATTGAAGATGGTAGAATTGAT

AAGTTTGTAGCTGATAGATATGCTTCTTGGAATACTGGAATAGGAGC

AGATATAATCGCTGGGAAAGCCGACTTCGCCAGTCTGGAAAAATA

TGCGCTTGAAAAAGGAGAAGTTACTGCCAGCTTAAGTTCCGGTCG

TCAAGAAATGTTGGAATCTATTGTAAACAATGTTTTATTTTCTCTGTAA

This gene was synthesized by assembling the oligonucleotides set forth below first into seven separate "primary fragments" (also referred to as "PFs"). The PFs were then assembled into three "secondary fragments ("SFs") which in turn were assembled into the full length gene. All oligonucleotides were obtained from IDT. All of the oligonucleotides used for gene construction are set forth in the table below.

| Name | Oligonucleotide Sequence (SEQ ID NOS 163-228, respectively, in order of appearance) | |
|---|---|---|
| 4329 On1 fwd | ATGGAGTTCTTTTCTAATATAGGTAAAATTCAGTATCAAGGTC | 43-mer |
| 4329 On2 rev | AATGGATCTGTAGATTTTGGACCTTGATACTGAATTTTA | 39-mer |

-continued

| Name | Oligonucleotide Sequence (SEQ ID NOS 163-228, respectively, in order of appearance) | |
|---|---|---|
| 4329 On3 fwd | CAAAATCTACAGATCCATTGTCTTTTAAATATTATAATCCAGA | 43-mer |
| 4329 On4 rev | GTTTTACCATTTATAACTTCTTCTGGATTATAATATTTAAAAGAC | 45-mer |
| 4329 On5 fwd | AGAAGTTATAAATGGTAAAACTATGAGAGAACATTTAAAATTT | 43-mer |
| 4329 On6 rev | ATAGTATGCCACCAAGACAAAGCAAATTTTAAATGTTCTCTCATA | 45-mer |
| 4329 On7 fwd | GCTTTGTCTTGGTGGCATACTATGGGTGGTGATGGTACTGATATG | 45-mer |
| 4329 On8 rev | TTATCAGTAGTACCACAACCGAACATATCAGTACCATCACCACCC | 45-mer |
| 4329 On9 fwd | TTCGGTTGTGGTACTACTGATAAAACTTGGGGTCAATCTGATC | 43-mer |
| 4329 On10 rev | GGCTTTTGCTCTAGCAGCTGGATCAGATTGACCCCAAGTT | 40-mer |
| 4329 On11 fwd | CAGCTGCTAGAGCAAAAGCCAAAGTAGATGCAGCCTTTGAAAT | 43-mer |
| 4329 On12 rev | ATCAATAGACAATTTATCCATAATTTCAAAGGCTGCATCTACTTT | 45-mer |
| 4329 On13 fwd | TATGGATAAATTGTCTATTGATTATTATTGTTTTCATGATAGAGA | 45-mer |
| 4329 On14 rev | AGAACCATATTCAGGAGACAAATCTCTATCATGAAAACAATAATA | 45-mer |
| 4329 On15 fwd | TTTGTCTCCTGAATATGGTTCTTTAAAAGCAACTAATGATCAA | 43-mer |
| 4329 On16 rev | AATATAATCCGTAACAATGTCCAATTGATCATTAGTTGCTTTTAA | 45-mer |
| 4329 On17 fwd | TTGGACATTGTTACGGATTATATTAAAGAAAAACAAGGTGATAAA | 45-mer |
| 4329 On18 rev | CGCAGTGCCCCACAAACATTTAAATTTATCACCTTGTTTTCTTT | 45-mer |
| 4329 On19 fwd | TTTAAATGTTTGTGGGCACTGCGAAATGTTTTGATCATCCACGT | 45-mer |
| 4329 On20 rev | ACTCGTCCCCGCACCATGCATAAAACGTGGATGATCAAAACATTT | 45-mer |
| 4329 On21 fwd | TTTATGCATGGTGCGGGGACGAGTCCTTCTGCTGATGTTTTTGCT | 45-mer |
| 4329 On22 rev | CTTCTTAATTTGAGCGGCAGAAAAAGCAAAAACATCAGCAGAAGG | 45-mer |
| 4329 On23 fwd | TTTTCTGCCGCTCAAATTAAGAAGGCATTGGAATCAACTGTTAAA | 45-mer |
| 4329 On24 rev | GAATACATACCCGTTCCCACCTAATTTAACAGTTGATTCCAATGC | 45-mer |
| 4329 On25 fwd | TTAGGTGGGAACGGGTATGTATTCTGGGGAGGAAGGGAAGGTTAT | 45-mer |
| 4329 On26 rev | CATATTAGTGTTTAATAATGTTTCATAACCTTCCCTTCCTCCCCA | 45-mer |
| 4329 On27 fwd | GAAACATTATTAAACACTAATATGGGTTTGGAATTGGATAATATG | 45-mer |
| 4329 On28 rev | TACAGCCATTTTCATCAATCTAGCCATATTATCCAATTCCAAACC | 45-mer |
| 4329 On29 fwd | GCTAGATTGATGAAAATGGCTGTAGAATACGGAAGGTCTATTGGT | 45-mer |
| 4329 On30 rev | TTCAATATAAAAGTCACCCTTAAAACCAATAGACCTTCCGTATTC | 45-mer |
| 4329 On31 fwd | TTTAAGGGTGACTTTTATATTGAACCAAAACCTAAAGAGCCTACT | 45-mer |
| 4329 On32 rev | AGTATCAAAATCATATTGATGTTTAGTAGGCTCTTTAGGTTTTGG | 45-mer |

-continued

| Name | Oligonucleotide Sequence (SEQ ID NOS 163-228, respectively, in order of appearance) | |
|---|---|---|
| 4329 On33 fwd | AAACATCAATATGATTTTGATACTGCTACAGTTTTGGGATTCTTG | 45-mer |
| 4329 On34 rev | ATCTTTATCCAGACCATATTTTCTCAAGAATCCCAAAACTGTAGC | 45-mer |
| 4329 On35 fwd | AGAAAATATGGTCTGGATAAAGATTTTAAAATGAATATAGAAGCT | 45-mer |
| 4329 On36 rev | ATGTTGTGCGAGTGTTGCATGATTAGCTTCTATATTCATTTTAAA | 45-mer |
| 4329 On37 fwd | AATCATGCAACACTCGCACAACATACTTTTCAACATGAATTGAGA | 45-mer |
| 4329 On38 rev | AAAAACTCCGTTATCTCTGGCAACTCTCAATTCATGTTGAAAAGT | 45-mer |
| 4329 On39 fwd | GTTGCCAGAGATAACGGAGTTTTTGGATCTATCGATGCAAACCAG | 45-mer |
| 4329 On40 rev | ATCCCATCCTAGCAAAACGTCTCCCTGGTTTGCATCGATAGATCC | 45-mer |
| 4329 On41 fwd | GGAGACGTTTTGCTAGGATGGGATACTGATCAATTTCCAACTAAC | 45-mer |
| 4329 On42 rev | CATACACATAGTAGTATCATAAATGTTAGTTGGAAATTGATCAGT | 45-mer |
| 4329 On43 fwd | ATTTATGATACTACTATGTGTATGTATGAAGTAATTAAGGCAGGA | 45-mer |
| 4329 On44 rev | GTTTAATCCGCCATTAGTAAAGCCTCCTGCCTTAATTACTTCATA | 45-mer |
| 4329 On45 fwd | GGCTTTACTAATGGCGGATTAAACTTTGATGCGAAGGCTAGGCGT | 45-mer |
| 4329 On46 rev | TATATCCTCTGGAGTGAAACTACCACGCCTAGCCTTCGCATCAAA | 45-mer |
| 4329 On47 fwd | GGTAGTTTCACTCCAGAGGATATATTCTATTCTTATATTGCTGGA | 45-mer |
| 4329 On48 rev | GAAACCTAACGCGAAAGCATCCATTCCAGCAATATAAGAATAGAA | 45-mer |
| 4329 On49 fwd | ATGGATGCTTTCGCGTTAGGTTTCAGGGCAGCACTAAAATTGATT | 45-mer |
| 4329 On50 rev | CTTATCAATTCTACCATCTTCAATCAATTTTAGTGCTGCCCT | 42-mer |
| 4329 On51 fwd | GAAGATGGTAGAATTGATAAGTTTGTAGCTGATAGATATGCTTCT | 45-mer |
| 4329 On52 rev | TGCTCCTATTCCAGTATTCCAAGAAGCATATCTATCAGCTACAAA | 45-mer |
| 4329 On53 fwd | TGGAATACTGGAATAGGAGCAGATATAATCGCTGGGAAAGCCGAC | 45-mer |
| 4329 On54 rev | ATATTTTTCCAGACTGGCGAAGTCGGCTTTCCCAGCGATTATATC | 45-mer |
| 4329 On55 fwd | TTCGCCAGTCTGGAAAAATATGCGCTTGAAAAAGGAGAAGTTACT | 45-mer |
| 4329 On56 rev | ACGACCGGAACTTAAGCTGGCAGTAACTTCTCCTTTTTCAAGCGC | 45-mer |
| 4329 On57 fwd | GCCAGCTTAAGTTCCGGTCGTCAAGAAATGTTGGAATCTAT | 41-mer |
| 4329 On58 rev | CAGAGAAAATAAAACATTGTTTACAATAGATTCCAACATTTCTTG | 45-mer |
| 4329 On59 fwd | ACTTGACTAACTGAAGCTTCATATGATGGAGTTCTTTTCTAATATAGGTAAAATT | 55-mer |
| 4329 On60 fwd | ACTTGACTACTAGTATGGAGTTCTTTTCTAATATAGGTAAAATT | 44-mer |
| 4329 On61 fwd | ACTTGACTAACTGAAGCTTCATATGTTGGACATTGTTACGGATTATATTAAAGAA | 55-mer |
| 4329 On62 fwd | ACTTGACTAACTGAAGCTTCATATGAAACATCAATATGATTTTGATACTGCTACA | 55-mer |
| 4329 On63 for | AGTTAAGTGAGTAAACTAGTGAATTCCAGAGAAAATAAAACATTGTTTACAATAGA | 56-mer |

| Name | Oligonucleotide Sequence (SEQ ID NOS 163-228, respectively, in order of appearance) | |
|---|---|---|
| 4329 On64 rev | AGTCAAGTCTCGAGCTACAGAGAAAATAAAACATTGTTTACAATAGA | 44-mer |
| 4329 On65 rev | AGTTAAGTGAGTAAACTAGTGAATTCCATATTAGTGTTTAATAATGT TTCATAACC | 56-mer |
| 4329 On66 rev | AGTTAAGTGAGTAAACTAGTGAATTCCATACACATAGTAGTATCAT AAATGTTAGT | 56-mer |

The 7 primary fragments ("PFs") were first separately assembled using polymerase chain reaction (PCR) mixture containing about 1×Pfu Ultra II reaction buffer (Agilent, La Jolla, Calif.), about 0.2 mM about , 0.04 µmol of assembly primers (see table below), about 0.2 µmol of end primers (see table below), and about 1 U Pfu Ultra II polymerase (Agilent, La Jolla, Calif.). The reaction conditions were 95° C. for 10 minutes, 30 cycles of 95° C. for 20 seconds, 44° C. for 30 seconds, and 72° C. for 15 seconds, and a final extension of 5 minutes at 72° C.

| Primary Fragment | Assembly Primers | 5' and 3' End Primers |
|---|---|---|
| PF1 | 4329 On1 fwd<br>4329 On2 rev<br>4329 On3 fwd<br>4329 On4 rev<br>4329 On5 fwd<br>4329 On6 rev<br>4329 On7 fwd<br>4329 On8 rev<br>4329 On9 fwd<br>4329 On10 rev | 4329 On1 fwd<br>4329 On10 rev |
| PF2 | 4329 On9 fwd<br>4329 On10 rev<br>4329 On11 fwd<br>4329 On12 rev<br>4329 On13 fwd<br>4329 On14 rev<br>4329 On15 fwd<br>4329 On16 rev<br>4329 On17 fwd<br>4329 On18 rev | 4329 On9 fwd<br>4329 On18 rev |
| PF3 | 4329 On17 fwd<br>4329 On18 rev<br>4329 On19 fwd<br>4329 On20 rev<br>4329 On21 fwd<br>4329 On22 rev<br>4329 On23 fwd<br>4329 On24 rev<br>4329 On25 fwd<br>4329 On26 rev | 4329 On17 fwd<br>4329 On26 rev |
| PF4 | 4329 On25 fwd<br>4329 On26 rev<br>4329 On27 fwd<br>4329 On28 rev<br>4329 On29 fwd<br>4329 On30 rev<br>4329 On31 fwd<br>4329 On32 rev<br>4329 On33 fwd<br>4329 On34 rev | 4329 On25 fwd<br>4329 On34 rev |
| PF5 | 4329 On33 fwd<br>4329 On34 rev<br>4329 On35 fwd<br>4329 On36 rev<br>4329 On37 fwd<br>4329 On38 rev<br>4329 On39 fwd<br>4329 On40 rev | 4329 On33 fwd<br>4329 On42 rev |
| PF6 | 4329 On41 fwd<br>4329 On42 rev<br>4329 On41 fwd<br>4329 On42 rev<br>4329 On43 fwd<br>4329 On44 rev<br>4329 On45 fwd<br>4329 On46 rev<br>4329 On47 fwd<br>4329 On48 rev<br>4329 On49 fwd<br>4329 On50 rev | 4329 On41 fwd<br>4329 On50 rev |
| PF7 | 4329 On49 fwd<br>4329 On50 rev<br>4329 On51 fwd<br>4329 On52 rev<br>4329 On53 fwd<br>4329 On54 rev<br>4329 On55 fwd<br>4329 On56 rev<br>4329 On57 fwd<br>4329 On58 rev | 4329 On49 fwd<br>4329 On58 rev |

Each assembled primary fragment was separately PCR purified using a Qiagen PCR purification kit (Qiagen, Valencia, Calif.) according to the manufacturer's directions and then reassembled into 3 secondary fragments ("SFs") in a PCR reaction containing about 1×Pfu Ultra II reaction buffer (Agilent, La Jolla, Calif.), about 0.2 mM dNTPs, about 0.1 µmol of each primary fragment (SF1=PF1+PF2+PF3; SF2=PF3+PF4+PF5;SF3=PF5+PF6+PF7), about 0.2 µmol of end primers (see table below), and about 1 U Pfu Ultra II polymerase (Agilent, La Jolla, Calif.). The reaction conditions were 95° C. for 10 minutes, 30 cycles of 95° C. for 20 seconds, 62° C. for 30 seconds, and 72° C. for 15 seconds, and a final extension of 5 minutes at 72° C.

| Secondary Fragment | Primary Fragments | 5' and 3' End Primers |
|---|---|---|
| SF1 | PF1<br>PF2<br>PF3 | 4329 On59 fwd (Tf1-5P1 Sf1-5P1)<br>4329 On65 rev (Sf1-3P1) |
| SF2 | PF3<br>PF4<br>PF5 | 4329 On61 fwd (Sf2-5P1)<br>4329 On66 rev (Sf2-3P1) |
| SF3 | PF5<br>PF6<br>PF7 | 4329 On62 fwd (Sf3-5P1)<br>4329 On63 rev (Tf1-3P1 Sf3 3P1) |

Each secondary fragment was PCR purified using a Qiagen PCR purification kit (Qiagen, Valencia, Calif.) according to the manufacturer's directions, and the final, full length gene was assembled in a PCR reaction containing 1×Pfu Ultra II reaction buffer (Agilent, La Jolla, Calif.), 0.2 mM dNTPs, 0.1

µmol of each secondary fragment (SF1+SF2+SF3), 0.2 µmol of end primers (4329 On60 fwd and 4329 On64 rev), and 1 U Pfu Ultra II polymerase (Agilent, La Jolla, Calif.). The reaction conditions were 95° C. for 10 minutes, 30 cycles of 95° C. for 20 seconds, 62° C. for 30 seconds, and 72° C. for 30 seconds, and a final extension of 5 minutes at 72° C. The final product was PCR purified using a Qiagen PCR purification kit (Qiagen, Valencia, Calif.) according to the manufacturer's directions and then cloned into pCR Blunt II-TOPO (Invitrogen, Carlsbad, Calif.) according to the manufacturer's directions. Sequence confirmation of the final construct was performed at GeneWiz (La Jolla, Calif.).

An additional variant of the native *R. flavefaciens* xylose isomerase gene (XI-R-COOP) was prepared in which all of the codons were optimized for expression in *Saccharomyces cerevisiae*. This variant gene was synthesized by IDT DNA Inc. and the sequence is set forth below as SEQ ID NO: 33.

SEQ ID NO: 33
ATGGAATTCTTCTCTAACATTGGTAAGATCCAATACCAAGGTCCAAAGT

CCACCGACCCATTGTCTTTCAAGTACTACAACCCAGAAGAAGTTATTA

ACGGTAAGACTATGAGAGAACACTTGAAGTTCGCTTTGTCCTGGTGGC

ACACCATGGGTGGTGACGGTACTGACATGTTCGGTTGTGGTACCACTG

ACAAGACCTGGGGTCAATCTGACCCAGCTGCTAGAGCTAAGGCTAAG

GTCGACGCTGCTTTCGAAATCATGGACAAGTTGTCCATTGACTACTAC

TGTTTCCACGACAGAGACTTGTCTCCAGAATACGGTTCCTTGAAGGCT

ACTAACGACCAATTGGACATCGTTACCGACTACATTAAGGAAAAGCA

AGGTGACAAGTTCAAGTGTTTGTGGGGTACTGCTAAGTGTTTCGACCAC

CCAAGATTCATGCACGGTGCTGGTACCTCTCCATCCGCTGACGTCTTC

GCTTTCTCTGCTGCTCAAATCAAGAAGGCTTTGGAATCCACTGTTAAGT

TGGGTGGTAACGGTTACGTCTTCTGGGGTGGTAGAGAAGGTTACGAAA

CCTTGTTGAACACTAACATGGGTTTGGAATTGGACAACATGGCTAGAT

TGATGAAGATGGCTGTTGAATACGGTAGATCTATTGGTTTCAAGGGTGA

CTTCTACATCGAACCAAAGCCAAAGGAACCAACCAAGCACCAATACGA

CTTCGACACTGCTACCGTCTTGGGTTTCTTGAGAAAGTACGGTTTGGACA

AGGACTTCAAGATGAACATTGAAGCTAACCACGCTACTTTGGCTCAACA

CACCTTCCAACACGAATTGAGAGTTGCTAGAGACAACGGTGTCTTCGG

TTCCATCGACGCTAACCAAGGTGACGTTTTGTTGGGTTGGGACACTGAC

CAATTCCCAACCAACATTTACGACACTACCATGTGTATGTACGAAGTCA

TCAAGGCTGGTGGTTTCACTAACGGTGGTTTGAACTTCGACGCTAAGGC

TAGAAGAGGTTCTTTCACCCCAGAAGACATTTTCTACTCCTACATCGCTG

GTATGGACGCTTTCGCTTTGGGTTTCAGAGCTGCTTTGAAGTTGATTGAA

GACGGTAGAATCGACAAGTTCGTTGCTGACAGATACGCTTCTTGGAACA

CTGGTATTGGTGCTGACATCATTGCTGGTAAGGCTGACTTCGCTTCCTTG

GAAAAGTACGCTTTGGAAAAGGGTGAAGTCACCGCTTCTTTGTCCTCTG

GTAGACAAGAAATGTTGGAATCCATCGTTAACAACGTCTTGTTCTCTT

TGTAA

Separately, the gene encoding xylose isomerase from *Piromyces* strain E2 was synthesized by IDT DNA, Inc. The sequence of this gene is set forth as SEQ ID NO: 34.

SEQ ID NO: 34
ACTAGTAAAAAAATGGCTAAGGAATATTTCCCACAAATTCAAAAGATTA

AGTTCGAAGGTAAGGATTCTAAGAATCCATTAGCCTTCCACTACTACGA

TGCTGAAAAGGAAGTCATGGGTAAGAAAATGAAGGATTGGTTACGTTT

CGCCATGGCCTGGTGGCACACTCTTTGCGCCGAAGGTGCTGACCAAT

TCGGTGGAGGTACAAAGTCTTTCCCATGGAACGAAGGTACTGATGCTA

TTGAAATTGCCAAGCAAAAGGTTGATGCTGGTTTCGAAATCATGCAAAA

GCTTGGTATTCCATACTACTGTTTCCACGATGTTGATCTTGTTTCCGAA

GGTAACTCTATTGAAGAATACGAATCCAACCTTAAGGCTGTCGTTGCTT

ACCTCAAGGAAAAGCAAAAGGAAACCGGTATTAAGCTTCTCTGGAGT

ACTGCTAACGTCTTCGGTCACAAGCGTTACATGAACGGTGCCTCCAC

TAACCCAGACTTTGATGTTGTCGCCCGTGCTATTGTTCAAATTAAGAAC

GCCATAGACGCCGGTATTGAACTTGGTGCTGAAAACTACGTCTTCTGG

GGTGGTCGTGAAGGTTACATGAGTCTCCTTAACACTGACCAAAAGCG

TGAAAAGGAACACATGGCCACTATGCTTACCATGGCTCGTGACTACG

CTCGTTCCAAGGGATTCAAGGGTACTTTCCTCATTGAACCAAAGCCA

ATGGAACCAACCAAGCACCAATACGATGTTGACACTGAAACCGCTAT

TGGTTTCCTTAAGGCCCACAACTTAGACAAGGACTTCAAGGTCAACAT

TGAAGTTAACCACGCTACTCTTGCTGGTCACACTTTCGAACACGAACT

TGCCTGTGCTGTTGATGCTGGTATGCTCGGTTCCATTGATGCTAACCGT

GGTGACTACCAAAACGGTTGGGATACTGATCAATTCCCAATTGATCAA

TACGAACTCGTCCAAGCTTGGATGGAAATCATCCGTGGTGGTGGTTTC

GTTACTGGTGGTACCAACTTCGATGCCAAGACTCGTCGTAACTCTAC

TGACCTCGAAGACATCATCATTGCCCACGTTTCTGGTATGGATGCTAT

GGCTCGTGCTCTTGAAAACGCTGCCAAGCTCCTCCAAGAATCTCCATT

ACACCAAGATGAAGAAGGAACGTTACGCTCCTTCGACAGTGGTATTG

GTAAGGACTTTGAAGATGGTAAGCTCACCCTCGAACAAGTTTACGAAT

ACGGTAAGAAGAACGGTGAACCAAAGCAAACTTCTGGTAAGCAAGAA

CTCTACGAAGCTATTGTTGCCATGTACCAATAGTAGCTCGAG

The amino acid sequence of the xylose isomerase from *Piromyces* strain E2 is set for in SEQ ID NO. 35

SEQ ID NO. 35
MAKEYFPQIQKIKFEGKDSKNPLAFHYYDAEKEVMGKKMKDWLRFAMAWW

HTLCAEGADQFGGGTKSFPWNEGTDAIEIAKQKVDAGFEIMQKLGIPYYC

FHDVDLVSEGNSIEEYESNLKAVVAYLKEKQKETGIKLLWSTANVFGHKR

YMNGASTNPDFDVVARAIVQIKNAIDAGIELGAENYVFWGGREGYMSLLN

TDQKREKEHMATMLTMARDYARSKGFKGTFLIEPKPMEPTKHQYDVDTET

AIGFLKAHNLDKDFKVNIEVNHATLAGHTFEHELACAVDAGMLGSIDANR

GDYQNGWDTDQFPIDQYELVQAWMEIIRGGGFVTGGTNFDAKTRRNSTDL

EDIIIAHVSGMDAMARALENAAKLLQESPYTKMKKERYASFDSGIGKDFE

DGKLTLEQVYEYGKKNGEPKQTSGKQELYEAIVAMYQ

For detection purposes, each gene was PCR amplified using a 3' oligonucleotide that added a 6-HIS tag (SEQ ID NO: 138) onto the c-terminal end of each xylose isomerase gene. The oligonucleotides used for this purpose are set forth below.

| Gene | Primer Name | Primer Sequence |
|---|---|---|
| XI-R-hotrod | 4329 On63 for (SEQ ID NO. 36) | agttaagtgagtaaactagtgaattccagagaaaataaaacattgtttacaataga |
|  | 4329-HIS REV (SEQ ID NO. 37) | agtcaagtctcgagtcaatggtgatggtggtgatgcagagaaaataaaacattgtttac |
| XI-R-native | KAS/5-XI-RF-NATIVE (SEQ ID NO. 38) | actagtatggaatttttcagcaatatcggtaaaattc |
|  | KAS/3-XI-RF-NATIVE-HIS (SEQ ID NO. 39) | ctcgagttacagactgaaaagaacgttatttacg |
| XI-R-coop | KAS/5-XI-RF-COOP (SEQ ID NO. 40) | actagtatggaattcttctctaacattgg |
|  | KAS/3-XI-RF-COOP-HIS (SEQ ID NO. 41) | ctcgagttacaaagagaacaagacgttgttaacgatgg |
| XI-P | XI-P_Native FL 5' (SEQ ID NO. 42) | actagtaaaaaaatggctaaggaatatttcccacaaattcaaaag |
|  | XI-P_Native FL 3'His-tag (SEQ ID NO. 43) | atgactcgagctactaatgatgatgatgatgatgttggtacatggcaacaatagcttcg |

Each xylose isomerase gene described above (plus or minus the HIS tag) was cloned into the yeast expression vector p426GPD (Mumberg et al., 1995, Gene 156: 119-122; obtained from ATCC #87361; PubMed: 7737504) using the SpeI and XhoI sites located at the 5' and 3' ends of each gene. Each of the bacterial vectors containing a xylose isomerase gene (with or without the 6-HIS c-terminal tag (SEQ ID NO: 138)) and the p426GPD yeast expression vector were digested with SpeI and XhoI. The generated fragments were gel extracted using a Qiagen gel purification kit (Qiagen, Valencia, Calif.), the p426GPD vector reaction was cleaned up using a Qiagen PCR purification kit. About 30 ng of each fragment was ligated to 50 ng of the p426GPD vector using T4 DNA ligase (Fermentas, Glen Burnie, Md.) in a 10 µl volume reaction overnight at 16° C. and transformed into NEB-5α competent cells (NEB, Ipswich, Mass.) and plated onto LB media with ampicillin (100 µg/ml). Constructs were confirmed by sequence analysis (GeneWiz, La Jolla, Calif.).

A haploid *Saccharomyces cerevisiae* strain (BY4742; ATCC catalog number 201389) was cultured in YPD media (10 g Yeast Extract, 20 g Bacto-Peptone, 20 g Glucose, 1 L total) at about 30° C. Separate aliquots of these cultured cells were transformed with a plasmid construct containing a xylose isomerase gene or with vector alone. Transformation was accomplished using the Zymo frozen yeast transformation kit (Catalog number T2001; Zymo Research Corp., Orange, Calif. 92867). To about 50 µl of cells was added approximately 0.5-1 µg plasmid DNA and the cells were cultured on SC drop out media with glucose minus uracil (about 20 g glucose; about 2.21 g SC drop-out mix [described below], about 6.7 g yeast nitrogen base, all in about 1 L of water); this mixture was cultured for 2-3 days at about 30° C.

SC drop-out mix contained the following ingredients (Sigma); all indicated weights are approximate:

| | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 2.63 g | Leucine |
| 0.9 g | Lysine |

-continued

| | |
|---|---|
| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 1.2 g | Valine |

For expression and activity analysis, cultures expressing the various xylose isomerase wild type and variant gene constructs were grown in about 100 ml SC-Dextrose (2%) at about 30° C. to an OD600 of about 4.0.

*S. cerevisiae* cultures were lysed using YPER-Plus reagent (Thermo Scientific, San Diego, Calif.; catalog number 78999) according to the manufacturer's instructions. Quantification of the lysates was performed using the Coomassie-Plus kit (Thermo Scientific, San Diego, Calif.; Catalog number 23236) as directed by the manufacturer. About 5-10 µg of total cell extract was used for SDS-gel [NuPage 4-12% Bis-Tris gels (Life Technologies, Carlsbad, Calif.)] and native gel electrophoresis and for native Western blot analyses.

SDS-PAGE gels were run according to the manufacturer's recommendation using NuPage MES-SDS Running Buffer at 1× concentration with the addition of NuPage antioxidant into the cathode chamber at a 1× concentration. Novex Sharp Protein Standards (Life Technologies, Carlsbad, Calif.) were used as standards. For Western analysis, gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with the 1:5000 dilution of primary antibody (Ms mAB to 6×His Tag (SEQ ID NO: 138), AbCam, Cambridge, Mass.) in 0.3% BSA (Fraction V, EMD, San Diego, Calif.) dissolved in 1×PBS and 0.05% Tween-20 with gentle shaking. Incubation was allowed to proceed for about 1 hour with gentle shaking. The membrane was then washed three times for 5 minutes each with 1×PBS and 0.05% Tween-20 with gentle shaking. The secondary antibody [Dnk pAb to Ms IgG (HRP), AbCam, Cambridge, Mass.] was used at 1:15000 dilution in 0.3% BSA and allowed to incubate for about 90 minutes at room temperature with gentle shaking. The membrane was washed three times for about 5 minutes using 1×PBS and 0.05% Tween-20 with gentle shaking. The membrane was then incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds.

The results are shown in FIG. 7. As can be seen, the wild type R. flavefaciens xylose isomerase gene protein and the wild type *Piromyces* xylose isomerase gene are both expressed in the soluble fraction of the cells. The expected size of the xylose isomerase *R. flavefaciens* polypeptide is approximately 49.8 kDa.

Example 10

In Vitro Xylose Isomerase Activity Assays

Enzyme assays of the various xylose isomerase variants were performed according to Kuyper et al. (FEMS Yeast Res., 4:69 [2003]) with a few modifications. Approximately 20 µg of soluble whole cell extract from each transformed cell line, prepared using Y-PER plus reagent as described above, was incubated in a solution containing about 100 mM Tris, pH 7.5, 10 mM $MgCl_2$, 0.15 mM NADH (Sigma, St. Louis, Mo.), and 2 U Sorbitol Dehydrogenase (SDH) (Roche, Indianapolis, Ind.) at about 30° C. To start the reaction, about 100 µl of xylose was added at various final concentrations of about 40 to about 500 mM. A Beckman DU-800 spectrophotometer was utilized with an Enzyme Mechanism software package (Beckman Coulter, Inc, Brea, Calif.), and the change in the A340 was monitored for 2-3 minutes. Assays were repeated as described above in the absence and in the presence of about 0 to about 50 mM xylitol, an inhibitor of xylose isomerase, in order to determine the K. Regular assays (no xylitol) were done independently about 5 to 10 times over the entire range of xylose concentrations and 2 times in the presence of the entire range of xylitol concentrations. The results are set forth in the table below.

| Enzyme | $K_m$ (mM) | Specific Activity (µmol min-1 mg-1) | $K_i$ (mM xylitol) |
|---|---|---|---|
| *Piromyces* xylose isomerase | 49 | 2.02 | 4.79 |
| *Ruminococcus* wild type xylose isomerase | 82.12 | 1.718 | 43.64 |
| *Ruminococcus* "hot rod" xylose isomerase | 103 | 1.31 | ND |
| *Ruminococcus* "codon optimized" xylose isomerase | 100 | 1.61 | ND |

Example 11

Construction of *Ruminococcus* Xylose Isomerase Chimeric Variants

Figure 8:
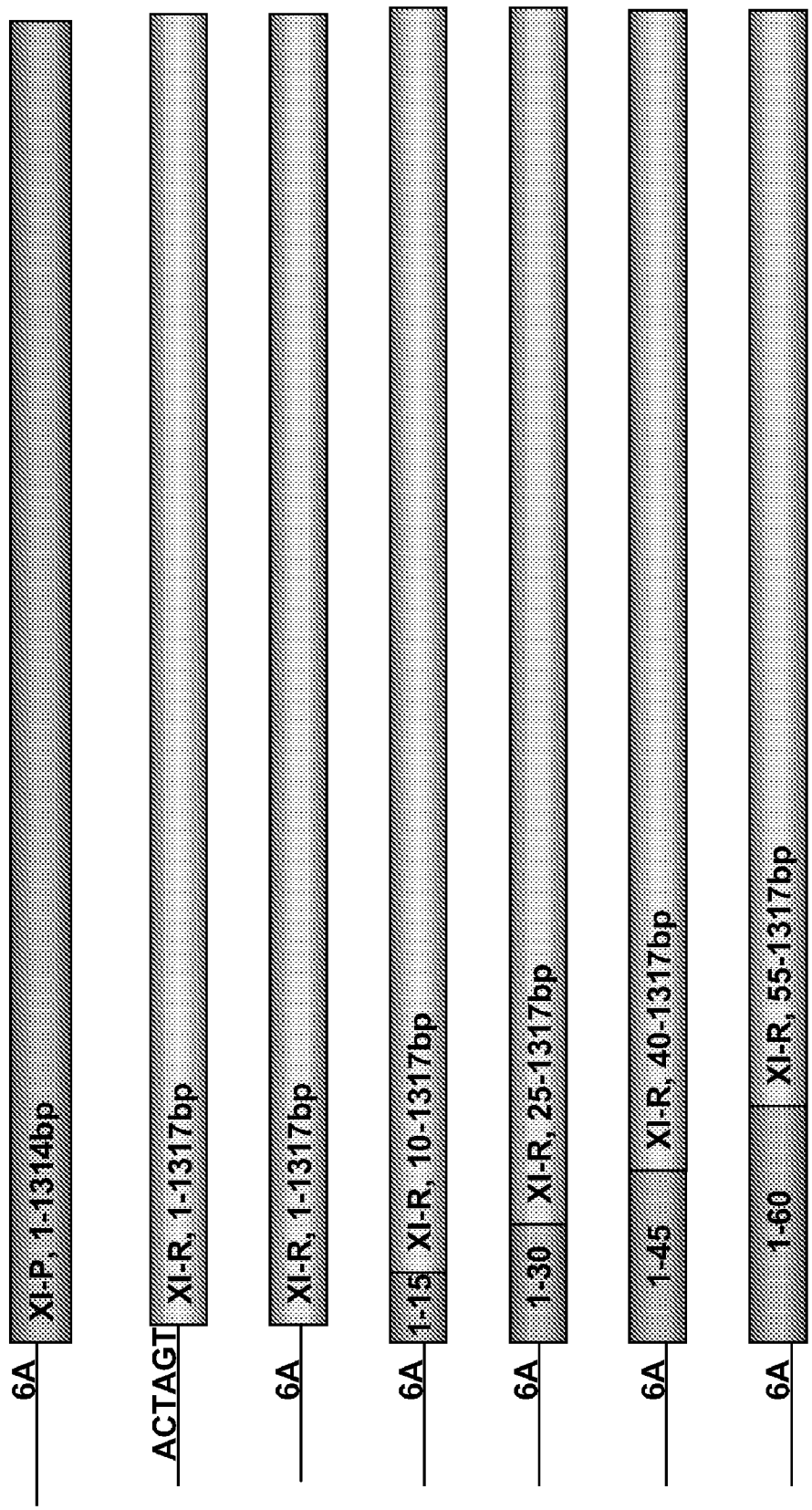
FIG. 8 illustrates schematic representations of native, modified and chimeric xylose isomerase genes.

Several xylose isomerase gene variants were designed and constructed in which 6 adenosine bases were added to each variant directly 5' of the ATG "start" codon. Additionally, 15, 20, 45 or 60 base pairs of the 5' end of the *Ruminococcus* xylose isomerase gene were replaced with various portions of the 5' end of the *Piromyces* xylose isomerase gene to create "chimeric" or "hybrid" xylose isomerase genes. Diagrams representative of non-limiting xylose isomerase chimeric variant gene embodiments is shown in FIG. 8.

PCR amplification was used to generate novel chimeric constructs. For all PCR reactions, approximately 0.2 µmol of each oligonucleotide was added to 25-30 ng of the appropriate purified DNA template with 0.2 mM dNTPs (5' and 3'), 1×Pfu Ultra II buffer and 1 unit (U) Pfu Ultra II polymerase (Agilent). The PCR reactions were thermocycled as follows; 95° C. for 10 minutes, followed by 30 cycles of 95° C. for 10 sec, 58° C. for 30 sec, and 72° C. for 30 seconds. A 5 minute 72° C. extension reaction completed the amplification rounds.

5' Oligonucleotides:

| Oligo Name | Sequence |
|---|---|
| KAS/XI-R-6A | actagtaaaaaaATGGAATTTTTCAGCAATATCGGTAAAATTC (SEQ ID NO. 44) |
| KAS/XI-R-P1-5 | actagtaaaaaaatggctaaggaatatTTCAGCAATATCGGTAAAATTCAG (SEQ ID NO. 45) |
| KAS/XI-R-P6-10 | ttcccacaaattcaaAAAATTCAGTATCAGGGACCAAAAAG (SEQ ID NO. 46) |
| KAS/XI-R-P1-10 | ACTAGTaaaaaaatggctaaggaatatttcccacaaattcaaAAAATTCAGTATCAGGGACCAAAAAG (SEQ ID NO. 47) |
| KAS/XI-R-P11-15 | aagattaagttcgaaGGACCAAAAAGTACTGATCCTCTCTC (SEQ ID NO. 48) |
| KAS/XI-R-P6-15 | ttcccacaaattcaaaagattaagttcgaaGGACCAAAAAGTACTGATCCTCTCTC (SEQ ID NO. 49) |
| KAS/XI-R-P1-15 | ACTAGTaaaaaaatggctaaggaatatttcccacaaattcaaaagattaagttc (SEQ ID NO. 50) |
| KAS/XI-R-P16-20 | ggtaaggattctaagGATCCTCTCTCATTTAAGTACTATAACCCTG (SEQ ID NO. 51) |
| KAS/XI-R-P10-20 | caaaagattaagttcgaaggtaaggattctaagGATCCTCTCTCATTTAAGTAC (SEQ ID NO. 52) |

3' Oligonucleotides:

```
KAS/3-XI-RF-NATIVE
                                  (SEQ ID NO. 53)
ctcgagttacagactgaaaagaacgttatttacg KAS/3-XI-RF-NATIVE-HIS
                                  (SEQ ID NO. 54)
ctcgagttacagactgaaaagaacgttatttacg
```

The novel XI-R constructs were generated using PCR with the relevant primers and template gene. The 5' primer KAS/XI-R-6A and either 3' primer KAS/3-XI-RF-NATIVE or 3' primer KAS/3-XI-RF-NATIVE-HIS were used in combination with the full length native *Ruminococcus* xylose isomerase (XI-R) gene to generate the constructs referred to as "XI-Rf-6A" and "XI-Rf-6AHis".

To generate the chimeric XI-Rp5 gene, the 5' primer KAS/XI-R-P1-5 and either 3' primer KAS/3-XI-RF-NATIVE or 3' primer KAS/3-XI-RF-NATIVE-HIS were used in combination with the full length native xylose isomerase *Ruminococ-* cus gene. The chimeric XI-Rp5 gene includes the first 5 amino acids of the *Piromyces* xylose isomerase (XI-P) polypeptide followed by amino acids 6 to 1323 of the native *Ruminococcus* xylose isomerase.

To generate the chimeric XI-Rp10 gene, the 5' primer KAS/XI-R-P6-10 and 3' primer KAS/3-XI-RF-NATIVE were first used to add nucleotides 16-30 from the XI-P gene to the 5' end of the XI-R gene keeping the remainder of the XI-R gene in-frame. The chimeric XI-Rp10 gene includes the first 10 amino acids of the *Piromyces* xylose isomerase followed by amino acids 11 to 438 of the *Ruminococcus* xylose isomerase. Following PCR purification of the resulting XI-Rp6-10 amplified product, 5' primer KAS/XI-R-P1-10 and either the 3' primer KAS/3-XI-RF-NATIVE or the 3' primer KAS/3-XI-RF-NATIVE-HIS oligonucleotides were used to add additional sequences.

To generate the chimeric XI-Rp15 gene, the 5' primer KAS/XI-R-P11-15 and 3' primer KAS/3-XI-RF-NATIVE were first used on the XI-Rp10 construct to add nucleotides 16 to 45 from the XI-P gene to the 5' end of the XI-R native gene. The chimeric XI-Rp15 gene includes the first 15 amino acid of the *Piromyces* xylose isomerase followed by amino acids 16 to 438 of the *Ruminococcus* xylose isomerase. Following PCR purification of the resulting XI-Rp6-15 amplified product, 5' primer KAS/XI-R-P1-15 either 3' primer KAS/3-XI-RF-NATIVE or 3' primer KAS/3-XI-RF-NATIVE-HIS oligonucleotides were used to add additional sequences.

To generate the chimeric XI-Rp20 gene, the 5' primer KAS/XI-R-P10-20 and 3' primer KAS/3-XI-RF-NATIVE were used on the XI-Rp15 construct to add nucleotides 30-60 to the 5' end of the XI-R native gene. The chimeric XI-Rp20 gene includes the first 20 amino acids of the *Piromyces* xylose isomerase followed by amino acids 21 to 438 of the *Ruminococcus* xylose isomerase. Following PCR purification of the resulting XI-Rp10-20 amplified product, 5' primer KAS/XI-R-P1-15 and either 3' primer KAS/3-XI-RF-NATIVE or 3' primer KAS/3-XI-RF-NATIVE-HIS oligonucleotides were used to add additional sequences.

Each of the novel chimeric xylose isomerase genes (with and without the c-terminal 6-HIS tag (SEQ ID NO: 138)) were cloned into the bacterial cloning vector pCR Blunt II TOPO (Life Technologies, Carlsbad, Calif.) according to the manufacturer's recommendations. Following sequence verification (GeneWiz, La Jolla, Calif.), the approximate 1330 bp SpeI-XhoI fragment from each construct was subcloned into the yeast expression vector p426GPD by first extracting each fragment from a gel slice using a gel purification kit (Qiagen, Valencia, Calif.), and then preparing the p426GPD vector for ligation by purifying it using a PCR purification kit (Qiagen, Valencia, Calif.), according to the manufacturer's instructions. About 30 ng of each of the chimeric genes was separately ligated to about 50 ng of the p426GPD vector using T4 DNA ligase (Fermentas, Glen Burnie, Md.) in a 10 µl volume reaction overnight at about 16° C., followed by transformation using standard protocols into NEB-5α competent cells (NEB, Ipswich, Mass.). The transformed cell culture was plated onto LB media with ampicillin (100 µg/ml). The constructs containing the chimeric genes were confirmed by sequence analysis (GeneWiz, La Jolla, Calif.).

A haploid *Saccharomyces cerevisiae* strain (BY4742; ATCC catalog number 201389) was cultured in YPD media (10 g Yeast Extract, 20 g Bacto-Peptone, 20 g Glucose, 1 L total) at about 30° C. Separate aliquots of these cultured cells were transformed with plasmid constructs containing the novel xylose isomerase chimeric genes as well as with the *Piromyces* and *Ruminococcus* native gene constructs described herein. Transformation was performed using the Zymo frozen yeast transformation kit (Catalog number T2001; Zymo Research Corp., Orange, Calif. 92867). Approximately about 0.5 µg to about 1 µg plasmid DNA was added to about 50 µl of cells, and the transformed cells were cultured on SC drop out media with glucose minus uracil (e.g., about 20 g glucose; about 2.21 g SC drop-out mix], about 6.7 g yeast nitrogen base, per 1 L of water) for 2-3 days at about 30° C.

*S. cerevisiae* cultures were lysed using YPER-Plus reagent (Thermo Scientific, San Diego, Calif.; catalog number 78999) according to the manufacturer's instructions. Quantification of the lysates was performed using the Coomassie-Plus kit (Thermo Scientific, San Diego, Calif., catalog number 23236) as directed by the manufacturer. About 5 to 10 µg of total cell extract was used for SDS-gel (NuPage 4-12% Bis-Tris gels, Life Technologies, Carlsbad, Calif.) and native gel electrophoresis and Western blot analyses. SDS-PAGE gels were run according to the manufacturer's recommendation using NuPage MES-SDS Running Buffer (Life Technologies, Carlsbad, Calif.) at 1× concentration with the addition of NuPage antioxidant to the cathode chamber at a 1× concentration. Novex Sharp Protein Standards (Life Technologies, Carlsbad, Calif.) were used as standards.

Figure 9:
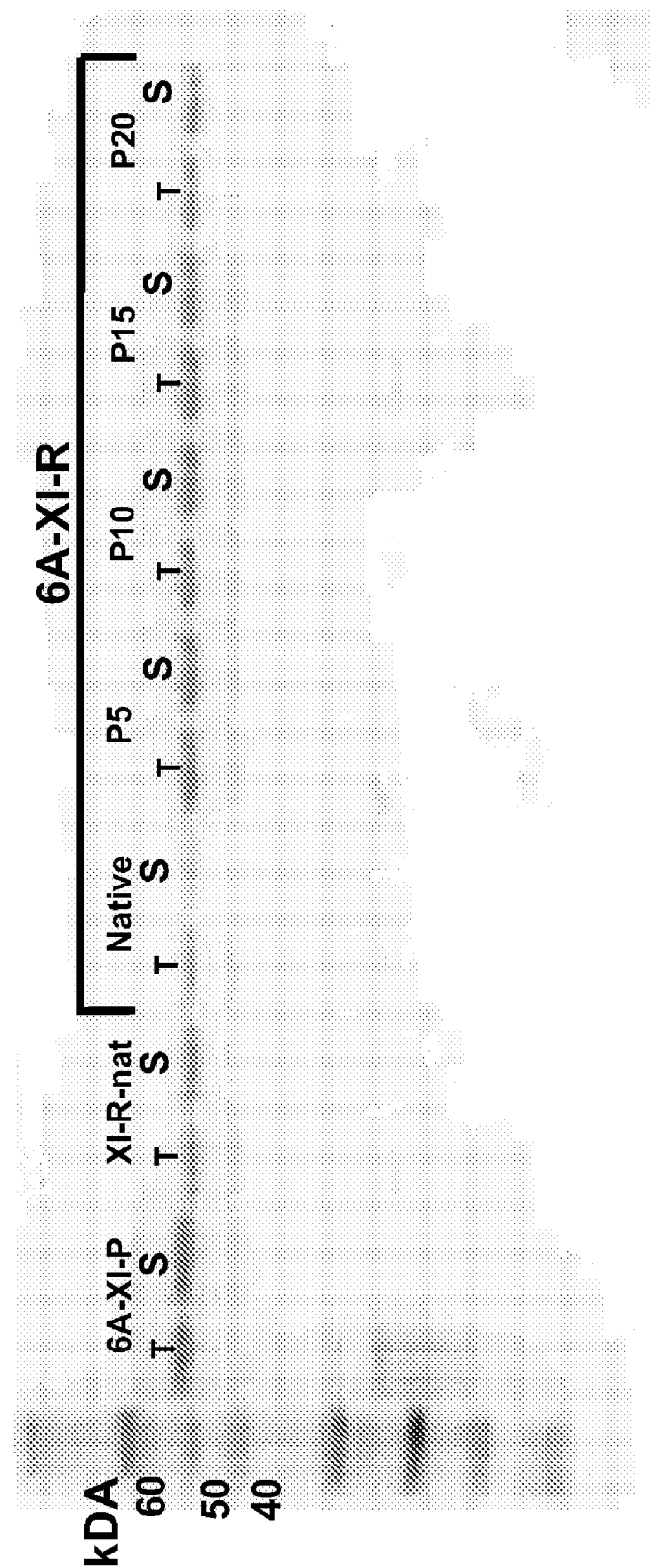
FIG. 9 shows a representative Western blot used to detect gene products.

For Western analysis, gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in about 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with an approximately 1:5000 dilution of primary antibody (anti-His mouse monoclonal antibody, AbCam, Cambridge, Mass.) in about 0.3% BSA (Fraction V, EMD, San Diego, Calif.) dissolved in 1×PBS and 0.05% Tween-20 with gentle shaking. Incubation was allowed to proceed for about 1 hour with gentle shaking. The membrane was then washed three times for about 5 minutes each with 1×PBS and 0.05% Tween-20 with gentle shaking. The secondary antibody (donkey anti mouse IgG polyclonal antibody linked to horse radish peroxidase, AbCam, Cambridge, Mass.) was used at about a 1:15000 dilution in 0.3% BSA and allowed to incubate for about 90 minutes at room temperature with gentle shaking. The membrane was washed three times for about 5 minutes each time using 1×PBS and 0.05% Tween-20 with gentle shaking. The membrane was then incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds. The expected size of the chimeric xylose isomerase constructs is approximately 49.8 kDa. The expected size of the xylose isomerase protein is approximately 50.2 kDa. The results of Western blot analysis are shown in FIG. 9. For each protein 2 lanes were run: T=total protein from whole cell extract, S=soluble portion of the whole cell extract.

As can be seen in FIG. 9, adding 6 adenosine bases directly upstream of the 5' end of the xylose isomerase *Ruminococcus* wild type gene did not improve expression of the polypeptide. However, replacing the 5' end of the *Ruminococcus* wild type xylose isomerase gene with 15, 30 or 45 of the 5' base pairs of the *Piromyces* wild type xylose isomerase gene improved expression of the enzyme.

Enzyme assays of the various novel xylose isomerase chimeric polypeptides were performed according to Kuyper et al. (FEMS Yeast Res., 4:69 [2003]) with a few modifications as described above. Approximately 20 μg of soluble whole cell extract from each transformed cell line was prepared using Y-PER plus reagent as described above was incubated in a solution containing about 100 mM Tris, pH 7.5, 10 mM MgCl$_2$, 0.15 mM NADH (Sigma, St. Louis, Mo.), and 2 U sorbitol dehydrogenase (SDH) (Roche, Indianapolis, Ind.) at about 30° C. To start the reaction, about 100 μl of xylose was added at various final concentrations of 40-500 mM. A Beckman DU-800 spectrophotometer was utilized with an Enzyme Mechanism software package (Beckman Coulter, Inc, Brea, Calif.), and the change in the A340 was monitored for 2-3 minutes. The results of the assays are set forth in the table below.

| Enzyme | $K_m$ (mM) | Specific Activity (μmol min-1 mg-1) | $K_i$ (mM xylitol) |
|---|---|---|---|
| XI-P | 49 | 2.02 | 4.79 |
| XI-Rnative | 82.12 | 1.72 | 43.64 |
| XI-Rp5 | 66.5 | 1.45 | ND |
| XI-Rp10 | 75.8 | 2.10 | ND |
| XI-Rp15 | 49.3 | 1.53 | ND |

The results indicate that substituting 30 base pairs of DNA from the 5' end of the *Ruminococcus* xylose isomerase gene with the first 15 base pairs of the *Piromyces* wild type xylose isomerase gene increased both the specific activity and the expression level to a level comparable to that of the wild type *Piromyces* xylose isomerase. The DNA and amino acid sequence for each chimeric gene is set forth below as SEQ ID NOs. 55 to 62. Small, bold "a" nucleotides indicated the 6 added adenosines. Large capital bold "A, T, G or C" nucleotides indicate the portion of the chimeric sequences donated by *Piromyces* and combined with the *Ruminococcus* sequence (e.g., small non-bold nucleotides).

```
SEQ ID NO. 55: XI-Rp5 DNA
aaaaaaATGGCTAAGGAATATTTCAGCAATATCGGTAAAATTCAGTATCA
GGGACCAAAAAGTACTGATCCTCTCTCATTTAAGTACTATAACCCTGAA
GAAGTCATCAACGGAAAGACAATGCGCGAGCATCTGAAGTTCGCTCTTT
GCATGGTGGCACACAATGGGCGGCGACGGAACAGATATTTCGGCTGCGG
CACAACAGACAAGACCTGGGGACAGTCCGATCCCGCTGCAAGAGCAAAG
GCTAAGGTTGACGCAGCATTCGAGATCATGGATAAGCTCTCCATTGACT
ACTATTGTTTCCACGATCGCGATCTTTCTCCCGAGTATGGCAGCCTCAA
GGCTACCAACGATCAGCTTGACATAGTTACAGACTATATCAAGGAGAAG
CAGGGCGACAAGTTCAAGTGCCTCTGGGGTACAGCAAAGTGCTTCGATC
ATCCAAGATTCATGCACGGTGCAGGTACATCTCCTTCTGCTGATGTATT
CGCTTTCTCAGCTGCTCAGATCAAGAAGGCTCTGGAGTCAACAGTAAAG
CTCGGCGGTAACGGTTACGTTTTCTGGGGCGGACGTGAAGGCTATGAGA
CACTTCTTAATACAAATATGGGACTCGAACTCGACAATATGGCTCGTCT
TATGAAGATGGCTGTTGAGTATGGACGTTCGATCGGCTTCAAGGGCGAC
TTCTATATCGAGCCCAAGCCCAAGGAGCCCACAAAGCATCAGTACGATT
TCGATACAGCTACTGTTCTGGGATTCCTCAGAAAGTACGGTCTCGATAA
GGATTTCAAGATGAATATCGAAGCTAACCACGCTACACTTGCTCAGCAT
ACATTCCAGCATGAGCTCCGTGTTGCAAGAGACAATGGTGTGTTCGGTT
CTATCGACGCAAACCAGGGCGACGTTCTTCTTGGATGGGATACAGACCA
GTTCCCCACAAATATCTACGATACAACAATGTGTATGTATGAAGTTATC
AAGGCAGGCGGCTTCACAAACGGCGGTCTCAACTTCGACGCTAAGGCAC
GCAGAGGGAGCTTCACTCCCGAGGATATCTTCTACAGCTATATCGCAGG
TATGGATGCATTTGCTCTGGGCTTCAGAGCTGCTCTCAAGCTTATCGAA
GACGGACGTATCGACAAGTTCGTTGCTGACAGATACGCTTCATGGAATA
CCGGTATCGGTGCAGACATAATCGCAGGTAAGGCAGATTTCGCATCTCT
TGAAAAGTATGCTCTTGAAAAGGGCGAGGTTACAGCTTCACTCTCAAGC
GGCAGACAGGAAATGCTGGAGTCTATCGTAAATAACGTTCTTTTCAGTC
TGTAA SEQ ID NO. 56: XI-Rp5 Polypeptide
MAKEYFSNIGKIQYQGPKSTDPLSFKYYNPEEVINGKTMREHLKFALSW
WHTMGGDGTDMFGCGTTDKTWGQSDPAARAKAKVDAAFEIMDKLSIDYY
CFHDRDLSPEYGSLKATNDQLDIVTDYIKEKQGDKFKCLWGTAKCFDHP
RFMHGAGTSPSADVFAFSAAQIKKALESTVKLGGNGYVFWGGREGYETL
LNTNMGLELDNMARLMKMAVEYGRSIGFKGDFYIEPKPKEPTKHQYDFD
TATVLGFLRKYGLDKDFKMNIEANHATLAQHTFQHELRVARDNGVFGSI
DANQGDVLLGWDTDQFPTNIYDTTMCMYEVIKAGGFTNGGLNFDAKARR
GSFTPEDIFYSYIAGMDAFALGFRAALKLIEDGRIDKFVADRYASWNTG
IGADIIAGKADFASLEKYALEKGEVTASLSSGRQEMLESIVNNVLFSL SEQ ID NO. 57: XI-Rp10 DNA
aaaaaaaTGGCTAAGGAATATTTCCCACAAATTCAACAGTATCAGGGAC
CAAAAAGTACTGATCCTCTCTCATTTAAGTACTATAACCCTGAAGAAGT
CATCAACGGAAAGACAATGCGCGAGCATCTGAAGTTCGCTCTTTCATGG
TGGCACACAATGGGCGGCGACGGAACAGATATGTTCGGCTGCGGCACAA
CAGACAAGACCTGGGGACAGTCCGATCCCGCTGCAAGAGCAAAGGCTAA
GGTTGACGCAGCATTCGAGATCATGGATAAGCTCTCCATTGACTACTAT
TGTTTCACACGATCGCGATCTTTCTCCCGAGTATGGCGCCTCAAGGCTA
CCAACGATCAGCTTGACATAGTTACAGACTATATCAAGGAGAAGCAGGG
CGACAAGTGTCAAGTGCCTCTGGGGTACAGCAAAGTGCTTCGATCATCC
AAATTCATGCACGGTGCAGGTACATCTCCTTCTGCTGATGTATTCGCTT
TCTCAGCTGCTCAGATCAAGAAGGCTCTGGAGTCAACAGTAAAGCTCGG
CGGTAACGGTTACGTTTTCTGGGGCGGACGTGAAGGCTATGAGACACTT
CTTAATACAAATATGGGACTCGAACTCGACAATATGGCTCGTCTTATGA
AGATGGCTGTTGAGTATGGACGTTCGATCGGCTTCAAGGGCGACTTCTA
TATCGAGCCCAAGCCCAAGGAGCCCACAAAGCATCA
GTACGATTTCGATACAGCTACTGTTCTGGGATTCCTCAGAAAGTACGGT
CTCGATAAGGATTTCAAGATGAATATCGAAGCTAACCACGCTACACTTG
```

-continued

```
CTCAGCATACATTCCAGCATGAGCTCCGTGTTGCAAGAGACAATGGTGT
GTTCGGTTCTATCGACGCAAACCAGGGCGACGTTCTTCTTGGATGGGAT
ACAGACCAGTTCCCCACAAATATCTACGATACAACAATGTGTATGTATG
AAGTTATCAAGGCAGGCGGCTTCACAAACGGCGGTCTCAACTTCGACGC
TAAGGCACGCAGAGGGAGCTTCACTCCCGAGGATATCTTCTACAGCTAT
ATCGCAGGTATGGATGCATTTGCTCTGGGCTTCAGAGCTGCTCTCAAGC
TTATCGAAGACGGACGTATCGACAAGTTCGTTGCTGACAGATACGCTTC
ATGGAATACCGGTATCGGTGCAGACATAATCGCAGGTAAGGCAGATTTC
GCATCTCTTGAAAAGTATGCTCTTGAAAAGGGCGAGGTTACAGCTTCAC
TCTCAAGCGGCAGACAGGAAATGCTGGAGTCTATCGTAAATAACGTTCT
TTTCAGTCTGTAA

SEQ ID NO. 58: XI-Rp10 Polypeptide
MAKEYFPQIQQYQGPKSTDPLSFKYYNPEEVINGKTMREHLKFALSWWH
TMGGDGTMDFGCGTTDKTWGQSDPAARAKAKVDAAFEIMDKLSIDYYCF
HDRDLSPEYGSLKATNDQLDIVTDYIKEKQGDKFKCLWGTAKCFDHPRF
MHGAGTSPSADVFAFSAAQIKKALESTVKLGGNGYVFWGGREGYETLLN
TNMGLELDNMARLMKMAVEYGRSIGFKGDFYIEPKPKEPTKHQYDFDTA
TVLGFLRKYGLDKDFKMNIEANHATLAQHTFQHELRVARDNGVFGSIDA
NQGDVLLGWDTDQFPTNIYDTTMCMYEVIKAGGFTNGGLNFDAKARRGS
FTPEDIFYSYIAGMDAFALGFRAALKLIEDGRIDKFVADRYASWNTGIG
ADIIAGKADFASLEKYALEKGEVTASLSSGRQEMLESIVNNVLFSL SEQ ID NO. 59: XI-Rp15 DNA
aaaaaaaTGGCTAAGGAATATTTCCCACAAATTCAAAAGATTAAGTTCG
AAAAAAGTACTGATCCTCTCTCATTTAAGTACTATAACCCTGAAGAAGT
CATCAACGGAAAGACAATGCGCGAGCATCTGAAGTTCGCTCTTTCATGG
TGGCACACAATGGGCGGCGACGGAACAGATATGTTCGGCTGCGGCACAA
CAGACAAGACCTGGGGACAGTCCGATCCCGCTGCAAGAGCAAAGGCTAA
GGTTGACGCAGCATTCGAGATCATGGATAAGCTCTCCATTGACTACTAT
TGTTTCCACGATCGCGATCTTTCTCCCGAGTATGGCAGCCTCAAGGCTA
CCAACGATCAGCTTGACATAGTTACAGACTATATCAAGGAGAAGCAGGG
CGACAAGTTCAAGTGCCTCTGGGGTACAGCAAAGTGCTTCGATCATCCA
AGATTCATGCACGGTGCAGGTACATCTCCTTCTGCTGATGTATTCGCTT
TCTCAGCTGCTCAGATCAAGAAGGCTCTGGAGTCAACAGTAAAGCTCGG
TCGGAACGGTTACGTTTTCTGGGGCGGACGTGAAGGCTATGAGACACTT
CTTAATACAAATATGGGACTCGAACTCGACAATATGGCTCGTCTTATGA
AGATGGCTGTTGAGTATGGACGTTCGATCGGCTTCAAGGGCGACTTCTA
TATCGAGCCCAAGCCCAAGGAGCCCACAAAGCATCAGTACGATTTCGAT
ACAGCTACTGTTCTGGGATTCCTCAGAAAGTACGGTCTCGATAAGGATT
TCAAGATGAATATCGAAGCTAACCACGCTACACTTGCTCAGCATACATT
CCAGCATGAGCTCCGTGTTGCAAGAGACAATGGTGTGTTCGGTTCTATC
GACGCAAACCAGGGCGACGTTCTTCTTGGATGGGATACAGACCAGTTCC
CCACAAATATCTACGATACAACAATGTGTATGTATGAAGTTATCAAGGC
AGGCGGCTTCACAAACGGCGGTCTCAACTTCGACGCTAAGGCACGCAGA
GGGAGCTTCACTCCCGAGGATATCTTCTACAGCTATATCGCAGGTATGG
ATGCATTTGCTCTGGGCTTCAGAGCTGCTCTCAAGCTTATCGAAGACGG
ACGTATCGACAAGTTCGTTGCTGACAGATACGCTTCATGGAATACCGGT
ATCGGTGCAGACATAATCGCAGGTAAGGCAGATTTCGCATCTCTTGAAA
AGTATGCTCTTGAAAAGGGCGAGGTTACAGCTTCACTCTCAAGCGGCAG
ACAGGAAATGCTGGAGTCTATCGTAAATAACGTTCTTTTCAGTCTGTAA SEQ ID NO. 60: XI-Rp15 Polypeptide
MAKEYFPQIQKIKFEKSTDPLSFKYYNPEEVINGKTMREHLKFALSWWH
TMGGDGTDMFGCGTTDKTWGQSDPAARAKAKVDAAFEIMDKLSIDYYCF
HDRDLSPEYGSLKATNDQLDIVTDYIKEKQGDKFKCLWGTAKCFDHPRF
MHGAGTSPSADVFAFSAAQIKKALESTVKLGGNGYVFWGGREGYETLLN
TNMGLELDNMARLMKMAVEYGRSIGFKGDFYIEPKPKEPTKHQYDFDTA
TVLGFLRKYGLDKDFKMNIEANHATLAQHTFQHELRVARDNGVFGSIDA
NQGDVLLGWDTDQFPTNIYDTTMCMYEVIKAGGFTNGGLNFDAKARRGS
FTPEDIFYSYIAGMDAFALGFRAALKLIEDGRIDKFVADRYASWNTGIG
ADIIAGKADFASLEKYALEKGEVTASLSSGRQEMLESIVNNVLFSL SEQ ID NO. 61: XI-Rp20 DNA
aaaaaaTGGCTAAGGAATATTTCCCACAAATTCAAAAGATTAAGTTCGAA
GGTAAGGATTCTAAGCTCTCATTTAAGTACTATAACCCTGAAGAAGTCAT
CAACGGAAAGACAATGCGCGAGCATCTGAAGTTCGCTCTTTCATGGTGG
CACACAATGGGCGGCGACGGAACAGATATGTTCGGCTGCGGCACAACAG
ACAAGACCTGGGGACAGTCCGATCCCGCTGCAAGAGCAAAGGCTAAGGT
TGACGCAGCATTCGAGATCATGGATAAGCTCTCCATTGACTACTATTGT
TTCCACGATCGCGATCTTTCTCCCGAGTATGGCAGCCTCAAGGCTACCA
ACGATCAGCTTGACATAGTTACAGACTATATCAAGGAGAAGCAGGGCGA
CAAGTTCAAGTGCCTCTGGGGTACAGCAAAGTGCTTCGATCATCCAAGA
TTCATGCACGGTGCAGGTACATCTCCTTCTGCTGATGTATTCGCTTTCT
CAGCTGCTCAGATCAAGAAGGCTCTGGAGTCAACAGTAAAGCTCGGCGG
TAACGGTTACGTTTTCTGGGGCGGACGTGAAGGCTATGAGACACTTCTT
AATACAAATATGGGACTCGAACTCGACAATATGGCTCGTCTTATGAAGA
TGGCTGTTGAGTATGGACGTTCGATCGGCTTCAAGGGCGACTTCTATAT
CGAGCCCAAGCCCAAGGAGCCCACAAAGCATCAGTACGATTTCGATACA
GCTACTGTTCTGGGATTCCTCAGAAAGTACGGTCTCGATAAGGATTTCA
AGATGAATATCGAAGCTAACCACGCTACACTTGCTCAGCATACATTCCA
GCATGAGCTCCGTGTTGCAAGAGACAATGGTGTGTTCGGTTCTATCGAC
TGCAAACCAGGGCGACGTTCTTCTTGGATGGGAACAGACCAGTTCCCCA
CAAATATCTACGATACAACAATGTGTATGTATGAAGTTATCAAGGCAGG
CGGCTTCACAAACGGCGGTCTCAACTTCGACGCTAAGGCACGCAGAGGG
AGCTTCACTCCCGAGGATATCTTCTACAGCTATATCGCAGGTATGGATG
CATTTGCTCTGGGCTTCAGAGCTGCTCTCAAGCTTATCGAAGACGGACG
TATCGACAAGTTCGTTGCTGACAGATACGCTTCATGGAATACCGGTATC
GGTGCAGACATAATCGCAGGTAAGGCAGATTTCGCATCTCTTGAAAAGT
```

```
ATGCTCTTGAAAAGGGCGAGGTTACAGCTTCACTCTCAAGCGGCAGACA

GGAAATGCTGGAGTCTATCGTAAATAACGTTCTTTTCAGTCTGTAA

SEQ ID NO. 62: XI-Rp20 Polypeptide
MAKEYFPQIQKIKFEGKDSKLSFKYYNPEEVINGKTMREHLKFALSWWH

FTMGGDGTDMGCGTTDKTWGQSDPAARAKAKVDAAFEIMDKLSIDYYCF

HDRDLSPEYGSLKATNDQLDIVTDYIKEKQGDKFKCLWGTAKCFDHPRF

MHGAGTSPSADVFAFSAAQIKKALESTVKLGGNGYVFWGGREGYETLLN

TNMGLELDNMARLMKMAVEYGRSIGFKGDFYIEPKPKEPTKHQYDFDTA

TVLGFLRKYGLDKDFKMNIEANHATLAQHTFQHELRVARDNGVFGSIDA

NQGDVLLGWDTDQFPTNIYDTTMCMYEVIKAGGFTNGGLNFDAKARRGS

FTPEDIFYSYIAGMDAFALGFRAALKLIEDGRIDKFVADRYASWNTGIG

ADIIAGKADFASLEKYALEKGEVTASLSSGRQEMLESIVNNVLFSL
```

Example 12

Production of Additional Xylose Isomerase Variants

A series of specific point mutations were made to the "hot rod" *Ruminococcus* xylose isomerase gene using site-directed mutagenesis. The particular point mutations that were generated are set forth in the table below.

| |
|---|
| W136F |
| F184S |
| G179A |
| G179A F184S |
| W136F G179A F184S |
| W136I G179A F184S |
| W136S G179A F184S |
| F87L W136F G179A F184S |
| F87M W136F G179A F184S |
| F87L W136F G179A F184S V214G |
| G179S F184A |
| F85S W136F G179A F184A V214G Q273T |
| F85S W136F G179A F184A V214 D257A |
| W136F G179A F184A |
| W136F G179A F184S D257E |

Site directed mutagenesis was performed as follows: About 50 ng of template DNA was added to 1×Pfu Ultra II buffer, 0.3 mM dNTPs, 0.3 µmol of the relevant mutagenesis primers depending on the mutant being constructed and 1 U Pfu Ultra 11 polymerase (Agilent, La Jolla, Calif.) in a 50 µl reaction mix. The sequence of the mutagenesis primers used is set forth in the table below. The "hot rod" *Ruminococcus* xylose isomerase gene was used as the template DNA for constructing single point mutation variants. Previously engineered mutants sometimes were used as "template" DNA to generate other mutants. The sequence of the oligonucleotides used to prepare each mutant is indicated in the table below. Each reaction was PCR cycled as follows: 95° C. 10 minutes followed by 30 rounds of 95° C. for 20 seconds, 55° C. for 30 seconds, and 72° C. for 5 minutes. A final 5 minute extension reaction at 72° C. was also included. Following PCR, 1.5 µl of Dpnl (NEB, Ipswich, Mass.) was added and allowed to digest the reaction mixture for 1 to 1.5 hours at 37° C. 5 µl of this mixture was then used to transform NEB-5a cells (NEB, Ipswich, Mass.) and plated onto LB media with ampicillin (100 µg/ml). (Table below discloses SEQ ID NOS 229-256, respectively, in order of appearance)

| | |
|---|---|
| GGCGACAAGTTCAAGTGCCTCTTCGGTACAGCAAAG | W136F_Forward |
| CTTTGCTGTACCGAAGAGGCACTTGAACTTGTCGCC | W136F_Reverse |
| TCGGCGGTAACGGTTACGTTAGCTGGGGCGGAC | F184S_Forward |
| GTCCGCCCCAGCTAACGTAACCGTTACCGCCGA | F184S_Reverse |
| AACAGTAAAGCTCGGCGCTAACGGTTACGTTTTCT | G179A_Forward |
| AGAAAACGTAACCGTTAGCGCCGAGCTTTACTGTT | G179A_Reverse |
| AACAGTAAAGCTCGGCGCTAACGGTTACGTTAGCTGGGGCGGAC | G179A-F184S_Forward |
| GTCCGCCCCAGCTAACGTAACCGTTAGCGCCGA | G179A-F184S_Reverse |
| GCTAAGGTTGACGCAGCAATGGAGATCATGGATAAGCTC | F85M_Forward |
| GAGCTTATCCATGATCTCCATTGCTGCGTCAACCTTAGC | F85M_Reverse |
| CTAAGGTTGACGCAGCATTAGAGATCATGGATAAGCTC | F85L_Forward |
| GAGCTTATCCATGATCTCTAATGCTGCGTCAACCTTAG | F85L_Reverse |
| AGCTAACCACGCTACACTTGCTACGCATACATTCCAGCATG | Q273T_Forward |
| CATGCTGGAATGTATGCGTAGCAAGTGTAGCGTGGTTAGCT | Q273T_Reverse |
| GCGACAAGTTCAAGTGCCTCATAGGTACAGCAAAGTGCTTCGA | W136I_Forward |
| TCGAAGCACTTTGCTGTACCTATGAGGCACTTGAACTTGTCGC | W136I_Reverse |
| GCGACAAGTTCAAGTGCCTCTCGGGTACAGCAA | W136S_Forward |
| TTGCTGTACCCGAGAGGCACTTGAACTTGTCGC | W136S_Reverse |
| GCTAACCACGCTACACTTGCTGGTCATACATTCCAGCAT | Q273G_Forward |
| ATGCTGGAATGTATGACCAGCAAGTGTAGCGTGGTTAGC | Q273G_Reverse |
| CCTCAGAAAGTACGGTCTCGCTAAGGATTTCAAGATGAATA | D257A_Forward |
| TATTCATCTTGAAATCCTTAGCGAGACCGTACTTTCTGAGG | D257A_Reverse |
| CCTCAGAAAGTACGGTCTCGAGAAGGATTTCAAGATGAATATC | D257E_Forward |
| GATATTCATCTTGAAATCCTTCTCGAGACCGTACTTTCTGAGG | D257E_Reverse |

```
GTCTTATGAAGATGGCTGGTGAGTATGGACGTTCGAT          V214G Forward
ATCGAACGTCCATACTCACCAGCCATCTTCATAAGAC          V214G Reverse GTCAACAGTAAAGCTCGGCAGTAACGGTTACGTTAGCTGG       G179S_Forward
CCAGCTAACGTAACCGTTACTGCCGAGCTTTACTGTTGAC       G179S_Reverse
```

Following sequence verification (GeneWiz, La Jolla, Calif.), the approximate 1330 bp SpeI-XhoI fragment from each construct was subcloned into the yeast expression vector p426GPD by first gel extracting each fragment using a Qiagen gel purification kit (Qiagen, Valencia, Calif.), and then preparing the p426GPD vector for ligation by purifying it using a Qiagen PCR purification kit according to the manufacturer's instructions. About 30 ng of each of the chimeric genes was separately ligated to about 50 ng of the p426GPD vector using T4 DNA ligase followed by transformation using known protocols into NEB-5α competent cells (NEB, Ipswich, Mass.). The transformed cells were plated onto LB media with ampicillin (100 µg/ml). Constructs containing the chimeric genes were confirmed by sequence analysis (GeneWiz, La Jolla, Calif.).

A haploid *Saccharomyces cerevisiae* strain (BY4742; ATCC catalog number 201389) was cultured in YPD media (10 g Yeast Extract, 20 g Bacto-Peptone, 20 g Glucose, 1 L total) at about 30° C. Separate aliquots of these cultured cells were transformed with a plasmid constructs containing the novel xylose isomerase chimeric genes as well as with the *Piromyces* and *Ruminococcus* native gene constructs made above. Transformation was accomplished using the Zymo frozen yeast transformation kit (Catalog number T2001; Zymo Research Corp., Orange, Calif. 92867). To about 50 µl of cells was added approximately 0.5-1 µg plasmid DNA and the cells were cultured on SC drop out media with glucose minus uracil (about 20 g glucose; about 2.21 g SC drop-out mix, about 6.7 g yeast nitrogen base, all in about 1 L of water); this mixture was cultured for 2-3 days at about 30° C.

Assays of the various novel xylose isomerase point mutation polypeptides were performed according to Kuyper et al. (FEMS Yeast Res., 4:69 [2003]) with a few modifications as described above. Approximately 20 µg of soluble whole cell extract from each transformed cell line was prepared using Y-PER plus reagent as described above was incubated in a solution containing about 100 mM Tris, pH 7.5, 10 mM Mg Cl¬ 2, 0.15 mM NADH (Sigma, St. Louis, Mo.), and 2 U Sorbitol Dehydrogenase (SDH) (Roche, Indianapolis, Ind.) at about 30° C. To start the reaction, about 100 µl of xylose was added at various final concentrations of 40-500 mM. A Beckman DU-800 spectrophotometer was utilized with an Enzyme Mechanism software package (Beckman Coulter, Inc, Brea, Calif.), and the change in the $A_{340}$ was monitored for 2-3 minutes. The results of the assays are shown in FIG. 10.

Figure 10:
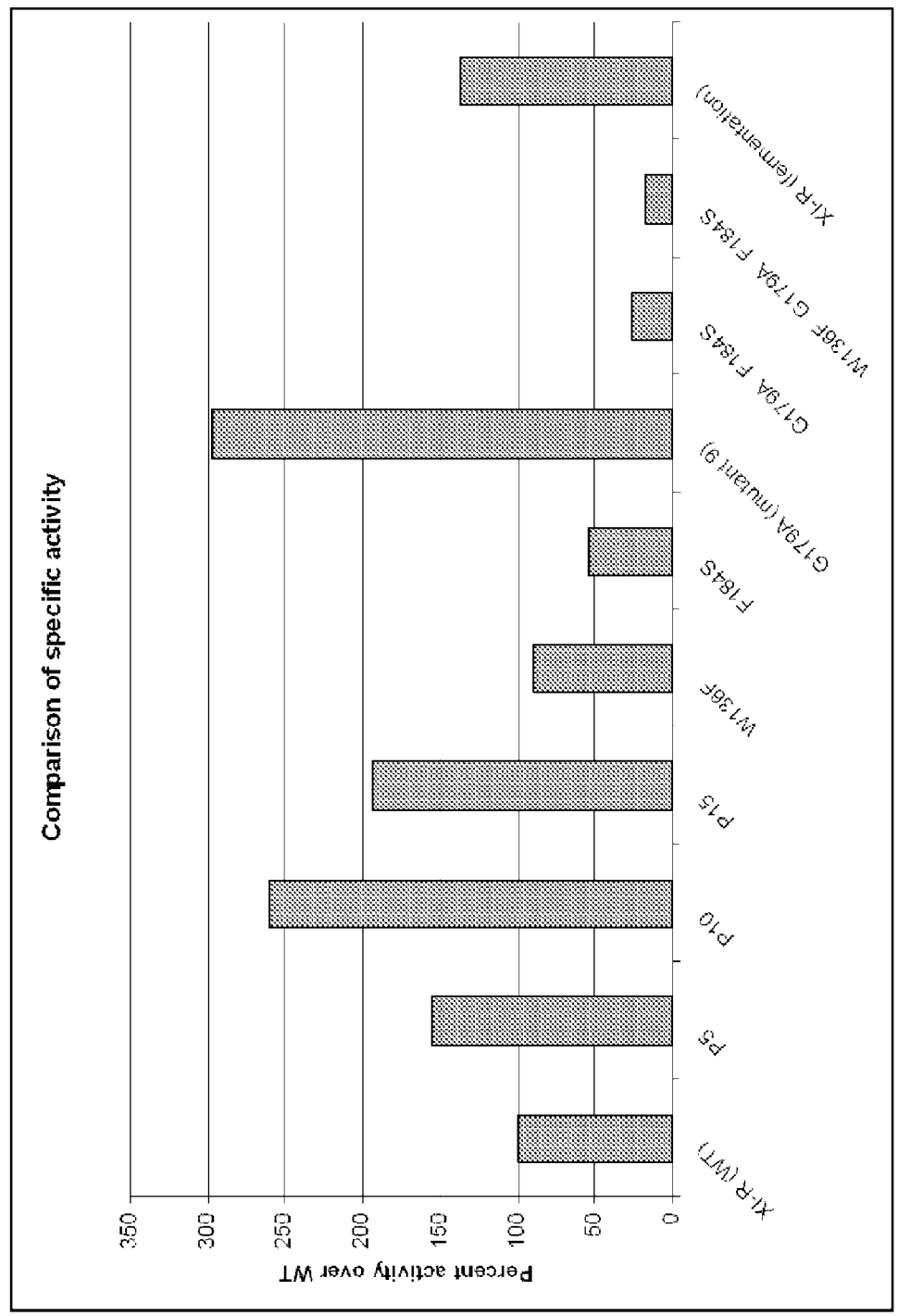
FIG. 10 graphically illustrates a comparison of specific activities of engineered mutant xylose isomerase enzymes.

Mutant G179A had the highest activity as compared to the *Ruminococcus* wild type xylose isomerase, as shown in FIG. 10. The kinetics of the G179A mutant were further analyzed using kinetic assays described herein, adding various concentrations of xylose ranging from about 40 to about 500 mM. The results of the kinetic assays, shown below, for the G179A mutant illustrate that the mutant xylose isomerase activity has a higher specific activity than the *Piromyces* xylose isomerase.

| Enzyme | Km (mM) | Specific Activity (µmol min-1 mg-1) |
|---|---|---|
| *Piromyces* xylose isomerase | 49 | 2.02 |
| *Ruminococcus* xylose isomerase wild type | 82.12 | 1.718 |
| *Ruminococcus* xylose isomerase G179A | 83.82 | 2.24 |

Example 13

In Vivo Evaluation of Xylose Isomerase Constructs

The yeast strain BY4742 was specifically engineered to more readily utilize xylose as a carbon source. The engineered strain was designed to include the following genetic modifications: the native Pho13 gene (alkaline phosphatase specific for p-nitrophenyl phosphate) was disrupted by inserting a construct containing the native TLK1 gene (Transketolase-1); the native aldose reductase gene (Gre3) was disrupted by inserting a construct containing the native high-affinity glucose transporter-7 gene (HXT7); the native glucose-repressible alcohol dehydrogenase II gene (adh2) was disrupted by inserting a construct containing the native xylulokinase gene (XYLK); and the native orotidine-5' phosphate decarboxylase gene (ura3) was disrupted by inserting a construct containing the native transaldolase 1 gene (TAL1). The resulting strain had the following genotype: pho13::TKL1, gre3::HXT7, adh-2::XYLK, ura3::TAL1. The final strain is referred to as the "C5" strain and was used for in vivo evaluation of the xylose isomerase variants.

The C5 strain was transformed using standard protocols with either p426GPD (as a control) or the chimeric variants XI-R, XI-Rp5, XI-Rp10, or XI-Rp15. The transformed cells were grown on SC-glucose minus uracil initially and then passaged onto SC-xylose minus uracil. Cultures of each of the above constructs were made in SC-xylose minus uracil—and grown for one week. The cultures were grown aerobically at 30° C. with 250 rpm agitation, 1 vvm sparge of process air, 21% O2. The pH was controlled at about 5.0 with 1N NaOH. Ethanol, glucose and xylose concentrations in the fermentation broth were monitored by a YSI 2700 BioAnalyzer during aerobic fermentation. At 24 hours elapsed fermentation time the fermentation was switched to anaerobic conditions. Before changing to anaerobic conditions, samples were taken to measure ethanol, glucose and xylose concentrations, and biomass was measured by OD600 nm and dry cell weight. At the start of anaerobic fermentation, 4 ml/L of 2.5 g/L ergosterol in EtOH, 0.4 ml/L Tween 80, and 0.01% AF-204 were added to each fermentor. Oxygen was purged with 100% N2 sparge at 1 vvm until percent O2 was below 1%. Aeration was then set at 0.25 vvm 100% N2.

Samples were taken every 24 to 48 hours and measured for ethanol concentration, glucose concentration, xylose concentration, and cell density (OD600 nm). The fermentation was harvested when xylose concentration was below 4 g/L in the XI-R strains, at 372 hours after commencing fermentation. The final sample also measured biomass by dry cell weight. The results are presented in the table below.

| Strain | $OD_{600\,nm}$ | Dry Cell Wt (g/L) | Ethanol (g/L) | Glucose (g/L) | Xylose (g/L) |
|---|---|---|---|---|---|
| XI-R | 7.72 | 2.20 | 15.65 | 0 | 3.14 |
| Vector | 7.34 | 1.78 | 6.705 | 0 | 23.21 |
| XI-R | 7.32 | 2.03 | 15.5 | 0 | 3.85 |
| Vector | 7.96 | 1.87 | 9.91 | 0 | 23.11 |

The data presented indicate that the *Ruminococcus* xylose isomerase containing yeast cells were able to utilize xylose as a carbon source, and the cells containing vector only (e.g., vector with no xylose isomerase gene) utilized very little xylose.

Industrial Yeast Strain Evaluation

To evaluate the activity of the various native, modified and engineered (e.g., mutant and/or chimeric) *Ruminococcus* xylose isomerases in a commercial yeast strain, the *Ruminococcus* wild type gene or *Ruminococcus* Rp10 and Rp15 chimeric constructs were inserted into a yeast vector containing a 2µ origin and a KANMX4 (G418R) cassette (cloned from vector HO-poly-KANMX4-HO; ATCC Cat. No. 87804; Voth et al., 2001 NAR 29(12): e59, DDBJ/EMBL/Gen Bank accession nos. AF324723-9). A commercially available industrial diploid strain of *Saccharomyces cerevisiae* (strain BF903; "Stillspirits" triple distilled yeast, Brewcraft, Albany, New Zealand; available at Hydrobrew, Oceanside, Calif.) was obtained and was made competent for transformation using known yeast cell transformation procedures. The transformed cells containing either vector alone or the various *Ruminococcus* xylose isomerase gene constructs were passaged in YPD medium containing about 100 µg/ml G418 (EMD, San Diego, Calif.), and about 2% glucose. Transformed yeast containing each construct were grown overnight aerobically in a 15 ml culture tube on YPD media containing 2% glucose. After about 24 hours, about 25 ml of YP media containing 2% glucose and 100 µg/ml G418 was seeded with the cells at an initial $OD_{600}$ of 0.5 in a 250 ml Erlenmeyer flask and grown aerobically at 30° C. The cultures were then passaged once every 7 days into fresh media, also at an initial $OD_{600}$ of 0.5. The fresh media contained increasing amounts of xylose and decreasing amounts of glucose as set forth below.

| Week | Glucose | Xylose |
|---|---|---|
| 1 | 1% | 1% |
| 2 | 0.50% | 1.50% |
| 3 | 0.25% | 1.75% |
| 4 | 0.10% | 1.90% |

Measurements were taken of the cell optical density ($OD_{600}$) to assess cell density and plated onto YPD with 100 µg/ml G418 to ensure that the plasmid was stable. Glucose, xylose and ethanol in the culture media were assayed using YSI 2700 Bioanalyzer instruments (World Wide Web uniform resource locator ysi.com), according to the manufacturer's recommendations. The strains were then grown overnight in YPD (with 100 µg/ml G418) and used to inoculate about 50 ml YP-xylose (with 100 µg/ml G418) into disposable 250 ml Erlenmeyer flasks with vented caps at an initial $OD_{600}$ of about 1. The cultures were allowed to grow aerobically at 30° C. at 200 rpm for 7 days. The results are shown in FIG. 11. The results shown in FIG. 11 indicate that the commercial yeast strain expressing the *Ruminococcus* xylose isomerase is more efficient at consuming xylose than the strain carrying the vector control only.

To evaluate ethanol production, the transformed cells containing either the vector control or the gene encoding native *Ruminococcus* xylose isomerase were grown overnight in YP glucose (with 100 µg/ml G418) and then used to inoculate serum bottles containing 50 ml YP plus xylose (with 100 µg/ml G418) at an initial $OD_{600}$ of about 1. The serum bottles were sealed with a butyl rubber stopper to prevent air exchange. As a result, the cultures became anaerobic once the available oxygen in the serum bottle was utilized. In general, anaerobiosis (e.g., the onset of anaerobic conditions) occurred a few hours after the culture was inoculated. Xylose utilization, ethanol production and cell growth were measured every twenty four hours. The results are shown in FIG. 12. The results suggest that yeast strains containing the *Ruminococcus* xylose isomerase, grew to a higher cell density and produced more ethanol using xylose as a carbon source than did cells carrying the vector only control (e.g., see FIG. 12).

Example 14

High Diversity Library of Xylose Isomerase of Variants

To generate additional *Ruminococcus* xylose isomerase variants, a high diversity library of mutants was generated using known molecular biology procedures. The library contained the combinations and permutations of substitutions listed in the table below. The *Ruminococcus* xylose isomerase variants listed below and highlighted in boldface type have been transformed into yeast strains, and are evaluated for growth and ethanol production on xylose media utilizing protocols described above. Yeast transformation of the variants listed below not highlighted in boldface is conducted and resulting variants are tested. In the table below "position" refers to the amino acid position in the *Ruminococcus* xylose isomerase amino acid sequence, "AA1" refers to the first of the considered amino acid substitutions for that position, "CODON1" refers to the nucleotide sequence selected for the amino acid chosen in "AA1", "AA2" refers to the second of the considered amino acid substitutions for that position, "CODON2" refers to the nucleotide sequence selected for the amino acid chosen in "AA2", "AA3" refers to the third of the considered amino acid substitutions for that position, "CODON3" refers to the nucleotide sequence selected for the amino acid chosen in "AA3", "AA4" refers to the fourth of the considered amino acid substitutions for that position and "CODON4" refers to the nucleotide sequence selected for the amino acid chosen in "AA4".

High Diversity Library of Xylose Isomerase of Variants

| Position | AA1 | CODON1 | AA2 | CODON2 | AA3 | CODON3 | AA4 | CODON4 | # substitutions | LIB1-A | LIB1-B |
|---|---|---|---|---|---|---|---|---|---|---|---|
| 3 | F | TTT | Y | TAT | | | | | 2 | 1 | 1 |
| 45 | L | TTG | M | ATG | | | | | 2 | 1 | 1 |
| 46 | S | TCT | A | GCT | | | | | 2 | 1 | 1 |
| 51 | M | ATG | L | TTG | | | | | 2 | 1 | 1 |
| 52 | G | GGT | C | TGT | | | | | 2 | 1 | 1 |
| 53 | G | GGT | A | GCT | | | | | 2 | 1 | 1 |
| 58 | M | ATG | Q | CAA | | | | | 2 | 1 | 1 |
| 85 | F | TTT | M | ATG | L | TTG | | | 3 | 1 | 3 |
| 101 | R | AGA | V | GTT | | | | | 2 | 1 | 1 |
| 107 | Y | TAT | G | GGT | | | | | 2 | 2 | 2 |
| 121 | T | ACT | V | GTT | | | | | 2 | 2 | 2 |
| 131 | K | AAA | G | GGT | | | | | 2 | 2 | 2 |
| 136 | W | TGG | F | TTT | | | | | 2 | 2 | 1 |
| 140 | K | AAA | N | AAT | | | | | 2 | 2 | 2 |
| 147 | F | TTT | Y | TAT | | | | | 2 | 2 | 2 |
| 179 | G | GGT | R | AGA | A | GCT | | | 3 | 1 | 3 |
| 184 | F | TTT | S | TCT | | | | | 2 | 1 | 1 |
| 204 | D | GAT | E | GAA | | | | | 2 | 2 | 2 |
| 214 | V | GTT | R | AGA | G | GGT | | | 3 | 1 | 1 |
| 257 | D | GAT | A | GCT | E | GAA | | | 3 | 1 | 1 |
| 273 | Q | CAA | F | TTT | T | ACT | G | GGT | 4 | 1 | 4 |
| 292 | I | ATT | V | GTT | | | | | 2 | 2 | 2 |
| 296 | Q | CAA | R | AGA | | | | | 2 | 1 | 1 |
| 345 | T | ACT | D | GAT | E | GAA | | | 3 | 3 | 3 |
| 373 | D | GAT | E | GAA | | | | | 2 | 2 | 2 |
| | | | | | | | | | 509607936 | 1536 | 27648 |

Number of possible variants: 5.096e+08
Expected completeness: 0.95
Required library size: 1.527e+09

The xylose isomerase mutants listed above are generated using oligonucleotides listed below and a 3 step PCR method, described in further detail below.
(Table below discloses SEQ ID NOS 257-336, respectively, in order of appearance)

| | |
|---|---|
| KAS/XI-LIB-for-1 | ctagaactagtaaaaaaatggctaaggaatattattctaatataggtaaaattcagtat |
| KAS/XI-LIB-for-2 | Actatgagagaacatttaaaatttgctatgtcttggtggcatactwt |
| KAS/XI-LIB-for-3 | Agagaacatttaaaatttgctttggcttggtggcatactwtgkgtg |
| KAS/XI-LIB-for-4 | Actatgagagaacatttaaaatttgctatggcttggtggcatactwtgkgtg |
| KAS/XI-LIB-for-5 | Ttgctttgtcttggtggcatactttgkgtgstgatg |

-continued

| | |
|---|---|
| KAS/XI-LIB-for-6 | Cttggtggcatactatgtgtgstgatggtactgats |
| KAS/XI-LIB-for-7 | Gtggcatactatgggtgctgatggtactgatatgt |
| KAS/XI-LIB-for-8 | Gtggcatactwtgkgtgctgatggtactgatcaat |
| KAS/XI-LIB-for-9 | Gcatactwtgkgtgstgatggtactgatcaattcggttgtggtact |
| KAS/XI-LIB-for-10 | gcaaaagccaaagtagatgcagccwtggaaattatggataaattgtctattg |
| KAS/XI-LIB-for-11 | ttatggataaattgtctattgattattattgttttcatgatgttgatttgtctcctgaatatggttctttaaaag |
| KAS/XI-LIB-for-12 | ttatggataaattgtctattgattattattgttttcatgatgttgatttgtctcctgaaggtggttctttaaaag |
| KAS/XI-LIB-for-13 | gttttcatgatagagatttgtctcctgaaggtggttctttaaaagcaactaatg |
| KAS/XI-LIB-for-14 | gttctttaaaagcaactaatgatcaattggacattgttgttgattatattaaagaaaaacaaggtgataaatttaaatg |
| KAS/XI-LIB-for-15 | gttctttaaaagcaactaatgatcaattggacattgttgttgattatattaaagaaaaacaaggtgatggttttaaatg |
| KAS/XI-LIB-for-16 | cggattatattaaagaaaaacaaggtgatggttttaaatgtttgtkkggcactgcgaawt |
| KAS/XI-LIB-for-17 | ttatattaaagaaaaacaaggtgataaatttaaatgtttgtttggcactgcgaawtgttttgat |
| KAS/XI-LIB-for-18 | Gtttgtggggcactgcgaattgttttgatcatcc |
| KAS/XI-LIB-for-19 | Ttttgatcatccacgttatatgcatggtgcgggga |
| KAS/XI-LIB-for-20 | Ggaatcaactgttaaattaggtagaaacgggtatgtattctggga |
| KAS/XI-LIB-for-21 | Gaatcaactgttaaattaggtgctaacgggtatgtattctggggag |
| KAS/XI-LIB-for-22 | Ggaatcaactgttaaattaggtagaaacgggtatgtatcttggga |
| KAS/XI-LIB-for-23 | Gaatcaactgttaaattaggtgctaacgggtatgtatcttggggag |
| KAS/XI-LIB-for-24 | Aaattaggtgggaacgggtatgtatcttggggaggaaggg |
| KAS/XI-LIB-for-25 | Cactaatatgggtttggaattggaaaatatggctagattgatgaaaatg |
| KAS/XI-LIB-for-26 | ggataatatggctagattgatgaaaatggctagagaatacggaaggtcta |
| KAS/XI-LIB-for-27 | Gctagattgatgaaaatggctggtgaatacggaaggtctattggtt |
| KAS/XI-LIB-for-28 | cagttttgggattcttgagaaaatatggtttggctaaagattttaaaatgaatatagaagcta |
| KAS/XI-LIB-for-29 | agttttgggattcttgagaaaatatggtttggaaaaagattttaaaatgaatatagaagctaa |
| KAS/XI-LIB-for-30 | atagaagctaatcatgcaacactcgcatttcatacttttcaacatgaattgagagtt |
| KAS/XI-LIB-for-31 | atagaagctaatcatgcaacactcgcaactcatacttttcaacatgaattgagagtt |
| KAS/XI-LIB-for-32 | agaagctaatcatgcaacactcgcaggtcatacttttcaacatgaattgagag |
| KAS/XI-LIB-for-33 | Taacggagttttggatctgttgatgcaaaccagggagacg |
| KAS/XI-LIB-for-34 | Taacggagttttggatctgttgatgcaaacagaggagacg |
| KAS/XI-LIB-for-35 | Ttttggatctatcgatgcaaacagaggagacgttttgctaggatggg |
| KAS/XI-LIB-for-36 | Aaggctaggcgtggtagtttcgatccagaggatatattctattc |
| KAS/XI-LIB-for-37 | Cgaaggctaggcgtggtagtttcgaaccagaggatatattctattctta |
| KAS/XI-LIB-for-38 | Cagggcagcactaaaattgattgaagaaggtagaattgataagtttg |
| KAS/XI-LIB-for-39 | Tgggaaagccgacttcgccagtttggaaaaatatg |
| KAS/XI-LIB-rev-1 | atactgaattttacctatattagaataatattccttagccatttttttactagttctag |
| KAS/XI-LIB-rev-2 | Awagtatgccaccaagacatagcaaattttaaatgttctctcatagt |
| KAS/XI-LIB-rev-3 | Cacmcawagtatgccaccaagccaaagcaaattttaaatgttctct |
| KAS/XI-LIB-rev-4 | cacmcawagtatgccaccaagccatagcaaattttaaatgttctctcatagt |

-continued

| | |
|---|---|
| KAS/XI-LIB-rev-5 | Catcascacmcaaagtatgccaccaagacaaagcaa |
| KAS/XI-LIB-rev-6 | Satcagtaccatcascacacatagtatgccaccaag |
| KAS/XI-LIB-rev-7 | Acatatcagtaccatcagcacccatagtatgccac |
| KAS/XI-LIB-rev-8 | Attgatcagtaccatcagcacmcawagtatgccac |
| KAS/XI-LIB-rev-9 | Agtaccacaaccgaattgatcagtaccatcascacmcawagtatgc |
| KAS/XI-LIB-rev-10 | Caatagacaatttatccataatttccawggctgcatctactttggcttttgc |
| KAS/XI-LIB-rev-11 | cttttaaagaaccatattcaggagacaaatcaacatcatgaaaacaataataatcaat agacaatttatccataa |
| KAS/XI-LIB-rev-12 | cttttaaagaaccaccttcaggagacaaatcaacatcatgaaaacaataataatcaat agacaatttatccataa |
| KAS/XI-LIB-rev-13 | cattagttgcttttaaagaaccaccttcaggagacaaatctctatcatgaaaac |
| KAS/XI-LIB-rev-14 | catttaaatttatcaccttgttttctttaatataatcaacaacaatgtccaattgatcattagttg cttttaaagaac |
| KAS/XI-LIB-rev-15 | catttaaaaccatcaccttgttttctttaatataatcaacaacaatgtccaattgatcattagtt gcttttaaagaac |
| KAS/XI-LIB-rev-16 | awttcgcagtgccmmacaaacatttaaaaccatcaccttgttttctttaatataatccg |
| KAS/XI-LIB-rev-17 | atcaaaacawttcgcagtgccaaacaaacatttaaatttatcaccttgttttctttaatataa |
| KAS/XI-LIB-rev-18 | Ggatgatcaaaacaattcgcagtgccccacaaac |
| KAS/XI-LIB-rev-19 | Tccccgcaccatgcatataacgtggatgatcaaaa |
| KAS/XI-LIB-rev-20 | Tccccagaatacatacccgtttctacctaatttaacagttgattcc |
| KAS/XI-LIB-rev-21 | Ctccccagaatacatacccgttagcacctaatttaacagttgattc |
| KAS/XI-LIB-rev-22 | Tccccaagatacatacccgtttctacctaatttaacagttgattcc |
| KAS/XI-LIB-rev-23 | Ctccccaagatacatacccgttagcacctaatttaacagttgattc |
| KAS/XI-LIB-rev-24 | Cccttcctccccaagatacatacccgttcccacctaattt |
| KAS/XI-LIB-rev-25 | Cattttcatcaatctagccatattttccaattccaaacccatattagtg |
| KAS/XI-LIB-rev-26 | Tagaccttccgtattctctagccattttcatcaatctagccatattatcc |
| KAS/XI-LIB-rev-27 | Aaccaatagaccttccgtattcaccagccattttcatcaatctagc |
| KAS/XI-LIB-rev-28 | tagcttctatattcattttaaaatctttagccaaaccatattttctcaagaatcccaaaactg |
| KAS/XI-LIB-rev-29 | ttagcttctatattcattttaaaatcttttccaaaccatattttctcaagaatcccaaaact |
| KAS/XI-LIB-rev-30 | aactctcaattcatgttgaaaagtatgaaatgcgagtgttgcatgattagcttctat |
| KAS/XI-LIB-rev-31 | aactctcaattcatgttgaaaagtatgagttgcgagtgttgcatgattagcttctat |
| KAS/XI-LIB-rev-32 | Ctctcaattcatgttgaaaagtatgacctgcgagtgttgcatgattagcttct |
| KAS/XI-LIB-rev-33 | Cgtctccctggtttgcatcaacagatccaaaaactccgtta |
| KAS/XI-LIB-rev-34 | Cgtctcctctgtttgcatcaacagatccaaaaactccgtta |
| KAS/XI-LIB-rev-35 | Cccatcctagcaaaacgtctcctctgtttgcatcgatagatccaaaa |
| KAS/XI-LIB-rev-36 | Gaatagaatatatcctctggatcgaaactaccacgcctagcctt |
| KAS/XI-LIB-rev-37 | Taagaatagaatatatcctctggttcgaaactaccacgcctagccttcg |
| KAS/XI-LIB-rev-38 | Caaacttatcaattctaccttcttcaatcaattttagtgctgccctg |
| KAS/XI-LIB-rev-39 | Catattttccaaactggcgaagtcggctttccca |
| KAS/FOR-XI-LIB | Cctgaaattattcccctacttgact |
| KAS/REV-XI-LIB | Ccttctcaagcaaggttttcagtat |

The nucleotide sequences of the oligonucleotides above include IUPAC nucleotide symbol designations, in some embodiments. The IUPAC nucleotide symbol designations used in the listing above and the nucleotides they represent are; m (A or C nucleotides), k (G or T nucleotides), s (C or G nucleotides), w (A or T nucleotides).

Oligonucleotides are prepared as 100 micromolar stocks to be diluted as needed for use as PCR and/or primer extension primers. Step 1 of the 3 step PCR protocol included initial primer extension reactions performed four times, each with a different concentration of mutant oligonucleotide (e.g., about 7.5 nanomolar, about 37.5 nanomolar, about 75 nanomolar, and about 150 nanomolar). An appropriate amount (e.g., dependent on the reaction) of each of the desired primers is contacted with Ruminococcus xylose isomerase nucleotide sequences, under PCR/primer extension conditions to generate the xylose isomerase mutant variants. The forward and reverse primers listed above are designated with "-for-" or "-rev-" as part of the primer name. A non-limiting example of the PCR/primer extension conditions utilized for generating the xylose isomerase mutant variants listed above include 200 micromolar of each deoxyribonucleotide (dNTP), 1×Pfu ultra II buffer, and 1 unit Pfu ultra II polymerase and a thermocycle profile of; (a) an initial 10 minute denaturation at 94° C., (b) 40 cycles of (i) 94° C. for 20 seconds, (ii) 56° C. for 30 seconds, and (iii) 72° C. for 45 seconds, and (c) a final extension at 72° C. for 5 minutes. The initial extension products are analyzed by gel electrophoresis on 1.2% Tris-acetate agarose gels. The reactions are column purified and the resultant purified nucleic acids are used for subsequent steps in the 3 step PCR protocol.

The second step of the 3 step protocol includes contacting the purified nucleic acids from the first step with Ruminococcus xylose isomerase gene primers (e.g., KAS/FOR-XI-LIB and KAS/REV-XI-LIB, as listed in the table above, under substantially similar PCR/primer extension conditions, with the modification of 5 units of Pfu ultra II polymerase instead of 1 unit. The PCR reactions also are performed four times, each with a differing amount of gene primers (e.g., about 20 nanomolar, about 100 nanomolar, about 2 micromolar and about 5 micromolar. The reaction products are analyzed by gel electrophoresis as described above and column purified in preparation for the final step of the 3 step PCR/primer extension protocol.

The final step of the 3 step protocol generated full length nucleic acids of xylose isomerase mutants. The column purified nucleic acid of the second step was contacted with about 200 nanomolar of each gene primer under extension conditions as described for the second step. The protocol described herein was used to generate a wide range of mutant xylose isomerase variants, each with between about 1 and about 9 mutations per gene.

Example 15

Construction of Mutant G179A with p10 or p15 Extensions

Site directed mutagenesis was performed as follows: 50 ng of the vector pBF348 (pCR Blunt II/XI-R-P10), pBF370 (pCR Blunt II/XI-R-P10-HIS), pBF349 (pCR Blunt II/XI-R-P15), or pBF370 (pCR Blunt II/XI-R-P10-HIS) was added to 1×Pfu Ultra II buffer, 0.3 mM dNTPs, 0.3 μmol mutagenesis primers [JML/5 (aacagtaaagctcggcgctaacggttacgttttct) and JML/6 (agaaaacgtaaccgttagcgccgagctttactgtt)], and 1 U Pfu Ultra II polymerase (Agilent, La Jolla, Calif.) in a 50 μl reaction mix. This reaction mixture was cycled as follows: (a) 95° C. 10 minutes, followed by (b) 30 rounds of (i) 95° C. for 20 seconds, (ii) 55° C. for 30 seconds, and (iii) 72° C. for 5 minutes. A final 5 minute extension reaction at 72° C. was also included. Following the cycling times, 1.5 μl of DpnI (NEB, Ipswich, Mass.) was added and allowed to digest the reaction mixture for 1 to 1.5 hours at 37° C. 5 μl of this mixture was then used to transform NEB-5α cells (NEB, Ipswich, Mass.) and plated onto LB media with kanamycin (35 μg/ml). The following plasmids were generated using the procedure described herein; pBF613 (XI-R-P15 with G179A mutation), pBF614 (XI-R-P15-HIS with G179A mutation), pBF615 (XI-R-P10 with G179A mutation), and pBF616 (XI-R-P10-HIS with G179A mutation), where XI=xylose isomerase, R=Ruminococcus, P=Piromyces, HIS=Histidine Tag, and the numbers that follow P indicate how many amino acids of the Piromyces xylose isomerase was fused to the 5' end of the Ruminococcus xylose isomerase gene.

Following sequence verification, the approximately 1330 base pair SpeI-XhoI fragment from each construct was subcloned into the yeast expression vector p426GPD. The generated xylose isomerase fragments were first gel extracted using a Qiagen gel purification kit (Qiagen, Valencia, Calif.), and the p426GPD vector reaction was cleaned up using a Qiagen PCR purification kit. 30 ng of the XI-fragments was ligated to 50 ng of the p426GPD vector using T4 DNA ligase (Fermentas, Glen Burnie, Md.) in a 10 μl volume reaction overnight at 16° C. and transformed into NEB-5α competent cells (NEB, Ipswich, Mass.) and plated onto LB media with ampicillin (100 μg/ml). Constructs were confirmed by sequence analysis. The following plasmids were generated using the procedure described herein: pBF677 (p426GPD/XI-R-P15_G179A), pBF678 (p426GPD/XI-R—P15-HIS_G179A), pBF679 (p426GPD/XI-R-P10_G179A), pBF680 (p426GPD/XI-R-P10-HIS_G179A).

Example 16

Additional Xylose Isomerase High Diversity Variants

An additional library of high diversity mutants containing changes not listed above also is generated. The table below lists positions in the Ruminococcus xylose isomerase gene at which one of two further amino acid codons is substituted to generate additional high diversity xylose isomerase variants. In the table below "XI-R position" refers to the amino acid position in the Ruminococcus xylose isomerase amino acid sequence, "AA1" refers to the first of two considered amino acid substitutions for that position, "CODON1" refers to the nucleotide sequence selected for the amino acid chosen in "AA1", "AA2" refers to the second of two considered amino acid substitutions for that position and "CODON2" refers to the nucleotide sequence selected for the amino acid chosen in "AA2". The nucleotide sequences for each codon are chosen using sequence and codon optimization methods described herein.

| XI-R position | AA1 | CODON1 | AA2 | CODON2 |
|---|---|---|---|---|
| 5 | S | TCT | P | CCA |
| 6 | N | AAT | Q | CAA |
| 42 | K | AAA | R | AGA |
| 54 | D | GAT | E | GAA |

| XI-R position | AA1 | CODON1 | AA2 | CODON2 |
|---|---|---|---|---|
| 56 | T | ACT | A | GCT |
| 84 | A | GCT | G | GGT |
| 137 | G | GGT | S | TCT |
| 141 | C | TGT | V | GTT |
| 180 | N | AAT | E | GAA |
| 181 | G | GGT | N | AAT |
| 203 | L | TTG | K | AAA |
| 205 | N | AAT | H | CAT |
| 208 | R | AGA | T | ACT |
| 209 | L | TTG | M | ATG |
| 210 | M | ATG | L | TTG |
| 211 | K | AAA | T | ACT |
| 215 | E | GAA | D | GAT |
| 252 | R | AGA | K | AAA |
| 253 | K | AAA | A | GCT |
| 254 | Y | TAT | H | CAT |
| 255 | G | GGT | N | AAT |
| 277 | Q | CAA | E | GAA |
| 299 | V | GTT | Y | TAT |
| 300 | L | TTG | Q | CAA |
| 301 | L | TTG | N | AAT |
| 344 | F | TTT | T | ACT |
| 346 | P | CCA | L | TTG |
| 372 | E | GAA | Q | CAA |
| 374 | G | GGT | S | TCT |
| 375 | R | AGA | P | CCA |

Example 17

Activation of the Entner-Doudoroff Pathway in Yeast Cells Using EDD and EDA Genes from *Pseudomonas aeruginosa* Strain PAO1

*Pseudomonas aeruginosa* strain PAO1 DNA was prepared using Qiagen DNeasy Blood and Tissue kit (Qiagen, Valencia, Calif.) according to the manufacture's instructions. The *P. aeruginosa* edd and eda constructs were isolated from *P. aeruginosa* genomic DNA using the following oligonucleotides:

The *P. aeruginosa* edd gene:

(SEQ ID NO: 63)
5'-aactgaactgactagtaaaaaaatgcaccctcgtgtgctcga agt-3'

(SEQ ID NO: 64)
5'-agtaaagtaaaagcttctactagcgccagccgttgaggctct-3'

The *P. aeruginosa* edd gene with 6-HIS c-terminal tag (SEQ ID NO: 138):

(SEQ ID NO63)
5'-aactgaactgactagtaaaaaaatgcaccctcgtgtgctcga agt-3'

(SEQ ID NO: 65)
5'-agtaaagtaaaagcttctactaatgatgatgatgatgatggcg ccagccgttgaggctc-3'

The *P. aeruginosa* eda gene:

(SEQ ID NO: 66)
5'-aactgaactgactagtaaaaaaatgcacaaccttgaacagaag acc-3'

(SEQ ID NO: 67)
5'-agtaaagtaactcgagctattagtgtctgcggtgctcggcgaa-3'

The *P. aeruginosa* eda gene with 6-HIS c-terminal tag (SEQ ID NO: 138):

(SEQ ID NO: 66)
5'-aactgaactgactagtaaaaaaatgcacaaccttgaacagaag acc-3'

(SEQ ID NO: 68)
5'-taaagtaactcgagctactaatgatgatgatgatgatggtgtctgcg gtgctcggcgaa-3'

All oligonucleotides set forth above were purchased from Integrated technologies ("IDT", Coralville, Iowa). These oligonucleotides were designed to incorporate a SpeI restriction endonuclease cleavage site upstream of a HindIII restriction endonuclease cleavage site or downstream of an XhoI restriction endonuclease cleavage site, with respect to the edd and eda gene constructs. These restriction endonuclease sites could be used to clone the edd and eda genes into yeast expression vectors p426GPD (ATCC accession number 87361) and p425GPD (ATCC accession number 87359). In addition to incorporating restriction endonuclease cleavage sites, the forward oligonucleotides also incorporate six consecutive A nucleotides (e.g., AAAAAA) immediately upstream of the ATG initiation codon. The six consecutive A nucleotides ensured that there was a conserved ribosome binding sequence for efficient translation initiation in yeast.

PCR amplification of the genes were performed as follows: about 100 ng of the genomic *P. aeruginosa* PAO1 DNA was added to 1×Pfu Ultra II buffer, 0.3 mM dNTPs, 0.3 μmol gene-specific primers (SEQ. ID. NOS: 63-68, and combinations as indicated), and 1 U Pfu Ultra II polymerase (Agilent, La Jolla, Calif.) in a 50 μl reaction mix. This was cycled as follows: 95° C. 10 minutes followed by 30 rounds of 95° C. for 20 seconds, 50° C. (eda amplifications) or 53° C. (edd amplifications) for 30 seconds, and 72° C. for 15 seconds (eda amplifications) or 30 seconds (edd amplifications). A final 5 minute extension reaction at 72° C. also was included. The about 670 bp (eda) or 1830 bp product (edd) was TOPO cloned into the pCR Blunt II TOPO vector (Life Technologies, Carlsbad, Calif.) according to the manufacturer's recommendations.

The nucleotide and amino acid sequences of the *P. aeruginosa* edd and eda genes are given below as SEQ ID NOS. 69-72.

*P. aeruginosa* edd nucleotide sequence: SEQ ID NO:69

```
ATGCACCCTCGTGTGCTCGAAGTCACCCGCCGCATCCAGGCCCGTAGCGC
GGCCACTCGCCAGCGCTACCTCGAGATGGTCCGGGCTGCGGCCAGCAAGG
GGCCGCACCGCGGCACCCTGCCGTGCGGCAACCTCGCCCACGGGGTCGCG
GCCTGTGGCGAAAGCGACAAGCAGACCCTGCGGCTGATGAACCAGGCCAA
CGTGGCCATCGTTTCCGCCTACAACGACATGCTCTCGGCGCACCAGCCGT
TCGAGCGCTTTCCGGGGCTGATCAAGCAGGCGCTGCACGAGATCGGTTCG
GTCGGCCAGTTCGCCGGCGGCGTGCCGGCCATGTGCGACGGGGTGACCCA
GGGCGAGCCGGGCATGGAACTGTCGCTGGCCAGCCGCGACGTGATCGCCA
TGTCCACCGCCATCGCGCTGTCTCACAACATGTTCGATGCAGCGCTGTGC
CTGGGTGTTTGCGACAAGATCGTGCCGGGCCTGCTGATCGGCTCGCTGCG
CTTCGGCCACCTGCCCACCGTGTTCGTCCCGGCCGGGCCGATGCCGACCG
GCATCTCCAACAAGGAAAAGGCCGCGGTGCGCCAACTGTTCGCCGAAGGC
AAGGCCACTCGCGAAGAGCTGCTGGCCTCGGAAATGGCCTCCTACCATGC
ACCCGGCACCTGCACCTTCTATGGCACCGCCAATACCAACCAGTTGCTGG
TGGAGGTGATGGGCCTGCACTTGCCCGGTGCCTCCTTCGTCAACCCGAAC
ACCCCCCTGCGCGACGAACTCACCCGCGAAGCGGCACGCCAGGCCAGCCG
GCTGACCCCCGAGAACGGCAACTACGTGCCGATGGCCGAGATCGTCGACG
AGAAGGCCATCGTCAACTCGGTGGTGGCGCTGCTCGCCACCGGCGGCTCG
ACCAACCACACCCTGCACCTGCTGGCGATCGCCCAGGCGGCGGGCATCCA
GTTGACCTGGCAGGACATGTCCGAGCTGTCCCATGTGGTGCCGACCCTGG
CGCGCATCTATCCGAACGGCCAGGCCGACATCAACCACTTCCAGGCGGCC
GGCGGCATGTCCTTCCTGATCCGCCAACTGCTCGACGGCGGGCTGCTTCA
CGAGGACGTACAGACCGTCGCCGGCCCCGGCCTGCGCCGCTACACCCGCG
AGCCGTTCCTCGAGGATGGCCGGCTGGTCTGGCGCGAAGGGCCGGAACGG
AGTCTCGACGAAGCCATCCTGCGTCCGCTGGACAAGCCGTTCTCCGCCGA
AGGCGGCTTGCGCCTGATGGAGGGCAACCTCGGTCGCGGCGTGATGAAGG
TCTCGGCGGTGGCGCCGGAACACCAGGTGGTCGAGGCGCCGGTACGGATC
TTCCACGACCAGGCCAGCCTGGCCGCGGCCTTCAAGGCCGGCGAGCTGGA
GCGCGACCTGGTCGCCGTGGTGCGTTTCCAGGGCCCGCGGGCGAACGGCA
TGCCGGAGCTGCACAAGCTCACGCCGTTCCTCGGGGTCCTGCAGGATCGT
GGCTTCAAGGTGGCGCTGGTCACCGACGGGCGCATGTCCGGGGCGTCGGG
CAAGGTGCCCGCGGCCATCCATGTGAGTCCGGAAGCCATCGCCGGCGGTC
CGCTGGCGCGCCTGCGCGACGGCGACCGGGTGCGGGTGGATGGGGTGAAC
GGCGAGTTGCGGGTGCTGGTCGACGACGCCGAATGGCAGGCGCGCAGCCT
GGAGCCGGCGCCGCAGGACGGCAATCTCGGTTGCGGCCGCGAGCTGTTCG
CCTTCATGCGCAACGCCATGAGCAGCGCGGAAGAGGGCGCCTGCAGCTTT
ACCGAGAGCCTCAACGGCTGGCGCTAGTAG
```

*P. aeruginosa* edd amino sequence: SEQ ID NO:70

```
MHPRVLEVTRRIQARSAATRQRYLEMVRAAASKGPHRGTLPCGNLAHGVA
ACGESDKQTLRLMNQANVAIVSAYNDMLSAHQPFERFPGLIKQALHEIGS
VGQFAGGVPAMCDGVTQGEPGMELSLASRDVIAMSTAIALSHNMFDAALC
LGVCDKIVPGLLIGSLRFGHLPTVFVPAGPMPTGISNKEKAAVRQLFAEG
KATREELLASEMASYHAPGTCTFYGTANTNQLLVEVMGLHLPGASFVNPN
TPLRDELTREAARQASRLTPENGNYVPMAEIVDEKAIVNSVVALLATGGS
TNHTLHLLAIAQAAGIQLTWQDMSELSHVVPTLARIYPNGQADINHFQAA
GGMSFLIRQLLDGGLLHEDVQTVAGPGLRRYTREPFLEDGRLVWREGPER
SLDEAILRPLDKPFSAEGGLRLMEGNLGRGVMKVSAVAPEHQVVEAPVRI
FHDQASLAAAFKAGELERDLVAVVRFQGPRANGMPELHKLTPFLGVLQDR
GFKVALVTDGRMSGASGKVPAAIHVSPEAIAGGPLARLRDGDRVRVDGVN
GELRVLVDDAEWQARSLEPAPQDGNLGCGRELFAFMRNAMSSAEEGACSF
TESLNGWR
```

*P. aeruginosa* eda nucleotide sequence: SEQ ID NO:71

```
ATGCACAACCTTGAACAGAAGACCGCCCGCATCGACACGCTGTGCCGGGA
GGCGCGCATCCTCCCGGTGATCACCATCGACCGCGAGGCGGACATCCTGC
CGATGGCCGATGCCCTCGCCGCCGGCGGCCTGACCGCCCTGGAGATCAC
CCTGCGCACGGCGCACGGGCTGACCGCCATCCGGCGCCTCAGCGAGGAG
CGCCCGCACCTGCGCATCGGCGCCGGCACCGTGCTCGACCCGCGGACCT
TCGCCGCCGCGGAAAAGGCCGGGGCGAGCTTCGTGGTCACCCCGGGTTG
CACCGACGAGTTGCTGCGCTTCGCCCTGGACAGCGAAGTCCCGCTGTTGC
CCGGCGTGGCCAGCGCTTCCGAGATCATGCTCGCCTACCGCCATGGCTA
CCGCCGCTTCAAGCTGTTTCCCGCCGAAGTCAGCGGCGGCCCGGCGGCG
CTGAAGGCGTTCTCGGGACCATTCCCCGATATCCGCTTCTGCCCCACCGG
AGGCGTCAGCCTGAACAATCTCGCCGACTACCTGGCGGTACCCAACGTGA
TGTGCGTCGGCGGCACCTGGATGCTGCCCAAGGCCGTGGTCGACCGCGGC
GACTGGGCCCAGGTCGAGCGCCTCAGCCGCGAAGCCCTGGAGCGCTTCGC
CGAGCACCGCAGACACTAATAG
```

*P. aeruginosa* eda amino sequence: SEQ ID NO:72

```
MHNLEQKTARIDTLCREARILPVITIDREADILPMADALAAGGLTALEIT
LRTAHGLTAIRRLSEERPHLRIGAGTVLDPRTFAAAEKAGASFVVTP
GCTDELLRFALDSEVPLLPGVASASEIMLAYRHGYRRFKLFPAEVS
GGPAALKAFSGPFPDIRFCPTGGVSLNNLADYLAVPNVMCVGGTW
MLPKAVVDRGDWAQVERLSREALERFAEHRRH
```

Cloning of PAO1 edd and eda Genes into Yeast Expression Vectors

Following sequence confirmation (GeneWiz), the about 670 bp SpeI-XhoI eda and about 1830 bp SpeI-HindIII edd fragments were cloned into the corresponding restriction sites in plasmids p425GPD and p426GPD vectors (Mumberg et al., 1995, Gene 156: 119-122; obtained from ATCC #87361;

PubMed: 7737504), respectively. Briefly, about 50 ng of SpeI-XhoI-digested p425GPD vector was ligated to about 50 ng of SpeI/XhoI-restricted eda fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin. Similarly, about 50 ng of SpeI-HindIII-digested p426GPD vector was ligated to about 42 ng of SpeI/HindIII-restricted edd fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin.

A haploid *Saccharomyces cerevisiae* strain (BY4742; ATCC catalog number 201389) was cultured in YPD media (10 g Yeast Extract, 20 g Bacto-Peptone, 20 g Glucose, 1 L total) at about 30° C. Separate aliquots of these cultured cells were transformed with a plasmid construct(s) containing the eda gene alone, the eda and edd genes, or with vector alone. Transformation was accomplished using the Zymo frozen yeast transformation kit (Catalog number T2001; Zymo Research Corp., Orange, Calif.). To 50 µl of cells was added approximately 0.5-1 µg plasmid DNA and the cells were cultured on SC drop out media with glucose minus leucine (eda), minus uracil and minus leucine (eda and edd) (about 20 g glucose; about 2.21 g SC drop-out mix [described below], about 6.7 g yeast nitrogen base, all in about 1 L of water); this mixture was cultured for 2-3 days at about 30° C. SC drop-out mix contained the following ingredients (Sigma); all indicated weights are approximate:

| | |
|---|---|
| 0.4 g | Adenine hemisulfate |
| 3.5 g | Arginine |
| 1 g | Glutamic Acid |
| 0.433 g | Histidine |
| 0.4 g | Myo-Inositol |
| 5.2 g | Isoleucine |
| 2.63 g | Leucine |
| 0.9 g | Lysine |
| 1.5 g | Methionine |
| 0.8 g | Phenylalanine |
| 1.1 g | Serine |
| 1.2 g | Threonine |
| 0.8 g | Tryptophan |
| 0.2 g | Tyrosine |
| 0.2 g | Uracil |
| 1.2 g | Valine |

Activity and Western Analyses

Cell lysates of the various EDD and EDA expressing strains were prepared as follows. About 50 to 100 ml of SCD-ura-leu media containing 10 mM MnCl2 was used to culture strains containing the desired plasmid constructs. When cultured aerobically, strains were grown in a 250 ml baffled shaker flask. When grown anaerobically, 400 µl/L Tween-80 (British Drug Houses, Ltd., West Chester, Pa.) plus 0.01 g/L Ergosterol (Alef Aesar, Ward Hill, Mass.) were added and the culture was grown in a 250 ml serum bottle outfitted with a butyl rubber stopper with an aluminum crimp cap. Each strain was inoculated at an initial $OD_{600}$ of about 0.2 and grown to an $OD_{600}$ of about 3-4. Cells were grown at 30° C. at 200 rpm.

Yeast cells were harvested by centrifugation at 1046×g (e.g., approximately 3000 rpm) for 5 minutes at 4° C. The supernatant was discarded and the cells were resuspended in 25 mL cold sterile water. This wash step was repeated once. Washed cell pellets were resuspended in 1 mL sterile water, transferred to 1.5 mL screw cap tube, and centrifuged at 16,100×g (e.g., approximately 13,200 rpm) for 3 minutes at 4° C.

Cell pellets were resuspended in about 800-1000 µl of freshly prepared lysis buffer (50 mM Tris-Cl pH 7.0, 10 mM MgCl2, 1× protease inhibitor cocktail EDTA-free (Thermo Scientific, Waltham, Mass.) and the tube filled with zirconia beads to avoid any headspace in the tube. The tubes were placed in a Mini BeadBeater (Bio Spec Products, Inc., Bartlesville, Okla.) and vortexed twice for 30 seconds at room temperature. The supernatant was transferred to a new 1.5 mL microcentrifuge tube and centrifuged twice to remove cell debris at 16,100×g (e.g., approximately 13,200 rpm) for 10 minutes, at 4° C. Quantification of the lysates was performed using the Coomassie-Plus kit (Thermo Scientific, San Diego, Calif.) as directed by the manufacturer.

| Strain | EDD | EDA |
|---|---|---|
| BF428 | p426GPD (vector control) | p425GPD (vector control) |
| BF604 | *E. coli* native | *E. coli* native |
| BF460 | *E. coli* native with 6-HIS | *E. coli* native with 6-HIS |
| BF591 | PAO1 native | PAO1 native |
| BF568 | PAO1 native with 6-HIS | PAO1 native with 6-HIS |
| BF592 | PAO1 native | *E. coli* native |
| BF603 | *E. coli* native | PAO1 native |

("6-HIS" in above table is disclosed as SEQ ID NO: 138)
About 5-10 µg of total cell extract was used for SDS-gel [NuPage 4-12% Bis-Tris gels (Life Technologies, Carlsbad, CA)] electrophoresis and Western blot analyses.

SDS-PAGE gels were performed according to the manufacturer's recommendation using NuPage MES-SDS Running Buffer at 1× concentration with the addition of NuPage antioxidant into the cathode chamber at a 1× concentration. Novex Sharp Protein Standards (Life Technologies, Carlsbad, Calif.) were used as standards. For Western analysis, gels were transferred onto a nitrocellulose membrane (0.45 micron, Thermo Scientific, San Diego, Calif.) using Western blotting filter paper (Thermo Scientific) using a Bio-Rad Mini Trans-Blot Cell (BioRad, Hercules, Calif.) system for approximately 90 minutes at 40V. Following transfer, the membrane was washed in 1×PBS (EMD, San Diego, Calif.), 0.05% Tween-20 (Fisher Scientific, Fairlawn, N.J.) for 2-5 minutes with gentle shaking. The membrane was blocked in 3% BSA dissolved in 1×PBS and 0.05% Tween-20 at room temperature for about 2 hours with gentle shaking. The membrane was washed once in 1×PBS and 0.05% Tween-20 for about 5 minutes with gentle shaking. The membrane was then incubated at room temperature with the 1:5000 dilution of primary antibody (Ms mAB to 6×His Tag (SEQ ID NO: 138), AbCam, Cambridge, Mass.) in 0.3% BSA (Fraction V, EMD, San Diego, Calif.) dissolved in 1×PBS and 0.05% Tween-20 with gentle shaking.

Incubation was allowed to proceed for about 1 hour with gentle shaking. The membrane was then washed three times for 5 minutes each with 1×PBS and 0.05% Tween-20 with gentle shaking. The secondary antibody [Dnk pAb to Ms IgG (HRP), AbCam, Cambridge, Mass.] was used at 1:15000 dilution in 0.3% BSA and allowed to incubate for about 90 minutes at room temperature with gentle shaking. The membrane was washed three times for about 5 minutes using 1×PBS and 0.05% Tween-20 with gentle shaking. The membrane incubated with 5 ml of Supersignal West Pico Chemiluminescent substrate (Thermo Scientific, San Diego, Calif.) for 1 minute and then was exposed to a phosphorimager (Bio-Rad Universal Hood II, Bio-Rad, Hercules, Calif.) for about 10-100 seconds.

The results of the Western blots, shown in FIGS. 13A and 13B. Included in the expression data are engineered and/or optimized versions of certain eda and edd genes. The genes were modified to include a C-terminal HIS tag to facilitate purification. The two letters refer to the EDD and EDA source, respectively. P is from *P. aeruginosa*, PAO1, E is from *E. coli*, Z is from *Zymomonas mobilis* ZM4, hot rod is the optimized version of *Zymomonas mobilis*, Harmonized is the codon harmonized version of *Zymomonas mobilis*, V refers to the vector(s). Both total crude extract and the solubilized extract are shown. The results presented in FIGS. 13A and 13B indicate that the PAO1 EDD protein is expressed and soluble in *S. cerevisiae*. The results also demonstrate that the *E. coli* EDA protein is expressed and soluble. It was not clear from these experiments if the PAO1 EDA was soluble in yeast.

Example 18

EDD and EDA Activity Assays

Cell lysates of the various EDD and EDA expressing strains were prepared as follows. About 50 to 100 ml of SCD-ura-leu media containing 10 mM MnCl2 was used. When cultured aerobically, strains were grown in a 250 ml baffled shake flask. When grown anaerobically, 400 µl/L Tween-80 (British Drug Houses, Ltd., West Chester, Pa.) plus 0.01 g/L Ergosterol (Alef Aesar, Ward Hill, Mass.) were added and the culture was grown in a 250 ml serum bottle outfitted with a butyl rubber stopper with an aluminum crimp cap. Each strain was inoculated at an initial $OD_{600}$ of about 0.2 and grown to an $OD_{600}$ of about 3-4. Cells were grown at 30° C. at 200 rpm.

Yeast cells were harvested by centrifugation at 1046×g (3000 rpm) for 5 minutes at 4° C. The supernatant was discarded and the cells were resuspended in 25 mL cold sterile water. This wash step was repeated once. Washed cell pellets were resuspended in 1 mL sterile water, transferred to 1.5 mL screw cap tube, and centrifuged at 16,100×g (13,200 rpm) for 3 minutes at 4° C. Cell pellets were resuspended in about 800-1000 µl of freshly prepared lysis buffer (50 mM Tris-Cl pH 7.0, 10 mM MgCl2, 1× protease inhibitor cocktail EDTA-free (Thermo Scientific, Waltham, Mass.) and the tube filled with zirconia beads to avoid any headspace in the tube. The tubes were placed in a Mini BeadBeater (Bio Spec Products, Inc., Bartlesville, Okla.) and vortexed twice for 30 seconds at room temperature. The supernatant was transferred to a new 1.5 mL microcentrifuge tube and centrifuged twice to remove cell debris at 16,100×g (13,200 rpm) for 10 minutes, at 4° C. Quantification of the lysates was performed using the Coomassie-Plus kit (Thermo Scientific, San Diego, Calif.) as directed by the manufacturer.

About 750 µg of crude extract was assayed using 1× assay buffer (50 mM Tris-Cl pH 7.0, 10 mM MgCl2), 3 U lactate dehydrogenase (5 µg/pL in 50 mM Tris-Cl pH 7.0), and 10 µl 1 mM 6-phosphogluconate dissolved in 50 mM Tris-Cl pH 7.0 were mixed in a reaction of about 400 µl. This reaction mix was transferred to a 1 ml Quartz cuvette and allowed to incubate about 5 minutes at 30° C. To this reaction, 100 µl of 1.5 mM NADH (prepared in 50 mM Tris-Cl pH 7.0) was added, and the change in $Abs_{340nm}$ over the course of 5 minutes at 30° C. was monitored in a Beckman DU-800 spectrophotometer using the Enzyme Mechanism software package (Beckman Coulter, Inc, Brea, Calif.).

The table below presents the relative specific activities for BY4742 strains expressing EDD and EDA from either *P. aeruginosa* (PAO1) or *E. coli* sources. The results presented in the table below indicate that each of the listed combinations of EDD and EDA genes, when expressed in *S. cerevisiae* strain BY4742, confers activity.

| Gene Combination | Km ($M^{-1}$) | Vmax (mmol $min^{-1}$) | Specific Activity (mmol $min^{-1}$ $mg^{-1}$) |
|---|---|---|---|
| EDD-P/EDA-P | $1.04 \times 10^{-3}$ | 0.21930 | 0.3451 |
| EDD-P/EDA-E | $2.06 \times 10^{-3}$ | 0.27280 | 0.3637 |
| EDD-E/EDA-P | $1.43 \times 10^{-3}$ | 0.09264 | 0.1235 |
| EDD-E/EDA-E | $0.839 \times 10^{-3}$ | 0.16270 | 0.2169 |

The data presented above is also presented graphically in FIG. 14. FIG. 14 graphically displays the relative activities of the various EDD/EDA combinations presented in the table above, as measured in assays using 750 micrograms of crude extract. From the height of the PE bar in FIG. 14, and the data presented in the table above, it is evident that the combinations conferring the highest level of activity were the EDD-P/EDA-E (e.g., PE) and EDD-P/EDA-P (e.g., PP) combinations.

Example 19

Improved Ethanol Yield from Yeast Strains Expressing EDD and EDA Constructs

Strains BF428 (vector control), BF591 (EDD-PAO1/EDA-PAO1), BF592 (EDD-PAO1/EDA-*E. coli*), BF603 (EDD-*E. coli*/EDA-PAO1) and BF604 (EDD-*E. coli*/EDA-*E. coli*) were inoculated into 15 ml SCD-ura-leu media containing 400 µl/L Tween-80 (British Drug Houses, Ltd., West Chester, Pa.) plus 0.01 g/L Ergosterol (EMD, San Diego, Calif.) in 20 ml Hungate tubes outfitted with a butyl rubber stopper and sealed with an aluminum crimped cap to prevent oxygen from entering the culture at an initial $OD_{600}$ of 0.5 and grown for about 20 hours. Glucose and ethanol in the culture media were assayed using YSI 2700 BioAnalyzer instruments (world wide web uniform resource locator ysi.com), according to the manufacturer's recommendations at 0 and 20 hours post inoculation. The results of the fermentation of glucose to ethanol are showing graphically in FIG. 15. The results presented in FIG. 15 indicate that the presence of the EDD/EDA combinations in *S. cerevisiae* increase the yield of ethanol produced, when compared to a vector-only control. The EDD/EDA combinations that showed the greatest fermentation efficiency in yeast were EDD-P/EDA-E (e.g., PE) and EDD-E/EDA-P (e.g., EP).

Example 20

Improved Ethanol Yield from Yeast Strains Expressing EDD and EDA from PAO1 in Fermentors A fermentation test of the strain BF591 [BY4742 with plasmids pBF290 (p426GPD-EDD_PAO1) and pBF292 (p425GPD-EDA_PAO1)] was conducted against BF428 (BY4742 p426GPD/p425GPD) control strain in 700 ml w.v. Multifors multiplexed fermentors. The fermentation medium was SC-Ura-Leu with about 2% glucose. Vessels were inoculated with about a 6.25% inoculum from overnight cultures grown in about 50 ml SC-Ura-Leu with about 2% glucose.

The cultures were grown aerobically at about 30° C. with about 250 rpm agitation, 1 vvm sparge of process air, (21% O2). The pH was controlled at around 5.0 with 0.25 N NaOH. Once glucose concentrations dropped below 0.5 g/L the fermentation was switched to anaerobic conditions. Before changing to anaerobic conditions, samples were taken to measure glucose concentrations and biomass by $OD_{600}$ as reported in Table B. Ethanol and glucose concentrations in the fermentation broth were monitored using YSI 2700 BioAnalyzer instruments.

The table below presents the elapsed fermentation time (EFT), the biomass and glucose at the start of anaerobic fermentation in a 400 ml fermentor. The edd and eda combinations carried by the strains are described above.

| Strain | EFT (hrs) | $OD_{600\,nm}$ | Glucose (g/L) |
|---|---|---|---|
| BF591 | 32 | 4.50 | .047 |
| BF428 | 27 | 4.81 | .062 |

At the beginning of the anaerobic portion of the fermentation, a bolus of 20 g/L glucose plus 3.35 g/L of yeast nitrogen base without amino acids was added to the fermentors. In addition, 4 ml/L of 2.5 g/L ergosterol in ethanol, 0.4 ml/L Tween 80, and 0.01% AF-204 were added to each fermentor. Oxygen was purged with 100% N2 sparged at about 1 vvm until pO2 was below 1%.

Samples were taken every 2 to 7 hours and measured for ethanol and glucose concentrations and $OD_{600}$. The fermentation was harvested when the glucose concentration was below 0.05 g/L, at 50 hours elapsed fermentation time (EFT). Ethanol and glucose concentrations and $OD_{600}$ of the final sample are reported in the table below.

| Strain | $OD_{600\,nm}$ | Ethanol (g/L) | Glucose (g/L) |
|---|---|---|---|
| BF591 | 5.6 | 17.1 | .04 |
| BF428 | 5.6 | 15.8 | 0 |

The data presented in the table above also is presented graphically in FIGS. 16A and 16B. FIG. 16A presents the fermentation data from strain BF428 (BY4742 with vector controls) and FIG. 16B presents the fermentation data from strain BF591 (BY4742 with EDD-PAO1/EDA-PAO1). Fermentation profiles for strains BF 428 and BF 591, grown on 2% dextrose, were calculated and are presented in the table below.

| Strain | Yx/s | Yp/s | Yp/x | Qp | qp |
|---|---|---|---|---|---|
| BF428 | 0.24 | 0.40 | 7.19 | 0.02 | 0.05 |
| BF591 | 0.23 | 0.43 | 7.44 | 0.02 | 0.07 |

Yx/s = OD/g glucose
Yp/s = q ethanol/g glucose
Yp/x = g ethanol/OD
Qp = g ethanol/Lh$^{-1}$
qp = g ethanol/ODh$^{-1}$ The results from the fermentation show that the BF591 has a higher ethanol yield (triangles, compare FIG. 16A and FIG. 16B) than the control BF428 strain. The calculated yield of ethanol was also determined to be higher in the engineered BF591 strain (0.43 g ethanol/g glucose) than that of the BF428 control strain (0.40 g ethanol/g glucose).

Example 21

Improved Ethanol Yield in a Tal1 Strain of *S. cerevisiae* Expressing EDD and EDA from PAO1

To generate BY4741 and BY4742 tal1 mutant strains, the following procedure was used:
Oligonucleotides (SEQ ID NO: 337)
350 - 5'-TAAAACGACGGCCAGTGAAT-3'

(SEQ ID NO: 338)
351 - 5'-TGCAGGTCGACTCTAGAGGAT-3'

(SEQ ID NO: 339)
352 - 5'-GTGTGCGTGTATGTGTACACCTGTATTTAATTTCCTTAC

TCGCGGGTTTTTCTAAAACGACGGCCAGTGAAT-3'

(SEQ ID NO: 340)
353 - 5'-TGTACCAGTCTAGAATTCTACCAACAAATGGGGAAAT

CAAAGTAACTTGGGCTGCAGGTCGACTCTAGAGGA-3'

All oligonucleotides set forth above were purchased from Integrated Technologies ("IDT", Coralville, Iowa). PCR amplification of the genes were performed as follows: about 50 ng of the pBFU-719 DNA (e.g., plasmid with unique 200-mer sequence) was added to 1×Pfu Ultra II buffer, 0.3 mM dNTPs, 0.3 µmol gene-specific primers (#350/#351 in the first round), and 1 U Pfu Ultra II polymerase (Agilent, La Jolla, Calif.) in a 50 µl reaction mix. The reaction mixture was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. A second round of PCR amplification was done using 50 ng of the first round PCR amplification with 1×Pfu Ultra 11 buffer, 0.3 mM dNTPs, 0.3 µmol gene-specific primers (#352/#353 in the second round), and 1 U Pfu Ultra II polymerase (Agilent, La Jolla, Calif.) in a 50 µl reaction mix. The second reaction mixture was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. The final PCR product was purified using the Zymo Research DNA Clean & Concentrator-25 kit (Zymo Research, Orange, Calif.).

Transformation was accomplished by a high-efficiency competency method. A 5 ml culture of the BY4742 or BY4741 strain was grown overnight at about 30° C. with shaking at about 200 rpm. A suitable amount of this overnight culture was added to 60 ml of YPD media to obtain an initial OD600 of about 0.2 (approximately 2×10$^6$ cells/ml). The cells were allowed to grow at 30° C. with agitation (about 200 rpm) until the $OD_{600}$ was about 1. The cells were then centrifuged at 3000 rpm for 5 min, washed with 10 ml sterile water and re-centrifuged. The cell pellet was resuspended in 1 ml sterile water, transferred to a 1.5 ml sterile microcentrifuge tube and spun down at 4000×g for about 5 minutes. This cell pellet was resuspended in 1 ml sterile 1×TE/LiOAC solution (10 mM Tris-HCl, 1 mM EDTA, 100 mM LiOAc, pH7.5) and re-centrifuged at about 4000×g for about 5 minutes. The cell pellet was resuspended in 0.25 ml 1×TE/LiOAc solution. For the transformation, 50 µl of these cells were aliquoted to a 1.5 ml microcentrifuge tube and about 1 µg purified PCR product and 5 µl of salmon sperm DNA that had been previously boiled for about 5 minutes and placed on ice. 300 µl of a sterile PEG solution was then added (40% PEG 3500, 10 mM Tris-HCl, 1 mM EDTA, 100 mM LiOAc, pH7.5). This mixture was allowed to incubate at 30° C. for about one hour with gentle mixing every 15 minutes. About 40 µl DMSO (Sigma, St. Louis, Mo.) was added to the incubating mixture, and the mixture heat shocked at about 42° C. for about 15 minutes. The cells were pelleted in a microcentrifuge at 13000 rpm for about 30 seconds and the supernatant removed. The cells were resuspended in 1 ml 1×TE (10 mM Tris-HCl, 1 mM EDTA, pH 7.5), centrifuged at 13000 rpm for about 30 seconds and resuspended in 1 ml 1×TE. About 100-200 µl of cells were plated onto SCD-URA media, as described above, and allowed to grow at about 30° C. for about 3 days. After 3 days, transformed colonies were streaked for single colonies on SCD-URA plates and allowed to grow at about 30° C. for about 3 days. From these plates, single colonies were streaked onto SCD agar plates (20 g/L agar in SCD media) containing 1 g/L 5-FOA (Research Products International Corp, Mt. Prospect, Ill.), and also inoculated into YPD liquid broth. The plates were allowed to grow at about 30° C. for about 4 days and the liquid culture was grown overnight at about 30° C. with agitation of about 200 rpm.

To confirm that integration of the construct was correct, genomic DNA was prepared from the YPD overnight cultures. Briefly, the yeast cells were pelleted by centrifugation at room temperature for 5 minutes at approximately 3000 rpm. The cell pellet was resuspended in 200 µl of breaking buffer (2% Triton X-100, 1% SDS, 100 mM NaCl, 10 mM Tris pH8, 1 mM EDTA) and placed into a 1.5 ml microcentrifuge tube containing about 200 µl glass beads and about 200 µl of phenol:chloroform:isoamyl alcohol (Ambion, Austin, Tex.). The mixture was vortexed for about 2 to 5 minutes at room temperature. About 200 µl of sterile water was then added and the mixture vortexed again. The mixture was centrifuged for about 10 minutes at about 13000 rpm and the aqueous layer transferred to a new microcentrifuge tube. About 1/10th of the aqueous layers volume of 3M NaOAc ((British Drug Houses, Ltd., West Chester, Pa.) was added to the aqueous layer and 2.5× the total volume of the mixture of ethanol was added and mixed well. The genomic DNA was then precipitated by placing the tubes at −80° C. for at least one hour (or in a dry ice/ethanol bath for about 30 minutes). The tubes were then centrifuged at about 13000 rpm for 5 minutes at about 4° C. to pellet the DNA. The DNA pellet was then washed two times or more times with about 200 µl of 70% ethanol and re-centrifuged. The DNA pellet was dried using vacuum assisted air drying and resuspended in about 50 to 200 µl 1×TE.

The genomic DNA isolated as described above was used in a PCR amplification reaction consisting of about 50 ng of the genomic DNA was added to 1×Pfu Ultra II buffer, 0.3 mM dNTPs, 0.3 µmol gene-specific primers (#276/#277), and 1 U Pfu Ultra II polymerase (Agilent, La Jolla, Calif.) in a 50 µl reaction mix. The reaction mix was cycled as follows: 95° C. 10 minutes followed by 30 rounds of 95° C. for 20 seconds, 60° C. for 30 seconds, and 72° C. for 45 seconds. A final 5 minute extension reaction at 72° C. was also included. A second round of PCR amplification was done using 50 ng of the first round PCR amplification with 1×Pfu Ultra II buffer, 0.3 mM dNTPs, 0.3 µmol gene-specific primers (#352/#353 in the second round), and 1 U Pfu Ultra II polymerase (Agilent, La Jolla, Calif.) in a 50 µl reaction mix. The second mixture was cycled as follows: 95° C. 10 minutes followed by 30 rounds of 95° C. for 20 seconds, 55° C. for 30 seconds, and 72° C. for about 30 seconds. A final 5 minute extension reaction at 72° C. was also included.

Positive colonies from the screen in YPD that had a PCR product of about 1600 bp indicating the insertion of the integration construct in the TAL1 locus, and that grew on the plates containing 5-FOA were grown overnight in YPD at about 30° C. with agitation of about 200 rpm. Genomic DNA was prepared as above and checked by PCR amplification using primers #276 and #277 (described below). Positive clones were identified which had a PCR product of 359 bp indicating the deletion of the tal1 locus and the remaining portion of the 200-mer tag. The strain carrying the correct traits was labeled as BF716. The BY4741 version was labeled as BF717.

Oligonucleotides

```
                                          (SEQ ID NO: 341)
#276 - 5'-GTCGACTGGAAATCTGGAAGGTTGGT-3'

(SEQ ID NO: 342)
#277 - 5'-GTCGACGCTTTGCTGCAAGGATTCAT-3'
```

The BY4742 tal1 strain was then made competent using the high efficiency competent method as described above. About 500 ng of plasmids pBF290 and pBF292 or with plasmids p426GPD and p425GPD were used to transform the BY4742 tal1 strain. The final transformation mixture was plated onto SCD-ura-leu plates and grown at about 30° C. for about 3 days. Strain BF716 (BY4742 tal1) with p426GPD/p425GPD was labeled as BF738. Strain BF716 with pBF290/pBF292 was labeled as BF741.

A fermentation test of the BF738 was conducted against BF741 in a 400 ml multiplexed fermentor. The fermentation medium utilized was SC -Ura -Leu with 2% glucose. Cultures were grown overnight in 50 ml SC -Ura -Leu 2% glucose and used to inoculate the fermentors at 4 to 5% inoculum. $OD_{600}$ readings of the inoculum are shown in the table below.

| Strain | $OD_{600\ nm}$ |
|---|---|
| BF741 (tal1 PP) | 3.70 |
| BF738 (tal1 VV) | 3.80 |

The cultures were grown aerobically at about 30° C. with about 250 rpm agitation, 0.5 vvm sparge of process air, 21% $O_2$. pH was controlled at 5.0 with 1N NaOH. Glucose concentrations in the fermentation broth were monitored by YSI 2700 BioAnalyzers during aerobic fermentation. Once glucose was depleted the fermentation was switched to anaerobic conditions. Before changing to anaerobic conditions samples were taken to measure glucose usage. Biomass was measured by monitoring the optical density of the growth medium at 600 nanometers (e.g., $OD_{600}$). EFT at glucose depletion, glucose concentrations and $OD_{600}$ are shown in the table below. The table below reports the amount of biomass in the fermentor and the amount of ethanol produced in grams per liter, after the specified amount of time (EFT), by the respective strains.

| Strain | EFT (hrs) | $OD_{600\ nm}$ | Glucose (g/L) |
|---|---|---|---|
| BF741 (tal1 PP) | 43.5 | 2.50 | 0.045 |
| BF738 (tal1 VV) | 31 | 2.95 | 0.192 |

At the beginning of anaerobic fermentation, about 19 g/L glucose, 3.7 g/L YNB, 4 ml/L of 2.5 g/L ergosterol (in ethanol), 0.4 ml/L Tween 80, and 0.01% AF-204 were added to each fermentor. Oxygen was purged with 100% $N_2$ sparged at 0.25 vvm for the remainder of the fermentation. Samples were taken every 4 to 12 hours and analyzed for ethanol production and glucose utilization using the YSI Bioanalyzers, and amount of biomass by $OD_{600}$. The fermentations were harvested when the glucose bolus was depleted. Anaerobic ethanol produced, anaerobic glucose consumption and $OD_{600}$ of the final sample are shown in the table below.

| Strain | $OD_{600\,nm}$ | Ethanol Produced (g/L) | Glucose Consumed (g/L) |
|---|---|---|---|
| BF741 (tal1 PP) | 3.75 | 8.1 | 18.99 |
| BF738 (tal1 VV) | 3.6 | 6.5 | 18.168 |

The results are also presented graphically in FIGS. 17A and 17B. FIG. 17A illustrates the fermentation data for strain BF738 (BY4742 tal1 with vector controls p426GPD and p425GPD) and FIG. 17B illustrates the fermentation data for strain BF741 (BY4742 tal1 with plasmids pBF290 (EDD-PAO1) and pBF292 (EDA-PAO1). The results presented above and in FIGS. 17A and 17B indicate that strain BF741, which expresses the activities encoded by the eda and edd genes, yields more ethanol than control strain BF738. Strain BF741 produced about 0.43 g ethanol per gram of glucose consumed whereas strain BF738 produced only 0.36 g ethanol per gram of glucose consumed. Fermentation profiles were calculated for strains BF738 and BF741 and are presented below.

| Strain | Yx/s | Yp/s | Yp/x | Qp | qp |
|---|---|---|---|---|---|
| BF738 | 0.198 | 0.358 | 3.76 | 0.371 | 0.103 |
| BF741 | 0.203 | 0.439 | 2.16 | 0.439 | 0.131 |

Yx/s = OD/g glucose,
Yp/s = q ethanol/g glucose,
Yp/x = g ethanol/OD
Qp = g ethanol/Lh$^{-1}$,
qp = g ethanol/ODh$^{-1}$ Example 22

Complementation and Improved Ethanol Yield in a pfk1 Strain of *S. cerevisiae* Expressing the EDA and EDD Genes from *P. aeruginosa*

Strain BF205 (YGR240C/BY4742, ATCC Cat. No. 4015893; PubMed: 10436161) was transformed with plasmids p426GPD and p425GPD or with plasmids pBF290 (p426GPD/EDD-PAO1) and pBF292 (p426GPD/EDA-PAO1), generating strains BF740 (vector controls) and BF743, respectively. Transformation was accomplished by a high-efficiency competency method using 500 ng of plasmids p426GPD and p425GPD or plasmids pBF290 and pBF292. Transformants were plated onto SCD-ura-leu agar plates and grown at about 30° C. for about 3 days. The final strains were named BF740 (BY4742 pfk1 with plasmids p426GPD and p425GPD) and BF743 (BY4742-pfk1, pBF290/pBF292).

A fermentation test of the control strain BF740 (BY4742 pfk1 with plasmids p426GPD and p425GPD) was conducted against BF743 (BY4742-pfk1, pBF290/pBF292) in 400 ml w.v. Multifors multiplexed fermentors. The fermentation medium was SC-Ura-Leu with 2% glucose. Vessels were inoculated with about a 10% inoculum from overnight cultures grown in about 50 ml SC-Ura-Leu with about 2% glucose and normalized to 0.5 $OD_{600}$. The actual inoculated ODs for the fermentations are shown in the table below.

| Strain | $OD_{600\,nm}$ |
|---|---|
| BF740 (pfk1 VV) | 0.571 |
| BF743 (pfk1 PP) | 0.535 |

The cultures were grown aerobically at about 30° C. with about 250 rpm agitation, 1 vvm sparge of process air, (21% $O_2$). The pH was controlled at around 5.0 with 0.25 N NaOH. Once glucose concentrations dropped below 0.5 g/L the fermentation was switched to anaerobic conditions. Before changing to anaerobic conditions, samples were taken to measure glucose concentrations and biomass by $OD_{600}$ as shown in the table below. The table below shows the beginning cell biomass and glucose concentration (in grams per liter of nutrient broth). Ethanol and glucose concentrations in the fermentation broth were monitored using a YSI 2700 BioAnalyzer.

| Strain | $OD_{600\,nm}$ | Ethanol (g/L) | Glucose (g/L) |
|---|---|---|---|
| BF740 | 5.94 | 5.67 | 0.033 |
| BF743 | 5.82 | 5.82 | 0.034 |

At the beginning of the anaerobic portion of the fermentation, a bolus of about 18 g/L glucose plus about 4 ml/L of 2.5 g/L ergosterol in Ethanol, 0.4 ml/L Tween 80, and 0.01% AF-204 were added to each fermentor. Oxygen was purged with 100% $N_2$ sparged at about 1 vvm until $pO_2$ was below 1%. Samples were taken every 4 to 8 hours and measured for ethanol and glucose concentrations and biomass ($OD_{600}$). The fermentation was harvested when the glucose concentration was below 0.05 g/L, at about 42 hours elapsed fermentation time (EFT). Ethanol and glucose concentrations and $OD_{600}$ of the final sample are shown in the table below.

| Strain | $OD_{600\,nm}$ | Ethanol (g/L) | Glucose (g/L) |
|---|---|---|---|
| BF740 | 6.4 | 5.07 | 14.6 |
| BF743 | 5.09 | 13.37 | 0.042 |

The results also are present graphically in FIGS. 18A and 18B. The results presented in FIG. 18A illustrate the fermentation data for strain BF740 grown on 2% dextrose and the results presented in FIG. 18B illustrate the fermentation data for strain BF743 grown on 2% dextrose. The results indicate that the BY4742 pfk1 mutant strain, BF740 cannot utilize glucose nor produce ethanol under anaerobic conditions. However, the engineered strain BF743 is capable of both utilizing glucose and producing ethanol under anaerobic conditions. Strain BF743 has a yield of about 0.39 g ethanol per gram of glucose consumed versus no yield in the control strain BF740. The fermentation profile for strains BF740 and BF743 are presented in the table below.

| Strain | Yx/s | Yp/s | Yp/x | Qp | qp |
|---|---|---|---|---|---|
| BF740 | 2.133 | −0.700 | −0.328 | −0.022 | −0.003 |
| BF743 | 0.264 | 0.390 | 1.483 | 0.178 | 0.035 |

Yx/s = OD/g glucose,
Yp/s = q ethanol/g glucose,
Yp/x = g ethanol/OD
Qp = g ethanol/Lh$^{-1}$,
qp = g ethanol/ODh$^{-1}$ Example 23

EDD and EDA Activities From Other Sources

The EDD and EDA genes also have been isolated from additional sources and tested for the ability to direct fermentation in yeast. The additional EDD and EDA genes have been isolated from *Shewanella oneidensis, Gluconobacter oxydans*, and *Ruminococcus flavefaciens*. Genomic DNA was purchased from ATCC for both *S. oneidensis* (Cat. No. 700550D) and *G. oxydans* (621 HD-5). *R. flavefaciens*, strain C94 (NCDO 2213) was also purchased from ATCC (Cat. No. 19208). To prepare genomic DNA, *R. flavefaciens* was grown in cooked meat media (Becton Dickinson, Franklin Lakes, N.J. USA) overnight at 37° C. and genomic DNA was isolated using a Qiagen DNeasy Blood and Tissue kit according to the manufacture's protocol. The eda and edd genes were PCR amplified from the corresponding genomic DNA using the following sets of PCR oligonucleotides. The nucleotide and amino acid sequences of eda and edd genes PCR amplified using the following sets of PCR oligonucleotide primers, also is given below.

The *S. oneidensis* edd gene:

```
                                     (SEQ. ID. NO: 73)
5'-GTTCACTGCactagtaaaaaaATGCACTCAGTCGTTCAATCTG-3'

(SEQ. ID. NO: 74)
5'-CTTCGAGATCTCGAGTTAGTAAAGTTCATCGATGGC-3'
```

The *S. oneidensis* eda gene:

```
                                     (SEQ. ID. NO: 75)
5'-GTTCACTGCactagtaaaaaaATGCTTGAGAATAACTGGTC-3'

(SEQ. ID. NO: 76)
5'-CTTCGAGATCTCGAGTTAAAGTCCGCCAATCGCCTC-3'
```

The *G. oxydans* edd gene:

```
                                     (SEQ. ID. NO: 77)
5'-GTTCACTGCactagtaaaaaaATGTCTCTGAATCCCGTCGTC-3'

(SEQ. ID. NO: 78)
5'-CTTCGAGATCTCGAGTTAGTGAATGTCGTCGCCAAC-3'
```

The *G. oxydans* eda gene:

```
                                     (SEQ. ID. NO: 79)
5'-GTTCACTGCactagtaaaaaaATGATCGATACTGCCAAACTC-3'

(SEQ. ID. NO: 80)
5'-CTTCGAGATCTCGAGTCAGACCGTGAAGAGTGCCGC-3'
```

The *R. flavefaciens* edd gene:

```
                                     (SEQ. ID. NO: 81)
5'-GTTCACTGCactagtaaaaaaATGAGCGATAATTTTTTCTGCG-3'

(SEQ. ID. NO: 82)
5'-CTTCGAGATCTCGAGCTATTTCCTGTTGATGATAGC-3'
```

*S. oneidensis* 6-phosphogluconate dehydratase (edd) (SEQ. ID. NO: 83):

ATGCACTCAGTCGTTCAATCTGTTACTGACAGAATTATTGCCCGTAGCA
AAGCATCTCGTGAAGCATACCTTGCTGCGTTAAACGATGCCCGTAACCA
TGGTGTACACCGAAGTTCCTTAAGTTGCGGTAACTTAGCCCACGGTTTT
GCGGCTTGTAATCCCGATGACAAAAATGCATTGCGTCAATTGACGAAGG
CCAATATTGGGATTATCACCGCATTCAACGATATGTTATCTGCACACCA
ACCCTATGAAACCTATCCTGATTTGCTGAAAAAAGCCTGTCAGGAAGTC
GGTAGTGTTGCGCAGGTGGCTGGCGGTGTTCCCGCCATGTGTGACGGCG
TGACTCAAGGTCAGCCCGGTATGAATTGAGCTTACTGAGCCGTGAAGT
GATTGCGATGGCAACCGCGGTTGGCTTATCACACAATATGTTTGATGGA
GCCTTACTCCTCGGTATTTGCGATAAAATTGTACCGGGTTTACTGATTG
GTGCCTTAAGTTTTGGCCATTTACCTATGTTGTTTGTGCCCGCAGGCCC
AATGAAATCGGGTATTCCTAATAAGGAAAAAGCTCGCATTCGTCAGCAA
TTTGCTCAAGGTAAGGTCGATAGAGCACAACTGCTCGAAGCGGAAGCCC
AGTCTTACCACAGTGCGGGTACTTGTACCTTCTATGGTACCGCTAACTC
AGAACCACTGATGCTCGAAGTGATGGGCTGCAATTGCCGGGTTCATCT
TTTGTGAATCCAGACGATCCACTGCGCGAAGCCTTAAACAAATGGCGG
CCAAGCAGGTTTGTCGTTTAACTGAACTAGGCACTCAATACAGTCCGAT
TGGTGAAGTCGTTAACGAAAAATCGATAGTGAATGGTATTGTTGCATTG
CTCGCGACGGGTGGTTCAACAAACTTAACCATGCACATTGTGGCGGCGG
CCCGTGCTGCAGGTATTATCGTCAACTGGGATGACTTTTCGGAATTATC
CGATGCGGTGCCTTTGCTGGCACGTGTTTATCCAAACGGTCATGCGGAT
ATTAACCATTTCCACGCTGCGGGTGGTATGGCTTTCCTTATCAAAGAAT
TACTCGATGCAGGTTTGCTGCATGAGGATGTCAATACTGTCGCGGGTTA
TGGTCTGCGCCGTTACACCCAAGAGCCTAAACTGCTTGATGGCGAGCTG
CGCTGGGTCGATGGCCCAACAGTGAGTTTAGATACCGAAGTATTAACCT
CTGTGGCAACACCATTCCAAAACAACGGTGGTTTAAAGCTGCTGAAGGG
TAACTTAGGCCGCGCTGTGATTAAAGTGTCTGCCGTTCAGCCACAGCAC
CGTGTGGTGGAAGCGCCCGCAGTGGTGATTGACGATCAAAACAAACTCG
ATGCGTTATTTAAATCCGGCGCATTAGACAGGGATTGTGTGGTGGTGGT
GAAAGGCCAAGGGCCGAAAGCCAACGGTATGCCAGAGCTGCATAAACTA
ACGCCGCTGTTAGGTTCATTGCAGGACAAAGGCTTTAAAGTGGCACTGA
TGACTGATGGTCGTATGTCGGGCGCATCGGGCAAAGTACCTGCGGCGAT
TCATTTAACCCCTGAAGCGATTGATGGCGGGTTAATTGCAAAGGTACAA
GACGGCGATTTAATCCGAGTTGATGCACTGACCGGCGAGCTGAGTTTAT
TAGTCTCTGACACCGAGCTTGCCACCAGAACTGCCACTGAAATTGATTT

```
ACGCCATTCTCGTTATGGCATGGGCGTGAGTTATTTGGAGTACTGCGT

TCAAACTTAAGCAGTCCTGAAACCGGTGCGCGTAGTACTAGCGCCATCG

ATGAACTTTACTAA
```

S. *oneidensis* 6-phosphogluconate dehydratase (edd)-Amino Acid sequence (SEQ. ID. NO: 84):

```
MHSVVQSVTDRIIARSKASREAYLAALNDARNHGVHRSSLSCGNLAHGFA

ACNPDDKNALRQLTKANIGIITAFNDMLSAHQPYETYPDLLKKACQEVGS

VAQVAGGVPAMCDGVTQGQPGMELSLLSREVIAMATAVGLSHNMFDGAL

LLGICDKIVPGLLIGALSFGHLPMLFVPAGPMKSGIPNKEKARIRQQFAQ

GKVDRAQLLEAEAQSYHSAGTCTFYGTANSNQLMLEVMGLQLPGSSF

VNPDDPLREALNKMAAKQVCRLTELGTQYSPIGEVVNEKSIVNGIVALL

ATGGSTNLTMHIVAAARAAGIIVNWDDFSELSDAVPLLARVYPNGHADI

NHFHAAGGMAFLIKELLDAGLLHEDVNTVAGYGLRRYTQEPKLLDGEL

RWVDGPTVSLDTEVLTSVATPFQNNGGLKLLKGNLGRAVIKVSAVQP

QHRVVEAPAVVIDDQNKLDALFKSGALDRDCVVVVKGQGPKANGMP

ELHKLTPLLGSLQDKGFKVALMTDGRMSGASGKVPAAIHLTPEAIDGG

LIAKVQDGDLIRVDALTGELSLLVSDTELATRTATEIDLRHSRYGMGREL

FGVLRSNLSSPETGARSTSAIDELY
```

G. *oxydans* 6-phosphogluconate dehydratase (edd) (SEQ. ID. NO: 85):

```
ATGTCTCTGAATCCCGTCGTCGAGAGCGTGACTGCCCGTATCATCGAGC

GTTCGAAAGTCTCCCGTCGCCGGTATCTCGCCCTGATGGAGCGCAACCG

CGCCAAGGGTGTGCTCCGGCCCAAGCTGGCCTGCGGTAATCTGGCGCAT

GCCATCGCAGCGTCCAGCCCCGACAAGCCGGATCTGATGCGTCCCACCG

GGACCAATATCGGCGTGATCACGACCTATAACGACATGCTCTCGGCGCA

TCAGCCGTATGCCGCTATCCCGAGCAGATCAAGCTGTTCGCCCGTGAA

GTCGGTGCGACGGCCCAGGTTGCAGGCGGCGCACCAGCAATGTGTGATG

GTGTGACGCAGGGGCAGGAGGGCATGGAACTCTCCCTGTTCTCCCGTGA

CGTGATCGCCATGTCCACGGCGGTCGGGCTGAGCCACGGCATGTTTGAG

GGCGTGGCGCTGCTGGGCATCTGTGACAAGATTGTGCCGGGCCTTCTGA

TGGGCGCGCTGCGCTTCGGTCATCTCCCGGCCATGCTGATCCCGGCAGG

GCCAATGCCGTCCGGTCTTCCAAACAAGGAAAAGCAGCGCATCCGCCAG

CTCTATGTGCAGGGCAAGGTCGGGCAGGACGAGCTGATGGAAGCGGAAA

ACGCCTCCTATCACAGCCCGGGCACCTGCACGTTCTATGGCACGGCCAA

TACGAACCAGATGATGGTCGAAATCATGGGTCTGATGATGCCGGACTCG

GCTTTCATCAATCCCAACACGAAGCTGCGTCAGGCAATGACCCGCTCGG

GTATTCACCGTCTGGCCGAAATCGGCCTGAACGGCGAGGATGTGCGCCC

GCTCGCTCATTGCGTAGACGAAAAGGCCATCGTGAATGCGGCGGTCGGG

TTGCTGGCGACGGGTGGTTCGACCAACCATTCGATCCATCTTCCTGCTA

TCGCCCGTGCCGCTGGTATCCTGATCGACTGGGAAGACATCAGCCGCCT
```
```
GTCGTCCGCGGTTCCGCTGATCACCCGTGTTTATCCGAGCGGTTCCGAG

GACGTGAACGCGTTCAACCGCGTGGGTGGTATGCCGACCGTGATCGCCG

AACTGACGCGCGCCGGGATGCTGCACAAGGACATTCTGACGGTCTCTCG

TGGCGGTTTCTCCGATTATGCCCGTCGCGCATCGCTGGAAGGCGATGAG

ATCGTCTACACCCACGCGAAGCCGTCCACGGACACCGATATCCTGCGCG

ATGTGGCTACGCCTTTCCGGCCCGATGGCGGTATGCGCCTGATGACTGG

TAATCTGGGCCGCGCGATCTACAAGAGCAGCGCTATTGCGCCCGAGCAC

CTGACCGTTGAAGCGCCGGCACGGGTCTTCCAGGACCAGCATGACGTCC

TCACGGCCTATCAGAATGGTGAGCTTGAGCGTGATGTTGTCGTGGTCGT

CCGGTTCCAGGGACCGGAAGCCAACGGCATGCCGGAGCTTCACAAGCTG

ACCCCGACTCTGGGCGTGCTTCAGGATCGCGGCTTCAAGGTGGCCCTGC

TGACGGATGGACGCATGTCCGGTGCGAGCGGCAAGGTGCCGGCCGCCAT

TCATGTCGGTCCCGAAGCGCAGGTTGGCGGTCCGATCGCCCGCGTGCGG

GACGGCGACATGATCCGTGTCTGCGCGGTGACGGGACAGATCGAGGCTC

TGGTGGATGCCGCCGAGTGGGAGAGCCGCAAGCCGGTCCCGCCGCCGCT

CCCGGCATTGGGAACGGGCCGCGAACTGTTCGCGCTGATGCGTTCGGTG

CATGATCCGGCCGAGGCTGGCGGATCCGCGATGCTGGCCCAGATGGATC

GCGTGATCGAAGCCGTTGGCGACGACATTCACTAA
```

G. *oxydans* 6-phosphogluconate dehydratase (edd)-Amino Acid sequence (SEQ. ID. NO: 86):

```
MSLNPVVESVTARIIERSKVSRRRYLALMERNRAKGVLRPKLACGNLA

HAIAASSPDKPDLMRPTGTNIGVITTYNDMLSAHQPYGRYPEQIKLFARE

VGATAQVAGGAPAMCDGVTQGQEGMELSLFSRDVIAMSTAVGLSHG

MFEGVALLGICDKIVPGLLMGALRFGHLPAMLIPAGPMPSGLPNKEKQ

RIRQLYVQGKVGQDELMEAENASYHSPGTCTFYGTANTNQMMVEIMG

LMMPDSAFINPNTKLRQAMTRSGIHRLAEIGLNGEDVRPLAHCVDEKA

IVNAAVGLLATGGSTNHSIHLPAIARAAGILIDWEDISRLSSAVPLITRV

YPSGSEDVNAFNRVGGMPTVIAELTRAGMLHKDILTVSRGGFSDYARR

ASLEGDEIVYTHAKPSTDTDILRDVATPFRPDGGMRLMTGNLGRAIYKS

SAIAPEHLTVEAPARVFQDQHDVLTAYQNGELERDVVVVVRFQGPEA

NGMPELHKLTPTLGVLQDRGFKVALLTDGRMSGASGKVPAAIHVGPE

AQVGGPIARVRDGDMIRVCAVTGQIEALVDAAEWESRKPVPPPLPAL

GTGRELFALMRSVHDPAEAGGSAMLAQMDRVIEAVGDDIH
```

R. *flavefaciens* phosphogluconate dehydratase/DHAD (SEQ. ID. NO: 87):

```
ATGAGCGATAATTTTTTCTGCGAGGGTGCGGATAAAGCCCCTCAGCGTT

CACTTTTCAATGCACTGGGCATGACTAAAGAGGAAATGAAGCGTCCCCT

CGTTGGTATCGTTTCTTCCTACAATGAGATCGTTCCCGGCCATATGAAC

ATCGACAAGCTGGTCGAAGCCGTTAAGCTGGGTGTAGCTATGGGCGGCG
```

```
GCACTCCTGTTGTTTTCCCTGCTATCGCTGTATGCGACGGTATCGCTAT

GGGTCACACAGGCATGAAGTACAGCCTTGTTACCCGTGACCTTATTGCC

GATTCTACAGAGTGTATGGCTCTTGCTCATCACTTCGACGCACTGGTAA

TGATACCTAACTGCGACAAGAACGTTCCCGGCCTGCTTATGGCGGCTGC

ACGTATCAATGTTCCTACTGTATTCGTAAGCGGCGGCCCTATGCTTGCA

GGCCATGTAAAGGGTAAGAAGACCTCTCTTTCATCCATGTTCGAGGCTG

TAGGCGCTTACACAGCAGGCAAGATAGACGAGGCTGAACTTGACGAATT

CGAGAACAAGACCTGCCCTACCTGCGGTTCATGTTCGGGTATGTATACC

GCTAACTCCATGAACTGCCTCACTGAGGTACTGGGTATGGGTCTCAGAG

GCAACGGCACTATCCCTGCTGTTTACTCCGAGCGTATCAAGCTTGCAAA

GCAGGCAGGTATGCAGGTTATGGAACTCTACAGAAAGAATATCCGCCCT

CTCGATATCATGACAGAGAAGGCTTTCCAGAACGCTCTCACAGCTGATA

TGGCTCTTGGATGTTCCACAAACAGTATGCTCCATCTCCCTGCTATCGC

CAACGAATGCGGCATAAATATCAACCTTGACATGGCTAACGAGATAAGC

GCCAAGACTCCTAACCTCTGCCATCTTGCACCGGCAGGCCACACCTACA

TGGAAGACCTCAACGAAGCAGGCGGAGTTTATGCAGTTCTCAACGAGCT

GAGCAAAAAGGGACTTATCAACACCGACTGCATGACTGTTACAGGCAAG

ACCGTAGGCGAGAATATCAAGGGCTGCATCAACCGTGACCCTGAGACTA

TCCGTCCTATCGACAACCCATACAGTGAAACAGGCGGAATCGCCGTACT

CAAGGGCAATCTTGCTCCCGACAGATGTGTTGTGAAGAGAAGCGCAGTT

GCTCCCGAAATGCTGGTACACAAAGGCCCTGCAAGAGTATTCGACAGCG

AGGAAGAAGCTATCAAGGTCATCTATGAGGGCGGTATCAAGGCAGGCGA

CGTTGTTGTTATCCGTTACGAAGGCCCTGCAGGCGGCCCCGGCATGAGA

GAAATGCTCTCTCCTACATCAGCTATACAGGGTGCAGGTCTCGGCTCAA

CTGTTGCTCTAATCACTGACGGACGTTTCAGCGGCGCTACCCGTGGTGC

GGCTATCGGACACGTATCCCCCGAAGCTGTAAACGGCGGTACTATCGCA

TATGTCAAGGACGGCGATATTATCTCCATCGACATACCGAATTACTCCA

TCACTCTTGAAGTATCCGACGAGGAGCTTGCAGAGCGCAAAAAGGCAAT

GCCTATCAAGCGCAAGGAGAACATCACAGGCTATCTGAAGCGCTATGCA

CAGCAGGTATCATCCGCAGACAAGGGCGCTATCATCAACAGGAAATAG
```

R. flavefaciens phosphogluconate dehydratase/DHAD-Amino Acid (SEQ. ID. NO: 88):

```
MSDNFFCEGADKAPQRSLFNALGMTKEEMKRPLVGIVSSYNEIVPGHMN

IDKLVEAVKLGVAMGGGTPVVFPAIAVCDGIAMGHTGMKYSLVTRDLIAD

STECMALAHHFDALVMIPNCDKNVPGLLMAAARINVPTVFVSGGPMLAG

HVKGKKTSLSSMFEAVGAYTAGKIDEAELDEFENKTCPTCGSCSGMYTAN

SMNCLTEVLGMGLRGNGTIPAVYSERIKLAKQAGMQVMELYRKNIRPLDI

MTEKAFQNALTADMALGCSTNSMLHLPAIANECGININLDMANEISAKTP

NLCHLAPAGHTYMEDLNEAGGVYAVLNELSKKGLINTDCMTVTGKTVGE

NIKGCINRDPETIRPIDNPYSETGGIAVLKGNLAPDRCVVKRSAVAPEML

VHKGPARVFDSEEEAIKVIYEGGIKAGDVVVIRYEGPAGGPGMREMLSP

TSAIQGAGLGSTVALITDGRFSGATRGAAIGHVSPEAVNGGTIAYVKDGD

IISIDIPNYSITLEVSDEELAERKKAMPIKRKENITGYLKRYAQQVSSAD

KGAIINRK
```

Pair wise homology comparisons for various edd proteins are presented in the table below. The comparisons were made using ClustalW software (ClustalW and ClustalX version 2; Larkin M. A., Blackshields G., Brown N. P., Chema R., McGettigan P. A., McWilliam H., Valentin F., Wallace I. M., Wilm A., Lopez R., Thompson J. D., Gibson T. J. and Higgins D. G., Bioinformatics 2007 23(21): 2947-2948). ClustalW is a free alignment tool available at the European Bioinformatics Institute website (e.g., world wide web uniform resource locator ebi.ac.uk, specific ClustalW location is ebi.ac.uk/Tools/clustalw2/index.html). PAO1=*Pseudomonas aeruginosa* PAO1, E.C.=*Eschericia coli*, S.O.=*S. oneidensis*, G.O.=*G. oxydans*, R.F.=*Ruminococcus flavefaciens*.

|       | PAO1 | E.C. | S.O. | G.O. | R.F. |
|-------|------|------|------|------|------|
| PAO1  | 100  | 62   | 62   | 55   | 29   |
| E.C.  | 62   | 100  | 66   | 56   | 30   |
| S.O.  | 62   | 66   | 100  | 56   | 28   |
| G.O.  | 55   | 56   | 56   | 100  | 28   |
| R.F.  | 29   | 30   | 28   | 28   | 100  |

*S. oneidensis* keto-hydroxyglutarate-aldolase/keto-deoxyphosphogluconate aldolase (eda) (SEQ. ID. NO: 89):

```
ATGCTTGAGAATAACTGGTCATTACAACCACAAGATATTTTTAAACGCAG

CCCTATTGTTCCTGTTATGGTGATTAACAAGATTGAACATGCGGTGCCCT

TAGCTAAAGCGCTGGTTGCCGGAGGGATAAGCGTGTTGGAAGTGACATT

ACGCACGCCATGCGCCCTTGAAGCTATCACCAAAATCGCCAAGGAAG

TGCCTGAGGCGCTGGTTGGCGCGGGGACTATTTTAAATGAAGCCCAGCT

TGGACAGGCTATCGCCGCTGGTGCGCAATTTATTATCACTCCAGGTGCG

ACAGTTGAGCTGCTCAAAGCGGGCATGCAAGGACCGGTGCCGTTAATTC

CGGGCGTTGCCAGTATTTCCGAGGTGATGACGGGCATGGCGCTGGGCTA

CACTCACTTTAAATTCTTCCCTGCTGAAGCGTCAGGTGGCGTTGATGCGC

TTAAGGCTTTCTCTGGGCCGTTAGCAGATATCCGCTTCTGCCCAACAGGT

GGAATTACCCCGAGCAGCTATAAAGATTACTTAGCGCTGAAGAATGTCGA

TTGTATTGGTGGCAGCTGGATTGCTCCTACCGATGCGATGGAGCAGGGCG

ATTGGGATCGTATCACTCAGCTGTGTAAAGAGGCGATTGGCGGACTTTAA
```

*S. oneidensis* keto-hydroxyglutarate-aldolase/keto-deoxyphosphogluconate aldolase (eda)-Amino Acid sequence (SEQ. ID. NO: 90):

```
MLENNWSLQPQDIFKRSPIVPVMVINKIEHAVPLAKALVAGGISVLEVTL

RTPCALEAITKIAKEVPEALVGAGTILNEAQLGQAIAAGAQFIITPGATV

ELLKAGMQGPVPLIPGVASISEVMTGMALGYTHFKFFPAEASGGVDAL

KAFSGPLADIRFCPTGGITPSSYKDYLALKNVDCIGGSWIAPTDAMEQG
DWDRITQLCKEAIGGL
```

*G. oxydans* keto-hydroxyglutarate-aldolase/keto-deoxy-phosphogluconate aldolase (eda) (SEQ. ID. NO: 91):

ATGATCGATACTGCCAAACTCGACGCCGTCATGAGCCGTTGTCCGGTCAT
GCCGGTGCTGGTGGTCAATGATGTGGCTCTGGCCCGCCCGATGGCCGAG
GCTCTGGTGGCGGGTGGACTGTCCACGCTGGAAGTCACGCTGCGCACGC
CCTGCGCCCTTGAAGCTATTGAGGAAATGTCGAAAGTACCAGGCGCGCTG
GTCGGTGCCGGTACGGTGCTGAATCCGTCCGACATGGACCGTGCCGTGAA
GGCGGGTGCGCGCTTCATCGTCAGCCCCGGCCTGACCGAGGCGCTGGC
AAAGGCGTCGGTTGAGCATGACGTCCCCTTCCTGCCAGGCGTTGCCAATG
CGGGTGACATCATGCGGGTCTGGATCTGGGTCTGTCACGCTTCAAGTTC
TTCCCGGCTGTGACGAATGGCGGCATTCCCGCGCTCAAGAGCTTGGCCA
GTGTTTTTGGCAGCAATGTCCGTTTCTGCCCCACGGGCGGCATTACGGAA
GAGAGCGCACCGGACTGGCTGGCGCTTCCCTCCGTGGCCTGCGTCGGCGG
ATCCTGGGTGACGGCCGGCACGTTCGATGCGGACAAGGTCCGTCAGCGC
GCCACGGCTGCGGCACTCTTCACGGTCTGA

*G. oxydans* keto-hydroxyglutarate-aldolase/keto-deoxy-phosphogluconate aldolase (eda)-Amino Acid (SEQ. ID. NO: 92):

MIDTAKLDAVMSRCPVMPVLVVNDVALARPMAEALVAGGLSTLEVTLRT
PCALEAIEEMSKVPGALVGAGTVLNPSDMDRAVKAGARFIVSPGLTEALA
KASVEHDVPFLPGVANAGDIMRGLDLGLSRFKFFPAVTNGGIPALKSLAS
VFGSNVRFCPTGGITEESAPDWLALPSVACVGGSWVTAGTFDADKVRQRA
TAAALFTV

Pair wise homology comparisons for various eda proteins are presented in the table below. The comparisons were made using ClustalW software (ClustalW and ClustalX version 2; Larkin M. A., Blackshields G., Brown N. P., Chema R., McGettigan P. A., McWilliam H., Valentin F., Wallace I. M., Wilm A., Lopez R., Thompson J. D., Gibson T. J. and Higgins D. G., Bioinformatics 2007 23(21): 2947-2948). PAO1=*Pseudomonas aeruginosa* PAO1, E.C.=*Eschericia coli*, S.O.=*S. oneidensis*, G.O.=*G. oxydans*, R.F.=*Ruminococcus flavefaciens*.

|      | PAO1 | E.C. | S.O. | G.O. |
| --- | --- | --- | --- | --- |
| PAO1 | 100  | 41   | 44   | 40   |
| E.C. | 41   | 100  | 60   | 46   |
| S.O. | 44   | 60   | 100  | 45   |
| G.O. | 40   | 46   | 45   | 100  |

All oligonucleotides set forth above were purchased from Integrated technologies ("IDT", Coralville, Iowa). These oligonucleotides were designed to incorporate a SpeI restriction endonuclease cleavage site upstream and an XhoI restriction endonuclease cleavage site downstream of the edd and eda gene constructs, such that the sites could be used to clone the genes into yeast expression vectors p426GPD (ATCC accession number 87361) and p425GPD (ATCC accession number 87359). In addition to incorporating restriction endonuclease cleavage sites, the forward oligonucleotides were designed to incorporate six consecutive A nucleotides immediately upstream of the ATG initiation codon.

PCR amplification of the genes were performed as follows: about 100 ng of the genomic DNA was added to 1×Pfu Ultra II buffer, 0.3 mM dNTPs, 0.3 µmol gene-specific primers and 1 U Pfu Ultra II polymerase (Agilent, La Jolla, Calif.) in a 50 µl reaction mix. The reaction mixture was cycled as follows: 95° C. 10 minutes followed by 30 rounds of 95° C. for 20 seconds, 50° C. (eda amplifications) or 53° C. (edd amplifications) for 30 seconds, and 72° C. for 15 seconds (eda amplifications) or 30 seconds (edd amplifications). A final 5 minute extension reaction at 72° C. was also included. Each amplified product was TOPO cloned into the pCR Blunt II TOPO vector (Life Technologies, Carlsbad, Calif.) according to the manufacturer's recommendations and the sequences verified (GeneWiz, La Jolla, Calif.).

Cloning of New edd and eda Genes into Yeast Expression Vectors

Each of the sequence-verified eda and edd fragments were subcloned into the corresponding restriction sites in plasmids p425GPD and p426GPD vectors (ATCC #87361; PubMed: 7737504). Briefly, about 50 ng of SpeI-XhoI-digested p425GPD vector was ligated to about 50 ng of SpeI/XhoI -restricted eda or edd fragment in a 10 µl reaction with 1×T4 DNA ligase buffer and 1 U T4 DNA ligase (Fermentas) overnight at 16° C. About 3 µl of this reaction was used to transform DH5α competent cells (Zymo Research) and plated onto LB agar media containing 100 µg/ml ampicillin. Final constructs were confirmed by restriction endonuclease digests and sequence verification (GeneWiz, La Jolla, Calif.).

In Vivo Assay to Determine Optimal EDD/EDA Combination

To determine the optimal EDD/EDA gene combinations, a yeast strain was developed to enable in vivo gene combination evaluation. Growth on glucose was impaired in this strain by disrupting both copies of phosphofructokinase (PFK), however, the strain could grow normally on galactose due to the presence of a single plasmid copy of the PFK2 gene under the control of a GAL1 promoter. The strain can only grow on glucose if a functional EDD/EDA is present in the cell. The strain was generated using strain BF205 (YGR240C/BY4742, ATCC Cat. No. 4015893; Winzeler E A, et al. Science 285: 901-906, 1999, PubMed: 10436161) as the starting strain.

PFK2 Expressing Plasmid

The plasmid expressing the PFK2 gene under the control of the GAL1 promoter, for use in the in vivo edd/eda gene combination evaluations, was constructed by first isolating the PFK2 gene. Primers JML/89 and JML/95 were used to amplify the PFK2 gene from BY4742 in a PCR reaction containing about 100 ng of the genomic DNA, 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reactions were cycled as follows: 95° C. for 10 minutes followed by 10 rounds of 95° C. for 20 seconds, 55° C. for 20 seconds, and 72° C. for 90 seconds and 25 rounds of 95° C. for 20 seconds, 62° C. for 20 seconds, and 72° C. for 90 seconds. A final 5 minute extension reaction at 72° C. was also included. Each amplified product was TOPO cloned into the pCR Blunt II TOPO vector (Life Technologies, Carlsbad, Calif.) according to the manufacturer's recommendations and sequence verified (GeneWiz, San Diego, Calif.). The sequences of JML/89 and JML/95 are given below.

JML/89

(SEQ ID NO: 343)
ACTAGTATGACTGTTACTACTCCTTTTGTGAATGGTAC

JML/95

(SEQ ID NO: 344)
CTCGAGTTAATCAACTCTCTTTCTTCCAACCAAATGGTC

The primers used were designed to include a unique SpeI restriction site at the 5' end of the gene and a unique XhoI restriction site at the 3' end of the gene. This SpeI-XhoI fragment (approximately 2900 bp) was cloned into the SpeI-XhoI sites of the yeast vector p416GAL (ATCC Cat. No. 87332; Mumberg D, et al., Nucleic Acids Res. 22: 5767-5768, 1994. PubMed: 7838736) in a 10 µl ligation reaction containing about 50 ng of the p416GAL plasmid and about 100 ng of the PFK2 fragment with 1× ligation buffer and 1 U T4 DNA ligase (Fermentas). This ligation reaction was allowed to incubate at room temperature for about one hour and was transformed into competent DH5α (Zymo Research, Orange, Calif.) and plated onto LB plates containing 100 µg/ml ampicillin. The final plasmid was verified by restriction digests and sequence confirmed (GeneWiz, San Diego, Calif.) and was called pBF744. Plasmid pBF744 was transformed in yeast strain BF205 (BY4742 pfk1) using the procedure outlined below. This resulting strain was called BF1477.

1. Inoculate 5mLs YPD with a single yeast colony. Grow O/N at 30° C.
2. Next day: add 50 µl culture to 450 µl fresh YPD, check A660. Add suitable amount of cells to 60 mLs fresh YPD to give an A660=0.2 ($2\times10^6$ cells/mL). Grow to A660=1.0 ($2\times10^7$ cells/mL), approximately 5 hours.
3. Boil a solution of 10 mg/ml salmon sperm DNA for 5 min, then quick chill on ice.
4. Spin down 50 mL cells at 3000 rpm for 5 min, wash in 10 mL sterile water, recentrifuge.
5. Resuspend in 1 mL sterile water. Transfer to 1.5 mL sterile microfuge tube, spin down.
6. Resuspend in 1 mL sterile TE/LiOAC solution. Spin down, resuspend in 0.25 mLs TE/LiOAc ($4\times10^9$ cells).
7. In a 1.5 mL microfuge tube, mix 50 µl yeast cells with 1-5 µg transforming DNA and 5 µl single stranded carrier DNA (boiled salmon sperm DNA).
8. Add 300 µl sterile PEG solution. Mix thoroughly. Incubate at 30° C. for 60 min with gentle mixing every 15 min.
9. Add 40 µl DMSO, mix thoroughly. Heat shock at 42° C. for 15 min.
10. Microfuge cells at 13000 rpm for 30 seconds, remove supernatant. Resuspend in 1 mL 1×TE, microfuge 30 sec. Resuspend in 1 mL 1×TE. Plate 100-200 µl on selective media (SCD-ura).

pfk2 Knockout Cassette

A knockout cassette for the PFK2 gene was constructed by first PCR amplifying about 300 bp of the 5' and 3' flanking regions of the PFK2 gene from S. cerevisiae, strain BY4742 using primers JML/85 and JML/87 and primers JML/86 and JML/88, respectively. These flanking regions were designed such that the 5' flanking region had a HindIII site at its 5' edge and a BamHI site at its 3' end. The 3' flanking region had a BamHI site at its 5' edge and a EcoRI site at its 3' edge. The nucleotide sequence of the PFK2 gene and the primers used for amplification of the PFK2 gene are given below.

S. cerevisiae PFK2 (from genomic sequence) SEW. ID. NO:121

ATGACTGTTACTACTCCTTTTGTGAATGGTACTTCTTATTGTACCGTCA
CTGCATATTCCGTTCAATCTTATAAAGCTGCCATAGATTTTTACACCAA
GTTTTTGTCATTAGAAAACCGCTCTTCTCCAGATGAAAACTCCACTTTA
TTGTCTAACGATTCCATCTCTTTGAAGATCCTTCTACGTCCTGATGAAA
AAATCAATAAAAATGTTGAGGCTCATTTGAAGGAATTGAACAGTATTAC
CAAGACTCAAGACTGGAGATCACATGCCACCCAATCCTTGGTATTTAAC
ACTTCCGACATCTTGGCAGTCAAGGACACTCTAAATGCTATGAACGCTC
CTCTTCAAGGCTACCCAACAGAACTATTTCCAATGCAGTTGTACACTTT
GGACCCATTAGGTAACGTTGTTGGTGTTACTTCTACTAAGAACGCAGTT
TCAACCAAGCCAACTCCACCACCAGCACCAGAAGCTTCTGCTGAGTCTG
GTCTTTCCTCTAAAGTTCACTCTTACACTGATTTGGCTTACCGTATGAA
AACCACCGACACCTATCCATCTCTGCCAAAGCCATTGAACAGGCCTCAA
AAGGCAATTGCCGTCATGACTTCCGGTGGTGATGCTCCAGGTATGAACT
CTAACGTTAGAGCCATCGTGCGTTCCGCTATCTTCAAAGGTTGTCGTGC
CTTTGTTGTCATGGAAGGTTATGAAGGTTTGGTTCGTGGTGGTCCAGAA
TACATCAAGGAATTCCACTGGGAAGACGTCCGTGGTTGGTCTGCTGAAG
GTGGTACCAACATTGGTACTGCCCGTTGTATGGAATTCAAGAAGCGCGA
AGGTAGATTATTGGGTGCCCAACATTTGATTGAGGCCGGTGTCGATGCT
TTGATCGTTTGTGGTGGTGACGGTTCTTTGACTGGTGCTGATCTGTTTA
GGATCAGAATGGCCTTCTTTGATCAGGAATTGTTGAAAACAAACAGAAT
TTCCAACGAACAATACGAAAGAATGAAGCATTTGAATATTTGCGGTACT
GTCGGTTCTATTGATAACGATATGTCCACCACGGATGCTACTATTGGTG
CTTACTCTGCCTTGGACAGAATCTGTAAGGCCATCGATTACGTTGAAGC
CACTGCCAACTCTCACTCAAGAGCTTTCGTTGTTGAAGTTATGGGTAGA
AACTGTGGTTGGTTAGCTTTATTAGCTGGTATCGCCACTTCCGCTGACT
ATATCTTTATTCCAGAGAAGCCAGCCACTTCCAGCGAATGGCAAGATCA
AATGTGTGACATTGTCTCCAAGCACAGATCAAGGGGTAAGAGAACCACC
ATTGTTGTTGTTGCAGAAGGTGCTATCGCTGCTGACTTGACCCCAATTT
CTCCAAGCGACGTCCACAAAGTTCTAGTTGACAGATTAGGTTTGGATAC
AAGAATTACTACCTTAGGTCACGTTCAAAGAGGTGGTACTGCTGTTGCT
TACGACCGTATCTTGGCTACTTTACAAGGTCTTGAGGCCGTTAATGCCG
TTTTGGAATCCACTCCAGACACCCCATCACCATTGATTGCTGTTAACGA
AAACAAATTGTTCGTAAACCATTAATGGAATCCGTCAAGTTGACCAAA
GCAGTTGCAGAAGCCATTCAAGCTAAGGATTTCAAGAGAGCTATGTCTT
TAAGAGACACTGAGTTCATTGAACATTTAAACAATTTCATGGCTATCAA
CTCTGCTGACCACAACGAACCAAAGCTACCAAAGGACAAGAGACTGAAG
ATTGCCATTGTTAATGTCGGTGCTCCAGCTGGTGGTATCAACTCTGCCG
TCTACTCGATGGCTACTTACTGTATGTCCCAAGGTCACAGACCATACGC
TATCTACAATGGTTGGTCTGGTTTGGCAAGACATGAAAGTGTTCGTTCT

-continued

```
TTGAACTGGAAGGATATGTTGGGTTGGCAATCCCGTGGTGGTTCTGAAA

TCGGTACTAACAGAGTCACTCCAGAAGAAGCAGATCTAGGTATGATTGC

TTACTATTTCCAAAAGTACGAATTTGATGGTTTGATCATCGTTGGTGGT

TTCGAAGCTTTTGAATCTTTACATCAATTAGAGAGAGCAAGAGAAAGTT

ATCCAGCTTTCAGAATCCCAATGGTCTTGATACCAGCTACTTTGTCTAA

CAATGTTCCAGGTACTGAATACTCTTTGGGTTCTGATACCGCTTTGAAT

GCTCTAATGGAATACTGTGATGTTGTTAAACAATCCGCTTCTTCAACCA

GAGGTAGAGCCTTCGTTGTCGATTGTCAAGGTGGTAACTCAGGCTATTT

GGCCACTTACGCTTCTTTGGCTGTTGGTGCTCAAGTCTCTTATGTCCCA

GAAGAAGGTATTTCTTTGGAGCAATTGTCCGAGGATATTGAATACTTAG

CTCAATCTTTTGAAAAGGCAGAAGGTAGAGGTAGATTTGGTAAATTGAT

TTTGAAGAGTACAAACGCTTCTAAGGCTTTATCAGCCACTAAATTGGCT

GAAGTTATTACTGCTGAAGCCGATGGCAGATTTGACGCTAAGCCAGCTT

ATCCAGGTCATGTACAACAAGGTGGTTTGCCATCTCCAATTGATAGAAC

AAGAGCCACTAGAATGGCCATTAAAGCTGTCGGCTTCATCAAAGACAAC

CAAGCTGCCATTGCTGAAGCTCGTGCTGCCGAAGAAAACTTCAACGCTG

ATGACAAGACCATTTCTGACACTGCTGCTGTCGTTGGTGTTAAGGGTTC

ACATGTCGTTTACAACTCCATTAGACAATTGTATGACTATGAAACTGAA

GTTTCCATGAGAATGCCAAAGGTCATTCACTGGCAAGCTACCAGACTCA

TTGCTGACCATTTGGTTGGAAGAAAGAGAGTTGATTAA
```

JML/85

(SEQ ID NO: 345)
AAGCTTTTAATTAATATAACGCTATGACGGTAGTTGAATGTTAAAAAC

JML/86

(SEQ ID NO: 346)
GAATTCTTAATTAAAGAGAACAAAGTATTTAACGCACATGTATAAATATTG

JML/87

(SEQ ID NO: 347)
GGATCCGCATGCGGCCGGCCAGCTTTTAATCAAGGAAGTAATAAATAAA
GGAC

JML/88

(SEQ ID NO: 348)
GGATCCGAGCTCGCGGCCGCAGCTTTTGAACAATGAATTTTTTGTTCCT
TTC

The nucleic acid fragments were amplified using the following conditions; about 100 ng of the BY4742 genomic DNA was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 58° C. for 30 seconds, and 72° C. for 20 seconds. A final 5 minute extension reaction at 72° C. was also included. Each amplified product was TOPO cloned into the pCR Blunt II TOPO vector (Life Technologies, Carlsbad, Calif.) according to the manufacturer's recommendations and the sequence of the construct was verified (GeneWiz, San Diego, Calif.). The resulting plasmids were named pBF648 (5' flanking region) and pBF649 (3' flanking region). A three fragment ligation was performed using about 100 ng of the 5' flanking region HindIII-BamHI fragment, about 100 ng of the 3' flanking region BamHI-EcoRI fragment and about 50 ng of pUC19 digested with HindIII and EcoRI in a 5 µl ligation reaction containing 1× ligation buffer and 1 U T4 DNA ligase (Fermentas). This reaction was incubated at room temperature for about one hour. About 2 µl of this reaction mix was used to transform competent DH5α cells (Zymo Research, Orange, Calif.) and plated onto LB agar media containing 100 µg/ml ampicillin. The final construct was confirmed by restriction endonuclease digests and sequence verification (GeneWiz, San Diego, Calif.), resulting in plasmid pBF653.

Lys 2 Gene Cloning

The Lys2 gene was isolated by PCR amplification from pRS317 (ATCC Cat. No. 77157; Sikorski R S, Boeke J D. Methods Enzymol. 194: 302-318, 1991. PubMed: 2005795) using primers JML/93 and JML/94. PCR amplification was performed as follows: about 25 ng of the pRS317 plasmid DNA was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reactions were cycled at: 95° C. 10 minutes followed by 10 rounds of 95° C. for 20 seconds, 55° C. for 30 seconds, and 72° C. for 2 minutes, followed by 25 more rounds of 95° C. for 20 seconds, 62° C. for 30 seconds, and 72° C. for 2 minutes. A final 5 minute extension reaction at 72° C. was also included. The amplified product was TOPO cloned into the pCR Blunt II TOPO vector as described herein, resulting in plasmid pBF656. The nucleotide sequence of Lys2 gene and the primers used for amplification of the Lys2 gene are given below.

JML/93

(SEQ ID NO: 349)
GCGGCCGCAGCTTCGCAAGTATTCATTTTAGACCCATG

JML/94

(SEQ ID NO: 350)
GGCCGGCCGGTACCAATTCCACTTGCAATTACATAAAAAATTCC

Lys 2 (from genomic sequence database), SEQ. ID. NO: 122

```
ATGACTAACGAAAAGGTCTGGATAGAGAAGTTGGATAATCCAACTCTTT

CAGTGTTACCACATGACTTTTTACGCCCACAACAAGAACCTTATACGAA

ACAAGCTACATATTCGTTACAGCTACCTCAGCTCGATGTGCCTCATGAT

AGTTTTTCTAACAAATACGCTGTCGCTTTGAGTGTATGGGCTGCATTGA

TATATAGAGTAACCGGTGACGATGATATTGTTCTTTATATTGCGAATAA

CAAAATCTTAAGATTCAATATTCAACCAACGTGGTCATTTAATGAGCTG

TATTCTACAATTAACAATGAGTTGAACAAGCTCAATTCTATTGAGGCCA

ATTTTTCCTTTGACGAGCTAGCTGAAAAAATTCAAAGTTGCCAAGATCT

GGAAAGGACCCCTCAGTTGTTCCGTTTGGCCTTTTTGGAAAACCAAGAT

TTCAAATTAGACGAGTTCAAGCATCATTTAGTGGACTTTGCTTTGAATT

TTGGATACCAGTAATAATGCGCAGTTTTGAACTTAATTTATAACAGCTT

ACTGTATTCGAATGAAAGAGTAACCATTGTTGCGGACCAATTTACTCAA

TATTTGACTGCTGCGCTAAGCGATCCATCCAATTGCATAACTAAAATCT

CTCTGATCACCGCATCATCCAAGGATAGTTTACCTGATCCAACTAAGAA

CTTGGGCTGGTGCGATTTCGTGGGGTGTATTCACGACATTTTCCAGGAC

AATGCTGAAGCCTTCCCAGAGAGAACCTGTGTTGTGGAGACTCCAACAC

TAAATTCCGACAAGTCCCGTTCTTTCACTTATCGCGACATCAACCGCAC
```

```
TTCTAACATAGTTGCCCATTATTTGATTAAAACAGGTATCAAAAGAGGT
GATGTAGTGATGATCTATTCTTCTAGGGGTGTGGATTTGATGGTATGTG
TGATGGGTGTCTTGAAAGCCGGCGCAACCTTTTCAGTTATCGACCCTGC
ATATCCCCCAGCCAGACAAACCATTTACTTAGGTGTTGCTAAACCACGT
GGGTTGATTGTTATTAGAGCTGCTGGACAATTGGATCAACTAGTAGAAG
ATTACATCAATGATGAATTGGAGATTGTTTCAAGAATCAATTCCATCGC
TATTCAAGAAAATGGTACCATTGAAGGTGGCAAATTGGACAATGGCGAG
GATGTTTTGGCTCCATATGATCACTACAAAGACACCAGAACAGGTGTTG
TAGTTGGACCAGATTCCAACCCAACCCTATCTTTCACATCTGGTTCCGA
AGGTATTCCTAAGGGTGTTCTTGGTAGACATTTTTCCTTGGCTTATTAT
TTCAATTGGATGTCCAAAAGGTTCAACTTAACAGAAAATGATAAATTCA
CAATGCTGAGCGGTATTGCACATGATCCAATTCAAAGAGATATGTTTAC
ACCATTATTTTTAGGTGCCCAATTGTATGTCCCTACTCAAGATGATATT
GGTACACCGGGCCGTTTAGCGGAATGGATGAGTAAGTATGGTTGCACAG
TTACCCATTTAACACCTGCCATGGGTCAATTACTTACTGCCCAAGCTAC
TACACCATTCCCTAAGTTACATCATGCGTTCTTTGTGGGTGACATTTTA
ACAAAACGTGATTGTCTGAGGTTACAAACCTTGGCAGAAAATTGCCGTA
TTGTTAATATGTACGGTACCACTGAAACACAGCGTGCAGTTTCTTATTT
CGAAGTTAAATCAAAAAATGACGATCCAAACTTTTTGAAAAAATTGAAA
GATGTCATGCCTGCTGGTAAAGGTATGTTGAACGTTCAGCTACTAGTTG
TTAACAGGAACGATCGTACTCAAATATGTGGTATTGGCGAAATAGGTGA
GATTTATGTTCGTGCAGGTGGTTTGGCCGAAGGTTATAGAGGATTACCA
GAATTGAATAAAGAAAATTTGTGAACAACTGGTTTGTTGAAAAAGATC
ACTGGAATTATTTGGATAAGGATAATGGTGAACCTTGGAGACAATTCTG
GTTAGGTCCAAGAGATAGATTGTACAGAACGGGTGATTTAGGTCGTTAT
CTACCAAACGGTGACTGTGAATGTTGCGGTAGGGCTGATGATCAAGTTA
AAATTCGTGGGTTCAGAATCGAATTAGGAGAAATAGATACGCACATTTC
CCAACATCCATTGGTAAGAGAAAACATTACTTTAGTTCGCAAAAATGCC
GACAATGAGCCAACATTGATCACATTTATGGTCCCAAGATTTGACAAGC
CAGATGACTTGTCTAAGTTCCAAAGTGATGTTCCAAAGGAGGTTGAAAC
TGACCCTATAGTTAAGGGCTTAATCGGTTACCATCTTTTATCCAAGGAC
ATCAGGACTTTCTTAAAGAAAAGATTGGCTAGCTATGCTATGCCTTCCT
TGATTGTGGTTATGGATAAACTACCATTGAATCCAAATGGTAAAGTTGA
TAAGCCTAAACTTCAATTCCCAACTCCCAAGCAATTAAATTTGGTAGCT
GAAAATACAGTTTCTGAAACTGACGACTCTCAGTTTACCAATGTTGAGC
GCGAGGTTAGAGACTTATGGTTAAGTATATTACCTACCAAGCCAGCATC
TGTATCACCAGATGATTCGTTTTTCGATTTAGGTGGTCATTCTATCTTG
GCTACCAAAATGATTTTTACCTTAAAGAAAAAGCTGCAAGTTGATTTAC
CATTGGGCACAATTTTCAAGTATCCAACGATAAAGGCCTTTGCCGCGGA
AATTGACAGAATTAAATCATCGGGTGGATCATCTCAAGGTGAGGTCGTC

GAAAATGTCACTGCAAATTATGCGGAAGACGCCAAGAAATTGGTTGAGA
CGCTACCAAGTTCGTACCCCTCTCGAGAATATTTTGTTGAACCTAATAG
TGCCGAAGGAAAAACAACAATTAATGTGTTTGTTACCGGTGTCACAGGA
TTTCTGGGCTCCTACATCCTTGCAGATTTGTTAGGACGTTCTCCAAAGA
ACTACAGTTTCAAAGTGTTTGCCCACGTCAGGGCCAAGGATGAAGAAGC
TGCATTTGCAAGATTACAAAAGGCAGGTATCACCTATGGTACTTGGAAC
GAAAAATTTGCCTCAAATATTAAAGTTGTATTAGGCGATTTATCTAAAA
GCCAATTTGGTCTTTCAGATGAGAAGTGGATGGATTTGGCAAACACAGT
TGATATAATTATCCATAATGGTGCGTTAGTTCACTGGGTTTATCCATAT
GCCAAATTGAGGGATCCAAATGTTATTTCAACTATCAATGTTATGAGCT
TAGCCGCCGTCGGCAAGCCAAAGTTCTTTGACTTTGTTTCCTCCACTTC
TACTCTTGACACTGAATACTACTTTAATTTGTCAGATAAACTTGTTAGC
GAAGGGAAGCCAGGCATTTTAGAATCAGACGATTTAATGAACTCTGCAA
GCGGGCTCACTGGTGGATATGGTCAGTCCAAATGGGCTGCTGAGTACAT
CATTAGACGTGCAGGTGAAAGGGGCCTACGTGGGTGTATTGTCAGACCA
GGTTACGTAACAGGTGCCTCTGCCAATGGTTCTTCAAACACAGATGATT
TCTTATTGAGATTTTTGAAAGGTTCAGTCCAATTAGGTAAGATTCCAGA
TATCGAAAATTCCGTGAATATGGTTCCAGTAGATCATGTTGCTCGTGTT
GTTGTTGCTACGTCTTTGAATCCTCCCAAAGAAAATGAATTGGCCGTTG
CTCAAGTAACGGGTCACCCAAGAATATTATTCAAAGACTACTTGTATAC
TTTACACGATTATGGTTACGATGTCGAAATCGAAAGCTATTCTAAATGG
AAGAAATCATTGGAGGCGTCTGTTATTGACAGGAATGAAGAAAATGCGT
TGTATCCTTTGCTACACATGGTCTTAGACAACTTACCTGAAAGTACCAA
AGCTCCGGAACTAGACGATAGGAACGCCGTGGCATCTTTAAAGAAAGAC
ACCGCATGGACAGGTGTTGATTGGTCTAATGGAATAGGTGTTACTCCAG
AAGAGGTTGGTATATATATTGCATTTTTAAACAAGGTTGGATTTTTACC
TCCACCAACTCATAATGACAAACTTCCACTGCCAAGTATAGAACTAACT
CAAGCGCAAATAAGTCTAGTTGCTTCAGGTGCTGGTGCTCGTGGAAGCT
CCGCAGCAGCTTAA
```

The knockout cassette was fully assembled by cloning the NotI-FseI LYS2 fragment from plasmid pBF656 into the NotI-FseI sites located between the 5' and 3' flanking PFK2 regions in plasmid pBF653. About 50 ng of plasmid pBF653 digested with NotI and FseI was ligated to about 100 ng of the NotI-FseI LYS2 fragment from plasmid pBF656 in a 5 μl reaction containing 1× ligation buffer and 1 U T4 DNA ligase (Fermentas) for about 1 hour at room temperature. About 2 μl of this reaction was used to transform competent DH5α (Zymo Research, Orange, Calif.) and plated on 100 μg/ml ampicillin. The structure of the final plasmid, pBF745, was confirmed by restriction enzyme digests. The approximately 5 kbp PacI fragment containing the LYS2 cassette and PFK2 flanking regions was gel extracted using the Zymoclean Gel DNA Recovery Kit (Zymo Research, Orange, Calif.) according to the manufacturer's conditions.

Strain BF1477 was transformed with the about 5 kbp PacI fragment using the method described above (LiOAc/PEG method) generating strain BF1411. Strain BF1411 has the ability to grow on galactose as a carbon source, but cannot grow on glucose. Various combinations of the EDD and EDA constructs can be expressed in this strain and monitored for growth on glucose. Strains which show growth on glucose (or the highest growth rate on glucose) can be further characterized to determine which combination of EDD and EDA genes is present. Using the strain and method described herein, libraries of EDD and EDA genes can be screened for improved activities and activity combinations in a host organism.

Example 24

Single Plasmid System for Industrial Yeast

A single plasmid system expressing EDD and EDA for industrial yeast was constructed as follows: The approximately 2800 bp fragment containing the GPD1 promoter, EDD-PAO1 gene and CYC1 terminator from plasmid pBF291 (p426GPD with EDD-PAO1) was PCR amplified using primers KAS/5'-BamHI-Pgpd and KAS/3'-NdeI-CYCt, described below. About 25 ng of the plasmid DNA was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 55° C. for 30 seconds, and 72° C. for 45 seconds. A final 5 minute extension reaction at 72° C. was also included. The amplified product was TOPO cloned into the pCR Blunt II TOPO vector, as described herein, and the final plasmid was sequence verified and designated, pBF475.

```
KAS/5'-BamHI-Pgpd
                                    (SEQ ID NO: 351)
GGATCCgtttatcattatcaatactcgccatttcaaag KAS/3'-NdeI-CYCt
                                    (SEQ ID NO: 352)
CATATGttgggtaccggccgcaaattaaagccttcgagcg
```

An approximately 1500 bp KANMX4 cassette was PCR amplified from plasmid pBF413 HO-poly-KanMX4-HO (ATCC Cat. No. 87804) using primers KAS/5'-Bam_NdeI-KANMX4 and KAS/3P-Sal_NheI-KANMX4, described below.

```
KAS/5'-Bam_NdeI-KANMX4
                                    (SEQ ID NO: 353)
GGATTCagtcagatCATATGggtaccccgggttaattaaggcgcgccag atctg KAS/3'-Sal_NheI-KANMX4
                                    (SEQ ID NO: 354)
GTCGACaggcctactgtacgGCTAGCgaattcgagctcgttttcgacact ggatggcggc
```

About 25 ng of plasmid pBF413 HO-poly-KanMX4-HO DNA was added to 1×Pfu Ultra II buffer, 0.3 mM dNTPs, 0.3 µmol gene-specific primers and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 55° C. for 30 seconds, and 72° C. for 30 seconds. A final 5 minute extension reaction at 72° C. was also included. The amplified product was TOPO cloned into the pCR Blunt II TOPO vector, as described herein. The resulting plasmid was sequence verified and designated, pBF465.

An approximately 225 bp ADH1 terminator was PCR amplified from the genome of BY4742 using primers KAS/5'-Xba-XhoI-ADHt and KAS/3'-StuI-ADH5. The sequence of primers KAS/5'-Xba-XhoI-ADHt and KAS/3'-StuI-ADH5 is given below.

```
KAS/5'-Xba-XhoI-ADHt
                                    (SEQ ID NO: 355)
tctagaCTCGAGtaataagcgaatttcttatgatttatg KAS/3'-StuI-ADH5
                                    (SEQ ID NO: 356)
aagcttAGGCCTggagcgatttgcaggcatttgc
```

About 100 ng of genomic DNA from BY4742 was added to 1×Pfu Ultra II buffer, 0.3 mM dNTPs, 0.3 µmol gene-specific primers and 1 U Pfu Ultra II polymerase (Agilent, La Jolla, Calif.) in a 50 µl reaction mix. The reaction was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector according to the manufacturer's recommendations and sequence verified. The resulting plasmid was designated pBF437.

The TEF2 promoter was PCR amplified from the genome of BY4742 using primers KAS/5'-Xba-XhoI-ADHt and KAS/3'-StuI-ADH5, described below.

```
KAS/5'-Bam-NheI-Ptef
                                    (SEQ ID NO: 357)
GGATCCgctagcACCGCGAATCCTTACATCACACCC KAS/3'-XbaI-SpeI-Ptef
                                    (SEQ ID NO: 358)
tctagaCTCGAGtaataagcgaatttcttatgatttatg
```

About 100 ng of genomic DNA from BY4742 was added to 1×Pfu Ultra II buffer, 0.3 mM dNTPs, 0.3 µmol gene-specific primers, and 1 U Pfu Ultra II polymerase (Agilent, La Jolla, Calif.) in a 50 µl reaction mix. This was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector (Life Technologies, Carlsbad, Calif.) according to the manufacturer's recommendations and sequence verified (GeneWiz, San Diego, Calif.). The resulting plasmid was called pBF440.

The EDA gene cassettes were constructed as follows: First the TEF2 promoter from the plasmid pBF440 was digested with BamHI and XbaI and was cloned into the BamHI and XbaI sites of pUC19 creating plasmid pBF480. Plasmid pBF480 was then digested with XbaI and HindIII and was ligated to the XbaI-HindIII fragment from plasmid pBF437 containing the ADH1 terminator, creating plasmid pBF521. Plasmid pBF521 was then digested with SpeI and XhoI and then ligated to either SpeI-XhoI fragment containing either the PAO1 eda gene from plasmid pBF292 or the E. coli eda gene from plasmid pBF268. The 2 plasmids generated, depending on the eda gene chosen, were designated pBF523 (e.g., containing the PAO1-eda) and pBF568 (e.g., containing the E. coli-eda), respectively. The approximately 1386 bp TEF-EDA-ADHt cassette from either plasmid pBF 523 or pBF568 was then gel extracted using the NheI-StuI sites.

The final vector was generated by first altering the NdeI site in pUC19 using the mutagenesis primers described below.

```
KAS/SDM-Nde1-pUC18-5
                                           (SEQ ID NO: 359)
gattgtactgagagtgcacaatatgcggtgtgaaatacc KAS/SDM-Nde1-pUC18-3
                                           (SEQ ID NO: 360)
ggtatttcacaccgcatattgtgcactctcagtacaatc
```

About 50 ng of pUC19 plasmid DNA was added to 1×Pfu Ultra II buffer, 0.3 mM dNTPs, 0.3 µmol SDM-specific primers and 1 U Pfu Ultra II polymerase (Agilent, La Jolla, Calif.) in a 50 µl reaction mix. The reaction was cycled at 95° C. for 10 minutes, followed by 15 rounds of 95° C. for 15 seconds, 55° C. for 40 seconds, and 72° C. for 3 minutes. A final 10 minute extension reaction at 72° C. was also included. The PCR reaction mixture was then digested with 30 U of Dpnl for about 2 hours and 5 µl of the digested PCR reaction mixture was used to transform competent DH5α (Zymo Research, Orange, Calif.) and plated onto LB plates containing 100 µg/ml ampicillin. The structure of the final plasmid, pBF421, was confirmed by restriction digests.

An approximately 1359 bp EcoRI fragment containing the 2µ yeast origin cassette was cloned into the EcoRI site of plasmid pBF421 in a 10 µl ligation reaction mixture containing 1× ligation buffer, 50 ng of EcoRI-digested pBF421 80 ng of EcoRI-digested 2p cassette, and 1 U T4 DNA ligase (Fermentas). The reaction was incubated at room temperature for about 2 hours and 3 µl of this was used to transform competent DH5α (Zymo Research, Orange, Calif.). The structure of the resultant plasmid, pBF429, was confirmed by restriction enzyme digests.

Plasmid pBF429 was then digested with BamHI and SalI and ligated to the BamHI-SalI KANMX4 cassette described above. The resultant plasmid, designated pBF515, was digested with BamHI and NdeI and ligated to the BamHI-NdeI fragment containing the 2802 bp GPD-EDD-CYCt fragment from pBF475. The resulting plasmid, designated pBF522, was digested with NheI-StuI and was ligated to the 1386 bp NheI-StuI TEF-EDA-ADHt fragment from plasmids pBF523 or pBF568,creating final plasmids pBF524 and pBF612.

Expression levels of each of the single plasmid eda/edd expression system vectors was assayed and compared against the original eda/edd two plasmid expression system vectors. The results, presented in FIG. 19, graphically illustrate edd/eda coupled assay kinetics for the single and two plasmid systems. The kinetics graphs for both expression systems show substantially similar enzyme kinetics over the major of the time course.

Example 25

Chimeric Xylose Isomerase Activities

Chimeric Xylose Isomerase nucleotide sequences and functional activities were generated that included an N-terminal portion of Xylose isomerase from one donor organism and a C-terminal portion of Xylose isomerase from a different donor organism. In some embodiments the second donor organism was a *Ruminococcus* bacteria. Given below are oligonucleotides utilized to isolate and modify a nucleotide sequence encoding a xylose isomerase activity. Also given below are non-limiting examples of native and chimeric nucleotide and amino acid sequences encoding xylose isomerase activities.

The native *Ruminococcus flavefaciens* nucleotide sequence (SEQ ID NO: 22) utilized to generate chimeric xylose isomerase activities is given below.

```
ATGGAATTTTTCAGCAATATCGGTAAAATTCAGTATCAGGGACCAAAAAG

TACTGATCCTCTCTCATTTAAGTACTATAACCCTGAAGAAGTCATCAAC

GGAAAGACAATGCGCGAGCATCTGAAGTTCGCTCTTTCATGGTGGCACA

CAATGGGCGGCGACGGAACAGATATGTTCGGCTGCGGCACAACAGACAA

GACCTGGGGACAGTCCGATCCCGCTGCAAGAGCAAAGGCTAAGGTTGAC

GCAGCATTCGAGATCATGGATAAGCTCTCCATTGACTACTATTGTTTCC

ACGATCGCGATCTTTCTCCCGAGTATGGCAGCCTCAAGGCTACCAACGA

TCAGCTTGACATAGTTACAGACTATATCAAGGAGAAGCAGGGCGACAAG

TTCAAGTGCCTCTGGGGTACAGCAAAGTGCTTCGATCATCCAAGATTCA

TGCACGGTGCAGGTACATCTCCTTCTGCTGATGTATTCGCTTTCTCAGC

TGCTCAGATCAAGAAGGCTCTGGAGTCAACAGTAAAGCTCGGCGGTAAC

GGTTACGTTTTCTGGGGCGGACGTGAAGGCTATGAGACACTTCTTAATA

CAAATATGGGACTCGAACTCGACAATATGGCTCGTCTTATGAAGATGGC

TGTTGAGTATGGACGTTCGATCGGCTTCAAGGGCGACTTCTATATCGAG

CCCAAGCCCAAGGAGCCCACAAAGCATCAGTACGATTTCGATACAGCTA

CTGTTCTGGGATTCCTCAGAAAGTACGGTCTCGATAAGGATTTCAAGAT

GAATATCGAAGCTAACCACGCTACACTTGCTCAGCATACATTCCAGCAT

GAGCTCCGTGTTGCAAGAGACAATGGTGTGTTCGGTTCTATCGACGCAA

ACCAGGGCGACGTTCTTCTTGGATGGGATACAGACCAGTTCCCCACAAA

TATCTACGATACAACAATGTGTATGTATGAAGTTATCAAGGCAGGCGGC

TTCACAAACGGCGGTCTCAACTTCGACGCTAAGGCACGCAGAGGGAGCT

TCACTCCCGAGGATATCTTCTACAGCTATATCGCAGGTATGGATGCATT

TGCTCTGGGCTTCAGAGCTGCTCTCAAGCTTATCGAAGACGGACGTATC

GACAAGTTCGTTGCTGACAGATACGCTTCATGGAATACCGGTATCGGTG

CAGACATAATCGCAGGTAAGGCAGATTTCGCATCTCTTGAAAAGTATGC

TCTTGAAAAGGGCGAGGTTACAGCTTCACTCTCAAGCGGCAGACAGGAA

ATGCTGGAGTCTATCGTAAATAACGTTCTTTTCAGTCTGTAA
```

The first 10 amino acids are underlined, and amino acids 11-15 are in bold font. The native sequence was originally cloned into a pUC57 vector, called pBF202, which was utilized as the PCR template for the 5' chimera constructs. The oligonucleotides used to generate the 5' replacement nucleotide sequences (e.g., oligonucleotides used to replace the first 10 amino acids of the *Ruminococcus* xylose isomerase protein) are given in the table below. In some embodiments, greater or fewer than 10 amino acids were replaced to maintain proper amino acid alignment between xylose isomerase activities.

| Name | Oligonucleotide sequence (SEQ ID NOS 361--374, respectively, in order of appearance) |
|---|---|
| KAS/5-XR_Cp10 | ACTAGTAAAAAATGAAAAATTACTTTCCAAATGTTCCAGAAGTACAGTATCAGGGACCAAAAAG |
| KAS/5-XR-O10 | ACTAGTAAAAAATGACTAAGGAATATTTCCCAACTATCGGCAAGATTCAGTATCAGGGACCAAAAAG |
| KAS/5-XR-Cth10 | ACTAGTAAAAAATGGAATACTTCAAAAATGTACCACAAATAAAACAGTATCAGGGACCAAAAAG |
| KAS/5-XR-Bth10 | ACTAGTAAAAAATGGCAACAAAAGAATTTTTTCCGGGAATTGAAAAGATTCAGTATCAGGGACCAAAAAG |
| KAS/5-XR-Bst10 | ACTAGTAAAAAATGGCTTATTTTCCGAATATCGGCAAGATTCAGTATCAGGGACCAAAAAG |
| KAS/5-XR-Bun10 | ACTAGTAAAAAATGGCTACCAAGGAATACTTCCCAGGTATTGGTAAGATCCAGTATCAGGGACCAAAAAG |
| KAS/5-XR-Cce10 | ACTAGTAAAAAATGTCAGAAGTATTTAGCGGTATTTCAAACATTCAGTATCAGGGACCAAAAAG |
| KAS/5-XR-RF10 | ACTAGTAAAAAATGGAATTTTTCAAGAACATAAGCAAGATCCAGTATCAGGGACCAAAAAG |
| KAS/5-XR-18P10 | ACTAGTAAAAAATGAGCGAATTTTTTACAGGCATTTCAAAGATCCAGTATCAGGGACCAAAAAG |
| KAS/5-XR-BV10 | ACTAGTAAAAAATGAAATTTTTTGAAAATGTCCCTAAGGTACAGTATCAGGGACCAAAAAG |
| KAS/XI-Re6-10 | CCTATTTTGACCAGCTCGATCGCGTTCAGTATCAGGGACCAAAAAGTACTGATCCTCTC |
| KAS/XI-Re1-10 | actagtaaaaaaATGCAAGCCTATTTTGACCAGCTCGATCGCGTTCAGTATCAGG |
| KAS/3-XI-RF-NATIVE | ctcgagttacagactgaaaagaacgttatttacg |
| KAS/3-XI-RF-Native-HISb | ctcgagttagtgatggtggtggtgatgcagactgaaaagaacgttatttacg |

In the table above the following abbreviations are used: Cp-*Clostridium phytofermentans*; O-*Orpinomyces*; Cth-*Clostridium thermohydrosulfuricum*, Bth-*Bacteroides thetaiotaomicron*, Bst-*Bacillus stearothermophilus*; Bun-*Bacillus uniformis*; Cce-*Clostridium cellulolyticum*; RF-*Ruminococcus flavefaciens* FD1, 18P10-*Ruminococcus* 18P13; BV10-*Clostridials genomosp* BVAB3 str UPII9-5; Re-*E. coli*.

All oligonucleotides set forth above were purchased from Integrated Technologies ("IDT", Coralville, Iowa). The oligonucleotides were designed to incorporate a SpeI restriction endonuclease cleavage site upstream and an XhoI restriction endonuclease cleavage site downstream of the new XI gene constructs, to allow cloning into the yeast expression vector p426GPD (ATCC accession number 87361), as described herein. In addition to incorporating restriction endonuclease cleavage sites, the forward oligonucleotides were designed to incorporate six consecutive A nucleotides immediately upstream of the ATG initiation codon.

PCR reactions to amplify the xylose isomerase genes were performed using about 40 ng of the pBF202 plasmid (containing the native XI-R gene in pUC57) DNA. The reactions were performed as described previously herein, using the oligonucleotide primers shown in the table above. Gene specific and for first and second rounds of PCR amplification were added at a final concentration of 0.3 µmol. The about 1350 bp products were TOPO cloned into the pCR Blunt II TOPO vector (Life Technologies, Carlsbad, Calif.) according to the manufacturer's recommendations and sequenced confirmed (GeneWiz, La Jolla, Calif.). For the 5' *E. coli* 10 amino acid extension, the PCR reactions also were performed in two steps with the following exceptions; the first reaction the nucleotides corresponding to amino acids 6-10 from the *E. coli* XI were added first using the 5' oligonucleotide KAS/XI-Re6-10 (see table above) using the 3' oligonucleotide KAS/3-XI-RF-NATIVE (see table above). Once the PCR product was confirmed by agarose gel electrophoresis, nucleic acid was purified using the Zymo Research DNA Clean & Concentrator-25 kit (Zymo Research, Orange, Calif.). In a second PCR reaction, about 40 ng of this cleaned PCR product was used in a second PCR reaction as outlined above but this time using the 5' oligonucleotide KAS/XI-Re1-10 and either KAS/3-XI-RF-NATIVE or KAS/3-XI-RF-Native-HISb, which generated the XI-R with 5' XI-*E. coli* extensions. These products were also TOPO cloned as detailed above and the sequence confirmed by sequence analysis. Following sequence confirmation, the approximately 1350 bp SpeI-XhoI fragments were cloned into the corresponding restriction sites in the p425GPD vectors, as described above.

Chimeric Xylose Isomerase Activities with a 5' 150 Amino Acid Replacement

Chimeric xylose isomerase proteins were also generated that included greater that 10 or 15 5' amino acid replacements, in some embodiments. Described herein are non-limiting examples of chimeric xylose isomerase activities with a replacement of approximately 150 5' amino acids from a different donor organism. The first 450 nucleotides of the native xylose isomerase sequence given above can be replaced with any of the sequences given in the table below to create chimeric xylose isomerase activities with approximately the 150 5' amino acids donated by a different organism than *Ruminococcus flavefaciens*.

| 5' Extension Source | Nucleotides |
|---|---|
| *Piromyces* (SEQ ID NO: 93) | ATGGCTAAGGAATATTTCCCACAAATTCAAAAGATTAAGTTCGA AGGTAAGGATTCTAAGAATCCATTAGCCTTCCACTACTACGAT GCTGAAAAGGAAGTCATGGGTAAGAAAATGAAGGATTGGTTAC GTTTCGCCATGGCCTGGTGGCACACTCTTTGCGCCGAAGGTG CTGACCAATTCGGTGGAGGTACAAAGTCTTTCCCATGGAACGA AGGTACTGATGCTATTGAAATTGCCAAGCAAAAGGTTGATGCT GGTTTCGAAATCATGCAAAAGCTTGGTATTCCATACTACTGTTT CCACGATGTTGATCTTGTTTCCGAAGGTAACTCTATTGAAGAAT ACGAATCCAACCTTAAGGCTGTCGTTGCTTACCTCAAGGAAAA GCAAAAGGAAACCGGTATTAAGCTTCTCTGGAGTACTGCTAAC GTCTTCGGTCACAAGCGTTACATGAAC |
| *Escherichia coli* (SEQ ID NO: 94) | ATGCAAGCCTATTTTGACCAGCTCGATCGCGTTCGTTATGAAG GCTCAAAATCCTCAAACCCGTTAGCATTCCGTCACTACAATCC CGACGAACTGGTGTTGGGTAAGCGTATGGAAGAGCACTTGCG TTTTGCCGCCTGCTACTGGCACACCTTCTGCTGGAACGGGGC GGATATGTTTGGTGTGGGGGCGTTTAATCGTCCGTGGCAGCA GCCTGGTGAGGCACTGGCGTTGGCGAAGCGTAAAGCAGATGT CGCATTTGAGTTTTTCCACAAGTTACATGTGCCATTTTATTGCT TCCACGATGTGGATGTTTCCCCTGAGGGCGCGTCGTTAAAAGA GTACATCAATAATTTTGCGCAAATGGTTGATGTCCTGGCAGGC AAGCAAGAAGAGCGGCGTGAAGCTGCTGTGGGGAACGGC CAACTGCTTTACAAACCCTCGCTACGGCGCG |
| *Clostridium phytofermentans* (SEQ ID NO: 95) | ATGAAAAATTACTTTCCAAATGTTCCAGAAGTAAAATACGAAGG CCCAAATTCAACGAATCCATTTGCTTTTAAATATTATGACGCAA ATAAAGTTGTAGCGGGTAAAACAATGAAAGAGCACTGTCGTTT TGCATTATCTTGGTGGCATACTCTTTGTGCAGGTGGTGCTGAT CCATTCGGTGTAACAACTATGGATAGAACCTACGGAAATATCA CAGATCCAATGGAACTTGCTAAGGCAAAAGTTGACGCTGGTTT CGAATTAATGACTAAATTAGGAATTGAATTCTTCTGTTTCCATG ACGCAGATATTGCTCCAGAAGGTGATACTTTTGAAGAGTCAAA GAAGAATCTTTTTGAAATCGTTGATTACATCAAAGAGAAGATGG ATCAGACTGGTATCAAGTTATTATGGGGTACTGCTAATAACTTT AGTCATCCAAGATTTATGCAT |
| *Orpinomyces* (SEQ ID NO: 96) | ATGACTAAGGAATATTTCCCAACTATCGGCAAGATTAGATTCGA AGGTAAGGATTCTAAGAATCCAATGGCCTTCCACTACTATGAT GCTGAAAAGGAAGTCATGGGTAAGAAAATGAAGGATTGGTTAC GTTTCGCCATGGCCTGGTGGCACACTCTTTGCGCCGATGGTG CTGACCAATTCGGTGTTGGTACTAAGTCTTTCCCATGGAATGA AGGTACTGACCCAATTGCTATTGCCAAGCAAAAGGTTGATGCT GGTTTTGAAATCATGACCAAGCTTGGTATTGAACACTACTGTTT CCACGATGTTGATCTTGTTTCTGAAGGTAACTCTATTGAAGAAT ACGAATCCAACCTCAAGCAAGTTGTTGCTTACCTTAAGCAAAA GCAACAAGAAACTGGTATTAAGCTTCTCTGGAGTACTGCCAAT GTTTTCGGTAACCCACGTTACATGAAC |
| *Clostridium thermohydrosulfuricum* (SEQ ID NO: 97) | ATGGAATACTTCAAAAATGTACCACAAATAAAATATGAAGGACC AAAATCAAACAATCCATATGCATTTAAATTTTACAATCCAGATGA AATAATAGACGGAAAACCTTTAAAAGAACACTTGCGTTTTTCAG TAGCGTACTGGCACACATTTACAGCCAATGGGACAGATCCATT TGGAGCACCCACAATGCAAAGGCCATGGGACCATTTTACTGAC CCTATGGATATTGCCAAAGCGAGAGTAGAAGCAGCCTTTGAAC TATTTGAAAAACTCGACGTACCATTTTTCTGTTTCCATGACAGA GATATAGCTCCGGAAGGAGAGACATTAAGGGAGACGAACAAA AATTTAGATACAATAGTTGCAATGATAAAAGACTACTTAAAGAC GAGCAAAACAAAAGTATTATGGGGCACAGCGAACCTTTTTTCA AATCCGAGATTTGTACAT |
| *Bacteroides thetaiotaomicron* (SEQ ID NO: 98) | ATGGCAACAAAAGAATTTTTTCCGGGAATTGAAAAGATTAAATT TGAAGGTAAAGATAGTAAGAACCCGATGGCATTCCGTTATTAC GATGCAGAGAAGGTGATTAATGGTAAAAAGATGAAGGATTGGC TGAGATTCGCTATGGCATGGTGGCACACATTGTGCGCTGAAG GTGGTGATCAGTTCGGTGGCGGAACAAAGCAATTCCCATGGA ATGGTAATGCAGATGCTATACAGGCAGCAAAAGATAAGATGGA TGCAGGATTTGAATTCATGCAGAAGATGGGTATCGAATACTATT GCTTCCATGACGTAGACTTGGTTTCGGAAGGTGCCAGTGTAGA AGAATACGAAGCTAACCTGAAAGAAATCGTAGCTTATGCAAAA CAGAAACAGGCAGAAACCGGTATCAAACTACTGTGGGGTACT GCTAATGTATTCGGTCACGCCCGCTATATGAAC |

-continued

| 5' Extension Source | Nucleotides |
|---|---|
| Bacillus stearothermophilus (SEQ ID NO: 99) | ATGGCTTATTTTCCGAATATCGGCAAGATTGCGTATGAAGGGC<br>CGGAGTCGCGCAATCCGTTGGCGTTTAAGTTTTATAATCCAGA<br>AGAAAAAGTCGGCGACAAAACAATGGAGGAGCATTTGCGCTTT<br>TCAGTGGCCTATTGGCATACGTTTACGGGGGATGGGTCGGAT<br>CCGTTTGGCGTCGGCAATATGATTCGTCCATGGAATAAGTACA<br>GCGGCATGGATCTGGCGAAGGCGCGCGTCGAGGCGGCGTTT<br>GAGCTGTTTGAAAAGCTGAACGTTCCGTTTTTCTGCTTCCATGA<br>CGTCGACATCGCGCCGGAAGGGGAAACGCTCAGCGAGACGT<br>ACAAAAATTTGGATGAAATTGTCGATATGATTGAAGAATACATG<br>AAAACAAGCAAAACGAAGCTGCTTTGGAATACGGCGAACTTGT<br>TCAGCCATCCGCGCTTCGTTCAC |
| Bacillus uniformis (SEQ ID NO: 100) | ATGGCTACCAAGGAATACTTCCCAGGTATTGGTAAGATCAAAT<br>TCGAAGGTAAGGAATCCAAGAACCCAATGGCCTTCAGATACTA<br>CGATGCTGACAAGGTTATCATGGGTAAGAAGATGTCTGAATGG<br>TTAAAGTTCGCTATGGCTTGGTGGCATACCTTGTGTGCTGAAG<br>GTGGTGACCAATTCGGTGGTGGTACCAAGAAATTCCCATGGAA<br>CGGTGAAGCTGACAAGGTCCAAGCTGCTAAGAACAAGATGGA<br>CGCTGGTTTCGAATTTATGCAAAAGATGGGTATTGAATACTACT<br>GTTTCCACGATGTTGACTTGTGTGAAGAAGCTGAAACCATCGA<br>AGAATACGAAGCTAACTTGAAGGAAATTGTTGCTTACGCTAAG<br>CAAAAGCAAGCTGAAACTGGTATCAAGCTATTATGGGGTACTG<br>CTAACGTCTTTGGTCATGCCAGATACATGAAC |
| Clostridium cellulolyticum (SEQ ID NO: 101) | ATGTCAGAAGTATTTAGCGGTATTTCAAACATTAAATTTGAAGG<br>AAGCGGGTCAGATAATCCATTAGCTTTTAAGTACTATGACCCTA<br>AGGCAGTTATCGGCGGAAAGACAATGGAAGAACATCTGAGATT<br>CGCAGTTGCCTACTGGCATACTTTTGCAGCACCAGGTGCTGAC<br>ATGTTCGGTGCAGGATCATATGTAAGACCTTGGAATACAATGT<br>CCGATCCTCTGGAAATTGCAAAATACAAAGTTGAAGCAAACTTT<br>GAATTCATTGAAAAGCTGGGAGCACCTTTCTTCGCTTTCCATG<br>ACAGGGATATTGCTCCTGAAGGCGACACACTCGCTGAAACAAA<br>TAAAAAACCTTGATACAATAGTTTCAGTAATTAAAGATAGAATGA<br>AATCCAGTCCGGTAAAGTTATTATGGGGAACTACAAATGCTTTC<br>GGAAACCCAAGATTTATGCAT |
| Ruminococcus flavefaciens FD1 (SEQ ID NO: 102) | ATGGAATTTTTCAAGAACATAAGCAAGATCCCTTACGAGGGCA<br>AGGACAGCACAAATCCTCTCGCATTCAAGTACTACAATCCTGA<br>TGAGGTAATTGACGGCAAGAAGATGCGTGACATTATGAAGTTT<br>GCTCTCTCATGGTGGCATACAATGGGCGGCGACGGAACAGAT<br>ATGTTCGGCTGCGGTACAGCTGACAAGACATGGGGCGAAAAT<br>GATCCTGCTGCAAGAGCTAAGGCTAAGGTTGACGCAGCTTTC<br>GAGATCATGCAGAAGCTCTCTATCGATTACTTCTGTTTCCACGA<br>CCGTGATCTTTCTCCTGAGTACGGCTCACTGAAGGACACAAAC<br>GCTCAGCTGGACATCGTTACAGATTACATCAAGGCTAAGCAGG<br>CTGAGACAGGTCTCAAGTGCCTCTGGGGTACAGCTAAGTGCTT<br>CGATCACCCAAGATTCATGCAC |
| Ruminococcus 18P13 (SEQ ID NO: 103) | ATGAGCGAATTTTTTACAGGCATTTCAAAGATCCCCTTTGAGG<br>GAAAGGCATCCAACAATCCCATGGCGTTCAAGTACTACAACCC<br>GGATGAGGTCGTAGGCGGCAAGACCATGCGGGAGCAGCTGA<br>AGTTTGCGCTGTCCTGGTGGCATACTATGGGGGGAGACGGTA<br>CGGACATGTTTGGTGTGGGTACCACCAACAAGAAGTTCGGCG<br>GAACCGATCCCATGGACATTGCTAAGAGAAAGGTAAACGCTGC<br>GTTTGAGCTGATGGACAAGCTGTCCATCGATTATTTCTGTTTCC<br>ACGACCGGGATCTGGCGCCGGAGGCTGATAATCTGAAGGAAA<br>CCAACCAGCGTCTGGATGAAATCACCGAGTATATTGCACAGAT<br>GATGCAGCTGAACCCGGACAAGAAGGTTCTGTGGGGTACTGC<br>AAATTGCTTCGGCAATCCCCGGTATATGCAT |
| Clostriales genomosp BVAB3 str UPII9-5 (SEQ ID NO: 104) | ATGAAATTTTTGAAAATGTCCCTAAGGTAAAATATGAGGGAAG<br>CAAGTCTACCAACCCGTTTGCATTTAAGTATTACAATCCTGAAG<br>CGGTGATTGCCGGTAAAAAAATGAAGGATCACCTGAAATTCGC<br>GATGTCCTGGTGGCACACCATGACGGCGACCGGGCAAGACCA<br>GTTCGGTTCGGGGACGATGAGCCGAATATATGACGGGCAAAC<br>TGAACCGCTGGCCTTGGCCAAAGCCCGAGTGGATGCGGCTTT<br>CGATTTCATGGAAAAATTAAATATCGAATATTTTGTTTCATGA<br>TGCCGACTTGGCTCCAGAAGGTAACAGTTTGCAGGAACGCAA<br>CGAAAATTTGCAGGAAATGGTGTCTTACCTGAAACAAAAGATG<br>GCCGGAACTTCGATTAAGCTTTTATGGGGAACCTCGAATTGTT<br>TCAGCAACCCTCGTTTTATGCAC |
| Bacillus stercoris (SEQ ID NO: 105) | ATGGCAACAAAAGAGTATTTTCCCGGAATAGGAAAAATCAAATT<br>CGAAGGCAAAGAAAGTAAGAATCCTATGGCATTCCGCTACTAC<br>GATGCGGAAAAAGTAATCATGGGCAAGAAGATGAAAGATTGGT<br>TGAAGTTCTCTATGGCATGGTGGCATACACTCTGTGCAGAGGG<br>TGGTGACCAGTTCGGCGGCGGAACGAAACATTTCCCCTGGAA |

| 5' Extension Source | Nucleotides |
|---|---|
| | CGGTGATGCCGATAAACTGCAGGCTGCCAAGAACAAAATGGA<br>TGCTGGTTTCGAGTTCATGCAGAAAATGGGCATCGAATATTAC<br>TGCTTCCACGATGTTGACCTTTGCGACGAGGCCGATACAATCG<br>AAGAGTACGAAGCAAACCTGAAAGCCATCGTTGCATACGCCAA<br>GCAAAAGCAGGAGGAAACAGGTATCAAACTGTTGTGGGGTAC<br>TGCCAACGTATTCGGTCATGCACGTTACATGAACG |
| Thermus thermophilus<br>(SEQ ID NO: 106) | ATGTACGAGCCCAAACCGGAGCACAGGTTTACCTTTGGCCTTT<br>GGACTGTGGGCAATGTGGGCCGTGATCCCTTCGGGGACGCG<br>GTTCGGGAGAGGCTGGACCCGGTTTACGTGGTTCATAAGCTG<br>GCGGAGCTTGGGGCCTACGGGGTAAACCTTCACGACGAGGAC<br>CTGATCCCGCGGGGCACGCCTCCTCAGGAGCGGGACCAGAT<br>CGTGAGGCGCTTCAAGAAGGCTCTCGATGAAACCGGCCTCAA<br>GGTCCCCATGGTCACCGCCAACCTCTTCTCCGACCCTGCTTTC<br>AAGGAC |

Xylose isomerase genes from additional bacteria were also utilized as the C-terminal portion of chimeric xylose isomerase activities. In some embodiments, the bacteria used as xylose isomerase nucleotide sequence donors were additional *Ruminococcus* bacteria. In certain embodiments, the bacteria used as xylose isomerase nucleotide sequences donors were *Clostridiales* bacteria. The native nucleotide and amino acid sequences of the additional xylose isomerase genes utilized to create chimeric xylose isomerase activities are given below. The 5' approximately 150 amino acids of the sequences below can be replaced as described above, using the sequences above, to create novel chimeric xylose isomerase activities.

Nucleotide Sequences

*Ruminococcus*_FD1 Xylose Isomerease (ZP_06143883.1, SEQ ID NO: 107)

ATGGAATTTTTCAAGAACATAAGCAAGATCCCTTACGAGGGCAAGGACA

GCACAAATCCTCTCGCATTCAAGTACTACAATCCTGATGAGGTAATTGA

CGGCAAGAAGATGCGTGACATTATGAAGTTTGCTCTCTCATGGTGGCAT

ACAATGGGCGGCGACGGAACAGATATGTTCGGCTGCGGTACAGCTGACA

AGACATGGGGCGAAAATGATCCTGCTGCAAGAGCTAAGGCTAAGGTTGA

CGCAGCTTTCGAGATCATGCAGAAGCTCTCTATCGATTACTTCTGTTTC

CACGACCGTGATCTTTCTCCTGAGTACGGCTCACTGAAGGACACAAACG

CTCAGCTGGACATCGTTACAGATTACATCAAGGCTAAGCAGGCTGAGAC

AGGTCTCAAGTGCCTCTGGGGTACAGCTAAGTGCTTCGATCACCCAAGA

TTCATGCACGGTGCAGGTACTTCACCATCCGCAGACGTATTCGCTTTCTC

AGCTGCACAGATCAAGAAGGCTCTCGAGTCTACTGTAAAGCTCGGCGGT

ACAGGCTACGTATTCTGGGGCGGACGTGAGGGTTATGAGACTCTCCTCA

ACACAAACATGGGCCTTGAGCTTGACAACATGGCTCGTCTCATGAAGAT

GGCTGTTGAGTACGGACGTTCTATCGGCTTCAAGGGCGATTTCTACATC

GAGCCTAAGCCAAAGGAGCCAACAAAGCACCAGTACGATTTCGATACTG

CTACTGTTCTCGGCTTCCTCAGAAAGTACGGTCTCGACAAGGATTTCAA

GATGAACATCGAAGCTAACCACGCTACACTGGCTCAGCACACATTCCAG

CACGAGCTCTGCGTAGCAAGAACAAACGGTGCTTTCGGTTCAATCGACG

CAAACCAGGGCGATCCTCTCCTCGGATGGGATACAGACCAGTTCCCGAC

-continued

AAATATCTATGACACAACAATGTGTATGTACGAAGTTATCAAGGCTGGC

GGCTTCACAAACGGCGGTCTCAACTTCGATGCAAAGGCAAGACGTGGAA

GCTTCACACCTGAGGATATCTTCTACAGCTACATTGCAGGTATGGATGC

ATTCGCTCTCGGCTACAAGGCTGCAAGCAAGCTCATCGCTGACGGACGT

ATCGACAGCTTCATTTCCGACCGCTACGCTTCATGGAGCGAGGGAATCG

GTCTCGACATCATCTCAGGCAAGGCTGATATGGCTGCTCTTGAGAAGTA

TGCTCTCGAAAAGGGCGAGGTTACAGACTCTATTTCCAGCGGCAGACAG

GAACTCCTCGAGTCTATCGTAAACAACGTTATATTCAATCTTTGA

*Ruminococcus*_18P13 Xylose Isomerease (CBL17278.1, SEQ ID NO: 108)

ATGAGCGAATTTTTTACAGGCATTTCAAAGATCCCCTTTGAGGGAAAGG

ATCCAACAATCCCATGGCGTTCAAGTACTACAACCCGGATGAGGTCGT

GGCGGCAAGACCATGCGGGAGCAGCTGAAGTTTGCGCTGTCCTGGTGG

ATACTATGGGGGGAGACGGTACGGACATGTTTGGTGTGGGTACCACCA

CAAGAAGTTCGGCGGAACCGATCCCATGGACATTGCTAAGAGAAAGGT

AACGCTGCGTTTGAGCTGATGGACAAGCTGTCCATCGATTATTTCTGT

TCCACGACCGGGATCTGGCGCCGGAGGCTGATAATCTGAAGGAAACCA

CCAGCGTCTGGATGAAATCACCGAGTATATTGCACAGATGATGCAGCT

AACCCGGACAAGAAGGTTCTGTGGGGTACTGCAAATTGCTTCGGCAAT

CCCCGGTATATGCATGGTGCCGGCACTGCGCCCAATGCGGACGTGTTTGC

ATTTGCAGCTGCGCAGATCAAAAAGGCAATTGAGATCACCGTAAAGCTG

GGTGGCAAGGGCTATGTATTCTGGGGCGGCAGAGAGGGCTACGAAACGC

TGCTGAACACCAATATGGGTCTGGAACTGGATAATATGGCACGGCTGCT

GCATATGGCAGTGGACTATGCAAGAAGCATCGGCTTTACCGGCGACTTC

TACATCGAGCCCAAGCCCAAGGAGCCTACCAAGCATCAGTATGATTTTG

ATACCGCAACCGTGATCGGCTTCCTGCGCAAGTATAATCTGGACAAGGA

CTTCAAGATGAACATCGAAGCCAACCACGCAACCCTTGCACAGCACACC

TTCCAGCATGAACTGCGGGTAGCACGGGAGAACGGCTTCTTTGGCTCCA

TCGATGCTAACCAGGGTGACACCCTGCTGGGCTGGGATACGGATCAGTT

-continued

CCCCACTAATACCTATGACGCAGCACTGTGTATGTACGAGGTACTCAAG

GCTGGCGGTTTTACCAATGGCGGTCTGAACTTTGACTCCAAGGCACGGC

GTGGATCCTTTGAGATGGAGGATATCTTCCACAGCTACATTGCCGGTAT

GGACACCTTTGCACTGGGTCTGAAGATTGCGCAGAAGATGATCGATGAC

GGACGGATCGACCAGTTCGTGGCTGATCGGTATGCAAGCTGGAACACCG

GCATCGGTGCGGATATCATTTCCGGCAAGGCAACCATGGCAGATTTGGA

GGCTTACGCACTGAGCAAGGGCGATGTGACCGCATCCCTCAAGAGCGGT

CGTCAGGAATTGCTGGAAAGCATCCTGAACAATATTATGTTCAATCTTT

AA

Clostridiales_genomosp_BVAB3_UPII9-5 Xylose Isomerease (YP_003474614.1, SEQ ID NO: 109)

ATGAAATTTTTTGAAAATGTCCCTAAGGTAAAATATGAGGGAAGCAAGT

CTACCAACCCGTTTGCATTTAAGTATTACAATCCTGAAGCGGTGATTGC

CGGTAAAAAAATGAAGGATCACCTGAAATTCGCGATGTCCTGGTGGCAC

ACCATGACGGCGACCGGGCAAGACCAGTTCGGTTCGGGGACGATGAGCC

GAATATATGACGGGCAAACTGAACCGCTGGCCTTGGCCAAAGCCCGAGT

GGATGCGGCTTTCGATTTCATGGAAAAATTAAATATCGAATATTTTTGT

TTTCATGATGCCGACTTGGCTCCAGAAGGTAACAGTTTGCAGGAACGCA

ACGAAAATTTGCAGGAAATGGTGTCTTACCTGAAACAAAAGATGGCCGG

AACTTCGATTAAGCTTTTATGGGGAACCTCGAATTGTTTCAGCAACCCT

CGTTTTATGCACGGGGCAGCCACATCTTGCGAAGCGGATGTGTTTGCTTG

GACCGCCACTCAGTTGAAAAATGCCATCGATGCTACCATCGCGCTTGGC

CGGTAAAGGCTATGTTTTCTGGGGCGGCGGGAAGGCTATGAAACCTTGC

TGAACACTGATGTCGGCCTGGAGATGGATAATTATGCAAGAATGCTGAA

AATGGCGGTTGCATATGCGCATTCTAAAGGTTATACGGGTGACTTTTAT

ATTGAACCTAAGCCAAAAGAACCCACTAAACATCAATATGATTTCGATG

TCGCCACTTGCGTTGCTTTCCTTGAAAAATACGATTTGATGCGTGATTT

TAAAGTAAACATTGAGGCTAATCACGCTACTTTGGCCGGTCATACTTTC

CAACATGAGTTACGCATGGCGCGTACCTTCGGGGTATTCGGCTCGGTTG

ATGCCAATCAGGGCGACAGCAATCTGGGCTGGGATACCGATCAGTTCCC

GGGCAATATTTATGATACGACTTTGGCCATGTATGAGATTTTGAAGGCC

GGTGGATTTACCAACGGAGGCTTGAACTTTGATCTAAAGTGCGTCGTC

CGTCATTTACCCCGGAAGATATTGCTTATGCTTATATTTTGGGCATGGA

TACGTTTGCCTTAGGCTTGATTAAGGCGCAACAGCTGATTGAGGATGGC

AGAATTGATCGTTTCGTAGCGGAAAAATATGCTAGTTATAAGTCGGGCA

TCGGTGCTGAAATCTTGAGTGGTAAAACCGGTTTGCCGGAATTGGAGGC

TTACGCATTGAAGAAAGGCGAGCCTAAGTTGTATAGTGGGCGGCAGGAA

TATCTTGAAAGTGTCGTTAATAACGTAATTTTCAACGGAAATCTTTGA

Amino Acid Sequences

Ruminococcus_FD1 Xylose Isomerease (SEQ ID NO: 110)

MEFFKNISKIPYEGKDSTNPLAFKYYNPDEVIDGKKMRDIMKFALSWWHT

MGGDGTDMFGCGTADKTWGENDPAARAKAKVDAAFEIMQKLSIDYFC

FHDRDLSPEYGSLKDTNAQLDIVTDYIKAKQAETGLKCLWGTAKCFDHP

RFMHGAGTSPSADVFAFSAAQIKKALESTVKLGGTGYVFWGGREGYET

LLNTNMGLELDNMARLMKMAVEYGRSIGFKGDFYIEPKPKEPTKHQYDF

DTATVLGFLRKYGLDKDFKMNIEANHATLAQHTFQHELCVARTNGAFGS

IDANQGDPLLGWDTDQFPTNIYDTTMCMYEVIKAGGFTNGGLNFDAKAR

RGSFTPEDIFYSYIAGMDAFALGYKAASKLIADGRIDSFISDRYASWSE

GIGLDIISGKADMAALEKYALEKGEVTDSISSGRQELLESIVNNVIFNL

Ruminococcus_18P13 Xylose Isomerease (SEQ ID NO: 111)

MSEFFTGISKIPFEGKASNNPMAFKYYNPDEVVGGKTMREQLKFALSWWH

TMGGDGTDMFGVGTTNKKFGGTDPMDIAKRKVNAAFELMDKLSIDYFCFH

DRDLAPEADNLKETNQRLDEITEYIAQMMQLNPDKKVLWGTANCFGNPRY

MHGAGTAPNADVFAFAAAQIKKAIEITVKLGGKGYVFWGGREGYETLLNT

NMGLELDNMARLLHMAVDYARSIGFTGDFYIEPKPKEPTKHQYDFDTATV

IGFLRKYNLDKDFKMNIEANHATLAQHTFQHELRVARENGFFGSIDANQG

DTLLGWDTDQFPTNTYDAALCMYEVLKAGGFTNGGLNFDSKARRGSFE

MEDIFHSYIAGMDTFALGLKIAQKMIDDGRIDQFVADRYASWNTGIGADI

ISGKATMADLEAYALSKGDVTASLKSGRQELLESILNNIMFN

Clostridiales_genomosp. BVAB3 str UPII9-5 Xylose Isomerease (SEQ ID NO: 112)

MKFFENVPKVKYEGSKSTNPFAFKYYNPEAVIAGKKMKDHLKFAMSWWHT

MTATGQDQFGSGTMSRIYDGQTEPLALAKARVDAAFDFMEKLNIEYFCFH

DADLAPEGNSLQERNENLQEMVSYLKQKMAGTSIKLLWGTSNCFSNPRF

MHGAATSCEADVFAWTATQLKNAIDATIALGGKGYVFWGGREGYETLLNT

DVGLEMDNYARMLKMAVAYAHSKGYTGDFYIEPKPKEPTKHQYDFDVAT

CVAFLEKYDLMRDFKVNIEANHATLAGHTFQHELRMARTFGVFGSVDAN

QGDSNLGWDTDQFPGNIYDTTLAMYEILKAGGFTNGGLNFDAKVRRPSFT

PEDIAYAYILGMDTFALGLIKAQQLIEDGRIDRFVAEKYASYKSGIGAEI

LSGKTGLPELEAYALKKGEPKLYSGRQEYLESVVNNVIFNGNL

Amino acid similarity comparisons were performed on the various xylose isomerase proteins whose sequences were analyzed to generate the chimeric xylose isomerase activity nucleotide sequences. The results of the amino acid similarity comparison are presented in the table below.

|  | Ruminococcus_FD1 | Ruminococcus_18P13 | Clostriales_BVAB3 |
|---|---|---|---|
| XI-R | 88 | 77 | 65.8 |
| *Piromyces* | 50.9 | 50 | 51.6 |
| *Clostridium phytofermentans* | 64.9 | 64.4 | 68.3 |
| *Thermus thermophilus* | 25.1 | 22.9 | 26.6 |
| *Orpinomyces* | 51.6 | 51.8 | 52.5 |
| *Bacteroides thetaiotaomicron* | 52.6 | 53 | 53 |
| *Escherichia coli* | 50.3 | 50.5 | 51.4 |
| *Clostridium thermohydrosulfuricum* | 60.7 | 61.3 | 59.8 |
| *Streptomyces rubiginosus* | 22.7 | 23.8 | 24.7 |
| *Thermotoga maritima* | 61 | 60 | 61.3 |
| *Thermotoga neopolitana* | 60.5 | 59.7 | 60.8 |
| *Streptomyces murinus* | 24.2 | 23 | 25.1 |
| *Lactobacillus pentosus* | 49.7 | 50.7 | 47.7 |
| *Bacillus stearothermophilus* | 55 | 57 | 56.5 |
| *Bacteroides uniformis* | 52.6 | 54.2 | 52.8 |
| *Clostridium cellulyticum* | 58.8 | 64.1 | 58.7 |
| Ruminococcus_FD1 | 100 | 77.1 | 65.6 |
| Ruminococcus_18P13 | 77.1 | 100 | 64 |
| Clostriales_BVAB3 | 65.6 | 64 | 100 |
| *Bacteroides stercoris* | 51.9 | 52.4 | 53 |

Example 26

Nucleotide and Amino Acid Sequences of Over Expressed Activities Useful for Increasing Sugar Transport and/or Sugar Metabolism As noted herein, increased or over expression of certain activities can result in increased ethanol production due to an increase in the utilization of the fermentation substrate, sometimes due to an increase in transport and/or metabolism of a desired sugar. Non-limiting examples of activities that can be over expressed to increase ethanol production by increasing sugar transport and/or metabolism include activities encoded by the genes gxf1, gxs1, hxt7, zwf1, gal2, sol3, sol4, the like, homologs thereof (e.g., *Candida albicans* Sol1p, *Schizosaccharomyces pombe* Sol1p, human PGLS and human H6PD), that can be expressed in a desired host organism, and combinations thereof. Nucleotide and amino acid sequences for some of these additional activities are given below. In some embodiments, 1, 2, 3, 4, 5, 6 or more of the non-limiting additional activities can be increased in expression or over expressed in an engineered host, thereby increasing transport and/or metabolism of a desired carbon source, wherein increased transport and/or metabolism of a desired carbon source results in increased ethanol production.

Nucleotide Sequences

*Debaryomyces hansenii* gxf1 (SEQ ID NO: 113)

ATGTCTCAAGAAGAATATAGTTCTGGGGTACAAACCCCAGTTTCTAACC

ATTCTGGTTTAGAGAAAGAAGAGCAACACAAGTTAGACGGTTTAGATGA

GGATGAAATTGTCGATCAATTACCTTCTTTACCAGAAAAATCAGCTAAGG

ATTATTTATTAATTTCTTTCTTCTGTGTATTAGTTGCATTTGGTGGTTTT

GTTTTCGGTTTCGATACTGGTACTATCTCAGGTTTCGTTAACATGAGTGA

TTACTTGGAAAGATTCGGTGAGCTTAATGCAGATGGTGAATATTTCTTAT

CTAATGTTAGAACTGGTTTGATTGTTGCTATTTTTAATGTTGGTTGTGCT

GTCGGTGGTATTTTCTTATCTAAGATTGCTGATGTTTATGGTAGAAGAAT

TGGTCTTATGTTTTCCATGATTATTTATGTGATTGGTATAATTGTTCAAA

TCTCAGCTTCTGACAAGTGGTATCAAATCGTTGTTGGTAGAGCTATTGCA

GGTTTAGCTGTTGGTACCGTTTCTGTCTTATCCCCATTATTCATTGGTGA

ATCAGCACCTAAAACCTTAAGAGGTACTTTAGTGTGTTGTTTCCAATTAT

GTATTACCTTAGGTATCTTCTTAGGTTACTGTACTACATATGGTACTAAA

ACCTACACCGACTCTAGACAATGGAGAATTCCATTAGGTTTATGTTTTGT

TTGGGCTATCATGTTGGTTATTGGTATGGTTTGCATGCCAGAATCACCAA

GATACTTAGTTGTCAAGAACAAGATTGAAGAAGCTAAGAAATCGATTGGT

AGATCCAACAAGGTTTCACCAGAAGATCCTGCTGTTTACACCGAAGTCCA

ATTGATTCAAGCAGGTATTGAAAGAGAAAGTTTAGCTGGTTCTGCCTCTT

GGACCGAATTGGTTACTGGTAAGCCAAGAATCTTTCGTAGAGTCATTATG

GGTATTATGTTACAATCTTTACAACAATTGACTGGTGACAACTATTTCTT

CTACTATGGTACTACTATTTTCCAAGCTGTCGGTATGACTGATTCCTTCC

AAACATCTATTGTTTTAGGTGTTGTTAACTTTGCATCTACATTTCTCGGT

ATCTACACAATTGAAAGATTCGGTAGAAGATTATGTTTGTTAACTGGTTC

TGTCTGTATGTTCGTTTGTTTCATCATTTACTCCATTTTGGGTGTTACAA

ACTTATATATTGATGGCTACGATGGTCCAACTTCGGTTCCAACCGGTGAT

GCGATGATTTTCATTACTACCTTATACATTTTCTTCTTCGCATCCACCTG

GGCTGGTGGTGTCTACTGTATCGTTTCCGAAACATACCCATTGAGAATTA

GATCTAAGGCCATGTCCGTTGCCACCGCTGCTAACTGGATTTGGGGTTTC

TTGATCTCTTTCTTCACTCCATTCATCACCTCGGCTATCCACTTCTACTA

CGGTTTCGTTTTCACAGGATGTTTGTTATTCTCGTTCTTTTACGTTTACT

TCTTTGTTGTTGAAACTAAGGGATTAACTTTAGAAGAAGTTGATGAATTG

TATGCCCAAGGTGTTGCCCCATGGAAGTCATCGAAATGGGTTCCACCAAC

CAAGGAAGAAATGGCCCATTCTTCAGGATATGCTGCTGAAGCCAAACCTC

ACGATCAACAAGTATAA

*Saccharomyces cerevisiae* gal2 (SEQ ID NO: 114)

```
ATGGCAGTTGAGGAGAACAATATGCCTGTTGTTTCACAGCAACCCCAAG
CTGGTGAAGACGTGATCTCTTCACTCAGTAAAGATTCCCATTTAAGCGC
ACAATCTCAAAAGTATTCTAATGATGAATTGAAAGCCGGTGAGTCAGGG
TCTGAAGGCTCCCAAAGTGTTCCTATAGAGATACCCAAGAAGCCCATGT
CTGAATATGTTACCGTTTCCTTGCTTTGTTTGTGTGTTGCCTTCGGCGG
CTTCATGTTTGGCTGGGATACCGGTACTATTTCTGGGTTTGTTGTCCAA
ACAGACTTTTTGAGAAGGTTTGGTATGAAACATAAGGATGGTACCCACT
ATTTGTCAAACGTCAGAACAGGTTTAATCGTCGCCATTTTCAATATTGG
ACTGTGCCTTTGGTGGTATTATACTTTCCAAGGTGGAGATATGTATGGC
CGTAAAAAGGGTCTTTCGATTGTCGTCTCGGTTTATATAGTTGGTATTA
TCATTCAAATTGCCTCTATCAACAAGTGGTACCAATATTTCATTGGTAG
AATCATATCTGGTTTGGGTGTCGGCGGCATCGCCGTCTTATGTCCTATG
TTGATCTCTGAAATTGCTCCAAAGCACTTGAGAGGCACACTAGTTTCTT
GTTATCAGCTGATGATTACTGCAGGTATCTTTTTGGGCTACTGTACTAA
TTACGGTACAAAGAGCTATTCGAACTCAGTTCAATGGAGAGTTCCATTA
GGGCTATGTTTCGCTTGGTCATTATTTATGATTGGCGCTTTGACGTTAG
TTCCTGAATCCCCACGTTATTTATGTGAGGTGAATAAGGTAGAAGACGC
CAAGCGTTCCATTGCTAAGTCTAACAAGGTGTCACCAGAGGATCCTGCC
GTCCAGGCAGAGTTAGATCTGATCATGGCCGGTATAGAAGCTGAAAAAC
TGGCTGGCAATGCGTCCTGGGGGGAATTATTTTCCACCAAGACCAAAGT
ATTTCAACGTTTGTTGATGGGTGTGTTTGTTCAAATGTTCCAACAATTA
ACCGGTAACAATTATTTTTTCTACTACGGTACCGTTATTTTCAAGTCAG
TTGGCCTGGATGATTCCTTTGAAACATCCATTGTCATTGGTGTAGTCAA
CTTTGCCTCCACTTTCTTTAGTTTGTGGACTGTCGAAAACTTGGGACAT
CGTAAATGTTTACTTTTGGGCGCTGCCACTATGATGGCTTGTATGGTCA
TCTACGCCTCTGTTGGTGTTACTAGATTATATCCTCACGGTAAAAGCCA
GCCATCTTCTAAAGGTGCCGGTAACTGTATGATTGTCTTTACCTGTTTT
TATATTTTCTGTTATGCCACAACCTGGGCGCCAGTTGCCTGGGTCATCA
CAGCAGAATCATTCCCACTGAGAGTCAAGTCGAAATGTATGGCGTTGGC
CTCTGCTTCCAATTGGGTATGGGGGTTCTTGATTGCATTTTTCACCCCA
TTCATCACATCTGCCATTAACTTCTACTACGGTTATGTCTTCATGGGCT
GGTTTGGTTGCCATGTTTTTTTATGTCTTTTTCTTTGTTCCAAAACTAA
AGGCCTATCGTTAGAAGAAATTCAAGAATTATGGGAAGAAGGTGTTTTA
CCTTGGAAATCTGAAGGCTGGATTCCTTCATCCAGAAGAGGTAATAATT
ACGATTTAGAGGATTTACAACATGACGACAAACCGTGGTACAAGGCCAT
GCTAGAATAA
```

*Saccharomyces cerevisiae* sol3 (SEQ ID NO: 115)

```
ATGGTGACAGTCGGTGTGTTTTCTGAGAGGGCTAGTTTGACCCATCAATT
GGGGGAATTCATCGTCAAGAAACAAGATGAGGCGCTGCAAAAGAAGTC
AGACTTTAAAGTTTCCGTTAGCGGTGGCTCTTTGATCGATGCTCTGTATG
AAAGTTTAGTAGCGGACGAATCACTATCTTCTCGAGTGCAATGGTCTAAA
TGGCAAATCTACTTCTCTGATGAAAGAATTGTGCCACTGACGGACGCTGA
CAGCAATTATGGTGCCTTCAAGAGAGCTGTTCTAGATAAATTACCCTCGA
CTAGTCAGCCAAACGTTTATCCCATGGACGAGTCCTTGATTGGCAGCGAT
GCTGAATCTAACAACAAAATTGCTGCAGAGTACGAGCGTATCGTACCTC
AAGTGCTTGATTTGGTACTGTTGGGCTGTGGTCCTGATGGACACACTTGT
TCCTTATTCCCTGGAGAAACACATAGGTACTTGCTGAACGAAACAACCA
AAAGAGTTGCTTGGTGCCACGATTCTCCCAAGCCTCCAAGTGACAGAAT
CACCTTCACTCTGCCTGTGTTGAAAGACGCCAAAGCCCTGTGTTTTGTG
GCTGAGGGCAGTTCCAAACAAAATATAATGCATGAGATCTTTGACTTGA
AAAACGATCAATTGCCAACCGCATTGGTTAACAAATTATTTGGTGAAAA
AACATCCTGGTTCGTTAATGAGGAAGCTTTTGGAAAAGTTCAAACGAAA
ACTTTTTAG
```

*Saccharomyces cerevisiae* zwf1 (SEQ ID NO: 116)

```
ATGAGTGAAGGCCCCGTCAAATTCGAAAAAAATACCGTCATATCTGTCT
TTGGTGCGTCAGGTGATCTGGCAAAGAAGAAGACTTTTCCCGCCTTATT
TGGGCTTTTCAGAGAAGGTTACCTTGATCCATCTACCAAGATCTTCGGT
TATGCCCGGTCCAAATTGTCCATGGAGGAGGACCTGAAGTCCCGTGTCC
TACCCCACTTGAAAAAACCTCACGGTGAAGCCGATGACTCTAAGGTCGA
ACAGTTCTTCAAGATGGTCAGCTACATTTCGGGAAATTACGACACAGAT
GAAGGCTTCGACGAATTAAGAACGCAGATCGAGAAATTCGAGAAAAGTG
CCAACGTCGATGTCCCACACCGTCTCTTCTATCTGGCCTTGCCGCCAAG
CGTTTTTTTGACGGTGGCCAAGCAGATCAAGAGTCGTGTGTACGCAGAG
AATGGCATCACCCGTGTAATCGTAGAGAAACCTTTCGGCCACGACCTGG
CCTCTGCCAGGGAGCTGCAAAAAAACCTGGGGCCCCTCTTTAAAGAAGA
AGAGTTGTACAGAATTGACCATTACTTGGGTAAAGAGTTGGTCAAGAAT
CTTTTAGTCTTGAGGTTCGGTAACCAGTTTTTGAATGCCTCGTGGAATA
GAGACAACATTCAAAGCGTTCAGATTTCGTTTAAAGAGAGGTTCGGCAC
CGAAGGCCGTGGCGGCTATTTCGACTCTATAGGCATAATCAGAGACGTG
ATGCAGAACCATCTGTTACAAATCATGACTCTCTTGACTATGGAAAGAC
CGGTGTCTTTGACCCGGAATCTATTCGTGACGAAAAGGTTAAGGTTCT
AAAGGCCGTGGCCCCCATCGACACGGACGACGTCCTCTTGGGCCAGTAC
GGTAAATCTGAGGACGGGTCTAAGCCCGCCTACGTGGATGATGACACTG
TAGACAAGGACTCTAAATGTGTCACTTTTGCAGCAATGACTTTCAACAT
CGAAAACGAGCGTTGGGAGGGCGTCCCCATCATGATGCGTGCCGGTAAG
GCTTTGAATGAGTCCAAGGTGGAGATCAGACTGCAGTACAAAGCGGTCG
CATCGGGTGTCTTCAAAGACATTCCAAATAACGAACTGGTCATCAGAGT
GCAGCCCGATGCCGCTGTGTACCTAAAGTTTAATGCTAAGACCCCTGGT
```

-continued
```
CTGTCAAATGCTACCCAAGTCACAGATCTGAATCTAACTTACGCAAGCA
GTGGGTACCAAGACTTTTGGATTCCAGAGGCTTACGAGTTGATAAGAGA
CGCCCTACTGGGTGACCATTCCAACTTTGTCAGAGATGACGAATTGGAT
ATCAGTTGGGGCATATTCACCCCATTACTGAAGCACATAGAGCGTCCGG
ACGGTCCAACACCGGAAATTTACCCCTACGGATCAAGAGGTCCAAGGG
ATTGAAGGAATATATGCAAAAACACAAGTATGTTATGCCCGAAAAGCAC
CCTTACGCTTGGCCCGTGACTAAGCCAGAAGATACGAAGGATAATTAG
```

Amino Acid Sequences

Debaryomyces hansenii gxf1 (SEQ ID NO: 117)

```
  1 MSQEEYSSGV QTPVSNHSGL EKEEQHKLDG LDEDEIVDQL
    PSLPEKSAKD YLLISFFCVL
 61 VAFGGFVFGF DTGTISGFVN MSDYLERFGE LNADGEYFLS
    NVRTGLIVAI FNVGCAVGGI
121 FLSKIADVYG RRIGLMFSMI IYVIGIIVQI SASDKWYQIV
    VGRAIAGLAV GTVSVLSPLF
181 IGESAPKTLR GTLVCCFQLC ITLGIFLGYC TTYGTKTYTD
    SRQWRIPLGL CFVWAIMLVI
241 GMVCMPESPR YLVVKNKIEE AKKSIGRSNK VSPEDPAVYT
    EVQLIQAGIE RESLAGSASW
301 TELVTGKPRI FRRVIMGIML QSLQQLTGDN YFFYYGTTIF
    QAVGMTDSFQ TSIVLGVVNF
361 ASTFLGIYTI ERFGRRLCLL TGSVCMFVCF IIYSILGVTN
    LYIDGYDGPT SVPTGDAMIF
421 ITTLYIFFFA STWAGGVYCI VSETYPLRIR SKAMSVATAA
    NWIWGFLISF FTPFITSAIH
481 FYYGFVFTGC LLFSFFYVYF FVVETKGLTL EEVDELYAQG
    VAPWKSSKWV PPTKEEMAHS
541 SGYAAEAKPH DQQV
```

Saccharomyces cerevisiae gal2 (SEQ ID NO: 118)

```
  1 MAVEENNMPV VSQQPQAGED VISSLSKDSH LSAQSQKYSN
    DELKAGESGS
 51 EGSQSVPIEI PKKPMSEYVT VSLLCLCVAF GGFMFGWDTG
    TISGFVVQTD
101 FLRRFGMKHK DGTHYLSNVR TGLIVAIFNI GCAFGGIILS
    KGGDMYGRKK
151 GLSIVVSVYI VGIIIQIASI NKWYQYFIGR IISGLGVGGI
    AVLCPMLISE
201 IAPKHLRGTL VSCYQLMITA GIFLGYCTNY GTKSYSNSVQ
    WRVPLGLCFA
251 WSLFMIGALT LVPESPRYLC EVNKVEDAKR SIAKSNKVSP
    EDPAVQAELD
301 LIMAGIEAEK LAGNASWGEL FSTKTKVFQR LLMGVFVQMF
    QQLTGNNYFF
351 YYGTVIFKSV GLDDSFETSI VIGVVNFAST FFSLWTVENL
    GHRKCLLLGA
401 ATMMACMVIY ASVGVTRLYP HGKSQPSSKG AGNCMIVFTC
    FYIFCYATTW
451 APVAWVITAE SFPLRVKSKC MALASASNWV WGFLIAFFTP
    FITSAINFYY
```

-continued
```
501 GYVFMGCLVA MFFYVFFFVP ETKGLSLEEI QELWEEGVLP
    WKSEGWIPSS
551 RRGNNYDLED LQHDDKPWYK AMLE
```

Saccharomyces cerevisiae zwf1 (SEQ ID NO: 119)

```
  1 MSEGPVKFEK NTVISVFGAS GDLAKKKTFP ALFGLFREGY
    LDPSTKIFGY
 51 ARSKLSMEED LKSRVLPHLK KPHGEADDSK VEQFFKMVSY
    ISGNYDTDEG
101 FDELRTQIEK FEKSANVDVP HRLFYLALPP SVFLTVAKQI
    KSRVYAENGI
151 TRVIVEKPFG HDLASARELQ KNLGPLFKEE ELYRIDHYLG
    KELVKNLLVL
201 RFGNQFLNAS WNRDNIQSVQ ISFKERFGTE GRGGYFDSIG
    IIRDVMQNHL
251 LQIMTLLTME RPVSFDPESI RDEKVKVLKA VAPIDTDDVL
    LGQYGKSEDG
301 SKPAYVDDDT VDKDSKCVTF AAMTFNIENE RWEGVPIMMR
    AGKALNESKV
351 EIRLQYKAVA SGVFKDIPNN ELVIRVQPDA AVYLKFNAKT
    PGLSNATQVT
401 DLNLTYASRY QDFWIPEAYE VLIRDALLGD HSNFVRDDEL
    DISWGIFTPL
451 LKHIERPDGP TPEIYPYGSR GPKGLKEYMQ KHKYVMPEKH
    PYAWPVTKPE
501 DTKDN
```

Saccharomyces cerevisiae sol3 (SEQ ID NO: 120)

```
  1 MVTVGVFSER ASLTHQLGEF IVKKQDEALQ KKSDFKVSVS
    GGSLIDALYE
 51 SLVADESLSS RVQWSKWQIY FSDERIVPLT DADSNYGAFK
    RAVLDKLPST
101 SQPNVYPMDE SLIGSDAESN NKIAAEYERI VPQVLDLVLL
    GCGPDGHTCS
151 LFPGETHRYL LNETTKRVAW CHDSPKPPSD RITFTLPVLK
    DAKALCFVAE
201 GSSKQNIMHE IFDLKNDQLP TALVNKLFGE KTSWFVNEEA
    FGKVQTKTF
```

Example 27

Cloning of Additional ZWF1 Candidate Genes

A variety of ZWF1 genes were cloned from *S. cerevisiae*, *Zymomonas mobilis*, *Pseudomonas fluorescens* (zwf1 and zwf2), and *P. aeruginosa* strain PAO1. The sequences of these additional ZWF1 genes are given below.

zwf1 from *P. fluorescens*

Amino Acid Sequence (SEQ. ID. NO: 123)

```
MTTTRKKSKALPAPPTTLFLFGARGDLVKRLLMPALYNLSRDGLLDEGLR
IVGVDHNAVSDAEFATLLEDFLRDEVLNKQGQGAAVDAAVWARLTRGINY
VQGDFLDDSTYAELAARIAASGTGNAVFYLATAPRFFSEVVRRLGSAGLL
```

EEGPQAFRRVVIEKPFGSDLQTAEALNGCLLKVMSEKQIYRIDHYLGKET

VQNILVSRFSNSLFEAFWNNHYIDHVQITAAETVGVETRGSFYEHTGALR

DMVPNHLFQLLAMVAMEPPAAFGADAVRGEKAKVVGAIRPWSVEEARANS

VRGQYSAGEVAGKALAGYREEANVAPDSSTETYVALKVMIDNWRWVGVPF

YLRTGKRMSVRDTEIVICFKPAPYAQFRDTEVERLLPTYLRIQIQPNEGM

WFDLLAKKPGPSLDMANIELGFAYRDFFEMQPSTGYETLIYDCLIGDQTL

FQRADNIENGWRAVQPFLDAWQQDASLQNYPAGVDGPAAGDELLARDG

RVWRPLG

Nucleotide Sequence (SEQ. ID. NO: 124)

ATGACCACCACGCGAAAGAAGTCCAAGGCGTTGCCGGCGCCGCCGACCA

CGCTGTTCCTGTTCGGCGCCCGCGGTGATCTGGTCAAGCGCCTGCTGAT

GCCGGCGCTGTACAACCTCAGCCGCGACGGTTTGCTGGATGAGGGGCTG

CGGATTGTCGGCGTCGACCACAACGCGGTGAGCGACGCCGAGTTCGCCA

CGCTGCTGGAAGACTTCCTTCGCGATGAAGTGCTCAACAAGCAAGGCCA

GGGGGCGGCGGTGGATGCCGCCGTCTGGGCCCGCCTGACCCGGGGCATC

AACTATGTCCAGGCGGATTTTCTCGACGACTCCACCTATGCCGAACTGG

CGGCGCGGATTGCCGCCAGCGGCACCGGCAACGCGGTGTTCTACCTGGC

GCACCGCACCGCGCTTCTTCAGTGAAGTGGTGCGCCCCTGGGCAGCGCC

GGGTTGCTGGAGGAGGGCCGCAGGCTTTTCGCCGGGTGGTGATCGAAA

AACCCTTCGGCTCCGACCTGCAGACCGCCGAAGCCCTCAACGGCTGCCT

GCTCAAGGTCATGAGCGAGAAGCAGATCTATCGCATCGACCATTACCTG

GGCAAGGAAACGGTCCAGAACATCCTGGTCAGCCGTTTTTCCAACAGCC

TGTTCGAGGCATTCTGGAACAACCATTACATCGACCACGTGCAGATCAC

CGCGGCGGAAACCGTCGGCGTGGAAACCCGTGGCAGCTTTTATGAACAC

ACCGGTGCCCTGCGGGACATGGTGCCCAACCACCTGTTCCAGTTGCTGG

CGATGGTGGCCATGGAGCCGCCCGCTGCCTTTGGCGCCGATGCGGTACG

TGGCGAAAAGGCCAAGGTGGTGGGGGCTATCCGCCCCTGGTCCGTGGAA

GAGGCCCGGGCCAACTCGGTGCGCGGCCAGTACAGCGCCGGTGAAGTGG

CCGGCAAGGCCCTGGCGGGCTACCGCGAGGAAGCCAACGTGGCGCCGGA

CAGCAGCACCGAAACCTACGTTGCGCTGAAGGTGATGATCGACAACTGG

CGCTGGGTCGGGGTGCCGTTCTACCTGCGCACCGGCAAGCGCATGAGTG

TGCGCGACACCGAGATCGTCATCTGCTTCAAGCCGGCGCCCTATGCACA

GTTCCGCGATACCGAGGTCGAGCGCCTGTTGCCGACCTACCTGCGGATC

CAGATCCAGCCCAACGAAGGCATGTGGTTCGACCTGCTGGCGAAAAAGC

CCGGGCCAGCCTGGACATGGCCAACATCGAACTGGGTTTTGCCTACCG

CGACTTTTTCGAGATGCAGCCCTCCACCGGCTACGAAACCCTGATCTAC

GACTGCCTGATCGGCGACCAGACCCTGTTCCAGCGCGCCGACAACATCG

AGAACGGCTGGCGCGCGGTGCAACCCTTCCTCGATGCCTGGCAACAGGA

CGCCAGCTTGCAGAACTACCCGGCGGGCGTGGATGGCCCGGCAGCCGGG

GATGAACTGCTGGCCCGGGATGGCCGCGTATGGCGACCCCTGGGGTGA zwf2 from *P. fluorescens*

Amino Acid Sequence (SEQ. ID. NO: 125)

MPSITVEPCTFALFGALGDLALRKLFPALYQLDAAGLLHDDTRILALARE

PGSEQEHLANIETELHKYVGDKDIDSQVLQRFLVRLSYLHVDFLKAEDYV

ALAERVGSEQRLIAYFATPAAVYGAICENLSRVGLNQHTRVVLEKPIGSD

LDSSRKVNDAVAQFFPETRIYRIDHYLGKETVQNLIALRFANSLFETQWN

QNYISHVEITVAEKVGIEGRWGYFDKAGQLRDMIQNHLLQLLCLIAMDPP

ADLSADSIRDEKVKVLKALAPISPEGLTTQVVRGQYIAGHSEGQSVPGYL

EEENSNTQSDTETFVALRADIRNWRWAGVPFYLRTGKRMPQKLSQIVIHF

KEPSHYIFAPEQRLQISNKLIIRLQPDEGISLRVMTKEQGLDKGMQLRSG

PLQLNFSDTYRSARIPDAYERLLLEVMRGNQNLFVRKDEIEAAWKWCDQL

IAGWKKSGDAPKPYAAGSWGPMSSIALITRDGRSWYGDI

Nucleotide Sequence (SEQ. ID. NO: 126)

ATGCCTTCGATAACGGTTGAACCCTGCACCTTTGCCTTGTTTGGCGCGC

TGGGCGATCTGGCGCTGCGTAAGCTGTTTCCTGCCCTGTACCAACTCGA

TGCCGCCGGTTTGCTGCATGACGACACGCGCATCCTGGCCCTGGCCCGC

GAGCCTGGCAGCGAGCAGGAACACCTGGCGAATATCGAAACCGAGCTGC

ACAAGTATGTCGGCGACAAGGATATCGATAGCCAGGTCCTGCAGCGTTT

TCTCGTTCCGCCTGAGCTACCTGCATGTGGACTTCCTCAAGGCCGAGGAC

TACGTCGCCCTGGCCGAACGTGTCGGCAGCGAGCAGCGCCTGATTGCCT

ACTTCGCCACGCCGGCGGCGGTGTATGGCGCGATCTGCGAAAACCTCTC

CCGGGTCGGGCTCAACCAGCACACCCGTGTGGTCCTGGAAAAACCCATC

GGCTCGGACCTGGATTCATCACGCAAGGTCAACGACGCGGTGGCGCAGT

TCTTCCCGGAAACCCGCATCTACCGGATCGACCACTACCTGGGCAAGGA

AACGGTGCAGAACCTGATTGCCCTGCGTTTCGCCAACAGCCTGTTCGAA

ACCCAGTGGAACCAGAACTACATCTCCCACGTGGAAATCACCGTGGCCG

AGAAGGTCGGCATCGAAGGTCGCTGGGGCTATTTCGACAAGGCCGGCCA

ACTGCGGGACATGATCCAGAACCACTTGCTGCAACTGCTCTGCCTGATC

GCGATGGACCCGCCGGCCGACCTTTCGGCCGACAGCATCCGCGACGAGA

AGGTCAAGGTGCTCAAGGCCCTGGCGCCCATCAGCCCGGAAGGCCTGAC

CACCCAGGTGGTGCGCGGCCAGTACATCGCCGGCCACAGCGAAGGCCAG

TCGGTGCCGGGCTACCTGGAGGAAGAAAACTCCAACACCCAGAGCGACA

CCGAGACCTTCGTCGCCCTGCGCGCCGATATCCGCAACTGGCGCTGGGC

CGGTGTGCCTTCTACCTGCGCACCGGCAAGCGCATGCCACAGAAGCTG

TCGCAGATCGTCATCCACTTCAAGGAACCCTCGCACTACATCTTCGCCC

CCGAGCAGCGCCTGCAGATCAGCAACAAGCTGATCATCCGCCTGCAGCC

GGACGAAGGTATCTCGTTGCGGGTGATGACCAAGGAGCAGGGCCTGGAC zwf1 from *P. aeruginosa*, PAO1
Amino Acid Sequence (SEQ. ID. NO: 127)

MPDVRVLPCTLALFGALGDLALRKLFPALYQLDRENLLHRDTRVLALARD
EGAPAEHLATLEQRLRLAVPAKEWDDVVWQRFRERLDYLSMDFLDPQAYV
GLREAVDDELPLVAYFATPASVFGGICENLAAAGLAERTRVVLEKPIGHD
LESSREVNEAVARFFPESRIYRIDHYLGKETVQNLIALRFANSLFETQWN
QNHISHVEITVAEKVGIEGRWGYFDQAGQLRDMVQNHLLQLLCLIAMDPP
SDLSADSIRDEKVKVLRALEPIPAEQLASRVVRGQYTAGFSDGKAVPGYL
EEEHANRDSDAETFVALRVDIRNWRWSGVPFYLRTGKRMPQKLSQIVIHF
KEPPHYIFAPEQRSLISNRLIIRLQPDEGISLQVMTKDQGLGKGMQLRTG
PLQLSFSETYHAARIPDAYERLLLEVTQGNQYLFVRKDEVEFAWKWCDQ
LIAGWERLSEAPKPYPAGSWGPVASVALVARDGRSWYGDF

Nucleotide Sequence (SEQ. ID. NO: 128)

ATGCCTGATGTCCGCGTTCTGCCTTGCACGTTAGCGCTGTTCGGTGCGC
TGGGCGATCTCGCCTTGCGCAAGCTGTTCCCGGCGCTCTACCAACTCGA
TCGTGAGAACCTGCTGCACCGCGATACCCGCGTCCTGGCCCTGGCCCGT
GACGAAGGCGCTCCCGCCGAACACCTGGCGACGCTGGAGCAGCGCCTGC
GCCTGGCAGTGCCGGCGAAGGAGTGGGACGACGTGGTCTGGCAGCGTTT
CCGCGAACGCCTCGACTACCTGAGCATGGACTTCCTCGACCCGCAGGCC
TATGTCGGCTTGCGCGAGGCGGTGGATGACGAACTGCCGCTGGTCGCCT
ACTTCGCCACGCCGGCCTCGGTGTTCGGCGGCATCTGCGAGAACCTCGC
CGCCGCCGGTCTCGCCGAGCGCACCCGGGTGGTGCTGGAGAAGCCCATC
GGTCATGACCTGGAGTCGTCCCGCGAGGTCAACGAGGCAGTCGCCCGGT
TCTTCCCGGAAAGCCGCATCTACCGGATCGACCATTACCTGGGCAAGGA
GACGGTGCAGAACCTGATCGCCCTGCGCTTCGCCAACAGCCTCTTCGAG
ACCCAGTGGAACCAGAACCACATCTCCCACGTGGAGATCACCGTGGCCG
AGAAGGTCGGCATCGAAGGCCGCTGGGGCTACTTCGACCAGGCCGGGCA
ACTGCGCGACATGGTGCAGAACCACCTGCTGCAACTGCTCTGCCTGATC
GCCATGGATCCGCCCAGCGACCTTTCGGCGGACAGCATTCGCGACGAGA
AGGTCAAGGTCCTCCGCGCCCTCGAGCCGATTCCCGCAGAACAACTGGC
TTCGCGCGTGGTGCGTGGGCAGTACACCGCCGGTTTCAGCGACGGCAAG
GCAGTGCCGGGCTACCTGGAGGAGGAACATGCGAATCGCGACAGCGACG
CGGAAACCTTCGTCGCCCTGCGCGTGGACATCCGCAACTGGCGCTGGTC

AGGGCATGCAACTGCGCAGCGGTCCGTTGCAGCTGAATTTTTCCGATA
CCTATCGCAGTGCACGGATCCCCGATGCCTACGAGCGGTTGTTGCTGGA
AAGTGATGCGCGGCAATCAGACCTGTTTGTGCGCAAAGATGAAATCGAA
CGCCGCGTGAAGTGGTGTGACCAGTTGATTGCGGGTGGAAGAAATCCG
GCGATGCGCCCAAGCCGTACGCGGCCGGGTCCTGGGGGCCGATGAGCTC
CATTGCACTGATCACGCGGGATGGGAGGTCTTGGTATGGCGATATCTaA zwf1 from *Z. mobilis*
Amino Acid Sequence (SEQ. ID. NO: 129)

MTNTVSTMILFGSTGDLSQRMLLPSLYGLDADGLLADDLRIVCTSRSEYD
TDGFRDFAEKALDRFVASDRLNDDAKAKFLNKLFYATVDITDPTQFGKLA
DLCGPVEKGIAIYLSTAPSLFEGAIAGLKQAGLAGPTSRLALEKPLGQDL
ASSDHINDAVLKVFSEKQVYRIDHYLGKETVQNLLTLRFGNALFEPLWNS
KGIDHVQISVAETVGLEGRIGYFDGSGSLRDMVQSHILQLVALVAMEPPA
HMEANAVRDEKVKVFRALRPINNDTVFTHTVTGQYGAGVSGGKEVAGYID
ELGQPSDTETFVAIKAHVDNWRWQGVPFYIRTGKRLPARRSEIVVQFKPV
PHSIFSSSGGILQPNKLRIVLQPDETIQISMMVKEPGLDRNGAHMREVWL
DLSLTDVFKDRKRRIAYERLMLDLIEGDATLFVRRDEVEAQWVWIDGIRE
GWKANSMKPKTYVSGTWGPSTAIALAERDGVTWYD

Nucleotide Sequence (SEQ. ID. NO: 130)

ATGACAAATACCGTTTCGACGATGATATTGTTTGGCTCGACTGGCGACC
TTTCACAGCGTATGCTGTTGCCGTCGCTTTATGGTCTTGATGCCGATGG
TTTGCTTGCAGATGATCTGCGTATCGTCTGCACCTCTCGTAGCGAATAC
GACACAGATGGTTTCCGTGATTTTGCAGAAAAAGCTTTAGATCGCTTTG
TCGCTTCTGACCGGTTAAATGATGACGCTAAAGCTAAATTCCTTAACAA
GCTTTTCTACGCGACGGTCGATATTACGGATCCGACCCAATTCGGAAAA
GTTAGCTGACCTTTGTGGCCCGTCGAAAAGGTATCGCCATTTATCTTT
GCGACTGCGCCTTCTTTGTTTGAAGGGGCAATCGCTGCCTGAAACAGGC
TGGTCTGGCTGGTCCAACTTCTCGCCTGGCGCTTGAAAAACCTTTAGGT
CAAGATCTTGCTTCTTCCGATCATATTAATGATGCGGTTTTGAAAGTTT
TCTCTGAAAAGCAAGTTTATCGTATTGACCATTATCTGGGTAAAGAAAC
GGTTCAGAATCTTCTGACCCTGCGTTTTGGTAATGCTTTGTTTGAACCG
CTTTGGAATTCAAAAGGCATTGACCACGTTCAGATCAGCGTTGCTGAAA
CGGTTGGTCTTGAAGGTCGTATCGGTTATTTCGACGGTTCTGGCAGCTT
GCGCGATATGGTTCAAAGCCATATCCTTCAGTTGGTCGCTTTGGTTGCA
ATGGAACCACCGGCTCATATGGAAGCCAACGCTGTTCGTGACGAAAAGG

-continued

```
TAAAAGTTTTCCGCGCTCTGCGTCCGATCAATAACGACACCGTCTTTAC

GCATACCGTTACCGGTCAATATGGTGCCGGTGTTTCTGGTGGTAAAGAA

GTTGCCGGTTACATTGACGAACTGGGTCAGCCTTCCGATACCGAAACCT

TTGTTGCTATCAAAGCGCATGTTGATAACTGGCGTTGGCAGGGTGTTCC

GTTCTATATCCGCACTGGTAAGCGTTTACCTGCACGTCGTTCTGAAATC

AGGGTGGTTCAGTTTAAACCTGTTCCGCATTCGATTTTCTCTTCTTCTG

GTATCTTGCAGCCGAACAAGCTGCGTATTGTCTTACAGCCTGATGAAAC

CATCCAGATTTCTATGATGGTGAAAGAACCGGGTCTTGACCGTAACGGT

GCGCATATGCGTGAAGTTTGGCTGGATCTTTCCCTCACGGATGTGTTTA

AAGACCGTAAACGTCGTATCGCTTATGAACGCCTGATGCTTGATCTTAT

CGAAGGCGATGCTACTTTATTTGTGCGTCGTGACGAAGTTGAGGCGCAG

TGGGTTTGGATTGACGGAATTCGTGAAGGCTGGAAAGCCAACAGTATGA

AGCCAAAAACCTATGTCTCTGGTACATGGGGCCTTCAACTGCTATAGC

TCTGGCCGAACGTGATGGAGTAACTTGGTATGACTGA
```

All the above genes were PCR amplified from their genomic DNA sources with and without c-terminal 6-HIS tags (SEQ ID NO: 138) and cloned into the yeast expression vector p426GPD for testing.

Assays of Candidate ZWF1 Genes

Strain BY4742 zwf1 (ATCC Cat. No. 4011971; Winzeler E A, et al. Science 285: 901-906, 1999. PubMed: 10436161) was used as the base strain for all ZWF1 assays. The assays were performed as follows: A 5 ml overnight of the strain expressing the ZWF1 gene was grown in SCD-ura. A 50 ml culture of the strain was then grown for about 18 hours from an initial $OD_{600}$ of about 0.2 until it had reached about $OD_{600}$ of about 4. The cells were centrifuged at 1046×g washed twice with 25 ml cold sterile water, and resuspended in 2 ml/g Yper Plus (Thermo Scientific) plus 1×protease inhibitors (EDTA-free). The cells were allowed to lyse at room temperature for about 30 minutes with constant rotation of the tubes. The lysate was centrifuged at 16,100×g for 10 minutes at 4° C. and the supernatants were transferred to a new 1.5 ml microcentrifuge tube. Quantification of the lysates was performed using the Coomassie-Plus kit (Thermo Scientific, San Diego, Calif.) as directed by the manufacturer.

Each kinetic assay was done using approximately 50 to 60 µg of crude extract in a reaction mixture containing 50 mM Tris-HCl, pH 8.9, and 1 mM NADP+ or NAD+. The reaction was started with 20 mM glucose-6-phosphate and the reaction was monitored at A340. The specific activity was measured as the µmol substrate/min/mg protein. The results of the assays are presented in the table below.

| Zwf1 | Cofactors | Vmax (µmol min$^{-1}$) | Km (M$^{-1}$) | Specific Activity (µmol min$^{-1}$ mg$^{-1}$) |
|---|---|---|---|---|
| S. cerevisiae | NAD+ | NA | NA | NA |
|  | NADP+ | 0.9523 | 0.4546 | 224.07 |
| S. cerevisiae + His | NAD+ | NA | NA | NA |
|  | NADP+ | 0.7267 | 0.4109 | 164.79 |
| ZM4 | NAD+ | NA | NA | NA |
|  | NADP+ | NA | NA | NA |
| ZM4 + His | NAD+ | 0.0213 | 0.0156 | 0.1267 |
|  | NADP+ | 0.0027 | 0.0140 | 0.0160 |
| P. fluorescens 1 | NAD+ | 0.0158 | 0.6201 | 0.3132 |
|  | NADP+ | 0.0213 | 0.8171 | 0.4208 |
| P. fluorescens 1 + His | NAD+ | 0.0126 | 4.9630 | 0.2473 |
|  | NADP+ | 0.0139 | 0.9653 | 0.2739 |
| P. fluorescens 2 | NAD+ | ND | ND | ND |
|  | NADP+ | NA | NA | NA |
| P. fluorescens 2 + His | NAD+ | NA | NA | NA |
|  | NADP+ | ND | ND | ND |
| PAO1 | NAD+ | NA | NA | NA |
|  | NADP+ | 0.0104 | 0.6466 | 0.1564 |
| PAO1 + His | NAD+ | 0.0074 | 0.0071 | 0.1098 |
|  | NADP+ | 0.0123 | 3.9050 | 0.1823 |

NA = cannot be calculated (substrate not used by enzyme)
ND = was not determined (either not enough crude available or cells did not grow)

Altering Cofactor Preference of S. cerevisiae ZWF1

ZWF1 from S. cerevisiae is an NADP+-only utilizing enzyme. Site-directed mutagenesis was used to alter of ZWF1 so that the altered ZWF1 could also utilize NAD+, thereby improving the REDOX balance within the cell. Site directed mutagenesis reactions were performed in the same manner for all mutations, and for mutants which include more than one mutation, each mutation was performed sequentially. About 50 ng of plasmid DNA was added to 1×Pfu Ultra II buffer, 0.3 mM dNTPs, 0.3 µmol site directed mutagenesis specific primers, and 1 U Pfu Ultra II polymerase (Agilent, La Jolla, Calif.) in a 50 µl reaction mix. The reaction was cycled at 95° C. for 10 minutes, followed by 15 rounds of 95° C. for 15 seconds, 55° C. for 40 seconds, and 72° C. for 3 minutes. A final 10 minute extension reaction at 72° C. was also included. The PCR reaction mixture was then digested with 30 U of DpnI for about 2 hours and 5 µl of the digested PCR reaction mixture was used to transform competent DH5α (Zymo Research, Orange, Calif.) and plated onto LB plates containing the appropriate antibiotics. The table below lists mutants generated in a first round of mutagenesis.

| Mutant # | zwf1_sc | Codon changes |
|---|---|---|
| 1 | A24G | GCA -> GGT |
| 2 | A24G/T28G | GCA -> GGT, ACT -> GGT |
| 3 | A51N | GCC -> AAT |
| 4 | A51D | GCC -> GAT |
| 5 | T28F | ACT -> TTT |
| 6 | K46R | AAG -> AGA |
| 7 | Y40L | TAC -> TTG |
| 8 | F33Y | TTT -> TAC |
| 9 | T28L | ACT -> TTG |
| 10 | V16L | GTC -> TTG |
| 11 | V13T | GTC -> ACT |
| 12 | L66E | CTA -> GAA |
| 13 | A24G/A51D | GCA -> GGT, GCC -> GAT |
| 14 | A24G/T28G/A51D | GCA -> GGT, ACT -> GGT, GCC -> GAT |
| 15 | R52D | CGG -> GAT |
| 16 | A51D/R52A | GCC -> GAT, CGG -> GCT |
| 17 | A24G/A51D/R52A | GCA -> GGT, GCC -> GAT, CGG -> GCT |
| 18 | A24G/T28G/ A51D/R52A | GCA -> GGT, ACT -> GGT, GCC -> GAT, CGG -> GCT |
| 19 | A51D/R52H | GCC -> GAT, CGG -> CAT |
| 20 | R52H | CGG -> CAT |
| 21 | D22R | GAT -> AGA |

The oligonucleotides, utilized to generate the mutants listed in the table above, are listed in the table below. All oligonucleotides were purchased from Integrated DNA Technologies (IDT).

| Mutation | Base plasmid | Oligo Name | Nucleotide sequence (SEQ ID NOS 375-412, respectively, in order of appearance) |
|---|---|---|---|
| 1 | pBF300 | ka/zwf1sc_A24Gfor | gtgcgtcaggtgatctgggtaagaagaagacttttccc |
| 1 | pBF300 | ka/zwf1sc_A24Grev | gggaaaagtcttcttcttacccagatcacctgacgcac |
| 2 | pBF300 | ka/zwf1sc_T28Gfor | gtgatctgggtaagaagaagggttttcccgccttatttgg |
| 2 | pBF300 | ka/zwf1sc_T28Grev | CCAAATAAGGCGGGAAAACCCTTCTTCTTAC CCAGATCAC |
| 3 | pBF300 | ka/zwf1sc_A51Nfor | ccttgatccatctaccaagatcttcggttataatcggtccaaattgtc cat |
| 3 | pBF300 | ka/zwf1sc_A51Nrev | atggacaatttggaccgattataaccgaagatcttggtagatggat caagg |
| 4 | pBF300 | ka/zwf1sc_A51Dfor | atctaccaagatcttcggttatgatcggtccaaattgtccatg |
| 4 | pBF300 | ka/zwf1sc_A51Drev | catggacaatttggaccgatcataaccgaagatcttggtagat |
| 5 | pBF300 | ka/zwf1sc_T28Ffor | ggtgatctggcaaagaagaagtttttcccgccttatttggg |
| 5 | pBF300 | ka/zwf1sc_T28Frev | cccaaataaggcgggaaaaaacttcttctttgccagatcacc |
| 6 | pBF300 | ka/zwf1sc_K46Rfor | taccttgatccatctaccagaatcttcggttatgcccggt |
| 6 | pBF300 | ka/zwf1sc_K46Rrev | accgggcataaccgaagattctggtagatggatcaaggta |
| 7 | pBF300 | ka/zwf1sc_Y39Lfor | gggcttttcagagaaggtttgcttgatccatctaccaaga |
| 7 | pBF300 | ka/zwf1sc_Y39Lrev | tcttggtagatggatcaagcaaaccttctctgaaaagccc |
| 8 | pBF300 | ka/zwf1sc_F33Yfor | gaagaagacttttcccgccttatacgggcttttcagagaag |
| 8 | pBF300 | ka/zwf1sc_F33Yrev | cttctctgaaaagcccgtataaggcgggaaaagtcttcttc |
| 9 | pBF300 | ka/zwf1sc_T28Lfor | gtcaggtgatctggcaaagaagaagttgtttcccgccttatttgg |
| 9 | pBF300 | ka/zwf1sc_T28Lrev | ccaaataaggcgggaaacaacttcttctttgccagatcacctgac |
| 10 | pBF300 | ka/zwf1sc_V16Lfor | cgaaaaaaatccgtcatatctttgtttggtgcgtcaggtgatctg |
| 10 | pBF300 | ka/zwf1sc_V16rev | cagatcacctgacgcaccaaacaaagatatgacggatttttttcg |
| 12 | pBF300 | ka/zwf1sc_L66Efor | gacctgaagtcccgtgtcgaaccccacttgaaaaaacc |
| 12 | pBF300 | ka/zwf1sc_L66Erev | ggttttttcaagtggggttcgacacgggacttcaggtc |
| 13 | pBF374 | ka/zwf1sc_A24Gfor | gtgcgtcaggtgatctgggtaagaagaagacttttccc |
| 13 | pBF374 | ka/zwf1sc_A24Grev | gggaaaagtcttcttcttacccagatcacctgacgcac |
| 14 | pBF374 | ka/zwf1sc_A24Gfor | gtgcgtcaggtgatctgggtaagaagaagacttttccc |
| 14 | pBF374 | ka/zwf1sc_A24Grev | gggaaaagtcttcttcttacccagatcacctgacgcac |
| 15 | pBF300 | KA/zwf1mut15for | accaagatcttcggttatgccgattccaaattgtccatggaggag |
| 15 | pBF300 | KA/zwf1mut15rev | ctcctccatggacaatttggaatcggcataaccgaagatcttggt |
| 16 | pBF374 | KA/zwf1mut16for | tccatctaccaagatcttcggttatgatgcttccaaattgtccatgga ggagac |
| 16 | pBF374 | KA/zwf1mut16rev | gtcctcctccatggacaatttggaagcatcataaccgaagatcttg gtagatgga |
| 17 | pBF441 | KA/zwf1mut16for | tccatctaccaagatcttcggttatgatgcttccaaattgtccatgga ggagac |
| 17 | pBF441 | KA/zwf1mut16rev | gtcctcctcctccatggacaatttggaagcatcataaccgaagatcttg gtagatgga |
| 18 | pBF442 | KA/zwf1mut16for | tccatctaccaagatcttcggttatgatgcttccaaattgtccatgga ggagac |
| 18 | pBF442 | KA/zwf1mut16rev | gtcctcctcctccatggacaatttggaagcatcataaccgaagatcttg gtagatgga |

-continued

| Base Mutation | plasmid | Oligo Name | Nucleotide sequence (SEQ ID NOS 375-412, respectively, in order of appearance) |
|---|---|---|---|
| 19 | pBF374 | KA/zwf1sc_mut19for | aagatcttcggttatgatcattccaaattgtccatggagg |
| 19 | pBF374 | KA/zwf1sc_mut19rev | cctccatggacaatttggaatgatcataaccgaagatctt |
| 20 | pBF300 | KA/zwf1sc_mut20for | aagatcttcggttatgcccattccaaattgtccatggagg |
| 20 | pBF300 | KA/zwf1sc_mut20rev | cctccatggacaatttggaatgggcataaccgaagatctt |

Initial kinetic screening of the ZWF1 mutants generated as described above, identified the following altered ZWF1 genes and preliminary cofactor phenotype.

| Mutant # | zwf1_sc | NAD+ usage | NADP+ usage |
|---|---|---|---|
| 1 | A24G | No | Yes |
| 2 | A24G/T28G | No | No |
| 3 | A51N | No | Yes |
| 4 | A51D | Yes | No |
| 5 | T28F | No | Yes |
| 6 | K46R | No | Yes |
| 7 | Y40L | No | Yes |
| 8 | F33Y | No | Yes |
| 9 | T28L | No | Yes |
| 10 | V16L | No | Yes |
| 11 | V13T | ND | ND |
| 12 | L66E | No | Yes |
| 13 | A24G/A51D | Yes | No |
| 14 | A24G/T28G/A51D | No | No |
| 15 | R52D | No | No |
| 16 | A51D/R52A | No | No |
| 17 | A24G/A51D/R52A | No | No |
| 18 | A24G/T28G/A51D/R52A | ND | ND |
| 19 | A51D/R52H | ND | ND |
| 20 | R52H | ND | ND |
| 21 | D22R | ND | ND |

ND = not determined

Mutants 4 (A51 D) and 13 (A24G/A51 D) were identified as mutants which enabled NAD+utilization with concomitant loss of NADP+utilization.

Cloning of SOL3

The SOL3 gene from S. cerevisiae was cloned as follows. The approximately 750 bp SOL3 gene was PCR amplified from the BY4742 genome using primers KAS/5-SOL3-NheI and KAS/3'-SOL3-SalI, shown below.

```
KAS/5-SOL3-NheI
                                     (SEQ ID NO: 413)
gctagcatggtgacagtcggtgtgttttctgag KAS/3'-SOL3-SalI
                                     (SEQ ID NO: 414)
gtcgacctaaaaagttttcgtttgaactttcc
```

About 100 ng of genomic DNA from S. cerevisiae strain BY4742 was added to 1×Pfu Ultra II buffer, 0.3 mM dNTPs, 0.3 μmol gene-specific primers, and 1 U Pfu Ultra II polymerase (Agilent, La Jolla, Calif.) in a 50 μl reaction mix. The reaction was cycled at 95° C. for 10 minutes, followed by 30 rounds of 95° C. for 20 seconds, 55° C. for 30 seconds, and 72° C. for 15 seconds. A final 5 minute extension reaction at 72° C. was also included. The amplified product was TOPO cloned into the pCR Blunt II TOPO vector (Life Technologies, Carlsbad, Calif.) according to the manufacturer's recommendations and sequence verified (GeneWiz, San Diego, Calif.). The resultant plasmid was designated pBF301. The sequence of the S. cerevisiae SOL3 gene is given below.

S. cerevisiae SOL3 (SEQ. ID. NO: 131)

ATGGTGACAGTCGGTGTGTTTTCTGAGAGGGCTAGTTTGACCCATCAATT

GGGGGAATTCATCGTCAAGAAACAAGATGAGGCGCTGCAAAAGAAGTCAG

ACTTTAAAGTTTCCGTTAGCGGTGGCTCTTTGATCGATGCTCTGTATGAA

AGTTTAGTAGCGGACGAATCACTATCTTCTCGAGTGCAATGGTCTAAATG

GCAAATCTACTTCTCTGATGAAAGAATTGTGCCACTGACGGACGCTGACA

GCAATTATGGTGCCTTCAAGAGAGCTGTTCTAGATAAATTACCCTCGACT

AGTCAGCCAAACGTTTATCCCATGGACGAGTCCTTGATTGGCAGCGATGC

TGAATCTAACAACAAAATTGCTGCAGAGTACGAGCGTATCGTACCTCAAG

TGCTTGATTTGGTACTGTTGGGCTGTGGTCCTGATGGACACACTTGTTCC

TTATTCCCTGGAGAAACACATAGGTACTTGCTGAACGAAACAACCAAAAG

AGTTGCTTGGTGCCACGATTCTCCCAAGCCTCCAAGTGACAGAATCACCT

TCACTCTGCCTGTGTTGAAAGACGCCAAAGCCCTGTGTTTTGTGGCTGAG

GGCAGTTCCAAACAAAATATAATGCATGAGATCTTTGACTTGAAAAACGA

TCAATTGCCAACCGCATTGGTTAACAAATTATTTGGTGAAAAAACATCCT

GGTTCGTTAATGAGGAAGCTTTTGGAAAAGTTCAAACGAAAACTTTTTAG

The NheI-SalI SOL3 gene fragment from plasmid pBF301 will be cloned into the SpeI-XhoI site in plasmids p413GPD and p423GPD (HIS3 marker-based plasmids; ATCC 87354 and ATCC 87355).

Testing of ZWF1/SOL3 Combinations in BY4742

A URA blaster cassette was digested with NotI and ligated into the MET17 integration cassette plasmid pBF691 to generate the Met17 knockout plasmid pBF772. Plasmid pBF772 was digested with PacI and linear fragments were purified by Zymo PCR purification kit (Zymo Research, Orange, Calif.) and concentrated in 10 μl ddH2O. LiCl2 high efficiency transformation was performed as shown described. About 1 μg linear MET17 knockout fragment was transformed into 50 μl fresh made BY4742 competent cells and cells were plated onto SCD-Ura plates at 30° C. for about 2-3 days. A single URA+ colony was streaked out on a SCD-Ura plate and grown at 30° C. for about 2-3 days. A single colony was inoculated overnight in YPD medium at 30° C. 50 μl of the overnight culture was then plated onto SCD complete -5FOA plates and incubated at 30° C. for about 3 days.

A single colony which grew on SCD complete-5FOA plates was then picked and inoculated in YPD medium and grown at 30° C. overnight. Yeast genomic DNA was extracted by YeaStar genomic extraction kit (Zymo Research, Orange, Calif.) and confirmation of the strain was confirmed by PCR using primers JML/237 and JML/238, shown below.

JML/237:
(SEQ ID NO: 415)
CCAACACTAAGAAATAATTTCGCCATTTCTTG

JML/238:
(SEQ ID NO: 416)
GCCAACAATTAAATCCAAGTTCACCTATTCTG

The PCR amplification was performed as follows: 10 ng of yeast genomic DNA with 0.1 μmol gene specific primers, 1×Pfu Ultra II buffer, 0.2 mmol dNTPs, and 0.2 U Taq DNA polymerase. The PCR mixture was cycled at 95° C. for 2 minutes, followed by 30 cycles of 95° C. for 20 seconds, 55° C. for 30 seconds and 72° C. for 45 seconds. A final step of 72° C. for 5 minutes was also included. The resultant strain was designated BF1618.

Strain BF1618 is undergoing transformation with the following plasmid combinations. Additionally, the affect of the ZWF1 mutant constructs will also be evaluated with and without SOL3 constructs. The table below shows the plasmid combinations being transformed into strain BF1618.

| Test Strain | EDD | EDA | ZWF1 | SOL3 |
|---|---|---|---|---|
| 1 | 2μ | 2μ | cen/ars | NONE |
| 2 | 2μ | 2μ | 2μ | NONE |
| 3 | 2μ | 2μ | cen/ars | cen/ars |
| 4 | 2μ | 2μ | 2μ | 2μ |
| 5 | 2μ | 2μ | NONE | cen/ars |
| 6 | 2μ | 2μ | NONE | 2μ |

Strains with improved ethanol production may benefit from two or more copies of the ZWF1 gene due to increased flux of the carbon towards the alternative pathway. A strain embodiment currently under construction has the phenotype; pfk1, ZWF1, SOL3, tal1, EDD-PAO1*, EDA-*E. coli**, where the "*" represents additional copies of the gene. It is believed that multiple copies of the EDD and EDA genes may provide additional increases in ethanol production.

Example 28

Identification of Additional Xylose Isomerase 5' Ends that can Increase Expression Levels of *Ruminococcus* Xylose Isomerase in Yeast To determine if the 5' end of other xylose isomerase genes could also be used to increase the expression of the *Ruminococcus* xylose isomerase in yeast, as demonstrated herein for the 5' end of *Piromyces* xylose isomerase, additional chimeric molecules were generated as described herein, using approximately 10 amino acids from the xylose isomerase genes described in Example 25. The alternate xylose isomerase gene 5' ends were selected from xylose isomerase sequences previously shown to be expressed and active inn yeast. The xylose isomerase gene donors and the 5' end of the nucleotide sequence from each are presented in the table below.

| | |
|---|---|
| *Clostridium phytofermentans* | ATGAAAAATTACTTTCCAAATGTTCCAGAAGTAAAATACGAAGGCCCAAATTCAACG<br>AATCCATTTGCTTTTAAATATTATGACGCAAATAAAGTTGTAGCGGGTAAAACAATG<br>AAAGAGCACTGTCGTTTTGCATTATCTTGGTGGCATACTCTTTGTGCAGGTGGTGC<br>TGATCCATTCGGTGTAACAACTATGGATAGAACCTACGGAAATATCACAGATCCAA<br>TGGAACTTGCTAAGGCAAAAGTTGACGCTGGTTTCGAATTAATGACTAAATTAGGA<br>ATTGAATTCTTCTGTTTCCATGACGCAGATATTGCTCCAGAAGGTGATACTTTTGAA<br>GAGTCAAAGAAGAATCTTTTTGAAATCGTTGATTACATCAAAGAGAAGATGGATCA<br>GACTGGTATCAAGTTATTATGGGGTACTGCTAATAACTTTAGTCATCCAAGATTTAT<br>GCAT (SEQ ID NO: 95) |
| *Orpinomyces* | ATGACTAAGGAATATTTCCCAACTATCGGCAAGATTAGATTCGAAGGTAAGGATTC<br>TAAGAATCCAATGGCCTTCCACTACTATGATGCTGAAAAGGAAGTCATGGGTAAGA<br>AAATGAAGGATTGGTTACGTTTCGCCATGGCCTGGTGGCACACTCTTTGCGCCGA<br>TGGTGCTGACCAATTCGGTGTTGGTACTAAGTCTTTCCCATGGAATGAAGGTACTG<br>ACCCAATTGCTATTGCCAAGCAAAAGGTTGATGCTGGTTTTGAAATCATGACCAAG<br>CTTGGTATTGAACACTACTGTTTCCACGATGTTGATCTTGTTTCTGAAGGTAACTCT<br>ATTGAAGAATACGAATCCAACCTCAAGCAAGTTGTTGCTTACCTTAAGCAAAAGCA<br>ACAAGAAACTGGTATTAAGCTTCTCTGGAGTACTGCCAATGTTTTCGGTAACCCAC<br>GTTACATGAAC (SEQ ID NO: 96) |
| *Clostridium thermohydrosulfuricum* | ATGGAATACTTCAAAAATGTACCACAAATAAAATATGAAGGACCAAAATCAAACAAT<br>CCATATGCATTTAAATTTTACAATCCAGATGAAATAATAGACGGAAAACCTTTAAAA<br>GAACACTTGCGTTTTTCAGTAGCGTACTGGCACACATTTACAGCCAATGGGACAGA<br>TCCATTTGGAGCACCCACAATGCAAAGGCCATGGGACCATTTTACTGACCCTATG<br>GATATTGCCAAAGCGAGAGTAGAAGCAGCCTTTGAACTATTTGAAAAACTCGACGT<br>ACCATTTTCTGTTTCCATGACAGAGATATAGCTCCGGAAGGAGAGACATTAAGGG<br>AGACGAACAAAAATTTAGATACAATAGTTGCAATGATAAAAGACTACTTAAAGACGA<br>GCAAAACAAAAGTATTATGGGGCACAGCGAACCTTTTTTCAAATCCGAGATTTGTA<br>CAT (SEQ ID NO: 97) |
| *Bacteroides thetaiotaomicron* | ATGGCAACAAAAGAATTTTTTCCGGGAATTGAAAAGATTAAATTTGAAGGTAAAGAT<br>AGTAAGAACCCGATGGCATTCCGTTATTACGATGCAGAGAAGGTGATTAATGGTAA<br>AAAGATGAAGGATTGGCTGAGATTCGCTATGGCATGGTGGCACACATTGTGCGCT<br>GAAGGTGGTGATCAGTTCGGTGGCGGAACAAAGCAATTCCCATGGAATGGTAATG<br>CAGATGCTATACAGGCAGCAAAAGATAAGATGGATGCAGGATTTGAATTCATGCAG<br>AAGATGGGTATCGAATACTATTGCTTCCATGACGTAGACTTGGTTTCGGAAGGTGC<br>CAGTGTAGAAGAATACGAAGCTAACCTGAAAGAAATCGTAGCTTATGCAAAACAGA<br>AACAGGCAGAAACCGGTATCAAACTACTGTGGGGTACTGCTAATGTATTCGGTCA<br>CGCCCGCTATATGAAC (SEQ ID NO: 98) |
| *Bacillus stearothermophilus* | ATGGCTTATTTTCCGAATATCGGCAAGATTGCGTATGAAGGGCCGGAGTCGCGCA<br>ATCCGTTGGCGTTTAAGTTTTATAATCCAGAAGAAAAAGTCGGCGACAAAACAATG |

-continued

|  |  |
|---|---|
|  | GAGGAGCATTTGCGCTTTTCAGTGGCCTATTGGCATACGTTTACGGGGGATGGGT<br>CGGATCCGTTTGGCGTCGGCAATATGATTCGTCCATGGAATAAGTACAGCGGCAT<br>GGATCTGGCGAAGGCGCGCGTCGAGGCGGCGTTTGAGCTGTTTGAAAAGCTGAA<br>CGTTCCGTTTTTCTGCTTCCATGACGTCGACATCGCGCCGGAAGGGGAAACGCTC<br>AGCGAGACGTACAAAAATTTGGATGAAATTGTCGATATGATTGAAGAATACATGAA<br>AACAAGCAAAACGAAGCTGCTTTGGAATACGGCGAACTTGTTCAGCCATCCGCGC<br>TTCGTTCAC (SEQ ID NO: 99) |
| Bacillus uniformis | ATGGCTACCAAGGAATACTTCCCAGGTATTGGTAAGATCAAATTCGAAGGTAAGGA<br>ATCCAAGAACCCAATGGCCTTCAGATACTACGATGCTGACAAGGTTATCATGGGTA<br>AGAAGATGTCTGAATGGTTAAAGTTCGCTATGCTTGGTGGCATACCTTGTGTGCT<br>GAAGGTGGTGACCAATTCGGTGGTGGTACCAAGAAATTCCCATGGAACGGTGAAG<br>CTGACAAGGTCCAAGCTGCTAAGAACAAGATGGACGCTGGTTTCGAATTTATGCAA<br>AAGATGGGTATTGAATACTACTGTTTCCACGATGTTGACTTGTGTGAAGAAGCTGA<br>AACCATCGAAGAATACGAAGCTAACTTGAAGGAAATTGTTGCTTACGCTAAGCAAA<br>AGCAAGCTGAAACTGGTATCAAGCTATTATGGGGTACTGCTAACGTCTTTGGTCAT<br>GCCAGATACATGAAC (SEQ ID NO: 100) |
| Clostridium cellulolyticum | ATGTCAGAAGTATTTAGCGGTATTTCAAACATTAAATTTGAAGGAAGCGGGTCAGA<br>TAATCCATTAGCTTTTAAGTACTATGACCCTAAGGCAGTTATCGGCGGAAAGACAA<br>TGGAAGAACATCTGAGATTCGCAGTTGCCTACTGGCATACTTTTGCAGCACCAGGT<br>GCTGACATGTTCGGTGCAGGATCATATGTAAGACCTTGGAATACAATGTCCGATCC<br>TCTGGAAATTGCAAAATACAAAGTTGAAGCAAACTTTGAATTCATTGAAAAGCTGG<br>GAGCACCTTTCTTCGCTTTCCATGACAGGGATATTGCTCCTGAAGGCGACACACTC<br>GCTGAAACAAATAAAAACCTTGATACAATAGTTTCAGTAATTAAAGATAGAATGAAA<br>TCCAGTCCGGTAAAGTTATTATGGGGAACTACAAATGCTTTCGGAAACCCAAGATT<br>TATGCAT (SEQ ID NO: 101) |
| Ruminococcus<br>flavefaciens FD1 | ATGGAATTTTTTCAAGAACATAAGCAAGATCCCTTACGAGGGCAAGGACAGCACAAA<br>TCCTCTCGCATTCAAGTACTACAATCCTGATGAGGTAATTGACGGCAAGAAGATGC<br>GTGACATTATGAAGTTTGCTCTCTCATGGTGGCATACAATGGGCGGCGACGGAAC<br>AGATATGTTCGGCTGCGGTACAGCTGACAAGACATGGGGCGAAAATGATCCTGCT<br>GCAAGAGCTAAGGCTAAGGTTGACGCAGCTTTCGAGATCATGCAGAAGCTCTCTA<br>TCGATTACTTCTGTTTCCACGACCGTGATCTTTCTCCTGAGTACGGCTCACTGAAG<br>GACACAAACGCTCAGCTGGACATCGTTACAGATTACATCAAGGCTAAGCAGGCTG<br>AGACAGGTCTCAAGTGCCTCTGGGGTACAGCTAAGTGCTTCGATCACCCAAGATT<br>CATGCAC (SEQ ID NO: 102) |
| Ruminococcus 18P13 | ATGAGCGAATTTTTTACAGGCATTTCAAAGATCCCCTTTGAGGGAAAGGCATCCAA<br>CAATCCCATGGCGTTCAAGTACTACAACCCGGATGAGGTCGTAGGCGGCAAGACC<br>ATGCGGGAGCAGCTGAAGTTTGCGCTGTCCTGGTGGCATACTATGGGGGGAGAC<br>GGTACGGACATGTTTGGTGTGGGTACCACCAACAAGAAGTTCGGCGGAACCGATC<br>CCATGGACATTGCTAAGAGAAAGGTAAACGCTGCGTTTGAGCTGATGGACAAGCT<br>GTCCATCGATTATTTCTGTTTCCACGACCGGGATCTGGCGCCGGAGGCTGATAAT<br>CTGAAGGAAACCAACCAGCGTCTGGATGAAATCACCGAGTATATTGCACAGATGA<br>TGCAGCTGAACCCGGACAAGAAGGTTCTGTGGGGTACTGCAAATTGCTTCGGCAA<br>TCCCCGGTATATGCAT (SEQ ID NO: 103) |
| Clostriales genomosp<br>BVAB3 str UPII9-5 | ATGAAATTTTTTGAAAATGTCCCTAAGGTAAAATATGAGGGAAGCAAGTCTACCAA<br>CCCGTTTGCATTTAAGTATTACAATCCTGAAGCGGTGATTGCCGGTAAAAAAATGA<br>AGGATCACCTGAAATTCGCGATGTCCTGGTGGCACACCATGACGGCGACCGGGC<br>AAGACCAGTTCGGTTCGGGGACGATGAGCCGAATATATGACGGGCAAACTGAACC<br>GCTGGCCTTGGCCAAAGCCCGAGTGGATGCGGCTTTCGATTTCATGGAAAAATTA<br>AATATCGAATATTTTTGTTTTCATGATGCCGACTTGGCTCCAGAAGGTAACAGTTTG<br>CAGGAACGCAACGAAAATTTGCAGGAAATGGTGTCTTACCTGAAACAAAAGATGG<br>CCGGAACTTCGATTAAGCTTTTATGGGGAACCTCGAATTGTTTCAGCAACCCTCGT<br>TTTATGCAC (SEQ ID NO: 104) |

The first 10 amino acids (30 bp) of XI-R was replaced with the 5' edge from the xylose isomerase genes presented in the table above using a single oligonucleotide in a PCR reaction, described herein. The oligonucleotides used for the PCR reactions are shown in the table below. The last 2 oligonucleotides were used as 3' oligonucleotides to amplify each resulting chimeric molecule with or without a c-terminal 6-HIS tag (SEQ ID NO: 138).

| Name | Oligonucleotide sequence (SEQ ID NOS 361-370 and 373-374, respectively, in order of appearance) |
|---|---|
| KAS/5-XR_Cp10 | ACTAGTAAAAAATGAAAAATTACTTTCCAAATGTTCCAGAAGTACAGTATCAGGGACCAAAAAG |
| KAS/5-XR-O10 | ACTAGTAAAAAATGACTAAGGAATATTTCCCAACTATCGGCAAGATTCAGTATCAGGGACCAAAA<br>AG |
| KAS/5-XR-Cth10 | ACTAGTAAAAAATGGAATACTTCAAAAATGTACCACAAATAAAACAGTATCAGGGACCAAAAAG |
| KAS/5-XR-Bth10 | ACTAGTAAAAAATGGCAACAAAAGAATTTTTTCCGGGAATTGAAAAGATTCAGTATCAGGGACCA<br>AAAAG |

-continued

| Name | Oligonucleotide sequence (SEQ ID NOS 361-370 and 373-374, respectively, in order of appearance) |
|---|---|
| KAS/5-XR-Bst10 | ACTAGTAAAAAATGGCTTATTTTCCGAATATCGGCAAGATTCAGTATCAGGGACCAAAAAG |
| KAS/5-XR-Bun10 | ACTAGTAAAAAATGGCTACCAAGGAATACTTCCCAGGTATTGGTAAGATCCAGTATCAGGGACCAAAAAG |
| KAS/5-XR-Cce10 | ACTAGTAAAAAATGTCAGAAGTATTTAGCGGTATTTCAAACATTCAGTATCAGGGACCAAAAAG |
| KAS/5-XR-RF10 | ACTAGTAAAAAATGGAATTTTTCAAGAACATAAGCAAGATCCAGTATCAGGGACCAAAAAG |
| KAS/5-XR-18P10 | ACTAGTAAAAAATGAGCGAATTTTTTACAGGCATTTCAAAGATCCAGTATCAGGGACCAAAAAG |
| KAS/5-XR-BV10 | ACTAGTAAAAAATGAAATTTTTTGAAAATGTCCCTAAGGTACAGTATCAGGGACCAAAAAG |
| KAS/3-XI-RF-NATIVE | CTCGAGTTACAGACTGAAAAGAACGTTATTTACG |
| KAS/3-XI-RF-NATIVE-HISb | CTCGAGTTAGTGATGGTGGTGGTGATGCAGACTGAAAAGAACGTTATTTACG |

Each new PCR product was TOPO cloned using a pCR Blunt II vector (Invitrogen), verified by sequencing and subcloned into p426GPD, also as described herein. The resulting plasmids were transformed into BY4742 (*S. cerevisiae*) and selected on SCD-ura medium. Assays to detect levels of expressed xylose isomerase were performed as described herein.

Results

Each of the new chimeric genes was evaluated for expression against the native *Ruminococcus* xylose isomerase gene. Each chimeric variant (e.g., 5' end of an alternate XI donor gene attached to the *Ruminococcus* acceptor gene) was evaluated under saturating xylose conditions (e.g., 500 mM), using 20 mg crude extract. The assays were repeated several times and the results are presented graphically in FIG. 21. As shown in FIG. 21, the 5' edge of 4 of the 10 genes tested showed increased expression in yeast, with respect to the native *Ruminococcus* xylose isomerase control. The 5' edges (e.g., 5' ends) that showed increased expression or improved the activity of the *Ruminococcus* xylose isomerase gene were from *Orpinomyces*, *Bacteroides thetaiotaomicron*, *Bacillus stearothermophilus*, and *B. uniformis*. These results suggest that exchanging the 5' edge of a xylose isomerase gene with low expression and/or activity for the 5' edge of a different xylose isomerase gene can be used as a method to improve the activity and/or expression of xylose isomerase genes when expressed in eukaryotes such as yeast. 5' edge nucleic acid sequences that can improve activity or expression are not necessarily associated with native xylose isomerase genes that themselves show high levels of expressions. Therefore, these results also suggest that an "ideal" chimera can be created for organism specific expression of xylose isomerase, using the method described herein with routine levels of experimentation to determine the best 5' edges and best acceptor gene combinations for a specific organism.

The top 4 chimeric variants (e.g., new 5' edges combined with the *Ruminococcus* xylose isomerase acceptor gene) were further analyzed using a full kinetic assay using varying xylose concentrations ranging from about 40 mM to about 500 mM. The results are presented in the table below.

| Samples | Km (M − 1) | Specific Activity mmol min-1 mg-1 |
|---|---|---|
| XI-R native | 75.03 | 2.171 |
| XI-R O10 (BF 1754) | 75.04 | 4.817 |
| XI-R Bth10 (BF 1755) | 66.70 | 4.185 |
| XI-R Bst10 (BF 1756) | 70.86 | 4.383 |
| XI-R Bun10 (BF 1757) | 90.14 | 5.000 |

These results demonstrate that each of these 5' edge replacements confers increased activity to the native XI-R enzyme, with the XI-R-Bun10 enzyme being the most active. The results of western blots are presented in FIG. 22. The western blot analysis presented in FIG. 22 shows the levels of expression of each chimeric construct in total crude extract and the soluble portion of the crude extract. The results of the western blot analysis are in good agreement with the results of the kinetic assays. G179A mutations, similar to those generated in the *Ruminococcus* native and chimeric genes described herein, are being generated for the 4 alternate 5' edge chimeras described in this example.

Example 29

Increased Expression of Ribulose-5-phosphate ketol-isomerase and Ribulose-5-phosphate-3-epimerase Ribulose-5-phosphate ketol-isomerase (RKI1) and ribulose-5-phosphate-3-epimerase (RPE1) catalyze reactions in the non-oxidative portion of the Pentose Phosphate pathway. Ribulose-5-phosphate ketol-isomerase catalyzes the interconversion of ribulose-5-phosphate and ribose-5-phosphate. Ribulose-5-phosphate-3-epimerase catalyzes the interconversion of ribulose-5-phosphate to xylulose-5-phosphate. Increasing the activity of one or both of these enzymes can lead to increased ethanol production. Ribulose-5-phosphate ketol-isomerase activity and ribulose-5-phosphate-3-epimerase activity each can be independently provided by a peptide. In some embodiments, the polypeptide is encoded by a heterologous nucleotide sequence introduced to a host microorganism. Nucleic acid sequences conferring Ribulose-5-phosphate ketol-isomerase activity and ribulose-5-phosphate-3- epimerase activity can be obtained from a number of sources, including, but not limited to *S. cerevisiae*, including but not limited to *Kluyveromyces, Pichia, Escherichia, Bacillus, Ruminococcus, Schizosaccharomyces*, and *Candida*.

Examples of an amino acid sequence of a polypeptide having ribulose-5-phosphate ketol-isomerase activity or ribulose-5-phosphate-3-epimerase activity, and a nucleotide sequence of a polynucleotide that encodes the respective polypeptide, are presented below. Increased activity of Ribulose-5-phosphate ketol-isomerase and Ribulose-5-phosphate-3-epimerase can be achieved using any suitable method. Non-limiting examples of methods suitable for adding, amplifying or over expressing ribulose-5-phosphate ketol-isomerase activity, ribulose-5-phosphate-3-epimerase activity, or ribulose-5-phosphate ketol-isomerase activity and ribulose-5-phosphate-3-epimerase activity include amplifying the number of RKI1 and/or RPE1 gene(s) in yeast following transformation with a high-copy number plasmid (e.g., such as one containing a 2 uM origin of replication), integration of multiple copies of RKI1 and/or RPE1 gene(s) into the yeast genome, over-expression of the RKI1 and/or RPE1 gene(s) directed by a strong promoter, the like or combinations thereof. Presence, absence or amount of 6-phosphogluconolactonase activity can be detected by any suitable method known in the art, including nucleic acid based analysis and western blot analysis.

RKI1 nucleotide sequence (SEQ ID NO: 417)

ATGGCTGCCGGTGTCCCAAAAATTGATGCGTTAGAATCTTTGGGCAATCC

TTTGGAGGATGCCAAGAGAGCTGCAGCATACAGAGCAGTTGATGAAAATT

TAAAATTTGATGATCACAAAATTATTGGAATTGGTAGTGGTAGCACAGTG

GTTTATGTTGCCGAAAGAATTGGACAATATTTGCATGACCCTAAATTTTA

TGAAGTAGCGTCTAAATTCATTTGCATTCCAACAGGATTCCAATCAAGAA

ACTTGATTTTGGATAACAAGTTGCAATTAGGCTCCATTGAACAGTATCCT

CGCATTGATATAGCGTTTGACGGTGCTGATGAAGTGGATGAGAATTTACA

ATTAATTAAAGGTGGTGGTGCTTGTCTATTTCAAGAAAAATTGGTTAGTA

CTAGTGCTAAAACCTTCATTGTCGTTGCTGATTCAAGAAAAAGTCACC

AAAACATTTAGGTAAGAACTGGAGGCAAGGTGTTCCCATTGAAATTGTAC

CTTCCTCATACGTGAGGGTCAAGAATGATCTATTAGAACAATTGCATGCT

GAAAAAGTTGACATCAGACAAGGAGGTTCTGCTAAAGCAGGTCCTGTTGT

AACTGACAATAATAACTTCATTATCGATGCGGATTTCGGTGAAATTTCC

GATCCAAGAAAATTGCATAGAGAAATCAAACTGTTAGTGGGCGTGGTGGA

AACAGGTTTATTCATCGACAACGCTTCAAAAGCCTACTTCGGTAATTCTG

ACGGTAGTGTTGAAGTTACCGAAAAGTGA

RKI1 amino acid sequence (SEQ ID NO: 418)

MAAGVPKIDALESLGNPLEDAKRAAAYRAVDENLKFDDHKIIGIGSGS

TVVYVAERIGQYLHDPKFYEVASKFICIPTGFQSRNLILDNKLQLGSIEQ

YPRIDIAFDGADEVDENLQLIKGGGACLFQEKLVSTSAKTFIVVADSRKK

SPKHLGKNWRQGVPIEIVPSSYVRVKNDLLEQLHAEKVDIRQGGSAKA

GPVVTDNNNFIIDADFGEISDPRKLHREIKLLVGVVETGLFIDNASKAYF

GNSDGSVEVTEK

RPE1 nucleotide sequence (SEQ ID NO: 419)

ATGGTCAAACCAATTATAGCTCCCAGTATCCTTGCTTCTGACTTCGCCA

ACTTGGGTTGCGAATGTCATAAGGTCATCAACGCCGGCGCAGATTGGTTA

CATATCGATGTCATGGACGGCCATTTTGTTCCAAACATTACTCTGGGCCA

ACCAATTGTTACCTCCCTACGTCGTTCTGTGCCACGCCCTGGCGATGCT

AGCAACACAGAAAAGAAGCCCACTGCGTTCTTCGATTGTCACATGATGG

TTGAAAATCCTGAAAAATGGGTCGACGATTTTGCTAAATGTGGTGCTGAC

CAATTTACGTTCCACTACGAGGCCACACAAGACCCTTTGCATTTAGTT

AAGTTGATTAAGTCTAAGGGCATCAAAGCTGCATGCGCCATCAAACC

TGGTACTTCTGTTGACGTTTTATTTGAACTAGCTCCTCATTTGGATATGG

CTCTTGTTATGACTGTGGAACCTGGGTTTGGAGGCCAAAAATTCATGG

AAGACATGATGCCAAAAGTGGAAACTTTGAGAGCCAAGTTCCCCCAT

TTGAATATCCAAGTCGATGGTGGTTTGGGCAAGGAGACCATCCCGAA

AGCCGCCAAAGCCGGTGCCAACGTTATTGTCGCTGGTACCAGTGTTT

TCACTGCAGCTGACCCGCACGATGTTATCTCCTTCATGAAAGAAGAAG

TCTCGAAGGAATTGCGTTCTAGAGATTTGCTAGATTAG

RPE1 amino acid sequence (SEQ ID NO: 420)

MVKPIIAPSILASDFANLGCECHKVINAGADWLHIDVMDGHFVPNITLG

QPIVTSLRRSVPRPGDASNTEKKPTAFFDCHMMVENPEKWVDDFAKC

GADQFTFHYEATQDPLHLVKLIKSKGIKAACAIKPGTSVDVLFELAPHLD

MALVMTVEPGFGGQKFMEDMMPKVETLRAKFPHLNIQVDGGLGKETIP

KAAKAGANVIVAGTSVFTAADPHDVISFMKEEVSKELRSRDLLD

Example 30

Xylulokinase Over Expression

As described herein, metabolism of xylose as a carbon source, either by xylose isomerase or the combination of xylose reductase and xylitol dehydrogenase, produces xylulose, which must be phosphorylated to enter the pentose phosphate pathway. Increased ethanol fermentation via the over expression of xylose isomerase or xylose reductase and xylitol dehydrogenase also may be further enhanced by the over expression of xylulokinase, in some embodiments. Presented herein are the nucleotide and amino acid sequence of the *S. cerevisiae* xylulokinase (XKS1) gene. The activity of xylulokinase was increased using methods described herein (e.g., strong promoter, multiple copies, the like and combinations thereof). The XKS1 gene of *S. cerevisiae* is functionally similar to the XYL3 gene of *Pichia stipitis*.

XKS1 (SEQ ID NO: 421)

ATGTTGTGTTCAGTAATTCAGAGACAGACAAGAGAGGTTTCCAACACAAT

GTCTTTAGACTCATACTATCTTGGGTTTGATCTTTCGACCCAACAACTGA

AATGTCTCGCCATTAACCAGGACCTAAAAATTGTCCATTCAGAAACAGTG

```
GAATTTGAAAAGGATCTTCCGCATTATCACACAAAGAAGGGTGTCTATAT
ACACGGCGACACTATCGAATGTCCCGTAGCCATGTGGTTAGAGGCTCTAG
ATCTGGTTCTCTCGAAATATCGCGAGGCTAAATTTCCATTGAACAAAGTT
ATGGCCGTCTCAGGGTCCTGCCAGCAGCACGGGTCTGTCTACTGGTCCTC
TCCAAGCCGAACTCTGTTAGAGCAATTGAATAAGAAACCGGAAAAAGATT
TATTGCACTACGTGAGCTCTGTAGCATTTGCAAGGCAAACCGCCCCCAAT
TGGCAAGACCACAGTACTGCAAAGCAATGTCAAGAGTTTGAAGAGTGCAT
AGGTGGGCCTGAAAAAATGGCTCAATTAACAGGGTCCAGAGCCCATTTTA
GATTTACTGGTCCTCAAATTCTGAAAATTGCACAATTAGAACCAGAAGCT
TACGAAAAAACAAAGACCATTTCTTTAGTGTCTAATTTTTTGACTTCTAT
CTTAGTGGGCCATCTTGTTGAATTAGAGGAGGCAGATGCCTGTGGTATGA
ACCTTTATGATATACGTGAAAGAAAATTCAGTGATGAGCTACTACATCTA
ATTGATAGTTCTTCTAAGGATAAAACTATCAGACAAAAATTAATGAGAGC
ACCCATGAAAAATTTGATAGCGGGTACCATCTGTAAATATTTTATTGAGA
AGTACGGTTTCAATACAAACTGCAAGGTCTCTCCCATGACTGGGGATAAT
TTAGCCACTATATGTTCTTTACCCCTGCGGAAGAATGACGTTCTCGTTTC
CCTAGGAACAAGTACTACAGTTCTTCTGGTCACCGATAAGTATCACCCCT
CTCCGAACTATCATCTTTTCATTCATCCAACTCTGCCAAACCATTATATG
GGTATGATTTGTTATTGTAATGGTTCTTTGGCAAGGGAGAGGATAAGAGA
CGAGTTAAACAAAGAACGGGAAAATAATTATGAGAAGACTAACGATTGGA
CTCTTTTTAATCAAGCTGTGCTAGATGACTCAGAAAGTAGTGAAAATGAA
TTAGGTGTATATTTTCCTCTGGGGAGATCGTTCCTAGCGTAAAAGCCAT
AAACAAAGGGTTATCTTCAATCCAAAAACGGGTATGATTGAAAGAGAGG
TGGCCAAGTTCAAAGACAAGAGGCACGATGCCAAAAATATTGTAGAATCA
CAGGCTTTAAGTTGCAGGGTAAGAATATCTCCCCTGCTTTCGGATTCAAA
CGCAAGCTCACAACAGAGACTGAACGAAGATACAATCGTGAAGTTTGATT
ACGATGAATCTCCGCTGCGGGACTACCTAAATAAAAGGCCAGAAAGGACT
TTTTTTGTAGGTGGGCTTCTAAAAACGATGCTATTGTGAAGAAGTTTGC
```

```
TCAAGTCATTGGTGCTACAAAGGGTAATTTTAGGCTAGAAACACCAAACT
CATGTGCCCTTGGTGGTTGTTATAAGGCCATGTGGTCATTGTTATATGAC
TCTAATAAAATTGCAGTTCCTTTTGATAAATTTCTGAATGACAATTTTCC
ATGGCATGTAATGGAAAGCATATCCGATGTGGATAATGAAAATTGGGATC
GCTATAATTCCAAGATTGTCCCCTTAAGCGAACTGGAAAAGACTCTCATC
TAA
```

XKS1 amino acid sequence (SEQ ID NO: 422)

MLCSVIQRQTREVSNTMSLDSYYLGFDLSTQQLKCLAINQDLKIVHSE
TVEFEKDLPHYHTKKGVYIHGDTIECPVAMWLEALDLVLSKYREAKFPL
NKVMAVSGSCQQHGSVYWSSQAESLLEQLNKKPEKDLLHYVSSVAF
ARQTAPNWQDHSTAKQCQEFEECIGGPEKMAQLTGSRAHFRFTGPQI
LKIAQLEPEAYEKTKTISLVSNFLTSILVGHLVELEEADACGMNLYDIRE
RKFSDELLHLIDSSSKDKTIRQKLMRAPMKNLIAGTICKYFIEKYGFNT
NCKVSPMTGDNLATICSLPLRKNDVLVSLGTSTTVLLVTDKYHPSPN
YHLFIHPTLPNHYMGMICYCNGSLARERIRDELNKERENNYEKTNDW
TLFNQAVLDDSESSENELGVYFPLGEIVPSVKAINKRVIFNPKTGMIE
REVAKFKDKRHDAKNIVESQALSCRVRISPLLSDSNASSQQRLNED
TIVKFDYDESPLRDYLNKRPERTFFVGGASKNDAIVKKFAQVIGATK
GNFRLETPNSCALGGCYKAMWSLLYDSNKIAVPFDKFLNDNFPWH
VMESISDVDNENWDRYNSKIVPLSELEKTLI

Example 31

Construction of the KanMX-ATβ1-L75Q Cassette

A unique disruption cassette suitable for use when auxotrophic markers are unavailable, such as in diploid industrial strains or haploids derived from such strains, was constructed to allow homologous recombination or integration of sequences in the absence of traditional auxotrophic marker selection. The primers used for amplification of nucleic acids utilized to generate the disruption cassette are described in the table below.

(Table discloses SEQ ID NOS 423-441, respectively, in order of appearance)

| | | |
|---|---|---|
| JML/51 | ACTAGTATGTCTGACAAGGAACAAACGAGC | 5'ScAto1SpeI |
| JML/52 | CTCGAGTTAAAAGATTACCCTTTCAGTAGATGGTAATG | 3'ScAto1XhoI |
| JML/55 | caagcctttggtggtacccagaatccagggttagctcc | ScATO(L75Q)_For |
| JML/56 | ggagctaaccctggattctgggtaccaccaaaggcttg | ScATO(L75Q)_Rev |
| JML/57 | ggtacaacgcatatgcagatgttgctacaaagcagaa | ScATO1G259D_For |
| JML/58 | ttctgctttgtagcaacatctgcatatgcgttgtacc | ScATO1G259D_Rev |

(Table discloses SEQ ID NOS 423-441, respectively, in order of appearance)

| | | |
|---|---|---|
| JML/59 | GACGACGTCTAGAAAAGAATACTGGAGAAATGAAAAGAAAAC | ReplacesJML/30 |
| JML/63 | GCATGCTTAATTAATGCGAGGCATATTTATGGTGAAGG | F'of5'FlankingRegionof ScURA3 |
| JML/64 | GGCCGGCCAGATCTGCGGCCGCGGCCAGCAAAACTAAAAAAC TGTATTATAAG | F'of3'FlankingRegionof ScURA3 |
| JML/65 | GCGGCCGCAGATCTGGCCGGCCGATTTATCTTCGTTTCCTGC AGGTTTTG | R'of5'FlankingRegionof ScURA3 |
| JML/66 | GAATTCTTAATTAACTTTTGTTCCACTACTTTTTGGAACTCT TG | R'of3FlankingRegionofSc URA3 |
| JML/67 | GCATGCGCGGCCGCACGTCGGCAGGCCCG | F'200mer-R |
| JML/68 | CGAAGGACGCGCGACCAAGTTTATCATTATCAATACTCGCCA TTTC | F'200mer-R-pGPD-ATO1-CYC |
| JML/69 | GAAATGGCGAGTATTGATAATGATAAACTTGGTCGCGCGTCC TTCG | R'pGPD-ATO1-CYC-200mer-R |
| JML/70 | GTCGACCCGCAAATTAAAGCCTTCGAGC | R-pGPD-ATO1-CYC |
| JML/71 | GTCGACGTACCCCCGGGTTAATTAAGGCG | F-KanMX |
| JML/72 | GTCGAAAACGAGCTCGAATTCGACGTCGGCAGGCCCG | F-KanMX-200mer-R |
| JML/73 | CGGGCCTGCCGACGTCGAATTCGAGCTCGTTTTCGAC | R-200mer-R-KanMX |
| JML/74 | GGATCCGCGGCCGCTGGTCGCGCGTCCTTCG | R-200mer-R |

ScATO1 was amplified from genomic DNA (gDNA) isolated from BY4742 with primers oJML51 and oJML52 and cloned into pCR Blunt II-TOPO (Invitrogen, Carlsbad, Calif.). Site Directed Mutagenesis (SDM) was performed on that plasmid with oJML55 and oJML56, as described herein. The mutagenized clone was re-amplified with primers oJML51 and oJML52 and cloned into pCR Blunt II-TOPO (Invitrogen, Carlsbad, Calif.), and designated ATO1-L75Q. ATO1-L75Q was subcloned into p416GPD using SpeI/XhoI restriction enzyme sites. The resulting plasmid was designated pJLVO48.

The 5' and 3' flanking regions of URA3 were amplified via PCR of the 5' regions with primers oJML63 and oJML65, the 3' region with primers oJML64 and oJML66. The amplified nucleic acids were annealed and re-amplified with oligonucleotides oJML63 and oJML66. The template used was TURBO gDNA. The PCR product was Topo cloned into pCR-Blunt II. The desired sequence was moved as an EcoRI-SphI fragment into vector pUC19 and designated pJLV63.

The R-KanMX fragment was made as follows: The KANMX fragment was first amplified from pBF524 with primers oJML71 and oJML73. The R-200-mer from plasmid pBF32 was then amplified using primers oJML72 and oJML74. The two fragments were annealed together and PCR amplified using primers oJML67 and oJML70 and topo cloned using pCR-Blunt II. The final plasmid construct was designated pJLV062. The R-P$_{TDH3}$-ATO1-L75Q construct was generated by amplifying a mixture of PCR oJML67-oJML69 (pBF32)+PCR oJML68-oJML70 (pJLVO48). The resulting plasmid was designated pJLV065. The R-PT$_{DH3}$-ATO1 L75Q (SalI/SphI) fragment from pJLV065 was ligated in a 3 piece ligation to the SalI/BamHIH(R-KanMX) fragment from pJLV063 into the BamHI/SphI site of pUC19. The entire R-KanMX-P$_{TDH3}$-ATO1-L75Q-R fragment was ligated as a NotI piece into the NotI site of pJLV63 and designated pJLV74. The letter "R" with reference to nucleic acid fragments, primers, plasmids and unique 200-mer sequence tags, refers to a unique 200-mer tag identification number. The unique sequence tags are described in Example 40. A table describing the intermediate and final plasmids is presented below.

| | | | |
|---|---|---|---|
| pJLV0035 | pBF493 | pCR-Topo BluntII-ScATO1 L75Q | PCR oJML51, oJML52 (SDM oJML55, oJML56 (Clone of ScATO1 Not Kept) |
| pJLV0048 | pBF506 | pRS416-ProGPD-ScATO1 L75Q | XhoI-SpeI (pRAS416-GPD) + XhoI-SpeI(pJLV035) |

-continued

| | | | |
|---|---|---|---|
| pJLV0061 | pBF604 | pCR-Topo BluntII-5' + 3' ScURA3 | PCR oJML63, oJML66 (PCR oJML63, oJML65 gDNA ScTURBO + PCR oJML64, oJML66 gDNA ScTURBO) |
| pJLV0062 | pBF605 | pCR-Topo BluntII-KanMX-200m-448 | PCR oJML71-oJML74 (PCR oJML71, oJML73 pBF524 + PCR oJML72, oJML74 pBF32) |
| pJLV0063 | pBF606 | pUC19-5 + 3' ScURA3 | EcoR1-SphI(pJLV0061) + EcoR1-SphI(pUC19) |
| pJLV0065 | pBF608 | pCR-Topo BluntII-200m448-ProGDP-ScATO1 L75Q | PCR oJML67-oJML70 (PCR oJML67-oJML59 (pBF32) + PCR oJML68-oJML70 (pJLV048)) |
| pJLV0070 | pBF650 | pUC19-200m448-ProGDP-ScATO1 L75Q-KanMX-200m448 | SalI/SphI (pJLV0065) + BamHI/SalI (pJLV0062) + SphI/BamHI (pUC19) |
| pJLV0074 | pBF654 | pUC19-5' URA3-200m448-ProGDP-ScATO1 L75Q-KanMX-200m448-3' URA3 | NotI(pJLV070) + NotI(pJLV063) |

Example 32

Construction of the ura3 Disruptions in Each Haploid

Haploid yeast strains were transformed with 2 to 3 µg of a PvuII, SphI digested ura3::R-KanMX-ATO1-L75Q-R disruption cassette using the high-efficiency Li-PEG procedure with a heat shock time of 8 minutes. Transformants were plated on YPD plus G418 (200 µg/ml) plates. Colonies were re-streaked onto ScD FOA plates. Single colonies were replica plated on ScD-ura, ScD+FOA, YPD, and YPD G418 200 µg/ml plates. Ura-FOA$^R$ G418$^R$ colonies were grown overnight in YPD. Genomic DNA was extracted and the presence of the KanMX-ATO1-L75Q gene in the URA3 loci was verified by PCR. 50 µl of each overnight culture was plated on ScD Acetate (2 g/L), pH 4.0, plates. Colonies were restreaked on ScD Acetate plates and single colonies grown overnight in YPD. Disruptions of the URA3 loci were verified by PCR with primers complementary to a region outside of the flanking region used for the disruption. The presence of the unique 200-mer sequence was verified by PCR with primers complementary to the 200-mer in combination with primers complementary to a region outside of the flanking region used for the disruption. The absence of the URA3 loci was verified by PCR that amplifies a 500 bp region of the Actin gene open reading frame and a 300 bp region of the URA3 open reading frame. The primers utilized for amplification and verification are presented, respectively, in the tables below.

Primers used for amplification of URA and Actin (SEQ ID NOS 442-445, respectively, in order of appearance)

| | | |
|---|---|---|
| JML/211 | GAGGGCACAGTTAAGCCGCTAAAGG | URA3 |
| JML/212 | GTCAACAGTACCCTTAGTATATTCTCCAGTAGCTA GGGAG | URA3 |
| JML/213 | CGTTACCCAATTGAACACGGTATTGTCAC | ACT1 |
| JML/214 | GAAGATTGAGCAGCGGTTTGCATTTC | ACT1 |

Primers used to verify the presence or absence of URA3 (SEQ ID NOS 434, 441 and 446-447, respectively, in order of appearance)

| | | |
|---|---|---|
| JML/67 | GCATGCgcggccgc ACGTCGGCAGGCC CG | F'200mer-R |
| JML/74 | GGATCCgcggccgc TGGTCGCGCGTCC TTCG | R-200mer-R |
| JML/102 | gagtcaaacgacg ttgaaattgaggct actgc | PCR to verify disruption of URA3 |
| JML/103 | GATTACTGCTGCTG TTCCAGCCCATATC CAAC | PCR to verify disruption of URA3 |

Example 33

EDA Gene Integration Method and Constructs

Plasmid DNA was digested with PacI using manufacturers suggestions. The digestions were purified using the GeneJET™ Gel Extraction Kit I (Fermentas). Each column was eluted with 20 µl of Elution buffer and multiple digests were combined. *S. cerevisiae* was transformed using the high-efficiency Li-PEG procedure with 2 to 3 µg of DNA and transformants were selected on ScD-ura solid media. Correct integrations were confirmed by PCR analysis with primers outside the flanking regions used as the disruption cassette and primers complementary to either the open reading frame of EDA or the 200-mer repeat. Oligonucleotide primers utilized for verification are described in the tables below.

Primers—Outside (SEQ ID NOS 448-451, respectively, in order of appearance)

| | | |
|---|---|---|
| YBR110.5 5' | GGCAATCAAATTGGGAACGAACAATG | JML/187 |
| 3' | CTCAAGGTATCCTCATGGCCAAGCAATAC | JML/188 |
| YDL075.5 5' | GGGTCTACAAACTGTTGTTGTCGAAGAAG ATG | JML/189 |
| 3' | CATTCAGTTCCAATGATTTATTGACAGTG CAC | JML/190 |

Primers—Repeat and EDA going out (SEQ ID NOS 452-454, respectively, in order of appearance)

| | | |
|---|---|---|
| JML/276 | CCTACCCGCCTCGGATCCCAGCTACC | R-repeat |
| JML/277 | GGTAGCTGGGATCCGAGGCGGGTAGG | R-repeat |
| JML/278 | CCTCCCGGCACAGCGTGTCGATGC | R at the 5'EDA |

PaEDA going out and similar primers for EcEDA (SEQ ID NOS 455-457, respectively, in order of appearance)

| | | |
|---|---|---|
| JML/297 | CGAAGCCCTGGAGCGCT TCGC | PCR for PaEDA going out at the 3' of the ORF |

```
JML/298  GTGGTCAGGATTGATTC   PCR for EcEDA Reverse
         TGCACTTGTTTTCCAG    at the 5' end JML/299  CGCGTGAAGCTGTAGAA   PCR for EcEDA Forward
         GGCGCTAAG           at the 3' end
```

The PCR reactions were performed in a final reaction volume of 25 μl using the following amplification profile; 1 cycle at 94 degrees C. for 2 minutes, followed by 35 cycles of 94 degrees C. for 30 seconds, 52 degrees C. for 30 second and 72 degrees C. for 2 minutes.

Construction of EDA Disruption Cassettes $P_{TDH3}$-PaEDA was amplified from pBF292 using primers oJML225 and oJML226, shown in the table below and Topo cloned in pCR Blunt II to make pJLV95. (SEQ ID NOS 458-459, respectively, in order of appearance)

```
JML/225  GAGCTCGGCCGCAAATTAAAGCCTT   3'cyCTERMINATOR
         CGAG

JML/226  GGCCGGCCGTTTATCATTATCAATA   5'PROMOTERgpd
         CTCGCCATTTCAAAGAATACG
```

The desired fragment was moved as a FseI-SacI piece into pBF730 or pBF731 (the integration cassette of either YBR110.5 or YDL075.5, respectively) to make plasmids pJLV114 and pJLV115, respectively. YBR110.5 is located inbetween loci YBR110 and YBR111, and YDL075.5 is located in between loci YDL075 and YDL076. The R-URA3-R sequence was moved into these plasmids as a NotI fragment to make pJLV119 and pJLV120. The resultant plasmids are described in the table below.

| | | | |
|---|---|---|---|
| pJLV0095 | pBF777 | pCR-Topo BluntII-PaEDA | PCR oJML225-oJML226 (pBF292) |
| pJLV0114 | pBF862 | pUC19-5'-YBR110.5-PGDP1-PaEDA-TCYC-3'YBR110.5 | FseI-SacI(pBF730) + FseI-SacI(pJLV95) |
| pJLV0115 | pBF863 | pUC19-5'-YDL075.5-PGDP1-PaEDA-TCYC-3'YDL075.5 | FseI-SacI(pBF731) + FseI-SacI(pJLV95) |
| pJLV0119 | pBF867 | pUC19-5'-YBR110.5-PGDP1-PaEDA-TCYC-R-URA3-R-3'YBR110.5 | NotI(pBF742) + NotI(pJLV114) |
| pJLV0120 | pBF868 | pUC19-5'-YDL075.5-PGDP1-PaEDA-TCYC-R-URA3-R-3'YDL075.5 | NotI(pBF742) + NotI(pJLV115) |

Example 34

Isolation and Evaluation of Additional EDA Genes

EDA genes isolated from a variety of sources were expressed in yeast and evaluated independently of EDA activity, to identify EDA activities suitable of inclusion in an engineered yeast strain. The EDA activities were was independently assessed by adding saturating amounts of over expressed *E. coli* EDD extracts to *S. cerevisiae* EDA extracts lacking EDD (Chemyan et al., Protein Science 16:2368-2377, 2007). The relative activities of EDAs, expressed in *S. cerevisiae*, were compared and ranked in this way. The activity of integrated EDAs in Thermosacc-Gold haploids, were also evaluated in this manner. The table below describes oligonucleotide primers used to isolate the various EDA genes.

| Name | Description | Sequence (SEQ ID NOS 75, 76, 79-80 and 460-473, respectively, in order of appearance) |
|---|---|---|
| KA/EDA-SoFor | Cloning primer for *Shewanella oneidensis* EDA | GTTCACTGCACTAGTAAAAAAATGCTTGAGAATAACTGGTC |
| KA/EDA-SoRev | Cloning primer for *Shewanella oneidensis* EDA | CTTCGAGATCTCGAGTTAAAGTCCGCCAATCGCCTC |
| KA/EDA-GoFor | Cloning primer for *Gluconobacter oxydans* EDA | GTTCACTGCACTAGTAAAAAAATGATCGATACTGCCAAACTC |
| KA/EDA-GoRev | Cloning primer for *Gluconobacter oxydans* EDA | CTTCGAGATCTCGAGTCAGACCGTGAAGAGTGCCGC |
| KA/EDA-BLFor | Cloning primer for *Bacilluis licheniformis* EDA | GTTCACTGCACTAGTAAAAAAATGGTATTGTCACACATCGAAG |
| KA/EDA-BLRev | Cloning primer for *Bacilluis licheniformis* EDA | CTTCGAGATCTCGAGTTACTGTTTTGCTGCTTCAACAAATTG |
| KA/EDA-BsFor | Cloning primer for *Bacillus subtilis* EDA | GTTCACTGCACTAGTAAAAAAATGGAGTCCAAAGTCGTTGAAAACC |
| KA/EDA-BsRev | Cloning primer for *Bacillus subtilis* EDA | CTTCGAGATCTCGAGTTACACTTGGAAAACAGCCTGCAAATCC |
| KA/EDA-PfFor | Cloning primer for *Pseudomonas fluorescens* EDA | GTTCACTGCACTAGTAAAAAAATGACAAACCTCGCCCCGACC |
| KA/EDA-PfRev | Cloning primer for *Pseudomonas fluorescens* EDA | CTTCGAGATCTCGAGTCAGTCCAGCAGGGCCAGG |
| KA/EDA-PsFor | Cloning primer for *Pseudomonas syringae* EDA | GTTCACTGCACTAGTAAAAAAATGACACAGAACGAAAATAATCAGCCGC |
| KA/EDA-PsRev | Cloning primer for *Pseudomonas syringae* EDA | CTTCGAGATCTCGAGTCAGTCAAACAGCGCCAGCGC |
| KA/EDA-SdFor | Cloning primer for *Saccharophagus degradans* EDA | GTTCACTGCACTAGTAAAAAAATGGCTATTACAAAAGAATTTTTAGCTCCAG |

-continued

| Name | Description | Sequence (SEQ ID NOS 75, 76, 79-80 and 460-473, respectively, in order of appearance) |
|---|---|---|
| KA/EDA-SdRev | Cloning primer for *Saccharaophagus degradans* EDA | CTTCGAGATCTCGAGTTAGCTAGAAATTTTAGCGGTA GTTGCC |
| KA/EDA-XaFor | Cloning primer for *Xanthamonas axonopodis* EDA | GTTCACTGCACTAGTAAAAAAATGACGATTGCCCAGA CCCAG |
| KA/EDA-XaRev | Cloning primer for *Xanthamonas axonopodis* EDA | CTTCGAGATCTCGAGTCAGCCCGCCCGCACC |
| KA/Nde IEDDfor | Cloning primer for *E. coli* EDD | GTTCACTGCCATATGAATCCACAATTGTTACGCGTAA CAAATCGAATCATTG |
| KA/Xho IEDDrev | Cloning primer for *E. coli* EDD | CTTCGAGATCTCGAGTTAAAAAGTGATACAGGTTGCG CCCTGTTCGGC |

Listed below are the amino acid sequences, nucleotide sequences and accession numbers of the EDA genes evaluated as described in this Example.

| Accession Number | Species | Strain Number | Nucleotide Sequence | Amino Acid Sequence |
|---|---|---|---|---|
| YP_526856.1 | *Saccharophagus degradans* | 2-40 | ATGGCTATTACAAAAGAATTTTTAGCTCCAGTTGGCGTAATGCCTGT TGTGGTTGTGGATCGTGTAGAAGATGCGGTGCCTATTACAAACGCAT TAAAAGCCGGCGGTATTAAAGCAGTTGAGATTACTTTACGTACTCCT GCGGCACTGGATGCTATTCGCGCTATTAAAGCTGAGTGTGAAGACAT CCTGGTGGGGGTAGGTACGGTTATTAACCATCAAAACCTTAAAGATA TTGCTGCAATTGGTGTTGATTTCGCCGTATCTCCTGGTTACACCCCA ACATTGCTGAAGCAAGCGCAAGATTTGGGCGTAGAAATGTTGCCTGG TGTAACTTCGCCTTCTGAAGTTATGCTTGGTATGGAGCTAGGTTTGT CTTGCTTCAAGCTATTCCCTGCGGTTGCAGTAGGTGGTTTGCCATTA CTTAAGTCTATTGGTGGCCCATTACCACAGGTTTCCTTCTGTCCAAC AGGCGGTTTGACTATCGATACTTTCACCGACTTCTTGGCATTGCCTA ACGTTGCTTGTGTGGGTGGTACTTGGTTGGTGCCTGCAGATGCTGTT GCAGCTAAAAACTGGCAAGCTATTACTGATATTGCGGCGGCAACTAC CGCTAAAATTTCTAGCTAA (SEQ ID NO: 474) | MAITKEFLAPVGVMPVV VVDRVEDAVPITNALKA GGIKAVEITLRTPAALD AIRAIKAECEDILVGVG TVINHQNLKDIAAIGVD FAVSPGYTPTLLKQAQD LGVEMLPGVTSPSEVML GMELGLSCFKLFPAVAV GGLPLLKSIGGPLPQVS FCPTGGLTIDTFTDFLA LPNVACVGGTWLVPADA VAAKNWQAITDIAAATT AKISS (SEQ ID NO: 475) |
| | *Xanthomonas axonopodis* pv. *Vasculorum* | ATCC 13902 | ATGACGATTGCCCAGACCCAGAACACCGCCGAACAGTTGCTGCGCGA TGCCGGCATCTTGCCCGTGGTCACCGTGGACACGCTGGATCAGGCGC GCCGCGTCGCCGATGCGTTGCTCGAAGGCGGCCTGCCCGCGATCGAG CTGACCCTTCGCACGCCAGTGGCGATCGACGCGCTGGCGATGCTCAA GCGCGAGCTTCCTAACATCTTGATCGGTGCCGGCACCGTGCTGAGCG AATTGCAGCTGCGTCAGTCGGTGGATGCCGGTGCAGACTTCCTGGTG ACCCCGGGCACGCCGGCGCCGCTGGCGCGCCTGCTGGCGGATGCGCC GATCCCGGCCGTTCCCGGCGCGGCCACTCCGACCGAGCTGCTGACCT TGATGGGTCTTGGCTTTCGCGTCTGCAAGCTGTTCCCGGCCACCGCC GTGGGCGGTCTGCAGATGCTCAGGGGCCTGGCCGGCCCGCTGTCCGA GCTCAAGCTGTGCCCCACCGGCGGCATCAGCGAGGCCAACGCCGCCG AGTTCCTGTCGCAGCCGAACGTGCTGTGCATCGGCGGTTCGTGGATG GTCCCCAAGGATTGGCTGGCGCACGGCCAATGGGACAAGGTCAAGGA AAGCTCGGCCAAGGCGGCGGCGATCGTGCGGCAGGTGCGGGCGGGCT GA (SEQ ID NO: 476) | MTIAQTQNTAEQLLRDA GILPVVTVDTLDQARRV ADALLEGGLPAIELTLR TPVAIDALAMLKRELPN ILIGAGTVLSELQLRQS VDAGADFLVTPGTPAPL ARLLADAPIPAVPGAAT PTELLTLMGLGFRVCKL FPATAVGGLQMLRGLAG PLSELKLCPTGGISEAN AAEFLSQPNVLCIGGSW MVPKDWLAHGQWDKVKE SSAKAAAIVRQVRAG (SEQ ID NO: 477) |
| AAO55695.1 | *Pseudomonas syringiae* | Pv. Tomato str DC3000 | ATGACACAGAACGAAAATAATCAGCCGCTCACCAGCATGGCGAACAA GATTGCCCGGATCGACGAACTCTGCGCCAAGGCAAAGATTCTGCCGG TCATCACCATTGCCCGTGATCAGGACGTATTGCCACTGGCCGACGCG CTGGCCGCTGGTGGCATGACGGCTCTGGAAATCACCCTGCGCTCGGC GTTCGGACTGAGTGCGATCCGCATTTTGCGCGAGCAGCGCCCAGAGC TGTGCACTGGCGCCGGGACCATTCTGGACCGCAAGATGCTGGCCGAC GCCGAGGCGGCGGGCTCGCAATTCATTGTGACCCCCGGCAGCACGCA GGAACTGTTGCAGGCGGCGCTCGACAGCCCGTTGCCCCTGTTGCCAG GCGTCAGCAGCGCGTCGGAAATCATGATCGGCTATGCCTTGGGTTAT CGCCGCTTCAAGCTGTTCCCGGCAGAAATCAGCGGCGGTGTGGCAGC GATCAAGGCCTTGGGCGGGCCTTTCAACGAGGTGCGTTTCTGCCCGA CGGGCGGCGTCAACGAGCAGAACCTCAAGAACTACATGGCCTTGCCC AACGTCATGTGCGTCGGCGGGACATGGATGATTGATAACGCCTGGGT CAAGAATGGCGACTGGGGCCGCATTCAGGAAGCCACGGCACAGGCGC TGGCGCTGTTTGACTGA (SEQ ID NO: 478) | MTQNENNQPLTSMANKI ARIDELCAKAKILPVIT IARDQDVLPLADALAAG GMTALEITLRSAFGLSA IRILREQRPELCTGAGT ILDRKMLADAEAAGSQF IVTPGSTQELLQAALDS PLPLLPGVSSASEIMIG YALGYRRFKLFPAEISG GVAAIKALGGPFNEVRF CPTGGVNEQNLKNYMAL PNVMCVGGTWMIDNAWV KNGDWGRIQEATAQALA LFD (SEQ ID NO: 479) |

| Accession Number | Species | Strain Number | Nucleotide Sequence | Amino Acid Sequence |
|---|---|---|---|---|
| NP_718073.1 | Shewanella oneidensis | MR-1 | ATGCTTGAGAATAACTGGTCATTACAACCACAAGATATTTTTAAACG CAGCCCTATTGTTCCTGTTATGGTGATTAACAAGATTGAACATGCGG TGCCCTTAGCTAAAGCGCTGGTTGCCGGAGGGATAAGCGTGTTGAA GTGACATTACGCACGCCATGCGCCCTTGAAGCTATCACCAAAATCGC CAAGGAAGTGCCTGAGGCGCTGGTTGGCGCGGGGACTATTTTAAATG AAGCCCAGCTTGGACAGGCTATCGCCGCTGGTGCGCAATTTATTATC ACTCCAGGTGCGACAGTTGAGCTGCTCAAAGCGGGCATGCAAGGACC GGTGCCGTTAATTCCGGGCGTTGCCAGTATTTCCGAGGTGATGACGG GCATGGCGCTGGGCTACACTCACTTTAAATTCTTCCCTGCTGAAGCG TCAGGTGGCGTTGATGCGCTTAAGGCTTTCTCTGGGCCGTTAGCAGA TATCCGCTTCTGCCCAACAGGTGGAATTACCCCGAGCAGCTATAAAG ATTACTTAGCGCTGAAGAATGTCGATTGTATTGGTGGCAGCTGGATT GCTCCTACCGATGCGATGGAGCAGGGCGATTGGGATCGTATCACTCA GCTGTGTAAAGAGGCGATTGGCGGACTTTAA (SEQ ID NO: 89) | MLENNWSLQPQDIFKRS PIVPVMVINKIEHAVPL AKALVAGGISVLEVTLR TPCALEAITKIAKEVPE ALVGAGTILNEAQLGQA IAAGAQFIITPGATVEL LKAGMQGPVPLIPGVAS ISEVMTGMALGYTHFKF FPAEASGGVDALKAFSG PLADIRFCPTGGITPSS YKDYLALKNVDCIGGSW IAPTDAMEQGDWDRITQ LCKEAIGGL (SEQ ID NO: 90) |
| YP_261692 | Pseudomonas fluorescens | Pf-5 | ATGACAAACCTCGCCCCGACCGTTTCCATGGCGGACAAAGTTGCCCT GATCGACAGCCTCTGCGCCAAGGCGCGGATCCTGCCGGTGATCACCA TTGCCCGCGAGCAGGATGTCCTGCCGCTGGCCGATGCCCTGGCGGCC GGCGGCCTGACCGCCCTGGAAGTGACCCTGCGTTCGCAGTTCGGCCT CAAGGCGATCCAGATCCTGCGCGAACAGCGCCCGGAGCTGGTGACCG GTGCCGGCACCGTGCTCGACCCGCAGATGCTGGTGGCCGCGGAAGCG CAGGTTCGCAGTTCATCGTCACCCCGGGCATCACCCGCGACCTGCT GCAAGCCAGCGTGGCCAGCCCGATTCCCCTGCTGCCGGGGATCAGCA ATGCCTCCGGGATCATGGAGGGTTATGCCCTGGGCTACCGCCGCTTC AAGCTGTTCCCGGCGGAAGTCAGTGGTGGCGTGGCGGCGATCAAGGC GATCAAGGCTCTGGGCGGCCCGTTCGGCGAGGTCAAGTTCTGCCCTACCGGCGGCG GGGTGGGTCCGGCCAATATCAAGAGCTACATGGCGCTCAAGAATGTGATG TGCGTCGGCAGTTGGATGCTCGATCCCGAGTGGATCAAGAACGG CGACTGGGCACGGATCCAGGAGTGCACGGCCGAGGCCCTGGCCCTGC TGGACTGA | MTNLAPTVSMADKVALI DSLCAKARILPVITIAR EQDVLPLADALAAGGLT ALEVTLRSQFGLKAIQI LREQRPELVTGAGTVLD PQMLVAAEAAGSQFIVT PGITRDLLQASVASPIP LLPGISNASGIMEGYAL GYRRFKLFPAEVSGGVA AIKALGGPFGEVKFCPT GGVGPANIKSYMALKNV MCVGGSWMLDPEWIKNG DWARIQECTAEALALLD (SEQ ID NO: 481) |
| ZP_03591973.1 | Bacillus subtilis | subtilis str. 168 | ATGGAGTCCAAAGTCGTTGAAAACCGTCTGAAAGAAGCAAAGCTGAT TGCAGTCATTCGTTCAAAGGATAAGCAGGAGGCCTGTCAGCAGATTG AGAGTTTATTAGATAAAGGGATTCGTGCAGTTGAAGTGACGTATACG ACCCCCGGGGCATCAGATATTATCGAATCCTTCCGTAATAGGGAAGA TATTTTAATTGGCGCGGGTACGGTCATCAGCGCGCAGCAAGCTGGGG AAGCTGCTAAGGCTGGCGCGCAGTTTATTGTCAGTCCGGGTTTTTCA GCTGATCTTGCTGAACATCTATCTTTTGTAAAGACACATTATATCCG CGGCGTCTTGACTCCGAGCGAAATTATGGAAGCGCTGACATTCGGTT TTACGACATTAAAGCTGTTCCCAAGCGGTGTGTTTGGCATTCCGTTT ATGAAAAATTTAGCGGGTCCTTTCCCGCAGGTGACCTTTATTCGAC AGGCGGGATACATCCGTCGAAGTGCCTGATTGGCTTAGAGCCGGAG CTGGCGCCGTCGGAGTCGGCAGCCAGTTGGGGCAGCTGTTCAAAAGAG GATTTGCAGGCTGTTTTCCAAGTGTAA (SEQ ID NO: 482) | MESKVVENRLKEAKLIA VIRSKDKQEACQQIESL LDKGIRAVEVTYTTPGA SDIIESFRNREDILIGA GTVISAQQAGEAAKAGA QFIVSPGFSADLAEHLS FVKTHYIPGVLTPSEIM EALTFGFTTLKLFPSGV FGIPFMKNLAGPFPQVT FIPTGGIHPSEVPDWLR AGAGAVGVGSQLGSCSK EDLQAVFQV (SEQ ID NO: 483) |
| YP_081150.2 | Bacillus licheniformis | ATCC 14580 | ATGGTATTGTCACACATCGAAGAACAAAAACTGATTGCGATCATCCG CGGATACAATCCGGAGGAGGCAGTGAGCATTGCCGGCGCTTAAAAG CGGGCGGCATCAGGCTTGTGGAGATTACGCTTAATTCCCCTCAAGCG ATCAAAGCGATTGAAGCGGTTTCAGCATTTTGGGGACGAAATGCT TGTCGGAGCGGGAACCGTACTTGATCCCGAATCTGCGAGAGCGGCGC TTTTAGCCGGCGCGCGGTTTATCCTGTCTCCGACCGTCAATGAAGAG ACGATCAAGCTGACAAAACGGTATGGAGCGGTCAGCATTCCAGGCGC TTTTACCCCGACTGAAATATTGACGGCGTATGAAAGCGGGGAAGACA TCATCAAGGTATTTCCCGGAACAATGGGGCCTGGCTATATCAAGGAT ATCCACGGACCGCTTCCGCATATTCCGCTGCTTCCGACTGGAGGAGT CGGATTGGAAAACCTTCACGAGTTTCTGCAGGCCGGTGCGGTCGGAG CGGGAATCGGCGGTTCGCTTGTTCGGGCTAATAAAGATGTTAATGAC GCGTTTTTAGAAGAGCTGTCCAAAAAAGCAAAGCAATTTGTTGAAGC AGCAAAACAGTAA (SEQ ID NO: 484) | MVLSHIEEQKLIAIIRG YNPEEAVSIAGALKAGG IRLVEITLNSPQAIKAI EAVSEHFGDEMLVGAGT VLDPESARAALLAGARF ILSPTVNEETIKLTKRY GAVSIPGAFTPTEILTA YESGGDIIKVFPGTMGP GYIKDIHGPLPHIPLLP TGGVGLENLHEFLQAGA VGAGIGGSLVRANKDVN DAFLEELSKKAKQFVEA AKQ (SEQ ID NO: 485) |
| YP_190869.1 | Gluconobacter oxydans | 62IH | ATGATCGATACTGCCAAACTCGACGCGTCATGAGCCGTTGTCCGGT CATGCCGGTGCTGGTGGTCAATGATGTGGCTCTGGCCCGCCGATGG CCGGAGCTCTGGTTGGCGGTGGACTGTCCACGCTGGAAGTCACGCTG CGCACGCCCTGCGCCCTTGAAGCTATTGAGGAAATGTCGAAAGTACC AGGCGCGCTGGTCGGTGCCGGTACGGTGCTGAATCCGTCCGACATGG ACCGTGCCGTGAAGGCGGGTGCGCGCTTCATCGTCAGCCCCGGCCTG ACCGAGGCGCTGGCAAAGGCGTCGGTTGAGCATGACGTCCCCTTCCT GCCAGGCGTTGCCAATGCGGGTGACATCATGCGGGGTCTGGATCTGG GTCTGTCACGCTTCAAGTTCTTCCCGGCTGTGACGAATGGCGGCATT CCCGCGCTCAAGAGCTTGGCCAGTGTTTTTGGCAGCAATGTCCGTTT CTGCCCCACGGGCGGCATTACGGAAGAGAGCGCACCGGACTGGCTGG CGCTTCCCTCCGTGGCCTGCGTCGGCGGATCCTGGGTGACGGCCGGC ACGTTCGATGCGGACAAGGTCCGTCAGCGCGCCACGGCTGCGGCACT CTTCACGGTCTGA (SEQ ID NO: 91) | MIDTAKLDAVMSRCPVM PVLVVNDVALARPMAEA LVAGGLSTLEVTLRTPC ALEAIEEMSKVPGALVG AGTVLNPSDMDRAVKAG ARFIVSPGLTEALAKAS VEHDVPFLPGVANAGDI MRGLDLGLSRFKFFPAV TNGGIPALKSLASVFGS NVRFCPTGGITEESAPD WLALPSVACVGGSWVTA GTFDADKVRQRATAAAL FTV (SEQ ID NO: 92) |

-continued

| Accession Number | Species | Strain Number | Nucleotide Sequence | Amino Acid Sequence |
|---|---|---|---|---|
| NP_251871.1 | P. aeruginosa | PAO1 Codon Optimized | ATGAAAAACTGGAAAACAAGTGCAGAATCAATCCTGACCACCGGCCC GGTTGTACCGGTTATCGTGGTAAAAAAACTGGAACACGCGGTGCCGA TGGCAAAAGCGTTGGTTGCTGGTGGGGTGCGCGTTCTGGAAGTGACT CTGCGTACCGAGTGTGCAGTTGACGCTATCCGTGCTATCGCCAAAGA AGTGCCTGAAGCGATTGTGGGTGCCGGTACGGTGCTGAATCCACAGC AGCTGGCAGAAGTCACTGAAGCGGGTGCACAGTTCGCAATTAGCCCG GTCTGACCGAGCCGCTGCTGAAAGCTGCTACCGAAGGGACTATTCC TCTGATTCCGGGGATCAGCACTGTTTCCGAACTGATGCTGGGTATGG ACTACGGTTTGAAAGAGTTCAAATTCTTCCCGGCTGAAGCTAACGGC GGCGTGAAAGCCCTGCAGGCGATCGCGGGTCCGTTCTCCCAGGTCCG TTTCTGCCCGACGGGTGGTATTTCTCCGGCTAACTACCGTGACTACC TGGCGCTGAAAAGCGTGCTGTGCATCGGTGGTTCCTGGCTGGTTCCG GCAGATGCGCTGGAAGCGGGCGATTACGACCGCATTACTAAGCTGGC GCGTGAAGCTGTAGAAGGCGCTAAGCTGTAA (SEQ ID NO: 486) | MKNWKTSAESILTTGPV VPVIVVKKLEHAVPMAK ALVAGGVRVLEVTLRTE CAVDAIRAIAKEVPEAI VGAGTVLNPQQLAEVTE AGAQFAISPGLTEPLLK AATEGTIPLIPGISTVS ELMLGMDYGLKEFKFFP AEANGGVKALQAIAGPF SQVRFCPTGGISPANYR DYLALKSVLCIGGSWLV PADALEAGDYDRITKLA REAVEGAKL (SEQ ID NO: 487) |
|  |  | PAO1-Ec5 | ATGAAAAACTGGAAACAGAAGACCGCCCGCATCGACACGCTGTGCCG GGAGGCGCGCATCCTCCCGGTGATCACCATCGACCGCGAGGCGGACA TCCTGCCGATGGCCGATGCCCTCGCCGCCGGCGGCCTGACCGCCCTG GAGATCACCCTGCGCACGGCGCACGGGCTGACCGCCATCCGGCGCCT CAGCGAGGAGCGCCCGCACCTGCGCATCGGCGCCGGCACCGTGCTCG ACCCGCGGACCTTCGCCGCCGCGAAAAGGCCGGGGCGAGCTTCGTG GTCACCCCGGGTTGCACCGACGAGTTGCTGCGCTTCGCCCTGGACAG CGAAGTCCCGCTGTTGCCCGGCGTGGCCAGCGCTTCCGAGATCATGC TCGCCTACCGCCATGGCTACCGCCGCTTCAAGCTGTTTCCCGCCGAA GTCAGCGGCGGCCCGGCGGCGCTGAAGGCGTTCTCGGGACCATTCCC CGATATCCGCTTCTGCCCCACCGGAGGCGTCAGCCTGAACAATCTCG CCGACTACCTGGCGGTACCCAACGTGATGTGCGTCGGCGGCACCTGG ATGCTGCCCAAGGCCGTGGTCGACCGCGGCGACTGGGCCCAGGTCGA GCGCCTCAGCCGCGAAGCCCTGGAGCGCTTCGCCGAGCACCGCAGAC ACTAATAGCTCGAGTTACTTTACT (SEQ ID NO: 488) | MKNWKQKTARIDTLCRE ARILPVITIDREADILP MADALAAGGLTALEITL RTAHGLTAIRRLSEERP HLRIGAGTVLDPRTFAA AEKAGASFVVTPGCTDE LLRFALDSEVPLLPGVA SASEIMLAYRHGYRRFK LFPAEVSGGPAALKAFS GPFPDIRFCPTGGVSLN NLADYLAVPNVMCVGGT WMLPKAVVDRGDWAQVE RLSREALERFAEHRRH (SEQ ID NO: 489) |
|  |  | PAO1-Ec10 | ATGAAAAACTGGAAAACAAGTGCAGAATCAATCGACACGCTGTGCCG GGAGGCGCGCATCCTCCCGGTGATCACCATCGACCGCGAGGCGGACA TCCTGCCGATGGCCGATGCCCTCGCCGCCGGCGGCCTGACCGCCCTG GAGATCACCCTGCGCACGGCGCACGGGCTGACCGCCATCCGGCGCCT CAGCGAGGAGCGCCCGCACCTGCGCATCGGCGCCGGCACCGTGCTCG ACCCGCGGACCTTCGCCGCCGCGGAAAAGGCCGGGGCGAGCTTCGTG GTCACCCCGGGTTGCACCGACGAGTTGCTGCGCTTCGCCCTGGACAG CGAAGTCCCGCTGTTGCCCGGCGTGGCCAGCGCTTCCGAGATCATGC TCGCCTACCGCCATGGCTACCGCCGCTTCAAGCTGTTTCCCGCCGAA GTCAGCGGCGGCCCGGCGGCGCTGAAGGCGTTCTCGGGACCATTCCC CGATATCCGCTTCTGCCCCACCGGAGGCGTCAGCCTGAACAATCTCG CCGACTACCTGGCGGTACCCAACGTGATGTGCGTCGGCGGCACCTGG ATGCTGCCCAAGGCCGTGGTCGACCGCGGCGACTGGGCCCAGGTCGA GCGCCTCAGCCGCGAAGCCCTGGAGCGCTTCGCCGAGCACCGCAGAC ACTAATAGCTCGAGTTACTTTACT (SEQ ID NO: 490) | MKNWKTSAESIDTLCRE ARILPVITIDREADILP MADALAAGGLTALEITL RTAHGLTAIRRLSEERP HLRIGAGTVLDPRTFAA AEKAGASFVVTPGCTDE LLRFALDSEVPLLPGVA SASEIMLAYRHGYRRFK LFPAEVSGGPAALKAFS GPFPDIRFCPTGGVSLN NLADYLAVPNVMCVGGT WMLPKAVVDRGDWAQVE RLSREALERFAEHRRH (SEQ ID NO: 491) |
|  |  | PAO1-Ec15 | ATGAAAAACTGGAAAACAAGTGCAGAATCAATCCTGACCACCGGCCG GGAGGCGCGCATCCTCCCGGTGATCACCATCGACCGCGAGGCGGACA TCCTGCCGATGGCCGATGCCCTCGCCGCCGGCGGCCTGACCGCCCTG GAGATCACCCTGCGCACGGCGCACGGGCTGACCGCCATCCGGCGCCT CAGCGAGGAGCGCCCGCACCTGCGCATCGGCGCCGGCACCGTGCTCG ACCCGCGGACCTTCGCCGCCGCGGAAAAGGCCGGGGCGAGCTTCGTG GTCACCCCGGGTTGCACCGACGAGTTGCTGCGCTTCGCCCTGGACAG CGAAGTCCCGCTGTTGCCCGGCGTGGCCAGCGCTTCCGAGATCATGC TCGCCTACCGCCATGGCTACCGCCGCTTCAAGCTGTTTCCCGCCGAA GTCAGCGGCGGCCCGGCGGCGCTGAAGGCGTTCTCGGGACCATTCCC CGATATCCGCTTCTGCCCCACCGGAGGCGTCAGCCTGAACAATCTCG CCGACTACCTGGCGGTACCCAACGTGATGTGCGTCGGCGGCACCTGG ATGCTGCCCAAGGCCGTGGTCGACCGCGGCGACTGGGCCCAGGTCGA GCGCCTCAGCCGCGAAGCCCTGGAGCGCTTCGCCGAGCACCGCAGAC ACTAATAGCTCGAGTTACTTTACT (SEQ ID NO: 492) | MKNWKTSAESILTTGRE ARILPVITIDREADILP MADALAAGGLTALEITL RTAHGLTAIRRLSEERP HLRIGAGTVLDPRTFAA AEKAGASFVVTPGCTDE LLRFALDSEVPLLPGVA SASEIMLAYRHGYRRFK LFPAEVSGGPAALKAFS GPFPDIRFCPTGGVSLN NLADYLAVPNVMCVGGT WMLPKAVVDRGDWAQVE RLSREALERFAEHRRH (SEQ ID NO: 493) |

EDA extracts were prepared using the following protocol.

Day 1

Grow 5 ml LB-Kan preps of BF1055 (BL21/DE3 with pET26b empty vector) and BF1706 (BL21DE3 with pET26b+*E. coli* EDD).

Grow 5 ml preps of each EDA construct expressed in *S. cerevisiae* in appropriate selective media (e.g. ScD-leu).

Day 2

Grow 50 ml LB-Kan prep of BF1055, 2% (v/v) inoculate.

Grow 50 ml prep of BF1706 using Novagen's Overnight Express (46.45 ml LB-Kan, 1 ml solution 1, 2.5 ml solution 2, 50 µl solution 3, 5 µl of 1M $MnCl_2$, 50 µl of 0.5 M $FeCl_2$), 2% (v/v) inoculate.

Grow 50 ml prep of each EDA construct expressed in *S. cerevisiae* in appropriate selective media+10 mM $MnCl_2$. Inoculate to $OD_{600}$ of 0.2.

Day 3

EDD extractions (adapted from Chernyan et al, Protein Science 16:2368-2377, 2007):

1) Pellet cells in 50 ml conical tubes, 4° C., 3,000 rpm, 10 mins, discard supernatant.
2) Resuspend in 2 ml degassed PDGH buffer (20 mM MES pH 6.5, 30 mM NaCl, 5 mM $MnCl_2$, 0.5 mM $FeCl_2$, 10 mM 2-mercaptoethanol, 10 mM cysteine, sparged with nitrogen gas). Move to hungate tube.
3) Add 0.1% Triton X-100, 10 ng/ml DNase, 10 µg/ml PMSF, 10 µg/ml TAME (Nα-(p-toluene sulfonyl)-L-arginine methyl ester), 100 µg/ml lysozyme.
4) Sparge hungate tube with nitrogen gas, cap and seal. Incubate 2 hours at 37° C., swirl occasionally.
5) Clarify by centrifugation in 2-ml tube, 4° C., 10 mins, 14,000 rpm. Keep supernatant.
6) Treat with 150 mM pyruvate and 10 mM sodium cyanoborohydride (work in hood) to inactivate aldolase activity. Incubate 30 mins at room temperature.
7) During incubation, pre-equilibrate PD-10 column from GE
   a. Remove top cap, pour off storage buffer.
   b. Cut off bottom tip, fit in 50 ml conical with adapter.
   c. Pour 5 ml of 20 mM MES buffer, pH 6.5 (total of 5 times). Discard flow-through.
8) Run sample through column, then add MES buffer to a total of 2.5 ml volume added. Discard flow-through.
9) Run 3.5 ml 20 mM MES pH 6.5 buffer to elute protein. Discard column in appropriate waste receptacle.
10) Perform Bradford assay (1:10 or 1:20 dilution).

EDA extractions:

1) Spin down in 50 ml conicals, 4° C., 3,400 rpm, 5 mins. Wash 2× with 25 ml water.
2) Resuspend in 1 ml lysis buffer (50 mM Tris-HCl, pH 7, 10 mM $MgCl_2$, 1× protease inhibitor.
3) Add 1 cap of zirconia beads, vortex 4-6 times, 15 sec bursts, ice in between.
4) Spin down cell debris, 4° C., 14,000 rpm, 10 mins. Save supernatant.
5) Perform Bradford assay (1:2 dilution).

Activity Assays:

Each reaction contains 50 mM Tris-HCl, pH 7, 10 mM $MgCl_2$, 0.15 mM NADH, 15 µg LDH, saturating amounts of EDD determined empirically (usually ~100 µg), 1-50 µg EDA (depending on level of activity), and 1 mM 6-phosphogluconate. Reactions are started by the addition of 6-phosphogluconate and monitored for 5 mins at 30° C.

Results

The *S. cerevisiae* strains tested for EDA activity are described in the table below. yCH strains are Thermosacc-based (Lallemand). BF strains are based on BY4742.

| Strain | Vector | Construct |
|---|---|---|
| BF542 | pBF150 | *Zymomonas mobilis* EDA |
| BF1689 | pBF892 | PAO1 + 5aa *E. coli* EDA |
| BF1691 | pBF894 | PAO1 + 10aa *E. coli* EDA |
| BF1693 | pBF896 | PAO1 + 15aa *E. coli* EDA |
| BF1721 | pBF909 | *Bacilluis licheniformis* EDA |
| BF1722 | pBF910 | *Bacillus subtilis* EDA |
| BF1723 | pBF911 | *Pseudomonas fluorescens* EDA |
| BF1724 | pBF912 | *Pseudomonas syringae* EDA |
| BF1725 | pBF913 | *Saccharophagus degradans* EDA |
| BF1726 | pBF914 | *Xanthamonas axonopodis* EDA |
| BF1727 | pBF766 | *Escherichia coli* EDA |
| BF1728 | pBF764 | *Pseudomonas aeruginosa* EDA |
| BF1729 | pBF729 | *Gluconobacter oxydans* EDA |
| BF1730 | pBF727 | *Shewanella oneidensis* EDA |
| BF1775 | pBF87 | p425GPD (empty vector) |
| BF1776 | pBF928 | PAO1 EDA codon optimized for *S. cerevisiae* |

*E. coli* expressed EDD was prepared and confirmed by western blot analysis as shown in FIG. 23. The expected size of EDD is approximately 66 kilodaltons (kDa). A band of approximately that size (e.g., as determined by the nearest sized protein standard of approximately 60 kDa) was identified by western blot. The *E. coli* expressed EDD was used with *S. cerevisiae* expressed EDA's to evaluate the EDA activities. The results of EDA kinetic assays are presented in the table below.

| EDD/EDA | slope | % max |
|---|---|---|
| EC/EC | 0.3467 | 100.00 |
| EC/SO | 0.1907 | 55.00 |
| EC/BS | 0.0897 | 25.87 |
| EC/GO | 0.0848 | 24.46 |
| EC/PCO | 0.084 | 24.23 |
| EC/PA | 0.0533 | 15.37 |
| EC/PE5 | 0.0223 | 6.43 |
| EC/PE10 | 0.0218 | 6.29 |
| EC/SD | 0.015 | 4.33 |
| EC/PS | 0.0135 | 3.89 |
| EC/BL | 0.0112 | 3.23 |
| EC/ZM | 0.0109 | 3.14 |
| EC/PF | 0.0082 | 2.37 |
| EC/V | 0.0074 | 2.13 |
| EC/XA | 0.0065 | 1.87 |
| EC/PE15 | 0.005 | 1.44 |

In the results presented above, the slope of the *E. coli* (EC) EDA is outside the linear range for accurate detection, and is therefore underestimated. For the other EDA's, when compared to the *E. coli* EDA, the calculated percentage of maximum activity (e.g., % max) is overestimated, however the slopes are accurate. The results of this experiment indicate that the *E. coli* EDA has higher activity as compared to the other EDA activities evaluated herein, and is approximately 16-fold more active than the EDA from *P. aeruginosa*. EDA's from *X. anoxopodis* and a chimera between *E. coli* EDA and *P. aeruginosa* (e.g., PE15) show less activity than the vector control. Codon-optimized EDA from *P. aeruginosa* showed a slight improvement over the native sequence, however chimeric versions (e.g., PE5, PE10, PE15) showed less activity than native. The experiments were repeated using 100 µg of EDD and 25 µg of EDA cell lysates in each reaction (unless otherwise noted, such as 5 µg of *E. coli* EDA). The reactions in the repeated experiment all were in the linear range of detection and the results of these additional kinetic assays are shown graphically in FIG. 24, and in the table below. *E. coli* EDA was again found to be the most active of those EDA's tested.

| EDA | slope | % max |
|---|---|---|
| EC | 0.462 | 100.00 |
| SO | 0.128 | 27.71 |
| GO | 0.0544 | 11.77 |
| PCO | 0.0539 | 11.67 |
| BS | 0.0505 | 10.93 |
| PA | 0.0273 | 5.91 |
| V | 0.0006 | 0.13 |

Example 35

Nucleotide and Amino Acid Sequence of *S. cerevisiae* Phosphoglucose Isomerase

Phosphoglucose isomerase (PGI1) activity was decreased or disrupted, in some embodiments, to favor the conversion of glucose-6-phosphate to gluconolactone-6-phosphate by the activity of ZWF1 (e.g., glucose-6-phosphate dehydrogenase). The nucleotide sequence of the *S. cerevisiae* PGI1 gene altered to decrease or disrupt phosphoglucose isomerase activity is shown below.

PGI1 nucleotide sequence (SEQ ID NO: 494)

ATGTCCAATAACTCATTCACTAACTTCAAACTGGCCACTGAATTGCCAGC

CTGGTCTAAGTTGCAAAAAATTTATGAATCTCAAGGTAAGACTTTGTCTG

TCAAGCAAGAATTCCAAAAAGATGCCAAGCGTTTTGAAAAATTGAACAAG

ACTTTCACCAACTATGATGGTTCCAAAATCTTGTTCGACTACTCAAAGAA

CTTGGTCAACGATGAAATCATTGCTGCATTGATTGAACTGGCCAAGGAGG

CTAACGTCACCGGTTTGAGAGATGCTATGTTCAAAGGTGAACACATCAAC

TCCACTGAAGATCGTGCGTCTACCACGTCGCATTGAGAAACAGAGCTAA

CAAGCCAATGTACGTTGATGGTGTCAACGTTGCTCCAGAAGTCGACTCTG

TCTTGAAGCACATGAAGGAGTTCTCTGAACAAGTTCGTTCTGGTGAATGG

AAGGGTTATACCGGTAAGAAGATCACCGATGTTGTTAACATCGGTATTGG

TGGTTCCGATTTGGGTCCAGTCATGGTCACTGAGGCTTTGAAGCACTACG

CTGGTGTCTTGGATGTCCACTTCGTTTCCAACATTGACGGTACTCACATT

GCTGAAACCTTGAAGGTTGTTGACCCAGAAACTACTTTGTTTTTGATTGC

TTCCAAGACTTTCACTACCGCTGAAACTATCACTAACGCTAACACTGCCA

AGAACTGGTTCTTGTCGAAGACAGGTAATGATCCATCTCACATTGCTAAG

CATTTCGCTGCTTTGTCCACTAACGAAACCGAAGTTGCCAAGTTCGGTAT

TGACACCAAAAACATGTTTGGTTTCGAAAGTTGGGTCGGTGGTCGTTACT

CTGTCTGGTCGGCTATTGGTTTGTCTGTTGCCTTGTACATTGGCTATGAC

AACTTTGAGGCTTTCTTGAAGGGTGCTGAAGCCGTCGACAACCACTTCAC

CCAAACCCCATTGGAAGACAACATTCCATTGTTGGGTGGTTTGTTGTCTG

TCTGGTACAACAACTTCTTTGGTGCTCAAACCCATTTGGTTGCTCCATTC

GACCAATACTTGCACAGATTCCCAGCCTACTTGCAACAATTGTCAATGGA

ATCTAACGGTAAGTCTGTTACCAGAGGTAACGTGTTTACTGACTACTCTA

CTGGTTCTATCTTGTTTGGTGAACCAGCTACCAACGCTCAACACTCTTTC

TTCCAATTGGTTCACCAAGGTACCAAGTTGATTCCATCTGATTTCATCTT

AGCTGCTCAATCTCATAACCCAATTGAGAACAAATTACATCAAAAGATGT

TGGCTTCAAACTTCTTTGCTCAAGCTGAAGCTTTAATGGTTGGTAAGGAT

GAAGAACAAGTTAAGGCTGAAGGTGCCACTGGTGGTTTGGTCCCACACAA

GGTCTTCTCAGGTAACAGACCAACTACCTCTATCTTGGCTCAAAAGATTA

CTCCAGCTACTTTGGGTGCTTTGATTGCCTACTACGAACATGTTACTTTC

ACTGAAGGTGCCATTTGGAATATCAACTCTTTCGACCAATGGGGTGTTGA

ATTGGGTAAAGTCTTGGCTAAAGTCATCGGCAAGGAATTGGACAACTCCT

CCACCATTTCTACCCACGATGCTTCTACCAACGGTTTAATCAATCAATTC

AAGGAATGGATGTGA

Example 36

Nucleotide and Amino Acid Sequence of *S. cerevisiae* 6-Phosphogluconate Dehydrogenase (Decarboxylating)

6-phosphogluconate dehydrogenase (decarboxylating) (GND1) activity was decreased or disrupted, in some embodiments, to minimize or eliminate the conversion of gluconate-6-phophate to ribulose-5-phosphate. The nucleotide sequence of the *S. cerevisiae* GND1 and GND2 genes altered to decrease or disrupt 6-phosphogluconate dehydrogenase (decarboxylating) activity is shown below.

GND1/YHR183W (SEQ ID NO: 495)

ATGTCTGCTGATTTCGGTTTGATTGGTTTGGCCGTCATGGGTCAAAATTT

GATCTTGAACGCTGCTGACCACGGTTTCACTGTTTGTGCTTACAACAGAA

CTCAATCCAAGGTCGACCATTTCTTGGCCAATGAAGCTAAGGGCAAATCT

ATCATCGGTGCTACTTCCATTGAAGATTTCATCTCCAAATTGAAGAGACC

TAGAAAGGTCATGCTTTTGGTTAAAGCTGGTGCTCCAGTTGACGCTTTGA

TCAACCAAATCGTCCCACTTTTGGAAAAGGGTGATATTATCATCGATGGT

GGTAACTCTCACTTCCCAGATTCTAATAGACGTTACGAAGAATTGAAGAA

GAAGGGTATTCTTTTCGTTGGTTCTGGTGTCTCCGGTGGTGAGGAAGGTG

CCCGTTACGGTCCATCTTTGATGCCAGGTGGTTCTGAAGAAGCTTGGCCA

CATATTAAGAACATCTTCCAATCCATCTCTGCTAAATCCGACGGTGAACC

ATGTTGCGAATGGGTTGGCCCAGCCGGTGCTGGTCACTACGTCAAGATGG

TTCACAACGGTATTGAATACGGTGATATGCAATTGATTTGTGAAGCTTAT

GACATCATGAAGAGATTGGGTGGGTTTACCGATAAGGAAATCAGTGACGT

TTTTGCCAAATGGAACAATGGTGTCTTGGATTCCTTCTTGGTCGAAATTA

CCAGAGATATTTTGAAATTCGACGACGTCGACGGTAAGCCATTAGTTGAA

AAAATCATGGATACTGCTGGTCAAAAGGGTACTGGTAAGTGGACTGCCAT

CAACGCCTTGGATTTGGGTATGCCAGTTACTTTGATTGGTGAAGCTGTCT

TTGCCCGTTGTCTATCTGCTTTGAAGAACGAGAGAATTAGAGCCTCCAAG

GTCTTACCAGGCCCAGAAGTTCCAAAAGACGCCGTCAAGGACAGAGAACA

ATTTGTCGATGATTTGGAACAAGCTTTGTATGCTTCCAAGATTATTTCTT

ACGCTCAAGGTTTCATGTTGATCCGTGAAGCTGCTGCTACTTATGGCTGG

AAACTAAACAACCCTGCCATCGCTTTGATGTGGAGAGGTGGTTGTATCAT

TAGATCTGTTTTCTTGGGTCAAATCACAAAGGCCTACAGAGAAGAACCAG

ATTTGGAAAACTTGTTGTTCAACAAGTTCTTCGCTGATGCCGTCACCAAG

GCTCAATCTGGTTGGAGAAAGTCAATTGCGTTGGCTACCACCTACGGTAT

CCCAACACCAGCCTTTTCCACCGCTTTGTCTTTCTACGATGGGTACAGAT

CTGAAAGATTGCCAGCCAACTTACTACAAGCTCAACGTGACTACTTTGGT

GCTCACACTTTCAGAGTGTTGCCAGAATGTGCTTCTGACAACTTGCCAGT

AGACAAGGATATCCATATCAACTGGACTGGCCACGGTGGTAATGTTTCTT

CCTCTACATACCAAGCTTAA

GND2/YGR256W (SEQ ID NO: 496)

ATGTCAAAGGCAGTAGGTGATTTAGGCTTAGTTGGTTTAGCCGTGATGGG

TCAAAATTTGATCTTAAACGCAGCGGATCACGGATTTACCGTGGTTGCT

TATAATAGGACGCAATCAAAGGTAGATAGGTTTCTAGCTAATGAGGCAA

AAGGAAAATCAATAATTGGTGCAACTTCAATTGAGGACTTGGTTGCGAA

ACTAAAGAAACCTAGAAAGATTATGCTTTTAATCAAAGCCGGTGCTCCG

GTCGACACTTTAATAAAGGAACTTGTACCACATCTTGATAAAGGCGACA

TTATTATCGACGGTGGTAACTCACATTTCCCGGACACTAACAGACGCTA

CGAAGAGCTAACAAAGCAAGGAATTCTTTTTGTGGGCTCTGGTGTCTCA

GGCGGTGAAGATGGTGCACGTTTTGGTCCATCTTTAATGCCTGGTGGGT

CAGCAGAAGCATGGCCGCACATCAAGAACATCTTTCAATCTATTGCCGC

CAAATCAAACGGTGAGCCATGCTGCGAATGGGTGGGGCCTGCCGGTTCT

GGTCACTATGTGAAGATGGTACACAACGGTATCGAGTACGGTGATATGC

AGTTGATTTGCGAGGCTTACGATATCATGAAACGAATTGGCCGGTTTAC

GGATAAAGAGATCAGTGAAGTATTTGACAAGTGGAACACTGGAGTTTTG

GATTCTTTCTTGATTGAAATCACGAGGGACATTTTAAAATTCGATGACG

TCGACGGTAAGCCATTGGTGGAAAAAATTATGGATACTGCCGGTCAAAA

GGGTACTGGTAAATGGACTGCAATCAACGCCTTGGATTTAGGAATGCCA

GTCACTTTAATTGGGGAGGCTGTTTTCGCTCGTTGTTTGTCAGCCATAA

AGGACGAACGTAAAAGAGCTTCGAAACTTCTGGCAGGACCAACAGTACC

AAAGGATGCAATACATGATAGAGAACAATTTGTGTATGATTTGGAACAA

GCATTATACGCTTCAAAGATTATTTCATATGCTCAAGGTTTCATGCTGA

TCCGCGAAGCTGCCAGATCATACGGCTGGAAATTAAACAACCCAGCTAT

TGCTCTAATGTGGAGAGGTGGCTGTATAATCAGATCTGTGTTCTTAGCT

GAGATTACGAAGGCTTATAGGGACGATCCAGATTTGGAAAATTTATTAT

TCAACGAGTTCTTCGCTTCTGCAGTTACTAAGGCCCAATCCGGTTGGAG

AAGAACTATTGCCCTTGCTGCTACTTACGGTATTCCAACTCCAGCTTTC

TCTACTGCTTTAGCGTTTTACGACGGCTATAGATCTGAGAGGCTACCAG

CAAACTTGTTACAAGCGCAACGTGATTATTTTGGCGCTCATACATTTAG

AATTTTACCTGAATGTGCTTCTGCCCATTTGCCAGTAGACAAGGATATT

CATATCAATTGGACTGGGCACGGAGGTAATATATCTTCCTCAACCTACC

AAGCTTAA

Example 37

Nucleotide and Amino Acid Sequence of *S. cerevisiae* Transaldolase

Transaldolase (TAL1) activity was increased in some embodiments, and in certain embodiments transaldolase activity was decreased or disrupted. Transaldolase converts sedoheptulose 7-phosphate and glyceraldehyde 3-phosphate to erythrose 4-phosphate and fructose 6-phosphate. The rationale for increasing or decreasing transaldolase activity is described herein with respect to various embodiments. The nucleotide sequence of the *S. cerevisiae* TAL1 gene altered to increase or decrease transaldolase activity, and the encoded amino acid sequence are shown below.

TAL1 nucleotide sequence (SEQ ID NO: 497)

ATGTCTGAACCAGCTCAAAAGAAACAAAAGGTTGCTAACAACTCTCTAG

AACAATTGAAAGCCTCCGGCACTGTCGTTGTTGCCGACACTGGTGATTTC

GGCTCTATTGCCAAGTTTCAACCTCAAGACTCCACAACTAACCCATCATT

GATCTTGGCTGCTGCCAAGCAACCAACTTACGCCAAGTTGATCGATGTTG

CCGTGGAATACGGTAAGAAGCATGGTAAGACCACCGAAGAACAAGTCGAA

AATGCTGTGGACAGATTGTTAGTCGAATTCGGTAAGGAGATCTTAAAGAT

TGTTCCAGGCAGAGTCTCCACCGAAGTTGATGCTAGATTGTCTTTTGACA

CTCAAGCTACCATTGAAAAGGCTAGACATATCATTAAATTGTTTGAACAA

GAAGGTGTCTCCAAGGAAAGAGTCCTTATTAAAATTGCTTCCACTTGGGA

AGGTATTCAAGCTGCCAAAGAATTGGAAGAAAAGGACGGTATCCACTGTA

ATTTGACTCTATTATTCTCCTTCGTTCAAGCAGTTGCCTGTGCCGAGGCC

CAAGTTACTTTGATTTCCCCATTTGTTGGTAGAATTCTAGACTGGTACAA

ATCCAGCACTGGTAAAGATTACAAGGGTGAAGCCGACCCAGGTGTTATTT

CCGTCAAGAAAATCTACAACTACTACAAGAAGTACGGTTACAAGACTATT

GTTATGGGTGCTTCTTTCAGAAGCACTGACGAAATCAAAAACTTGGCTGG

TGTTGACTATCTAACAATTTCTCCAGCTTTATTGGACAAGTTGATGAACA

GTACTGAACCTTTCCCAAGAGTTTTGGACCCTGTCTCCGCTAAGAAGGAA

GCCGGCGACAAGATTTCTTACATCAGCGACGAATCTAAATTCAGATTCGA

CTTGAATGAAGACGCTATGGCCACTGAAAAATTGTCCGAAGGTATCAGAAA

ATTCTCTGCCGATATTGTTACTCTATTCGACTTGATTGAAAAGAAAGTTA

CCGCTTAA

TAL1 amino acid sequence (SEQ ID NO: 498)

MSEPAQKKQKVANNSLEQLKASGTVVVADTGDFGSIAKFQPQDSTTNPSL

ILAAAKQPTYAKLIDVAVEYGKKHGKTTEEQVENAVDRLLVEFGKEILKI

VPGRVSTEVDARLSFDTQATIEKARHIIKLFEQEGVSKERVLIKIASTWE

GIQAAKELEEKDGIHCNLTLLFSFVQAVACAEAQVTLISPFVGRILDWYK

```
SSTGKDYKGEADPGVISVKKIYNYYKKYGYKTIVMGASFRSTDEIKNLAG

VDYLTISPALLDKLMNSTEPFPRVLDPVSAKKEAGDKISYISDESKFRFD

LNEDAMATEKLSEGIRKFSADIVTLFDLIEKKVTA
```

Example 38

Nucleotide and Amino Acid Sequence of S. cerevisiae Transketolase

Transketolase (TKL1 and TKL2) activity was increased in some embodiments, and in certain embodiments transaldolase activity was decreased or disrupted. Transketolase converts xylulose-5-phosphate and ribose-5-phosphate to sedoheptulose-7-phosphate and glyceraldehyde-3-phosphate. The rationale for increasing or decreasing transketolase activity is described herein with respect to various embodiments. The nucleotide sequence of the S. cerevisiae TKL1 gene altered to increase or decrease transketolase activity, and the encoded amino acid sequence are shown below.

TKL1 nucleotide sequence (SEQ ID NO: 499)

```
ATGACTCAATTCACTGACATTGATAAGCTAGCCGTCTCCACCATAAGAA

TTTTGGCTGTGGACACCGTATCCAAGGCCAACTCAGGTCACCCAGGTGC

TCCATTGGGTATGGCACCAGCTGCACACGTTCTATGGAGTCAAATGCGC

ATGAACCCAACCAACCCAGACTGGATCAACAGAGATAGATTTGTCTTGT

CTAACGGTCACGCGGTCGCTTTGTTGTATTCTATGCTACATTTGACTGG

TTACGATCTGTCTATTGAAGACTTGAAACAGTTCAGACAGTTGGGTTCC

AGAACACCAGGTCATCCTGAATTTGAGTTGCCAGGTGTTGAAGTTACTA

CCGGTCCATTAGGTCAAGGTATCTCCAACGCTGTTGGTATGGCCATGGC

TCAAGCTAACCTGGCTGCCACTTACAACAAGCCGGGCTTTACCTTGTCT

GACAACTACACCTATGTTTTCTTGGGTGACGGTTGTTTGCAAGAAGGTA

TTTCTTCAGAAGCTTCCTCCTTGGCTGGTCATTTGAAATTGGGTAACTT

GATTGCCATCTACGATGACAACAAGATCACTATCGATGGTGCTACCAGT

ATCTCATTCGATGAAGATGTTGCTAAGAGATACGAAGCCTACGGTTGGG

AAGTTTTGTACGTAGAAAATGGTAACGAAGATCTAGCCGGTATTGCCAA

GGCTATTGCTCAAGCTAAGTTATCCAAGGACAAACCAACTTTGATCAAA

ATGACCACAACCATTGGTTACGGTTCCTTGCATGCCGGCTCTCACTCTG

TGCACGGTGCCCCATTGAAAGCAGATGATGTTAAACAACTAAAGAGCAA

ATTCGGTTTCAACCCAGACAAGTCCTTTGTTGTTCCACAAGAAGTTTAC

GACCACTACCAAAAGACAATTTTAAAGCCAGGTGTCGAAGCCAACAACA

AGTGGAACAAGTTGTTCAGCGAATACCAAAAGAAATTCCCAGAATTAGG

TGCTGAATTGGCTAGAAGATTGAGCGGCCAACTACCCGCAAATTGGGAA

TCTAAGTTGCCAACTTACACCGCCAAGGACTCTGCCGTGGCCACTAGAA

AATTATCAGAAACTGTTCTTGAGGATGTTTACAATCAATTGCCAGAGTT

GATTGGTGGTTCTGCCGATTTAACACCTTCTAACTTGACCAGATGGAAG

GAAGCCCTTGACTTCCAACCTCCTTCTTCCGGTTCAGGTAACTACTCTG

GTAGATACATTAGGTACGGTATTAGAGAACACGCTATGGGTGCCATAAT

GAACGGTATTTCAGCTTTCGGTGCCAACTACAAACCATACGGTGGTACT

TTCTTGAACTTCGTTTCTTATGCTGCTGGTGCCGTTAGATTGTCCGCTT

TGTCTGGCCACCCAGTTATTTGGGTTGCTACACATGACTCTATCGGTGT

CGGTGAAGATGGTCCAACACATCAACCTATTGAAACTTTAGCACACTTC

AGATCCCTACCAAACATTCAAGTTTGGAGACCAGCTGATGGTAACGAAG

TTTCTGCCGCCTACAAGAACTCTTTAGAATCCAAGCATACTCCAAGTAT

CATTGCTTTGTCCAGACAAAACTTGCCACAATTGGAAGGTAGCTCTATT

GAAAGCGCTTCTAAGGGTGGTTACGTACTACAAGATGTTGCTAACCCAG

ATATTATTTTAGTGGCTACTGGTTCCGAAGTGTCTTTGAGTGTTGAAGC

TGCTAAGACTTTGGCCGCAAAGAACATCAAGGCTCGTGTTGTTTCTCTAC

CAGATTTCTTCACTTTTGACAAACAACCCCTAGAATACAGACTATCAGTC

TTACCAGACAACGTTCCAATCATGTCTGTTGAAGTTTTGGCTACCACATG

TTGGGGCAAATACGCTCATCAATCCTTCGGTATTGACAGATTTGGTGCCT

CCGGTAAGGCACCAGAAGTCTTCAAGTTCTTCGGTTTCACCCCAGAAGGT

GTTGCTGAAAGAGCTCAAAAGACCATTGCATTCTATAAGGGTGACAAGCT

AATTTCTCCTTTGAAAAAAGCTTTCTAA
```

TKL1 amino acid sequence (SEQ ID NO: 500)

```
MTQFTDIDKLAVSTIRILAVDTVSKANSGHPGAPLGMAPAAHVLWSQMRM

NPTNPDWINRDRFVLSNGHAVALLYSMLHLTGYDLSIEDLKQFRQLGSRT

PGHPEFELPGVEVTTGPLGQGISNAVGMAMAQANLAATYNKPGFTLSDNY

TYVFLGDGCLQEGISSEASSLAGHLKLGNLIAIYDDNKITIDGATSISFD

EDVAKRYEAYGWEVLYVENGNEDLAGIAKAIAQAKLSKDKPTLIKMTTTI

GYGSLHAGSHSVHGAPLKADDVKQLKSKFGFNPDKSFVVPQEVYDHYQKT

ILKPGVEANNKWNKLFSEYQKKFPELGAELARRLSGQLPANWESKLPTYT

AKDSAVATRKLSETVLEDVYNQLPELIGGSADLTPSNLTRWKEALDFQPP

SSGSGNYSGRYIRYGIREHAMGAIMNGISAFGANYKPYGGTFLNFVSYAA

GAVRLSALSGHPVIWVATHDSIGVGEDGPTHQPIETLAHFRSLPNIQVWR

PADGNEVSAAYKNSLESKHTPSIIALSRQNLPQLEGSSIESASKGGYVLQ

DVANPDIILVATGSEVSLSVEAAKTLAAKNIKARVVSLPDFFTFDKQPLE

YRLSVLPDNVPIMSVEVLATTCWGKYAHQSFGIDRFGASGKAPEVFKFFG

FTPEGVAERAQKTIAFYKGDKLISPLKKAF
```

Example 39

Nucleotide and Amino Acid Sequences of Additional
EDD Genes Evaluated for Activity

| Accession Number | Species | Strain Number | NUCLEOTIDE SEQUENCE | Amino Acid Sequence |
|---|---|---|---|---|
| YP_526855.1 | Saccharophagus degradans | 2-40 | ATGAATAGCGTAATCGAAGCTGTAACTCAGCGAATTATTGAGCGCAGT CGACATTCTCGTCAGGCGTATTTGAATTTAATGCGCAACACCATGGAG CAGCATCCTCCTAAAAAGCGTCTATCTTGCGGCAATTTGGCTCATGCCT ATGCAGCATGTGGTCAATCCGATAAGCAAACAATTCGTTTAATGCAAA GTGCAAACATAAGTATTACTACGGCATTTAACGATATGCTTTCGGCGC ATCAGCCTTTAGAAACATACCCTCAAATAATCAAAGAAACTGCGCGTG CAATGGGTTCAACTGCTCAAGTTGCAGGCGGCGTGCCGGCAATGTGTG ATGGTGTAACTCAAGGCCAGCCCGGTATGGAGCTGAGTTTGTTTAGCC GCGAAGTTGTAGCAATGGCTACAGCAGTAGGCCTTTCGCACAATATGT TTGATGGCAATATGTTTTTGGGTGTATGCGATAAAATTGTTCCTGGCAT GCTAATTGGCGCGTTGCAGTTTGGTCATATTCCTGGGGTGTTTGTGCCT GCCGGACCAATGCCTTCTGGTATTCCCAACAAAGAAAAGCAAAAGTT CGTCAGCAATATGCGGCGGGCATTGTGGGGAAGATAAGCTTTTAGAA ACCGAGTCGGCTTCCTATCACAGTGCAGGCACGTGTACTTTTTACGGTA CAGCGAATACAAACCAAATGATGGTTGAAATGTTGGGTGTTCAGTTGC CTGGCTCGTCGTTTGTTTACCCCGGTACTGAGTTGCGTGATGCCTTAAC GAGAGCTGCTGTTGAAAAGTTGGTAAAAATCACAGATTCAGCCGGTAA CTACCGTCCGCTCTACGAAGTCATTACGGAAAAATCCATCGTCAATTC AATAATTGGTTTGTTGGCTACCGGCGGTTCTACTAACCACACGCTACAC ATTGTTGCTGTGGCTCGCGCTGCGGGTATAGAGGTTACGTGGGCAGAT ATGGACGAGCTTTCGCGTGCTGTGCCATTACTTGCACGTGTTTACCCTA ACGGCGAAGCTGATGTTAACCAATTCCAGCAGGCTGGCGGCATGGCTT ATTTAGTAAGAGAGCTGCGCAGCGGCGGTTTGCTAAATGAAGATGTGG TTACTATTATGGGTGAGGGCCTCGAGGCCTACGAAAAAGAGCCCATGC TTAACGATAAGGGGCAGGCTGAATGGGTAAATGATGTACCTGTTAGCC GCGACGATACCGTTGTGCGTCCAGTTACCTCGCCTTTCGATAAAGAGG GTGGGTTGCGTCTACTCAAGGGTAACTTAGGGCAGGGCGTAATCAAAA TTTCTGCGGTAGCGCCAGAAAATCGCGTTGTTGAGGCCCCATGTATTGT ATTCGAGGCCCAAGAAGAGCTAATAGCTGCGTTTAAGCGTGGTGAGCT CGAAAAAGACTTTGTTGCGGTAGTGCGCTTCCAAGGGCCTTCTGCCAA TGGCATGCCAGAACTTCATAAAATGACCCCGCCTTTAGGTGTGCTTCA AGATAAGGGTTTCAAGGTAGCGTTAGTTACCGATGGCAGAATGTCTGG TGCATCTGGTAAAGTGCCGGCCGGTATACACTTGTCGCCAGAAGCGAG CCGTGGTGGCCTGTTGAATAAGCTGCGCACGGGTGATGTGATTCGCTT CGATGCCGAAGCGGGCGTTATTCAAGCGCTTGTTAGTGATGAAGAGTT AGCTGCGCGTGAGCCAGCTGTGCAACCGGTCGTGGAGCAGAACCTCGG ACGCTCTCTGTTTGGTGGTTTGCGCGATTTGGCTGGTGTATCGCTACAA GGCGGAACAGTTTTCGATTTTGAAAGAGAGTTTGGCGAAAAATAG (SEQ ID NO: 501) | MNSVIEAVTQRIIERSR HSRQAYLNLMRNTME QHPPKKRLSCGNLAHA YAACGQSDKQTIRLMQ SANISITTAFNDMLSAH QPLETYPQIIKETARAM GSTAQVAGGVPAMCD GVTQGQPGMELSLFSR EVVAMATAVGLSHNM FDGNMFLGVCDKIVPG MLIGALQFGHIPGVFVP AGPMPSGIPNKEKAKV RQQYAAGIVGEDKLLE TESASYHSAGTCTFYGT ANTNQMMVEMLGVQL PGSSFVYPGTELRDALT RAAVEKLVKITDSAGN YRPLYEVITEKSIVNSII GLLATGGSTNHTLHIVA VARAAGIEVTWADMD ELSRAVPLLARVYPNGE ADVNQFQQAGGMAYL VRELRSGGLLNEDVVTI MGEGLEAYEKEPMLND KGQAEWVNDVPVSRD DTVVRPVTSPFDKEGGL RLLKGNLGQGVIKISAV APENRVVEAPCIVFEAQ EELIAAFKRGELEKDFV AVVRFQGPSANGMPEL HKMTPPLGVLQDKGFK VALVTDGRMSGASGKV PAGIHLSPEASKGGLLN KLRTGDVIRFDAEAGVI QALVSDEELAAREPAV QPVVEQNLGRSLFGGL RDLAGVSLQGGTVFDF EREFGEK (SEQ ID NO: 502) |
| NP_642389.1 | Xanthomonas axonopodis | Pv. citri str. 306 | ATGAGCCTGCATCCGAATATCCAAGCCGTCACCGACCGTATCCGCAAG CGCAGTGCTCCCTCGCGCGCGGCGTATCTGGCCGGCCTCGATGCCGCC CTGCGTGAGGGCCCGTTCCGTAGCCGGTTGAGCTGCGGCAATCTCGCG CATGGCTTCGCTGCGTCCGAGCCGGGCGACAAATCGCGCCTGCGCGGT GCGGCCACGCCGAACCTGGGCATCATCACTGCCTATAACGACATGTTG TCGGCACATCAGCCGTTCGAGCACTACCCGCAGCTGATCCGCGAAACC GCGCGCTCACTTGGCGCCACTGCGCAGGTGGCCGGCGGCGTGCCGGCG ATGTGTGACGGCGTGACCCAGGGCCGCGCCGGCATGGAGCTGTCGCTG TTCTCGCGCGACAACATCGCTCAGGCTGCGGCCATTGGCCTGAGCCAT GACATGTTCGACAGCGTGGTGTACCTGGGGGTGTGCGACAAGATCGTG CCGGGTCTGCTGATCGGTGCGCTGGCGTTTGGCCATTTGCCCGGCGATCT TCATGCCGGCTGGTCCGATGACCCCGGGCATCCCGAACAAGCAGAAAG CCGAAGTCCGCGAACGCTACGCCGCTGGCGAAGCCACCCGCGCCGAAT TGCTGGAGGCCGAATCCTCGTCTTATCACTCGCCCGGCACCTGCACCTT TTACGGCACGGCGAACTCCAACCAGGTGTTGCTCGAAGCGATGGGCGT GCAGTTGCCCGGCGCCTCGTTCGTCAATCCGGAGCTGCCGCTGCGCGA TGCACTGACCCGCGAAGGCACCGCACGCGCATTGGCGATCTCCGCGCT GGGCGATGACTTCCGCCCGTTCGGTCGTTTGATCGACGAACGGGCCAT CGTCAATGCCGTGGTCGCGCTGATGGCGACCGGCGGTTCGACCAACCA CACCATCCACTGGATCGCGGTCGCTGCGGCCATCGTGTTGAC CTGGGACGACATGGATCTGATCTCGCAGACCGTGCCGCTGTTGACACG CATCTACCCGAACGGCGAAGCCGACGTGAACCGCTTCCAGGCCGCAGG CGGCACGGCGTTCGTGTTCCGCGAATTGATGGACGCCGGCTACATGCA CGACGACCTGCCGACCATCGTCGAAGGCGGCATGCGCGCGTACGTCAA CGAACCGCGCCTGCAGGACGGCAAGGTGACCTACGTGCCCGGCACCG GTATTACCGACGACAGCGTCGCGCGTCCGGTCAGCGATGCATTCG AATCACAAGGCGGCCTGCGCCTGCTGCGCGGCAACCTCGGCCGCTCGT TGATCAAGCTGTCGGCGGTCAAGCCGCAGCACCGCAGCATCCAAGCGC CAGCGGTGGTGATCGACACCCCGCAAGTGCTCAACAAACTGCATGCGG CGGGCGTACTGCCGCACGATTTCGTGGTGGTACTGCGCTATCAGGGCC | MSLHPNIQAVTDRIRKR SAPSRAAYLAGIDAALR EGPFRSRLSCGNLAHGF AASEPTDKSRLRGAATP NLGIITAYNDMLSAHQP FEHYPQLIRETARSLGA TAQVAGGVPAMCDGV TQGRAGMELSLFSRDNI AQAAIGLSHDMFDSV VYLGVCDKIVPGLLIGA LAFGHLPAIFMPAGPMT PGIPNKQKAEVRERYA AGEATRAELLEAESSSY HSPGTCTFYGTANSNQ VLLEAMGVQLPGASFV NPELPLRDALTREGTAR ALAISALGDDFRPFGRLI DERAIVNAVVALMATG GSTNHTIHWIAVARAA GIVLTWDDMDLISQTVP LLTRIYPNGEADVNRFQ AAGTAFVFRELMDAG YMHDDLPTIVEGGMRA YVNEPRLQDGKVTYVP GTATADDSVARPVSD AFESQGGLRLLRGNLG RSLIKLSAVKPQHRSIQ APAVVIDTPQVLNKLH AAGVLPHDFVVVLRYQ GPRANGMPELHSMAPL |

| Accession Number | Species | Strain Number | NUCLEOTIDE SEQUENCE | Amino Acid Sequence |
|---|---|---|---|---|
| | | | CACGCGCAAACGGCATGCCGGAGCTGCATTCGATGGCGCCGCTACTGG<br>GCCTGCTGCAGAACCAGGGCCGGCGCGTGGCGTTGGTCACCGACGGCC<br>GTCTGTCCGGCGCCTCGGGCAAGTTCCCGGCGGCGATCCACATGACCC<br>CGGAAGCCGCACGCGGCGGCCCGATCGGGCGCGTACGCGAAGGCGAC<br>ATCGTGCGACTGGACGGCGAAGCCGGCACCTTGGAAGTGCTGGTTTCG<br>GCCGAAGAATGGGCATCGCGCGAGGTCGCACCGAACACTGCCGTTGGC<br>CGGCAACGACCTGGGCCGCAACCTGTTCGCCATCAACCGCCAGGTGGT<br>TGGCCCGGCCGACCAGGGCGCGATTTCCATTTCCTGCGGCCCGACCCA<br>TCCGGACGGTGCGCTGTGGAGCTACGACGCCGAGTACGAACTCGGTGC<br>CGATGCAGCTGCAGCCGCCGCGCCGCACGAGTCCAAGGACGCCTGA<br>(SEQ ID NO: 503) | LGLLQNQGRRVALVTD<br>GRLSGASGKFPAAIHMT<br>PEAARGGPIGRVREGDI<br>VRLDGEAGTLEVLVSA<br>EEWASREVAPNTALAG<br>NDLGRNLFAINRQVVG<br>PADQGAISISCGPTHPD<br>GALWSYDAEYELGAD<br>AAAAAAPHESKDA<br>(SEQ ID NO: 504) |
| NP_791117.1 | Pseudomonas syringae | Pv. tomato str. DC3000 | ATGCATCCCCGCGTCCTTGAAGTAACCGAGCGGCTCATTGCTCGCAGT<br>CGCGATACCCGTCAGCGCTACCTTCAATTGATTCGAGGCGCAGCAGC<br>GATGGCCCGATGCGCGGCAAGCTTCAATGTGCCAACTTTGCTCACGGC<br>GTCGCCGCCTGCGGACCGGAGGACAAGCAAAGCCTGCGTTTGATGAAC<br>GCCGCCAACGTGGCAATCGTCTCTTCCTACAATGAAATGCTCTCGGCG<br>CATCAGCCCTACGAGCACTTTCCTGCACAGATCAAACAGGCGTTACGT<br>GACATTGGTTCGGTCGGTCAGTTTGCCGGCGGCGTGCCTGCCATGTGC<br>GATGGCGTGACTCAGGGTGAGCCGGGCATGGAACTGGCCATTGCCAGC<br>CGCGAAGTGATTGCCATGTCCACGGCAATTGCCTTGTCACACAATATG<br>TTCGACGCCGCCATGATGCTGGGTATCTGCGACAAGATCGTCCCCGGC<br>CTGATGATGGGGGCGTTGCGTTTCGGTCATCTGCCGACCATCTTCGTGC<br>CGGGCGGGCCGATGGTGTCAGGTATCTCCAACAAGGAAAAAGCCGAC<br>GTACGGCAGCGTTACGCTGAAGGCAAGGCCAGCCGTGAAGAGCTGCT<br>GGACTCGGAAATGAAGTCCTATCACGGCCCGGGAACCTGCACGTTCTA<br>CGGCACCGCCAACACCAATCAGTTGGTGATGGAAGTCATGGGCATGCA<br>CCTTCCCGGTGCCTCGTTCGTCAATCCCTACACCACTGCGTGATGCG<br>CTGACAGCTGAAGCGGCTCGTCAGGTCACGCGTCTGACCATGCAAAGC<br>GGCAGTTTCATGCCGATTGGTGAAATCGTCGACGAGCGCTCGCTGGTC<br>AATTCCATCGTTGCGCTGCACGCCACCGGCGGCTCGACCAACCACACG<br>CTGCACATGCCGGCGATTGCTCAGGCTGCGGGTATTCAGCTGACCTGG<br>CAGGACATGGCCGACCTCTCCGAAGTGGTGCCGACCCTCAGTCACGTC<br>TACCCCAACGGCAAGGCCGACATCAACCATTTCCAGGCCGCAGGCGGC<br>ATGTCTTTCCTGATTCGCGAGCTGCTGGCAGCCGGTCTGCTGCACGAA<br>AACGTTAACACCGTGGCCGGTTATGGCCTGAGCCGCTACACCAAAGAG<br>CCATTCCTGGAGGATGGCAAACTGGTCTGGCGTGAAGGCCCGCTGGAC<br>AGCCTGGATGAAAACATCCTGCGCCCGGTGGCGCGTCCGTTCTCCCCT<br>GAAGGCGGTTTGCGGGTCATGGAAGGCAACCTGGGTCGCGGTGTCATG<br>AAAGTATCGGCCGTTGCGCTGGAGCATCAGATTGTCGAAGCGCCAGCC<br>CGAGTGTTTCAGGATCAGAAGGAGCTGGCCGATGCGTTCAAGGCCGGC<br>GAGCTGGAATGTGATTTCGTCGCCGTCATGCGTTTTCAGGGCCCGCGCT<br>GCAACGGCATGCCCGAACTGCACAAGATGACCCCGTTTCTGGGCGTGC<br>TGCAGGATCGTGGTTTCAAAGTGGCGCTGGTCACCGATGGACGGATGT<br>CGGGCGCCTCAGGCAAGATTCCGGCGGCGATTCACGTCTGCCCGGAAG<br>CGTTCGATGGTGGCCCGTTGGCACTGGTACGCGACGGCGATGTGATCC<br>GCGTGGATGGCGTAAAAGGCACGTTACAGTGCTGGTCGAAGCGTCA<br>GAATTGGCCGCCCGAGAACCGGCCATCAACCAGATCGACAACAGTGTC<br>GGCTGCGGTCGCGAGCTTTTTGGATTCATGCGCATGGCCTTCAGCTCCG<br>CAGAGCAAGGCGCCAGCGCCTTTACCTCTAGTCTGGAGACGCTCAAGT<br>GA (SEQ ID NO: 505) | MHPRVLEVTERLIARSR<br>DTRQRYLQLIRGAASD<br>GPMRGKLQCANFAHG<br>VAACGPEDKQSLRLMN<br>AANVAIVSSYNEMLSA<br>HQPYEHFPAQIKQALRD<br>IGSVGQFAGGVPAMCD<br>GVTQGEPGMELAIASRE<br>VIAMSTAIALSHNMFDA<br>AMMLGICDKIVPGLMM<br>GALRFGHLPTIFVPGGP<br>MVSGISNKEKADVRQR<br>YAEGKASREELLDSEM<br>KSYHGPGTCTFYGTAN<br>TNQLVMEVMGMHLPG<br>ASFVNPYTPLRDALTAE<br>AARQVTRLTMQSGSFM<br>PIGEIVDERSLVNSIVAL<br>HATGGSTNHTLHMPAI<br>AQAAGIQLTWQDMAD<br>LSEVVPTLSHVYPNGK<br>ADINHFQAAGGMSFLIR<br>ELLAAGLLHENVNTVA<br>GYGLSRYTKEPFLEDG<br>KLVWREGPLDSLDENIL<br>RPVARPFSPEGGLRVME<br>GNLGRGVMKVSAVAL<br>EHQIVEAPARVFQDQK<br>ELADAFKAGELECDFV<br>AVMRFQGPRCNGMPEL<br>HKMTPFLGVLQDRGFK<br>VALVTDGRMSGASGKI<br>PAAIHVCPEAFDGGPLA<br>LVRDGDVIRVDGVKGT<br>LQVLVEASELAAREPAI<br>NQIDNSVGCGRELFGF<br>MRMAFSSAEQGASAFT<br>SSLETLK<br>(SEQ ID NO: 506) |
| YP_261706.1 | Pseudomonas fluorescens | Pf-5 | ATGCATCCCCGCGTTCTTGAGGTCACCGAACGGCTTATCGCCCGTAGTC<br>GCGCCACTCGCCAGGCCTATCTCGCGCTGATCCGCGATGCCGCCAGCG<br>ACGGGCCCGCAGCGGGGCAAGCTGCAATGTGCGAACTTCGCCACGGC<br>GTGGCCGGTTGCGGCACCGACGACAAGCACAACCTGCGGATGATGAA<br>TGCGGCCAACGTGGCAATTGTTTCGTCATATAACGACATGTTGTCGGC<br>GCACCAGCCTTACGAGGTGTTCCCCGAGCAGATCAAGCGCGCCCTGCG<br>CGAGATCGGCTCGGTGGGCCAGTTCGCCGGCGGCACCCCGGCCATGTG<br>CGATGGCGTGACCCAGGGCGAGGCCGGTATGGAACTGAGCCTGCCGA<br>GCCGTGAAGTGATCGCCCTGTCTACGGCGGTGGCCCTCTCTCACAACA<br>TGTTCGATGCCGCGCTGATGCTGGGGATCTGCGACAAGATTGTCCCGG<br>GGTTGATGATGGGCGCTCTGCGCTTCGGTCACCTGCCGACCATCTTCGT<br>TCCCGGCGGGCCCATGGTCTCGGGCATTTCCAACAAGCAGAAAGCCGA<br>CGTGCGCCAGCGTTACGCCGAAGGCAAGGCCAGCCGCGAGGAACTGC<br>TGGAGTCGGAAATGAAGTCCTACCACAGCCCCGGCACCTGCACTTTCT<br>ACGGCACCGCCAACACCAACCAGTTGCTGATGGAAGTGATGGGCCTGC<br>ACCTGCCGGGCGCCTCTTTCGTCAACCCCAATACGCCGCTGCGCGACG<br>CCCTGACCCATGAGGCGGCGCAGCAGGTCACGCGCCTGACCAAGCAG<br>AGCGGGGCCTTCATGCCGATTGGCGAGATCGTCGACGAGCGCGTGCTG<br>GTCAACTCCATCGTTGCCCTGCACGCCACGGGCGGCTCCACCAACCAC<br>ACCCTGCACATGCCGGCGATTGCCCAGGCGGCGGGCATCCAGCTGACC<br>TGGCAGGACATGGCCGACCTCTCCGAGGTGGTGCCGACCCTGTCCCAC<br>GTCTATCCCAACGGCAAGGCCGATATCAACCACTTCCAGGCGGCGGGC<br>GGCATGTCTTTCCTGATCCGCGAGCTGCTGGAAGCCGGCCTGCTCCAC<br>GAAGACGTCAATACCGTGGCCGGCCGCGGCCTGAGCCGCTATACCCAG<br>GAACCCTTCCTGGACAACGGCAAGCTGGTGTGGCGCGACGGCCCGATT | MHPRVLEVTERLIARSR<br>ATRQAYLALIRDAASD<br>GPQRGKLQCANFAHGV<br>AGCGTDDKHNLRMMN<br>AANVAIVSSYNDMLSA<br>HQPYEVFPEQIKRALRE<br>IGSVGQFAGGTPAMCD<br>GVTQGEAGMELSLPSR<br>EVIALSTAVALSHNMFD<br>AALMLGICDKIVPGLM<br>MGALRFGHLPTIFVPGG<br>PMVSGISNKQKADVRQ<br>RYAEGKASREELLESE<br>MKSYHSPGTCTFYGTA<br>NTNQLLMEVMGLHLPG<br>ASFVNPNTPLRDALTHE<br>AAQQVTRLTKQSGAFM<br>PIGEIVDERVLNSIVAL<br>HATGGSTNHTLHMPAI<br>AQAAGIQLTWQDMAD<br>LSEVVPTLSHVYPNGK<br>ADINHFQAAGGMSFLIR<br>ELLEAGLLHEDVNTVA<br>GRGLSRYTQEPFLDNG<br>KLVWRDGPIESLDENIL |

| Accession Number | Species | Strain Number | NUCLEOTIDE SEQUENCE | Amino Acid Sequence |
|---|---|---|---|---|
| | | | GAAAGCCTGGACGAAAACATCCTGCGCCCGGTGGCCCGGGCGTTCTCT<br>GCGGAGGGCGGCTTGCGGGTCATGAAGGCAACCTCGGTCGCGGCGT<br>GATGAAGGTTTCCGCCGTGGCCCCGGAGCACCAGATCGTCGAGGCCC<br>GGCCGTGGTGTTCCAGGACCAGCAGGACCTGGCCGATGCCTTCAAGGC<br>CGGCCTGCTGGAGAAGGACTTCGTCGCGGTGATGCGCTTCCAGGGCCC<br>GCGCTCCAACGGCATGCCCGAGCTGCACAAGATGACCCCCTTCCTCGG<br>GGTGCTGCAGGACCGCGGCTTCAAGGTGGCGCTGGTCACCGACGGGGC<br>CATGTCCGGCGCTTCGGGCAAGATTCCGGCAGCGATCCATGTCAGCCC<br>CGAAGCCCAGGTGGGTGGCGCGCTGGCCCGGGTGCTGGACGGCGATA<br>TCATCCGAGTGGATGGCGTCAAGGGCACCCTGGAGCTTAAGGTAGACG<br>CCGCAGAATTCGCCGCCCGGGAGCCGGCCAAGGGCCTGCTGGGCAAC<br>AACGTTGGCACCGGCCGCGAACTCTTCGCCTTCATGCGCATGGCCTTC<br>AGCTCGGCAGAGCAGGGCGCCAGCGCCTTTACCTCTGCCCTGGAGACG<br>CTCAAGTGA (SEQ ID NO: 507) | RPVARAFSAEGGLRVM<br>EGNLRGVMKVSAVAP<br>EHQIVEAPAVVFQDQQ<br>DLADAFKAGLLEKDFV<br>AVMRFQGPRSNGMPEL<br>HKMTPFLGVLQDRGFK<br>VALVTDGRMSGASGKI<br>PAAIHVSPEAQVGGAL<br>ARVLDGDIIRVDGVKG<br>TLELKVDAAEFAAREP<br>AKGLLGNNVGTGRELF<br>AFMRMAFSSAEQGASA<br>FTSALETLK<br>(SEQ ID NO: 508) |
| ZP_0359148.1 | Bacillus subtilis | subtilis str. 168 | ATGGCAGAATTACGCAGTAATATGATCACACAAGGAATCGATAGAGCT<br>CCGCACCGCAGTTTGCTTCGTGCAGCAGGGGTAAAAGAAGAGGATTTC<br>GGCCAAGCCGTTTATTGCGTGTGTAATTCATACATTGATATCGTTCCCG<br>GTCATGTTCACTTGCAGGAGTTTGGGAAAATCGTAAAAGAAGCAATCA<br>GAGAAGCAGGGGGCGTTCCGTTTGAATTTAATACCATTGGGGTAGATG<br>ATGGCATCGCAATGGGGCATATCGGTATGAGATATTCGCTGCCAAGCC<br>GTGAAATTATCGCAGACTCTGTGGAAACGGTTGTATCCGCACACTGGT<br>TTGACGGAATGGTCTGTATTCCGAACTGCGACAAAATCACACCGGGAA<br>TGCTTATGGCGGCAATGCGCATCAACATTCCGACGATTTTTGTCAGCG<br>GCGGACCGATGGCGGCAGGAAGAACAAGTTACGGGCGAAAAATCTCC<br>CTTTCCTCAGTATTCGAAGGGTAGGCGCCTACCAAGCAGGGAAAATC<br>AACGAAAACGAGCTTCAAGAACTAGAGCAGTTCGGATGCCCAACGTG<br>CGGGTCTTGCTCAGGCATGTTTACGGCGAACTCAATGAACTGTCTGTC<br>AGAAGCACTTGGTCTTGCTTTGCCGGGTAATGGAACCATTCTGGCAAC<br>ATCTCCGGAACGCAAAGAGTTTGTGAGAAAATCGGCTGCGCAATTAAT<br>GGAAACGATTCGCAAAGATATCAAACCGCGTGATATTGTTACAGTAAA<br>AGCGATTGATAACGCGTTTGCACTCGATATGGCGCTCGGAGGTTCTAC<br>AAATACCGTTCTTCATACCCTTGCCCTTGCAAACGAAGCCGGCGTTGA<br>ATACTCTTTAGAAACGCATTAACGAAGTCGCTGAGCGCGTGCCGCACTT<br>GGCTAAGCTGGCGCCTGCATCGGATGTGTTTATTGAAGATCTTCACGA<br>AGCGGGCGGCGTTTCAGCGGCTCTGAATGAGCTTTCGAAGAAAGAAG<br>GAGCGCTTCATTTAGATGCGCTGACTGTTACAGGAAAAACTCTTGGAG<br>AAACCATTGCCGGACATGAAGTAAAGGATTATGACGTCATTCACCCGC<br>TGGATCAACCATTCACTGAAAAGGGAGGCCTTGCTGTTTTATTCGGTA<br>ATCTAGCTCCGGACGGCGCTATCATTAAAACAGGCGGCGTACAGAATG<br>GGATTACAAGACACGAAGGGCCGGTCGTATTCGATTCTCAGGACG<br>AGGCGCTTGACGGCATTATCAACCGAAAGTAAAAGAAGGCGACGTT<br>GTCATCATCAGATACGAAGGCCCAAAAGGCGGACCTGGCATGCCGGA<br>AATGCTGGCGCCAACATCCCAAATCGTTGGAATGGGACTCGGGCCAAA<br>AGTGGCATTGATTACGGACGACGTTTTTCCGGAGCCTCCCGTGGCCT<br>CTCAATCGGCCACGTATCACCTGAGGCCGCTGAGGGCGGGCCGCTTGC<br>CTTTGTTGAAAACGGAGACCATATTATCGTTGATATTGAAAAACGCAT<br>CTTGGATGTACAAGTGCCAGAAGAAGAGTGGGAAAAACGAAAAGCGA<br>ACTGGAAAGGTTTTGAACCGAAAGTGAAAACCGGCTACCTGGCACGTT<br>ATTCTAAACTTGTGACAAGTGCCAACACCGGCGGTATTATGAAAATCT<br>AG (SEQ ID NO: 509) | MAELRSNMITQGIDRAP<br>HRSLLRAAGVKEEDFG<br>KPFIAVCNSYIDIVPGHV<br>HLQEFGKIVKEAIREAG<br>GVPFEFNTIGVDDGIAM<br>GHIGMRYSLPSREIIADS<br>VETVVSAHWFDGMVCI<br>PNCDKITPGMLMAAMR<br>INIPTIFVSGGPMAAGRT<br>SYGRKISLSSVFEGVGA<br>YQAGKINENELQELEQF<br>GCPTCGSCSGMFTANS<br>MNCLSEALGLALPGNG<br>TILATSPERKEFVRKSA<br>AQLMETIRKDIKPRDIV<br>TVKAIDNAFALDMALG<br>GSTNTVLHTLALANEA<br>GVEYSLERINEVAERVP<br>HLAKLAPASDVFIEDLH<br>EAGGVSAALNELSKKE<br>GALHLDALTVTGKTLG<br>ETIAGHEVKDYDVIHPL<br>DQPFTEKGGLAVLFGN<br>LAPDGAIIKTGGVQNGI<br>TRHEGPAVVFDSQDEA<br>LDGIINRKVKEGDVVIIR<br>YEGPKGGPGMPEMLAP<br>TSQIVGMGLGPKVALIT<br>DGRFSGASRGLSIGHVS<br>PEAAEGGPLAFVENGD<br>HIIVDIEKRILDVQVPEE<br>EWEKRKANWKGFEPK<br>VKTGYLARYSKLVTSA<br>NTGGIMKI<br>(SEQ ID NO: 510) |
| YP_091897.1 | Bacillus licheniformis | ATCC 14580 | ATGACAGGTTTACGCAGTGACATGATTACAAAAGGGATCGACAGAGC<br>GCCGCACCGCAGTTTGCTGCGCGCGGCTGGGGTAAAAGAAGAGGACTT<br>CGGCCAAACCGTTTATTGCGTTTGCAATCATCATCGATATCGTACCG<br>GGTCATGTCCATTTGCAGGAGTTTGGAAAAATCGTCAAAGAGGCGATC<br>AGAGAGGCCGGCGGTGTTCCGTTTGAATTTAATACAATCGGGGTCGAC<br>GACGGAATTGCGATGGGGCACATCGGAATGAGGTATTCTCTCCCGAGC<br>CGCGAAATCATCGCAGATTCAGTGGAAACGGTTGTATCGGCGCACTGG<br>TTTGACGGAATGGTATGTATTCCAAACTGTGATAAAATCACACCGGGC<br>ATGATCATGGCGGCAATGCGATCAACATTCCGACCGTGTTTGTCAGC<br>GGGGGGCCGATGGAAGCGGGAAGAACGAGCGACGGACGAAAAATCTC<br>GCTTTCCTCTGTATTTGAAGGCGTTGGCGCTTATCAATCAGGCAAAATC<br>GATGAGAAGGACTTCGAGGAGCTTGAACAGTTCGGCTGTCCGACTTGC<br>GGATCATGCTCGGGCATGTTTACGGCGAACTCGATGAACTGTCTTTCTG<br>AAGCTCTTGGCATCGCCATGCCGGGCAACGGCACCATTTTGGCGACAT<br>CGCCCGACCGCAGGGAATTTGCCAAACAGTCGGCCCGCCAGCTGATGG<br>AGCTGATCAAGTCGGATATCAAACCGCGCGACATCGTGACCGAAAAA<br>GCGATCGACAACGCGTTCGCTTTAGACATGGCGCTCGGCGGATCAACG<br>AATACGATCCTTCATACGCTTGCGATCGCCAATGAAGCGGGTGTAGAC<br>TATTCGCTTGAACGGATCAATGAGGTAGCGGCAAGGGTTCCGCATTTA<br>TCGAAGCTTGCGCCTTCCGATGTGTTTATTGAAGATTTGCATGAAGGC<br>GGCGGTGTTTCAGCCGTCTTAAACGAGCTGTCGAAAAAGAAGGC<br>GCGCTTCACTTGGATACGCTGACTGTAACGGGAAAAACGCTTGGCGAA<br>AATATTGCCGGACGCGAAGTGAAAGATTACGAGGTCATTCATCCGATC<br>GATCAGCCGTTTTCAGAGCAAGGCGGACTCGCCGTCCTGTTCGGCAAC<br>CTGGCTCCTGACGGTGCGATCATTAAAACGGGCGGCGTCCAAGACGGG | MTGLRSDMITKGIDRAP<br>HRSLLRAAGVKEEDFG<br>KPFIAVCNHHRYRTVP<br>HLQEFGKIVKEAIREAG<br>GVPFEFNTIGVDDGIAM<br>GHIGMRYSLPSREIIADS<br>VETVVSAHWFDGMVCI<br>PNCDKITPGMIMAAMRI<br>NIPTVFVSGGPMEAGRT<br>SDGRKISLSSVFEGVGA<br>YQSGKIDEKGLEELEQF<br>GCPTCGSCSGMFTANS<br>MNCLSEALGIAMPGNG<br>TILATSPDRREFAKQSA<br>RQLMELIKSDIKPRDIVT<br>EKAIDNAFALDMALGG<br>STNTILHTLAIANEAGV<br>DYSLERINEVAARVPHL<br>SKLAPSDVFIEDLHEA<br>GGVSAVLNELSKKEGA<br>LHLDTLTVTGKTLGENI<br>AGREVKDYEVIHPIDQP<br>FSEQGGLAVLFGNLAP<br>DGAIIKTGGVQDGITRH<br>EGPAVVFDSQEEALDGI |

| Accession Number | Species | Strain Number | NUCLEOTIDE SEQUENCE | Amino Acid Sequence |
|---|---|---|---|---|
| | | | ATTACCCGCCATGAAGGACCTGCGGTTGTCTTTGATTCACAGGAAGAA GCGCTTGACGGCATCATCAACCGTAAAGTAAAAGCGGGAGATGTCGTC ATCATCCGCTATGAAGGCCCTAAAGGCGGACCGGGAATGCCTGAAATG CTTGCGCCGACTTCACAGATCGTCGGAATGGGCCTCGGCCCGAAAGTC GCCTTGATTACCGACGGCCGTTTTCAGGAGCCGTCTTTCGA TCGGCCACGTTTCACCGGAAGCAGCCGAAGGCGGCCCGCTTGCTTTCG TAGAAAACGGCGACCATATCGTTGTCGATATCGAAAGCGGATTTTAA ACATCGAAATCTCCGATGAGGAATGGGAAAAAAGAAAAGCAAACTGG CCCGGCTTTGAACCGAAAGTGAAAACGGGCTATCTCGCCAGGTATTCA AAGCTTGTGACATCTGCCAATACCGGCGGCATTATGAAAATCTAG (SEQ ID NO: 511) | INRKVKAGDVVIIRYEG PKGGPGMPEMLAPTSQI VGMGLGPKVALITDGR FSGASRGLSIGHVSPEA AEGGPLAFVENGDHIV VDIEKRILNIEISDEEWE KRKANWPGFEPKVKTG YLARYSKLVTSANTGGI MKI (SEQ ID NO: 512) |
| NP_0718074.1 | Sewanella oneidensis | MR-1 | ATGCACTCAGTCGTTCAATCTGTTACTGACAGAATTATTGCCCGTAGCA AAGCATCTCGTGAAGCATACTTGCTGCGTTAAACGATGCCCGTAACC ATGGTGTACACCGAAGTTCCTTAAGTTGCGGTAACTTAGCCCACGGTTT TGCGGCTTGTAATCCCGATGACAAAAATGCATTGCGTCAATTGACGAA GGCCAATATTGGGATTATCACCGCATTCAACGATATGTTATCTGCACA CCAACCCTATGAAACCTATCCTGATTTGCTGAAAAAAGCCTGTCAGGA AGTCGGTAGTGTTGCGCAGGTGGCTGGCGGTGTTCCCGCCATGTGTGA CGGCGTGACTCAAGGTCAGCCCGGTATGGAATTGAGCTTACTGAGCCG TGAAGTGATTGCGATGGCAACCGCGGTTGGCTTATCACACAATATGTT TGATGGAGCCTTACTCCTCGGTATTTGCGATAAAATTGTACCGGGTTTA CTGATTGGTGCCTTAAGTTTTGGCCATTTACCTATGTTGTTTGTGCCCG CAGGCCCAATGAAATCGGGTATTCCTAATAAGGAAAAAGCTCGCATTC GTCAGCAATTTGCTCAAGGTAAGGTCGATAGAGCACAACTGCTCGAAG CGGAAGCCCAGTCTTACACAGTGCGGGTACTTGTACCTTCTATGGTA CCGCTAACTCGAACCAACTGATGCTCGAAGTGATGGGGCTGCAATTGC CGGGTTCATCTTTTGTGAATCCAGACGATCCACTGCGCGAAGCCTTAA ACAAAATGGCGGCCAAGCAGGTTTGTCGTTTAACTGAACTAGGCACTC AATACAGTCCGATTGGTGAAGTCGTTAACGAAAAATCGATAGTGAATG GTATTGTTGCATTGCTCGCGACGGTGGTTCAACAAACTTAACCATGC ACATTGTGGCGGCGGCCCGTGCTGCAGGTATTATCGTCAACTGGGATG ACTTTTCGGAATTATCCGATGCGGTGCCTTTGCTGGCACGTGTTTATCC AAACGGTCATGCGGATATTAACCATTTCCACGCTGCGGGTGGTATGGC TTTCTTTATCAAAGAATTACTCGATGCAGGTTTGCTGCATGAGGATGTC AATACTGTCGCGGGTTATGGTCTGCGCCGTTACACCCAAGAGCCTAAA CTGCTTGATGGCGAGCTGCGCTGGGTCGATGGCCCAACAGTGAGTTTA GATACCGAAGTATTAACCTCTGTGGCAACACCATTCCAAAACAACGGT GGTTTAAAGCTGCTGAAGGGTAACTTAGGCCGCGCTGTGATTAAAGTG TCTGCCGTTCAGCCACAGCACCGTGTGGAAGCGCCCGCAGTGGTG ATTGACGATCAAAACAAACTCGATGCGTTATTTAAATCCGGCGCATTA GACAGGGATTGTGTGGTGGTGGTGAAAGGCCAAGGGCCGAAAGCCAA CGGTATGCCAGAGCTGCATAAACTAACGCCGCTGTTAGGTTCATTGCA GGACAAAGGCTTTAAAGTGGCACTGATGACTGATGGTCGTATGTCGGG CGCATCGGGCAAAGTACCTGCGGCGATTCATTTAACCCCTGAAGCGAT TGATGGCGGGTTAATTGCAAAGGTACAAGACGGCGATTTAATCCGAGT TGATGCACTGACCGGCGAGTGAGTTTATTAGTCTCTGACACCGAGCT TGCCACCAGAACTGCCACTGAAATTGATTTACGCCATTCTCGTTATGGC ATGGGGCGTGAGTTATTGGAGTACTGCGTTCAAACTTAAGCAGTCCT GAAACCGGTGCGCGTAGTACTAGCGCCATCGATGAACTTTACTAA (SEQ ID NO: 83) | MHSVVQSVTDRIIARSK ASREAYLAALNDARNH GVHRSSLSCGNLAHGF AACNPDDKNALRQLTK ANIGIITAFNDMLSAHQ PYETYPDLLKKACQEV GSVAQVAGGVPAMCD GVTQGQPGMELSLLSR EVIAMATAVGLSHNMF DGALLLGICDKIVPGLLI GALSFGHLPMLFVPAGP MKSGIPNKEKARIRQQF AQGKVDRAQLLEAEAQ SYHSAGTCTFYGTANS NQLMLEVMGLQLPGSS FVNPDDPLREALNKMA AKQVCRLTELGTQYSPI GEVVNEKSIVNGIVALL ATGGSTNLTMHIVAAA RAAGIIVNWDDFSELSD AVPLLARVYPNGHADI NHFHAAGGMAFLIKEL LDAGLLHEDVNTVAGY GLRRYTQEPKLLDGEL RWVDGPTVSLDTEVLT SVATPFQNNGGLKLLK GNLGRAVIKVSAVQPQ HRVVEAPAVVIDDQNK LDALFKSGALDRDCVV VVKGQGPKANGMPEL HKLTPLLGSLQDKGFK VALMTDGRMSGASGK VPAAIHLTPEAIDGGLIA KVQDGDLIRVDALTGE LSLLVSDTELATRTATEI DLRHSRYGMRELFGV LRSNLSSPETGARSTSAI DELY (SEQ ID NO: 84) |
| YP_190870.1 | Gluconobacter oxydans | 621H | ATGTCTCTGAATCCCGTCGTCGAGAGCGTGACTGCCCGTATCATCGAG CGTTCGAAAGTCTCCCGTCGCCGGTATCTCGCCCTGATGGAGCGCAAC CGCGCCAAGGGTGTGCTCCGGCCCAAGCTGGCCTGCGGTAATCTGGCG CATGCCATCGCAGCGTCCAGCCCCGACAAGCCGGATCTGATGCGTCCC ACCGGGACCAATATCGGCGTGATCACGACCTATAACGACATGCTCTCG GCGCATCAGCCGTATGGCCGCTATCCCGAGCAGATCAAGCTGTTCGCC CGTGAAGTCGGTGCGCAGGTCGCCCAGGTTGCAGGCGGCGCACCAGCGT GTGATGGTGTGACGCAGGGGCAGGAGGGCATGGAACTCTCCCTGTT CTCCCGTGACGTGATCGCCATGTCCACGGCGGTCGGGCTGAGCCACGG CATGTTTGAGGGCGTGGCCGCTGCTGGGCATCTGTGACAAGATTGTGCC GGGCCTTCTGATGGGCGCGCTGCGCTTCGGTCATCTCCCGGCCATGCTG ATCCCGGCAGGGCCAATGCCGTCTGGGCCGTTTCCAAACAAGGAAAAGCA GCGCATCCGCCAGCTCTATGTGCAGGGCAAGGTCGGGCAGGACGAGCT GATGGAAGCTGGAAAACGCCTCCTATCACAGCCCGGGCACCTGCACGTT CTATGGCACGGCCAATACGAACCAGATGATGGTCGAAATCATGGGTCT GATGATGCCGGACTCGGCTTTCATCAATCCCAACACGAAGCTGCGTCA GGCAATGACCCGCTCGGGTATTCACCGTCTGGCCGAAATCGGCCTGAA CGGCGAGGATGTGCGCCCGCTCGCTCATTGCGTAGACGAAAAGGCCAT CGTGAATGCGGCGGTCGGGTTGCTGGCGACGGGTGGTTCGACCAACCA TTCCATCCATCTTCCTGCTATAGCGGCGGGTATCCTGATCGAC TGGGAAGACATCAGCCGCCTGTCGTCCGCGGTTCCGCTGATCACCCGT GTTTATCCGAGCGGTTCCGAGGACGTGAACGCGTTCAACCGCGTGGGT GGTATGCCGACCGTGATCGCCGAACTGACGCGCGCCGGGATGCTGCAC AAGGACATTCTGACGGTCTCTCGTGGCCGGTTTCTCCGATTATGCCCGTC GCGCATCGCTGGAAGGCGATGAGATCGTCTACACCCACGCGAAGCCGT | MSLNPVVESVTARIIER SKVSRRRYLALMERNR AKGVLRPKLACGNLAH AIAASSPDKPDLMRPTG TNIGVITTYNDMLSAHQ PYGRYPEQIKLFAREVG ATAQVAGGAPAMCDG VTQGQEGMELSLFSRD VIAMSTAVGLSHGMFE GVALLGICDKIVPGLLM GALRFGHLPAMLIPAGP MPSGLPNKEKQRIRQLY VQGKVGQDELMEAEN ASYHSPGTCTFYGTANT NQMMVEIMGLMMPDS AFINPNTKLRQAMTRSG IHRLAEIGLNGEDVRPL AHCVDEKAIVNAAVGL LATGGSTNHSIHLPAIA RAAGILIDWEDISRLSSA VPLITRVYPSGSEDVNA FNRVGGMPTVIAELTR AGMLHKDILTVSRGGF SDYARRASLEGDEIVYT HAKPSTDTDILRDVATP |

-continued

| Accession Number | Species | Strain Number | NUCLEOTIDE SEQUENCE | Amino Acid Sequence |
|---|---|---|---|---|
| | | | CCACGGACACCGATATCCTGCGCGATGTGGCTACGCCTTTCCGGCCCG ATGGCGGTATGCGCCTGATGACTGGTAATCTGGGCCGCGCGATCTACA AGAGCAGCGCTATTGCGCCCGAGCACCTGACCGTTGAAGCGCCGGCAC GGGTCTTCCAGGACCAGCATGACGTCCTCACGGCCTATCAGAATGGTG AGCTTGAGCGTGATGTTGTCGTGGTCGTCCGGTTCCAGGGACCGGAAG CCAACGGCATGCCGGAGCTTCACAAGCTGACCCCGACTCTGGGCGTGC TTCAGGATCGCGGCTTCAAGGTGGCCCTGCTGACGGATGGACGCATGT CCGGTGCGAGCGGCAAGGTGCCGGCCGCCATTCATGTCGGTCCCGAAG CGCAGGTTGGCGGTCCGATCGCCCGCGTGCGGGACGGCGACATGATCC GTGTCTGCGCGGTGACGGGACAGATCGAGGCTCTGGTGGATGCCGCCG AGTGGGAGAGCCGCAAGCCGGTCCCGCCGCCGCTCCCGGCATTGGGA ACGGGCCGCGAACTGTTCGCGCTGATGCGTTCGGTGCATGATCCGGCC GAGGCTGGCGGATCCGCGATGCTGGCCCAGATGGATCGCGTGATCGAA GCCGTTGGCGACGACATTCACTAA (SEQ ID NO: 85) | FRPDGGMRLMTGNLGR AIYKSSAIAPEHLTVEAP ARVFQDQHDVLTAYQN GELERDVVVVRFQGP EANGMPELHKLTPTLG VLQDRGFKVALLTDGR MSGASGKVPAAIHVGP EAQVGGPIARVRDGDM IRVCAVTGQIEALVDAA EWESRKPVPPPLPALGT GRELFALMRSVHDPAE AGGSAMLAQMDRVIEA VGDDIH (SEQ ID NO: 86) |
| ZP_06145432.1 | Ruminococcus flavefaciens | FD-1 | ATGAGCGATAATTTTTTCTGCGAGGGTGCGGATAAAGCCCCTCAGCGT TCACTTTTCAATGCACTGGGCATGACTAAAGAGGAAATGAAGCGTCCC CTCGTTGGTATCGTTTCTTCCTACAATGAGATCGTTCCCGGCCATATGA ACATCGACAAGCTGGTCGAAGCCGTTAAGCTGGGTGTAGCTATGGGCG GCGGCACTCCTGTTGTTTTCCCTGCTATCGCTGTATGCGACGGTATCGC TATGGGTCACACAGGCATGAAGTACAGCCTTGTTACCCGTGACCTTAT TGCCGATTCTACAGAGTGTATGGCTCTTGCTCATCACTTCGACGCACTG GTAATGATACCTAACTGCGACAAGAACGTTCCCGGCCTGCTTATGGCG GCTGCACGTATCAATGTTCCTACTGTATTCGTAAGCGGCGGCCCTATGC TTGCAGGCCATGTAAAGGGTAAGAAGACCTCTCTTTCATCCATGTTCG AGGCTGTAGGCGCTTACACAGCAGGCAAGATAGACGAGGCTGAACTT GACGAATTCGAGAACAAGACCTGCCCTACCTGCGGTTCATGTTCGGGT ATGTATACCGCTAACTCCATGAACTGCCTCACTGAGGTACTGGGTATG GGTCTCAGAGGCAACGGCACTATCCCTGCTGTTTACTCCGAGCGTATC AAGCTTGCAAAGCAGGCAGGTATGCAGGTTATGGAACTCTACAGAAA GAATATCCGCCCTCTCGATATCATGACAGAGAAGGCTTTCCAGAACGC TCTCACAGCTGATATGGCTCTTGGATGTTCCACAAACAGTATGCTCCAT CTCCCTGCTATCGCCAACGAATGCGGCATAAATATCAACCTTGACATG GCTAACGAGATAAGCGCCAAGACTCCTAACCTCTGCCATCTTGCACCG GCAGGCCACACCTACATGGAAGGCGTCAACGAAGCAGGCGGAGTTTA TGCAGTTCTCAACGAGCTGAGCAAAAAGGGACTTATCAACACCGACTG CATGACTGTTACAGGCAAGACCGTAGGCGAGAATATCAAGGGCTGCAT CAACCGTGACCCTGAGACTATCCGTCCTATCGACAACCCATACAGTGA AACAGGCGGAATCGCCGTACTCAAGGGCAATCTTGCTCCCGACAGATG TGTTGTGAAGAGAAGCGCAGTTGCTCCCGAAATGCTGGTACACAAAGG CCCTGCAAGAGTATTCGACAGCGAGGAAGAAGCTATCAAGGTCATCTA TGAGGGCGGTATCAAGGCAGGCGACGTTGTTGTTATCCGTTACGAAGG CCCTGCAGGCGGCCCCGGCATGAGAGAAATGCTCTCTCCTACATCAGC TATACAGGGTGCAGGTCTCGGCTCAACTGTTGCTCTAATCACTGACGG ACGTTTCAGCGGCGCTACCCGTGGTGCGGCTATCGGACACGTATCCCC CGAAGCTGTAAACGGCGGTACTATCGCATATGTCAAGGACGGCGATAT TATCTCCATCGACATACCGAATTACTCCATCACTCTTGAAGTATCCGAC GAGGAGCTTGCAGAGCGCAAAAAGGCAATGCCTATCAAGCGCAAGGA GAACATCACAGGCTATCTGAAGCGCTATGCACAGCAGGTATCATCCGC AGACAAGGGCGCTATCATCAACAGGAAATAG (SEQ ID NO: 87) | MSDNFFCEGADKAPQR SLFNALGMTKEEMKRP LVGIVSSYNEIVPGHMN IDKLVEAVKLGVAMGG GTPVVFPAIAVCDGIAM GHTGMKYSLVTRDLIA DSTECMALAHHFDALV MIPNCDKNVPGLLMAA ARINVPTVFVSGGPMLA GHVKGKKTSLSSMFEA VGAYTAGKIDEAELDE FENKTCPTCGSCSGMY TANSMNCLTEVLGMGL RGNGTIPAVYSERIKLA KQAGMQVMELYRKNI RPLDIMTEKAFQNALTA DMALGCSTNSMLHLPA IANECGININLDMANEIS AKTPNLCHLAPAGHTY MEGVNEAGGVYAVLN ELSKKGLINTDCMTVT GKTVGENIKGCINRDPE TIRPIDNPYSETGGIAVL KGNLAPDRCVVKRSAV APEMLVHKGPARVFDS EEEAIKVIYEGGIKAGD VVVIRYEGPAGGPGMR EMLSPTSAIQGAGLGST VALITDGRFSGATRGAA IGHVSPEAVNGGTIAYV KDGDIISIDIPNYSITLE VSDEELAERKKAMPIKR KENITGYLKRYAQQVS SADKGAIINRK (SEQ ID NO: 88) |

Example 40

Unique 200-mer Nucleotide Sequences Used for Integration Constructs

| 200-mer Number | Sequence (SEQ ID NOS 513-531, respectively, in order of appearance) |
|---|---|
| 30 | CACGCACGGACCGACCGTCACCGGACCGTTTCGCGCGACGTGCGCGAGGCTCCGACACGAAA GACGGGCCCCCTATTGCGCTCATGTCGGCCGCACCCCTGCGTAAAGTCAGATACGTGCGCCA CCCGAGCCGGGACCGCCCTGAGCGCATGGTCCGGGCGGCGTGGCAAGCGCAGGAGGGCGTGC CCCGTTCGCTAGGCA |
| 44 | ACGTATGTCGGCTGATCGTACACGCCGACCAGCGCAGTCGGCGTACTCAGGCGTTCCGAGTA GCTCACATCTGTGGGCCCCGGCGTACCTTCGGCAGGGTTATGCGACGGGGCGGCAGGCTTGC GCTGGCGTCGGGAATCACCGCGAACTTGACCCGCGCCGGTTCCGTATCGGTCCGCTGCGGCC GTGCTCCGCAGTCGA |
| 45 | TGCAGTCCGCCCAGCCGGCCGTGTAGCACGGCCGACTGCAGGTGCGACGTGCTAGGGGCCAG CACGCGAGCGGCCCTACCACGGGTCGTGTGGGCGCATGACCGCCGGCCGGGTCTCGGCACG |

| 200-mer Number | Sequence (SEQ ID NOS 513-531, respectively, in order of appearance) |
|---|---|
| | GGGCGACGCGGTGCTCCTAGGCTAGCAGGGCCTCACCGGGTGATCCCCCGTGTAGCGCCGCA CAACACCCCCTGCGA |
| 49 | TGCCCGCATACCGCCCGCCCACTGGGGATCCTCCGGCGCTGTCGCGCTATGCGCGTCCATCC TGGTCGGACGGGCTCGGGCCCCGGACCAAACCGCAGCGGCCCCTGGCAGCGACTAAGGGCGC CGTCTCACCCTAGACTTCTTAATCGGGGTGTCCCGGTAGGCCGGGAGTAGCCTCGGCGGGCT AGCCGCGTGACTATA |
| 78 | GCGGGTTAGTCCCCGTCGGACGTCATGCATACAGTCGGGGCTGGCGAGACAGGAGGCTACAG GGGGCGCCCGGAGGAACACACGTGGGACTAAGACGTCGGTCCGTGTGCCCCCGAACCGGCGT GCTCATCGTAGGACTGGGAAGTCCGTACCGCGTGGCTCGTACCTCGCGGTCTGAGTCCGACA CCCGCTGACGCCGGA |
| 13 | CTGAGACGACTCCCGCACTACGGATCGCGAGCGTAGACTCAGCCCGGACTCTCACGCGACCT CGGACGCGGCCTAATGTCTCGACTCGCGGTCCGCTGAAGGTCTCGGGGCACGCGAGACGCGG GGTCAGGCCGGGGGGATCCCCGCACACACTCAGTCGCGGCGAACGGAGTCCCGTGGCCTGGC TAGGGATCGTGGGTA |
| 60 | GGGGCGTCCACTCTGGCTCGGTAGAGCGCTGGGCTCCGCGCGACTGCGCGCACCCATCGGTT TGGCGCGACGCACCGTGGACTCCTGGGCTAGAGGGCGGGTCCCCGCCATACCCCGTTCTCGT GCCGGCTGGGTAGGACCGGAGTGACGGCTGTGGCCGGCGACTCGGGCGCGCACTGTAGTCGG ATCTGGGCGGGCAGA |
| 92 | GTCGGGCGCGCGTCAGTCCACGCGTTAAACACTGGCCGACGACACGACGGGATCCGGGCACG CCCCGAGAGCGCGTGTTCGCGCGAGTCGATCGGGAGGCCGCAGCGTGTCGAGCCCAGACCCC GCTCTAGCGTGGCCATCGCGGTGCTAAGTGGGGCGGCCGGGTCCTATACACGCTTACCGATA GTCAAGTTTGCGTGA |
| 127 | GTCTTAGGGCCCAGGGACCGCACGGGTCGACCGCGCGACTGGTCGGAGCTTGCGCGTCTACG CCACTCGGCGGCCCCGACGGGGATGCCGCGGAATGTCCGCCGGCGTATGCGGCTCAAGCCG GACCGTCGGACTGCGAAGCGCCGTGAGCACCCCTCGACCTGACCGGACGCGGCGCACCCGTC CGAGTATCGTCGCGA |
| 153 | TCGGGTCTCGCCCGGCGCTAGTCCAGCCGTAGCGCTCTCCGGCGATCACCCCGGAGCACTCT GGAGCCGAGCGGTCGGGTCTGTTGGGCGCGCCGCGGCTACGGACGGCTCGACTCACTGGCGC TCGACCCCGTATCCCCCGTCTCGGACGACGCACCGTTGCGCGGGAACGATCGGCGGCGCTCA CACGCACGATCGGAA |
| 299 | CTTAAGGCTGGCGCACCATGAGGGCGCGCCACGTCCGACCCGCAGCCCGCGCGTAGTAGCC TAGCCGGGCGGGGTTCCTCCCGTGCGTCACCTAGCACGGGGCCTGGCACCGAACGCGAGCCC GTCCGGTCACCGCGGCGGGTCTGCGGACGTCCCCGGTCGCTCGGCTCGGAGTCCCCGCTGGG GATCGCGTCGGGACA |
| 317 | CGACGCGTAGCACTCGCGGACCTAGGGCGCGCGAGTCGGGGGAGCCCGCGGTGCGACGCTC GGGGAGGAGCTCGCATGCCCAAGGCACGATCTAGGGGGGGGTACGGGGGGCGTCCGTCCGAG CGCCGGGACTGCGATCCGGGGCCACATGCTAACCGGCGGAAGGGGGACCTAACCGGTGTGG ACTCCGGGTAATCCA |
| 319 | CGGGGGGCTGACACGTCTCGGATCGCCCCGTCAGTCAGCCCCCTAGTCCCGGACAGGACGTC GGAGGTCGAGTCCGCACTGTCGGGCCTGCTCGTGGGCACGGCAGGACGCGTCCCCATGGTCA GCCGCCGTGCGATACCTCGCCACGACTCTGAGCCGGGCGCGAGCGTGAGAGCCCGAGCCGCG GTACACGGGGCGTCA |
| 529 | GCGAGCTCGCTCTCGACTCCGGGCTCCCGTGCTGACACGGGTGCGACCCCGCGGCGATTGT CCGCACGCCTGTCGGACGACGTCGGCCCGTCGTAGTGCCGGTCAGAGGCAGGGGGGCTGCTC GCGCTGGCCGCCTCGTCGCGCGTGGACCCTATGGGGGATCACGCGTGGGGTCGGGATCGGGG ACCGCGCGACTTGGA |
| 651 | CGCGCCCCGTAACGGACGCGGTGAGTCGAGCTTACGCGGCTAGGGCCGAGTCGTGTTAGCGT CTCGCGTAAGCGAATGCCACGTCCCCCGCCGCCCGTCGCGCAGCTGGCTACGCAACGCCTCC GCGGCCTCCGTAGCGAGTGCGTGGGACGCTGGCCGTCCGCGTGTTCCGGGACCTGGATGCGG GAGGGACCTAAGGCA |
| 677 | AGAACGTGCGGTCGTCCCCACGCACGGGATGACGGACGGGGTAGACGGGCGTCGTGCGCGCG GGTAGCGTAACCGGTTACAGTCCCCGCAACGCTCTAGCTCCGGCCCTCGCTTAGGAGTTCGC GGCCGAGACATGAGGTGGTCCGGACGGCAGGGGGTCGCGGAGACCGTGGAGCCGATTCTGCC GGACGCCACGTCCCA |
| 708 | CGGGACGCCCCGTACCGTGTACGAAGCCCCGGTCGGTCGGCGGATCGTAGATCCCGGAGCCG ACGCCTTGAACCCGGCTTTCCCAGCGACTCGCGCCCCCACTGGGTCCCTCGGGACCCCGCTC CCCCCAGACGCATACAGCCCGCAAGCGGGGGCAGTCTCGGACCGCCCGGACACTGGCCTTAG GCACCGTGGGCTCGA |
| 717 | GTGTCCGGGGCGCATCGGAGCTGTCCGACCGAGTTCCGGGGACGGCGCACGTTGTGCCGGCC TCAGACGGAGCCTGTAGCCCCCGGACAGTGTGTGCCCGCCCACTACGGGTTAGGCACGGGGT TGGTCGGCACGCGTCCTCCGCGTGTCACGGACCGATGCAGACCGCTGGCCGGGAGGTCGCCC CCCCAGGGGTGCACA |

-continued 200-mer
Number Sequence (SEQ ID NOS 513-531, respectively, in order of appearance)

719    CGCGCAGCACGCACGTCCGGGGCACGCGCGGCTCGGAGGGTCCGGGCTGGGACGGGAGGTTT
GGAGTCGCGTGCGCGTAGCAGCGCACCCGCCTGGTCGCCGGGTCTAGTAGGGCTGGGTTACG
GAGGACGTGCAGGCGACCCCAACCGTTGACGACGGGTCCGACCACGCCTTTAGCCGTGGCGT
GTCCGTCGCGAGCCA

Example 41

Evaluation of Additional Xylose Isomerase Genes

As noted above, additional xylose isomerase genes were identified and isolated and chimeric versions generated in certain embodiments. Presented below are the results of activity assays of three candidate xylose isomerase genes from *R. flavefaciens*, FD-1, *Ruminococcus* 18P13, and *Clostridiales genomosp.*, when expressed in *S. cerevisiae*.

The candidate xylose isomerase enzymes (XI's) were assayed as total soluble crude extracts (prepared as described herein in YPER-PLUS reagent and quantified with the Coomasie-Plus kit). 100 µg of each extract was compared for the candidate XI's alongside the original XI-R (e.g., *Ruminococcus* xylose isomerase) native construct. The *Clostridiales* enzyme was further characterized at 1974 µg to confirm the presence of activity. The results in this experiment are presented as the slope of the activity at saturating xylose concentrations (500 mM). The results are show in FIG. 25. The *R. flavefaciens*, FD-1 XI activity shows the highest activity of the candidates tested, and shows higher activity than the XI-R native construct used as a control. The two candidate genes from *Ruminococcus* strains were further characterized in an enzyme assay using xylose concentrations between 40 and 500 nM. Michaelis Mentin plots were generated for each candidate in order to determine $K_m$ and specific activity levels as compared to the native XI-R enzyme. The results are presented in the table below. The *R. flavefaciens*, FD-1 XI activity shows a greater than 2 fold specific activity than the native XI control activity.

| Enzyme Source | Km | Specific Activity (umol min$^{-1}$ mg$^{-1}$) |
|---|---|---|
| XI-R native | 42.57 nM | 0.9605 |
| *R. flavefaciens* FD-1 | 71.91 nM | 2.3045 |
| *Ruminococcus* 18P13 | 65.11 Nm | 0.20448 |

Example 42

Examples of Embodiments

Provided hereafter are certain non-limiting embodiments of the technology.

A1. An engineered microorganism that comprises:
(a) a functional Embden-Meyerhoff glycolysis pathway that metabolizes six-carbon sugars under aerobic fermentation conditions, and
(b) a genetic modification that reduces an Embden-Meyerhoff glycolysis pathway member activity upon exposure of the engineered microorganism to anaerobic fermentation conditions,
whereby the engineered microorganism preferentially metabolizes six-carbon sugars by the Enter-Doudoroff pathway under the anaerobic fermentation conditions.

A2. The engineered microorganism of embodiment A1, wherein the genetic modification is insertion of a promoter into genomic DNA in operable linkage with a polynucleotide that encodes the Embden-Meyerhoff glycolysis pathway member activity.

A3. The engineered microorganism of embodiment A1, wherein the genetic modification is provision of a heterologous promoter polynucleotide in operable linkage with a polynucleotide that encodes the Embden-Meyerhoff glycolysis pathway member activity.

A4. The engineered microorganism of embodiment A1, wherein the genetic modification is a deletion or disruption of a polynucleotide that encodes, or regulates production of, the Embden-Meyerhoff glycolysis pathway member, and the microorganism comprises a heterologus nucleic acid that includes a polynucleotide encoding the Embden-Meyerhoff glycolysis pathway member operably linked to a polynucleotide that down-regulates production of the member under anaerobic fermentation conditions.

A5. The engineered microorganism of any one of embodiments A1-A4, wherein the Embden-Meyerhoff glycolysis pathway member activity is a phosphofructokinase activity.

A6. The engineered microorganism of any one of embodiments A1-A5, which microorganism comprises an added or altered five-carbon sugar metabolic activity.

A7. The engineered microorganism of embodiment A6, wherein the microorganism comprises an added or altered xylose isomerase activity.

A8. The engineered microorganism of any one of embodiments A1-A7, wherein the microorganism comprises an added or altered five-carbon sugar transporter activity.

A9. The engineered microorganism of embodiment A8, wherein the transporter activity is a transporter facilitator activity.

A10. The engineered microorganism of embodiment A8, wherein the transporter activity is an active transporter activity.

A11. The engineered microorganism of any one of embodiments A1-A10, wherein the microorganism comprises an added or altered carbon dioxide fixation activity.

A12. The engineered microorganism of embodiment A11, wherein the microorganism comprises an added or altered phosphoenolpyruvate (PEP) carboxylase activity.

A13. The engineered microorganism of any one of embodiments A1-A12, wherein the microorganism comprises a genetic modification that reduces or removes an alcohol dehydrogenase 2 activity.

A14. The engineered microorganism of any one of embodiments A1-A13, wherein the microorganism comprises a genetic modification described in any one of embodiments B1-B208.

B1. An engineered microorganism that comprises a genetic modification that inhibits cell division upon exposure to a change in fermentation conditions, wherein:

the genetic modification comprises introduction of a heterologous promoter operably linked to a polynucleotide encoding a polypeptide that regulates the cell cycle of the microorganism; and the promoter activity is altered by the change in fermentation conditions.

B2. The engineered microorganism of embodiment B1, wherein the genetic modification induces cell cycle arrest.

B3. The engineered microorganism of embodiment B1 or B2, wherein the change in fermentation conditions is a switch to anaerobic fermentation conditions.

B4. The engineered microorganism of embodiment B1 or B2, wherein the change in fermentation conditions is a switch to an elevated temperature.

B5. The engineered microorganism of any one of embodiments B1-B4, wherein the polypeptide that regulates the cell cycle has thymidylate synthase activity.

B6. The engineered microorganism of any one of embodiments B1-B5, wherein the promoter activity is reduced by the change in fermentation conditions.

B100. An engineered microorganism that comprises a genetic modification that inhibits cell division and/or cell proliferation upon exposure of the microorganism to a change in fermentation conditions.

B101. The engineered microorganism of embodiment B100, wherein the change in fermentation conditions is a switch to anaerobic fermentation conditions.

B102. The engineered microorganism of embodiment B100, wherein the change in fermentation conditions is a switch to an elevated temperature.

B103. The engineered microorganism of any one of embodiments B100-B102, wherein the genetic modification induces cell cycle arrest upon exposure to the change in fermentation conditions.

B104. The engineered microorganism of any one of embodiments B100-B103, wherein the genetic modification reduces thymidylate synthase activity upon exposure to the change in fermentation conditions.

B200. The engineered microorganism of any one of embodiments B1-B104, wherein the genetic modification is a temperature sensitive mutation.

B201. The engineered microorganism of any one of embodiments B1-B200, wherein the microorganism comprises an added or altered five-carbon sugar metabolic activity.

B202. The engineered microorganism of embodiment B201, wherein the microorganism comprises an added or altered xylose isomerase activity.

B203. The engineered microorganism of any one of embodiments B1-B202, wherein the microorganism comprises an added or altered five-carbon sugar transporter activity.

B204. The engineered microorganism of embodiment B203, wherein the transporter activity is a transporter facilitator activity.

B205. The engineered microorganism of embodiment B203, wherein the transporter activity is an active transporter activity.

B206. The engineered microorganism of any one of embodiments B1-B205, wherein the microorganism comprises an added or altered carbon dioxide fixation activity.

B207. The engineered microorganism of embodiment B206, wherein the microorganism comprises an added or altered phosphoenolpyruvate (PEP) carboxylase activity.

B208. The engineered microorganism of any one of embodiments B1-B207, wherein the microorganism comprises a genetic modification that reduces or removes an alcohol dehydrogenase 2 activity.

B300. The engineered microorganism of any one of embodiments A1-B208, wherein the microorganism is an engineered yeast.

B301. The engineered microorganism of embodiment B300, wherein the yeast is a *Saccharomyces* yeast.

B302. The engineered microorganism of embodiment B301, wherein the *Saccharomyces* yeast is *S. cerevisiae*.

C1. A method for manufacturing a target product produced by an engineered microorganism, which comprises:
(a) culturing an engineered microorganism of any one of embodiments A1-B302 under aerobic conditions; and
(b) culturing the engineered microorganism after (a) under anaerobic conditions, whereby the engineered microorganism produces the target product.

C2. The method of embodiment C1, wherein the target product is ethanol.

C3. The method of embodiment C1, wherein the target product is succinic acid.

C4. The method of any one of embodiments C1-C3, wherein the host microorganism from which the engineered microorganism is produced does not produce a detectable amount of the target product.

C5. The method of any one of embodiments C1-C4, wherein the culture conditions comprise fermentation conditions.

C6. The method of any one of embodiments C1-C5, wherein the culture conditions comprise introduction of biomass.

C7. The method of any one of embodiments C1-C6, wherein the culture conditions comprise introduction of a six-carbon sugar.

C8. The method of embodiment C7, wherein the sugar is glucose.

C9. The method of any one of embodiments C1-C8, wherein the culture conditions comprise introduction of a five-carbon sugar.

C10. The method of embodiment C9, wherein the sugar is xylose.

C11. The method of any one of embodiments C1-C10, wherein the target product is produced with a yield of greater than about 0.3 grams per gram of glucose added.

C12. The method of any one of embodiments C1-C11, which comprises purifying the target product from the cultured microorganisms.

C13. The method of embodiment C12, which comprises modifying the target product, thereby producing modified target product.

C14. The method of any one of embodiments C1-C13, which comprises placing the cultured microorganisms, the target product or the modified target product in a container.

C15. The method of embodiment C14, which comprises shipping the container.

D1. A method for producing a target product by an engineered microorganism, which comprises:
(a) culturing an engineered microorganism of any one of embodiments A1-B302 under a first set of fermentation conditions; and
(b) culturing the engineered microorganism after (a) under a second set of fermentation conditions different than the first set of fermentation conditions, whereby the second set of fermentation conditions inhibits cell division and/or cell proliferation of the engineered microorganism.

D2. The method of embodiment D1, wherein the second set of fermentation conditions comprises anaerobic fermentation conditions and the first set of fermentation conditions comprises aerobic fermentation conditions.

D3. The method of embodiment D1, wherein the second set of fermentation conditions comprises an elevated temperature as compared to the temperature in the first set of fermentation conditions.

D4. The method of any one of embodiments D1-D3, wherein the genetic modification inhibits the cell cycle of the engineered microorganism upon exposure to the second set of fermentation conditions.

D5. The method of any one of embodiments D1-D4, wherein the genetic modification induces cell cycle arrest upon exposure to the second set of fermentation conditions.

D6. The method of any one of embodiments D1-D5, wherein the genetic modification inhibits thymidylate synthase activity upon exposure to the change in fermentation conditions.

D7. The method of embodiment D6, wherein the genetic modification comprises a temperature sensitive mutation.

D8. The method of any one of embodiments D1-D7, wherein the microorganism comprises an added or altered five-carbon sugar metabolic activity.

D9. The method of embodiment D8, wherein the microorganism comprises an added or altered xylose isomerase activity.

D10. The method of any one of embodiments D1-D9, wherein the microorganism comprises an added or altered five-carbon sugar transporter activity.

D11. The method of embodiment D10, wherein the transporter activity is a transporter facilitator activity.

D12. The method of embodiment D10, wherein the transporter activity is an active transporter activity.

D13. The method of any one of embodiments D1-D12, wherein the microorganism comprises an added or altered carbon dioxide fixation activity.

D14. The method of embodiment D13, wherein the microorganism comprises an added or altered phosphoenolpyruvate (PEP) carboxylase activity.

D15. The method of any one of embodiments D1-D14, wherein the microorganism comprises a genetic modification that reduces or removes an alcohol dehydrogenase 2 activity.

D16. The method of any one of embodiments D1-D15, wherein the microorganism is an engineered yeast.

D17. The method of embodiment D16, wherein the yeast is a *Saccharomyces* yeast.

D18. The method of embodiment D17, wherein the *Saccharomyces* yeast is *S. cerevisiae*.

D19. The method of any one of embodiments D1-D18, wherein the target product is ethanol.

D20. The method of any one of embodiments D1-D18, wherein the target product is succinic acid.

E1. A method for manufacturing an engineered microorganism, which comprises:
  (a) introducing a genetic modification to a host microorganism that reduces an Embden-Meyerhoff glycolysis pathway member activity upon exposure of the engineered microorganism to anaerobic conditions; and
  (b) selecting for engineered microorganisms that (i) metabolize six-carbon sugars by the Embden-Meyerhoff glycolysis pathway under aerobic fermentation conditions, and (ii) preferentially metabolize six-carbon sugars by the Enter-Doudoroff pathway under the anaerobic fermentation conditions.

E2. The method of embodiment E1, wherein the genetic modification is insertion of a promoter into genomic DNA in operable linkage with a polynucleotide that encodes the Embden-Meyerhoff glycolysis pathway member activity.

E3. The method of embodiment E1, wherein the genetic modification is provision of a heterologous promoter polynucleotide in operable linkage with a polynucleotide that encodes the Embden-Meyerhoff glycolysis pathway member activity.

E4. The method of embodiment E1, wherein the genetic modification is a deletion or disruption of a polynucleotide that encodes, or regulates production of, the Embden-Meyerhoff glycolysis pathway member, and the microorganism comprises a heterologous nucleic acid that includes a polynucleotide encoding the Embden-Meyerhoff glycolysis pathway member operably linked to a polynucleotide that downregulates production of the member under anaerobic fermentation conditions.

E5. The method of any one of embodiments E1-E4, wherein the Embden-Meyerhoff glycolysis pathway member activity is a phosphofructokinase activity.

E6. The method of any one of embodiments E1-E5, which comprises introducing a genetic alteration that adds or alters a five-carbon sugar metabolic activity.

E7. The method of embodiment E6, wherein the genetic alteration adds or alters a xylose isomerase activity.

E8. The method of any one of embodiments E1-E7, which comprises introducing a genetic modification that adds or alters a five-carbon sugar transporter activity.

E9. The method of embodiment E8, wherein the transporter activity is a transporter facilitator activity.

E10. The method of embodiment E8, wherein the transporter activity is an active transporter activity.

E11. The method of any one of embodiments E1-E10, which comprises introducing a genetic modification that adds or alters a carbon dioxide fixation activity.

E12. The method of embodiment E11, which comprises introducing a genetic modification that adds or alters a phosphoenolpyruvate (PEP) carboxylase activity.

E13. The method of any one of embodiments E1-E12, which comprises introducing a genetic modification that reduces or removes an alcohol dehydrogenase 2 activity.

E14. The method of any one of embodiments E1-E13, which comprises introducing a genetic modification described in any one of embodiments B1-B208.

F1. A method for manufacturing an engineered microorganism, which comprises:
  (a) introducing a genetic modification to a host microorganism that inhibits cell division upon exposure to a change in fermentation conditions, thereby producing engineered microorganisms; and
  (b) selecting for engineered microorganisms with inhibited cell division upon exposure of the engineered microorganisms to the change in fermentation conditions.

F2. The method of embodiment F2, wherein the change in fermentation conditions comprises a change to anaerobic fermentation conditions.

F3. The method of embodiment F1, wherein the change in fermentation conditions comprises a change to an elevated temperature.

F4. The method of any one of embodiments F1-F3, wherein the genetic modification inhibits the cell cycle of the engineered microorganism upon exposure to the change in fermentation conditions.

F5. The method of any one of embodiments F1-F4, wherein the genetic modification induces cell cycle arrest upon exposure to the second set of fermentation conditions.

F6. The method of any one of embodiments F1-F5, wherein the genetic modification inhibits thymidylate synthase activity upon exposure to the change in fermentation conditions.

F7. The method of embodiment F6, wherein the genetic modification comprises a temperature sensitive mutation.

F8. The method of any one of embodiments F1-F7, wherein the genetic modification adds or alters a five-carbon sugar metabolic activity.

F9. The method of embodiment F8, wherein the genetic modification adds or alters a xylose isomerase activity.

F10. The method of any one of embodiments F1-F9, wherein the genetic modification adds or alters a five-carbon sugar transporter activity.

F11. The method of embodiment F10, wherein the transporter activity is a transporter facilitator activity.

F12. The method of embodiment F10, wherein the transporter activity is an active transporter activity.

F13. The method of any one of embodiments F1-F12, wherein the genetic modification adds or alters a carbon dioxide fixation activity.

F14. The method of embodiment F13, wherein the genetic modification adds or alters a phosphoenolpyruvate (PEP) carboxylase activity.

F15. The method of any one of embodiments F1-F14, wherein the genetic modification reduces or removes an alcohol dehydrogenase 2 activity.

F16. The method of any one of embodiments E1-E14 and F1-F15, wherein the microorganism is an engineered yeast.

F17. The method of embodiment F16, wherein the yeast is a *Saccharomyces* yeast.

F18. The method of embodiment F17, wherein the *Saccharomyces* yeast is *S. cerevisiae*.

G1. A nucleic acid, comprising a polynucleotide that encodes a polypeptide from *Ruminococcus* flavefaciens possessing a xylose to xylulose xylose isomerase activity.

G2. The nucleic acid of embodiment G1, wherein the polynucleotide includes one or more substituted codons.

G3. The nucleic acid of embodiment G2, wherein the one or more substituted codons are yeast codons.

G4. The nucleic acid of any one of embodiments G1 to G3, wherein the polynucleotide includes a nucleotide sequence of SEQ ID NO: 29, 30, 32 or 33, fragment thereof, or sequence having 50% identity or greater to the foregoing.

G5. The nucleic acid of any one of embodiments G1 to G4, wherein the polypeptide includes an amino acid sequence of SEQ ID NO: 31, fragment thereof, or sequence having 75% identity or greater to the foregoing.

G6. The nucleic acid of any one of embodiments G1 to G5, wherein a stretch of contiguous nucleotides of the polynucleotide is from another organism.

G7. The nucleic acid of embodiment G6, wherein the stretch of contiguous nucleotides from the other organism is from a nucleotide sequence that encodes a polypeptide possessing a xylose isomerase activity.

G8. The nucleic acid of embodiment G5 or G6, wherein the other organism is a fungus.

G9. The nucleic acid of embodiment G8, wherein the fungus is a *Piromyces* fungus.

G10. The nucleic acid of embodiment G9, wherein the fungus is a *Piromyces* strain E2.

G11. The nucleic acid of embodiment G10, wherein the stretch of contiguous nucleotides from the other organism is from SEQ ID NO: 34, or sequence having 50% identity or greater to the foregoing.

G12. The nucleic acid of embodiment G10, wherein the stretch of contiguous nucleotides from the other organism encodes an amino acid sequence from SEQ ID NO: 35, or sequence having 75% identity or greater to the foregoing.

G13. The nucleic acid of any one of embodiments G6 to G12, wherein the stretch of contiguous nucleotides from the other organism is about 1% to about 30% of the total number of nucleotides in the polynucleotide that encodes the polypeptide possessing xylose isomerase activity.

G14. The nucleic acid of embodiment G13, wherein about 30 contiguous nucleotides from the polynucleotide from *R. flavefaciens* are replaced by about 10 to about 20 nucleotides from the other organism.

G15. The nucleic acid of embodiment G13 or G14, wherein the contiguous stretch of polynucleotides from the other organism are at the 5' end of the polynucleotide.

G16. The nucleic acid of any one of embodiments G6 to G15, wherein the polynucleotide includes a nucleotide sequence of SEQ ID NO: 55, 56, 57, 59 or 61, fragment thereof, or sequence having 50% identity or greater to the foregoing.

G17. The nucleic acid of any one of embodiments G6 to G15, wherein the polynucleotide encodes a polypeptide that includes an amino acid sequence of SEQ ID NO: 58, 60 or 62, fragment thereof, or sequence having 75% identity or greater to the foregoing.

G18. The nucleic acid of any one of embodiments G1 to G17, which comprises one or more point mutations.

G19. The nucleic acid of embodiment G18, wherein the point mutation is at a position corresponding to position 179 of the *R. flavefaciens* polypeptide having xylose isomerase activity.

G20. The nucleic acid of embodiment G19, wherein the point mutation is a glycine 179 to alanine point mutation.

H1. An expression vector comprising a polynucleotide that encodes a polypeptide from *Ruminococcus flavefaciens* possessing a xylose to xylulose xylose isomerase activity.

H2. The expression vector of embodiment H1, wherein the polynucleotide includes one or more substituted codons.

H3. The expression vector of embodiment H2, wherein the one or more substituted codons are yeast codons.

H4. The expression vector of any one of embodiments H1 to H3, wherein the polynucleotide includes a nucleotide sequence of SEQ ID NO: 29, 30, 32 or 33, fragment thereof, or sequence having 50% identity or greater to the foregoing.

H5. The expression vector of any one of embodiments H1 to H4, wherein the polypeptide includes an amino acid sequence of SEQ ID NO: 31, fragment thereof, or sequence having 75% identity or greater to the foregoing.

H6. The expression vector of any one of embodiments H1 to H5, wherein a stretch of contiguous nucleotides of the polynucleotide is from another organism.

H7. The expression vector of embodiment H6, wherein the stretch of contiguous nucleotides from the other organism is from a nucleotide sequence that encodes a polypeptide possessing a xylose isomerase activity.

H8. The expression vector of embodiment H5 or H6, wherein the other organism is a fungus.

H9. The expression vector of embodiment H8, wherein the fungus is a *Piromyces* fungus.

H10. The expression vector of embodiment H9, wherein the fungus is a *Piromyces* strain E2.

H11. The expression vector of embodiment H10, wherein the stretch of contiguous nucleotides from the other organism is from SEQ ID NO: 34, or sequence having 50% identity or greater to the foregoing.

H12. The expression vector of embodiment H10, wherein the stretch of contiguous nucleotides from the other organism encodes an amino acid sequence from SEQ ID NO: 35, or sequence having 75% identity or greater to the foregoing.

H13. The expression vector of any one of embodiments H6 to H12, wherein the stretch of contiguous nucleotides from the other organism is about VA to about 30% of the total number of nucleotides in the polynucleotide that encodes the polypeptide possessing xylose isomerase activity.

H14. The expression vector of embodiment H13, wherein about 30 contiguous nucleotides from the polynucleotide from *R. flavefaciens* are replaced by about 10 to about 20 nucleotides from the other organism.

H15. The expression vector of embodiment H13 or H14, wherein the contiguous stretch of polynucleotides from the other organism are at the 5' end of the polynucleotide.

H16. The expression vector of any one of embodiments H6 to H15, wherein the polynucleotide includes a nucleotide sequence of SEQ ID NO: 55, 56, 57, 59 or 61, fragment thereof, or sequence having 50% identity or greater to the foregoing.

H17. The expression vector of any one of embodiments H6 to H15, wherein the polynucleotide encodes a polypeptide that includes an amino acid sequence of SEQ ID NO: 58, 60 or 62, fragment thereof, or sequence having 75% identity or greater to the foregoing.

H18. The expression vector of any one of embodiments H1 to H17, which comprises one or more point mutations.

H19. The expression vector of embodiment H18, wherein the point mutation is at a position corresponding to position 179 of the *R. flavefaciens* polypeptide having xylose isomerase activity.

H20. The expression vector of embodiment H19, wherein the point mutation is a glycine 179 to alanine point mutation.

H21. The expression vector of any one of embodiments, H1 to H20, comprising a regulatory nucleotide sequence in operable linkage with the polynucleotide.

H22. The expression vector of embodiment J25, wherein the regulatory nucleotide sequence comprises a promoter sequence.

H23. The expression vector of embodiment J26, wherein the promoter sequence is an inducible promoter sequence.

H24. The expression vector of embodiment J26, wherein the promoter sequence is a constitutively active promoter sequence.

H25. A method for preparing an expression vector of any one of embodiments H1 to H24, comprising: (i) providing a nucleic acid that contains a regulatory sequence, and (ii) inserting the polynucleotide into the nucleic acid in operable linkage with the regulatory sequence.

I1. A nucleic acid, comprising a polynucleotide that includes a first stretch of contiguous nucleic acids from a first organism and a second stretch of contiguous nucleic acids from a second organism, wherein the polynucleotide encodes a polypeptide possessing a xylose to xylulose xylose isomerase activity.

I2. The nucleic acid of embodiment I1, wherein the first organism and the second organism are the same species.

I3. The nucleic acid of embodiment I1, wherein the first organism and the second organism are different species.

I4. The nucleic acid of any one of embodiments I1 to I3, wherein the first stretch of contiguous nucleotides and the second stretch of contiguous nucleotides independently are selected from nucleotide sequence that encodes a polypeptide having xylose isomerase activity.

I5. The nucleic acid of any one of embodiments I1 to I4, wherein the first organism is a bacterium.

I6. The nucleic acid of embodiment I5, wherein the bacterium is a *Ruminococcus* bacterium.

I7. The nucleic acid of embodiment I6, wherein the bacterium is a *Ruminococcus flavefaciens* bacterium.

I8. The nucleic acid of any one of embodiments I5 to I7, wherein the stretch of contiguous nucleotides is from SEQ ID NO: 29, 30, 32, 33, or a sequence having 50% identity or greater to the foregoing.

I9. The nucleic acid of embodiment I8, wherein the stretch of contiguous nucleotides from the other organism encodes an amino acid sequence from SEQ ID NO: 31, or a sequence having 75% identity or greater to the foregoing.

I10. The nucleic acid of any one of embodiments I1 to I9, wherein the second organism is a fungus.

I11. The nucleic acid of embodiment I10, wherein the fungus is a *Piromyces* fungus.

I12. The nucleic acid of embodiment I11, wherein the fungus is a *Piromyces* strain E2 fungus.

I13. The nucleic acid of any one of embodiments I10 to I12, wherein the stretch of contiguous nucleotides is from SEQ ID NO: 34, or a sequence having 50% identity or greater to the foregoing.

I14. The nucleic acid of embodiment I13, wherein the stretch of contiguous nucleotides from the other organism encodes an amino acid sequence from SEQ ID NO: 35, or a sequence having 75% identity or greater to the foregoing.

I15. The nucleic acid of any one of embodiments I1 to I14, wherein the polynucleotide includes one or more substituted codons.

I16. The nucleic acid of embodiment I15, wherein the one or more substituted codons are yeast codons.

I17. The nucleic acid of any one of embodiments I1 to I16, wherein the stretch of contiguous nucleotides from the first organism or second organism is about 1% to about 30% of the total number of nucleotides in the polynucleotide that encodes the polypeptide possessing xylose isomerase activity.

I18. The nucleic acid of embodiment I17, wherein the stretch of contiguous nucleotides from the second organism is about 1% to about 30% of the total number of nucleotides in the polynucleotide.

I19. The nucleic acid of embodiment I18, wherein the contiguous stretch of polynucleotides from the second organism are at the 5' end of the polynucleotide.

I20. The nucleic acid of any one of embodiments I1 to I19, wherein the polynucleotide includes a nucleotide sequence of SEQ ID NO: 55, 56, 57, 59 or 61, fragment thereof, or sequence having 50% identity or greater to the foregoing.

I21. The nucleic acid of any one of embodiments I1 to I20, wherein the polynucleotide encodes a polypeptide that includes an amino acid sequence of SEQ ID NO: 58, 60 or 62, fragment thereof, or sequence having 75% identity or greater to the foregoing.

I22. The nucleic acid of any one of embodiments I1 to I21, which comprises one or more point mutations.

I23. The nucleic acid of embodiment I22, wherein the point mutation is at a position corresponding to position 179 of the *R. flavefaciens* polypeptide having xylose isomerase activity.

I24. The nucleic acid of embodiment I23, wherein the point mutation is a glycine 179 to alanine point mutation.

J1. An expression vector, comprising a polynucleotide that includes a first stretch of contiguous nucleotides from a first organism and a second stretch of contiguous nucleotides from a second organism, wherein the polynucleotide encodes a polypeptide possessing a xylose to xylulose xylose isomerase activity.

J2. The expression vector of embodiment J1, wherein the first organism and the second organism are the same.

J3. The expression vector of embodiment J1, wherein the first organism and the second organism are different.

J4. The expression vector of any one of embodiments J1 to J3, wherein the first stretch of contiguous nucleotides and the second stretch of contiguous nucleotides independently are selected from nucleotide sequence that encodes a polypeptide having xylose isomerase activity.

J5. The expression vector of any one of embodiments J1 to J4, wherein the first organism is a bacterium.

J6. The expression vector of embodiment J5, wherein the bacterium is a *Ruminococcus* bacterium.

J7. The expression vector of embodiment J6, wherein the bacterium is a *Ruminococcus* flavefaciens bacterium.

J8. The expression vector of any one of embodiments J5 to J7, wherein the stretch of contiguous nucleotides is from SEQ ID NO: 29, 30, 32, 33, or a sequence having 50% identity or greater to the foregoing.

J9. The expression vector of embodiment J8, wherein the stretch of contiguous nucleotides from the other organism encodes an amino acid sequence from SEQ ID NO: 31, or a sequence having 75% identity or greater to the foregoing.

J10. The expression vector of any one of embodiments J1 to J9, wherein the second organism is a fungus.

J11. The expression vector of embodiment J10, wherein the fungus is a *Piromyces* fungus.

J12. The expression vector of embodiment J11, wherein the fungus is a *Piromyces* strain E2 fungus.

J13. The expression vector of any one of embodiments J10 to J12, wherein the stretch of contiguous nucleotides is from SEQ ID NO: 34, or a sequence having 50% identity or greater to the foregoing.

J14. The expression vector of embodiment J13, wherein the stretch of contiguous nucleotides from the other organism encodes an amino acid sequence from SEQ ID NO: 35, or a sequence having 75% identity or greater to the foregoing.

J15. The expression vector of any one of embodiments J1 to J14, wherein the polynucleotide includes one or more substituted codons.

J16. The expression vector of embodiment J15, wherein the one or more substituted codons are yeast codons.

J17. The expression vector of any one of embodiments J1 to J16, wherein the stretch of contiguous nucleotides from the first organism or second organism is about 1% to about 30% of the total number of nucleotides in the polynucleotide that encodes the polypeptide possessing xylose isomerase activity.

J18. The expression vector of embodiment J17, wherein the stretch of contiguous nucleotides from the second organism is about 1% to about 30% of the total number of nucleotides in the polynucleotide.

J19. The expression vector of embodiment J18, wherein the contiguous stretch of polynucleotides from the second organism are at the 5' end of the polynucleotide.

J20. The expression vector of any one of embodiments J1 to J19, wherein the polynucleotide includes a nucleotide sequence of SEQ ID NO: 55, 56, 57, 59 or 61, fragment thereof, or sequence having 50% identity or greater to the foregoing.

J21. The expression vector of any one of embodiments J1 to J20, wherein the polynucleotide encodes a polypeptide that includes an amino acid sequence of SEQ ID NO: 58, 60 or 62, fragment thereof, or sequence having 75% identity or greater to the foregoing.

J22. The expression vector of any one of embodiments J1 to J21, which comprises one or more point mutations.

J23. The expression vector of embodiment J22, wherein the point mutation is at a position corresponding to position 179 of the *R. flavefaciens* polypeptide having xylose isomerase activity.

J24. The expression vector of embodiment J23, wherein the point mutation is a glycine 179 to alanine point mutation.

J25. The expression vector of any one of embodiments, J1 to J24, comprising a regulatory nucleotide sequence in operable linkage with the polynucleotide.

J26. The expression vector of embodiment J25, wherein the regulatory nucleotide sequence comprises a promoter sequence.

J27. The expression vector of embodiment J26, wherein the promoter sequence is an inducible promoter sequence.

J28. The expression vector of embodiment J26, wherein the promoter sequence is a constitutively active promoter sequence.

J29. A method for preparing an expression vector of any one of embodiments J1 to J28, comprising: (i) providing a nucleic acid that contains a regulatory sequence, and (ii) inserting the polynucleotide into the nucleic acid in operable linkage with the regulatory sequence.

K1. A microbe comprising a polynucleotide of the nucleic acid of any one of embodiments G1 to G20 or any one of embodiments I1 to I24.

K2. A microbe comprising an expression vector of any one of embodiments H1 to H20 or any one of embodiments J1 to J24.

K3. The microbe of embodiment K1 or K2, which is a yeast.

K4. The microbe of embodiment K3, which is a *Saccharomyces* yeast.

K5. The microbe of embodiment K4, which is a *Saccharomyces cerevisiae* yeast.

L1. A method, comprising contacting a microbe of any one of embodiments K1 to K5 with a feedstock comprising a five carbon molecule under conditions for generating ethanol.

L2. The method of embodiment L1, wherein the five carbon molecule comprises xylose.

L3. The method of embodiment L1 or L2, wherein about 15 grams per liter of ethanol or more is generated within about 372 hours.

L4. The method of any one of embodiments L1 to L3, wherein about 2.0 grams per liter dry cell weight is generated within about 372 hours.

M1. A composition comprising an engineered yeast comprising heterologous polynucleotide subsequences that encode a phosphogluconate dehydratase enzyme, a 2-keto-3-deoxygluconate-6-phosphate aldolase enzyme and a xylose isomerase enzyme.

M2. The composition of embodiment M1, wherein the yeast is a *Saccharomyces* spp. yeast.

M3. The composition of embodiment M2, wherein the yeast is a *Saccharomyces cerevisiae* yeast strain.

M3. The composition of any one of embodiments M1 to M3, wherein the polynucleotide subsequences encoding the phosphogluconate dehydratase enzyme and the 3-deoxygluconate-6-phosphate aldolase enzyme independently are from an *Escherichia* spp. microbe or *Pseudomonas* spp. microbe.

M4. The composition of embodiment M3, wherein the *Escherichia* spp. microbe is an *Escherichia coli* strain.

M5. The composition of embodiment M3 or M4, wherein the *Pseudomonas* spp. microbe is a *Pseudomonas aeruginosa* strain.

M6. The composition of any one of embodiments M1 to M5, wherein the polynucleotide subsequence that encodes the phosphogluconate dehydratase enzyme is an EDD gene.

M7. The composition of any one of embodiments M1 to M5, wherein the polynucleotide subsequence that encodes the 2-keto-3-deoxygluconate-6-phosphate aldolase enzyme is an EDA gene.

M8. The composition of any one of embodiments M1 to M7, wherein the xylose isomerase enzyme is a chimeric enzyme.

M8.1. The composition of embodiment M8, wherein a first portion of the polynucleotide subsequence that encodes the chimeric xylose isomerase enzyme is from a first microbe and a second portion of the polynucleotide subsequence that encodes the chimeric xylose isomerase enzyme is from a second microbe.

M8.2. The composition of embodiment M8 or M8.1, wherein the first microbe, the second microbe, or the first microbe and the second microbe independently are selected from one or more of the group consisting of *Clostridiales* spp., *Ruminococcus* spp., *Thermus* spp., *Bacillus* spp., *Clostridium* spp., *Orpinomyces* spp., *Escherichia* spp. and *Piromyces* spp. microbes.

M8.3. The composition of embodiment M8.2, wherein the first microbe, the second microbe, or the first microbe and the second microbe independently are selected from one or more of the group consisting of *Clostridiales_genomosp.* BVAB3 str UPII9-5, *Ruminococcus flavefaciens*, *Ruminococcus_FD1*, *Ruminococcus_18P13*, *Thermus thermophilus*, *Bacillus stercoris*, *Clostridium cellulolyticum*, *Bacillus uniformis*, *Bacillus stearothermophilus*, *Bacteroides thetaiotaomicron*, *Clostridium thermohydrosulfuricum*, *Orpinomyces*, *Clostridium phytofermentans*, *Escherichia coli* and *Piromyces* strain E2.

M8. The composition of any one of embodiments M1 to M7, wherein 80% or more of the polynucleotide subsequence that encodes the xylose isomerase enzyme is from a *Ruminococcus* spp. microbe xylose isomerase-encoding sequence.

M9. The composition of embodiment M8, wherein all of the polynucleotide subsequence that encodes the xylose isomerase enzyme is from a *Ruminococcus* spp. microbe xylose isomerase-encoding sequence.

M10. The composition of any one of embodiments M8 to M9, wherein the *Ruminococcus* spp. microbe is a *Ruminococcus flavefaciens* strain.

M11. The composition of any one of embodiments M8 to M10, wherein the polynucleotide subsequence that encodes the xylose isomerase enzyme is chimeric and includes a sequence that encodes a xylose isomerase from another microbe.

M12. The composition of embodiment M11, wherein the other microbe is a fungus.

M13. The composition of embodiment M12, wherein the fungus is an anaerobic fungus.

M14. The composition of embodiment M12, wherein the fungus is a *Piromyces* spp. fungus.

M15. The composition of embodiment M14, wherein the *Piromyces* spp. fungus is a *Piromyces* strain E2.

M16. The composition of any one of embodiments M1 to M15, wherein the yeast expresses a glucose-6-phosphate dehydrogenase enzyme, a glucose-6-phosphate dehydrogenase enzyme, or a glucose-6-phosphate dehydrogenase enzyme and a glucose-6-phosphate dehydrogenase enzyme.

M17. The composition of embodiment M16, wherein the polynucleotide subsequences that encode the glucose-6-phosphate dehydrogenase enzyme, the glucose-6-phosphate dehydrogenase enzyme, or the glucose-6-phosphate dehydrogenase enzyme and the glucose-6-phosphate dehydrogenase enzyme are from a yeast.

M18. The composition of embodiment M17, wherein the yeast from which the polynucleotide subsequence or subsequences are derived is a *Saccharomyces* spp. yeast.

M19. The composition of embodiment 18, wherein the yeast is a *Saccharomyces cerevisiae* strain.

M20. The composition of any one of embodiments M16 to M19, wherein the yeast over-expresses an endogenous glucose-6-phosphate dehydrogenase enzyme, an endogenous glucose-6-phosphate dehydrogenase enzyme, or an endogenous glucose-6-phosphate dehydrogenase enzyme and an endogenous glucose-6-phosphate dehydrogenase enzyme.

M21. The composition of any one of embodiments M16 to M20, wherein the glucose-6-phosphate dehydrogenase enzyme is expressed from a ZWF gene.

M22. The composition of embodiment M21, wherein the ZWF gene is a ZWF1 gene.

M23. The composition of any one of embodiments M16 to M22, wherein the glucose-6-phosphate dehydrogenase enzyme is expressed from a SOL gene.

M24. The composition of embodiment M23, wherein the SOL gene is a SOL3 gene.

M25. The composition of any one of embodiments M1 to M25, wherein the yeast includes a polynucleotide subsequence that encodes a glucose transporter.

M26. The composition of embodiment M25, wherein the polynucleotide subsequence that encodes the glucose transporter is from a yeast.

M27. The composition of embodiment M25 or M26, wherein the yeast over-expresses one or more endogenous glucose transport enzymes.

M28. The composition of any one of embodiments M25 to M27, wherein the glucose transporter is encoded by a one or more of a GAL2, GSX1 and GXF1 gene.

M29. The composition of any one of embodiments M1 to M28, wherein the yeast includes a genetic alteration that reduces the activity of an endogenous phosphofructokinase (PFK) enzyme activity.

M29. The composition of embodiment M29, wherein the PFK enzyme is a PFK-2 enzyme.

M30. The composition of any one of embodiments M1 to M29, wherein the yeast includes one or more extra copies of an endogenous promoter, or a heterologous promoter operable in a yeast, wherein the promoter is in operable connection with one or more of the polynucleotide subsequences.

M31. The composition of embodiment M30, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

M32. The composition of any one of embodiments M1 to M31, wherein the polynucleotide subsequences, the promoters, or the polynucleotide subsequences and the promoters are not integrated in the yeast nucleic acid.

M33. The composition of embodiment M32, wherein the polynucleotide subsequences, the promoters, or the polynucleotide subsequences and the promoters are in one or more plasmids.

M34. The composition of any one of embodiments M1 to M31, wherein the polynucleotide subsequences, the promoters, or the polynucleotide subsequences and the promoters are integrated in genomic DNA of the yeast.

M35. The composition of embodiment M34, wherein the polynucleotide subsequences, the promoters, or the polynucleotide subsequences and the promoters are integrated in a transposition integration event, in a homologous recombination integration event, or in a transposition integration event and a homologous recombination integration event.

M36. The composition of embodiment M35, wherein the transposition integration event includes transposition of an operon comprising two or more of the polynucleotide subsequences, the promoters, or the polynucleotide subsequences and the promoters.

M37. The composition of embodiment 34, wherein the homologous recombination integration event includes homologous recombination of an operon comprising two or more of the polynucleotide subsequences, the promoters, or the polynucleotide subsequences and the promoters.

N1. A method, comprising contacting an engineered yeast of any one of embodiments M1 to M37 with a feedstock that contains one or more hexose sugars and one or more pentose sugars under conditions in which the microbe synthesizes ethanol.

N2. The method of embodiment N1, wherein the engineered yeast synthesizes ethanol to about 85% to about 99% of theoretical yield.

N3. The method of embodiment N1 or N2, comprising recovering ethanol synthesized by the engineered yeast.

N4. The method of any one of embodiments, N1 to N3, wherein the conditions are fermentation conditions.

O1. A composition comprising a nucleic acid comprising heterologous polynucleotides that encode a phosphogluconate dehydratase enzyme, a 2-keto-3-deoxygluconate-6-phosphate aldolase enzyme and a xylose isomerase enzyme.

O2. The composition of embodiment O1, wherein the yeast is a *Saccharomyces* spp. yeast.

O3. The composition of embodiment O2, wherein the yeast is a *Saccharomyces cerevisiae* yeast strain.

O3.1. The composition of any one of embodiments O1 to O3, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

O4. The composition of embodiment O3, wherein the *Escherichia* spp. microbe is an *Escherichia coli* strain.

O5. The composition of embodiment O3 or O4, wherein the *Pseudomonas* spp. microbe is a *Pseudomonas aeruginosa* strain.

O6. The composition of any one of embodiments O1 to O5, wherein the polynucleotide that encodes the phosphogluconate dehydratase enzyme is an EDD gene.

O7. The composition of any one of embodiments O1 to O5, wherein the polynucleotide that encodes the 2-keto-3-deoxygluconate-6-phosphate aldolase enzyme is an EDA gene.

O8. The composition of any one of embodiments O1 to O7, wherein the xylose isomerase enzyme is a chimeric enzyme.

O8.1. The composition of embodiment O8, wherein a first portion of the polynucleotide that encodes the chimeric xylose isomerase enzyme is from a first microbe and a second portion of the polynucleotide that encodes the chimeric xylose isomerase enzyme is from a second microbe.

O8.2. The composition of embodiment O8 or O8.1, wherein the first microbe, the second microbe, or the first microbe and the second microbe independently are selected from one or more of the group consisting of *Clostridiales* spp., *Ruminococcus* spp., *Thermus* spp., *Bacillus* spp., *Clostridium* spp., *Orpinomyces* spp., *Escherichia* spp. and *Piromyces* spp. microbes.

O8.3. The composition of embodiment O8.2, wherein the first microbe, the second microbe, or the first microbe and the second microbe independently are selected from one or more of the group consisting of Clostridiales_genomosp. BVAB3 str UPII9-5, *Ruminococcus flavefaciens*, *Ruminococcus*_FD1, *Ruminococcus*_18P13, *Thermus thermophilus*, *Bacillus stercoris*, *Clostridium cellulolyticum*, *Bacillus uniformis*, *Bacillus stearothermophilus*, *Bacteroides thetaiotaomicron*, *Clostridium thermohydrosulfuricum*, *Orpinomyces*, *Clostridium phytofermentans*, *Escherichia coli* and *Piromyces* strain E2.

O8. The composition of any one of embodiments O1 to O7, wherein 80% or more of the polynucleotide that encodes the xylose isomerase enzyme is from a *Ruminococcus* spp. microbe xylose isomerase-encoding sequence.

O9. The composition of embodiment O8, wherein all or a portion of the polynucleotide that encodes the xylose isomerase enzyme is from a *Ruminococcus* spp. microbe xylose isomerase-encoding sequence.

O10. The composition of any one of embodiments O8 to O9, wherein the *Ruminococcus* spp. microbe is a *Ruminococcus flavefaciens* strain.

O11. The composition of any one of embodiments O8 to O10, wherein the polynucleotide that encodes the xylose isomerase enzyme is chimeric and includes a sequence that encodes a xylose isomerase from another microbe.

O11.1. The composition of any one of embodiments O8 to O11, wherein the portion of the polynucleotide from the *Ruminococcus* spp. microbe xylose isomerase is 3' with respect to the portion of the polynucleotide from another microbe.

O12. The composition of embodiment O11 or O11.1, wherein the other microbe is a fungus.

O13. The composition of embodiment O12, wherein the fungus is an anaerobic fungus.

O14. The composition of embodiment O12, wherein the fungus is a *Piromyces* spp. fungus.

O15. The composition of embodiment O14, wherein the *Piromyces* spp. fungus is a *Piromyces* strain E2.

O16. The composition of any one of embodiments O1 to O15, wherein the nucleic acid includes one or more polynucleotides that encode a glucose-6-phosphate dehydrogenase enzyme, a 6-phosphogluconolactonase enzyme, or a glucose-6-phosphate dehydrogenase enzyme and a 6-phosphogluconolactonase enzyme.

O17. The composition of embodiment O16, wherein the one or more polynucleotides that encode the glucose-6-phosphate dehydrogenase enzyme, the 6-phosphogluconolactonase enzyme, or the glucose-6-phosphate dehydrogenase enzyme and the 6-phosphogluconolactonase enzyme are from a yeast.

O18. The composition of embodiment O17, wherein the yeast from which the polynucleotide or polynucleotides are derived is a *Saccharomyces* spp. yeast.

O19. The composition of embodiment O18, wherein the yeast is a *Saccharomyces cerevisiae* strain.

O20. The composition of any one of embodiments O16 to O19, wherein the nucleic acid includes one or more polynucleotides that encode an endogenous glucose-6-phosphate dehydrogenase enzyme, an endogenous 6-phosphogluconolactonase enzyme, or an endogenous glucose-6-phosphate dehydrogenase enzyme and an endogenous 6-phosphogluconolactonase enzyme.

O21. The composition of any one of embodiments O16 to O20, wherein the glucose-6-phosphate dehydrogenase enzyme is expressed from a ZWF gene.

O22. The composition of embodiment O21, wherein the ZWF gene is a ZWF1 gene.

O23. The composition of any one of embodiments O16 to O22, wherein the 6-phosphogluconolactonase enzyme is expressed from a SOL gene.

O24. The composition of embodiment O23, wherein the SOL gene is a SOL3 gene.

O25. The composition of any one of embodiments O1 to O24, wherein the nucleic acid includes one or more polynucleotides that encode one or more glucose transporters.

O26. The composition of embodiment O25, wherein the polynucleotide that encodes the one or more glucose transporters is from a yeast.

O27. The composition of embodiment O25 or O26, wherein the one or more glucose transporters is encoded by a one or more of a GAL2, GSX1 and GXF1 gene.

O28. The composition of any one of embodiments O1 to O27, wherein the nucleic acid includes one or more polynucleotides that encode a transketolase enzyme, transaldolase enzyme, or a transketolase enzyme and transaldolase enzyme.

O29. The composition of embodiment O28, wherein the transketolase enzyme is encoded by a TKL1 coding sequence or a TKL2 coding sequence.

O30. The composition of embodiment O28, wherein the transaldolase is encoded by a TAL coding sequence.

O31. The composition of any one of embodiments O28 to O30, wherein the transketolase enzyme or the transaldolase enzyme is from a yeast.

O32. The composition of any one of embodiments O1 to O31, wherein the nucleic acid includes one or more promoters operable in a yeast, wherein the promoter is in operable connection with one or more of the polynucleotides.

O33. The composition of embodiment O32, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

O34. The composition of any one of embodiments O1 to O33, wherein the nucleic acid includes one or more polynucleotides that homologously combine in a gene of a host that encodes a phosphofructokinase (PFK) enzyme, phosphoglucoisomerase (PGI) enzyme or 6-phosphogluconate dehydrogenase (decarboxylating) enzyme.

O35. The composition of embodiment O34, wherein the phosphofructokinase (PFK) enzyme is a PFK-2 enzyme or PFK-1 enzyme.

O35.1. The composition of embodiment O34, wherein the 6-phosphogluconate dehydrogenase (decarboxylating) enzyme is encoded by a GND-1 gene or a GND-2 gene.

O36. The composition of embodiment O34, wherein the PGI is encoded by a PGI-1 gene.

O37. The composition of any one of embodiments O1 to O6, wherein the nucleic acid is one or two separate nucleic acid molecules.

O38. The composition of embodiment O37, wherein each nucleic acid molecule includes one or two or more of the polynucleotide subsequences, one or two or more of the promoters, or one or two or more of the polynucleotide subsequences and one or two or more of the promoters.

O39. The composition of embodiment O37 or O38, wherein each of the one or two nucleic acid molecules are in circular form.

O40. The composition of embodiment O37 or O38, wherein each of the one or two nucleic acid molecules are in linear form.

O41. The composition of any one of embodiments O37 to O40, wherein each of the one or two nucleic acid molecules functions as an expression vector.

O42. The composition of any one of embodiments O37 to O41, wherein each of the one or two nucleic acid molecules includes flanking sequences for integrating the polynucleotides, the promoter sequences, or the polynucleotides and the promoter sequences in the nucleic acid into genomic DNA of a host organism.

P1. The composition comprising an engineered yeast that includes an alteration that adds or increases a phosphogluconate dehydratase activity, a 2-keto-3-deoxygluconate-6-phosphate aldolase activity and a xylose isomerase activity.

P2. The composition of embodiment P1, wherein the yeast is a *Saccharomyces* spp. yeast.

P3. The composition of embodiment P2, wherein the yeast is a *Saccharomyces cerevisiae* yeast strain.

P4. The composition of any one of embodiments P1 to P3 that includes heterologous polynucleotides that encode a phosphogluconate dehydratase enzyme, a 2-keto-3-deoxygluconate-6-phosphate aldolase enzyme and a xylose isomerase enzyme.

P5. The composition of embodiment P4, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

P6. The composition of embodiment P5, wherein the *Escherichia* spp. microbe is an *Escherichia coli* strain.

P7. The composition of embodiment P5, wherein the *Pseudomonas* spp. microbe is a *Pseudomonas aeruginosa* strain.

P8. The composition of any one of embodiments P4 to P7, wherein the polynucleotide that encodes the phosphogluconate dehydratase enzyme is an EDD gene.

P9. The composition of any one of embodiments P4 to P7, wherein the polynucleotide that encodes the 2-keto-3-deoxygluconate-6-phosphate aldolase enzyme is an EDA gene.

P10. The composition of any one of embodiments P1 to P9, wherein the xylose isomerase enzyme is a chimeric enzyme.

P11. The composition of embodiment P10, wherein a first portion of the polynucleotide that encodes the chimeric xylose isomerase enzyme is from a first microbe and a second portion of the polynucleotide that encodes the chimeric xylose isomerase enzyme is from a second microbe.

P12. The composition of embodiment P10 or P11, wherein the first microbe, the second microbe, or the first microbe and the second microbe independently are selected from one or more of the group consisting of *Clostridiales* spp., *Ruminococcus* spp., *Thermus* spp., *Bacillus* spp., *Clostridium* spp., *Orpinomyces* spp., *Escherichia* spp. and *Piromyces* spp. microbes.

P13. The composition of embodiment P12, wherein the first microbe, the second microbe, or the first microbe and the second microbe independently are selected from one or more of the group consisting of *Clostridiales_genomosp.* BVAB3 str UPI19-5, *Ruminococcus flavefaciens*, *Ruminococcus_*FD1, *Ruminococcus_*18P13, *Thermus thermophilus*, *Bacillus stercoris*, *Clostridium* cellulolyticum, *Bacillus uniformis*, *Bacillus stearothermophilus*, *Bacteroides thetaiotaomicron*, *Clostridium thermohydrosulfuricum*, *Orpinomyces*, *Clostridium phytofermentans*, *Escherichia coli* and *Piromyces* strain E2.

P14. The composition of any one of embodiments P10 to P13, wherein 80% or more of the polynucleotide that encodes the xylose isomerase enzyme is from a *Ruminococcus* spp. microbe xylose isomerase-encoding sequence.

P15. The composition of embodiment P14, wherein all or a portion of the polynucleotide that encodes the xylose isomerase enzyme is from a *Ruminococcus* spp. microbe xylose isomerase-encoding sequence.

P16. The composition of embodiment P15, wherein the *Ruminococcus* spp. microbe is a *Ruminococcus flavefaciens* strain.

P17. The composition of any one of embodiments P10 to P16, wherein the polynucleotide that encodes the xylose isomerase enzyme is chimeric and includes a sequence that encodes a xylose isomerase from another microbe.

P18. The composition of any one of embodiments P10 to P17, wherein the portion of the polynucleotide from the *Ruminococcus* spp. microbe xylose isomerase is 3' with respect to the portion of the polynucleotide from another microbe.

P19. The composition of embodiment P17 or P18, wherein the other microbe is a fungus.

P20. The composition of embodiment P19, wherein the fungus is an anaerobic fungus.

P21. The composition of embodiment P20, wherein the fungus is a *Piromyces* spp. fungus.

P22. The composition of embodiment P21, wherein the *Piromyces* spp. fungus is a *Piromyces* strain E2.

P23. The composition of any one of embodiments P1 to P22, wherein one or more of the following activities are added or increased: a glucose-6-phosphate dehydrogenase activity, a 6-phosphogluconolactonase activity, or a glucose-6-phosphate dehydrogenase activity and a 6-phosphogluconolactonase activity.

P24. The composition of embodiment P24, wherein the yeast comprises one or more heterologous polynucleotides that encode one or more of the following enzymes, or wherein the yeast comprises multiple copies of endogenous polynucleotides that encode one or more of the following enzymes: glucose-6-phosphate dehydrogenase enzyme, 6-phosphogluconolactonase enzyme, or glucose-6-phosphate dehydrogenase enzyme and 6-phosphogluconolactonase enzyme.

P25. The composition of embodiment P24, wherein the one or more polynucleotides that encode the glucose-6-phosphate dehydrogenase enzyme, the 6-phosphogluconolactonase enzyme, or the glucose-6-phosphate dehydrogenase enzyme and the 6-phosphogluconolactonase enzyme are from a yeast.

P26. The composition of embodiment P25, wherein the yeast is a *Saccharomyces* spp. yeast.

P27. The composition of embodiment P26, wherein the yeast is a *Saccharomyces cerevisiae* strain.

P28. The composition of any one of embodiments P24 to P27, wherein the glucose-6-phosphate dehydrogenase enzyme is expressed from a ZWF gene.

P29. The composition of embodiment P28, wherein the ZWF gene is a ZWF1 gene.

P30. The composition of any one of embodiments P24 to P29, wherein the 6-phosphogluconolactonase enzyme is expressed from a SOL gene.

P31. The composition of embodiment P31, wherein the SOL gene is a SOL3 gene.

P32. The composition of any one of embodiments P1 to P31, wherein the nucleic acid includes one or more polynucleotides that encode one or more glucose transporters.

P33. The composition of embodiment P32, wherein the polynucleotide that encodes the one or more glucose transporters is from a yeast.

P34. The composition of embodiment P32 or P33, wherein the one or more glucose transporters is encoded by a one or more of a GAL2, GSX1 and GXF1 gene.

P35. The composition of any one of embodiments P1 to P34, wherein the yeast includes one or more added activities or increased activities selected from the group consisting of transketolase activity, transaldolase activity, or a transketolase activity and transaldolase activity.

P36. The composition of embodiment P35, wherein the yeast includes one or more heterologous polynucleotides that encodes one or more of the following enzymes, or includes multiple copies of polynucleotides that encode one or more of the following enzymes: transketolase enzyme, transaldolase enzyme, or a transketolase enzyme and transaldolase enzyme P37. The composition of embodiment P36, wherein the transketolase enzyme is encoded by a TKL1 coding sequence or a TKL2 coding sequence.

P38. The composition of embodiment P36, wherein the transaldolase is encoded by a TAL coding sequence.

P39. The composition of any one of embodiments P36 to P38, wherein the transketolase enzyme or the transaldolase enzyme is from a yeast.

P40. The composition of any one of embodiments P1 to P39, wherein the nucleic acid includes one or more promoters operable in a yeast, wherein the promoter is in operable connection with one or more of the polynucleotides.

P41. The composition of embodiment P40, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

P42. The composition of any one of embodiments P1 to P41, wherein the yeast includes a reduction in one or more of the following activities: phosphofructokinase (PFK) activity, phosphoglucoisomerase (PGI) activity, 6-phosphogluconate dehydrogenase (decarboxylating) activity or combination thereof.

P43. The composition of embodiment P42, wherein the yeast includes an alteration in one or more polynucleotides that inhibits production of one or more enzymes selected from the group consisting of phosphofructokinase (PFK) enzyme, phosphoglucoisomerase (PGI) enzyme, 6-phosphogluconate dehydrogenase (decarboxylating) enzyme or combination thereof.

P44. The composition of embodiment P43, wherein the phosphofructokinase (PFK) enzyme is a PFK-2 enzyme or PFK-1 enzyme.

P44.1. The composition of embodiment P43, wherein the 6-phosphogluconate dehydrogenase (decarboxylating) enzyme is encoded by a GND-1 gene or GND-2 gene.

P45. The composition of embodiment P43, wherein the PGI is encoded by a PGI-1 gene.

P46. The composition of any one of embodiments P1 to P45, wherein the polynucleotides, the promoters, or the polynucleotides and the promoters are not integrated in the yeast nucleic acid.

P47. The composition of embodiment P46, wherein the polynucleotides, the promoters, or the polynucleotides and the promoters are in one or more plasmids.

P48. The composition of any one of embodiments P1 to P47, wherein the polynucleotide subsequences, the promoters, or the polynucleotide subsequences and the promoters are integrated in genomic DNA of the yeast.

P49. The composition of embodiment P48, wherein the polynucleotides, the promoters, or the polynucleotides and the promoters are integrated in a transposition integration event, in a homologous recombination integration event, or in a transposition integration event and a homologous recombination integration event.

P50. The composition of embodiment P49, wherein the transposition integration event includes transposition of an operon comprising two or more of the polynucleotide subsequences, the promoters, or the polynucleotide subsequences and the promoters.

P51. The composition of embodiment P49, wherein the homologous recombination integration event includes homologous recombination of an operon comprising two or more of the polynucleotide subsequences, the promoters, or the polynucleotide subsequences and the promoters.

Q1. A method, comprising contacting an engineered yeast of any one of embodiments P1 to P51 with a feedstock that contains one or more hexose sugars and one or more pentose sugars under conditions in which the microbe synthesizes ethanol.

Q2. The method of embodiment Q1, wherein the engineered yeast synthesizes ethanol to about 85% to about 99% of theoretical yield.

Q3. The method of embodiment Q1 or Q2, comprising recovering ethanol synthesized by the engineered yeast.

Q4. The method of any one of embodiments Q1 to Q3, wherein the conditions are fermentation conditions.

R1. A composition comprising a nucleic acid comprising heterologous polynucleotides that encode a phosphogluconate dehydratase enzyme, a 2-keto-3-deoxygluconate-6-phosphate aldolase enzyme and a 6-phosphogluconolactonase enzyme.

R2. The composition of embodiment R1, wherein the yeast is a *Saccharomyces* spp. yeast.

R3. The composition of embodiment R2, wherein the yeast is a *Saccharomyces cerevisiae* yeast strain.

R3.1. The composition of any one of embodiments R1 to R3, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

R4. The composition of embodiment R3, wherein the *Escherichia* spp. microbe is an *Escherichia coli* strain.

R5. The composition of embodiment R3 or R4, wherein the *Pseudomonas* spp. microbe is a *Pseudomonas aeruginosa* strain.

R6. The composition of any one of embodiments R1 to R5, wherein the polynucleotide that encodes the phosphogluconate dehydratase enzyme is an EDD gene.

R7. The composition of any one of embodiments R1 to R5, wherein the polynucleotide that encodes the 2-keto-3-deoxygluconate-6-phosphate aldolase enzyme is an EDA gene.

R8. The composition of any one of embodiments R1 to R7, wherein the 6-phosphogluconolactonase enzyme is expressed from a SOL gene.

R9. The composition of embodiment R8, wherein the SOL gene is a SOL3 gene.

R10. The composition of any one of embodiments R1 to R9, wherein the nucleic acid includes a polynucleotide that encodes a glucose-6-phosphate dehydrogenase enzyme.

R11. The composition of embodiment R10, wherein the polynucleotide that encodes the glucose-6-phosphate dehydrogenase enzyme is from a yeast.

R12. The composition of embodiment R11, wherein the yeast is a *Saccharomyces* spp. yeast.

R13. The composition of embodiment R12, wherein the yeast is a *Saccharomyces cerevisiae* strain.

R14. The composition of any one of embodiments R10 to R13, wherein the nucleic acid includes a polynucleotide that encode an endogenous glucose-6-phosphate dehydrogenase enzyme.

R15. The composition of any one of embodiments R10 to R14, wherein the glucose-6-phosphate dehydrogenase enzyme is expressed from a ZWF gene.

R16. The composition of embodiment R15, wherein the ZWF gene is a ZWF1 gene.

R17. The composition of any one of embodiments R1 to R16, wherein the nucleic acid includes one or more promoters operable in a yeast, wherein the promoter is in operable connection with one or more of the polynucleotides.

R18. The composition of embodiment R17, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

R19. The composition of any one of embodiments R1 to R18, wherein the nucleic acid includes one or more polynucleotides that homologously combine in a gene of a host that encodes a phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

R20. The composition of embodiment R19, wherein the transketolase enzyme is encoded by a TKL-1 coding sequence or a TKL-2 coding sequence.

R21. The composition of embodiment R19, wherein the transaldolase is encoded by a TAL-1 coding sequence.

R22. The composition of embodiment R19, wherein the phosphofructokinase (PFK) enzyme is a PFK-2 enzyme or PFK-1 enzyme.

R23. The composition of embodiment R19, wherein the 6-phosphogluconate dehydrogenase (decarboxylating) enzyme is encoded by a GND-1 gene or a GND-2 gene.

R24. The composition of embodiment R19, wherein the PGI is encoded by a PGI-1 gene.

R25. The composition of any one of embodiments R1 to R24, wherein the nucleic acid is one or two separate nucleic acid molecules.

R26. The composition of embodiment R25, wherein each nucleic acid molecule includes one or two or more of the polynucleotide subsequences, one or two or more of the promoters, or one or two or more of the polynucleotide subsequences and one or two or more of the promoters.

R27. The composition of embodiment R25 or R26, wherein each of the one or two nucleic acid molecules are in circular form.

R28. The composition of embodiment R25 or R26, wherein each of the one or two nucleic acid molecules are in linear form.

R29. The composition of any one of embodiments R25 to R28, wherein each of the one or two nucleic acid molecules functions as an expression vector.

R30. The composition of any one of embodiments R25 to R29, wherein each of the one or two nucleic acid molecules includes flanking sequences for integrating the polynucleotides, the promoter sequences, or the polynucleotides and the promoter sequences in the nucleic acid into genomic DNA of a host organism.

S1. A composition comprising an engineered yeast that includes an alteration that adds or increases a phosphogluconate dehydratase activity, a 2-keto-3-deoxyglucose-6-phosphate aldolase activity and a 6-phosphogluconolactonase activity.

S2. The composition of embodiment S1, wherein the yeast is a *Saccharomyces* spp. yeast.

S3. The composition of embodiment S2, wherein the yeast is a *Saccharomyces cerevisiae* yeast strain.

S4. The composition of any one of embodiments S1 to S3 that includes heterologous polynucleotides that encode a phosphogluconate dehydratase enzyme, a 2-keto-3-deoxygluconate-6-phosphate aldolase enzyme and a 6-phosphogluconolactonase enzyme.

S5. The composition of embodiment S4, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

S6. The composition of embodiment S5, wherein the *Escherichia* spp. microbe is an *Escherichia coli* strain.

S7. The composition of embodiment S5, wherein the *Pseudomonas* spp. microbe is a *Pseudomonas aeruginosa* strain.

S8. The composition of any one of embodiments S4 to S7, wherein the polynucleotide that encodes the phosphogluconate dehydratase enzyme is an EDD gene.

S9. The composition of any one of embodiments S4 to S7, wherein the polynucleotide that encodes the 2-keto-3-deoxygluconate-6-phosphate aldolase enzyme is an EDA gene.

S10. The composition of any one of embodiments S4 to S9, wherein the 6-phosphogluconolactonase enzyme is expressed from a SOL gene.

S11. The composition of embodiment S10, wherein the SOL gene is a SOL3 gene.

S12. The composition of any one of embodiments S4 to S11, wherein a glucose-6-phosphate dehydrogenase activity is added or increased.

S13. The composition of embodiment S12, wherein the yeast comprises a heterologous polynucleotide that encodes a glucose-6-phosphate dehydrogenase enzyme, or wherein the yeast comprises multiple copies of an endogenous polynucleotide that encodes a glucose-6-phosphate dehydrogenase enzyme.

S14. The composition of embodiment S13, wherein the polynucleotide that encodes the glucose-6-phosphate dehydrogenase enzyme is from a yeast.

S15. The composition of embodiment S14, wherein the yeast is a *Saccharomyces* spp. yeast.

S16. The composition of embodiment S15, wherein the yeast is a *Saccharomyces cerevisiae* strain.

S17. The composition of any one of embodiments S13 to S17, wherein the glucose-6-phosphate dehydrogenase enzyme is expressed from a ZWF gene.

S18. The composition of embodiment S17, wherein the ZWF gene is a ZWF1 gene.

S19. The composition of any one of embodiments S1 to S18, wherein the nucleic acid includes one or more promoters operable in a yeast, wherein the promoter is in operable connection with one or more of the polynucleotides.

S20. The composition of embodiment S19, wherein the promoter is selected from promoters that regulate glucose phosphate dehydrogenase (GSD), translation elongation factor (TEF-1), phosphoglucokinase (SGK-1) and triose phosphate dehydrogenase (TDH-1).

S21. The composition of any one of embodiments S1 to S20, wherein the yeast includes a reduction in one or more of the following activities: phosphofructokinase (PFK) activity, phosphoglucoisomerase (PGI) activity, 6-phosphogluconate dehydrogenase (decarboxylating) activity, transketolase activity, transaldolase activity, or combination thereof.

S22. The composition of embodiment S21, wherein the yeast includes an alteration in one or more polynucleotides that inhibits production of one or more enzymes selected from the group consisting of phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

S23. The composition of embodiment S22, wherein the transketolase enzyme is encoded by a TKL-1 coding sequence or a TKL-2 coding sequence.

S24. The composition of embodiment S22, wherein the transaldolase is encoded by a TAL-1 coding sequence.

S25. The composition of embodiment S22, wherein the phosphofructokinase (PFK) enzyme is a PFK-2 enzyme or PFK-1 enzyme.

S26. The composition of embodiment S22, wherein the 6-phosphogluconate dehydrogenase (decarboxylating) enzyme is encoded by a GND-1 gene or GND-2 gene.

S27. The composition of embodiment S22, wherein the PGI is encoded by a PGI-1 gene.

S28. The composition of any one of embodiments S1 to S27, wherein the polynucleotides, the promoters, or the polynucleotides and the promoters are not integrated in the yeast nucleic acid.

S29. The composition of embodiment S28, wherein the polynucleotides, the promoters, or the polynucleotides and the promoters are in one or more plasmids.

S30. The composition of any one of embodiments S1 to S29, wherein the polynucleotide subsequences, the promoters, or the polynucleotide subsequences and the promoters are integrated in genomic DNA of the yeast.

S31. The composition of embodiment S30, wherein the polynucleotides, the promoters, or the polynucleotides and the promoters are integrated in a transposition integration event, in a homologous recombination integration event, or in a transposition integration event and a homologous recombination integration event.

S32. The composition of embodiment S31, wherein the transposition integration event includes transposition of an operon comprising two or more of the polynucleotide subsequences, the promoters, or the polynucleotide subsequences and the promoters.

S33. The composition of embodiment S31, wherein the homologous recombination integration event includes homologous recombination of an operon comprising two or more of the polynucleotide subsequences, the promoters, or the polynucleotide subsequences and the promoters.

T1. A method, comprising contacting an engineered yeast of any one of embodiments S1 to S33 with a feedstock that contains one or more hexose sugars under conditions in which the microbe synthesizes ethanol.

T2. The method of embodiment T1, wherein the engineered yeast synthesizes ethanol to about 85% to about 99% of theoretical yield.

T3. The method of embodiment T1 or T2, comprising recovering ethanol synthesized by the engineered yeast.

T4. The method of any one of embodiments T1 to T3, wherein the conditions are fermentation conditions.

U1. A composition comprising an engineered yeast that includes an alteration that adds or increases a xylose isomerase activity and a glucose transporter activity.

U2. The composition of embodiment U1, wherein the yeast is a *Saccharomyces* spp. yeast.

U3. The composition of embodiment U2, wherein the yeast is a *Saccharomyces cerevisiae* yeast strain.

U4. The composition of any one of embodiments U1 to U3 that includes heterologous polynucleotides that encode a xylose isomerase enzyme and a glucose transport enzyme.

U5. The composition of any one of embodiments U1 to U4, wherein the xylose isomerase enzyme is a chimeric enzyme.

U6. The composition of embodiment U5, wherein a first portion of the polynucleotide that encodes the chimeric xylose isomerase enzyme is from a first microbe and a second portion of the polynucleotide that encodes the chimeric xylose isomerase enzyme is from a second microbe.

U7. The composition of embodiment U5 or U6, wherein the first microbe, the second microbe, or the first microbe and the second microbe independently are selected from one or more of the group consisting of *Clostridiales* spp., *Ruminococcus* spp., *Thermus* spp., *Bacillus* spp., *Clostridium* spp., *Orpinomyces* spp., *Escherichia* spp. and *Piromyces* spp. microbes.

U8. The composition of embodiment U7, wherein the first microbe, the second microbe, or the first microbe and the second microbe independently are selected from one or more of the group consisting of *Clostridiales_genomosp.* BUAB3 str UUII9-5, *Ruminococcus flavefaciens, Ruminococcus*_FD1, *Ruminococcus*_18U13, *Thermus thermophilus, Bacillus stercoris, Clostridium cellulolyticum, Bacillus uniformis, Bacillus stearothermophilus, Bacteroides thetaiotaomicron, Clostridium thermohydrosulfuricum, Orpinomyces, Clostridium phytofermentans, Escherichia coli* and *Piromyces* strain E2.

U9. The composition of any one of embodiments U5 to U8, wherein 80% or more of the polynucleotide that encodes the xylose isomerase enzyme is from a *Ruminococcus* spp. microbe xylose isomerase-encoding sequence.

U10. The composition of embodiment U9, wherein all or a portion of the polynucleotide that encodes the xylose isomerase enzyme is from a *Ruminococcus* spp. microbe xylose isomerase-encoding sequence.

U11. The composition of embodiment U10, wherein the *Ruminococcus* spp. microbe is a *Ruminococcus flavefaciens* strain.

U12. The composition of any one of embodiments U5 to U12, wherein the polynucleotide that encodes the xylose isomerase enzyme is chimeric and includes a sequence that encodes a xylose isomerase from another microbe.

U13. The composition of any one of embodiments U5 to U12, wherein the portion of the polynucleotide from the *Ruminococcus* spp. microbe xylose isomerase is 3' with respect to the portion of the polynucleotide from another microbe.

U14. The composition of embodiment U12 or U13, wherein the other microbe is a fungus.

U15. The composition of embodiment U14, wherein the fungus is an anaerobic fungus.

U16. The composition of embodiment U15, wherein the fungus is a *Piromyces* spp. fungus.

U17. The composition of embodiment U16, wherein the *Piromyces* spp. fungus is a *Piromyces* strain E2.

U18. The composition of any one of embodiments U4 to U17, wherein the polynucleotide that encodes the one or more glucose transporters is from a yeast.

U19. The composition of embodiment U18, wherein the one or more glucose transporters is encoded by a one or more of a GAL2, GSX1 and GXF1 gene.

U20. The composition of any one of embodiments U1 to U19, wherein the yeast includes one or more added activities or increased activities selected from the group consisting of transketolase activity, transaldolase activity, or a transketolase activity and transaldolase activity.

U21. The composition of embodiment U20, wherein the yeast includes one or more heterologous polynucleotides that encodes one or more of the following enzymes, or includes multiple copies of polynucleotides that encode one or more of the following enzymes: transketolase enzyme, transaldolase enzyme, or a transketolase enzyme and transaldolase enzyme U22. The composition of embodiment U21, wherein the transketolase enzyme is encoded by a TKL1 coding sequence or a TKL2 coding sequence.

U23. The composition of embodiment U21, wherein the transaldolase is encoded by a TAL coding sequence.

U24. The composition of any one of embodiments U21 to U23, wherein the transketolase enzyme or the transaldolase enzyme is from a yeast.

U25. The composition of any one of embodiments U1 to U24, wherein the nucleic acid includes one or more promoters operable in a yeast, wherein the promoter is in operable connection with one or more of the polynucleotides.

U26. The composition of embodiment U25, wherein the promoter is selected from promoters that regulate glucose phosphate dehydrogenase (GUD), translation elongation factor (TEF-1), phosphoglucokinase (UGK-1) and triose phosphate dehydrogenase (TDH-1).

U27. The composition of any one of embodiments U1 to U26, wherein the polynucleotides, the promoters, or the polynucleotides and the promoters are not integrated in the yeast nucleic acid.

U28. The composition of embodiment U27, wherein the polynucleotides, the promoters, or the polynucleotides and the promoters are in one or more plasmids.

U29. The composition of any one of embodiments U1 to U28, wherein the polynucleotide subsequences, the promoters, or the polynucleotide subsequences and the promoters are integrated in genomic DNA of the yeast.

U30. The composition of embodiment U29, wherein the polynucleotides, the promoters, or the polynucleotides and the promoters are integrated in a transposition integration event, in a homologous recombination integration event, or in a transposition integration event and a homologous recombination integration event.

U31. The composition of embodiment U30, wherein the transposition integration event includes transposition of an operon comprising two or more of the polynucleotide subsequences, the promoters, or the polynucleotide subsequences and the promoters.

U32. The composition of embodiment U30, wherein the homologous recombination integration event includes homologous recombination of an operon comprising two or more of the polynucleotide subsequences, the promoters, or the polynucleotide subsequences and the promoters.

V1. A method, comprising contacting an engineered yeast of any one of embodiments U1 to U32 with a feedstock that contains one or more pentose sugars under conditions in which the microbe synthesizes ethanol.

V2. The method of embodiment V1, wherein the engineered yeast synthesizes ethanol to about 85% to about 99% of theoretical yield.

V3. The method of embodiment V1 or V2, comprising recovering ethanol synthesized by the engineered yeast.

W1. A composition comprising a synthetic nucleic acid that includes a polynucleotide selected from the group of twenty (20) polynucleotides (SEQ ID NOS 513-531, respectively, in order of appearance) consisting of:

```
CACGCACGGACCGACCGTCACCGGACCGTTTCGCGCGACGTGCGCGAGG
CTCCGACACGAAAGACGGGCCCCCTATTGCGCTCATGTCGGCCGCACCC
CTGCGTAAAGTCAGATACGTGCGCCACCCGAGCCGGGACCGCCCTGAGC
GCATGGTCCGGGCGGCGTGGCAAGCGCAGGAGGGCGTGCCCCGTTCGCT
AGGCA

ACGTATGTCGGCTGATCGTACACGCCGACCAGCGCAGTCGGCGTACTCA
GGCGTTCCGAGTAGCTCACATCTGTGGGCCCCGGCGTACCTTCGGCAGG
GTTATGCGACGGGGCGGCAGGCTTGCGCTGGCGTCGGGAATCACCGCGA
ACTTGACCCGCGCCGGTTCCGTATCGGTCCGCTGCGGCCGTGCTCCGCA
GTCGA

TGCAGTCCGCCCAGCCGGCCGTGTAGCACGGCCGACTGCAGGTGCGACG
TGCTAGGGGCCAGCACGCGAGCGGCCCTACCACGGGTCGTGTGGGCGC
ATGACCGCCGGCCGGGTCTCGGCACGGGGCGACGCGGTGCTCCTAGGCT
AGCAGGGCCTCACCGGGTGATCCCCCGTGTAGCGCCGCACAACACCCCC
TGCGA

TGCCCGCATACCGCCCGCCCACTGGGGATCCTCCGGCGCTGTCGCGCTA
TGCGCGTCCATCCTGGTCGGACGGGCTCGGGCCCCGGACCAAACCGCAG
CGGCCCCTGGCAGCGACTAAGGGCGCCGTCTCACCCTAGACTTCTTAAT
```

-continued

CGGGGTGTCCCGGTAGGCCGGGAGTAGCCTCGGCGGGCTAGCCGCGTGA
CTATA

GCGGGTTAGTCCCCGTCGGACGTCATGCATACAGTCGGGGCTGGCGAGA
CAGGAGGCTACAGGGGGCGCCCGGAGGAACACACGTGGGACTAAGACGT
CGGTCCGTGTGCCCCCGAACCGGCGTGCTCATCGTAGGACTGGGAAGTC
CGTACCGCGTGGCTCGTACCTCGCGGTCTGAGTCCGACACCCGCTGACG
CCGGA

CTGAGACGACTCCCGCACTACGGATCGCGAGCGTAGACTCAGCCCGGAC
TCTCACGCGACCTCGGACGCGGCCTAATGTCTCGACTCGCGGTCCGCTG
AAGGTCTCGGGGCACGCGAGACGCGGGGTCAGGCCGGGGGGATCCCCGC
ACACACTCAGTCGCGGCGAACGGAGTCCCGTGGCCTGGCTAGGGATCGT
GGGTA

GGGGCGTCCACTCTGGCTCGGTAGAGCGCTGGGCTCCGCGCGACTGCGC
GCACCCATCGGTTTGGCGCGACGCACCGTGGACTCCTGGGCTAGAGGGC
GGGTCCCCGCCATACCCCGTTCTCGTGCCGGCTGGGTAGGACCGGAGTG
ACGGCTGTGGCCGGCGACTCGGGCGCGCACTGTAGTCGGATCTGGGCGG
GCAGA

GTCGGGCGCGCGTCAGTCCACGCGTTAAACACTGGCCGACGACACGACG
GGATCCGGGCACGCCCCGAGAGCGCGTGTTCGCGCGAGTCGATCGGGAG
GCCGCAGCGTGTCGAGCCCAGACCCCGCTCTAGCGTGGCCATCGCGGTG
CTAAGTGGGGCGGCCGGGTCCTATACACGCTTACCGATAGTCAAGTTTG
CGTGA

GTCTTAGGGCCCAGGGACCGCACGGGTCGACCGCGCGACTGGTCGGAGC
TTGCGCGTCTACGCCACTCGGCGGCCCCGACGGGGATGCCGCGGAATG
TCCGCCGGCGTATGCGGCTCAAGCCGGACCGTCGGACTGCGAAGCGCCG
TGAGCACCCCTCGACCTGACCGGACGCGGCGCACCCGTCCGAGTATCGT
CGCGA

TCGGGTCTCGCCCGGCGCTAGTCCAGCCGTAGCGCTCTCCGGCGATCAC
CCCGGAGCACTCTGGAGCCGAGCGGTCGGGTCTGTTGGGCGCGCCGCGG
CTACGGACGGCTCGACTCACTGGCGCTCGACCCCGTATCCCCGTCTCG
GACGACGCACCGTTGCGCGGGAACGATCGGCGGCGCTCACACGCACGAT
CGGAA

CTTAAGGCTGGCGCACCATGAGGGCCGCGCCACGTCCGACCCGCAGCCC
GCGCGTAGTAGCCTAGCCGGGCGGGGTTCCTCCCGTGCGTCACCTAGCA
CGGGGCCTGGCACCGAACGCGAGCCCGTCCGGTCACCGCGGCGGGTCTG
CGGACGTCCCCGGTCGCTCGGCTCGGAGTCCCCGCTGGGGATCGCGTCG
GGACA

CGACGGCGTAGCACTCGCGGACCTAGGGCGCGCGAGTCGGGGGAGCCCG
CGGTGCGACGCTCGGGGAGGAGCTCGCATGCCCAAGGCACGATCTAGGG
GGGGGTACGGGGGGCGTCCGTCCGAGCGCCGGGACTGCGATCCGGGGCC
ACATGCTAACCGGCGGAAGGGGGGACCTAACCGGTGTGGACTCCGGGTA
ATCCA

CGGGGGGCTGACACGTCTCGGATCGCCCCGTCAGTCAGCCCCCTAGTCC
CGGACAGGACGTCGGAGGTCGAGTCCGCACTGTCGGGCCTGCTCGTGGG
CACGGCAGGACGCGTCCCCATGGTCAGCCGCCGTGCGATACCTCGCCAC
GACTCTGAGCCGGGCGCGAGCGTGAGAGCCCGAGCCGCGGTACACGGGG
CGTCA

GCGAGCTCGCTCTCGACTCCGGGCTCCCGTGCTGACACGGGGTGCGACC
CCGCGGCGATTGTCCGCACGCCTGTCGGACGACGTCGGCCCGTCGTAGT
GCCGGTCAGAGGCAGGGGGGCTGCTCGCGCTGGCCGCCTCGTCGCGCGT
GGACCCTATGGGGGATCACGCGTGGGGTCGGGATCGGGACCGCGCGAC
TTGGA

CGCGCCCCGTAACGGACGCGGTGAGTCGAGCTTACGCGGCTAGGGCCGA
GTCGTGTTAGCGTCTCGCGTAAGCGAATGCCACGTCCCCCGCCGCCCGT
CGCGCAGCTGGCTACGCAACGCCTCCGCGGCCTCCGTAGCGAGTGCGTG
GGACGCTGGCCGTCCGCGTGTTCCGGGACCTGGATGCGGGAGGGACCTA
AGGCA

AGAACGTGCGGTCGTCCCCACGCACGGGATGACGGACGGGGTAGACGGG
CGTCGTGCGCGGGTAGCGTAACCGGTTACAGTCCCCGCAACGCTCTA
GCTCCGGCCCTCGCTTAGGAGTTCGCGGCCGAGACATGAGGTGGTCCGG
ACGGCAGGGGGTCGCGGAGACCGTGGAGCCGATTCTGCCGGACGCCACG
TCCCA

CGGGACGCCCCGTACCGTGTACGAAGCCCCGGTCGGTCGCGGATCGTA
GATCCCGGAGCCGACGCCTTGAACCCGGCTTTCCCAGCGACTCGCGCCC
CCACTGGGTCCCTCGGGACCCCGCTCCCCCCAGACGCATACAGCCCGCA
AGCGGGGGCAGTCTCGGACCGCCCGGACACTGGCCTTAGGCACCGTGGG
CTCGA

-continued

GTGTCCGGGGCGCATCGGAGCTGTCCGACCGAGTTCCGGGGACGGCGCA
CGTTGTGCCGGCCTCAGACGGAGCCTGTAGCCCCCGGACAGTGTGTGCC
CGCCCACTACGGGTTAGGCACGGGGTTGGTCGGCACGCGTCCTCCGCGT
GTCACGGACCGATGCAGACCGCTGGCCGGGAGGTCGCCCCCCCAGGGGT
GCACA

CGCGCAGCACGCACGTCCGGGGCACGCGCGGCTCGGAGGGTCCGGGCTG
GGACGGGAGGTTTGGAGTCGCGTGCGCGTAGCAGCGCACCCGCCTGGTC
GCCGGGTCTAGTAGGGCTGGGTTACGGAGGACGTGCAGGCGACCCCAAC
CGTTGACGACGGGTCCGACCACGCCTTTAGCCGTGGCGTGTCCGTCGCG
AGCCA

W2. A microorganism comprising a polynucleotide that includes a sequence selected from the group of twenty (20) sequences (SEQ ID NOS 513-531, respectively, in order of appearance) consisting of CACGCACGGACCGACCGTCACCGGACCGTTTCGCGCGACGTGCGCGAGG
CTCCGACACGAAAGACGGGCCCCCTATTGCGCTCATGTCGGCCGCACCC
CTGCGTAAAGTCAGATACGTGCGCCACCCGAGCCGGGACCGCCCTGAGC
GCATGGTCCGGGCGGCGTGGCAAGCGCAGGAGGGCGTGCCCCGTTCGCT
AGGCA ACGTATGTCGGCTGATCGTACACGCCGACCAGCGCAGTCGGCGTACTCA
GGCGTTCCGAGTAGCTCACATCTGTGGGCCCCGGCGTACCTTCGGCAGG
GTTATGCGACGGGGCGGCAGGCTTGCGCTGGCGTCGGGAATCACCGCGA
ACTTGACCCGCGCCGGTTCCGTATCGGTCCGCTGCGGCCGTGCTCCGCA
GTCGA TGCAGTCCGCCCAGCCGGCCGTGTAGCACGGCCGACTGCAGGTGCGACGT
GCTAGGGGCCAGCACGCGAGCGGCCCTACCACGGGTCGTGTGGGGCGCAT
GACCGCCGGCCGGGTCTCGGCACGGGGCGACGCGGTGCTCCTAGGCTAGC
AGGGCCTCACCGGGTGATCCCCGTGTAGCGCCGCACAACACCCCCTGCGA TGCCCGCATACCGCCCGCCCACTGGGGATCCTCCGGCGCTGTCGCGCTAT
GCGCGTCCATCCTGGTCGGACGGGCTCGGGCCCCGGACCAAACCGCAGCG
GCCCCTGGCAGCGACTAAGGGCGCCGTCTCACCCTAGACTTCTTAATCGG
GGGTGTCCCGGTAGGCCGGGAGTAGCCTCGGCGGCTAGCCGCGTGACTATA GCGGGTTAGTCCCCGTCGGACGTCATGCATACAGTCGGGGCTGGCGAGAC
AGGAGGCTACAGGGGGCGCCCGGAGGAACACACGTGGGACTAAGACGTCG
GTCCGTGTGCCCCGAACCGGCGTGCTCATCGTAGGACTGGGAAGTCCGT
ACCGCGTGGCTCGTACCTCGCGGTCTGAGTCCGACACCCGCTGACGCCGGA CTGAGACGACTCCCGCACTACGGATCGCGAGCGTAGACTCAGCCCGGACT
CTCACGCGACCTCGGACGCGGCCTAATGTCTCGACTCGCGGTCCGCTGAA
GGTCTCGGGGCACGCGAGACGCGGGGTCAGGCCGGGGGGATCCCCGCACA
CACTCAGTCGCGGCGAACGGAGTCCCGTGGCCTGGCTAGGGATCGTGGGTA GGGGCGTCCACTCTGGCTCGGTAGAGCGCTGGGCTCCGCGCGACTGCGCG
CACCCATCGGTTTGGCGCGACGCACCGTGGACTCCTGGGCTAGAGGGCGG
TCCCCGCCATACCCCGTTCTCGTGCCGGCTGGGTAGGACCGGAGTGACG
GCTGTGGCCGGCGACTCGGGCGCGCACTGTAGTCGGATCTGGGCGGGCAGA GTCGGGCGCGCGTCAGTCCACGCGTTAAACACTGGCCGACGACACGACGG
ATCCGGGCACGCCCCGAGAGCGCGTGTTCGCGCGAGTCGATCGGGAGGC
CGCAGCGTGTCGAGCCCAGACCCCGCTCTAGCGTGGCCATCGCGGTCTA
AGTGGGGCGGCCGGGTCCTATACACGCTTACCGATAGTCAAGTTTGCGTGA GTCTTAGGGCCCAGGGACCGCACGGGTCGACCGCGCGACTGGTCGGAGCT
TGCGCGTCTACGCCACTCGGCGGCCCCGACGGGGATGCCGCGGAATGTC
CGCCGGCGTATGCGGCTCAAGCCGGACCGTCGGACTGCGAAGCGCCGTGA
GCACCCCTCGACCTGACCGGACGCGGCGCACCCGTCCGAGTATCGTCGCGA TCGGGTCTCGCCCGGCGCTAGTCCAGCCGTAGCGCTCTCCGGCGATCACC
CCGGAGCACTCTGGAGCCGAGCGGTCGGGTCTGTTGGGCGCGCCGCGGCT
GACGGACGGCTCGACTCACTGGCCTCGACCCCGTATCCCCGTCTCGGAC
GACGCACCGTTGCGCGGGAACGATCGGCGGCGCTCACACGCACGATCGGAA CTTAAGGCTGGCGCACCATGAGGGCCGCGCCACGTCCGACCCGCAGCCG
CGCGTAGTAGCCTAGCCGGGCGGGTTCCTCCCGTGCGTCACCTAGCACG
GGGCCTGGCACCGAACGCGAGCCCGTCCGGTCACCGCGGCGGGTCTGCGG
GACGTCCCCGGTCGCTCGGCTCGGAGTCCCCGCTGGGGATCGCGTCGGGACA CGACGGCGTAGCACTCGCGGACCTAGGGCGCGCGAGTCGGGGGAGCCCGC
GGTGCGACGCTCGGGGAGGAGCTCGCATGCCCAAGGCACGATCTAGGGGG
GGGTACGGGGGCGTCCGTCCGAGCGCCGGGACTGCGATCCGGGGCCACA
TTGCTAACCGGCGGAAGGGGGGACCTAACCGGTGTGGACTCCGGGTAATCCA

```
CGGGGGGCTGACACGTCTCGGATCGCCCCGTCAGTCAGCCCCCTAGTCCC
GGACAGGACGTCGGAGGTCGAGTCCGCACTGTCGGGCCTGCTCGTGGGCA
CGGCAGGACGCGTCCCCATGGTCAGCCGCCGTGCGATACCTCGCCACGAC
TCTGAGCCGGGCGCGAGCGTGAGAGCCCGAGCCGCGGTACACGGGGCGTCA

GCGAGCTCGCTCTCGACTCCGGGCTCCCGTGCTGACACGGGGTGCGACCC
CGCGGCGATTGTCCGCACGCCTGTCGGACGACGTCGGCCCGTCGTAGTGC
CGGTCAGAGGCAGGGGGGCTGCTCGCGCTGGCCGCCTCGTCGCGCGTGGA
CCCTATGGGGGATCACGCGTGGGGTCGGGATCGGGGACCGCGCGACTTGGA

CGCGCCCCGTAACGGACGCGGTGAGTCGAGCTTACGCGGCTAGGGCCGAG
TCGTGTTAGCGTCTCGCGTAAGCGAATGCCACGTCCCCCGCCGCCCGTCG
CGCAGCTGGCTACGCAACGCCTCCGCGGCCTCCGTAGCGAGTGCGTGGGA
CGCTGGCCGTCCGCGTGTTCCGGGACCTGGATGCGGGAGGGACCTAAGGCA

AGAACGTGCGGTCGTCCCCACGCACGGGATGACGGACGGGGTAGACGGGC
GTCGTGCGCGCGGGTAGCGTAACCGGTTACAGTCCCCGCAACGCTCTAGC
TCCGGCCCTCGCTTAGGAGTTCGCGGCCGAGACATGAGGTGGTCCGGACG
GCAGGGGGTCGCGGAGACCGTGGAGCCGATTCTGCCGGACGCCACGTCCCA

CGGGACGCCCCGTACCGTGTACGAAGCCCCGGTCGGTCGGCGGATCGTAG
ATCCCGGAGCCGACGCCTTGAACCCGGCTTTCCCAGCGACTCGCGCCCCC
ACTGGGTCCCTCGGGACCCCGCTCCCCCCAGACGCATACAGCCCGCAAGC
GGGGGCAGTCTCGGACCGCCCGGACACTGGCCTTAGGCACCGTGGGCTCGA

GTGTCCGGGGCGCATCGGAGCTGTCCGACCGAGTTCCGGGGACGGCGCAC
GTTGTGCCGGCCTCAGACGGAGCCTGTAGCCCCCGGACAGTGTGTGCCCG
CCCACTACGGGTTAGGCACGGGGTTGGTCGGCACGCGTCCTCCGCGTGTC
ACGGACCGATGCAGACCGCTGGCCGGGAGGTCGCCCCCCCAGGGGTGCACA

CGCGCAGCACGCACGTCCGGGGCACGCGCGGCTCGGAGGGTCCGGGCTGG
GACGGGAGGTTTGGAGTCGCGTGCGCGTAGCAGCGCACCCGCCTGGTCGC
CGGGTCTAGTAGGGCTGGGTTACGGAGGACGTGCAGGCGACCCCAACCGT
TGACGACGGGTCCGACCACGCCTTTAGCCGTGGCGTGTCCGTCGCGAGCCA
```

W3. A method comprising detecting the presence or absence of a nucleotide sequence identification tag in a microorganism, wherein the nucleotide sequence is selected from the group of twenty (20) nucleotide sequences (SEQ ID NOS 513-531, respectively, in order of appearance) consisting of

```
CACGCACGGACCGACCGTCACCGGACCGTTTCGCGCGACGTGCGCGAGGCT
CCGACACGAAAGACGGGCCCCCTATTGCGCTCATGTCGGCCGCACCCCTGC
GTAAAGTCAGATACGTGCGCCACCCGAGCCGGGACCGCCCTGAGCGCATGG
TCCGGGCGGCGTGGCAAGCGCAGGAGGGCGTGCCCCGTTCGCTAGGCA

ACGTATGTCGGCTGATCGTACACGCCGACCAGCGCAGTCGGCGTACTCAGG
CGTTCCGAGTAGCTCACATCTGTGGGCCCCGGCGTACCTTCGGCAGGGTTA
TGCGACGGGCGGCAGGCTTGCGCTGGCGTCGGGAATCACCGCGAACTTGA
CCCGCGCCGGTTCCGTATCGGTCCGCTGCGGCCGTGCTCCGCAGTCGA

TGCAGTCCGCCCAGCCGGCCGTGTAGCACGGCCGACTGCAGGTGCGACGTG
CTAGGGGCCAGCACGCGAGCGGCCCTACCACGGGTCGTGTGGGGCGCATGA
CCGCCGGCCGGGTCTCGGCACGGGGCGACGCGGTGCTCCTAGGCTAGCAGG
GCCTCACCGGGTGATCCCCCGTGTAGCGCCGCACAACACCCCCTGCGA

TGCCCGCATACCGCCCGCCCACTGGGGATCCTCCGGCGCTGTCGCGCTATG
CGCGTCCATCCTGGTCGGACGGGCTCGGGCCCCGGACCAAACCGCAGCGGC
CCCTGGCAGCGACTAAGGGCGCCGTCTCACCCTAGACTTCTTAATCGGGGT
GTCCCGGTAGGCCGGGAGTAGCCTCGGCGGGCTAGCCGCGTGACTATA

GCGGGTTAGTCCCCGTCGGACGTCATGCATACAGTCGGGGCTGGCGAGACA
GGAGGCTACAGGGGGCGCCCGGAGGAACACACGTGGGACTAAGACGTCGGT
CCGTGTGCCCCCGAACCGGCGTGCTCATCGTAGGACTGGGAAGTCCGTACC
GCGTGGCTCGTACCTCGCGGTCTGAGTCCGACACCCGCTGACGCCGGA

CTGAGACGACTCCCGCACTACGGATCGCGAGCGTAGACTCAGCCCGGACTC
TCACGCGACCTCGGACGCGGCCTAATGTCTCGACTCGCGGTCCGCTGAAGG
TCTCGGGGCACGCGAGACGCGGGGTCAGGCCGGGGGGATCCCCGCACACAC
TCAGTCGCGGCGAACGGAGTCCCGTGGCCTGGCTAGGGATCGTGGGTA

GGGGCGTCCACTCTGGCTCGGTAGAGCGCTGGGCTCCGCGCGACTGCGCGC
ACCCATCGGTTTGGCGCGACGCACCGTGGACTCCTGGGCTAGAGGGCGGGT
CCCCGCCATACCCCGTTCTCGTGCCGGCTGGGTAGGACCGGAGTGACGGCT
GTGGCCGGCGACTCGGGCGCGCACTGTAGTCGGATCTGGGCGGGCAGA
```

```
GTCGGGCGCGCGTCAGTCCACGCGTTAAACACTGGCCGACGACACGACGGG
ATCCGGGCACGCCCCGAGAGCGCGTGTTCGCGCGAGTCGATCGGGAGGCCG
CACGCGTGTCGAGCCCAGACCCGCTCTAGCGTGGCCATCGCGGTGCTAAG
TGGGGCGGCCGGGTCCTATACACGCTTACCGATAGTCAAGTTTGCGTGA

GTCTTAGGGCCCAGGGACCGCACGGGTCGACCGCGCGACTGGTCGGAGCTT
GCGCGTCTACGCCACTCGGCGGCCCCGACGGGGGATGCCGCGGAATGTCCG
CCGGCGTATGCGGCTCAAGCCGGACCGTCGGACTGCGAAGCGCCGTGAGCA
CCCCTCGACCTGACCGGACGCGGCGCACCCGTCCGAGTATCGTCGCGA

TCGGGTCTCGCCCGGCGCTAGTCCAGCCGTAGCGCTCTCCGGCGATCACCC
CGGAGCACTCTGGAGCCGAGCGGTCGGGTCTGTTGGGCGCGCCGCGGCTAC
AGGCGGCTCGACTCACTGGCGCTCGACCCCGTATCCCCCGTCTCGGACGAC
GCACCGTTGCGCGGGAACGATCGGCGGCGCTCACACGCACGATCGGAA

CTTAAGGCTGGCGCACCATGAGGGCCGCGCCACGTCCGACCCGCAGCCCGC
GCGTAGTAGCCTAGCCGGGCGGGGTTCCTCCCGTGCGTCACCTAGCACGGG
GCCTGGCACCGAACGCGAGCCCGTCCGGTCACCGCGGCGGGTCTGCGGACG
TCCCCGGTCGCTCGGCTCGGAGTCCCCGCTGGGGATCGCGTCGGGACA

CGACGGCGTAGCACTCGCGGACCTAGGGCGCGCGAGTCGGGGGAGCCCGCG
GTGCGACGCTCGGGGAGGAGCTCGCATGCCCAAGGCACGATCTAGGGGGGG
GTACGGGGGCGTCCGTCCGAGCGCCGGGACTGCGATCCGGGGCCACATGC
TAACCGGCGGAAGGGGGGACCTAACCGGTGTGGACTCCGGGTAATCCA

CGGGGGGCTGACACGTCTCGGATCGCCCCGTCAGTCAGCCCCCTAGTCCCG
GACAGGACGTCGGAGGTCGAGTCCGCACTGTCGGGCCTGCTCGTGGGCACG
GCAGGACGCGTCCCCATGGTCAGCCGCCGTGCGATACCTCGCCACGACTCT
GAGCCGGGCGCGAGCGTGAGAGCCCGAGCCGCGGTACACGGGGCGTCA

GCGAGCTCGCTCTCGACTCCGGGCTCCCGTGCTGACACGGGGTGCGACCCC
GCGGCGATTGTCCGCACGCCTGTCGGACGACGTCGGCCCGTCGTAGTGCCG
GTCAGAGGCAGGGGGGCTGCTCGCGCTGGCCGCCTCGTCGCGCGTGGACCC
TATGGGGGATCACGCGTGGGGTCGGGATCGGGGACCGCGCGACTTGGA

CGCGCCCCGTAACGGACGCGGTGAGTCGAGCTTACGCGGCTAGGGCCGAGT
GCTGTTAGCGTCTCGCGTAAGCGAATGCCACGTCCCCCGCCGCCCGTCGCG
CAGCTGGCTACGCAACGCCTCCGCGGCCTCCGTAGCGAGTGCGTGGGACGC
TGGCCGTCCGCGTGTTCCGGGACCTGGATGCGGGAGGGACCTAAGGCA

AGAACGTGCGGTCGTCCCCACGCACGGGATGACGGACGGGGTAGACGGGCG
TCGTGCGCGCGGGTAGCGTAACCGGTTACAGTCCCCGCAACGCTCTAGCTC
CGGCCCTCGCTTAGGAGTTCGCGGCCGAGACATGAGGTGGTCCGGACGGCA
GGGGTCGCGGAGACCGTGGAGCCGATTCTGCCGGACGCCACGTCCCA

CGGGACGCCCCGTACCGTGTACGAAGCCCCGGTCGGTCGGCGGATCGTAGA
TCCCGGAGCCGACGCCTTGAACCCGGCTTTCCCAGCGACTCGCGCCCCAC
TGGGTCCCTCGGGACCCCGCTCCCCCCAGACGCATACAGCCCGCAAGCGGG
GGCAGTCTCGGACCGCCCGGACACTGGCCTTAGGCACCGTGGGCTCGA

GTGTCCGGGGCGCATCGGAGCTGTCCGACCGAGTTCCGGGGACGGCGCACG
TTGTGCCGGCCTCAGACGGAGCCTGTAGCCCCCGGACAGTGTGTGCCCGCC
ACTACGGGTTAGGCACGGGGTTGGTCGGCACGCGTCCTCCGCGTGTCACG
GACCGATGCAGACCGCTGGCCGGGAGGTCGCCCCCCCAGGGGTGCACA

CGCGCAGCACGCACGTCCGGGGCACGCGCGGCTCGGAGGGTCCGGGCTGGG
ACGGGAGGTTTGGAGTCGCGTGCGCGTAGCAGCGCACCCGCCTGGTCGCCG
GGTCTAGTAGGGCTGGGTTACGGAGGACGTGCAGGCGACCCCAACCGTTGA
CGACGGGTCCGACCACGCCTTTAGCCGTGGCGTGTCCGTCGCGAGCCA
```

W4. The method of embodiment W3, wherein the microorganism includes two or more different identification tags.

W5. The method of embodiment W3, wherein the microorganism includes multiple copies of one or more of the identification tags.

X1. A composition comprising a nucleic acid comprising heterologous polynucleotides that encode a phosphogluconate dehydratase enzyme and a 2-keto-3-deoxygluconate-6-phosphate aldolase enzyme, and one or more polynucleotides that homologously combine in a gene of a host that encodes a 6-phosphogluconate dehydrogenase (decarboxylating) enzyme.

X2. The composition of embodiment X1, wherein the yeast is a *Saccharomyces* spp. yeast.

X3. The composition of embodiment X2, wherein the yeast is a *Saccharomyces cerevisiae* yeast strain.

X3.1. The composition of any one of embodiments X1 to X3, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

X4. The composition of embodiment X3, wherein the *Escherichia* spp. microbe is an *Escherichia coli* strain.

X5. The composition of embodiment X3 or X4, wherein the *Pseudomonas* spp. microbe is a *Pseudomonas aeruginosa* strain.

X6. The composition of any one of embodiments X1 to X5, wherein the polynucleotide that encodes the phosphogluconate dehydratase enzyme is an EDD gene.

X7. The composition of any one of embodiments X1 to X5, wherein the polynucleotide that encodes the 2-keto-3-deoxygluconate-6-phosphate aldolase enzyme is an EDA gene.

X8. The composition of any one of embodiments X1 to X7, wherein the nucleic acid includes a polynucleotide that encodes a 6-phosphogluconolactonase enzyme.

X8.1. The composition of embodiment X8, wherein the polynucleotide that encodes the 6-phosphogluconolactonase enzyme is from a yeast.

X8.2. The composition of embodiment X8.1, wherein the yeast is a *Saccharomyces* spp. yeast.

X8.3. The composition of embodiment X8.2, wherein the yeast is a *Saccharomyces cerevisiae* strain.

X8.4. The composition of any one of embodiments X8 to X8.3, wherein the 6-phosphogluconolactonase enzyme is expressed from a SOL gene.

X9. The composition of embodiment X8.4, wherein the SOL gene is a SOL3 gene.

X10. The composition of any one of embodiments X1 to X9, wherein the nucleic acid includes a polynucleotide that encodes a glucose-6-phosphate dehydrogenase enzyme.

X11. The composition of embodiment X10, wherein the polynucleotide that encodes the glucose-6-phosphate dehydrogenase enzyme is from a yeast.

X12. The composition of embodiment X11, wherein the yeast is a *Saccharomyces* spp. yeast.

X13. The composition of embodiment X12, wherein the yeast is a *Saccharomyces cerevisiae* strain.

X14. The composition of any one of embodiments X10 to X13, wherein the nucleic acid includes a polynucleotide that encode an endogenous glucose-6-phosphate dehydrogenase enzyme.

X15. The composition of any one of embodiments X10 to X14, wherein the glucose-6-phosphate dehydrogenase enzyme is expressed from a ZWF gene.

X16. The composition of embodiment X15, wherein the ZWF gene is a ZWF1 gene.

X17. The composition of any one of embodiments X1 to X16, wherein the nucleic acid includes one or more promoters operable in a yeast, wherein the promoter is in operable connection with one or more of the polynucleotides.

X18. The composition of embodiment X17, wherein the promoter is selected from promoters that regulate glucose phosphate dehydrogenase (GPD), translation elongation factor (TEF-1), phosphoglucokinase (PGK-1) and triose phosphate dehydrogenase (TDH-1).

X19. The composition of any one of embodiments X1 to X18, wherein the nucleic acid includes one or more polynucleotides that homologously combine in a gene of a host that encodes a phosphofructokinase (PFK) enzyme, phosphoglucoisomerase (PGI) enzyme, transketolase enzyme, transaldolase enzyme, or combination thereof.

X20. The composition of embodiment X19, wherein the transketolase enzyme is encoded by a TKL-1 coding sequence or a TKL-2 coding sequence.

X21. The composition of embodiment X19, wherein the transaldolase is encoded by a TAL-1 coding sequence.

X22. The composition of embodiment X19, wherein the phosphofructokinase (PFK) enzyme is a PFK-2 enzyme or PFK-1 enzyme.

X23. The composition of any one of embodiments X1 to X22, wherein the 6-phosphogluconate dehydrogenase (decarboxylating) enzyme is encoded by a GND-1 gene or a GND-2 gene.

X24. The composition of embodiment X19, wherein the PGI is encoded by a PGI-1 gene.

X25. The composition of any one of embodiments X1 to X24, wherein the nucleic acid is one or two separate nucleic acid molecules.

X26. The composition of embodiment X25, wherein each nucleic acid molecule includes one or two or more of the polynucleotide subsequences, one or two or more of the promoters, or one or two or more of the polynucleotide subsequences and one or two or more of the promoters.

X27. The composition of embodiment X25 or X26, wherein each of the one or two nucleic acid molecules are in circular form.

X28. The composition of embodiment X25 or X26, wherein each of the one or two nucleic acid molecules are in linear form.

X29. The composition of any one of embodiments X25 to X28, wherein each of the one or two nucleic acid molecules functions as an expression vector.

X30. The composition of any one of embodiments X25 to X29, wherein each of the one or two nucleic acid molecules includes flanking sequences for integrating the polynucleotides, the promoter sequences, or the polynucleotides and the promoter sequences in the nucleic acid into genomic DNA of a host organism.

Y1. A composition comprising an engineered yeast that includes an alteration that adds or increases a phosphogluconate dehydratase activity and a 2-keto-3-deoxygluconate-6-phosphate aldolase activity, and an alteration that reduces a 6-phosphogluconate dehydrogenase (decarboxylating) activity.

Y2. The composition of embodiment Y1, wherein the yeast is a *Saccharomyces* spp. yeast.

Y3. The composition of embodiment Y2, wherein the yeast is a *Saccharomyces cerevisiae* yeast strain.

Y4. The composition of any one of embodiments Y1 to Y3, wherein the yeast includes an altered gene that encodes a 6-phosphogluconate dehydrogenase (decarboxylating) enzyme.

Y4.1. The composition of any one of embodiments Y1 to Y4 where the yeast includes heterologous polynucleotides, or multiple copies of endogenous polynucleotides, that encode a phosphogluconate dehydratase enzyme and a 2-keto-3-deoxygluconate-6-phosphate aldolase enzyme.

Y5. The composition of embodiment Y4, wherein the polynucleotides encoding the phosphogluconate dehydratase enzyme and the 3-deoxygluconate-6-phosphate aldolase enzyme independently are from an *Escherichia* spp. microbe or *Pseudomonas* spp. microbe.

Y6. The composition of embodiment Y5, wherein the *Escherichia* spp. microbe is an *Escherichia coli* strain.

Y7. The composition of embodiment Y5, wherein the *Pseudomonas* spp. microbe is a *Pseudomonas aeruginosa* strain.

Y8. The composition of any one of embodiments Y4 to Y7, wherein the polynucleotide that encodes the phosphogluconate dehydratase enzyme is an EDD gene.

Y9. The composition of any one of embodiments Y4 to Y7, wherein the polynucleotide that encodes the 2-keto-3-deoxygluconate-6-phosphate aldolase enzyme is an EDA gene.

Y10. The composition of any one of embodiments Y1 to Y11, wherein a glucose-6-phosphate dehydrogenase activity is added or increased.

Y10.1. The composition of embodiment Y10, wherein the yeast comprises a heterologous polynucleotide that encodes a 6-phosphogluconolactonase enzyme, or wherein the yeast comprises multiple copies of an endogenous polynucleotide that encodes a 6-phosphogluconolactonase enzyme.

Y10.2. The composition of embodiment Y10.1, wherein the polynucleotide that encodes the 6-phosphogluconolactonase enzyme enzyme is from a yeast.

Y10.3. The composition of embodiment Y10.2, wherein the yeast is a *Saccharomyces* spp. yeast.

Y10.4. The composition of embodiment Y10.3, wherein the yeast is a *Saccharomyces cerevisiae* strain.

Y10.5. The composition of any one of embodiments Y10 to Y10.4, wherein the 6-phosphogluconolactonase enzyme is expressed from a SOL gene.

Y11. The composition of embodiment Y10.4, wherein the SOL gene is a SOL3 gene.

Y12. The composition of any one of embodiments Y4 to Y11, wherein a glucose-6-phosphate dehydrogenase activity is added or increased.

Y13. The composition of embodiment Y12, wherein the yeast comprises a heterologous polynucleotide that encodes a glucose-6-phosphate dehydrogenase enzyme, or wherein the yeast comprises multiple copies of an endogenous polynucleotide that encodes a glucose-6-phosphate dehydrogenase enzyme.

Y14. The composition of embodiment Y13, wherein the polynucleotide that encodes the glucose-6-phosphate dehydrogenase enzyme is from a yeast.

Y15. The composition of embodiment Y14, wherein the yeast is a *Yaccharomyces* spp. yeast.

Y16. The composition of embodiment Y15, wherein the yeast is a *Yaccharomyces cerevisiae* strain.

Y17. The composition of any one of embodiments Y13 to Y17, wherein the glucose-6-phosphate dehydrogenase enzyme is expressed from a ZWF gene.

Y18. The composition of embodiment Y17, wherein the ZWF gene is a ZWF1 gene.

Y19. The composition of any one of embodiments Y1 to Y18, wherein the nucleic acid includes one or more promoters operable in a yeast, wherein the promoter is in operable connection with one or more of the polynucleotides.

Y20. The composition of embodiment Y19, wherein the promoter is selected from promoters that regulate glucose phosphate dehydrogenase (GYD), translation elongation factor (TEF-1), phosphoglucokinase (YGK-1) and triose phosphate dehydrogenase (TDH-1).

Y21. The composition of any one of embodiments Y1 to Y20, wherein the yeast includes a reduction in one or more of the following activities: phosphofructokinase (PFK) activity, phosphoglucoisomerase (PGI) activity, transketolase activity, transaldolase activity, or combination thereof.

Y22. The composition of embodiment Y21, wherein the yeast includes an alteration in one or more polynucleotides that inhibits production of one or more enzymes selected from the group consisting of phosphofructokinase (PFK) enzyme, phosphoglucoisomerase (PGI) enzyme, 6-phosphogluconate dehydrogenase (decarboxylating) enzyme, transketolase enzyme, transaldolase enzyme, or combination thereof.

Y23. The composition of embodiment Y22, wherein the transketolase enzyme is encoded by a TKL-1 coding sequence or a TKL-2 coding sequence.

Y24. The composition of embodiment Y22, wherein the transaldolase is encoded by a TAL-1 coding sequence.

Y25. The composition of embodiment Y22, wherein the phosphofructokinase (PFK) enzyme is a PFK-2 enzyme or PFK-1 enzyme.

Y26. The composition of any one of embodiments Y4 to Y25, wherein the 6-phosphogluconate dehydrogenase (decarboxylating) enzyme is encoded by a GND-1 gene or GND-2 gene.

Y27. The composition of embodiment Y22, wherein the PGI is encoded by a PGI-1 gene.

Y28. The composition of any one of embodiments Y1 to Y27, wherein the polynucleotides, the promoters, or the polynucleotides and the promoters are not integrated in the yeast nucleic acid.

Y29. The composition of embodiment Y28, wherein the polynucleotides, the promoters, or the polynucleotides and the promoters are in one or more plasmids.

Y30. The composition of any one of embodiments Y1 to Y29, wherein the polynucleotide subsequences, the promoters, or the polynucleotide subsequences and the promoters are integrated in genomic DNA of the yeast.

Y31. The composition of embodiment Y30, wherein the polynucleotides, the promoters, or the polynucleotides and the promoters are integrated in a transposition integration event, in a homologous recombination integration event, or in a transposition integration event and a homologous recombination integration event.

Y32. The composition of embodiment Y31, wherein the transposition integration event includes transposition of an operon comprising two or more of the polynucleotide subsequences, the promoters, or the polynucleotide subsequences and the promoters.

Y33. The composition of embodiment Y31, wherein the homologous recombination integration event includes homologous recombination of an operon comprising two or more of the polynucleotide subsequences, the promoters, or the polynucleotide subsequences and the promoters.

Z1. A method, comprising contacting an engineered yeast of any one of embodiments Y1 to Y33 with a feedstock that contains one or more hexose sugars under conditions in which the microbe synthesizes ethanol.

Z2. The method of embodiment Z1, wherein the engineered yeast synthesizes ethanol to about 85% to about 99% of theoretical yield.

Z3. The method of embodiment Z1 or Z2, comprising recovering ethanol synthesized by the engineered yeast.

Z4. The method of any one of embodiments Z1 to Z3, wherein the conditions are fermentation conditions.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. An engineered *Saccharomyces cerevisiae* yeast comprising a chimeric enzyme having xylose isomerase activity, wherein:
   the C-terminal region of the chimeric enzyme comprises at least 5 contiguous amino acids from a *Ruminococcus* spp. xylose isomerase enzyme; and
   the N-terminal region of the chimeric enzyme comprises at least 5 contiguous amino acids from a fungal xylose isomerase enzyme.

2. The engineered *Saccharomyces cerevisiae* yeast of claim 1, wherein the *Ruminococcus* spp. xylose isomerase enzyme is from a *Ruminococcus flavefaciens* strain.

3. The engineered *Saccharomyces cerevisiae* yeast of claim 2, wherein the *Ruminococcus flavefaciens* strain is selected from the group consisting of *Ruminococcus flavefaciens* strain 17, *Ruminococcus flavefaciens* strain Siijpesteijn 1948, and *Ruminococcus flavefaciens* strain FD1.

4. The engineered *Saccharomyces cerevisiae* yeast of claim 2, wherein the at least 5 contiguous amino acids from the *Ruminococcus* spp. xylose isomerase enzyme are from SEQ ID NO: 31.

5. The engineered *Saccharomyces cerevisiae* yeast of claim 1, wherein the fungal xylose isomerase enzyme is from a fungus selected from the group consisting of an *Aspergillus* spp., *Thraustochytrium* spp., *Schizochytrium* spp., *Rhizopus* spp., *Orpinomyces* spp, and *Piromyces* spp.

6. The engineered *Saccharomyces cerevisiae* yeast of claim 5, wherein the fungal xylose isomerase enzyme is from a *Piromyces* spp.

7. The engineered *Saccharomyces cerevisiae* yeast of claim 6, wherein the *Piromyces* spp, is a *Piromyces* strain E2.

8. The engineered *Saccharomyces cerevisiae* yeast of claim 7, wherein the at least 5 contiguous amino acids from the fungal xylose isomerase enzyme are from SEQ ID NO: 35.

9. The engineered *Saccharomyces cerevisiae* yeast of claim 5, wherein the fungal xylose isomerase enzyme is from an *Orpinomyces* spp.

10. The engineered *Saccharomyces cerevisiae* yeast of claim 1, comprising a heterologous phosphogluconate dehydratase enzyme and a heterologous 3-deoxygluconate-6-phosphate aldolase enzyme.

11. The engineered *Saccharomyces cerevisiae* yeast of claim 10, wherein the phosphogluconate dehydratase enzyme and the 3-deoxygluconate-6-phosphate aldolase enzyme independently are encoded by a polynucleotide from an *Escherichia* spp, or *Pseudomonas* spp.

12. The engineered *Saccharomyces cerevisiae* yeast of claim 11, wherein the phosphogluconate dehydratase enzyme is encoded by a polynucleotide from a *Pseudomonas aeruginosa* strain.

13. The engineered *Saccharomyces cerevisiae* yeast of claim 12, wherein the phosphogluconate dehydratase enzyme comprises an amino acid sequence of SEQ ID NO 70.

14. The engineered *Saccharomyces cerevisiae* yeast of claim 1, wherein the C-terminal region of the chimeric enzyme comprises the contiguous amino acid sequence of the *Ruminococcus* spp. xylose isomerase enzyme less 5 to 30 contiguous N-terminal amino acids of the *Ruminococcus* spp. xylose isomerase enzyme.

15. The engineered *Saccharomyces cerevisiae* yeast of claim 14, wherein the N-terminal region of the chimeric enzyme comprises 5 to 30 contiguous N-terminal amino acids from the fungal xylose isomerase enzyme.

16. The engineered *Saccharomyces cerevisiae* yeast of claim 15, wherein the fungal xylose isomerase enzyme is from an *Orpinomyces* spp, fungus or *Piromyces* spp, fungus.

17. The engineered *Saccharomyces cerevisiae* yeast of claim 2, wherein the C-terminal region of the chimeric enzyme comprises the contiguous amino acid sequence of the Ruminococcus flavefaciens xylose isomerase enzyme less 5 to 30 contiguous N-terminal amino acids of the Ruminococcus flavefaciens xylose isomerase enzyme.

18. The engineered Saccharomyces cerevisiae yeast of claim 17, wherein the N-terminal region of the chimeric enzyme comprise 5 to 30 contiguous N-terminal amino acids from the fungal xylose isomerase enzyme.

19. The engineered Saccharomyces cerevisiae yeast of claim 18, wherein the fungal xylose isomerase enzyme is from an Orpinomyces spp, fungus or Piromyces spp, fungus.

* * * * *

UNITED STATES PATENT AND TRADEMARK OFFICE
CERTIFICATE OF CORRECTION

Page 1 of 2

PATENT NO. : 8,093,037 B2
APPLICATION NO. : 13/045841
DATED : January 10, 2012
INVENTOR(S) : Stephen Picataggio, Kirsty Anne Lily Salmon and Jose Miguel LaPlaza It is certified that error appears in the above-identified patent and that said Letters Patent is hereby corrected as shown below:

In column 725, line 34, correct claim 1 to read as follows:

1. An engineered Saccharomyces cerevisiae yeast comprising a chimeric enzyme having xylose isomerase activity, wherein:

the C-terminal region of the chimeric enzyme comprises at least 5 contiguous amino acids from a Ruminococcus spp[[,]]. xylose isomerase enzyme; and the N-terminal region of the chimeric enzyme comprises at least 5 contiguous amino acids from a fungal xylose isomerase enzyme.

In column 725, line 43, correct claim 2 to read as follows:

2. The engineered Saccharomyces cerevisiae yeast of claim 1, wherein the Ruminococcus spp[[,]]. xylose isomerase enzyme is from a Ruminococcus flavefaciens strain.

In column 725, line 51, correct claim 4 to read as follows:

4. The engineered Saccharomyces cerevisiae yeast of claim 2, wherein the at least 5 contiguous amino acids from the Ruminococcus spp[[,]]. xylose isomerase enzyme are from SEQ ID NO: 31.

In column 725, line 55, correct claim 5 to read as follows:

5. The engineered Saccharomyces cerevisiae yeast of claim 1, wherein the fungal xylose isomerase enzyme is from a fungus selected from the group consisting of an Aspergillus spp., Thraustochytrium spp., Schizochytrium spp., Rhizopus spp., Orpinomyces spp[[,]]., and Piromyces spp.

In column 725, line 63, correct claim 7 to read as follows:

7. The engineered Saccharomyces cerevisiae yeast of claim 6, wherein the Piromyces spp[[,]]. is a Piromyces strain E2.

Signed and Sealed this
Twelfth Day of June, 2012

David J. Kappos
*Director of the United States Patent and Trademark Office*

CERTIFICATE OF CORRECTION (continued)
U.S. Pat. No. 8,093,037 B2

In column 726, line 36, correct claim 10 to read as follows:

10. The engineered Saccharomyces cerevisiae yeast of claim 1, comprising a heterologous phosphogluconate dehydratase enzyme and a heterologous <u>2-keto-</u>3-deoxygluconate-6-phosphate aldolase enzyme.

In column 726, line 40, correct claim 11 to read as follows:

11. The engineered Saccharomyces cerevisiae yeast of claim 10, wherein the phosphogluconate dehydratase enzyme and the <u>2-keto-</u>3-deoxygluconate-6-phosphate aldolase enzyme independently are encoded by a polynucleotide from an Escherichia spp[[,]]<u>.</u> or Pseudomonas spp.

In column 726, line 52, correct claim 14 to read as follows:

14. The engineered Saccharomyces cerevisiae yeast of claim 1, wherein the C-terminal region of the chimeric enzyme comprises the contiguous amino acid sequence of the Ruminococcus spp[[,]]<u>.</u> xylose isomerase enzyme less 5 to 30 contiguous N-terminal amino acids of the Ruminococcus spp[[,]]<u>.</u> xylose isomerase enzyme.

In column 726, line 62, correct claim 16 to read as follows:

16. The engineered Saccharomyces cerevisiae yeast of claim 15, wherein the fungal xylose isomerase enzyme is from an Orpinomyces spp[[,]]<u>.</u> fungus or Piromyces spp[[,]]<u>.</u> fungus.

In column 728, line 1, correct claim 19 to read as follows:

19. The engineered Saccharomyces cerevisiae yeast of claim 18, wherein the fungal xylose isomerase enzyme is from an Orpinomyces spp[[,]]<u>.</u> fungus or Piromyces spp[[,]]<u>.</u> fungus.